United States Patent
Park et al.

(10) Patent No.: US 9,837,618 B2
(45) Date of Patent: *Dec. 5, 2017

(54) COMPOUND AND ORGANIC ELECTROLUMINESCENCE DEVICE INCLUDING THE SAME

(71) Applicant: DOOSAN CORPORATION, Seoul (KR)

(72) Inventors: Ho Cheol Park, Suwon-si (KR); Hyung Chan Bae, Yongin-si (KR); Min Sik Eum, Yongin-si (KR); Young Mi Beak, Yongin-si (KR); Chang Jun Lee, Ansan-si (KR); Jin Yong Shin, Yongin-si (KR); Tae Hyung Kim, Yongin-si (KR)

(73) Assignee: DOOSAN CORPORATION, Seoul (KR)

( * ) Notice: Subject to any disclaimer, the term of this patent is extended or adjusted under 35 U.S.C. 154(b) by 167 days.

This patent is subject to a terminal disclaimer.

(21) Appl. No.: 14/421,679

(22) PCT Filed: Aug. 13, 2013

(86) PCT No.: PCT/KR2013/007282
§ 371 (c)(1),
(2) Date: May 1, 2015

(87) PCT Pub. No.: WO2014/027822
PCT Pub. Date: Feb. 20, 2014

(65) Prior Publication Data
US 2015/0236272 A1  Aug. 20, 2015

(30) Foreign Application Priority Data

Aug. 17, 2012  (KR) .................. 10-2012-0090244

(51) Int. Cl.
| H01L 51/50 | (2006.01) |
| H01L 51/00 | (2006.01) |
| C07D 487/04 | (2006.01) |
| C09K 11/06 | (2006.01) |

(52) U.S. Cl.
CPC ........ *H01L 51/0072* (2013.01); *C07D 487/04* (2013.01); *C09K 11/06* (2013.01); *H01L 51/0052* (2013.01); *H01L 51/0054* (2013.01); *H01L 51/0056* (2013.01); *H01L 51/0061* (2013.01); *H01L 51/0071* (2013.01); *C09K 2211/1044* (2013.01); *C09K 2211/1048* (2013.01); *C09K 2211/1051* (2013.01); *C09K 2211/1059* (2013.01); *C09K 2211/1062* (2013.01); *C09K 2211/1066* (2013.01); *C09K 2211/1074* (2013.01); *C09K 2211/1077* (2013.01); *C09K 2211/1081* (2013.01); *H01L 51/5016* (2013.01); *H01L 51/5056* (2013.01); *H01L 51/5088* (2013.01); *H01L 2251/308* (2013.01)

(58) Field of Classification Search
None
See application file for complete search history.

(56) References Cited

FOREIGN PATENT DOCUMENTS

| CN | 102449106 |   | 5/2012 |   |
|---|---|---|---|---|
| CN | 104736537 | A | 6/2015 |   |
| JP | 10502374 | A | 3/1998 |   |
| JP | 2007088016 | A | 4/2007 |   |
| JP | 2010205982 | A | 9/2010 |   |
| JP | 2011506475 | A | 3/2011 |   |
| JP | 2011526610 | A | 10/2011 |   |
| JP | 2012-01513 | * | 1/2012 | ............ H01L 51/50 |
| JP | 2012001513 |   | 1/2012 |   |
| JP | 2012140365 | A | 7/2012 |   |
| JP | 2015502953 | A | 1/2015 |   |
| KR | 10-2011-0014752 | A | 2/2011 |   |
| KR | 10-2011-0083442 | A | 7/2011 |   |
| KR | 10-2012-0044517 | A | 5/2012 |   |
| WO | 2009136586 | A1 | 11/2009 |   |
| WO | 2010107244 | A2 | 9/2010 |   |
| WO | 2011136755 | A1 | 11/2011 |   |
| WO | 2012/039561 | A1 | 3/2012 |   |
| WO | 2012039561 | A1 | 3/2012 |   |
| WO | 2012050371 | A1 | 4/2012 |   |
| WO | 2012/067425 | A1 | 5/2012 |   |

OTHER PUBLICATIONS

Bosch, Joan et al., Rearrangement under alkaline conditions of compounds related to tetracyclic Strychnos indole alkaloids Heterocycles (1984), 22(3), 561-4 (STN Abstract Only).*
International Searching Authority, International Search Report of PCT/KR2013/007282, dated Nov. 29, 2013. [PCT/ISA/210].
Japanese Patent Office; Communication dated Feb. 10, 2016 in counterpart application No. 2015-527368.
Sikharulidze et al."Pyrrolocarbazoles. 4. Acetylation of 3Hpyrrolo[2.3-c]carbazole" Chemistry of Heterocyclic Compounds, Apr. 1981, vol. 17, Issue 4, pp. 357-360 (9 pages total).
State Intellectual Property Office of the P.R.C.; Communication dated Nov. 3, 2015 in counterpart application No. 201380053772.5.
Chinese Patent Office, Communication dated Aug. 3, 2016 in counterpart Chinese Application No. 201380053772.5.

* cited by examiner

*Primary Examiner* — Gregory Clark
(74) *Attorney, Agent, or Firm* — Sughrue Mion, PLLC

(57) ABSTRACT

The present invention relates to a novel indole-based compound having excellent hole injection and transport capabilities, light-emitting capabilities, and the like, and an organic electroluminescence device which includes the indole-based compound in one or more organic material layers thereof so as to improve characteristics such as light-emitting efficiency, driving voltage, and lifespan.

9 Claims, No Drawings

COMPOUND AND ORGANIC ELECTROLUMINESCENCE DEVICE INCLUDING THE SAME

CROSS REFERENCE TO RELATED APPLICATIONS

This application is a National Stage of International Application No. PCT/KR2013/007282, filed Aug. 13, 2013, claiming priority based on Korean Patent Application No. 10-2012-0090244, filed Aug. 17, 2012, the contents of all of which are incorporated herein by reference in their entirety.

TECHNICAL FIELD

The present invention relates to a novel compound and an organic electroluminescence device including the same.

BACKGROUND ART

When voltage is applied between two electrodes of the organic electroluminescence device, holes are injected into the organic material layer at the anode and electrons are injected into the organic material layer at the cathode, the injected holes and electrons meet each other to form an exciton, and when the formed exciton falls down to a bottom state, light is emitted. Materials used as the organic material layer may be classified into a light-emitting material, a hole injection material, a hole transporting material, an electron transporting material, an electron injection material, and the like according to the function.

The light-emitting materials may be divided into blue, green, and red light-emitting materials according to the light-emitting color, and into yellow and orange light-emitting materials required for implementing a much better natural color. Further, a host/dopant system may be used as a light-emitting material in order to enhance color purity and light-emitting efficiency through an energy transfer.

Dopant materials may be divided into a fluorescent dopant using an organic material and a phosphorescent dopant in which a metal complex compound including heavy atoms such as Ir and Pt is used. Since the development of the phosphorescent dopant may theoretically enhance light-emitting efficiency by up to 4 times compared to the development of the fluorescent dopant, studies on not only phosphorescent dopants, but also phosphorescent hosts have been conducted.

As the hole transporting material, the hole injection material, the electron transporting layer, and the like, NPB, BCP, Alq$_3$ and the like have been widely known until now, and as the light-emitting material, anthracene derivatives have been used. In particular, in the light-emitting material, metal complex compounds including Ir and having a great advantage in terms of enhancing the efficiency, such as Firpic, Ir(ppy)$_3$ and (acac)Ir(btp)$_2$, are used as blue, green and red phosphorescent dopant materials, and CBP is used as a phosphorescent host material.

However, since light-emitting materials in the related art have good light-emitting characteristics, but have low glass transition temperature, and thus poor thermal stability, these materials fall short of a level that sufficiently satisfies the lifespan of the organic electroluminescence device.

DISCLOSURE

Technical Problem

An object of the present invention is to provide a novel compound which has excellent light-emitting capabilities, hole transport capabilities, hole injection capabilities, and the like, and thus may be used as a material for a light-emitting layer, a material for a hole transporting layer, and a material for a hole injection layer.

Further, another object of the present invention is to provide an organic electroluminescence device which includes the novel compound, and thus has low driving voltage, high light-emitting efficiency, and an enhanced lifespan.

Technical Solution

In order to achieve the objects, the present invention provides a compound represented by the following Formula 1.

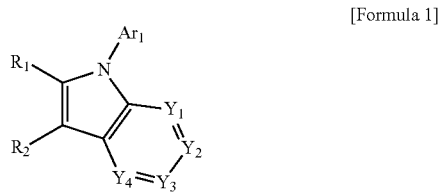

[Formula 1]

In Formula 1, $Y_1$ to $Y_4$ are each independently N or $CR_3$, and one of $Y_1$ and $Y_2$, $Y_2$ and $Y_3$ and $Y_3$ and $Y_4$ forms a fused ring represented by the following Formula 2,

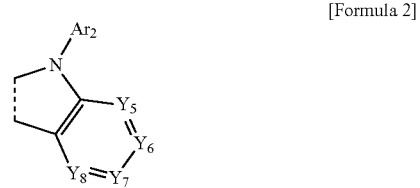

[Formula 2]

in Formula 2, $Y_5$ to $Y_8$ are each independently N or $CR_4$, and the dotted line means a site where a fusion (condensation) with the compound of Formula 1 occurs, $Ar_1$ and $Ar_2$ are each independently selected from the group consisting of a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and in this case, one or more of $Ar_1$ and $Ar_2$ are represented by the following Formula 3,

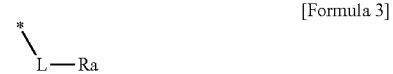

[Formula 3]

in Formula 3, L is a single bond or phenylene,

Ra is selected from the group consisting of structures represented by the following S-1 to S-17,

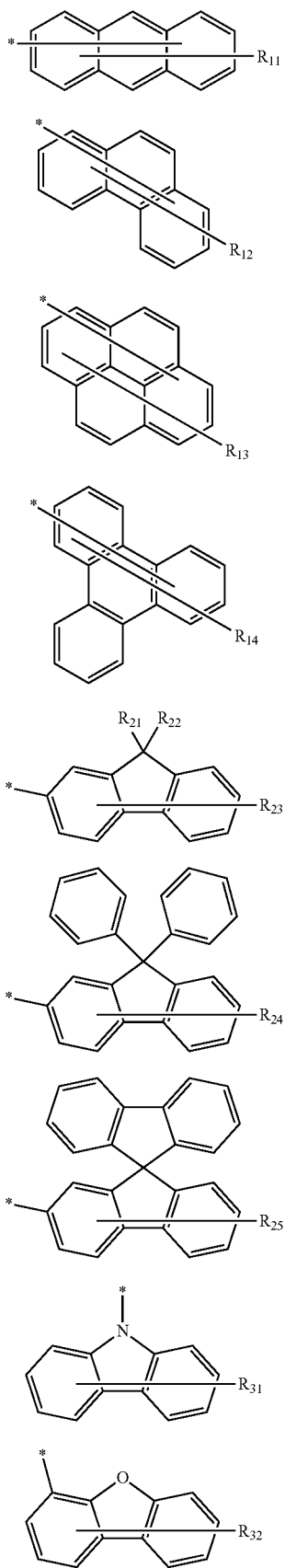

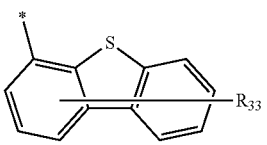

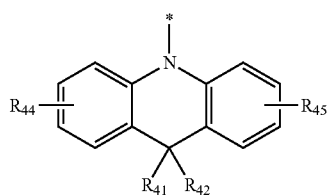

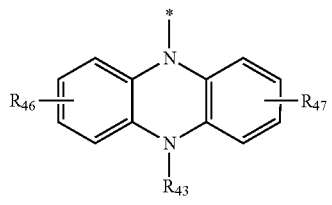

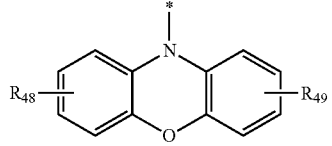

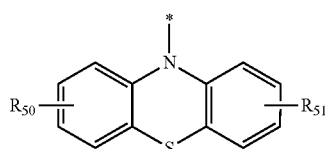

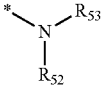

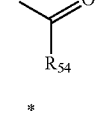

in the structure, $R_{11}$ to $R_{14}$, $R_{21}$ to $R_{25}$, $R_{31}$ to $R_{33}$, and $R_{41}$ to $R_{56}$ are each independently selected from the group consisting of hydrogen, deuterium, halogen, nitro, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and the * sign means a site which is bonded to L, $R_1$ to $R_4$ are each independently selected from the group consisting of hydrogen, deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may form a fused ring with an adjacent group, the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_1$ to $R_4$, $R_{11}$ to $R_{14}$, $R_{21}$ to $R_{25}$, $R_{31}$ to $R_{33}$, and $R_{41}$ to $R_{56}$ may be each independently substituted with one or more selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group. Here, when the groups are substituted with a plurality of substituents, the respective substituents may be the same as or different from each other.

Also, the present invention provides a compound selected from the group consisting of compounds represented by the following Formulae 4 to 9.

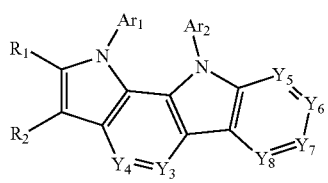

[Formula 4]

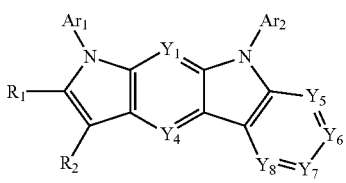

[Formula 5]

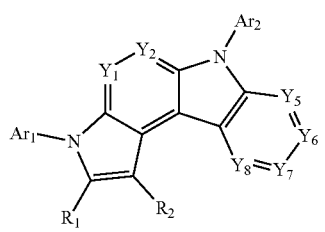

[Formula 6]

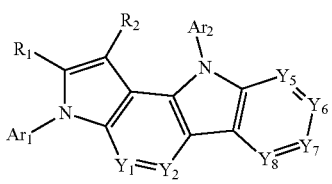

[Formula 7]

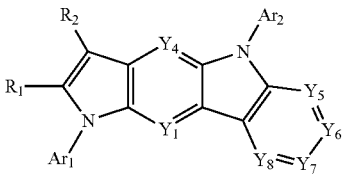

[Formula 8]

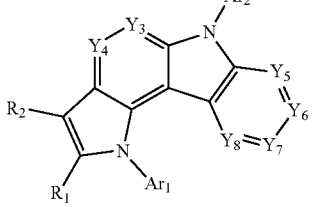

[Formula 9]

In Formulae 4 to 9, $Y_1$ to $Y_4$ are each independently N or $CR_3$, and $Y_5$ to $Y_8$ are each independently N or $CR_4$, $Ar_1$ and $Ar_2$ are different from each other, and are a $C_6$ to $C_{60}$ aryl group or a heteroaryl group having 5 to 60 nuclear atoms, and in this case, one or more of $Ar_1$ and $Ar_2$ are represented by the following Formula 3,

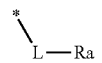

[Formula 3]

in Formula 3, L is a single bond or phenylene, $R_1$ to $R_4$ and Ra are each independently selected from the group consisting of hydrogen, deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may form a fused ring with an adjacent group, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_1$ to $R_4$ and Ra may be each independently substituted with one or more selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

Here, $Ar_1$ and $Ar_2$ are different from each other, one or both thereof may be represented by Formula 3, and in this case, it is preferred that Ra of Formula 3 is selected from the group consisting of structures represented by the following S-1 to S-17.

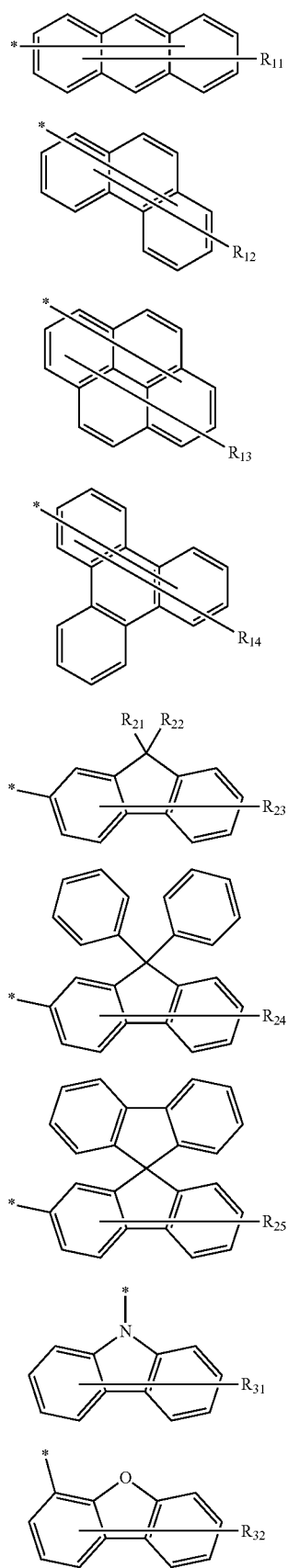

In the structure, $R_{11}$ to $R_{14}$, $R_{21}$ to $R_{25}$, $R_{31}$ to $R_{33}$, and $R_{41}$ to $R_{56}$ are each independently selected from the group consisting of hydrogen, deuterium, halogen, nitro, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and the * sign means a site which is bonded to L, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_{11}$ to $R_{14}$, $R_{21}$ to $R_{25}$, $R_{31}$ to $R_{33}$, and $R_{41}$ to $R_{56}$ may be each independently substituted with one or more selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

The alkyl used in the present invention means a monovalent functional group obtained by removing a hydrogen atom from a linear or branched, saturated hydrocarbon having 1 to 40 carbon atoms, and non-limiting examples thereof include methyl, ethyl, propyl, isobutyl, sec-butyl, pentyl, iso-amyl, hexyl, and the like.

The alkenyl used in the present invention means a monovalent functional group obtained by removing a hydrogen atom from a linear or branched, unsaturated hydrocarbon having 2 to 40 carbon atoms, which has one or more carbon-carbon double bonds. Non-limiting examples thereof include vinyl, allyl, isopropenyl, 2-butenyl, and the like.

The alkynyl used in the present invention means a monovalent functional group obtained by removing a hydrogen atom from a linear or branched, unsaturated hydrocarbon having 2 to 40 carbon atoms, which has one or more carbon-carbon triple bonds. Non-limiting examples thereof include ethynyl, 2-propynyl, and the like.

The cycloalkyl used in the present invention means a monovalent functional group obtained by removing a hydrogen atom from a monocyclic or polycyclic non-aromatic hydrocarbon (saturated cyclic hydrocarbon) having 3 to 40 carbon atoms. Non-limiting examples thereof include cyclopropyl, cyclopentyl, cyclohexyl, norbornyl, adamantine, and the like.

The heterocycloalkyl used in the present invention means a monovalent functional group obtained by removing a hydrogen atom from a non-aromatic hydrocarbon (saturated cyclic hydrocarbon) having 3 to 40 nuclear atoms, and one or more carbons in the ring, preferably 1 to 3 carbons are substituted with a heteroatom such as N, O, or S. Non-limiting examples thereof include morpholine, piperazine, and the like.

The aryl used in the present invention means a monovalent functional group obtained by removing a hydrogen atom from an aromatic hydrocarbon having 6 to 60 carbon atoms of a single ring or a combination of two or more rings. In this case, the two or more rings may be simply pendant to each other or pendant to each other in a fused form. Non-limiting examples thereof include phenyl, biphenyl, terphenyl, naphthyl, phenanthryl, anthryl, and the like.

The heteroaryl used in the present invention is a monovalent functional group obtained by removing a hydrogen atom from a monoheterocyclic or polyheterocyclic aromatic hydrocarbon having 5 to 60 nuclear atoms, and one or more carbons in the ring, preferably 1 to 3 carbons are substituted with a heteroatom such as nitrogen (N), oxygen (O), sulfur (S), or selenium (Se). In this case, the two or more rings may be simply pendant to each other or pendant to each other in a fused form in the heteroaryl, and furthermore, the heteroaryl may also include a fused form with an aryl group. Non-limiting examples of the heteroaryl include: a six-membered monocyclic ring such as pyridyl, pyrazinyl, pyrimidinyl, pyridazinyl, and triazinyl; a polycyclic ring such as phenoxathienyl, indolizinyl, indolyl, purinyl, quinolyl, benzothiazole, and carbazolyl; and 2-furanyl, N-imidazolyl, 2-isoxazolyl, 2-pyridinyl, 2-pyrimidinyl, and the like.

The alkyloxy used in the present invention means a monovalent functional group represented by RO—, and R is an alkyl having 1 to 40 carbon atoms, and may include a linear, branched, or cyclic structure. Non-limiting examples of the alkyloxy include methoxy, ethoxy, n-propoxy, 1-propoxy, t-butoxy, n-butoxy, pentoxy, and the like.

The aryloxy used in the present invention means a monovalent functional group represented by R'O—, and R' is an aryl having 6 to 60 carbon atoms. Non-limiting examples of the aryloxy include phenyloxy, naphthyloxy, diphenyloxy, and the like.

The alkylsilyl used in the present invention means a silyl substituted with an alkyl having 1 to 40 carbon atoms, the arylsilyl means a silyl substituted with an aryl having 6 to 60 carbon atoms, and the arylamine means an amine substituted with an aryl having 6 to 60 carbon atoms.

The fused ring used in the present invention means a fused aliphatic ring, a fused aromatic ring, a fused heteroaliphatic ring, a fused heteroaromatic ring, or a combined form thereof.

Meanwhile, the present invention provides an organic electroluminescence device including an anode, a cathode, and an organic material layer including one or more layers interposed between the anode and the cathode, in which at least one of the organic material layers including or more layers includes the compound represented by Formula 1.

In this case, the organic material layer including one or more layers, which includes the compound represented by Formula 1, is selected from the group consisting of a hole transporting layer, a hole injection layer, and a light-emitting layer, and may be preferably a hole transporting layer and/or a light-emitting layer, and more preferably a phosphorescent light-emitting layer.

Specifically, the compound represented by Formula 1 may be a phosphorescent host material of a phosphorescent light-emitting layer.

BEST MODE

Hereinafter, the present invention will be described.
1. Novel Compound

A novel compound according to the present invention is a compound having a basic structure in which a specific substituent is bonded to a fused indole derivative, and is represented by Formula 1.

The compound of Formula 1 according to the present invention may be usefully applied as a material for a hole injection layer and a hole transporting layer of an organic electroluminescence device because a specific substituent ($R_1$ to $R_4$, $Ar_1$, and $Ar_2$) is introduced into an indole derivative having a broad singlet energy level and a high triplet energy level to effectively adjust the energy level and maximize the hole blocking capabilities and hole injection/transport capabilities. In addition, the compound of Formula 1 according to the present invention may exhibit excellent light-emitting characteristics as a linking group is modified, and thus may also be usefully applied as a material for the light-emitting layer of the organic electroluminescence device.

That is, the compound of Formula 1 according to the present invention may enhance phosphorescent characteristics of the organic electroluminescence device, and simultaneously, enhance hole injection/transport capabilities, light-emitting efficiency, driving voltage, lifespan characteristics, and the like thereof. Furthermore, according to the kind of substituent group (substitution product) to be introduced, electron transport capabilities may also be enhanced. Therefore, the compound of Formula 1 according to the present invention may be used as a material for an organic material layer, preferably a material for a light-emitting layer (a blue, green and/or red phosphorescent host material), a material for a hole transporting layer, and a material for a hole injection layer, of the organic electroluminescence device.

Specifically, various substituent group (substitution products), particularly, an aryl group and/or a heteroaryl group, are introduced into the compound represented by Formula 1 according to the present invention to significantly increase the molecular weight of the compound and enhance the glass transition temperature, and accordingly, the compound represented by Formula 1 may have thermal stability higher than that of the existing light-emitting material (for example, CBP). Therefore, an organic electroluminescence device including the compound of Formula 1 according to the present invention may be greatly enhanced in terms of performance and lifespan characteristics. The organic electroluminescence device with performance and lifespan characteristics enhanced as described above may resultantly maximize performance of a full-color organic light-emitting panel.

In the compound of Formula 1 according to the present invention, one or more of $Ar_1$ and $Ar_2$ are represented by Formula 3, and in this case, it is preferred that Formula 3 is selected from the group consisting of structures represented by the following A1 to A100. In this case, the * sign means a site which is bonded to N (nitrogen).

A1
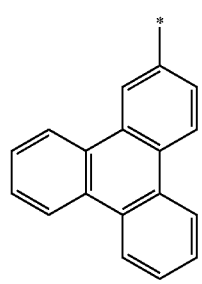

A2
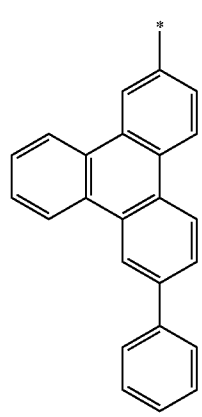

A3
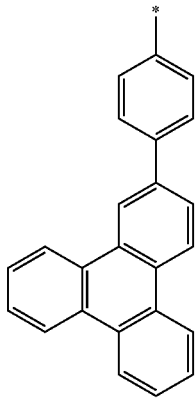

A4
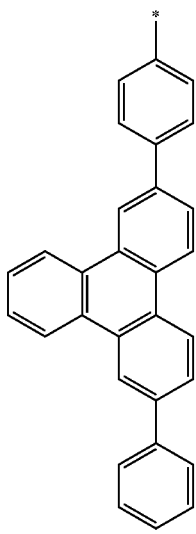

A5
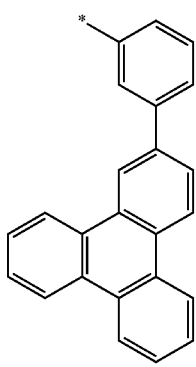

A6
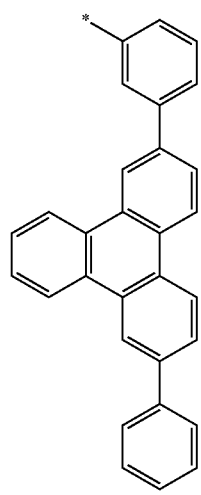
A7
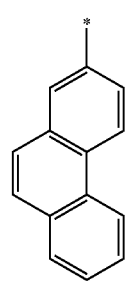
A8
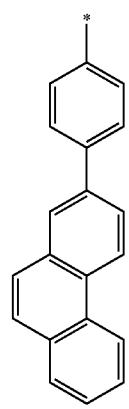
A9
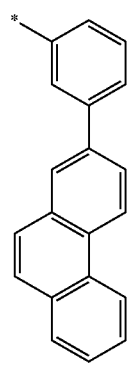
A10
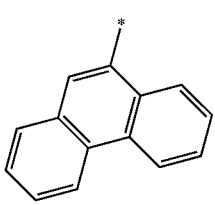
A11
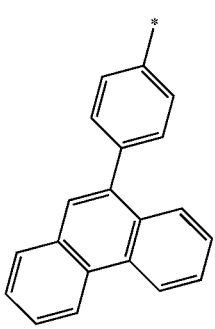
A12
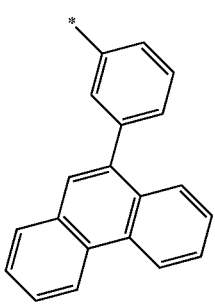
A13
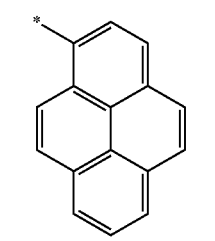
A14

A15 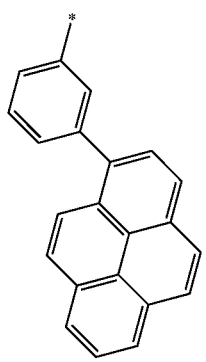
A16 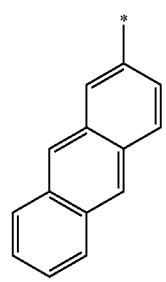
A17 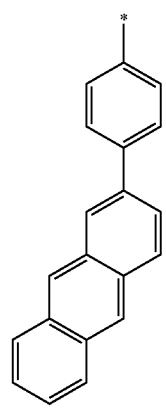
A18 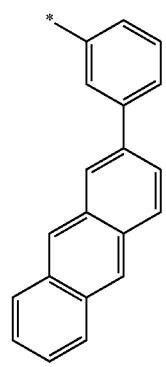
A19 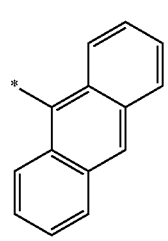
A20 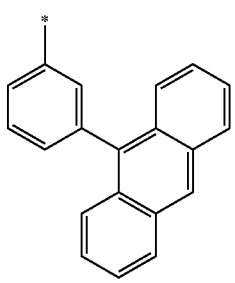
A21 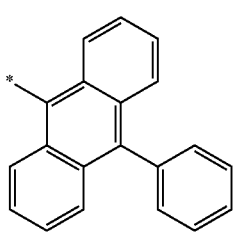
A22 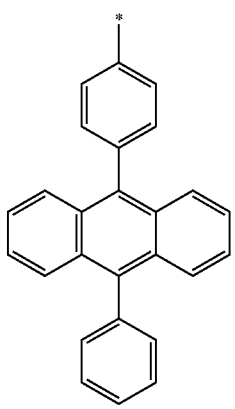
A23 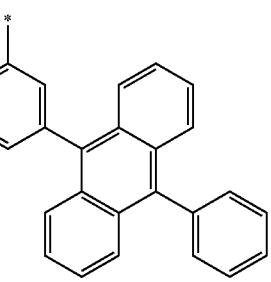
A24 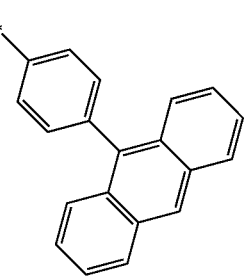

A25 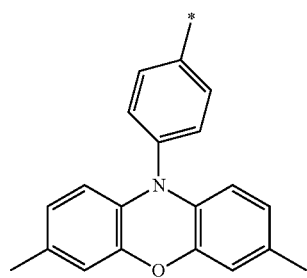
A26 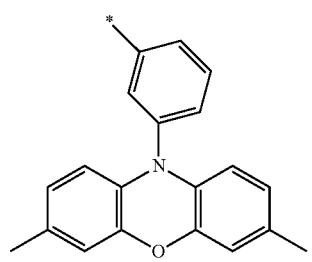
A27 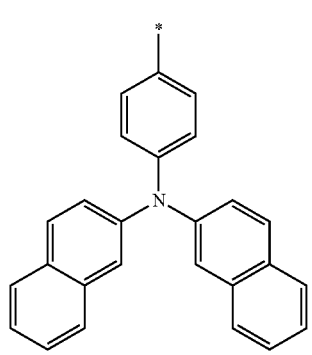
A28 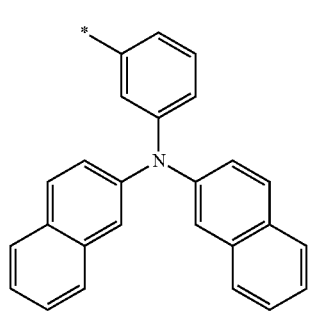
A29 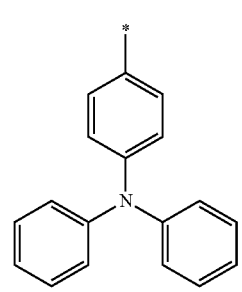
A30 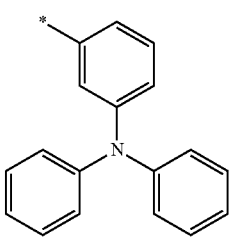
A31 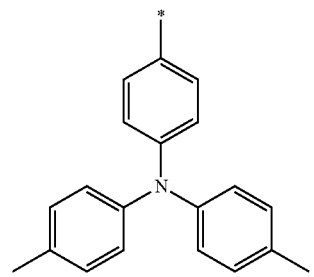
A32 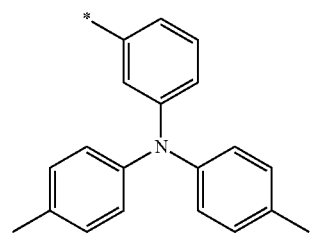
A33 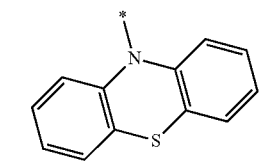
A34 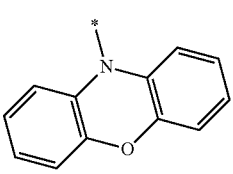
A35 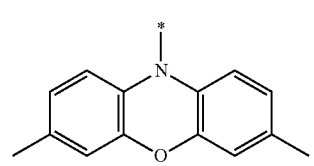
A36 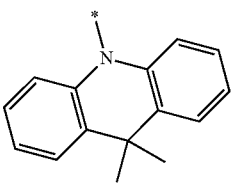

A37 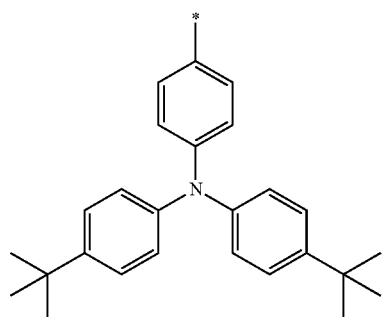
A38 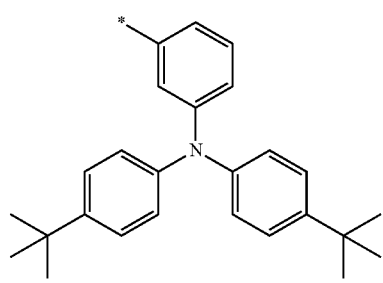
A39 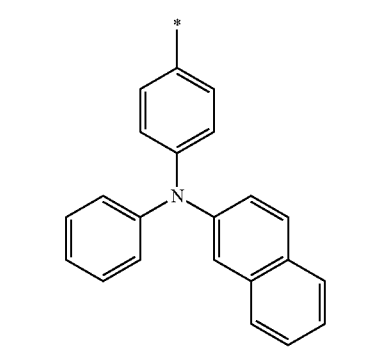
A40 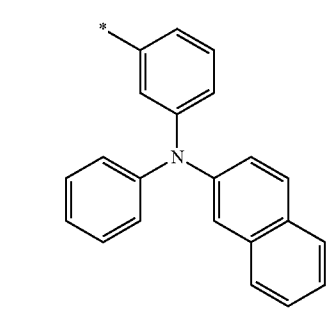
A41 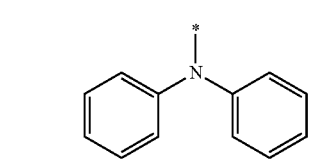
A42 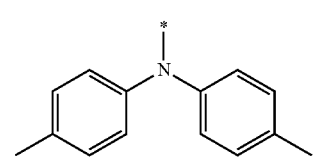
A43 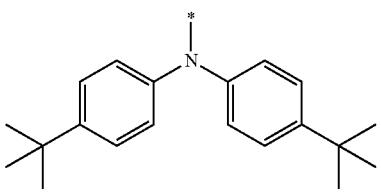
A44 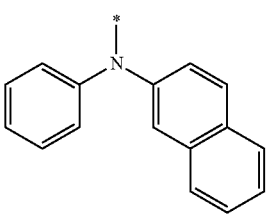
A45 
A46 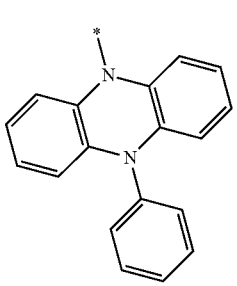
A47 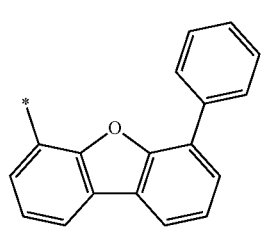
A48 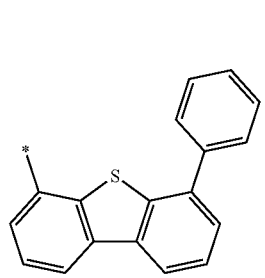
A49 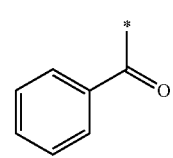

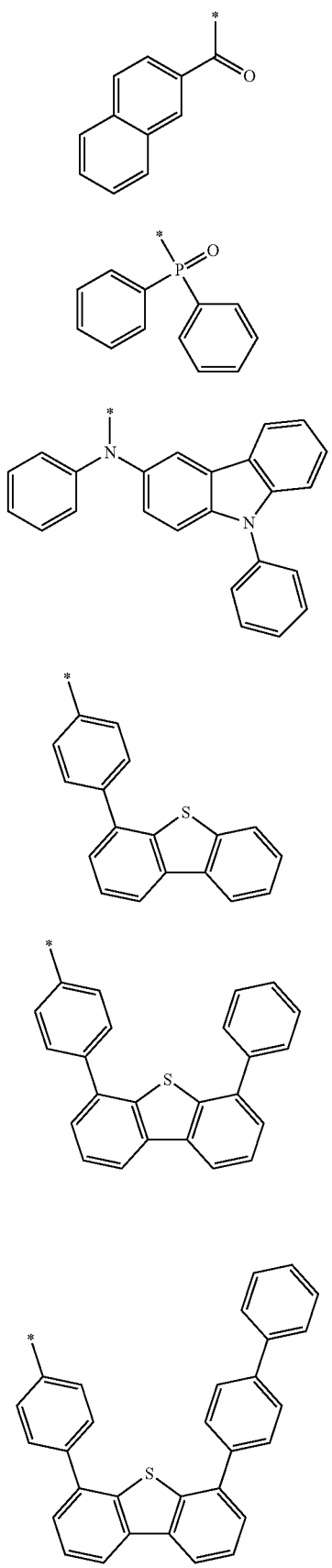
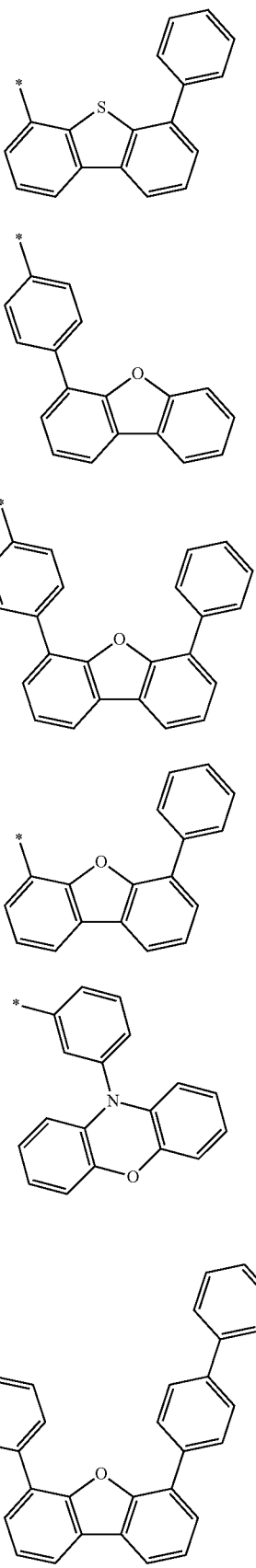

-continued
A62
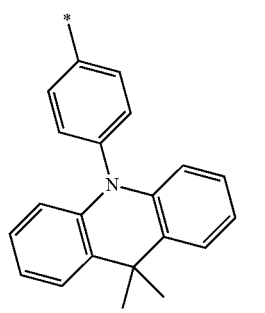
A63
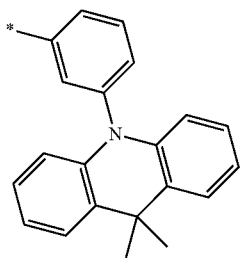
A64
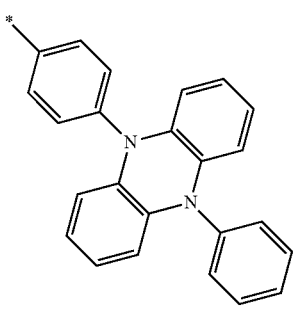
A65
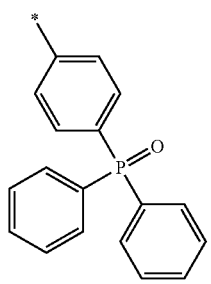
A66
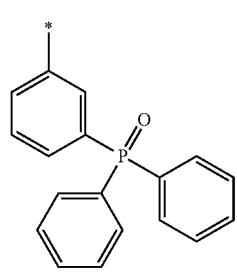
-continued
A67
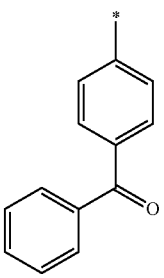
A68
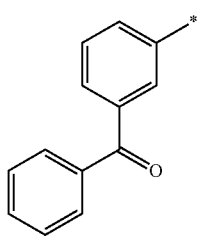
A69
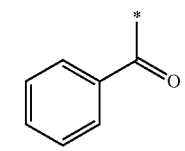
A70
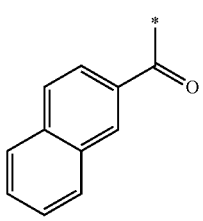
A71
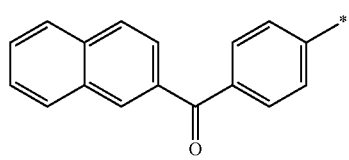
A72
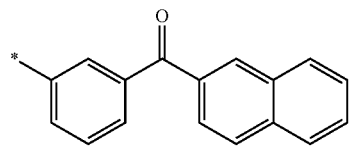
A73
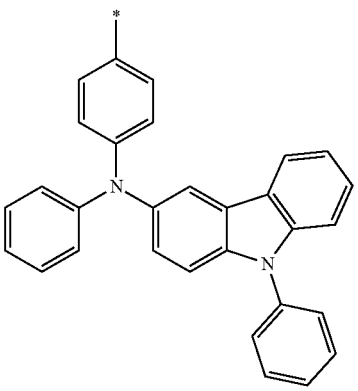

-continued
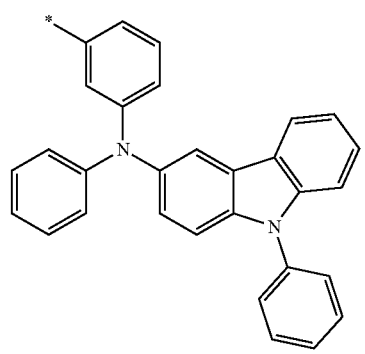
A74
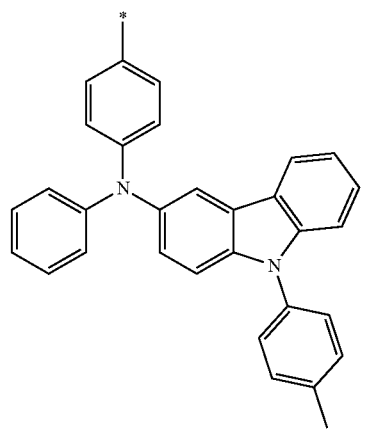
A75
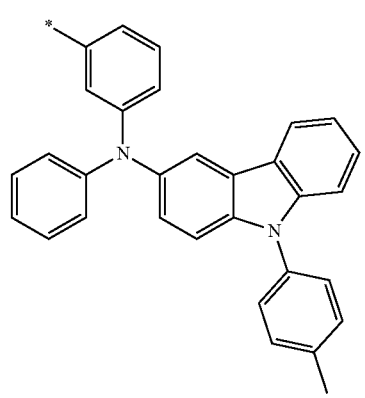
A76
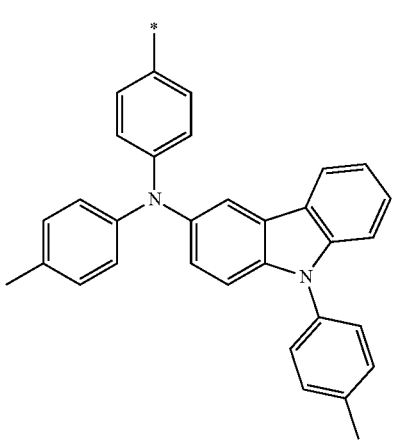
A77
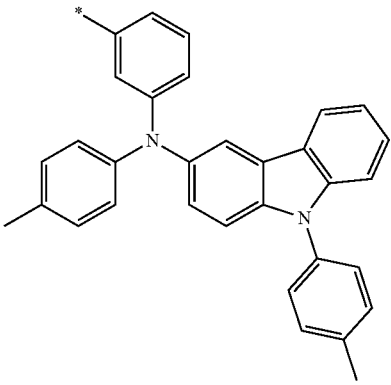
A78
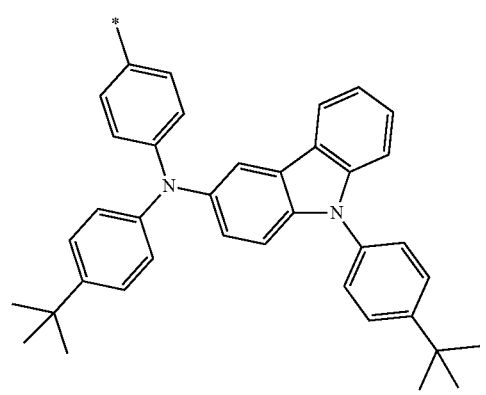
A79
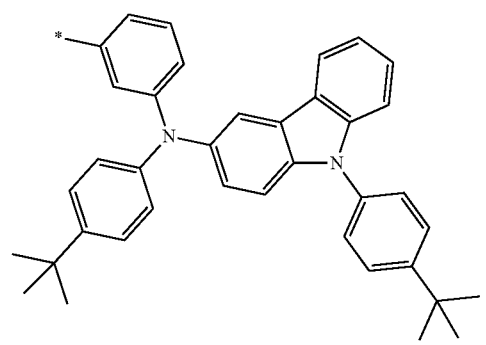
A80
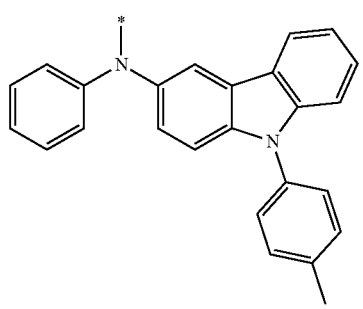
A81

A82
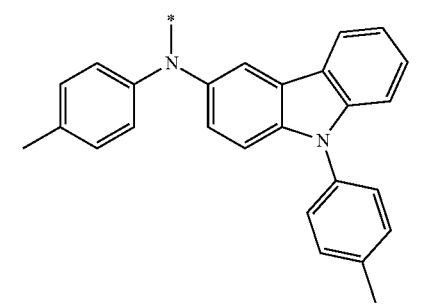
A83
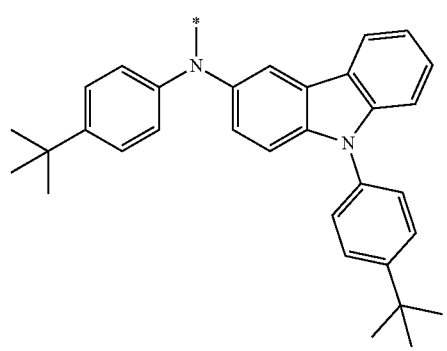
A84
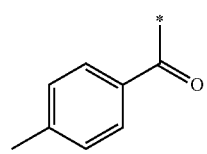
A85
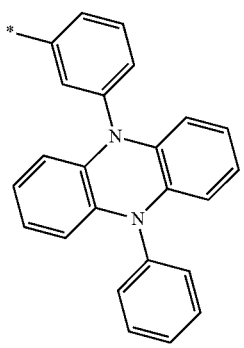
A86
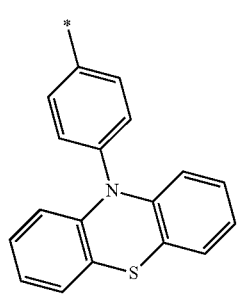
A87
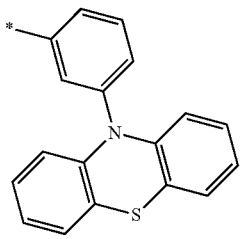
A88
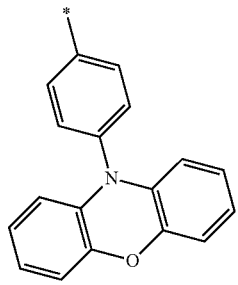
A89
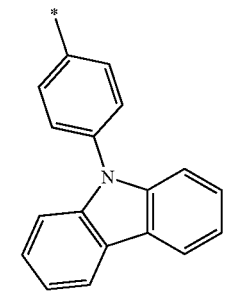
A90
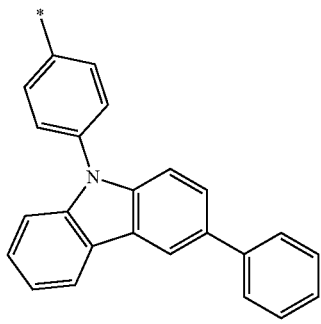
A91
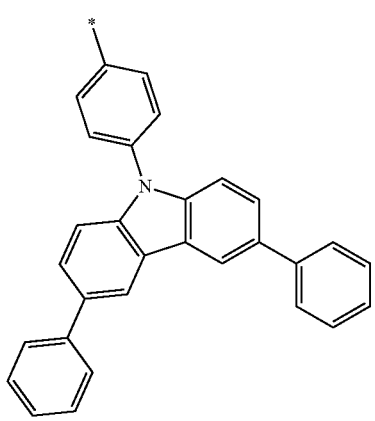

-continued
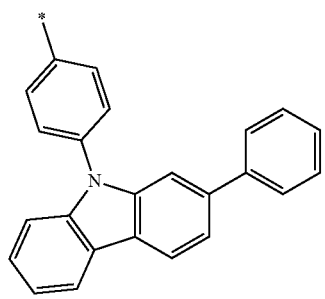
A92
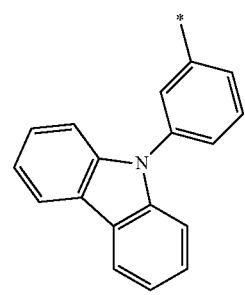
A93
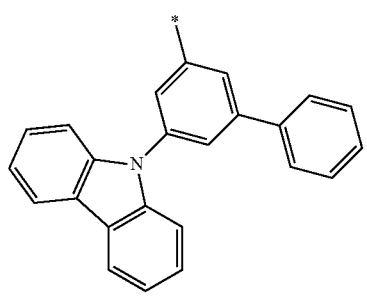
A94
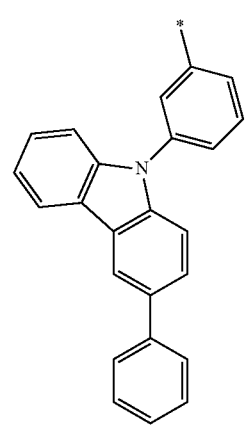
A95
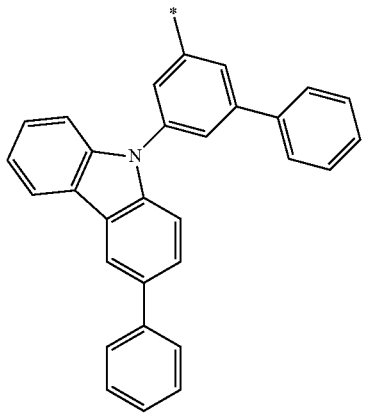
A96
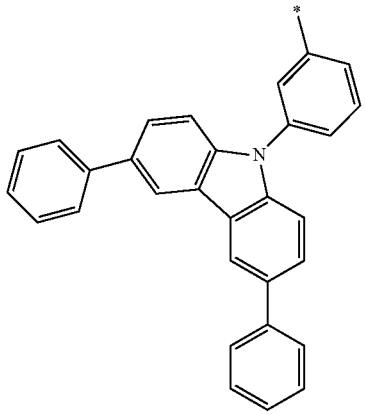
A97
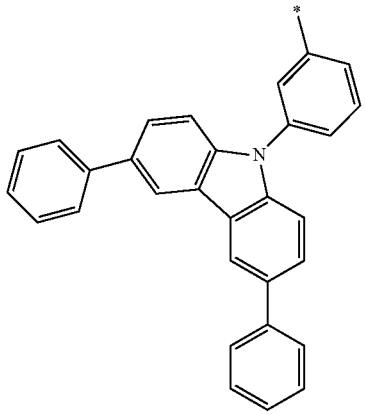
A98
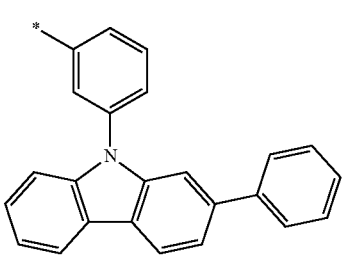
A99

-continued

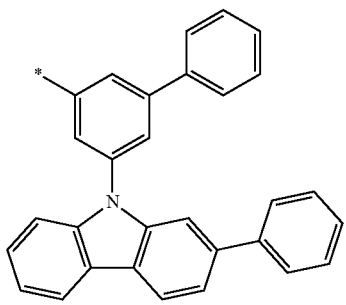

A100

Further, in consideration of performance and lifespan characteristics of the organic electroluminescence device, in the compound of Formula 1 according to the present invention, it is preferred that what does not form a fused ring in $Y_1$ to $Y_4$ is $CR_3$ (for example, when $Y_1$ and $Y_2$ forms a fused ring, both $Y_3$ and $Y_4$ are $CR_3$), and what does not form a fused ring in $Y_5$ to $Y_8$ is $CR_4$ (for example, when $Y_5$ and $Y_6$ forms a fused ring, both $Y_7$ and $Y_8$ are $CR_4$). In this case, $R_3$ and $R_4$ may be the same as or different from each other.

Specifically, it is preferred that the compound of Formula 1 according to the present invention is selected from the group consisting of compounds represented by the following Formulae 4 to 9.

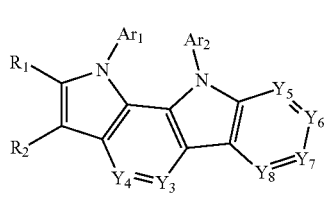

[Formula 4]

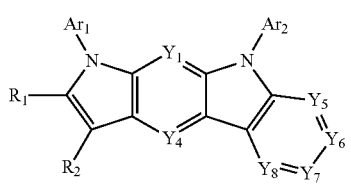

[Formula 5]

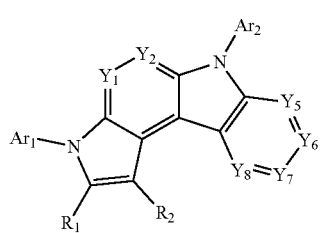

[Formula 6]

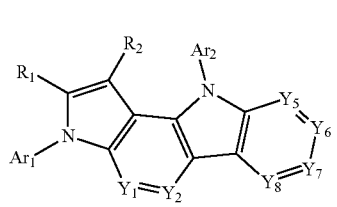

[Formula 7]

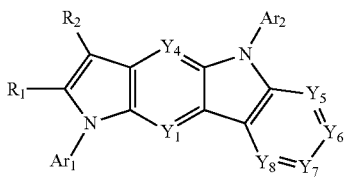

[Formula 8]

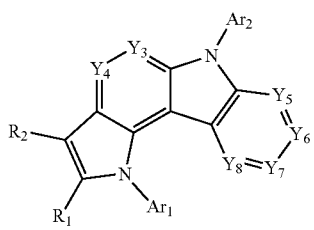

[Formula 9]

In Formulae 4 to 9, $Ar_1$ and $Ar_2$, $Y_1$ to $Y_8$, and $R_1$ to $R_4$ are the same as those defined above.

Specific examples of the compound represented by Formula 1 according to the present invention include the following Examples (Inv1 to Inv1328), but are not limited thereto.

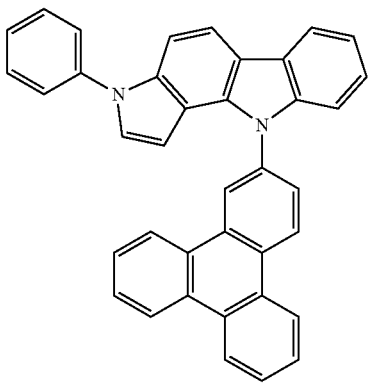

Inv1

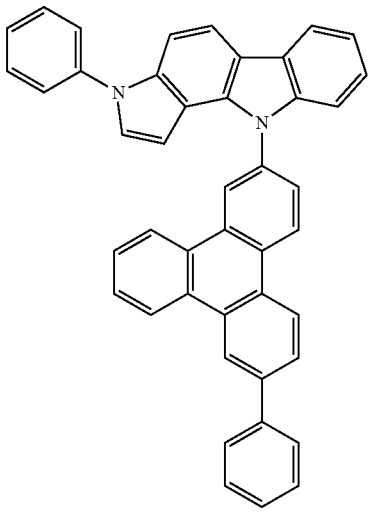

Inv2

Inv3
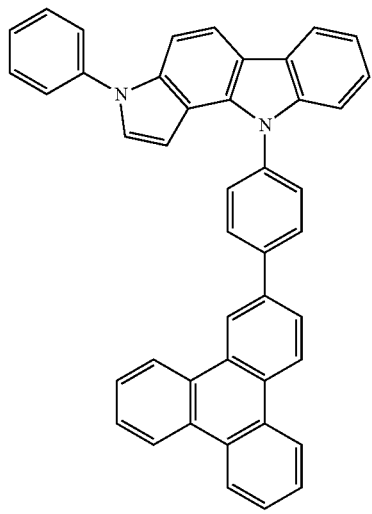
Inv4
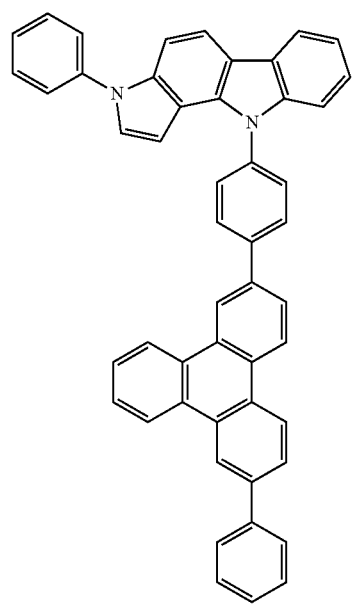
Inv5
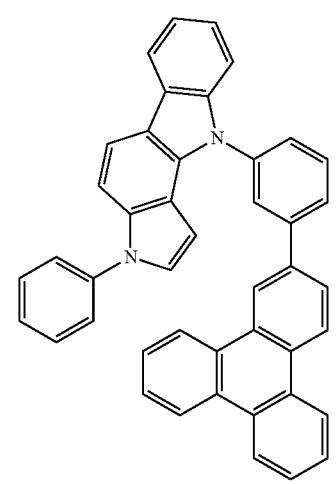
Inv6
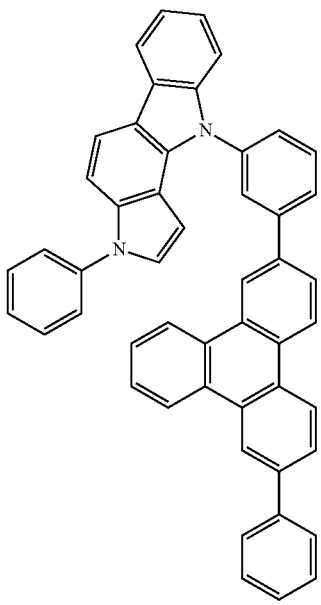
Inv7
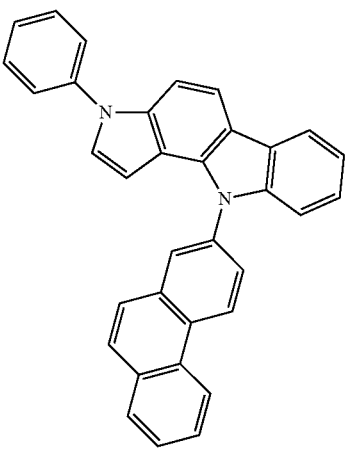
Inv8
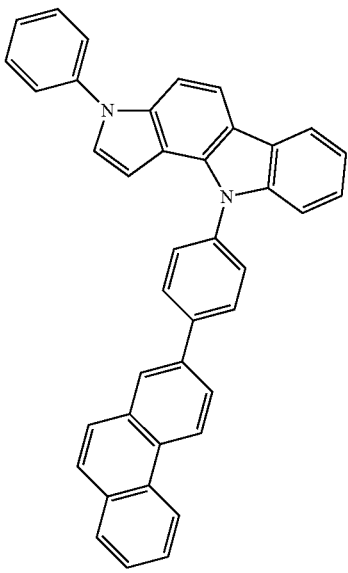

Inv9
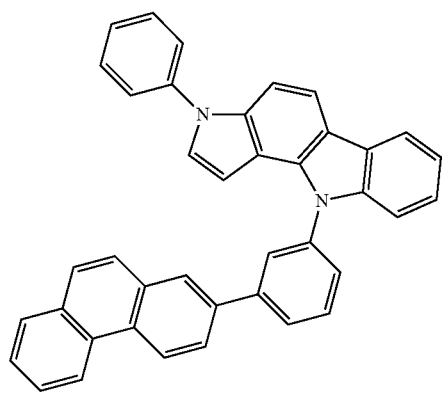
Inv10
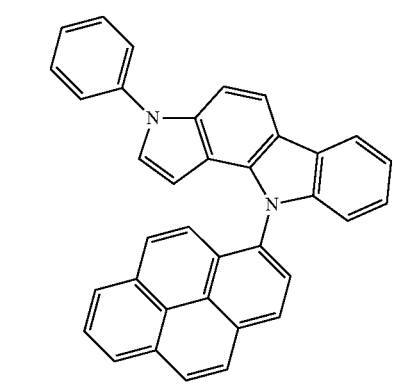
Inv11
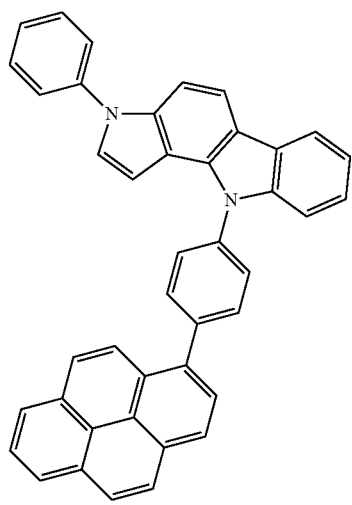
Inv12
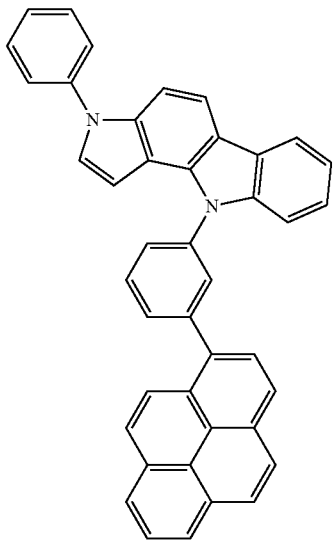
Inv13
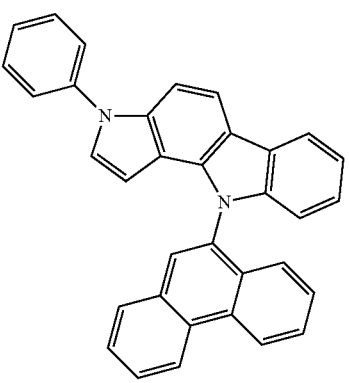
Inv14
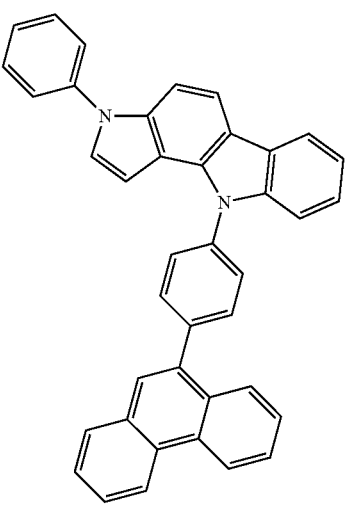

Inv15
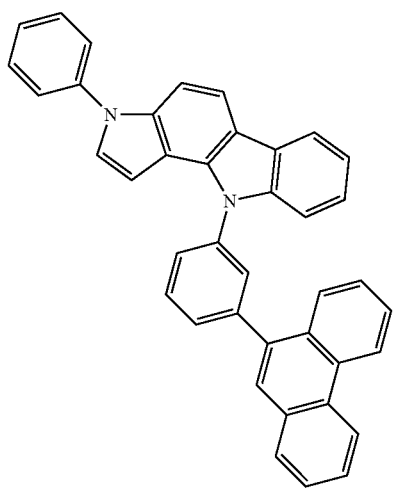
Inv16
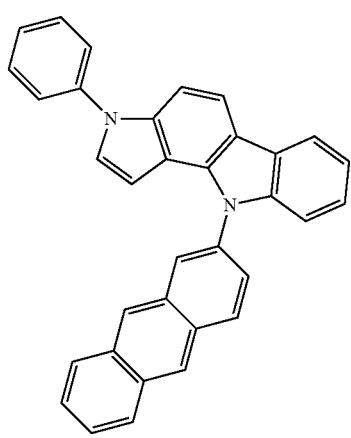
Inv17
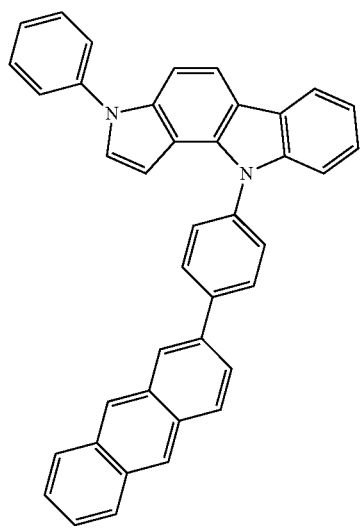
Inv18
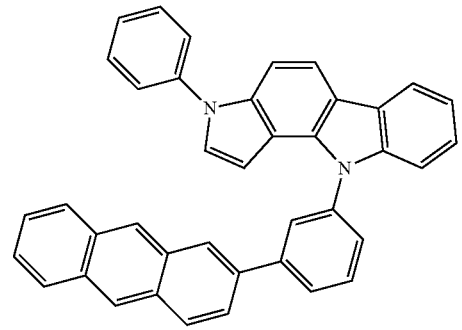
Inv19
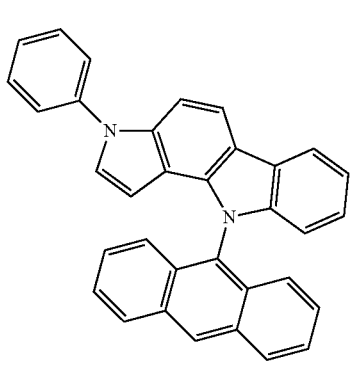
Inv20
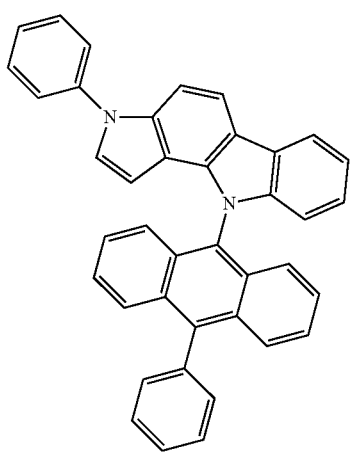

Inv21
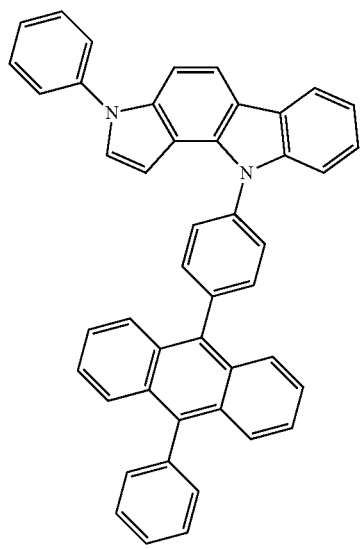
Inv22
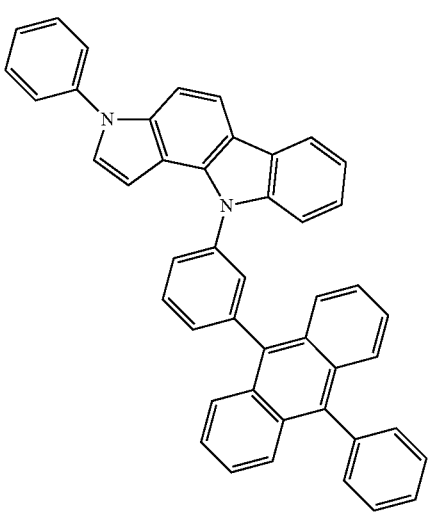
Inv23
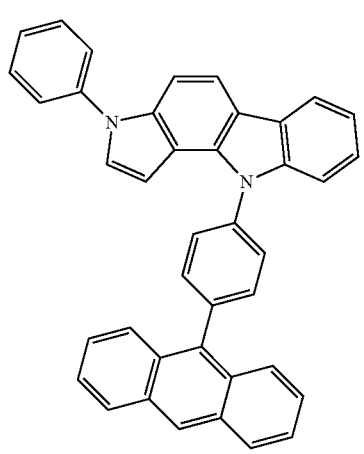
Inv24
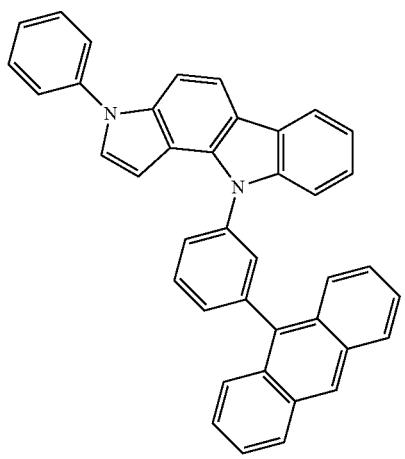
Inv25
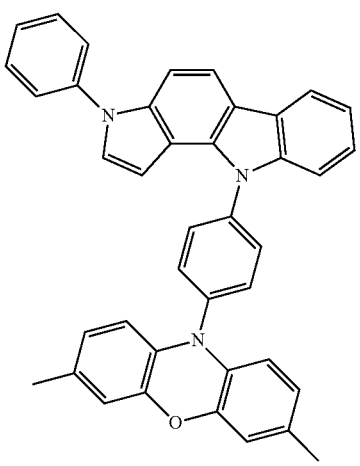
Inv26
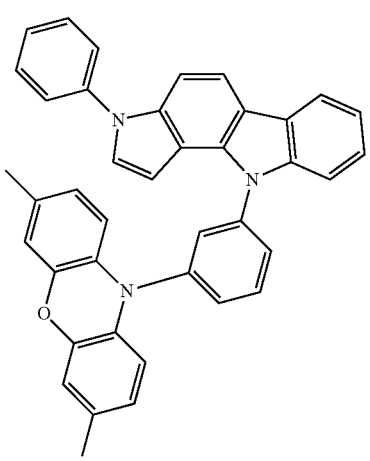

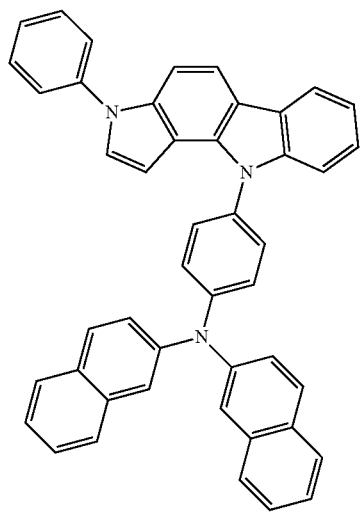
Inv27
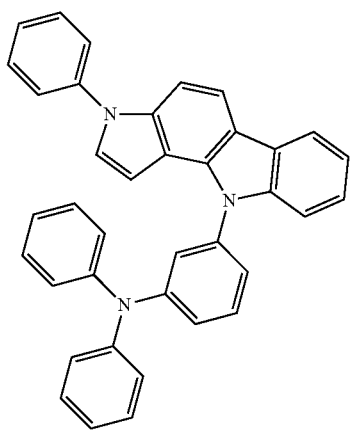
Inv30
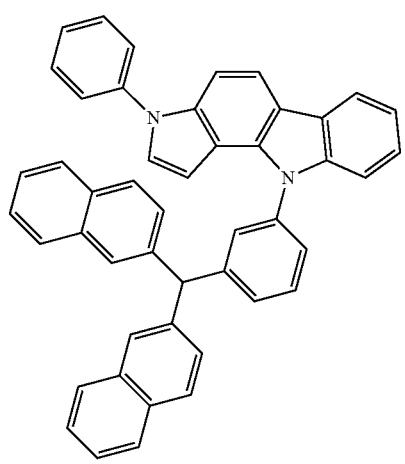
Inv28
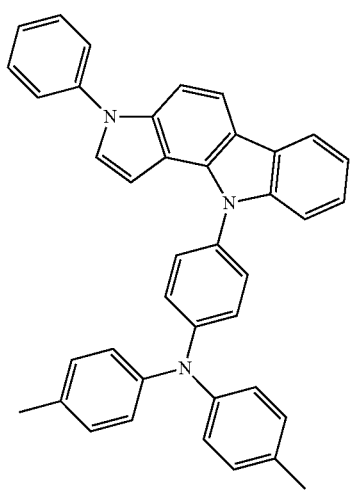
Inv31
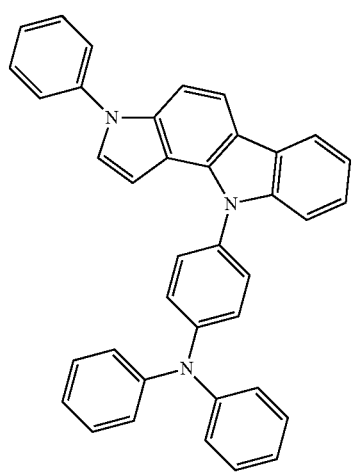
Inv29
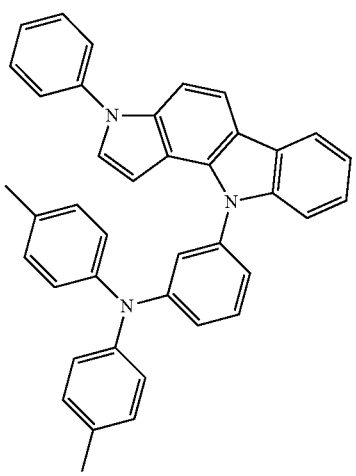
Inv32

Inv33
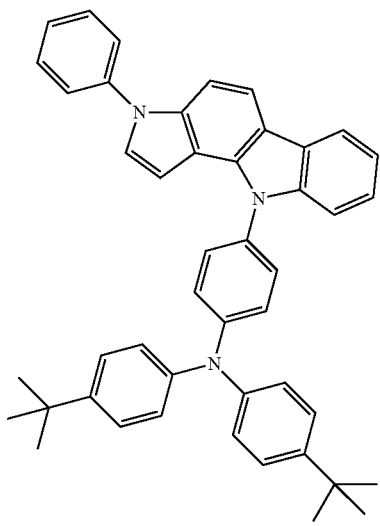
Inv34
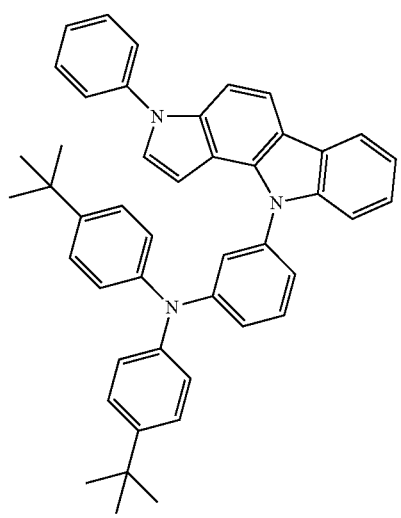
Inv35
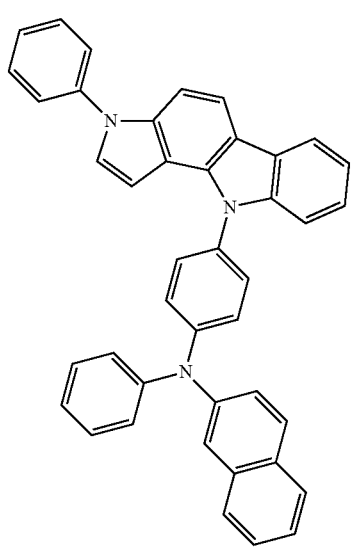
Inv36
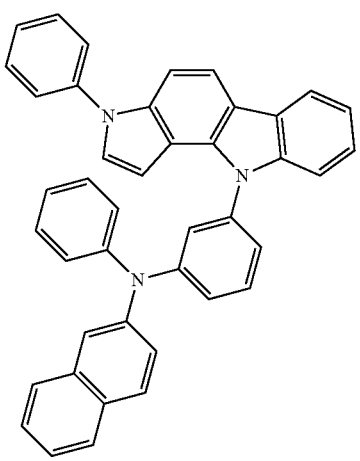
Inv37
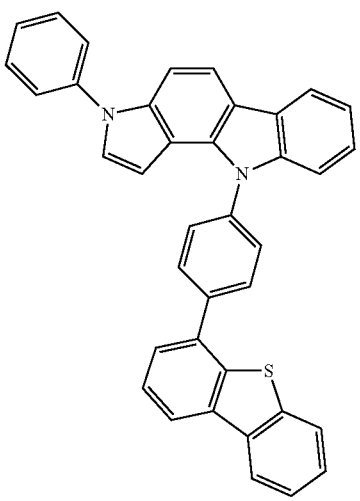
Inv38
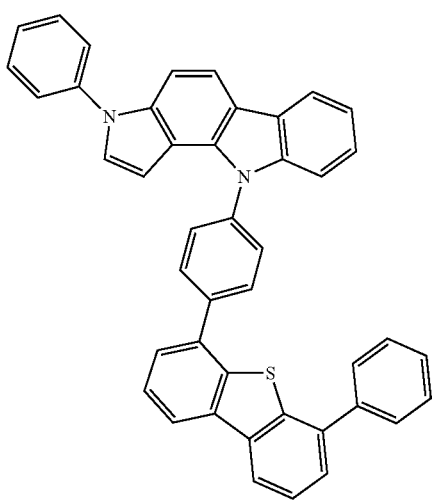

-continued
Inv39
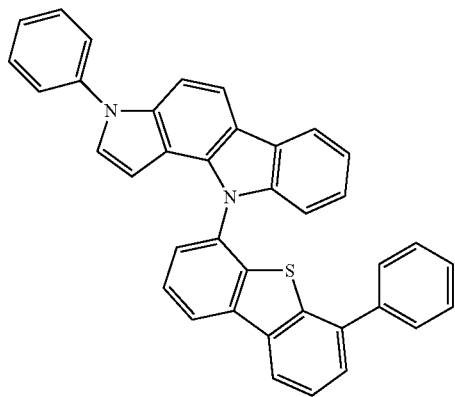
Inv40
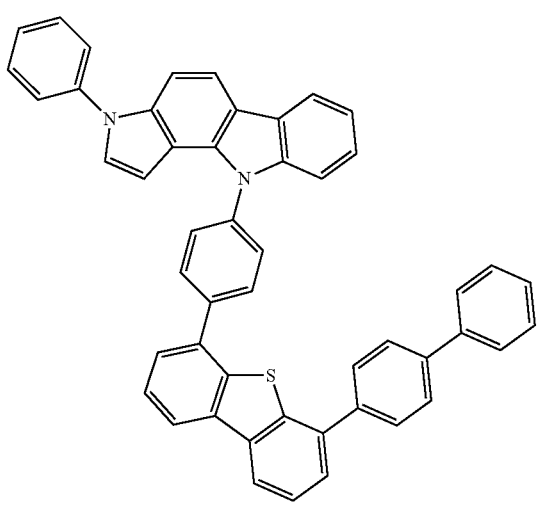
Inv41
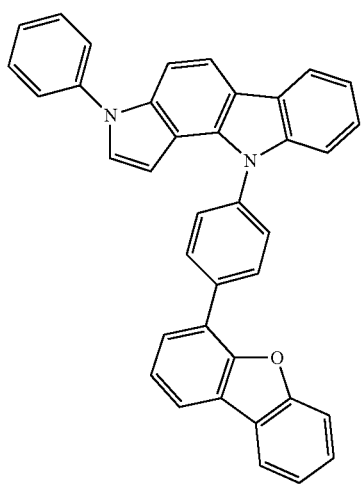
Inv42
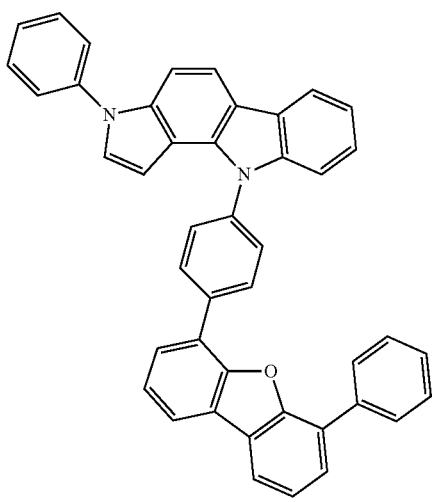
Inv43
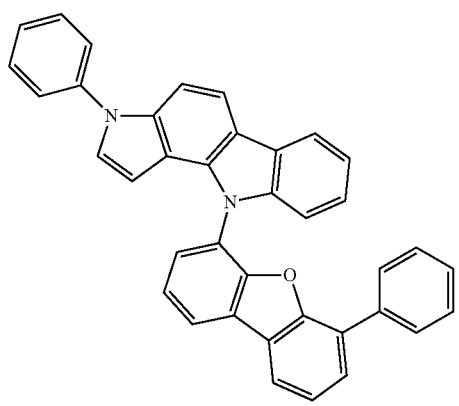
Inv44

Inv45
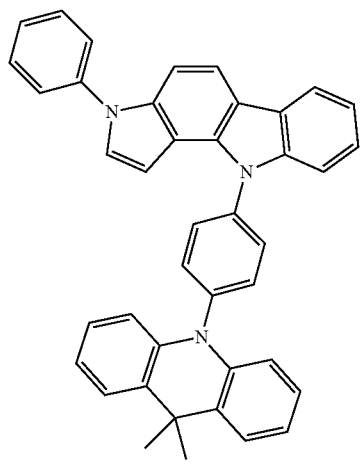
Inv46
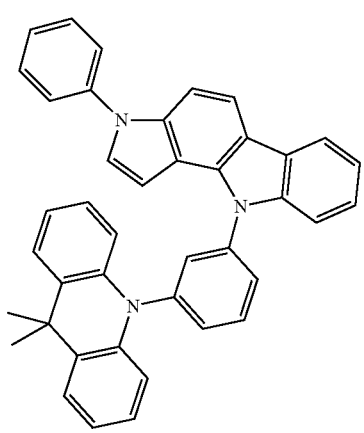
Inv47
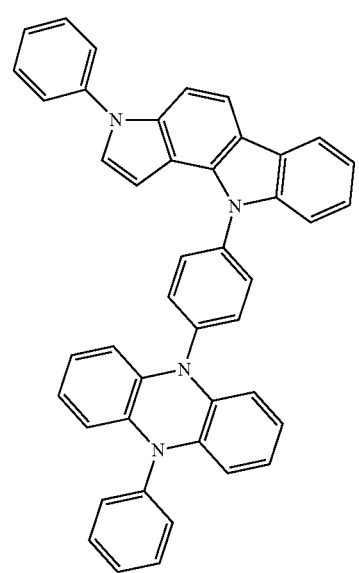
Inv48
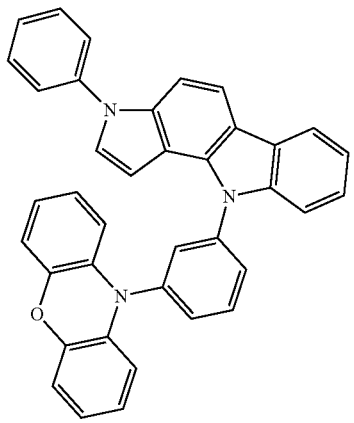
Inv49
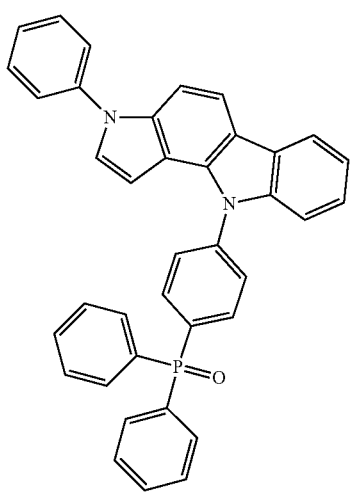
Inv50
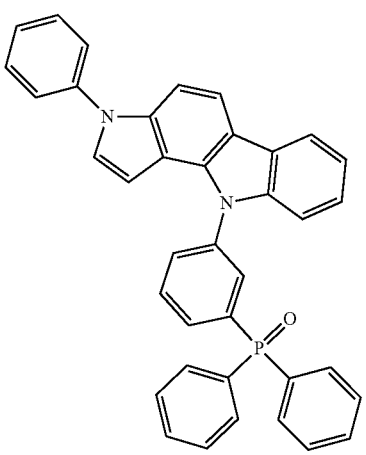

Inv51
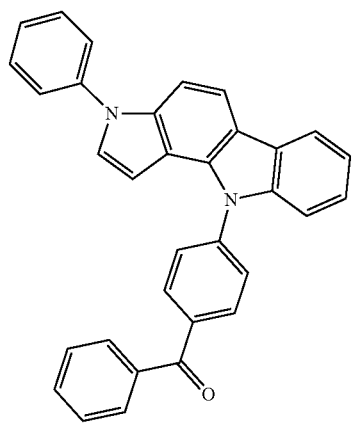
Inv52
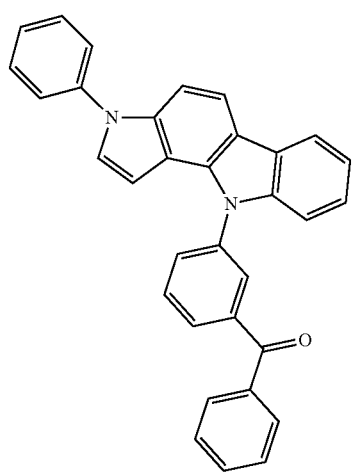
Inv53
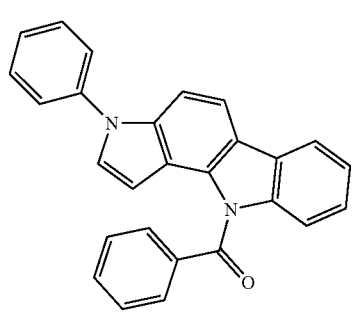
Inv54
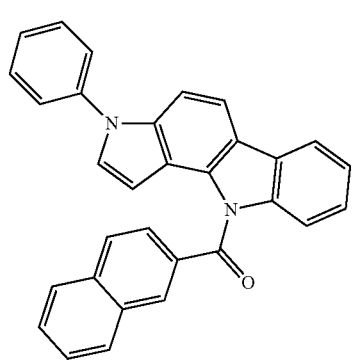
Inv55
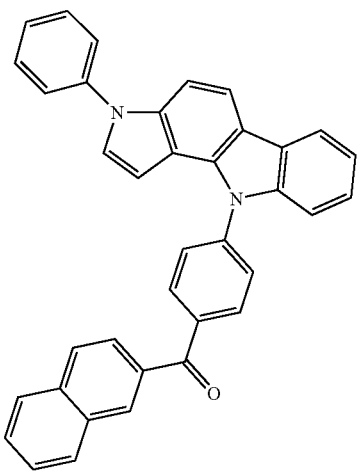
Inv56
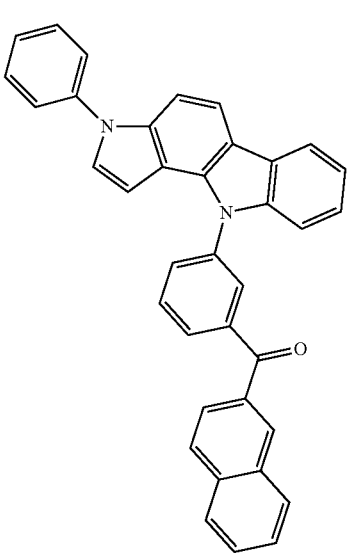
Inv57
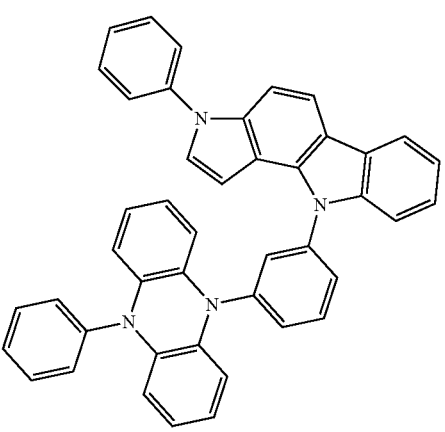

-continued
Inv58
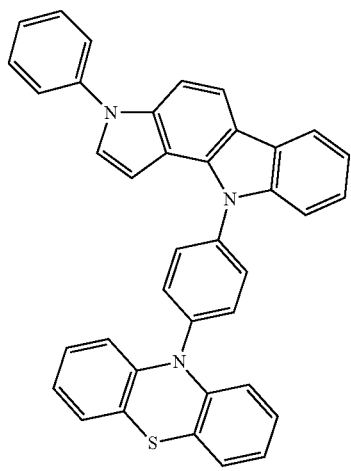
Inv59
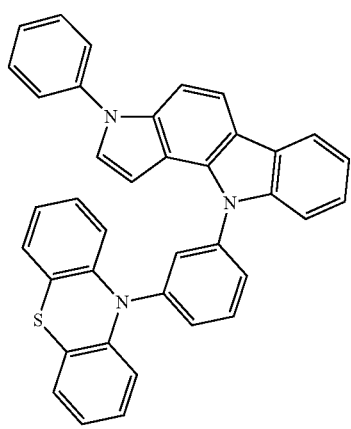
Inv60
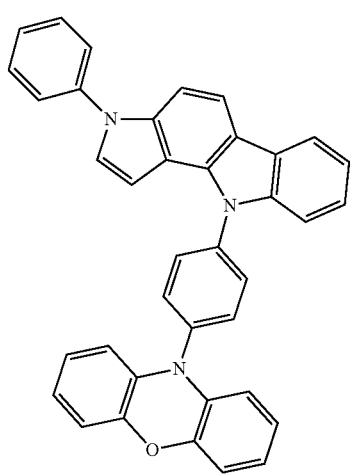
-continued
Inv61
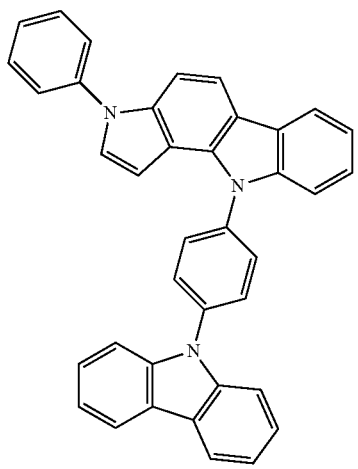
Inv62
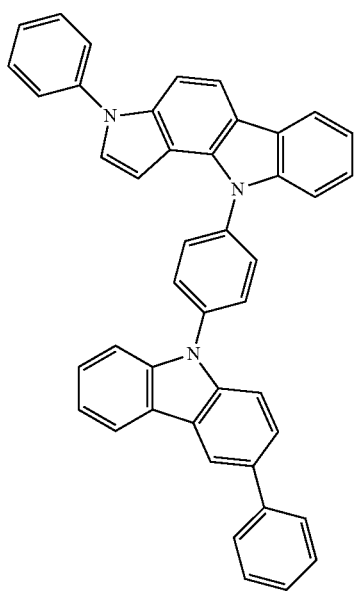
Inv63
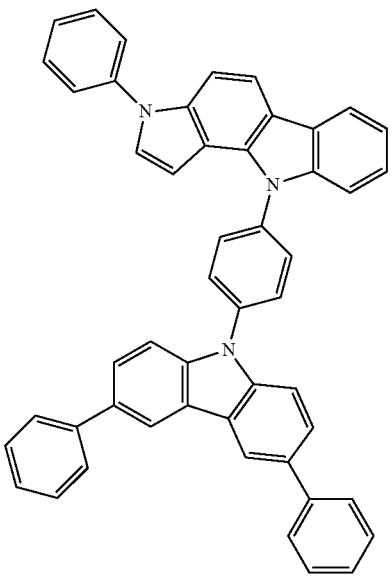

Inv64
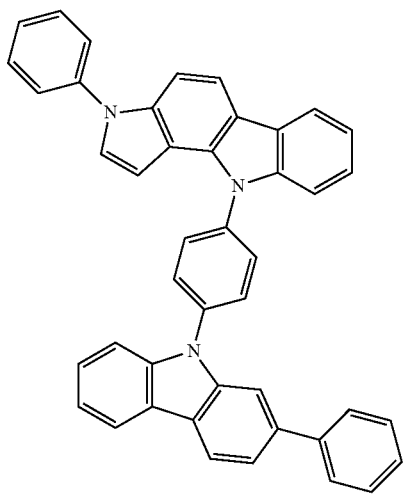
Inv67
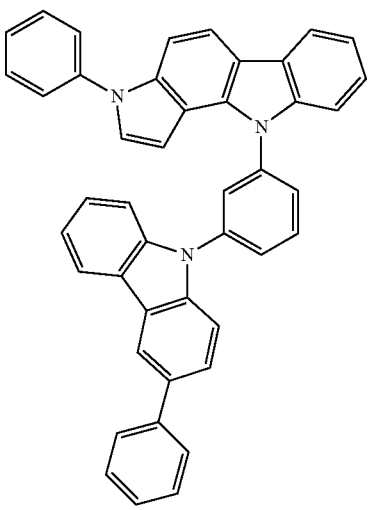
Inv65
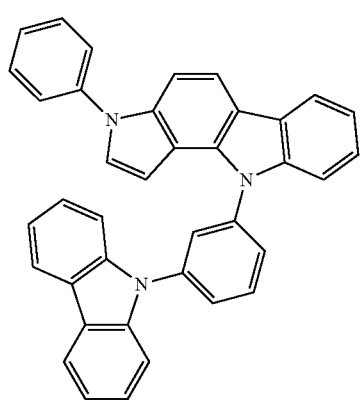
Inv68
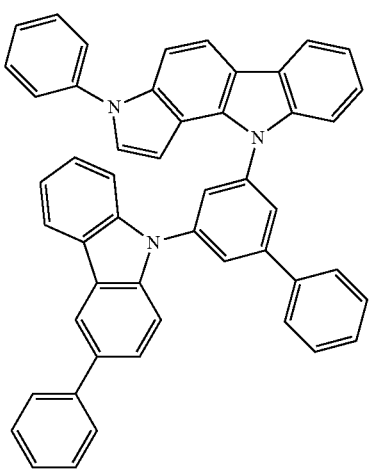
Inv66
Inv69
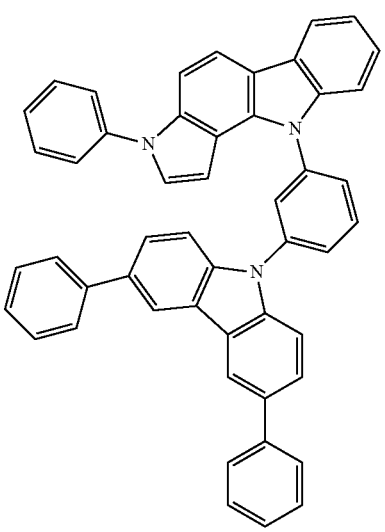

-continued
Inv70
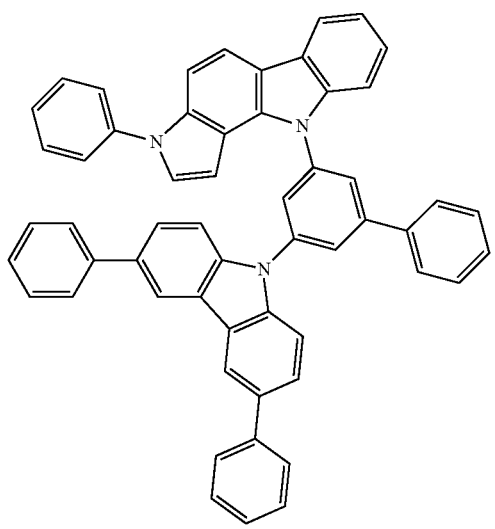
Inv71
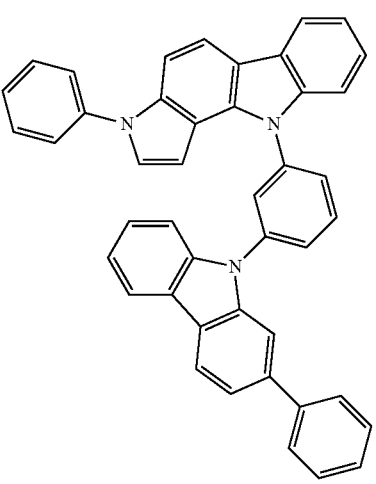
Inv72
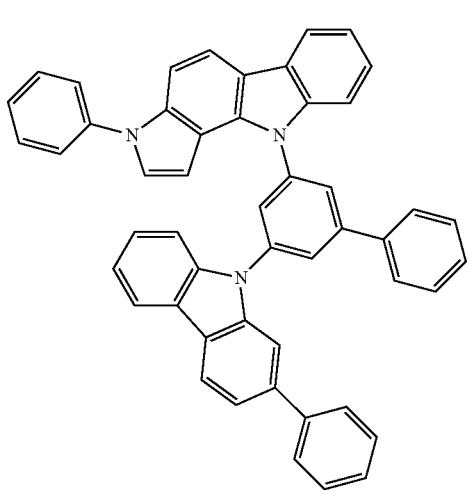
-continued
Inv73
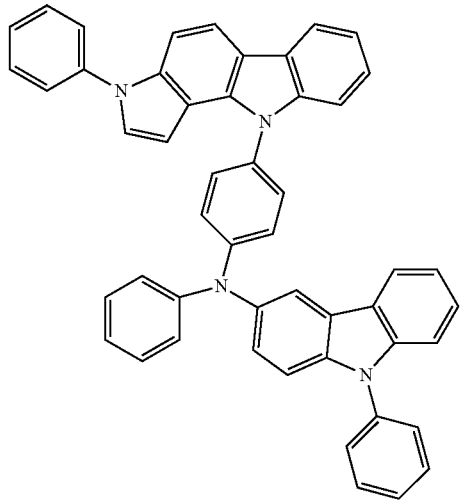
Inv74
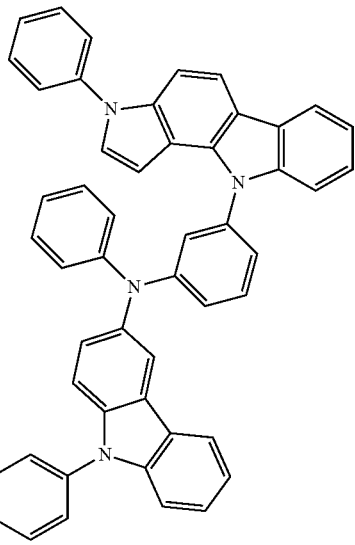
Inv75
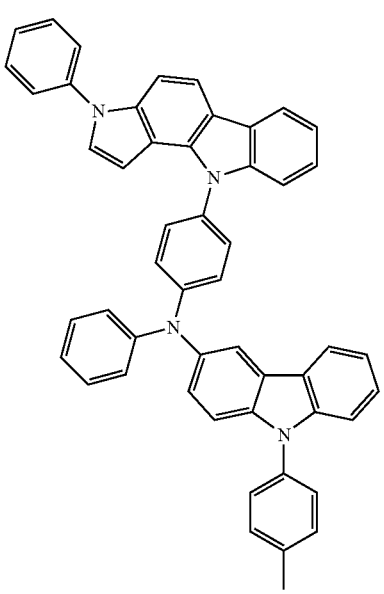

Inv76
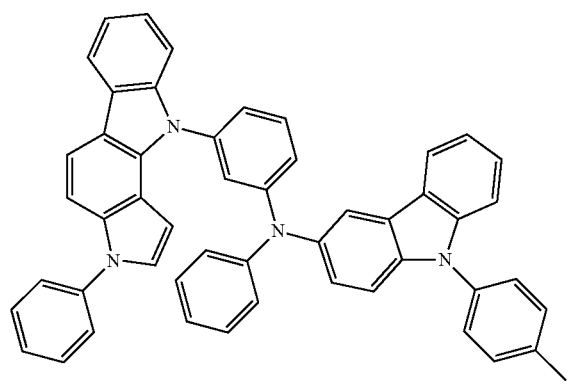
Inv77
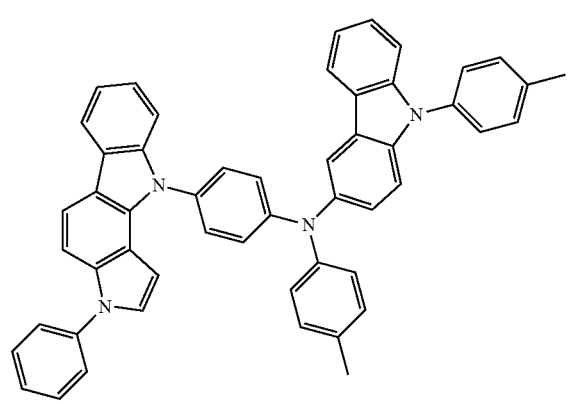
Inv78
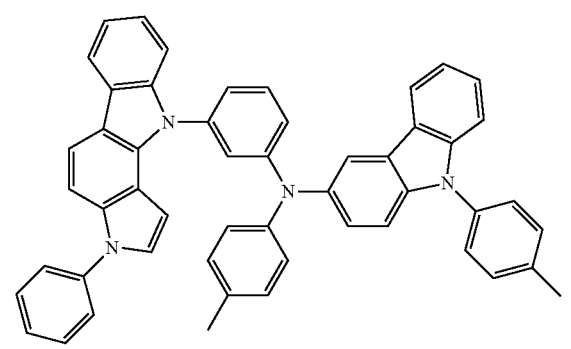
Inv79
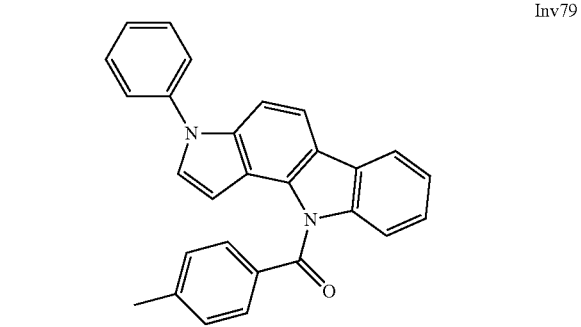
Inv80
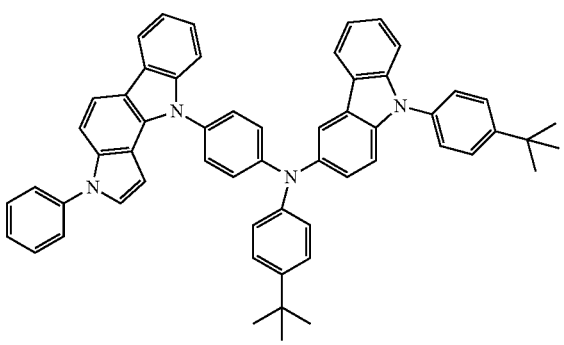
Inv81
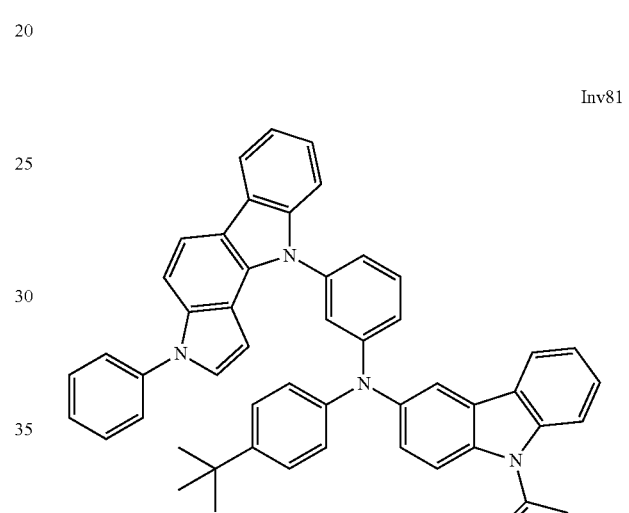
Inv82
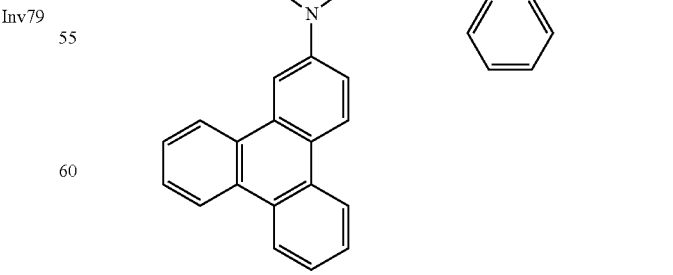

Inv83
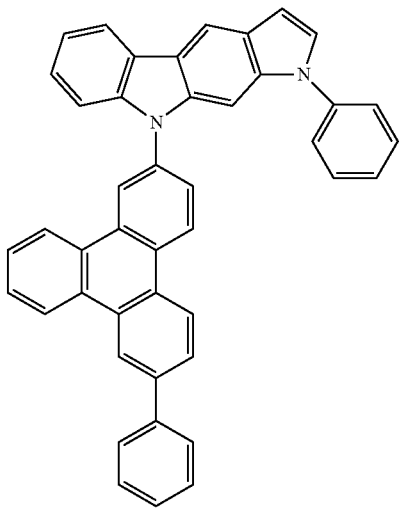
Inv84
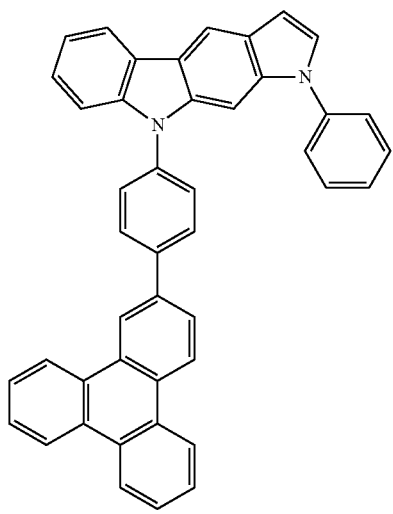
Inv85
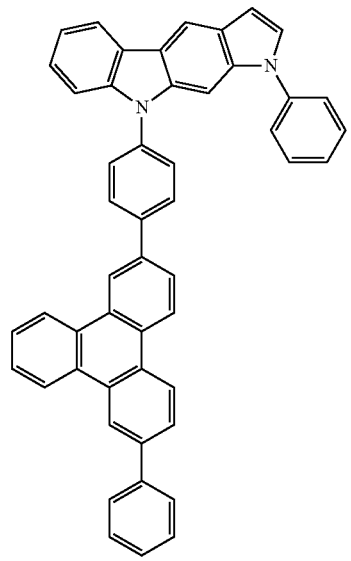
Inv86
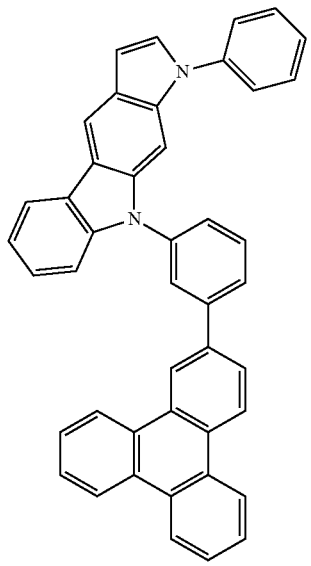
Inv87
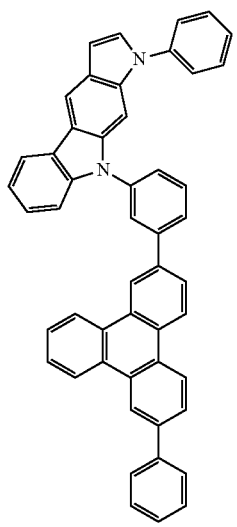
Inv88
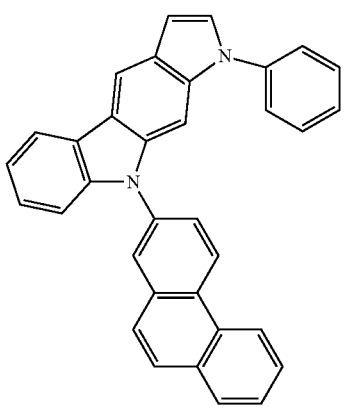

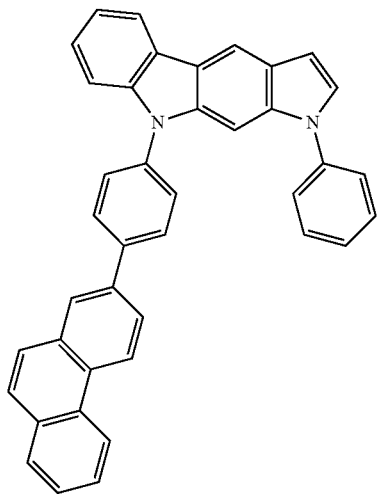
Inv89
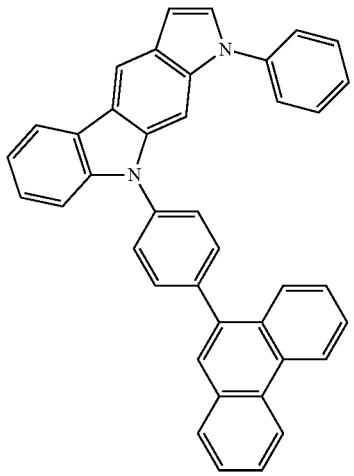
Inv92
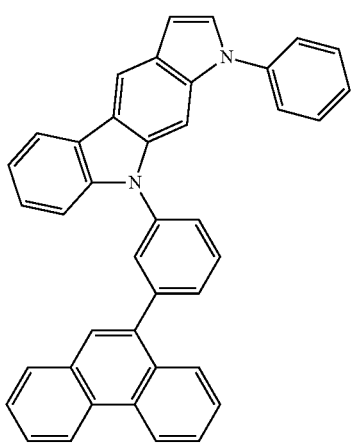
Inv90
Inv93
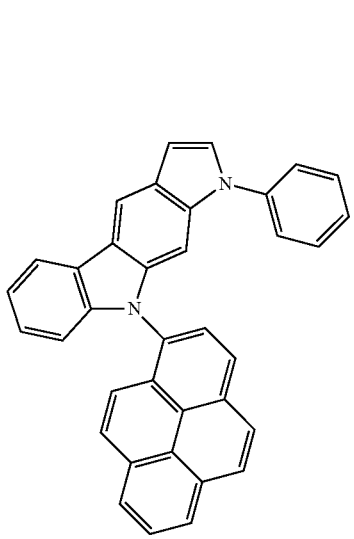
Inv91
Inv94

-continued
Inv95
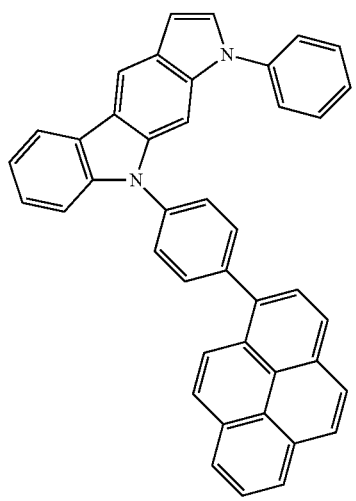
Inv96
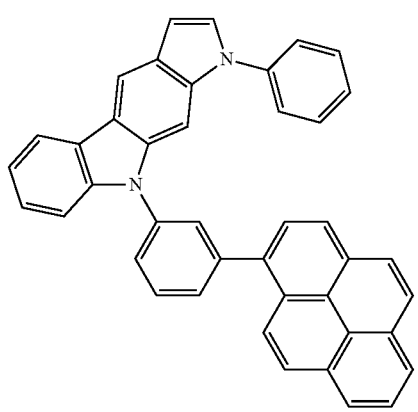
Inv97
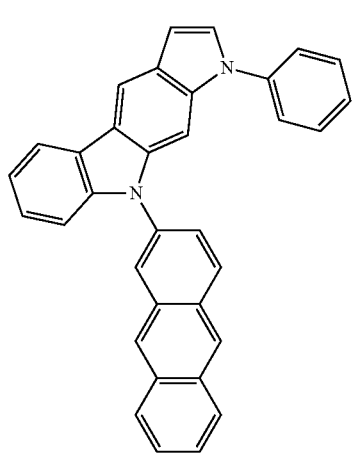
-continued
Inv98
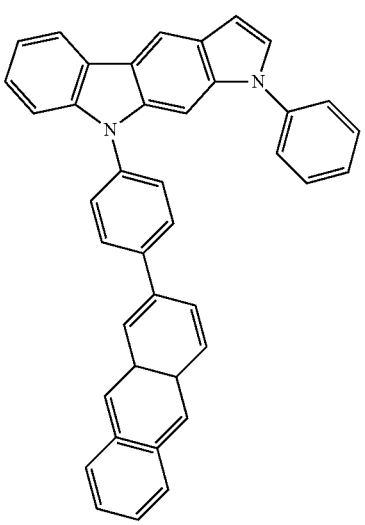
Inv99
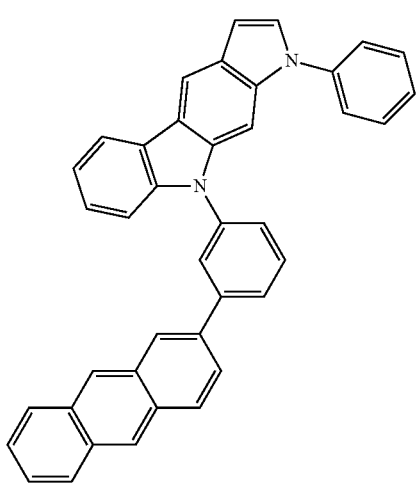
Inv100
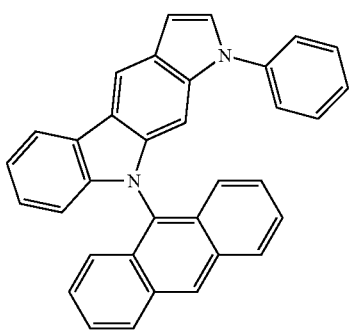

Inv101
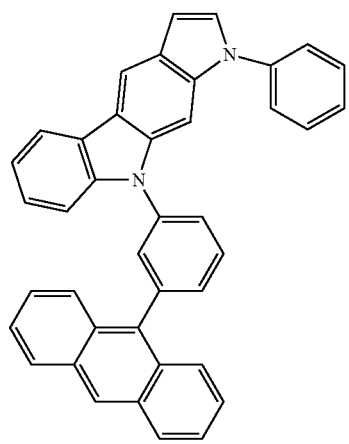
Inv104
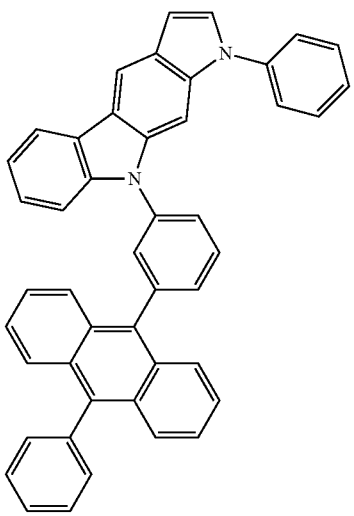
Inv102
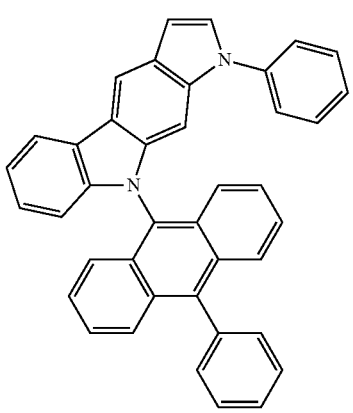
Inv105
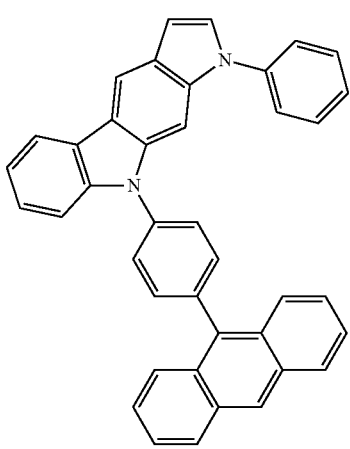
Inv103
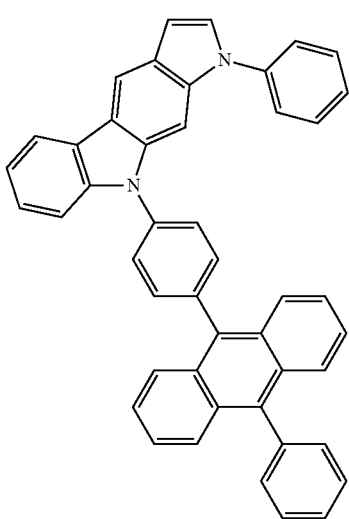
Inv106
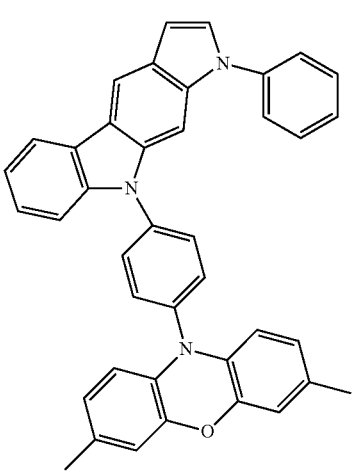

Inv107
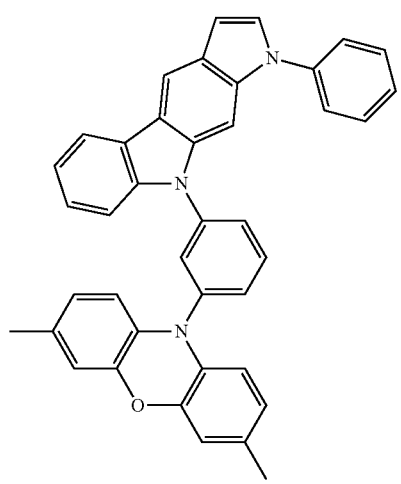
Inv108
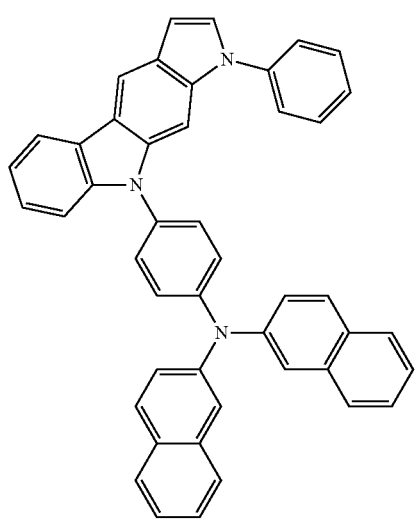
Inv109
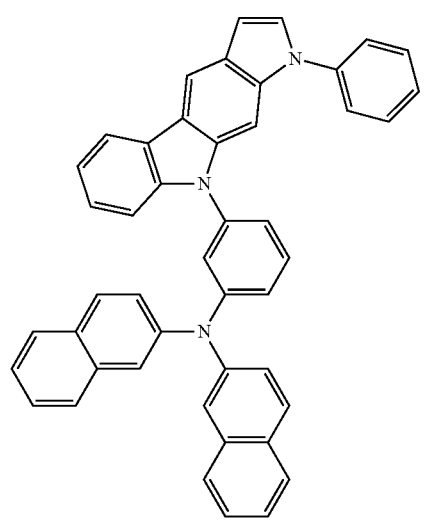
Inv110
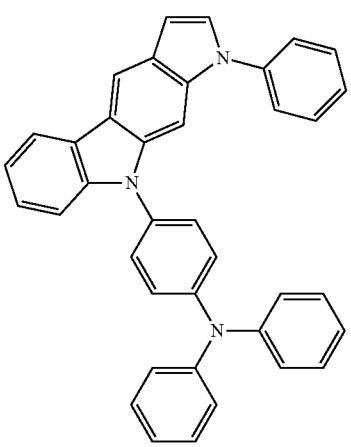
Inv111
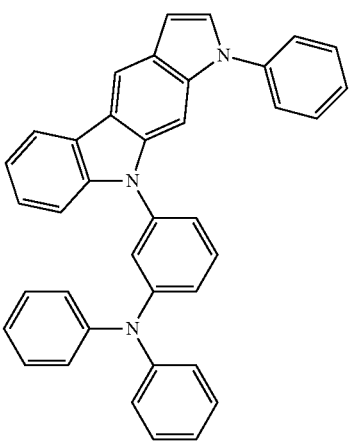
Inv112
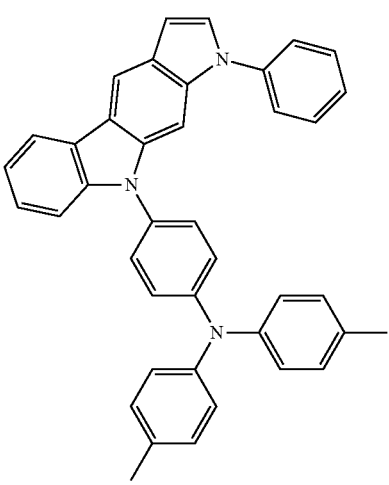

Inv113
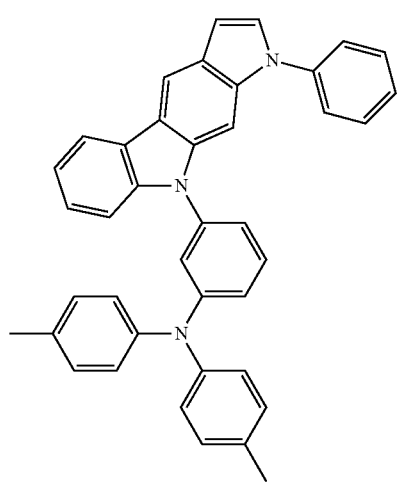
Inv114
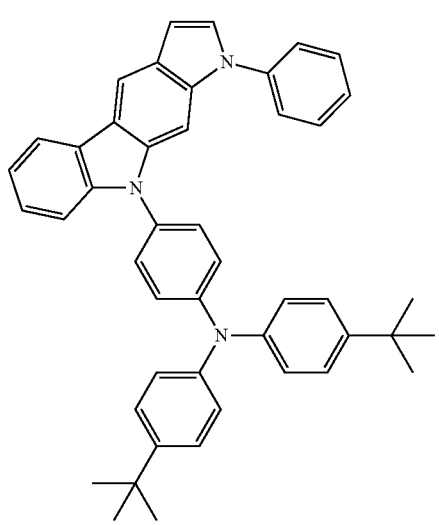
Inv115
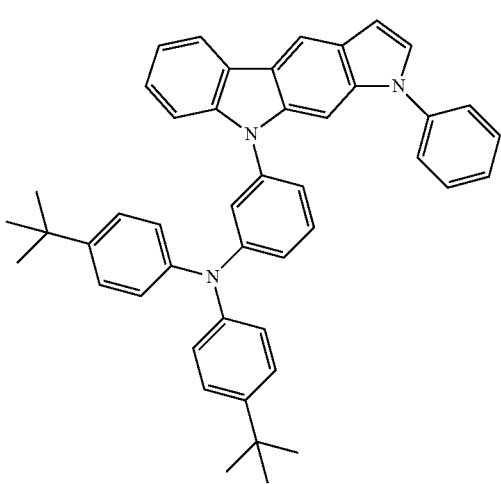
Inv116
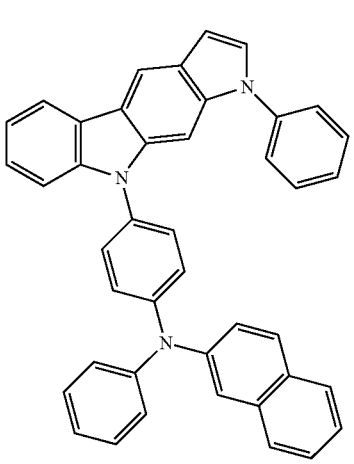
Inv117
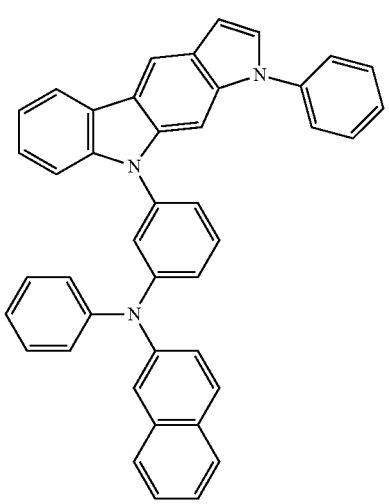
Inv118
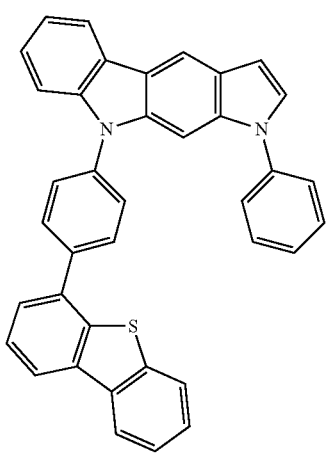

Inv119

Inv120

Inv121

Inv122

Inv123

Inv124

Inv125
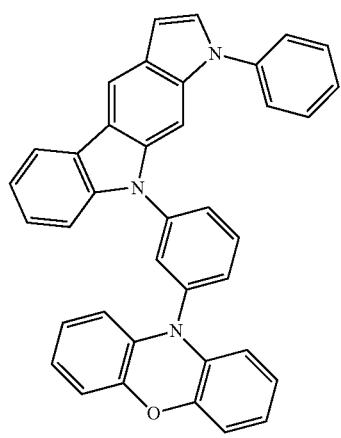
Inv126
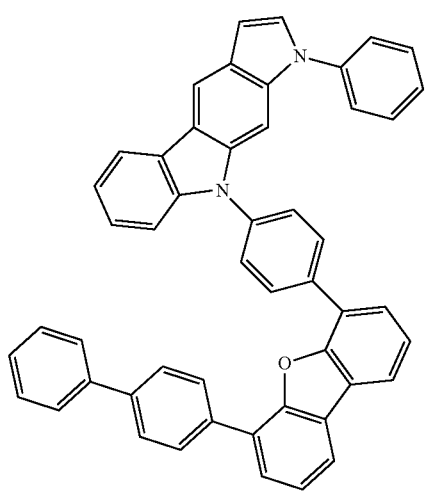
Inv127
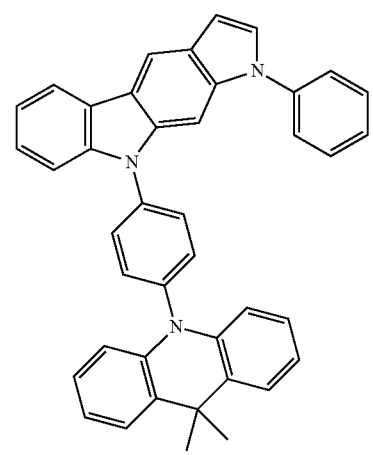
Inv128
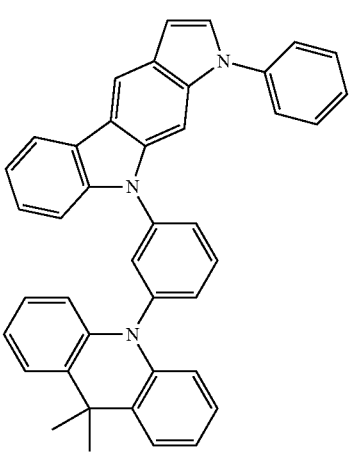
Inv129
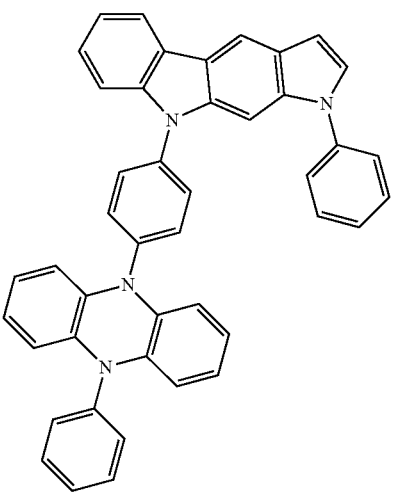
Inv130
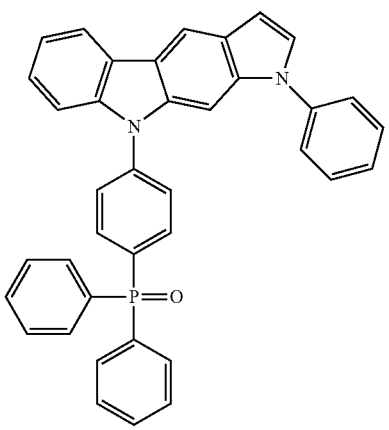

Inv131
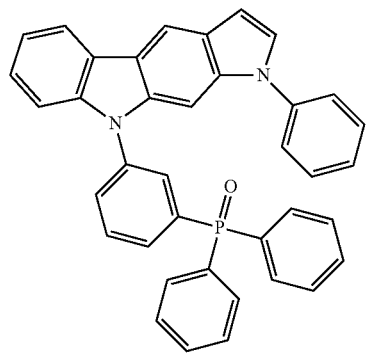
Inv132
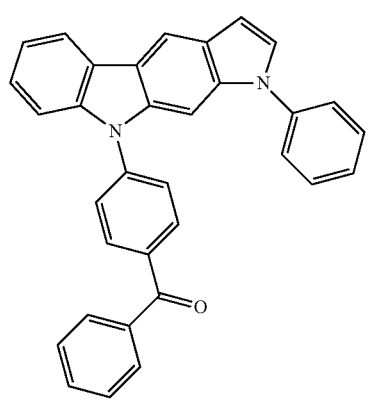
Inv133
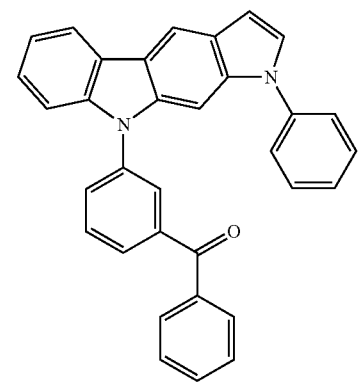
Inv134
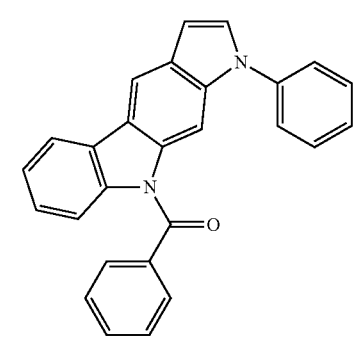
Inv135
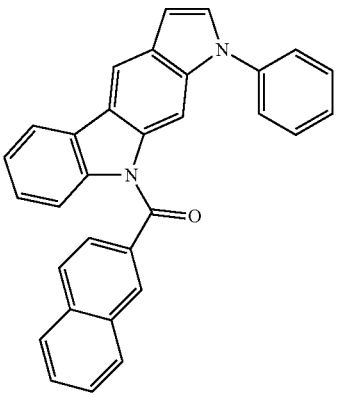
Inv136
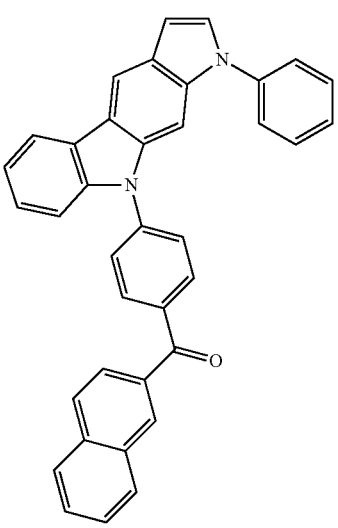
Inv137
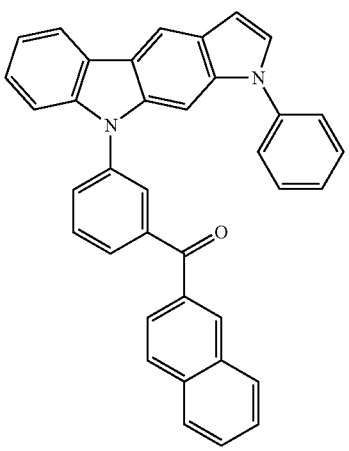

Inv138
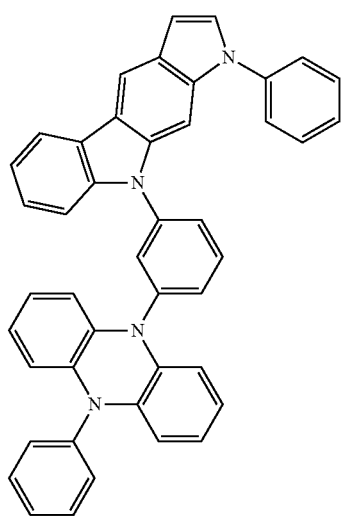
Inv139
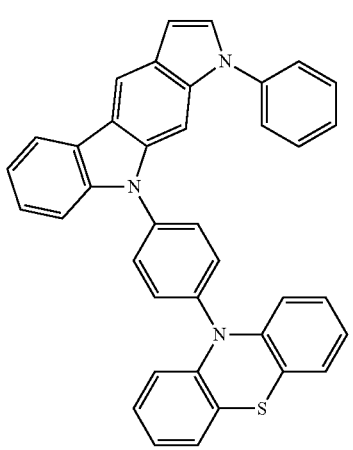
Inv140
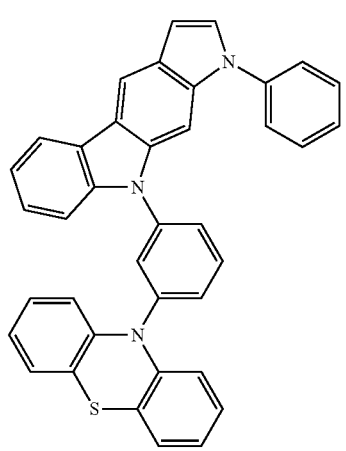
Inv141
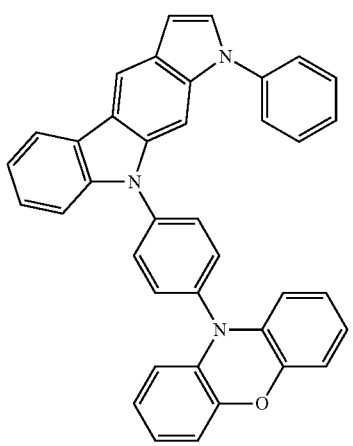
Inv142
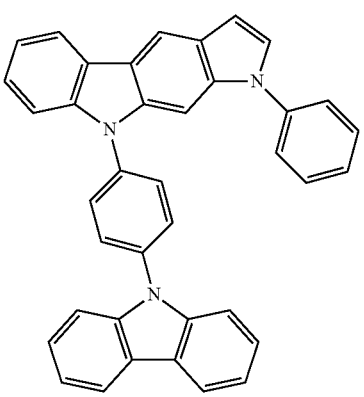
Inv143
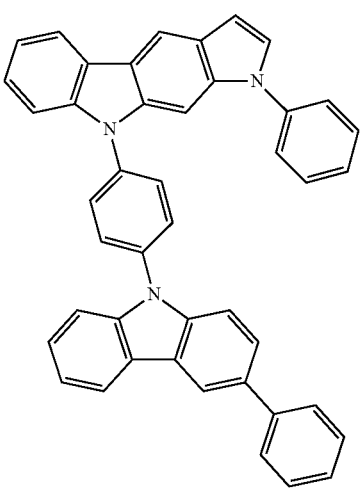

Inv144
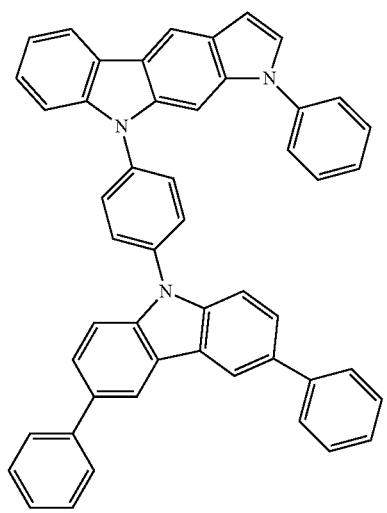
Inv145
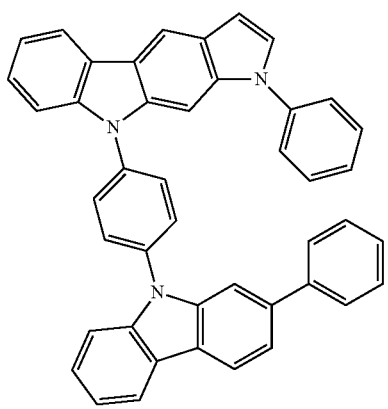
Inv146
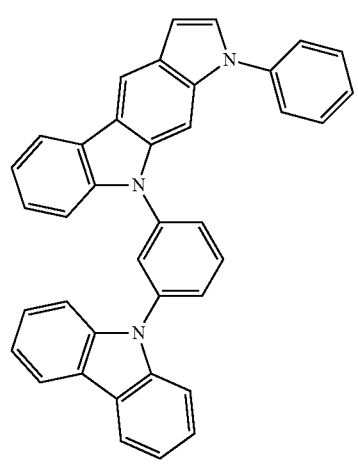
Inv147
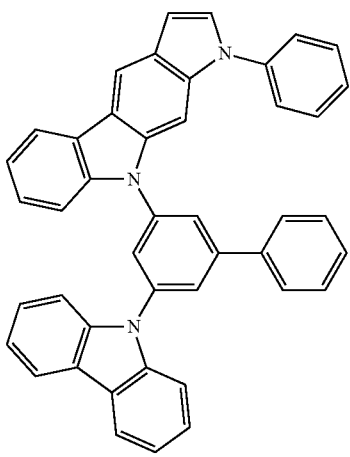
Inv148
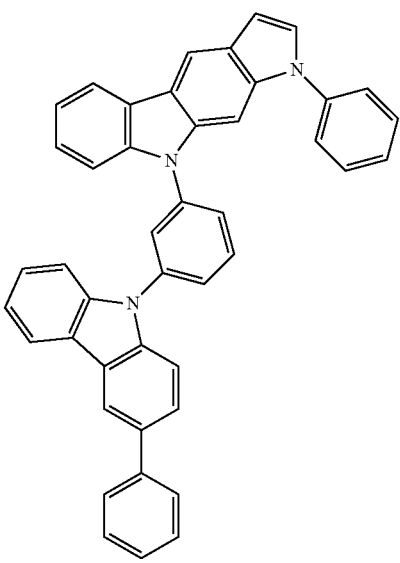
Inv149
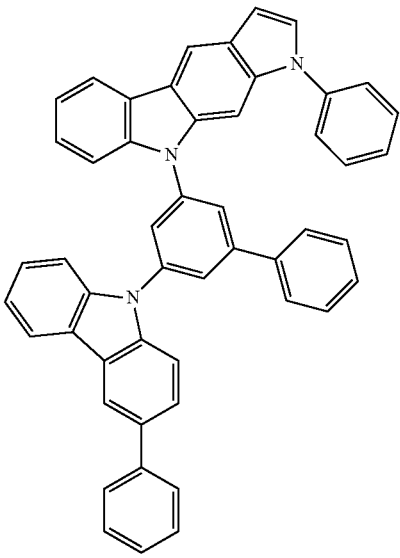

Inv150
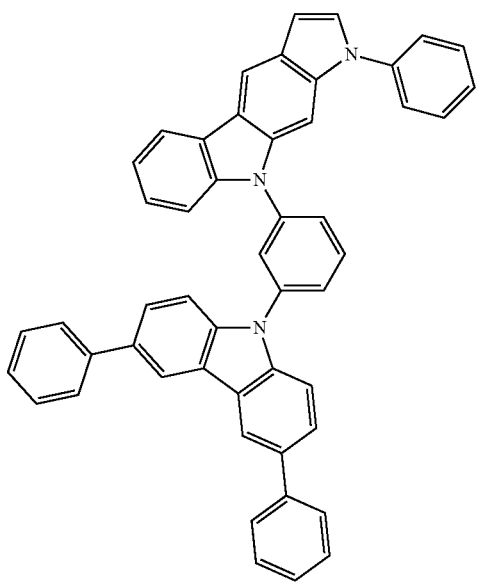
Inv151
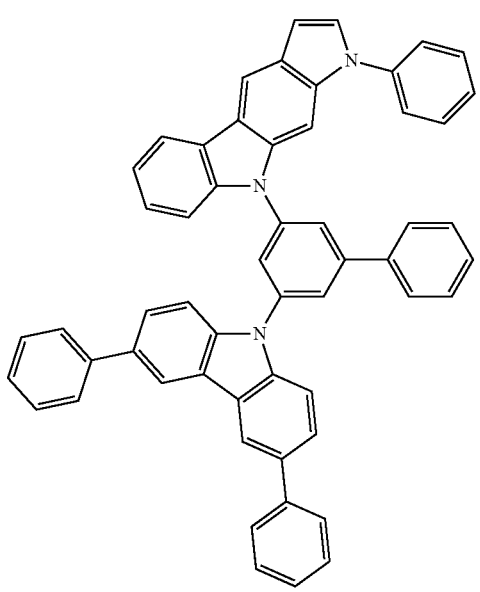
Inv152
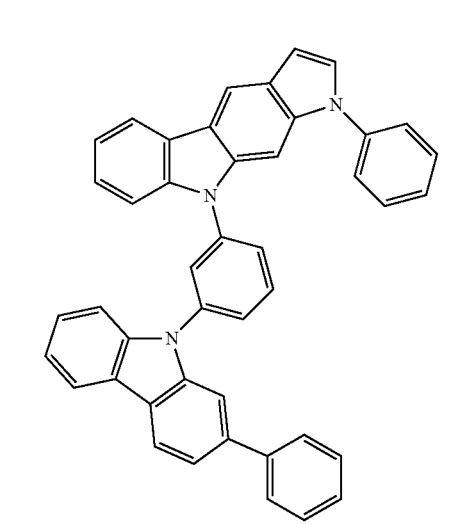
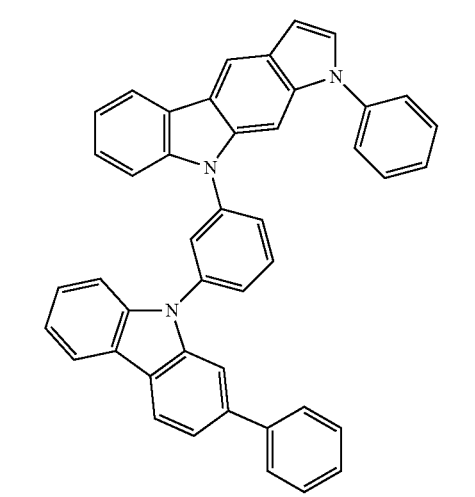
Inv153
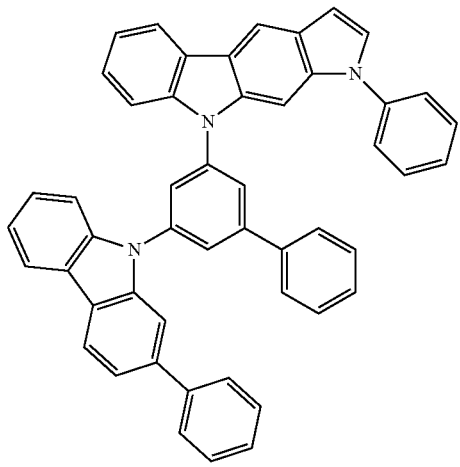
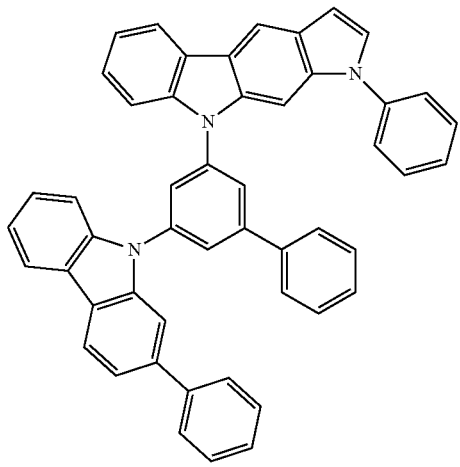
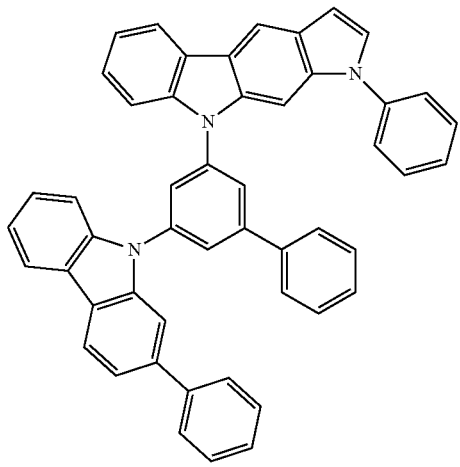
Inv154
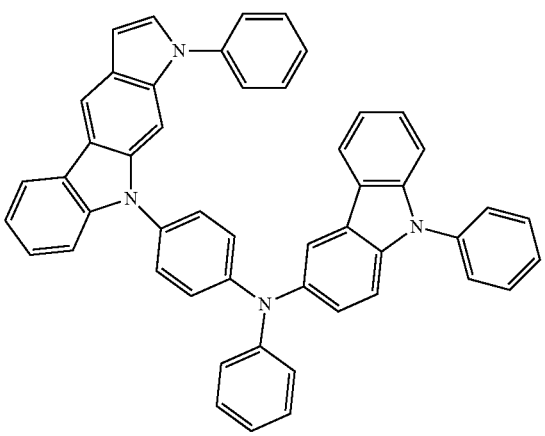

Inv155
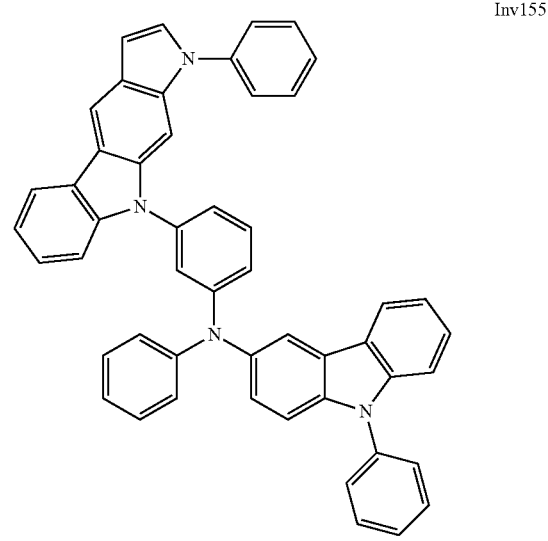

Inv156
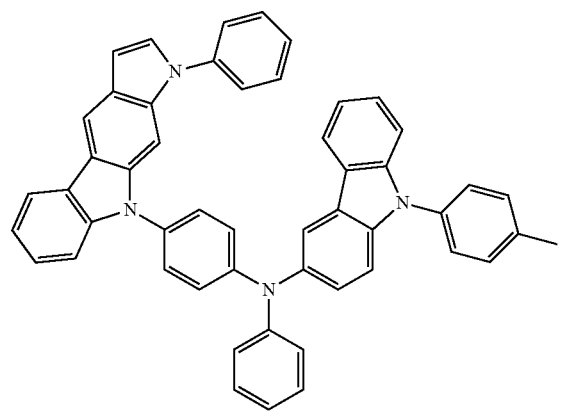
Inv159
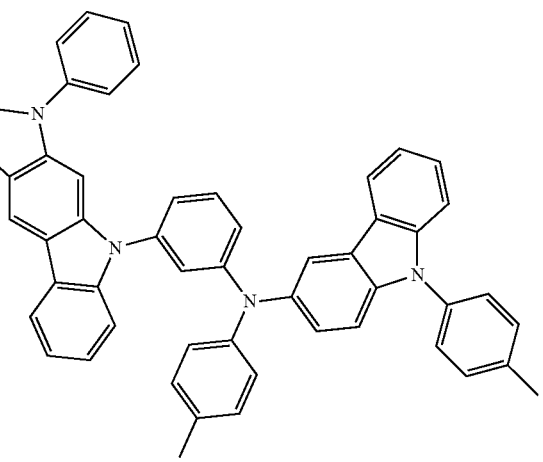
Inv157
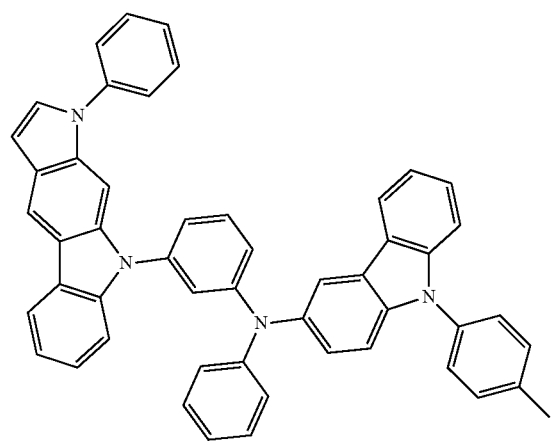
Inv160
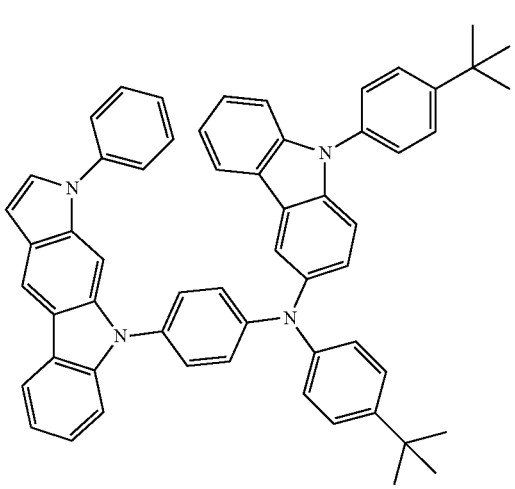
Inv158
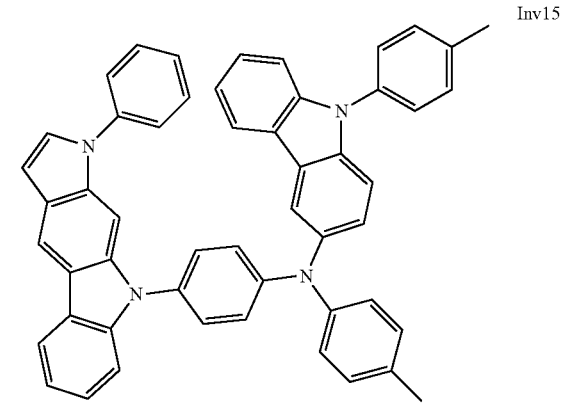
Inv161
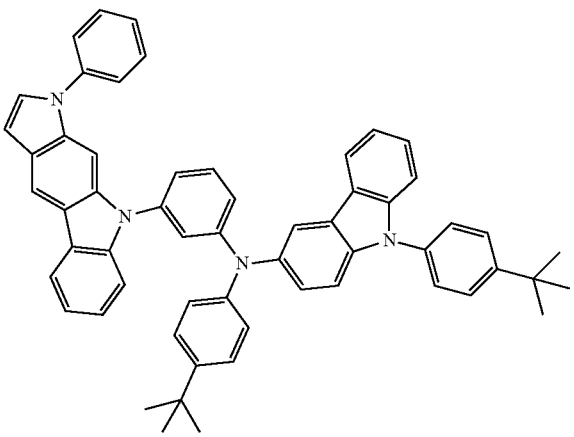

-continued
Inv162
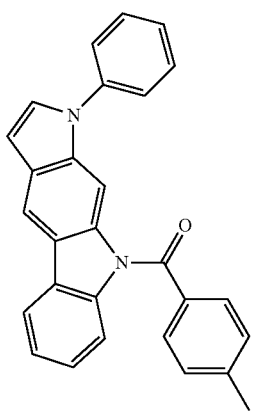
Inv165
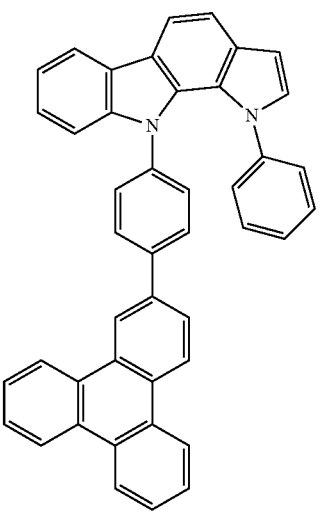
Inv163
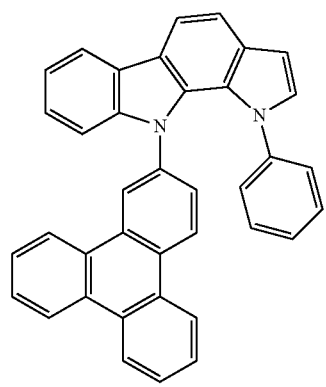
Inv166
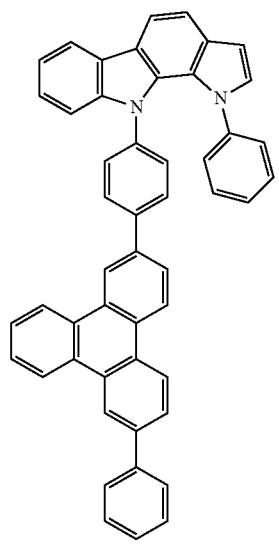
Inv164
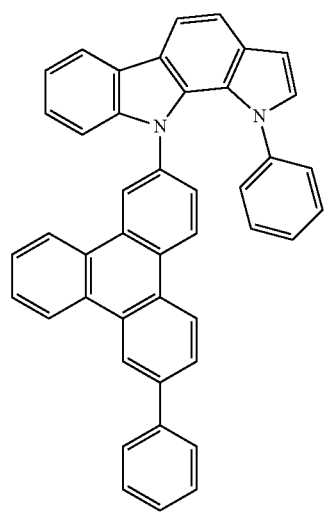
Inv167
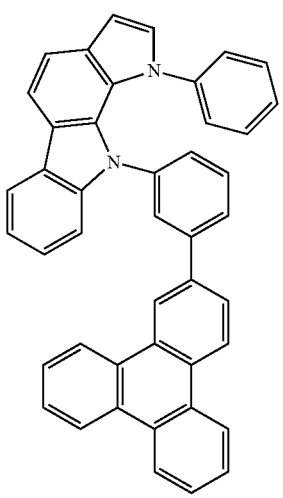

Inv168
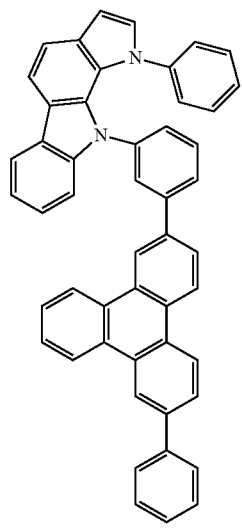
Inv169
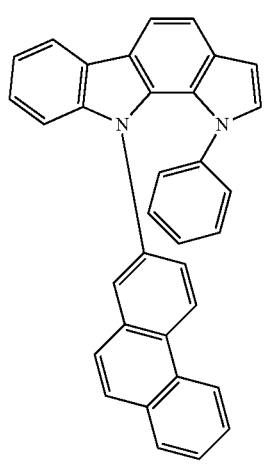
Inv170
Inv171
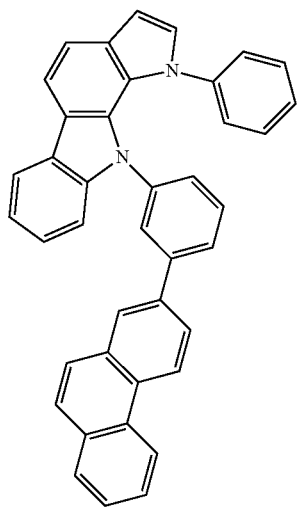
Inv172
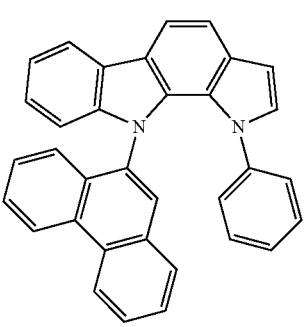
Inv173
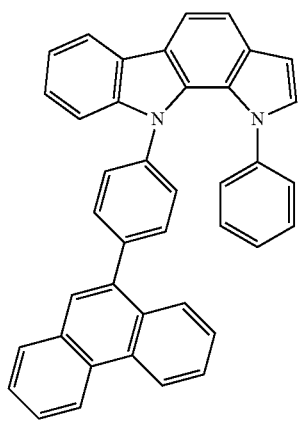

Inv174
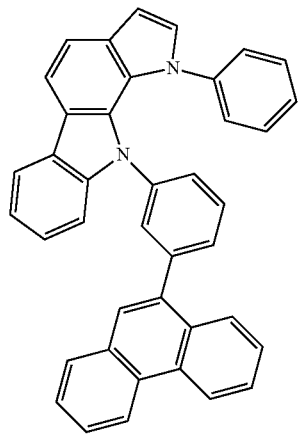
Inv177
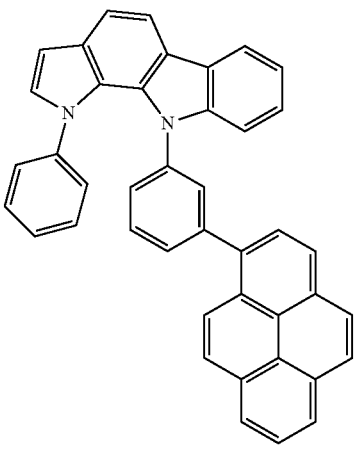
Inv175
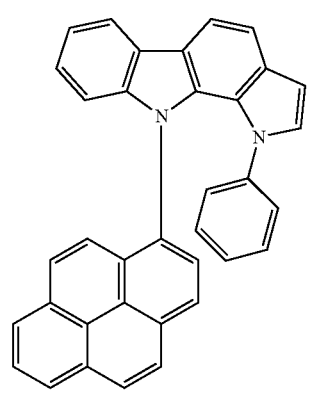
Inv178
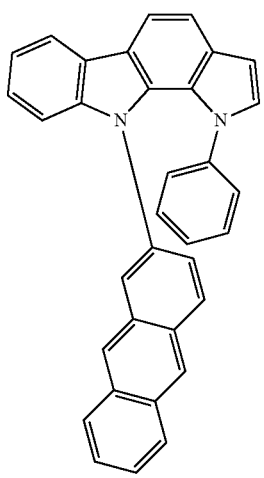
Inv176
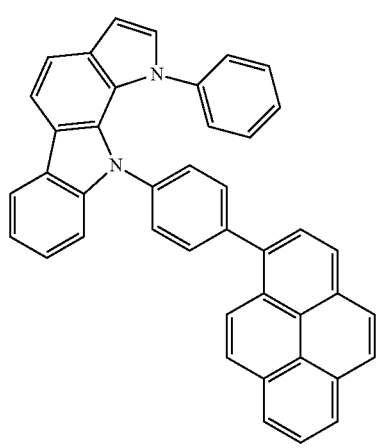
Inv179
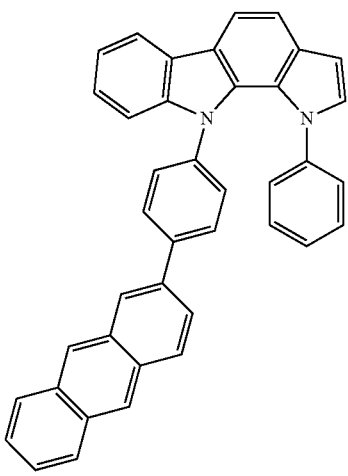

Inv180
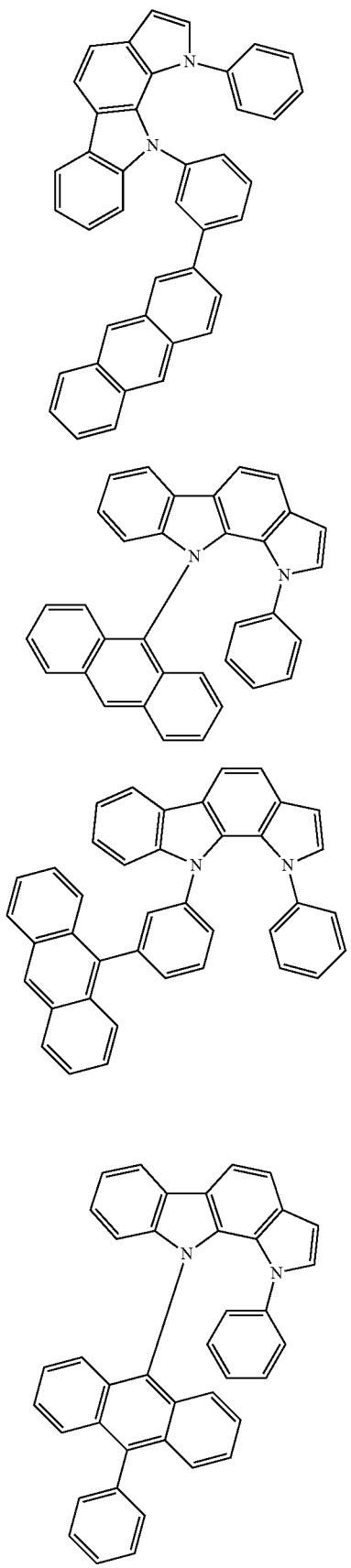
Inv181
Inv182
Inv183
Inv184
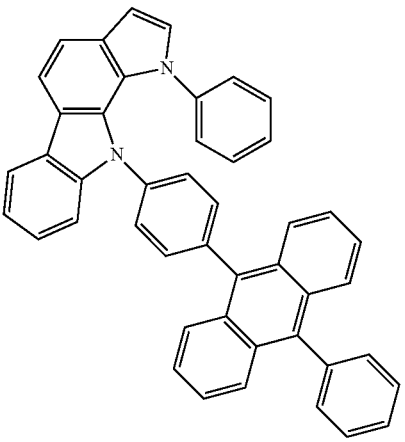
Inv185
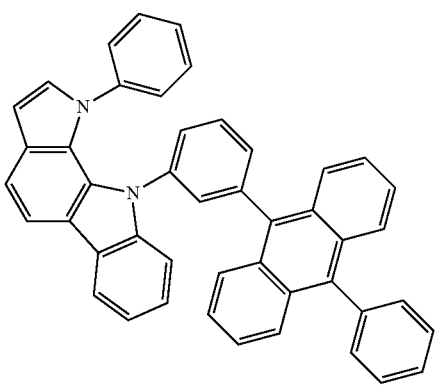
Inv186
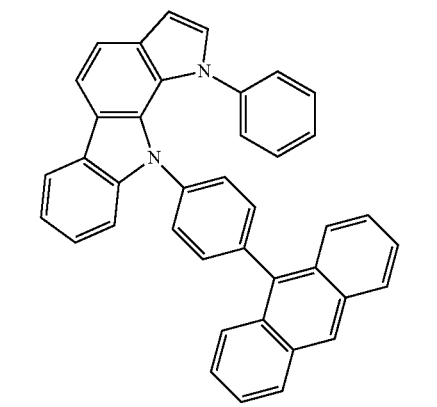
Inv187
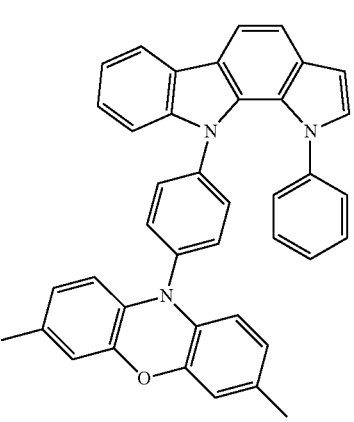

Inv188
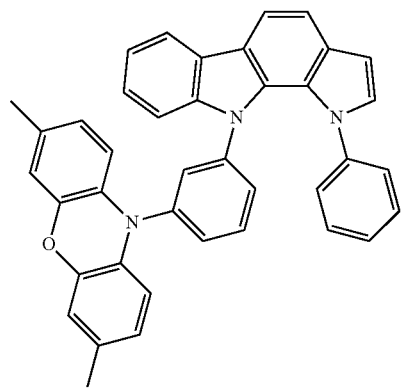
Inv189
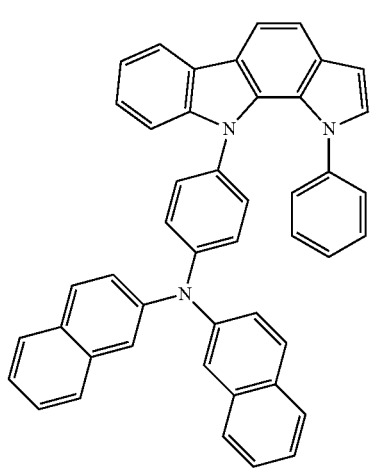
Inv190
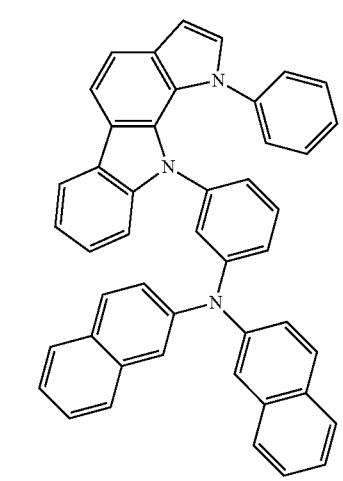
Inv191
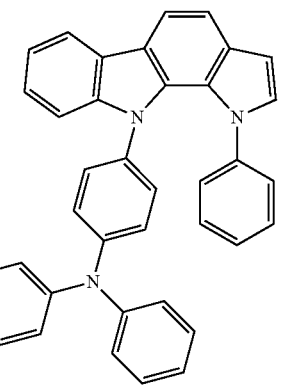
Inv192
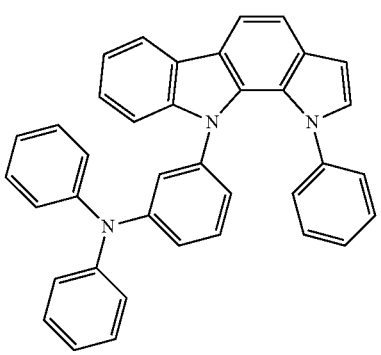
Inv193
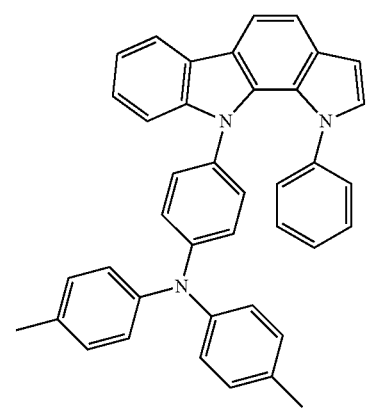
Inv194
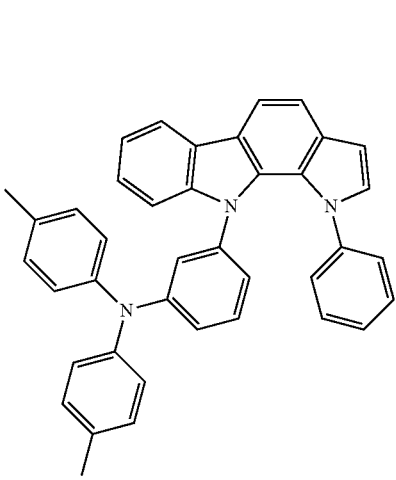

Inv195
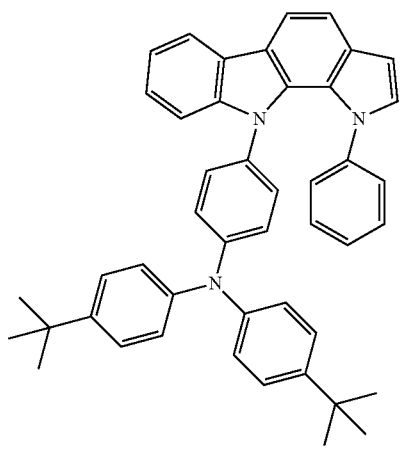
Inv196
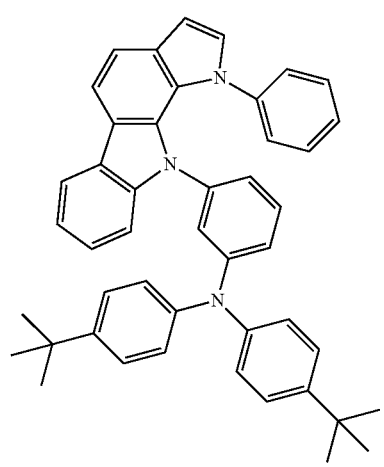
Inv197
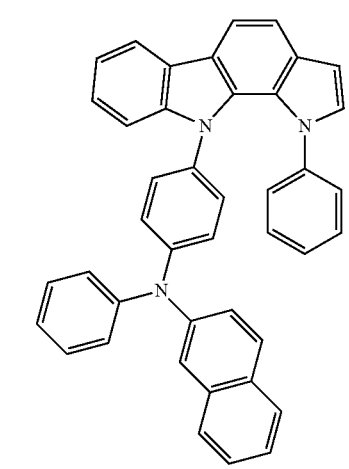
Inv198
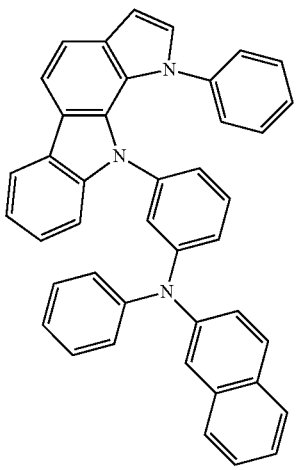
Inv199
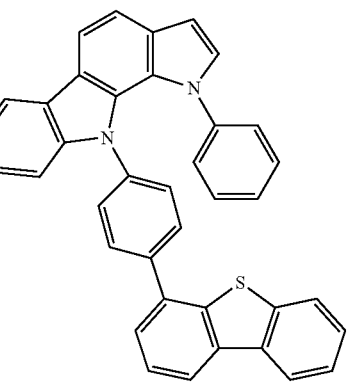
Inv200
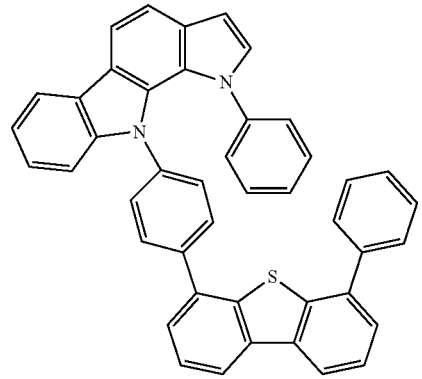
Inv201
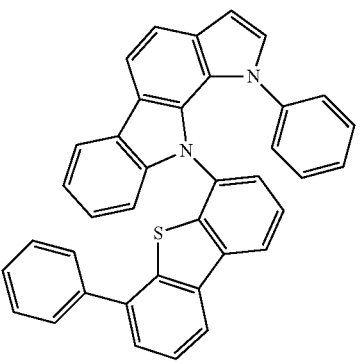

Inv202
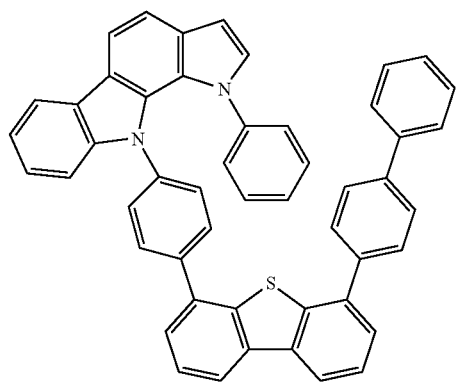
Inv203
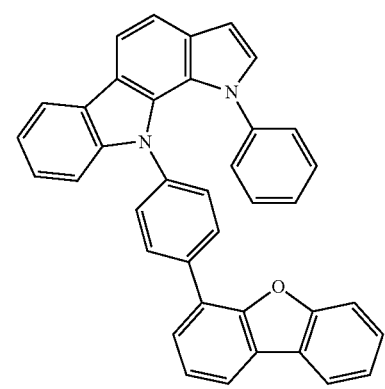
Inv204
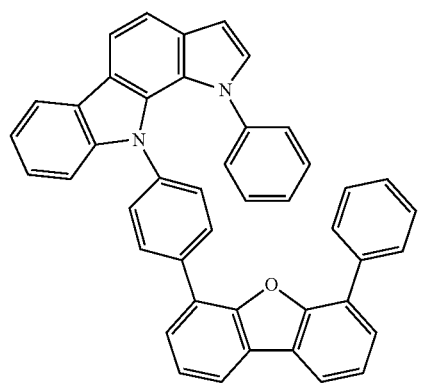
Inv205
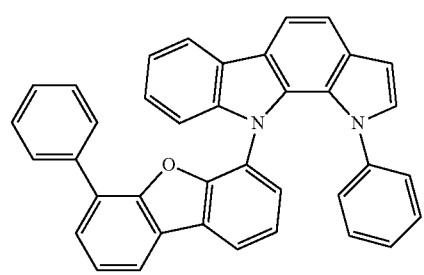
Inv206
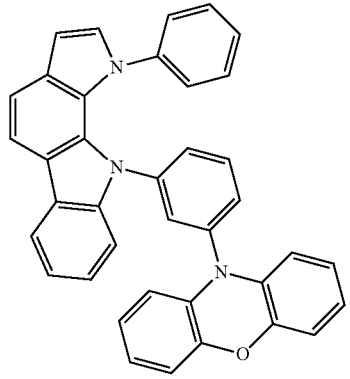
Inv207
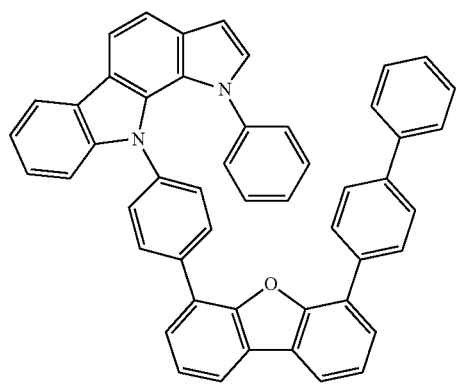
Inv208
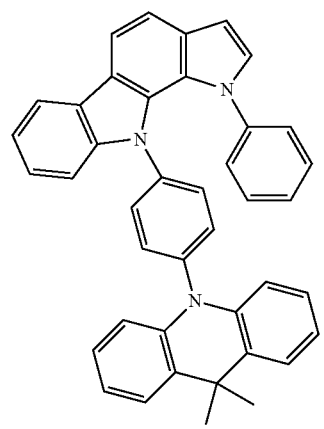
Inv209
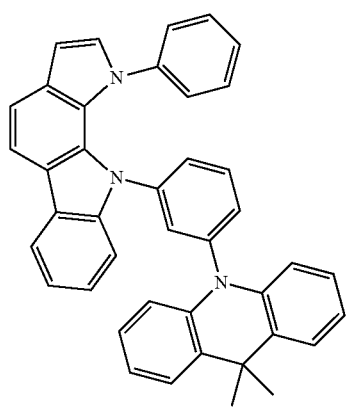

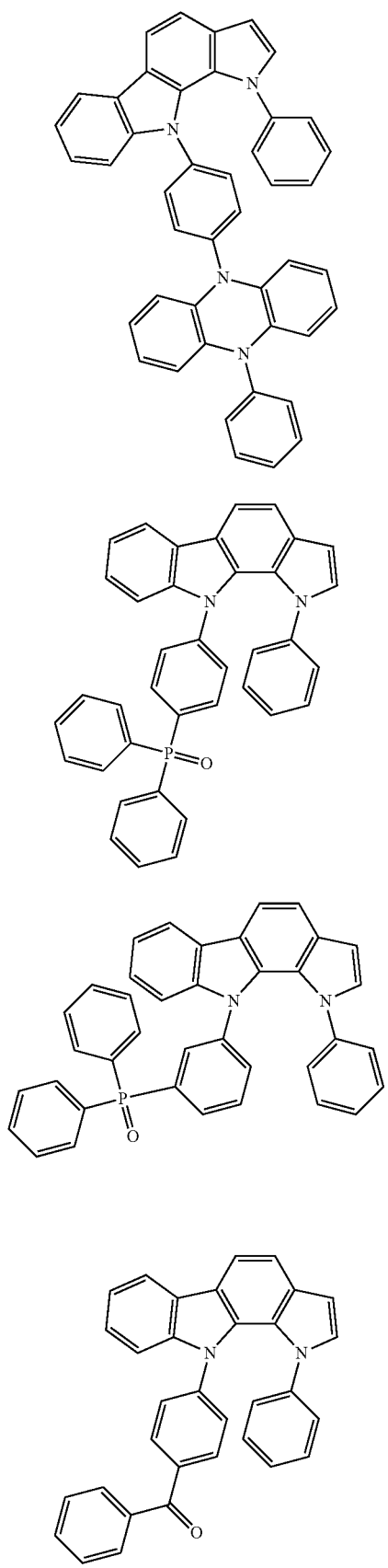

Inv219
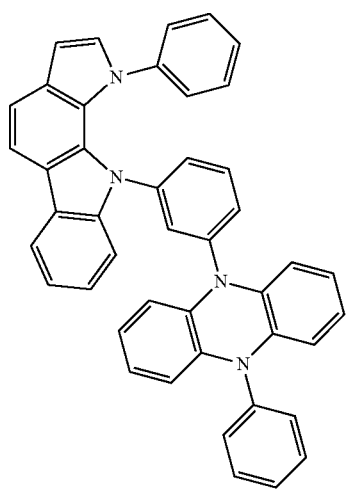
Inv220
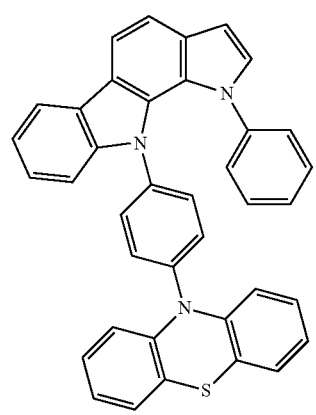
Inv221
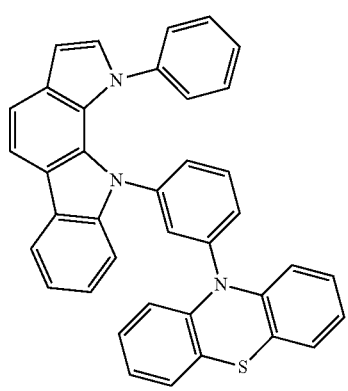
Inv222
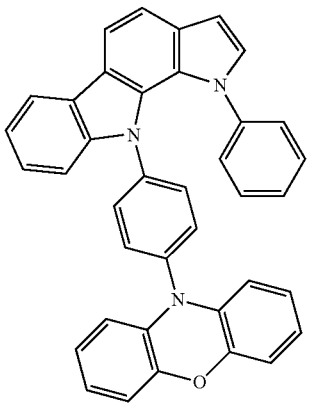
Inv223
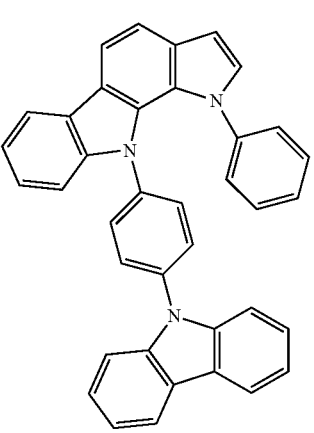
Inv224
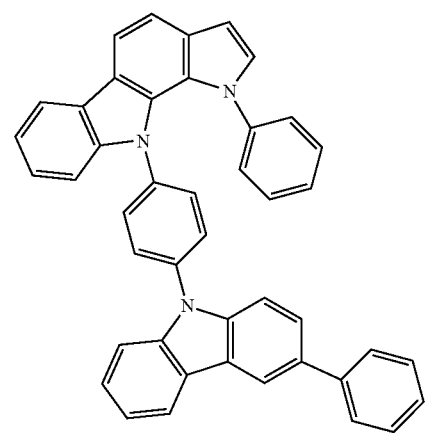

Inv225
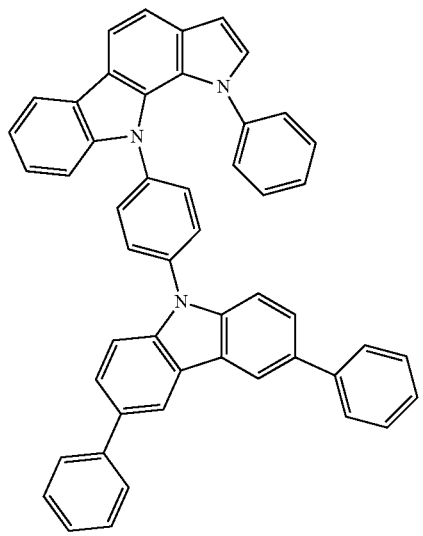
Inv226
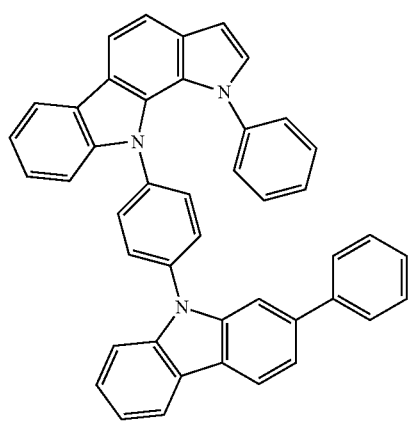
Inv227
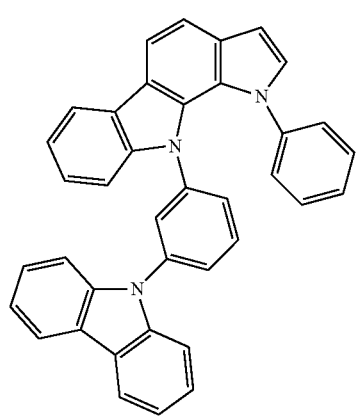
Inv228
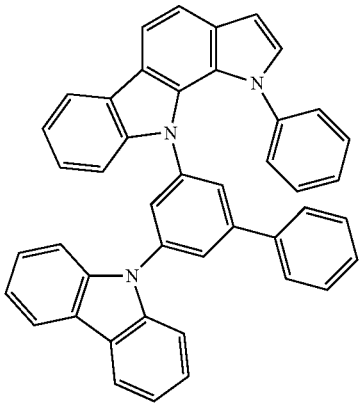
Inv229
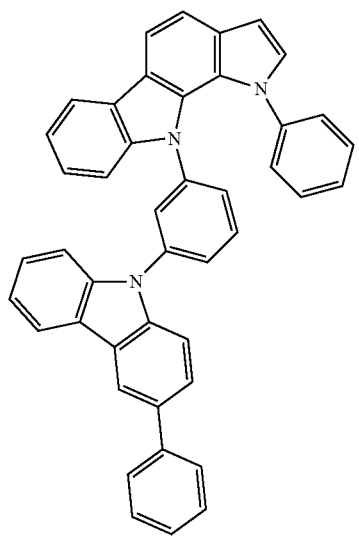
Inv230
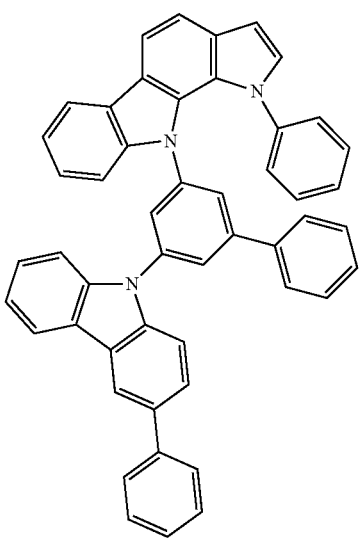

-continued
Inv231
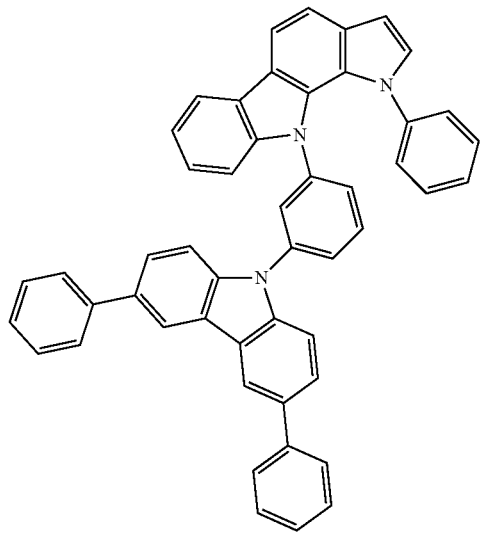
Inv232
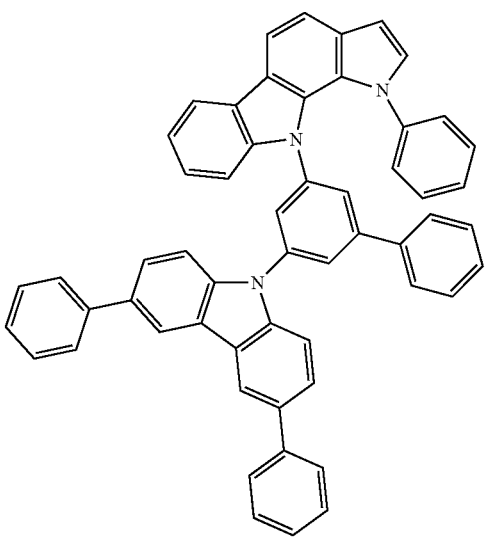
Inv233
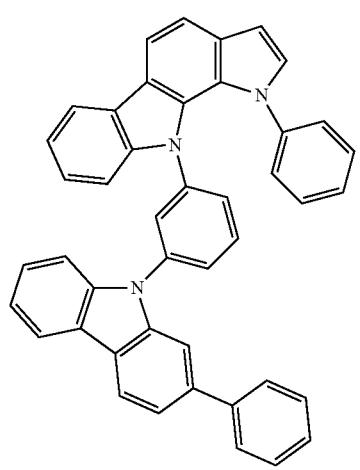
Inv234
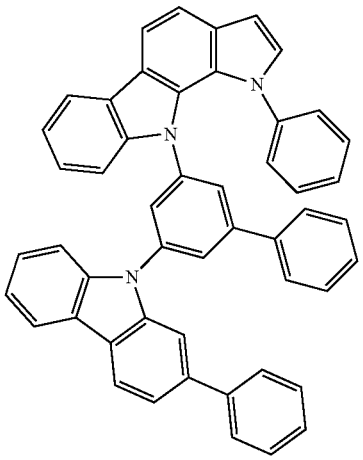
Inv235
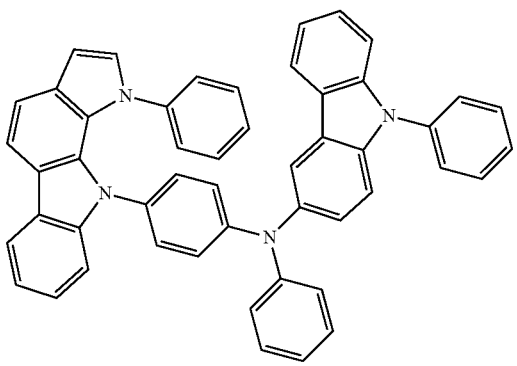
Inv236
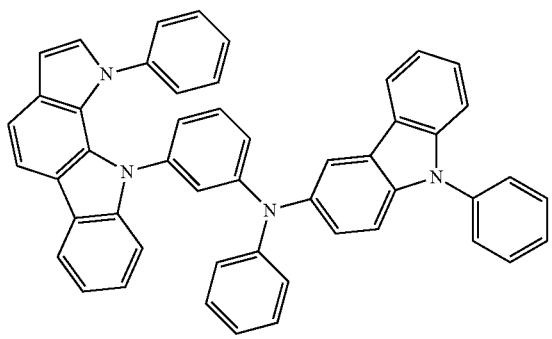

Inv237
Inv241
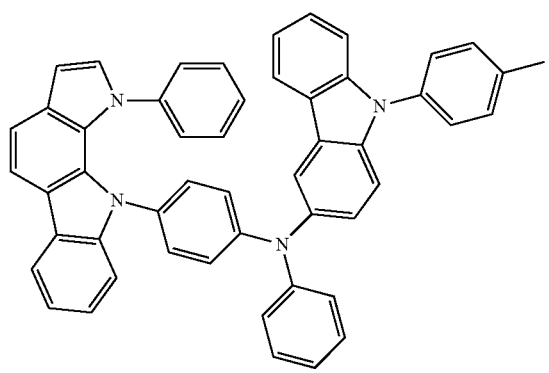
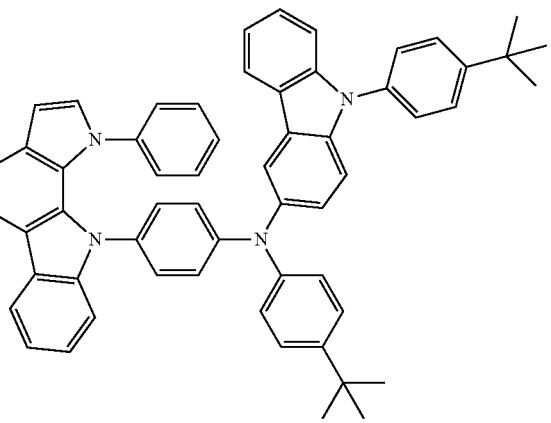
Inv238
Inv242
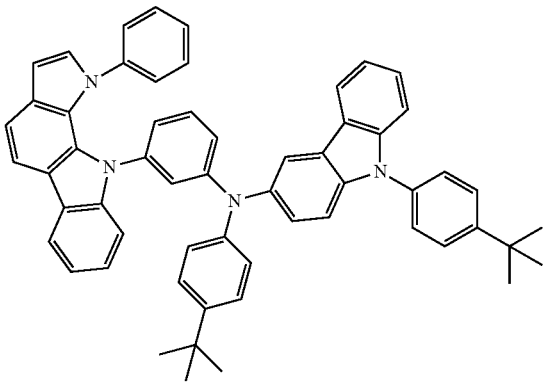
Inv239
Inv243
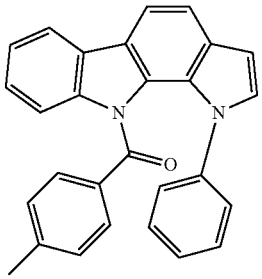
Inv240
Inv244
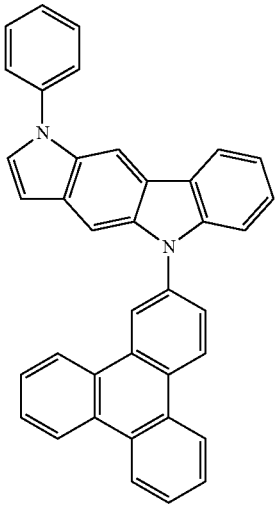

Inv245
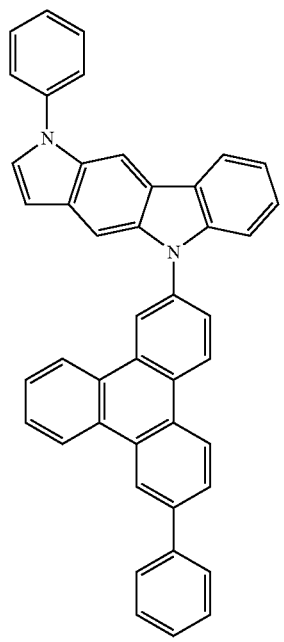
Inv246
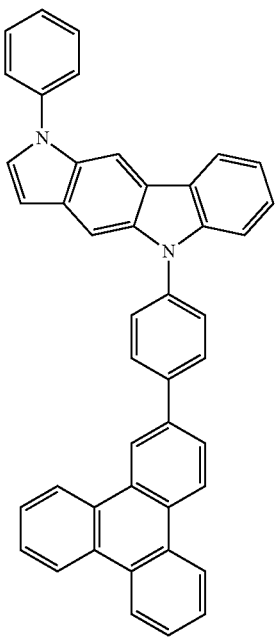
Inv247
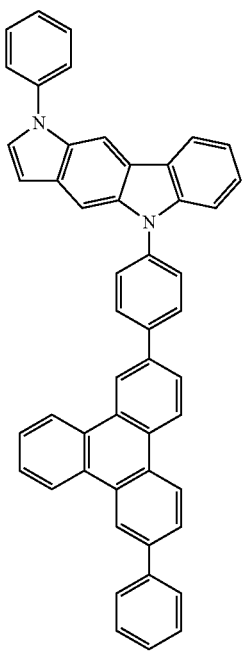
Inv248
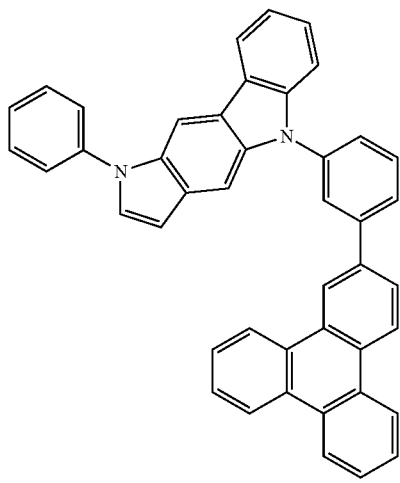

Inv249
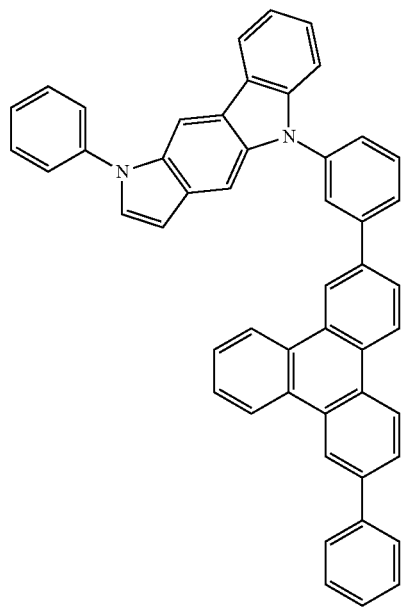
Inv250
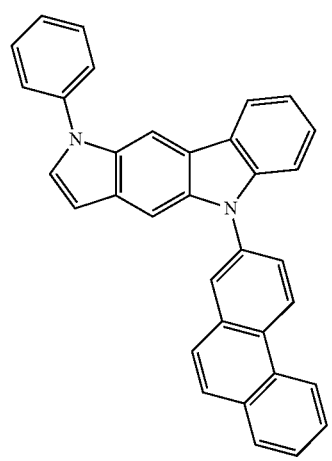
Inv251
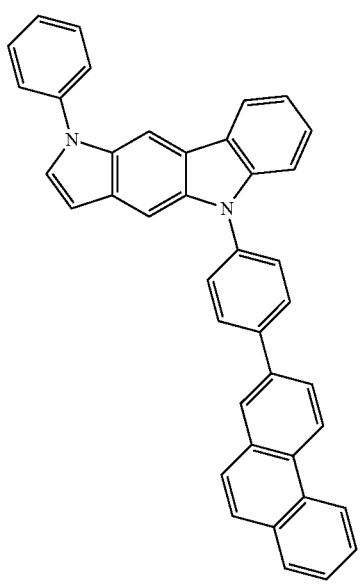
Inv252
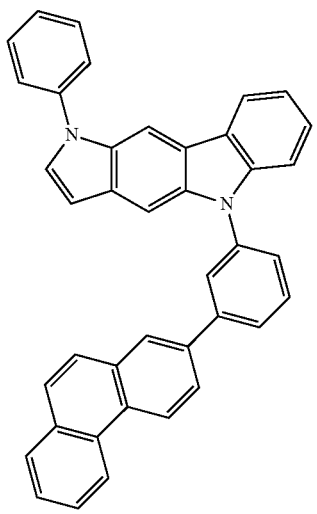
Inv253
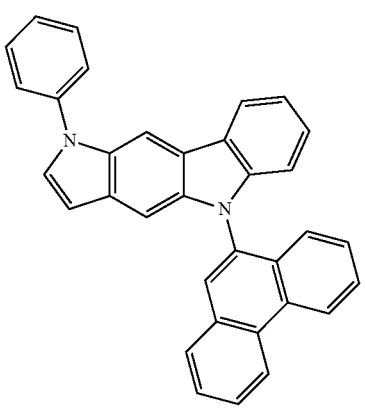
Inv254
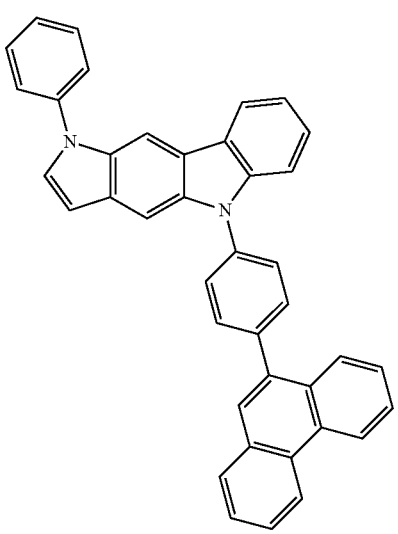

Inv255
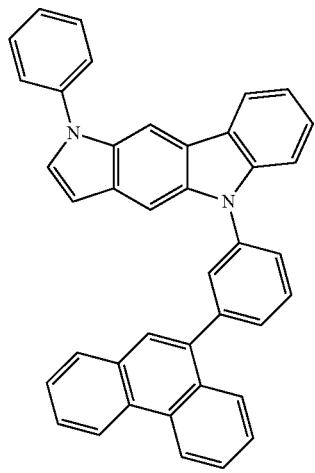
Inv256
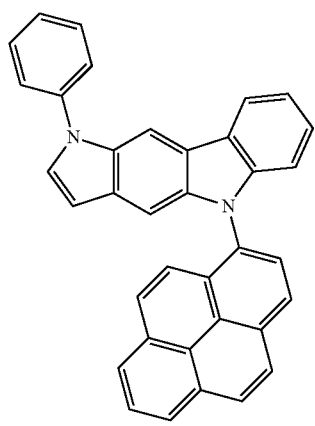
Inv257
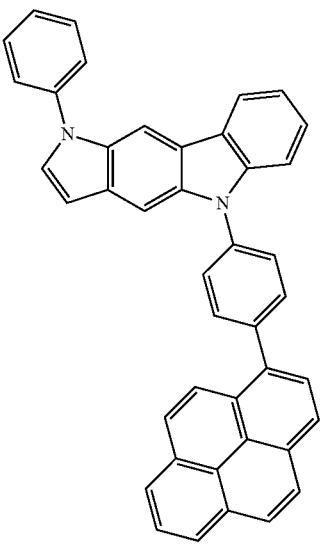
Inv258
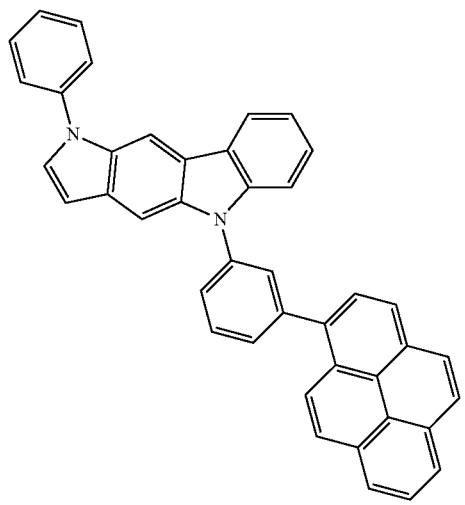
Inv259
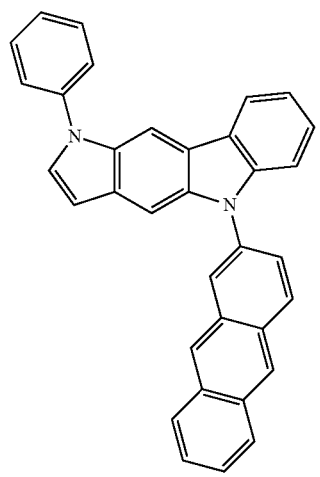
Inv260
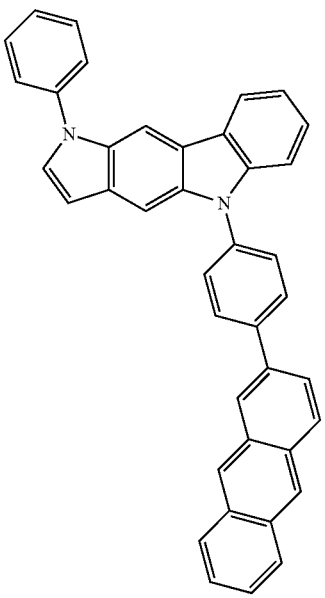

Inv261
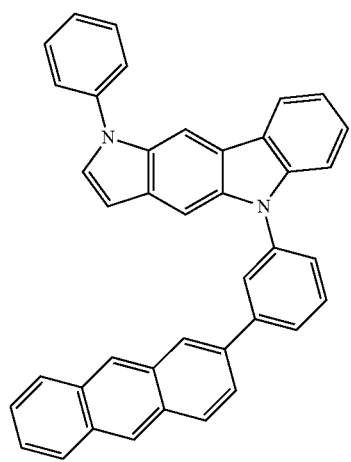
Inv262
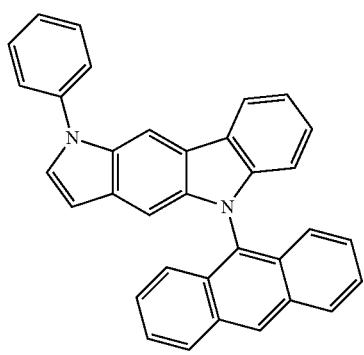
Inv263
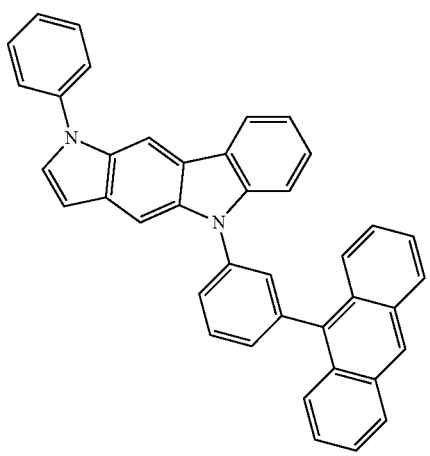
Inv264
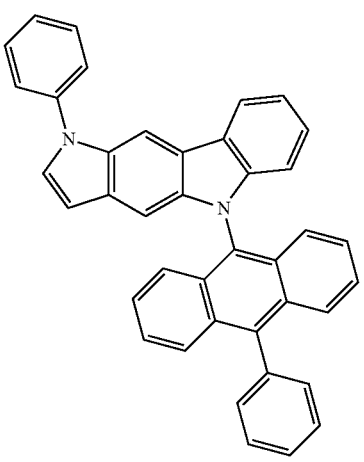
Inv265
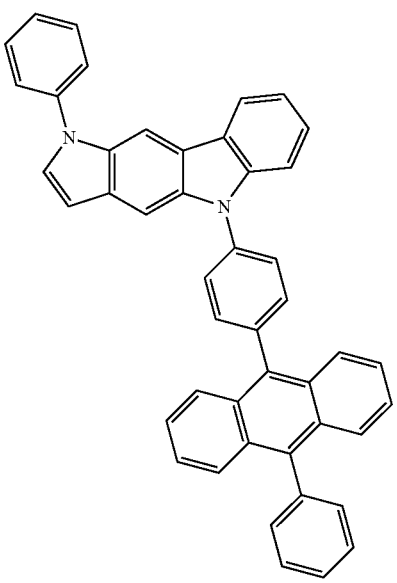
Inv266
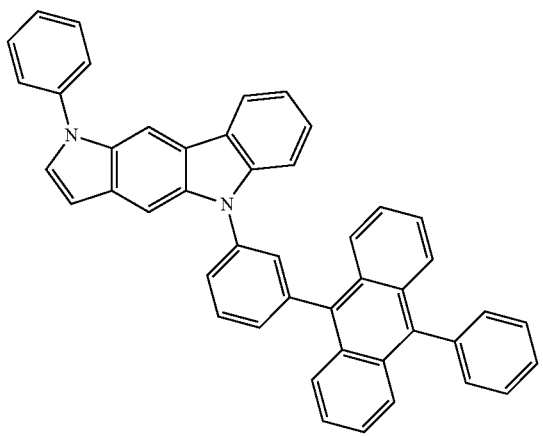

Inv267
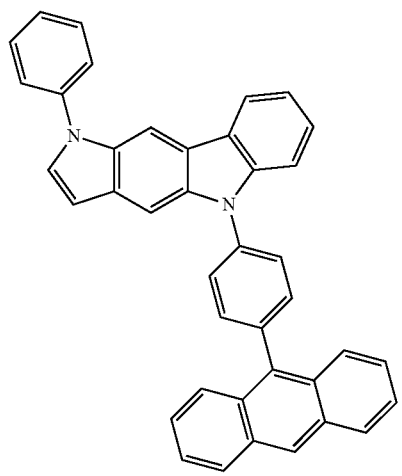
Inv268
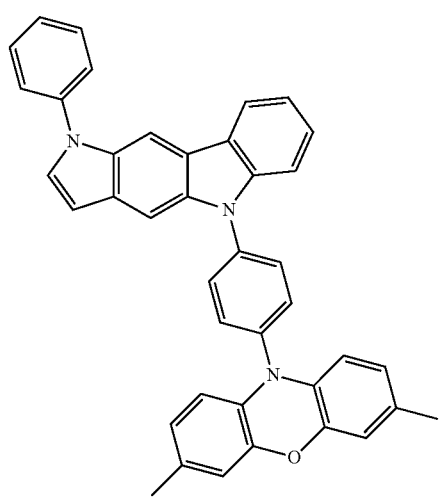
Inv269
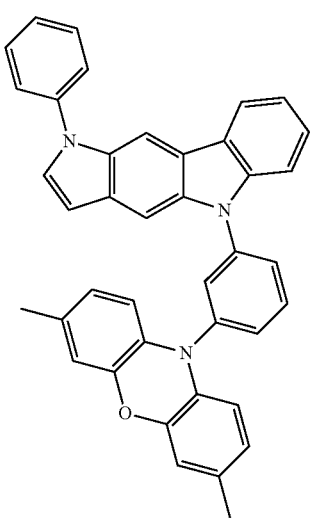
Inv270
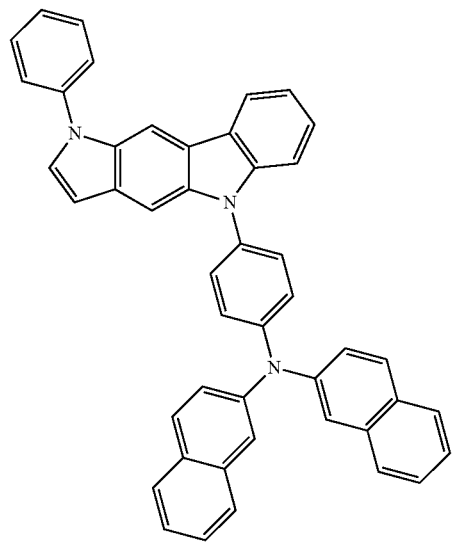
Inv271
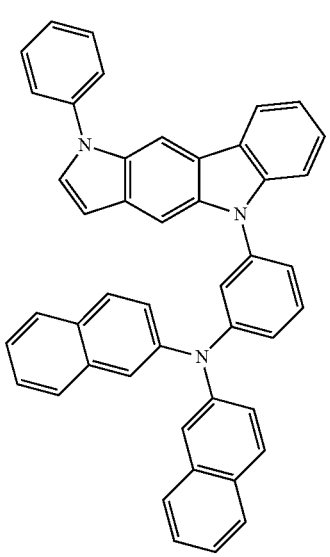
Inv272
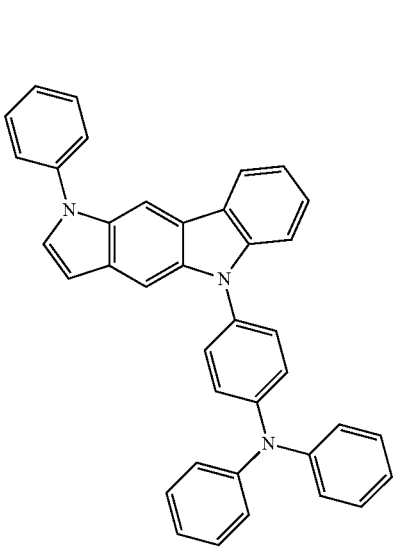

Inv273
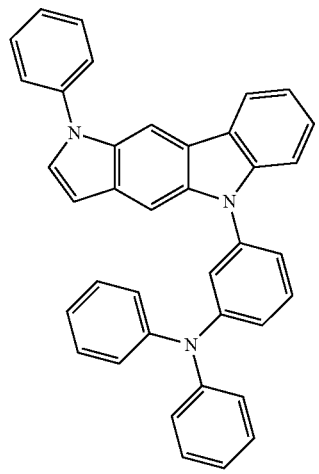
Inv274
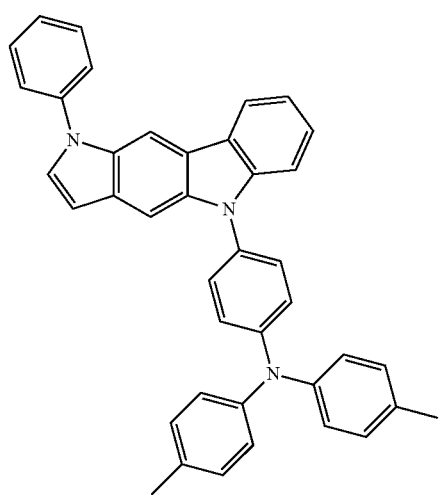
Inv275
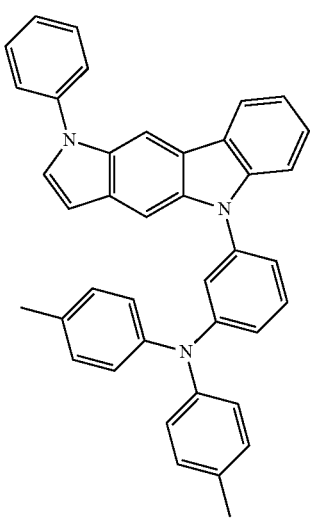
Inv276
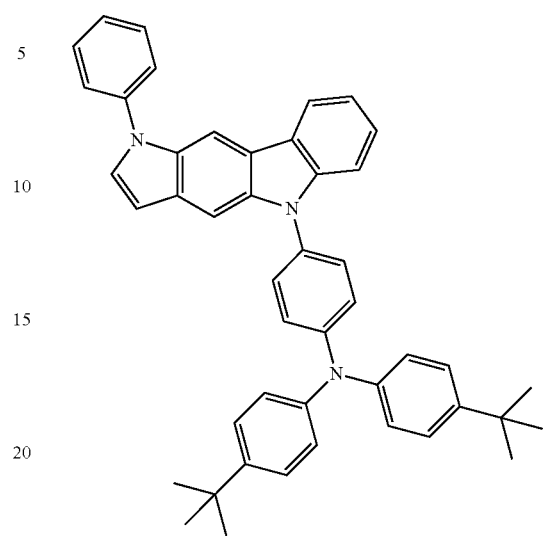
Inv277
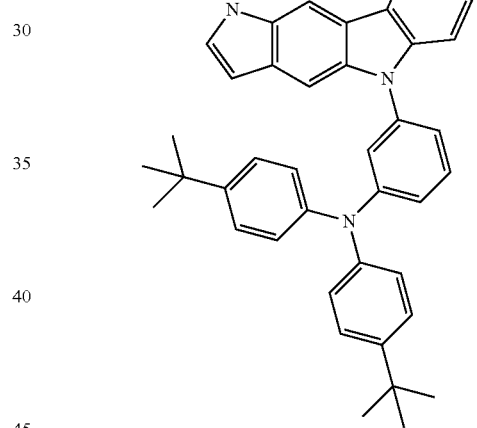
Inv278
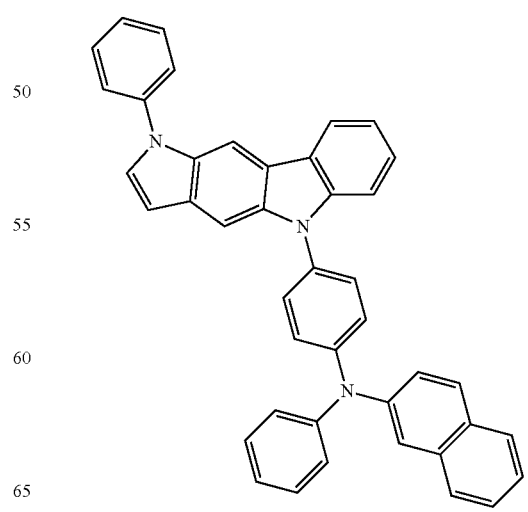

-continued
Inv279
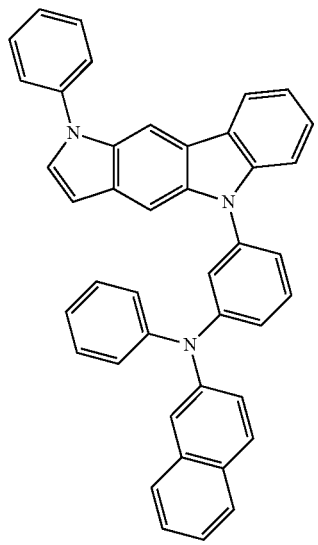
Inv282
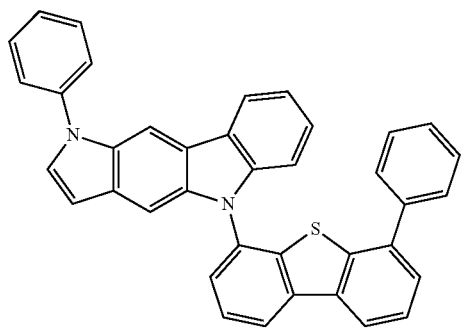
Inv280
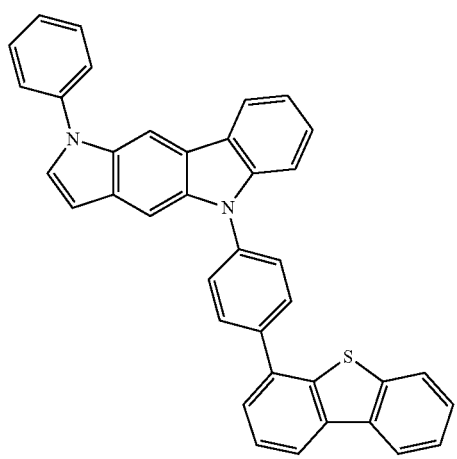
Inv283
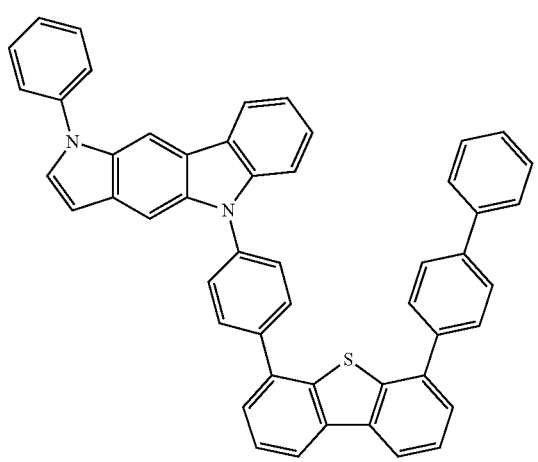
Inv281
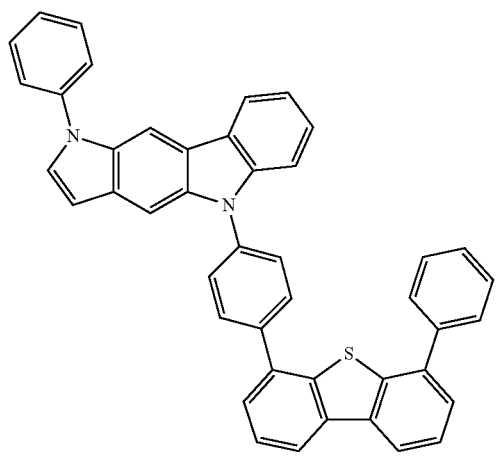
Inv284
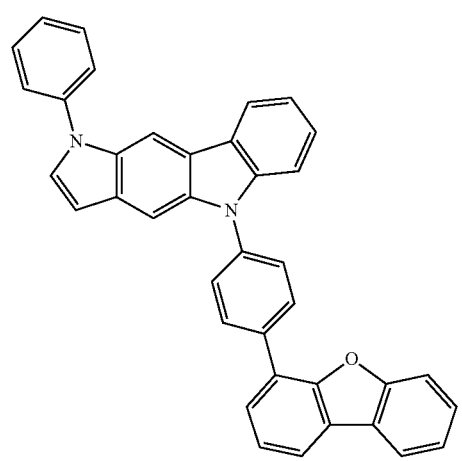

Inv285
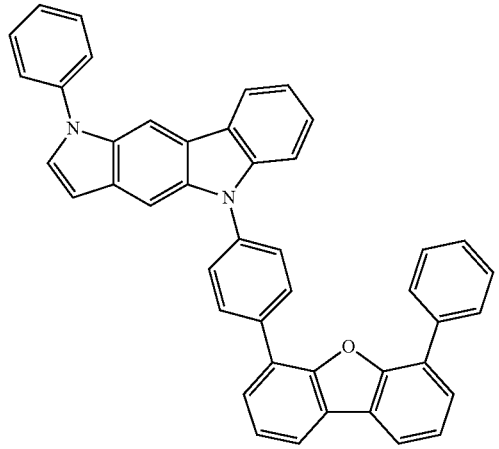
Inv288
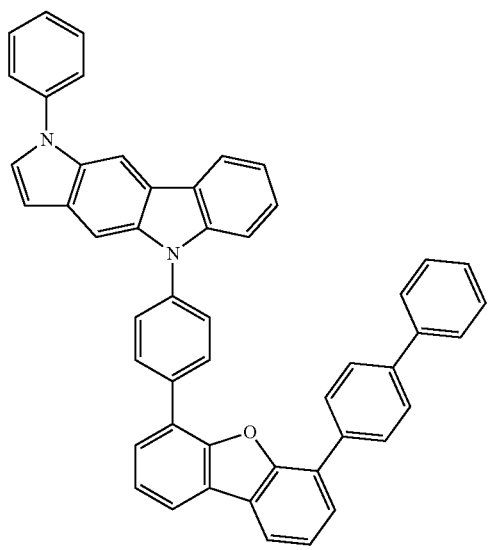
Inv286
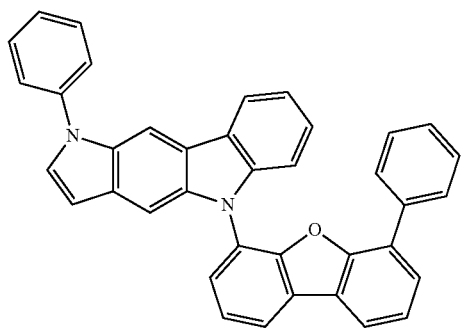
Inv289
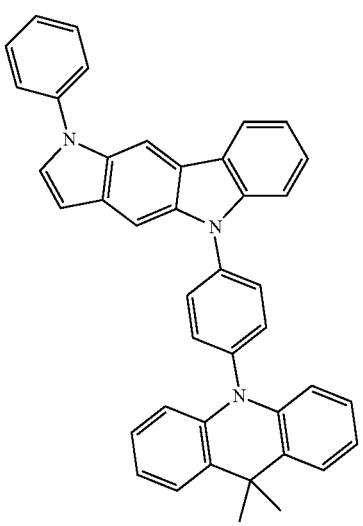
Inv287
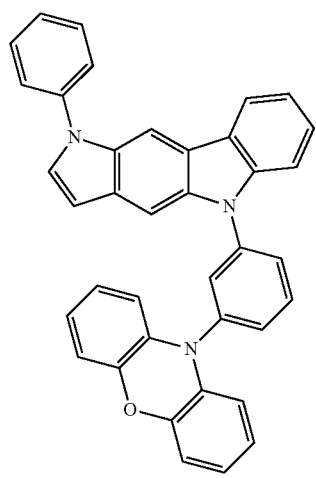
Inv290
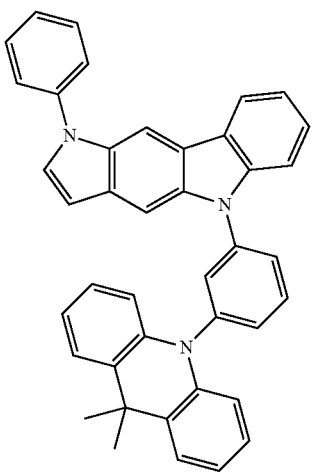

Inv291
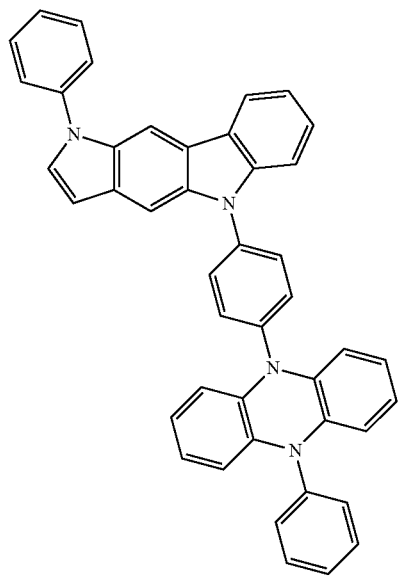
Inv292
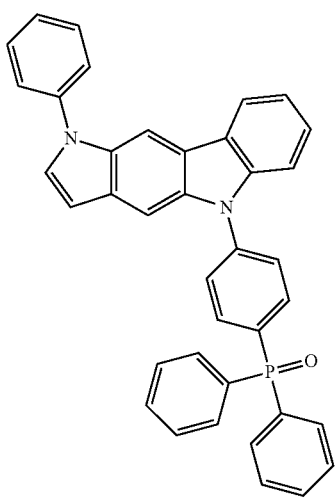
Inv293
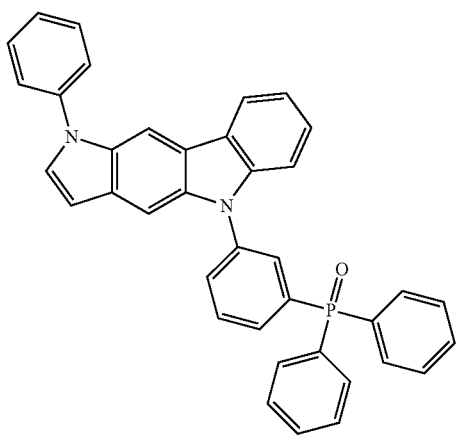
Inv294
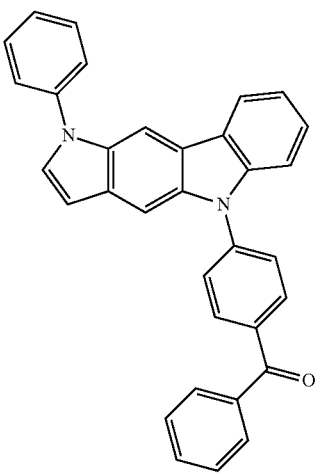
Inv295
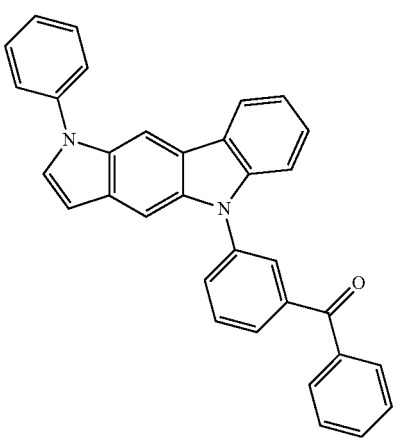
Inv296
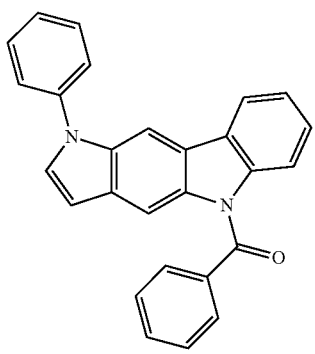

-continued
Inv297
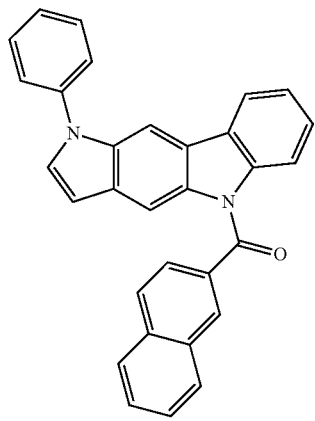
Inv298
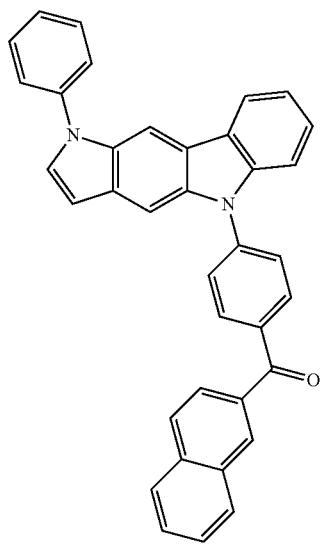
Inv299
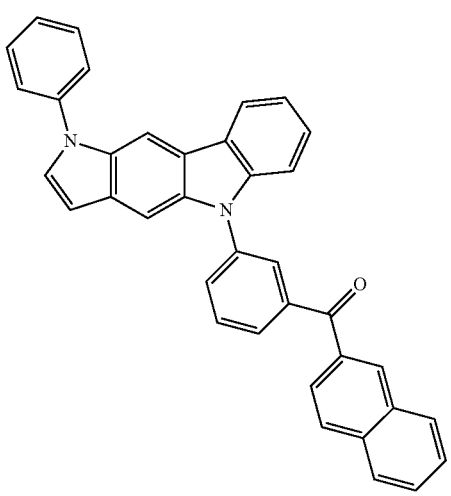
-continued
Inv300
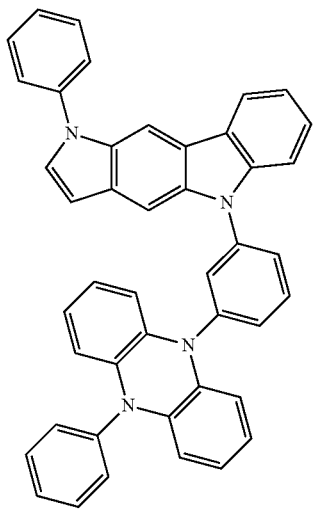
Inv301
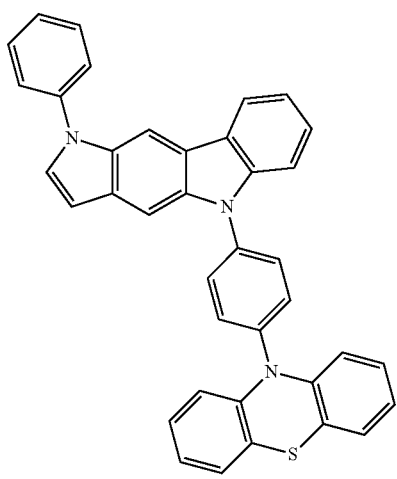
Inv302
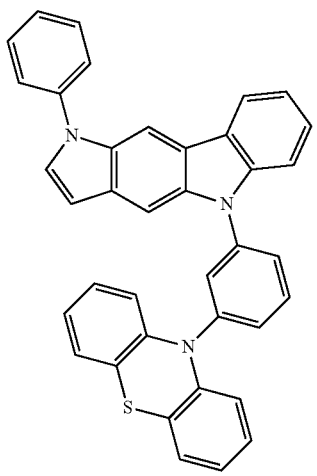

-continued
Inv303
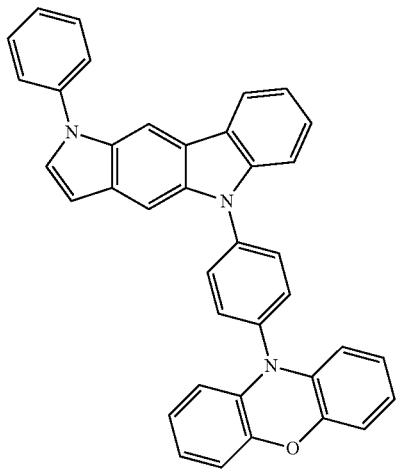
Inv304
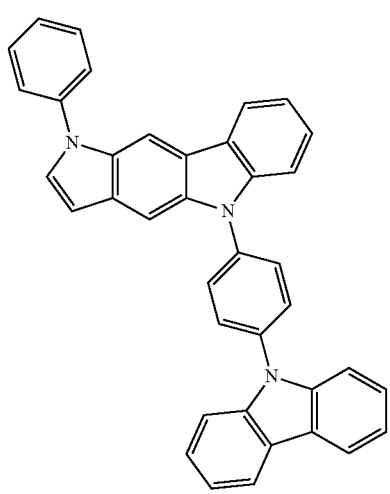
Inv305
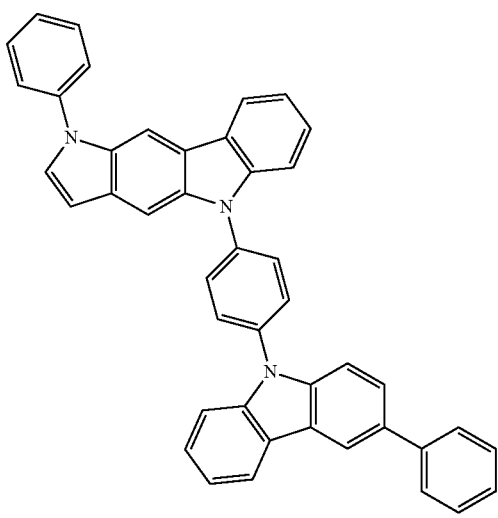
-continued
Inv306
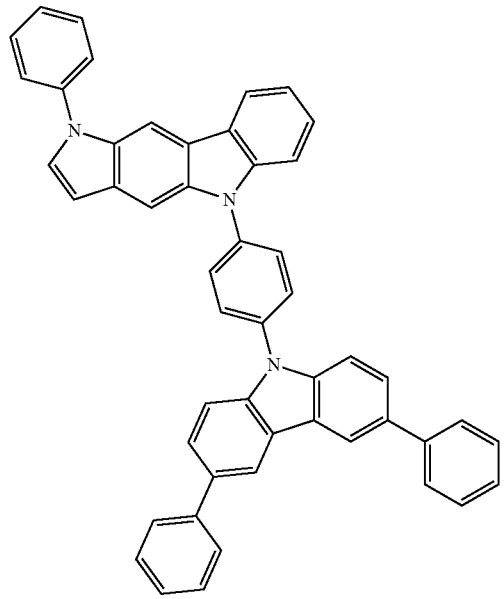
Inv307
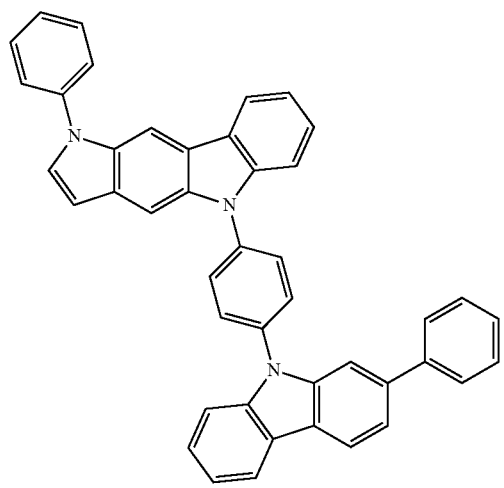
Inv308
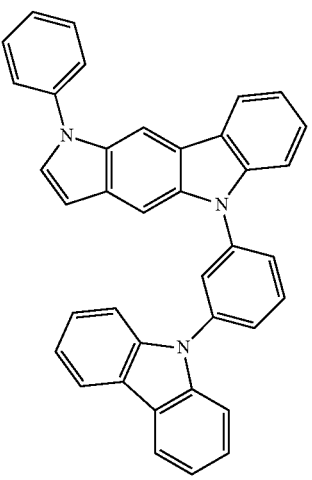

Inv309
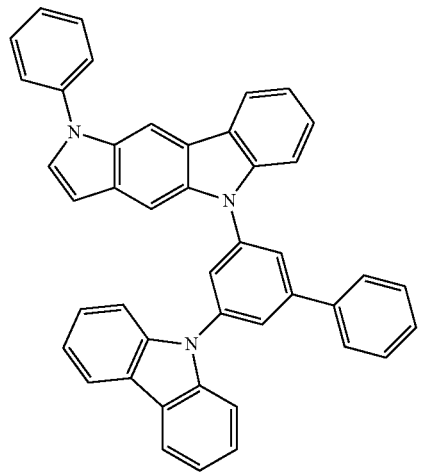
Inv310
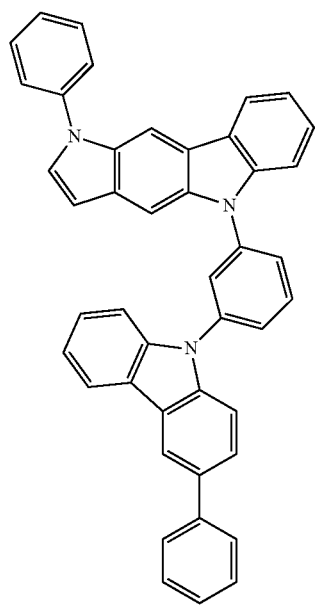
Inv311
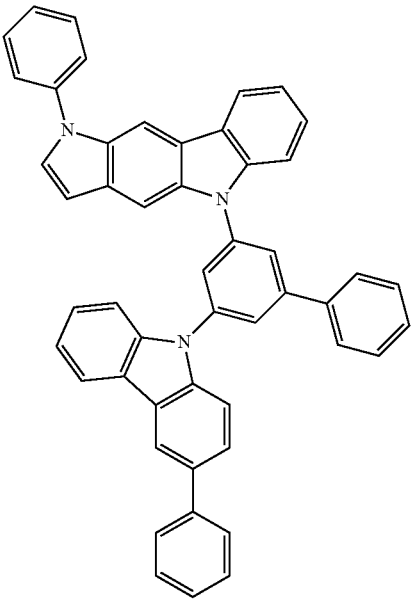
Inv312
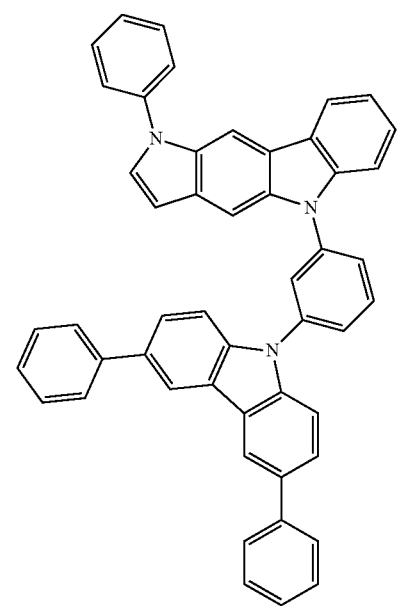

-continued
Inv313
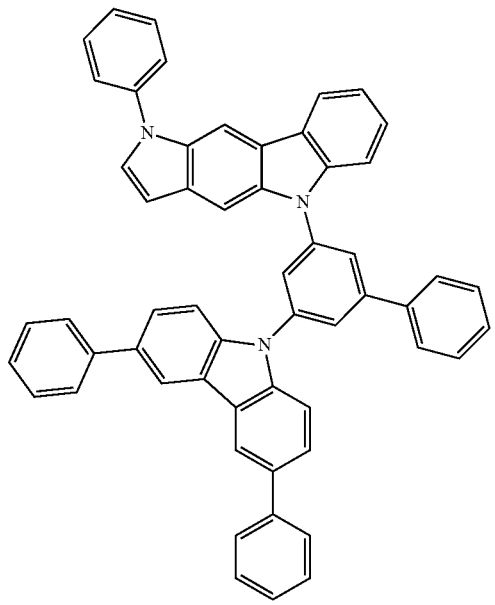
Inv315
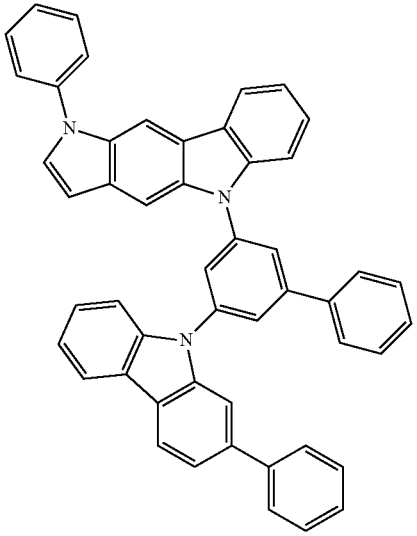
Inv316
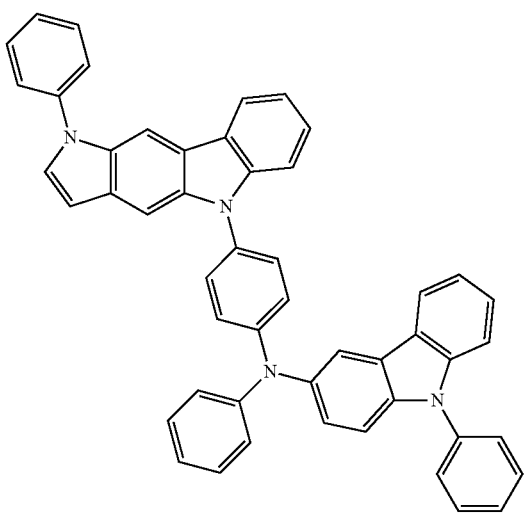
Inv314
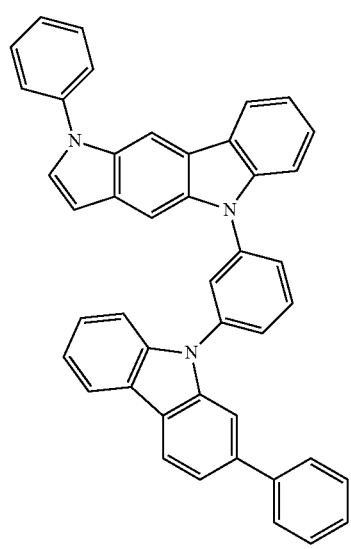
Inv317
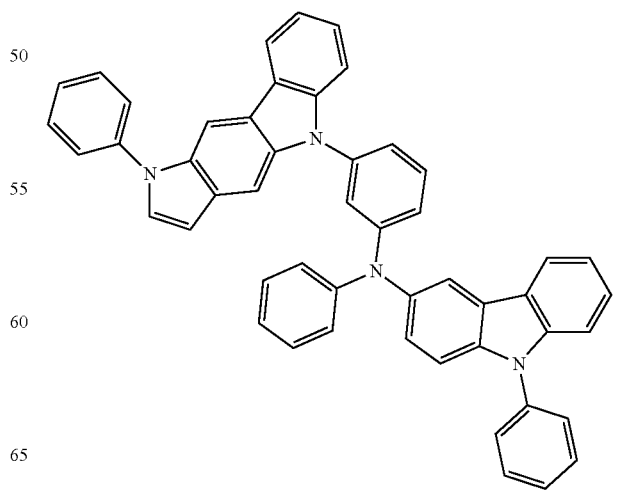

Inv318
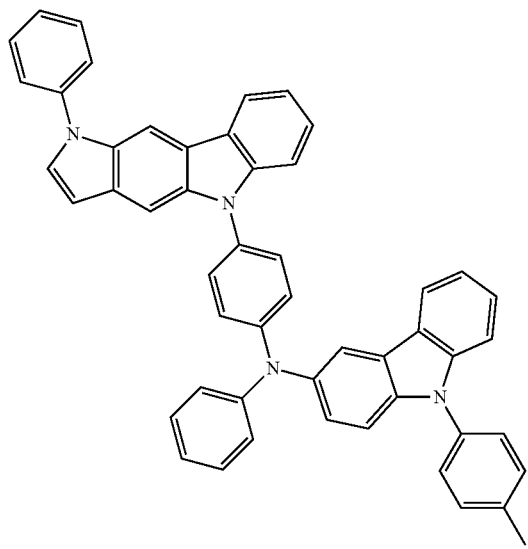
Inv320
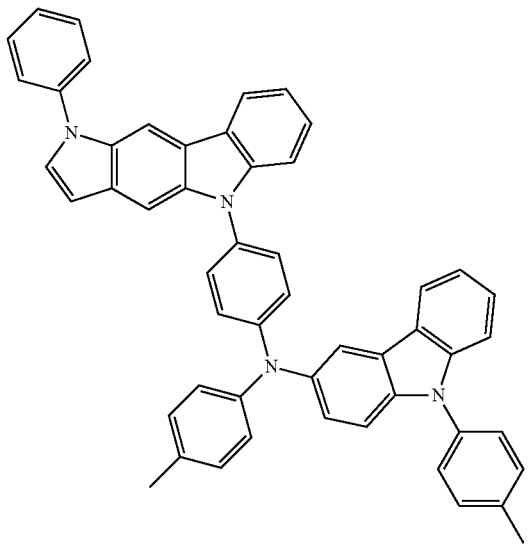
Inv319
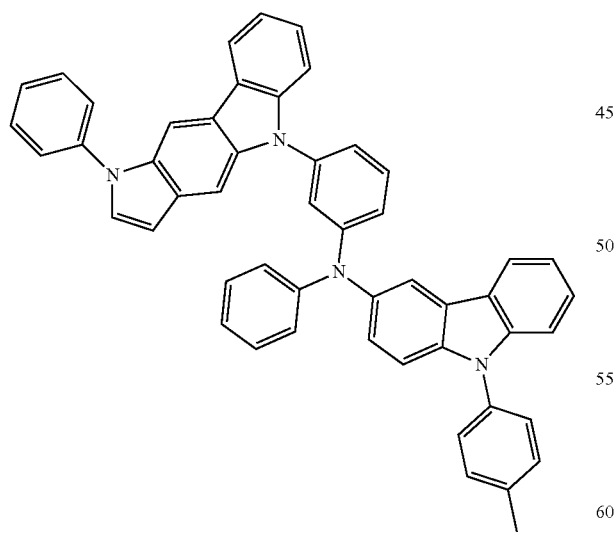
Inv321
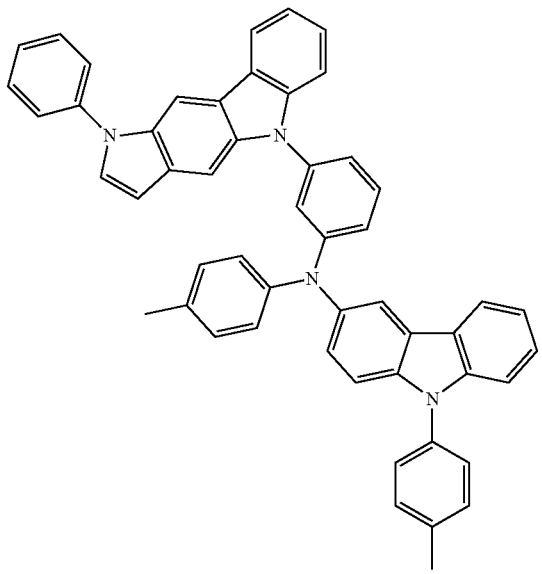

Inv322
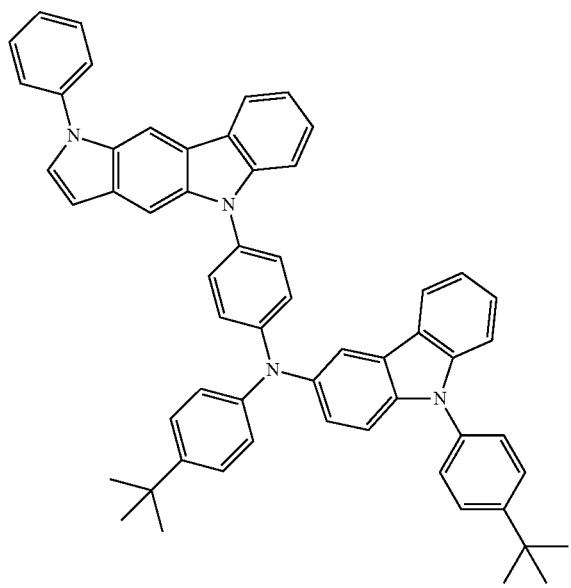
Inv323
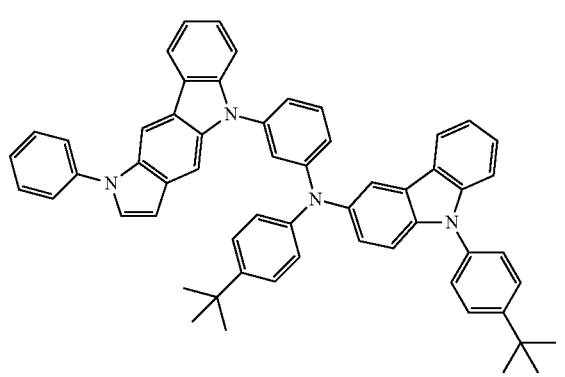
Inv324
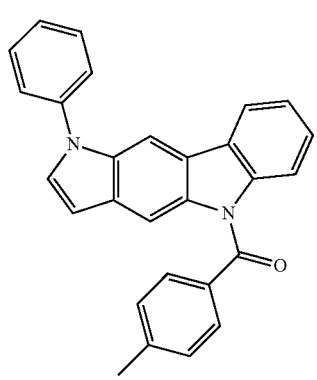
Inv325
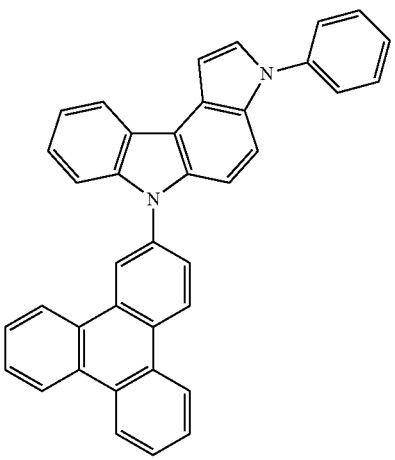
Inv326
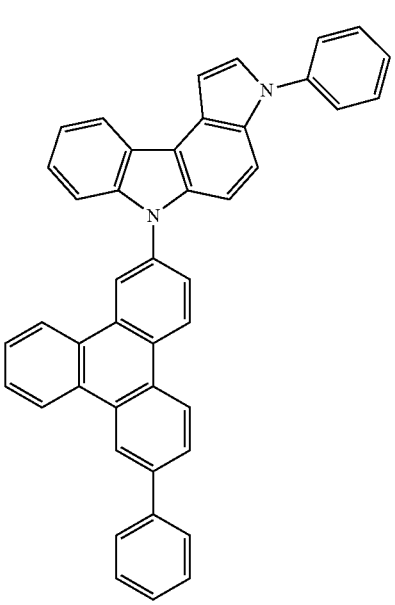
Inv327
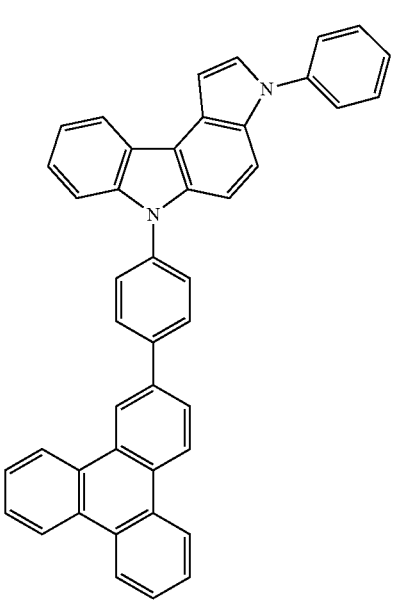

Inv328
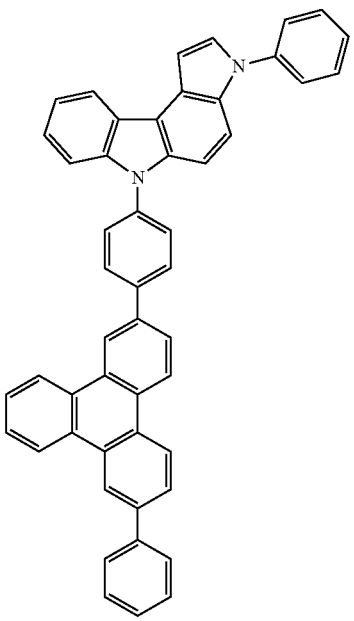
Inv331
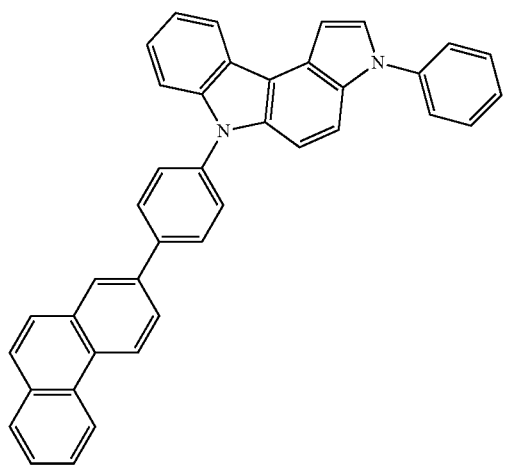
Inv329
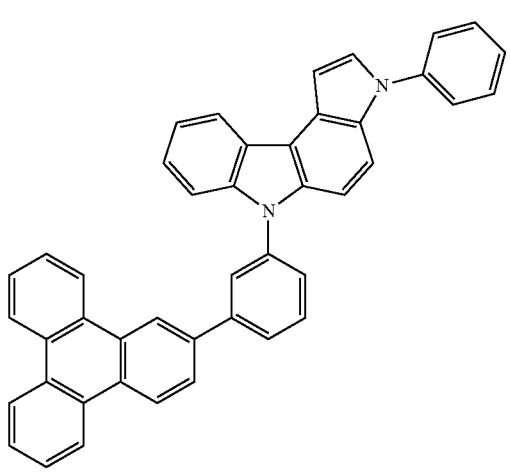
Inv332
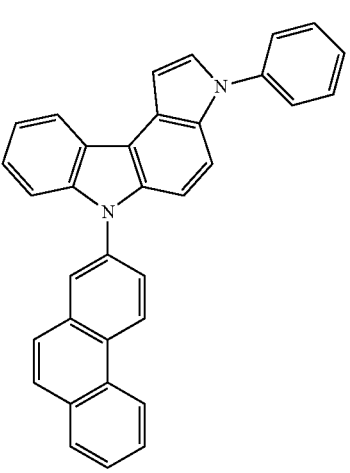
Inv330
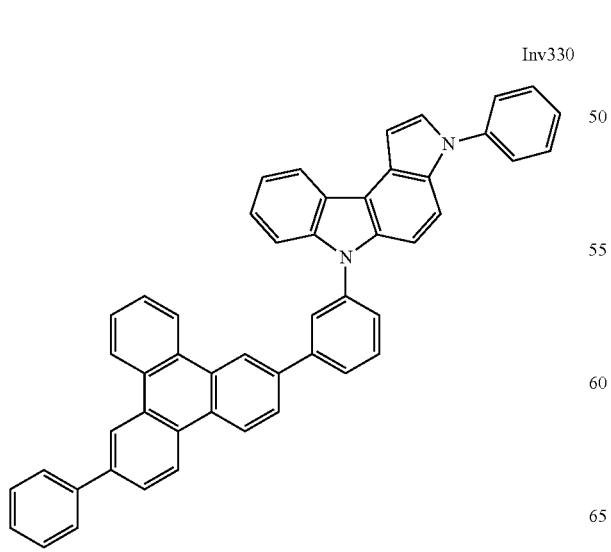
Inv333
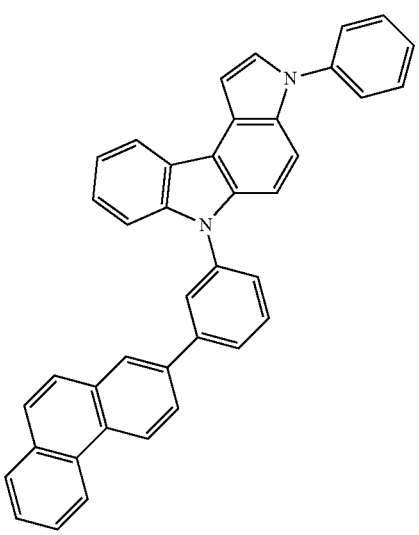

Inv334
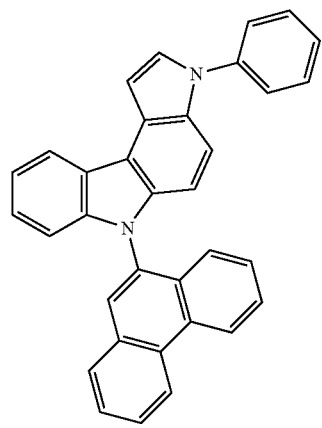
Inv335
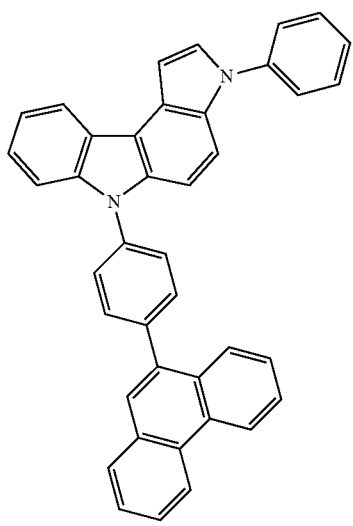
Inv336
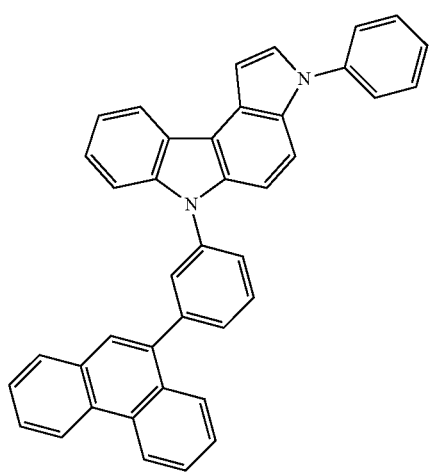
Inv337
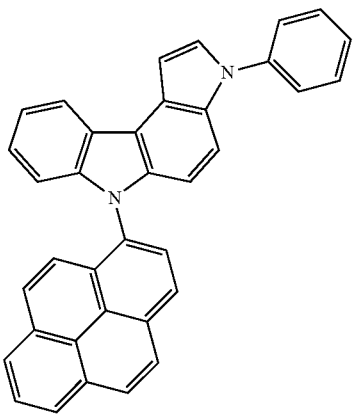
Inv338
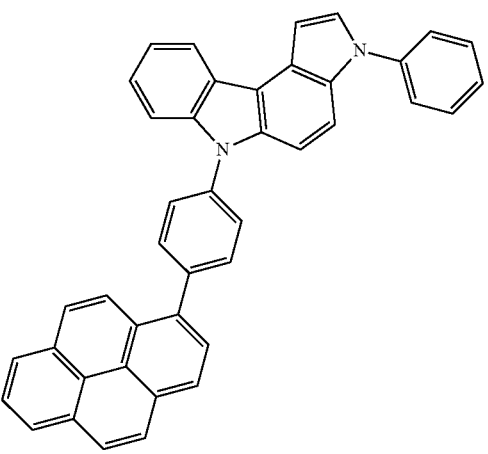
Inv339
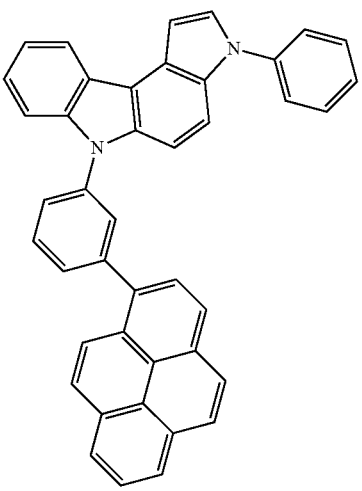

-continued
Inv340
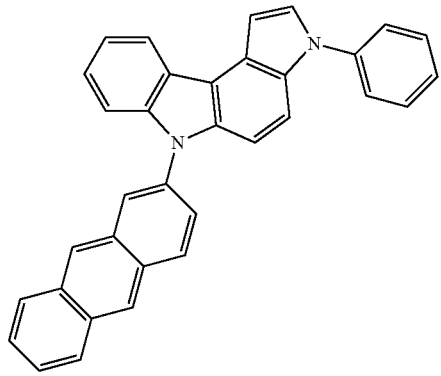
Inv343
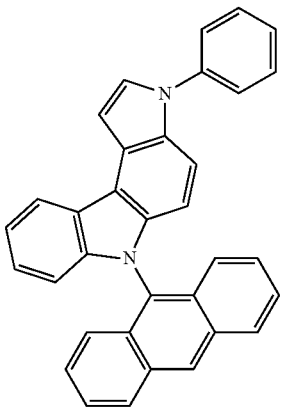
Inv341
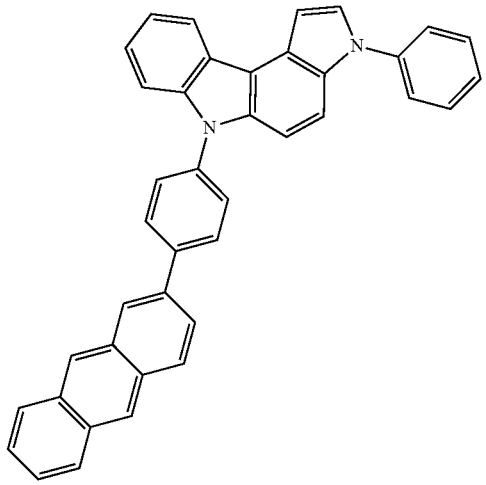
Inv344
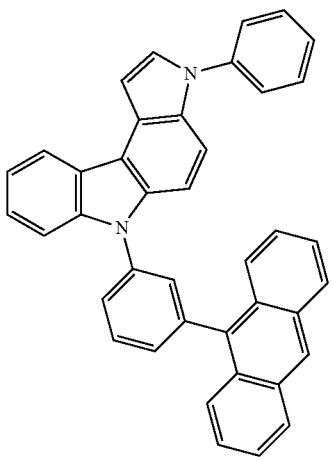
Inv342
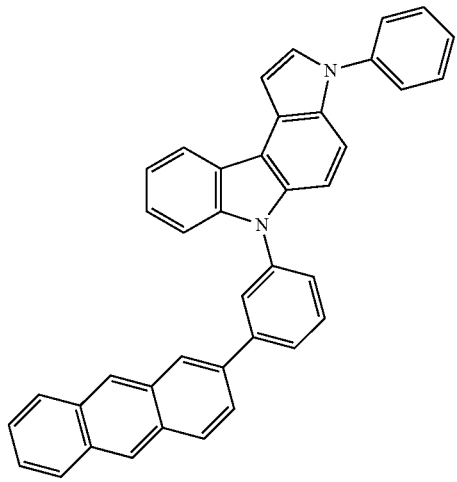
Inv345
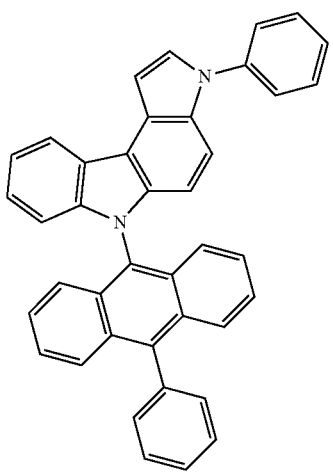

Inv346
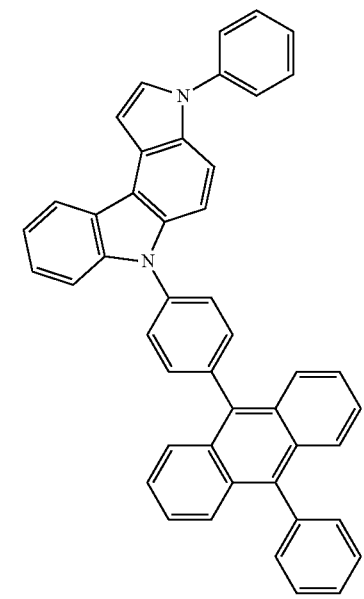
Inv347
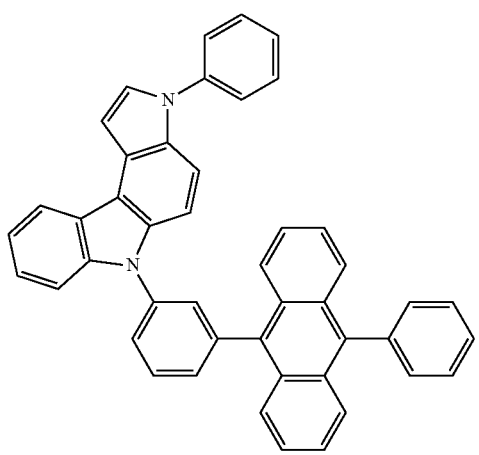
Inv348
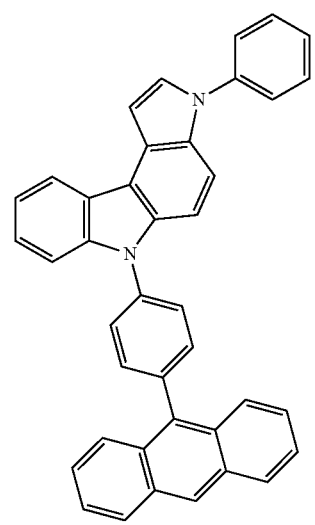
Inv349
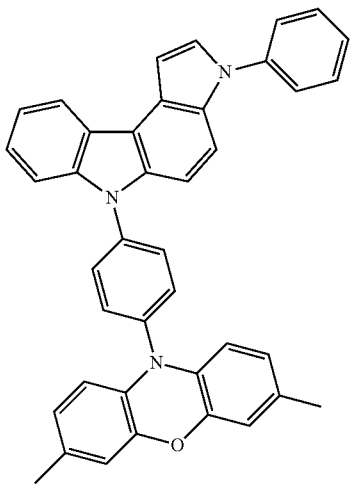
Inv350
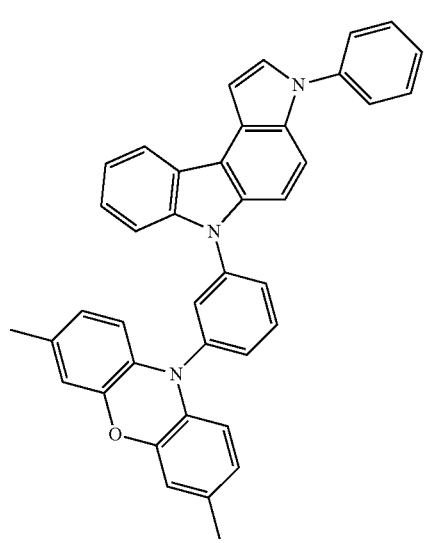
Inv351
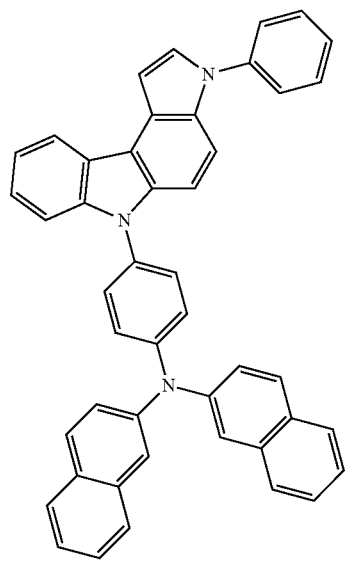

Inv352
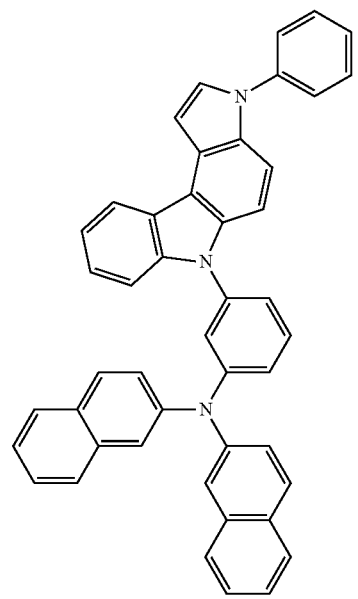
Inv353
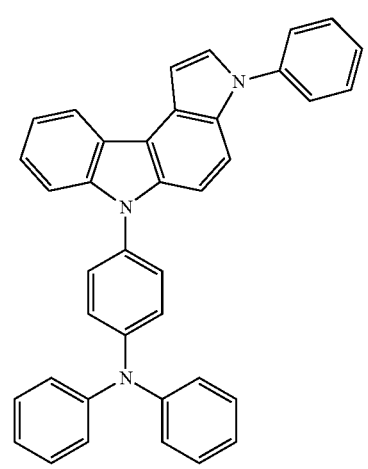
Inv354
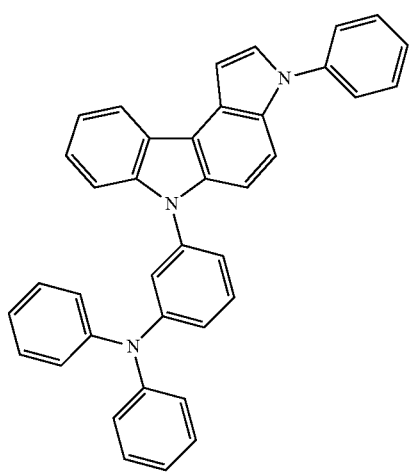
Inv355
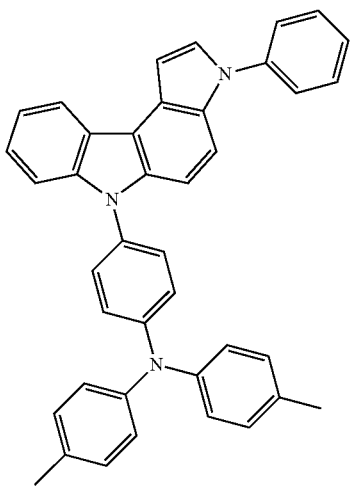
Inv356
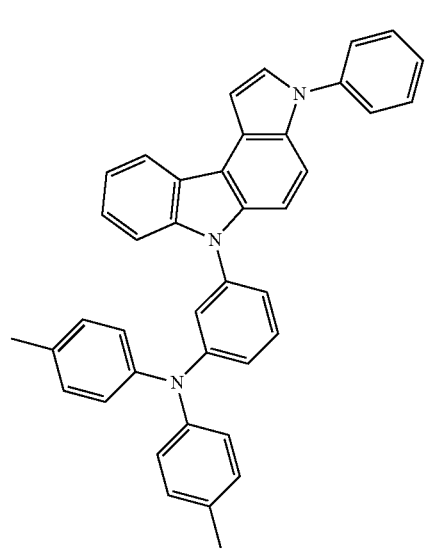
Inv357
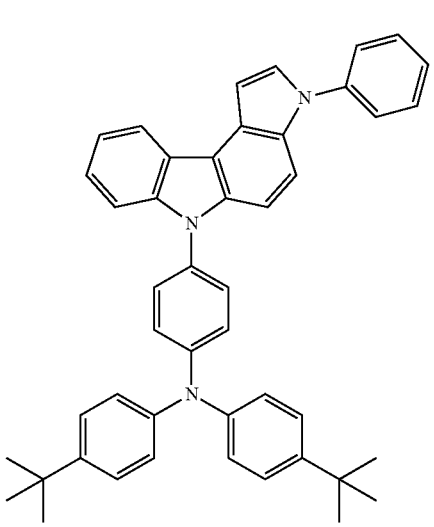

-continued
Inv358
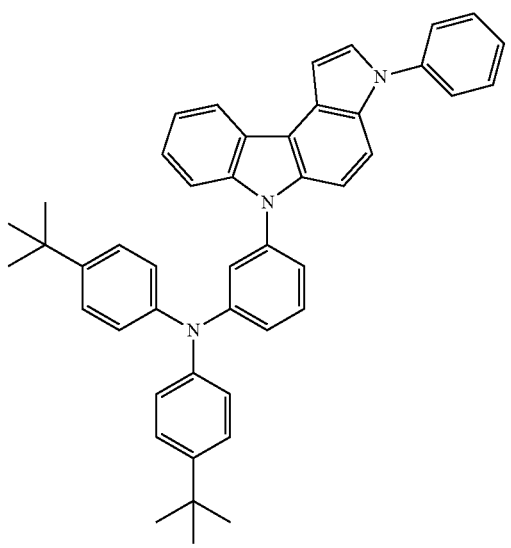
Inv359
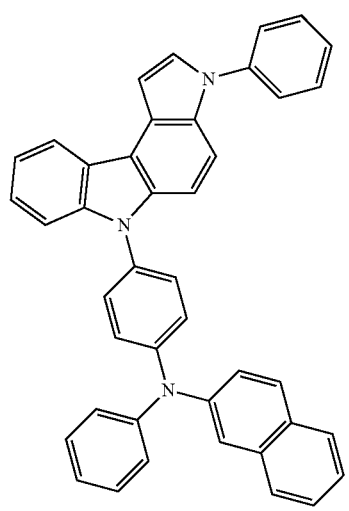
Inv360
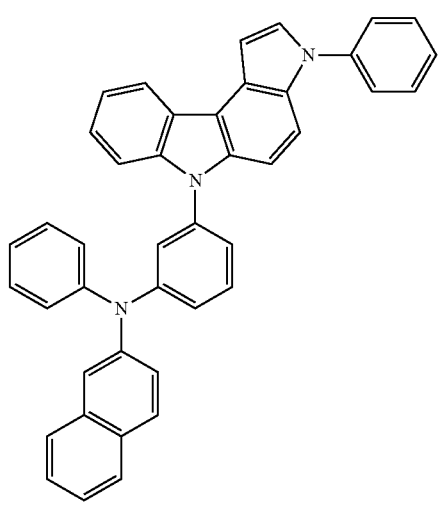
-continued
Inv361
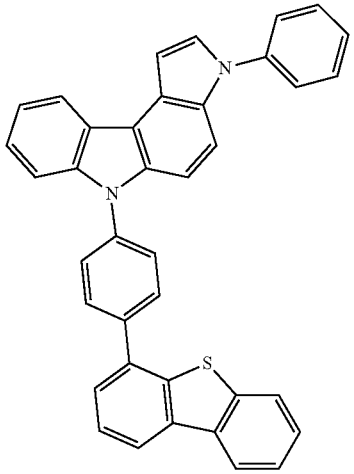
Inv362
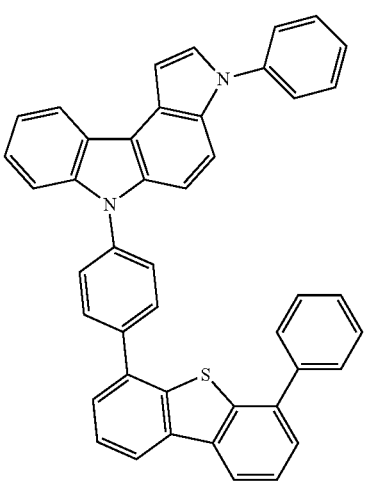
Inv363
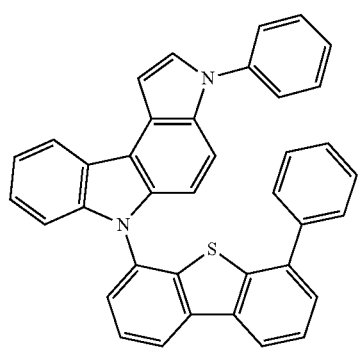

Inv364
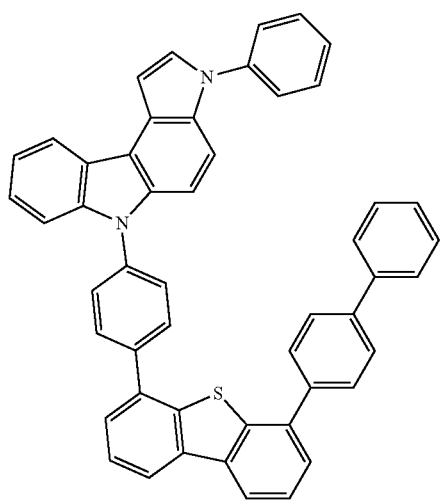
Inv365
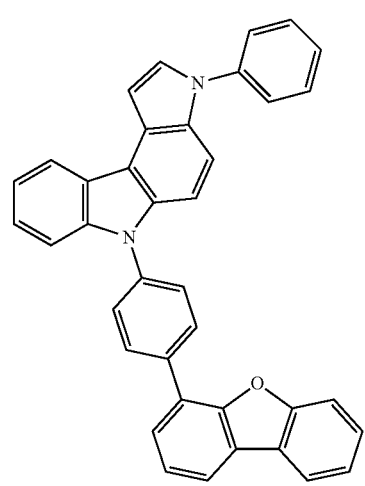
Inv366
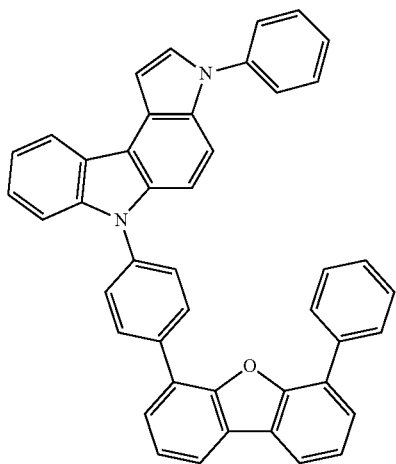
Inv367
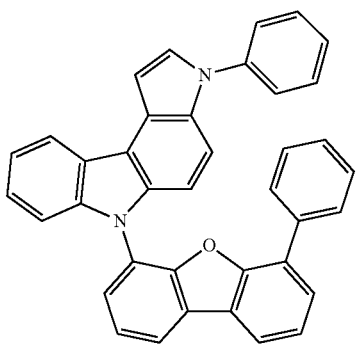
Inv368
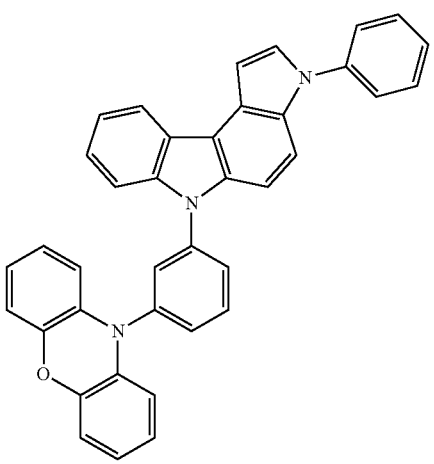
Inv369
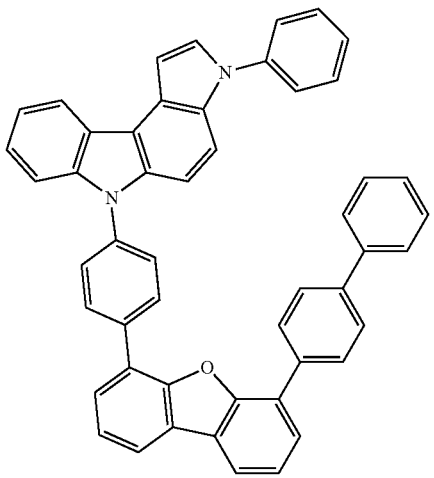

Inv370
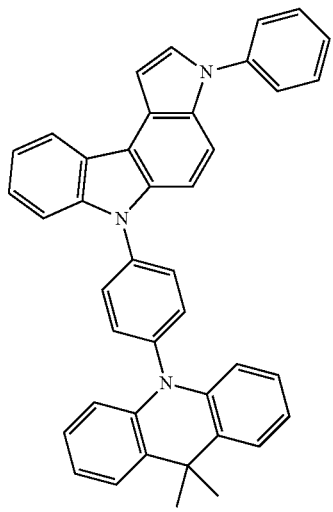
Inv371
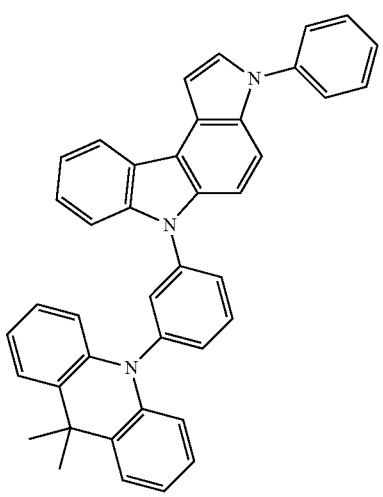
Inv372
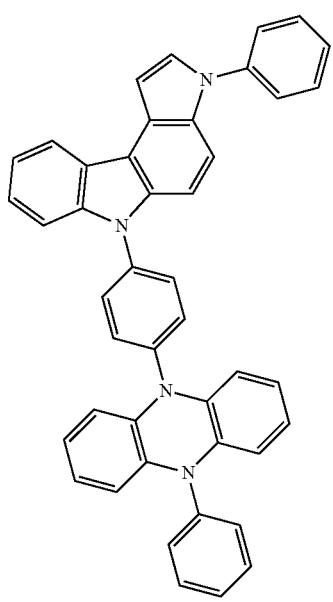
Inv373
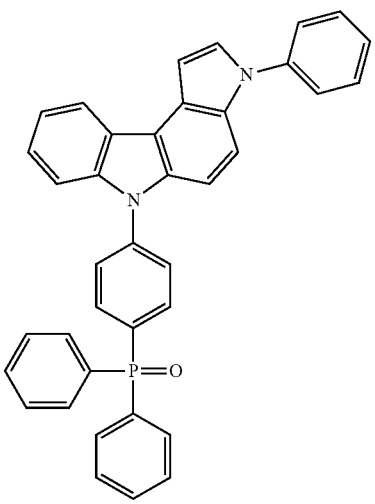
Inv374
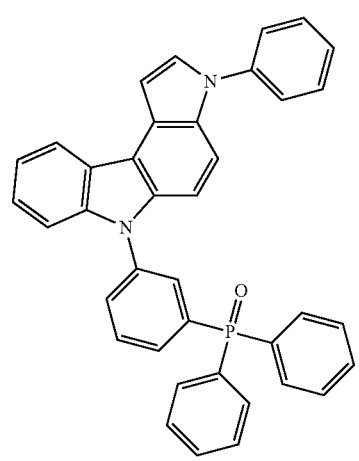
Inv375
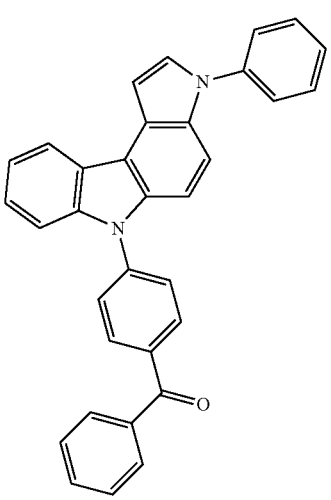

Inv376
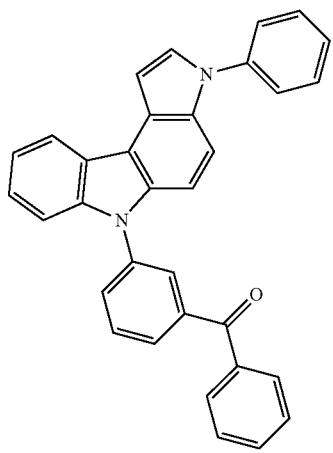
Inv377
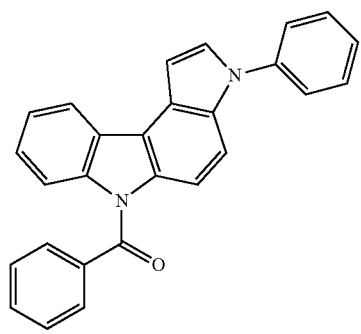
Inv378
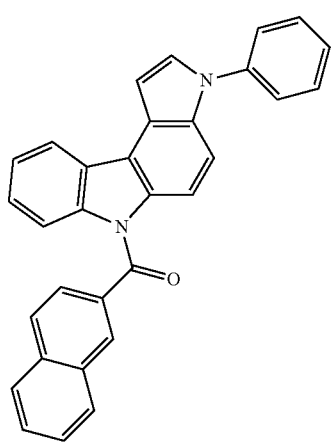
Inv379
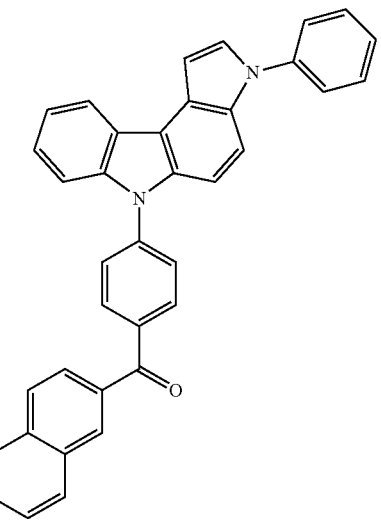
Inv380
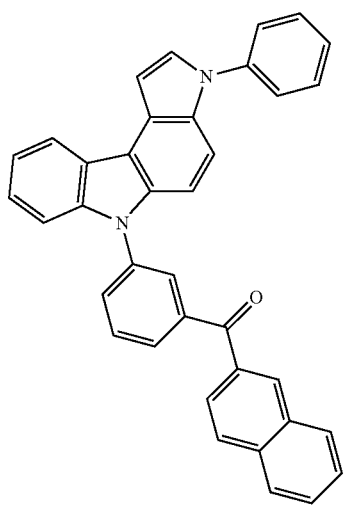
Inv381
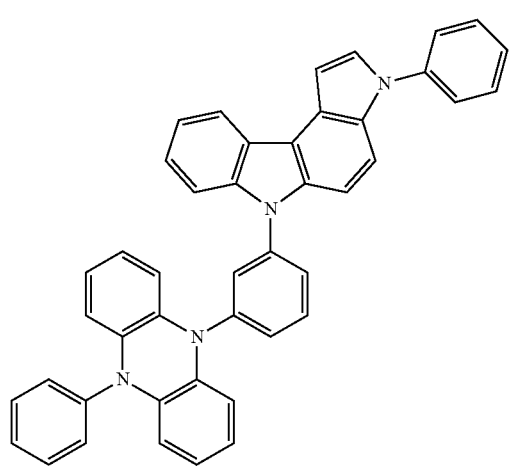

Inv382
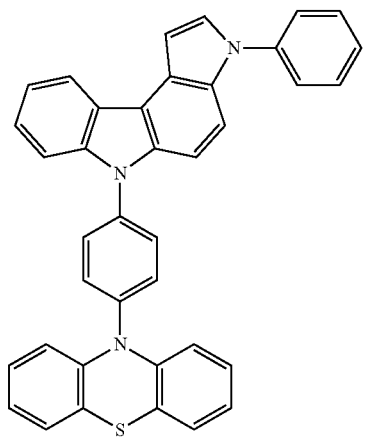
Inv383
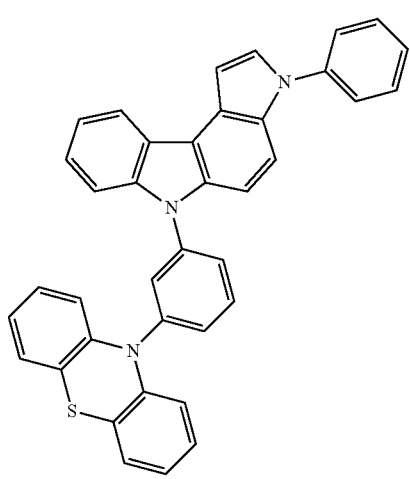
Inv384
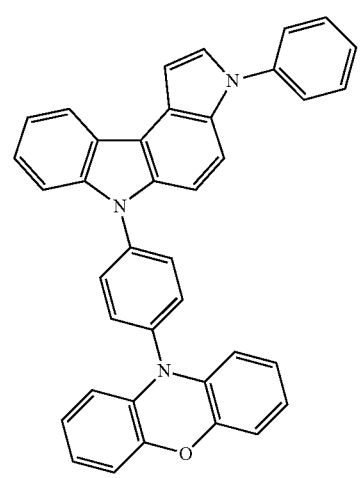
Inv385
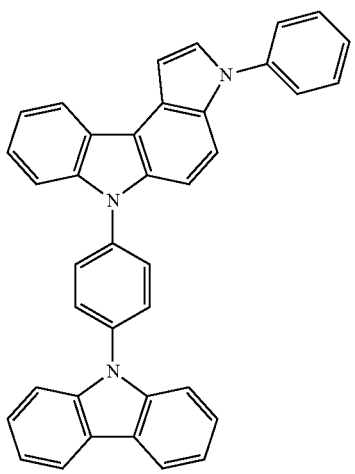
Inv386
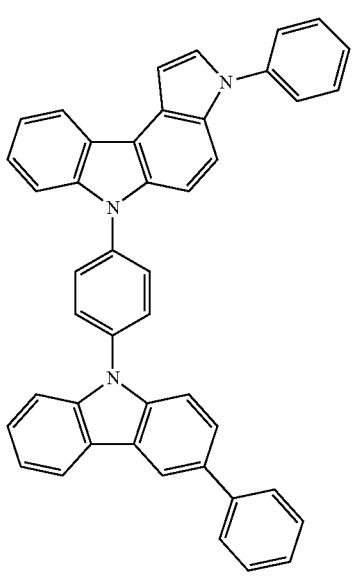
Inv387
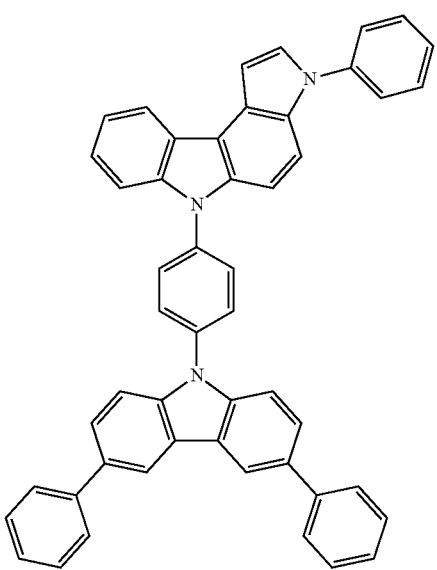

Inv388
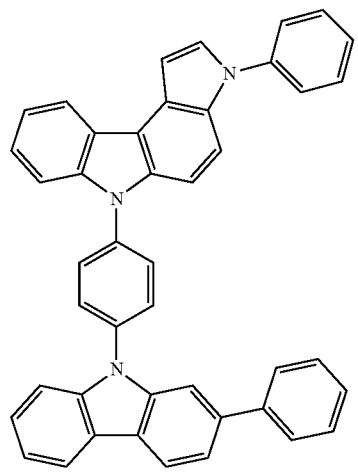
Inv389
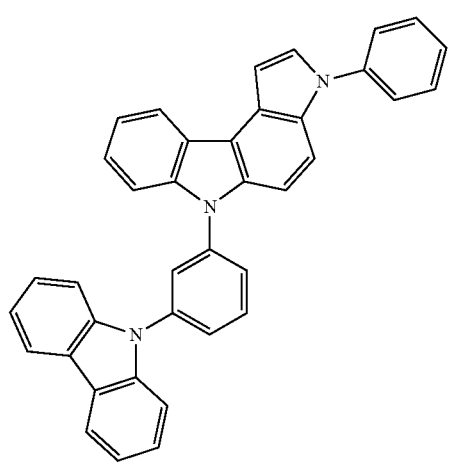
Inv390
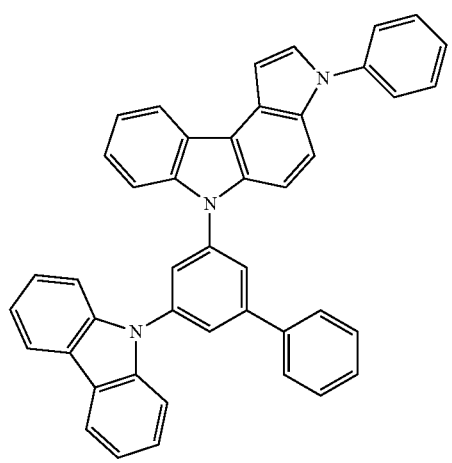
Inv391
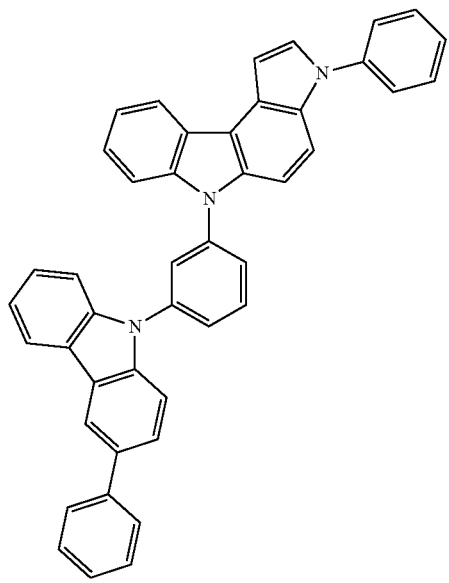
Inv392
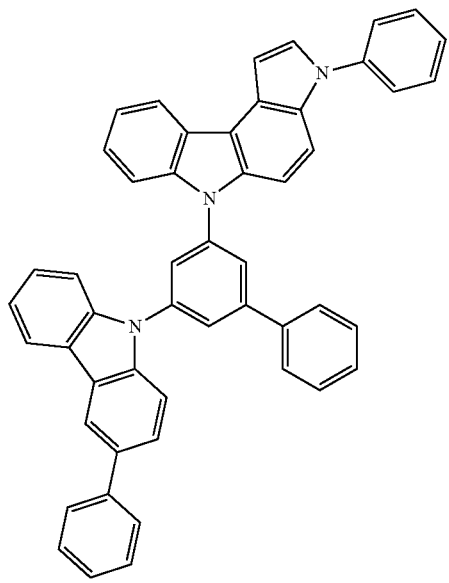

Inv393
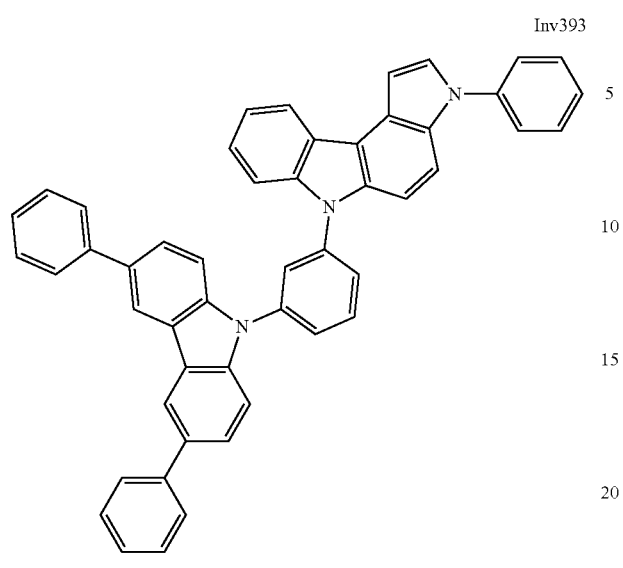
Inv394
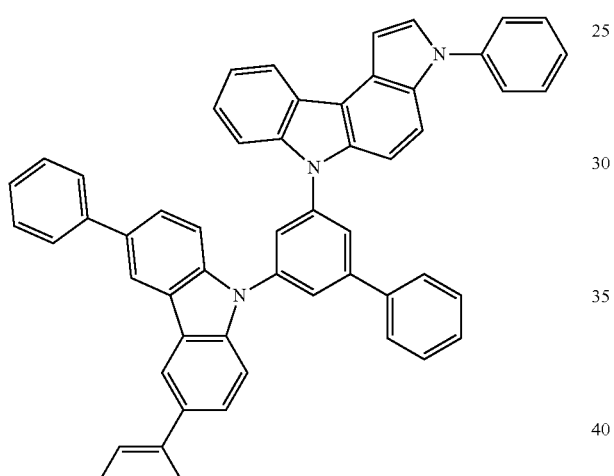
Inv395
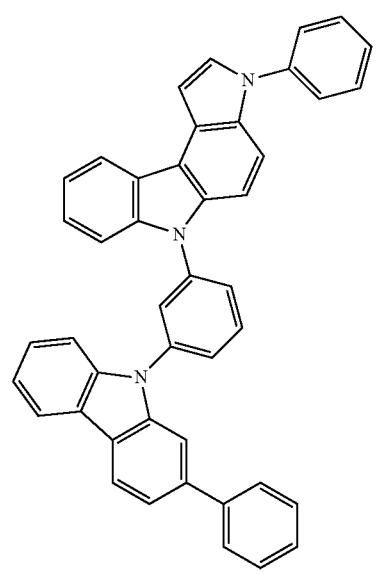
Inv396
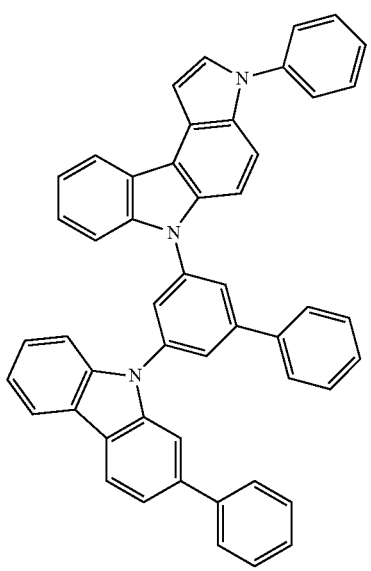
Inv397
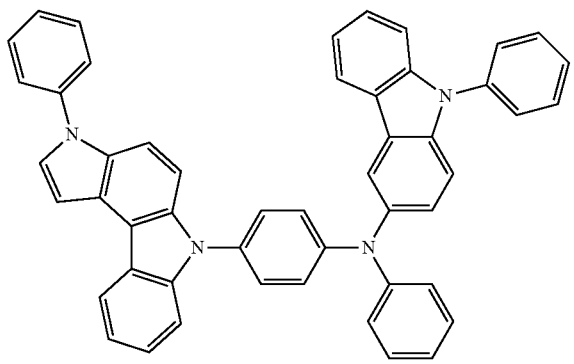
Inv398
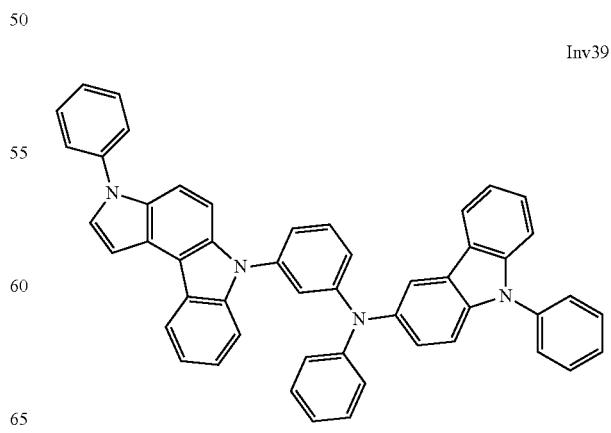

Inv399
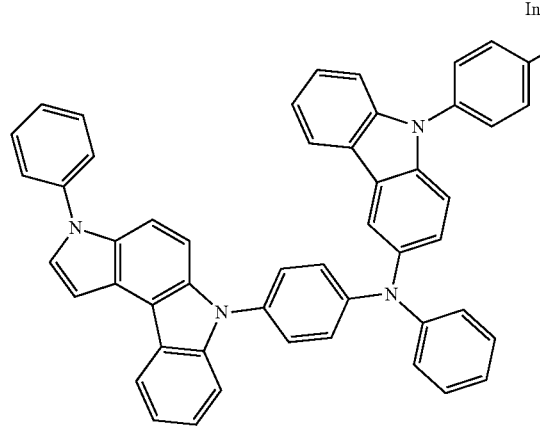
Inv400
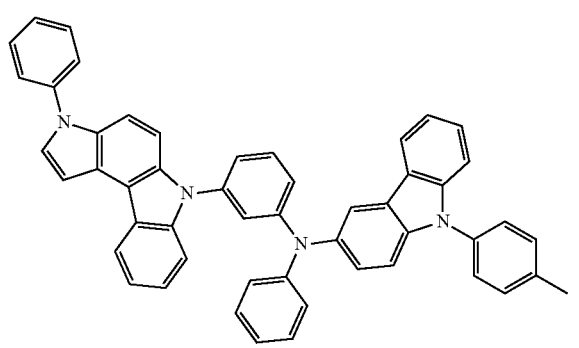
Inv401
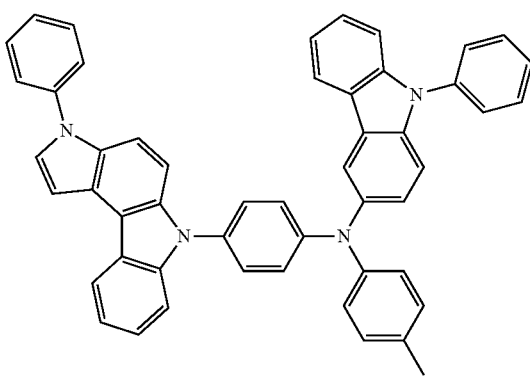
Inv402
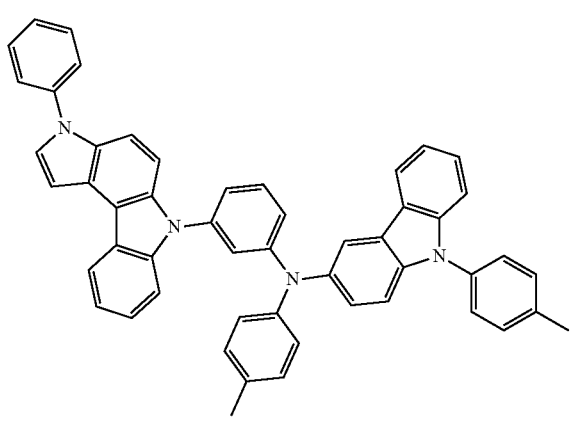
Inv403
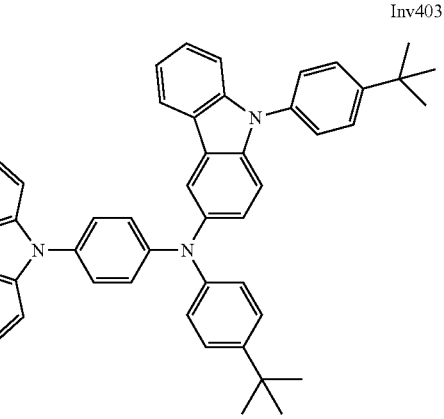
Inv404
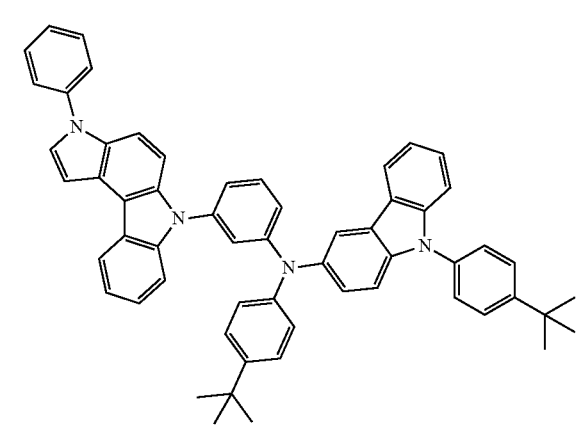
Inv405
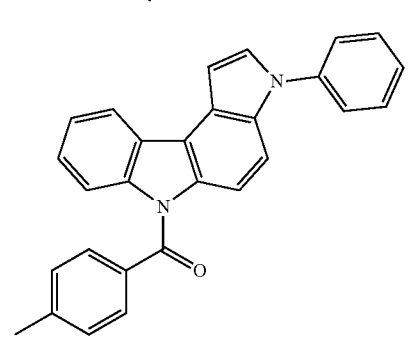
Inv406
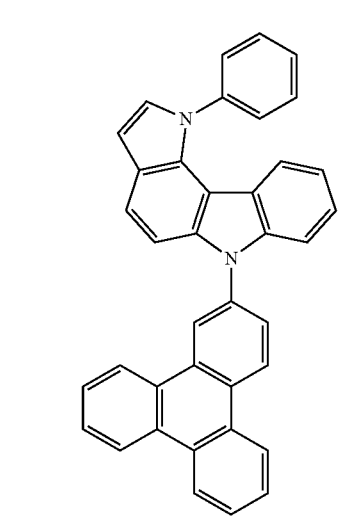

Inv407
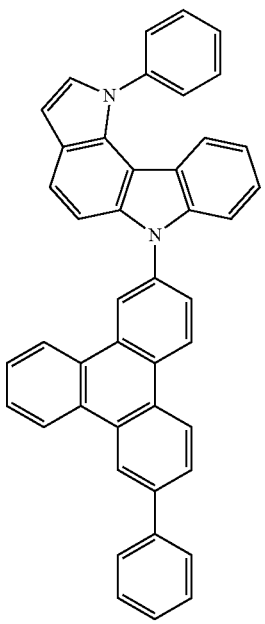
Inv408
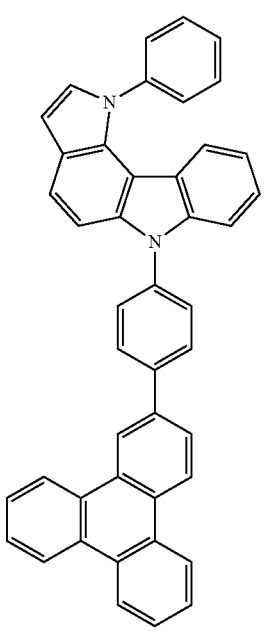
Inv409
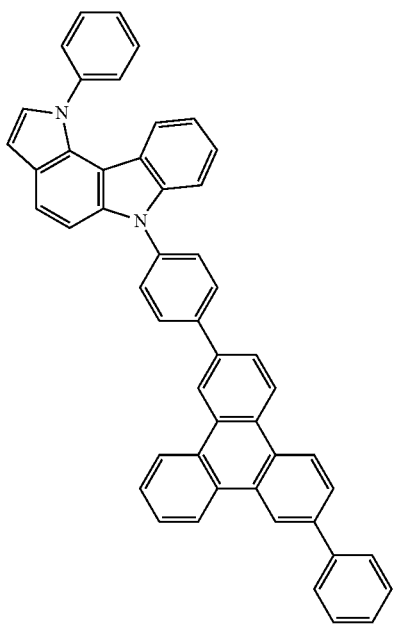
Inv410
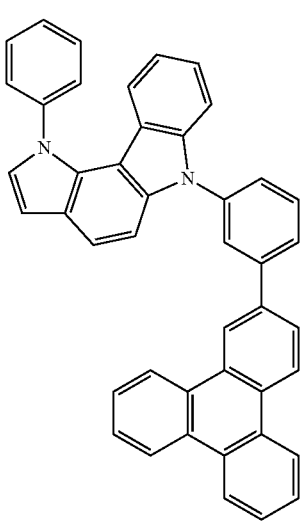

Inv411
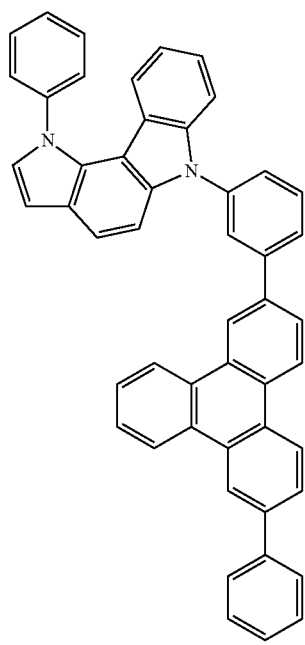
Inv412
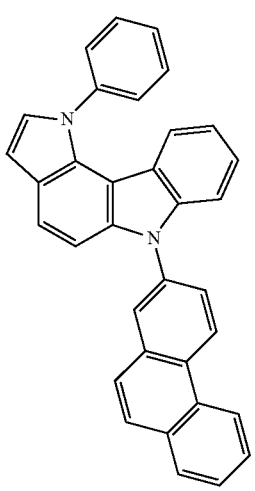
Inv413
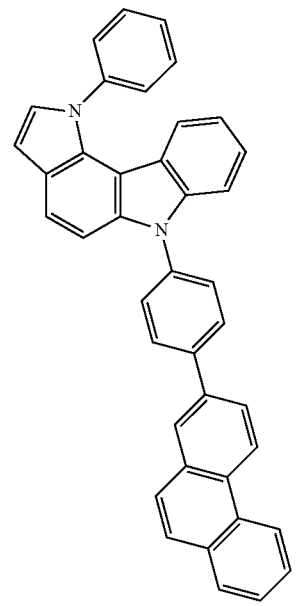
Inv414
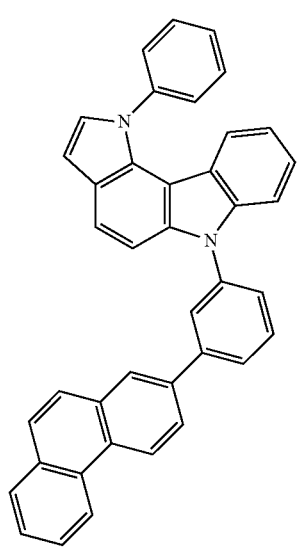
Inv415
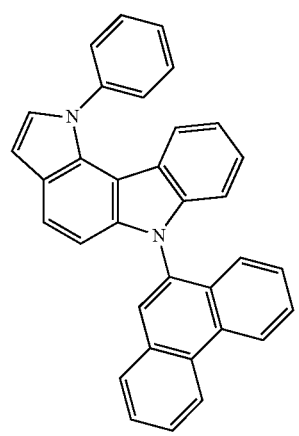

Inv416
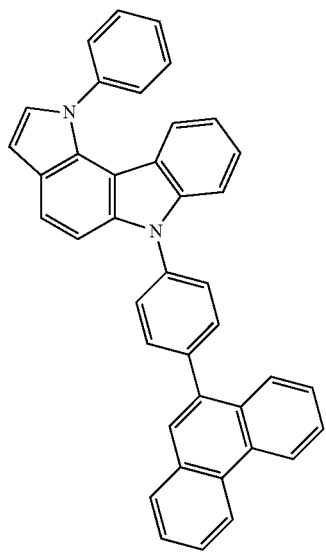
Inv417
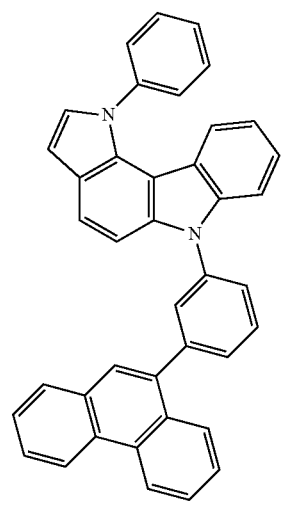
Inv418
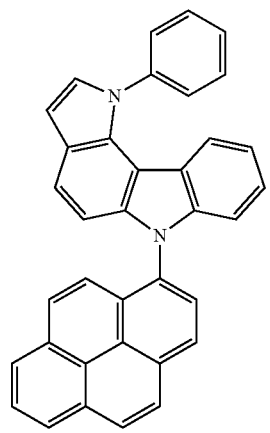
Inv419
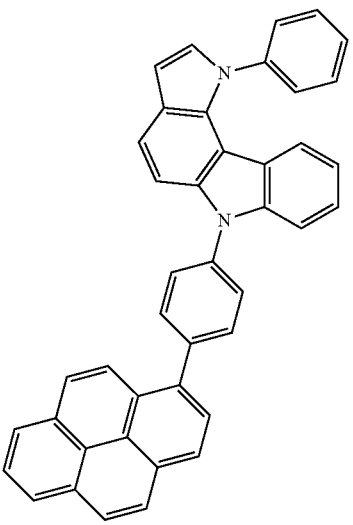
Inv420
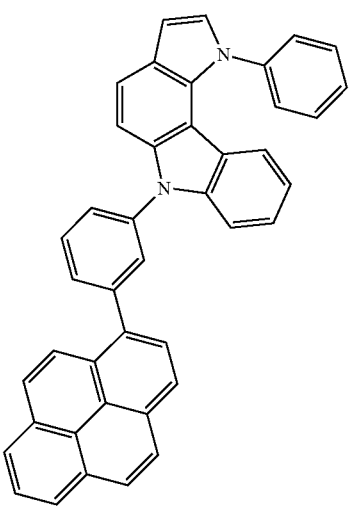
Inv421
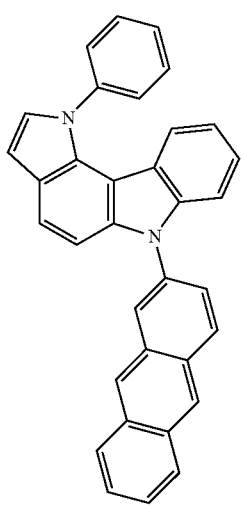

-continued
Inv422
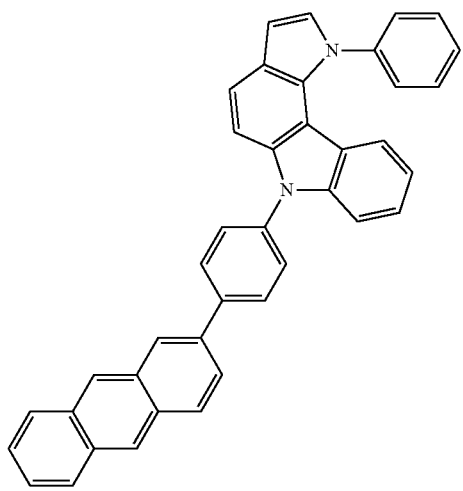
Inv423
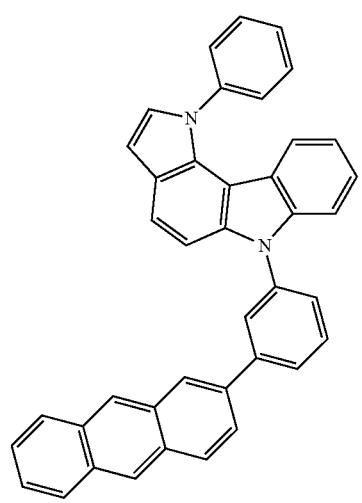
Inv424
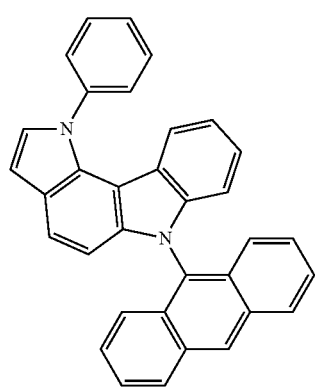
-continued
Inv425
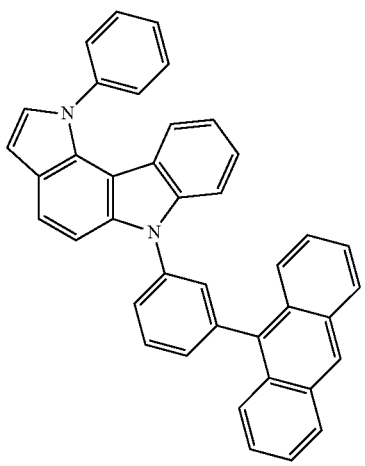
Inv426
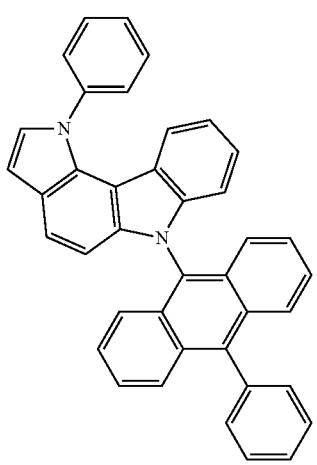
Inv427
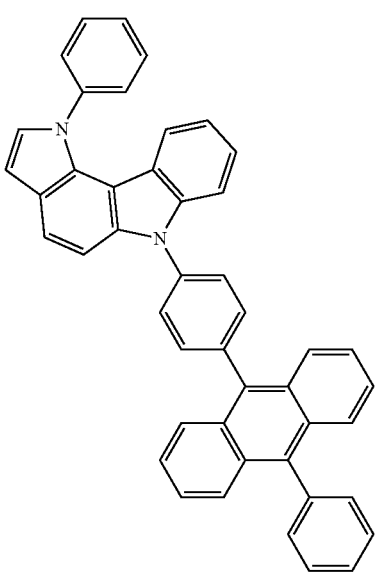

Inv428
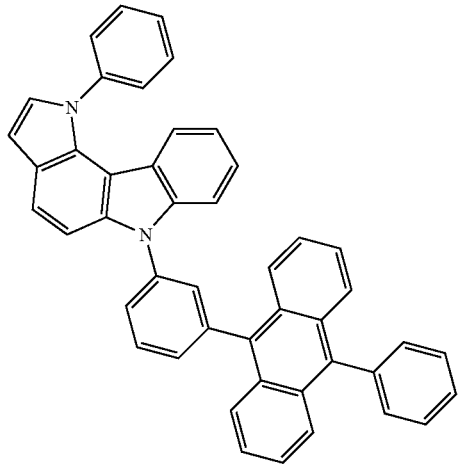
Inv429
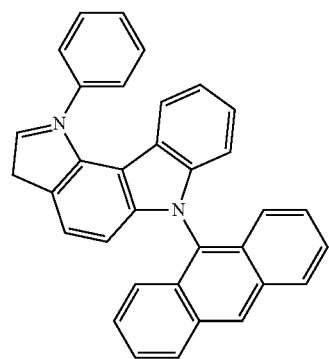
Inv430
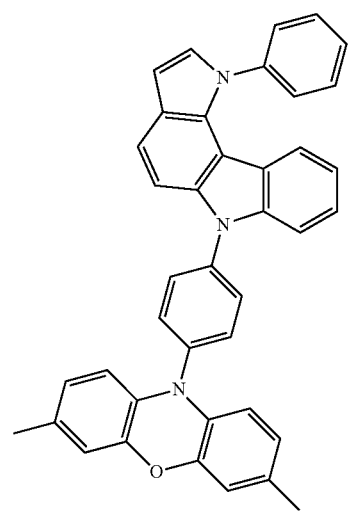
Inv431
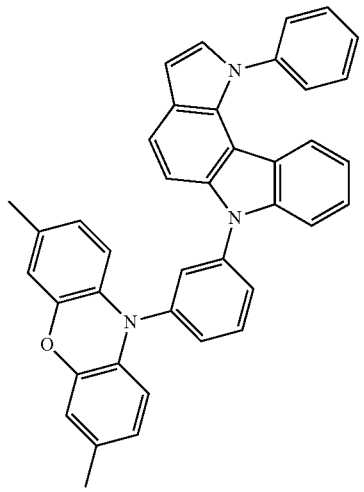
Inv432
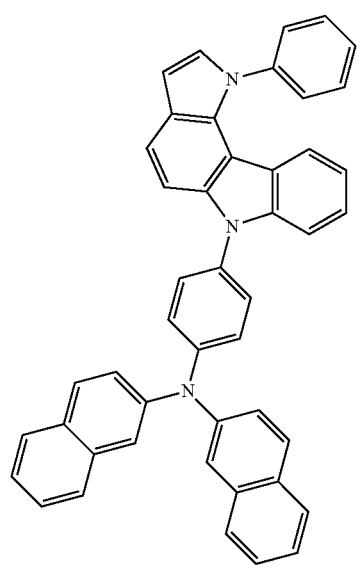
Inv433
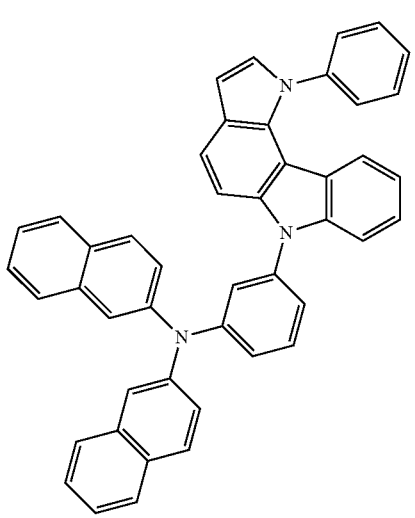

Inv434
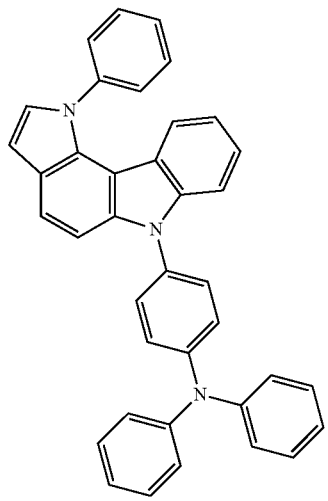
Inv435
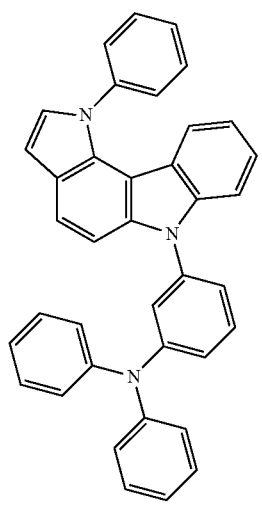
Inv436
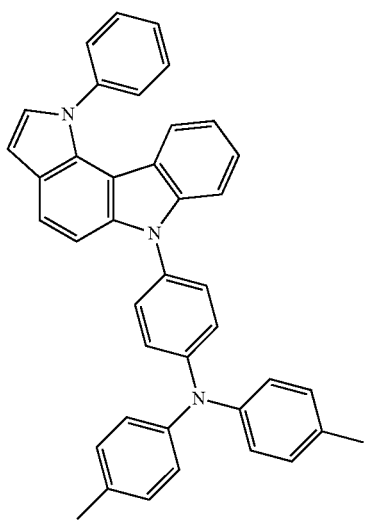
Inv437
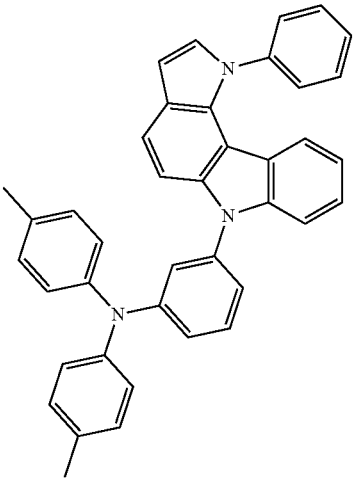
Inv438
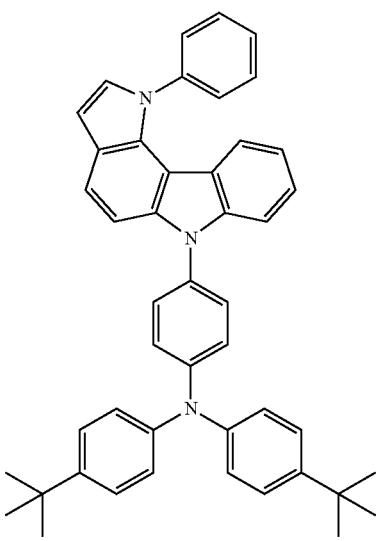
Inv439
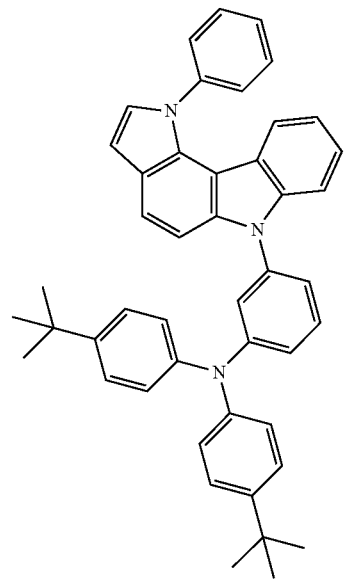

Inv440
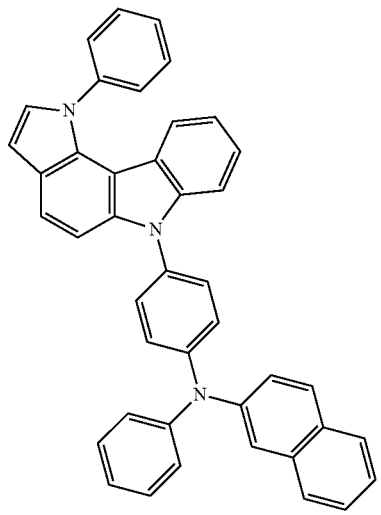
Inv441
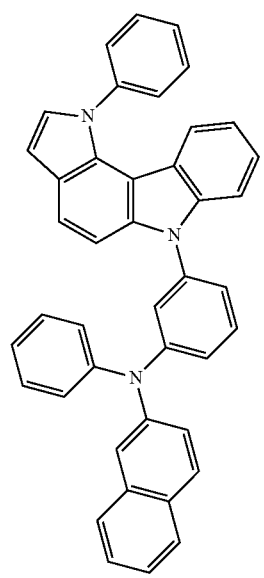
Inv442
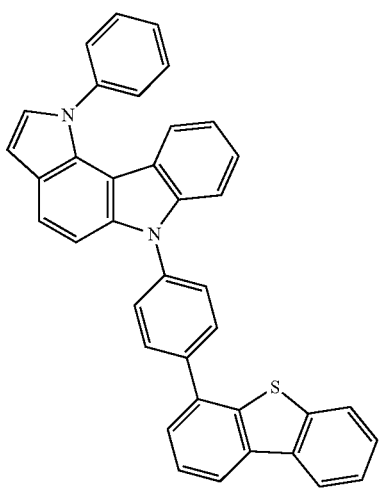
Inv443
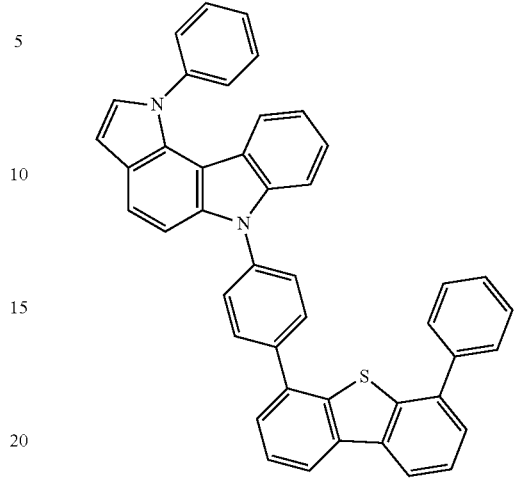
Inv444
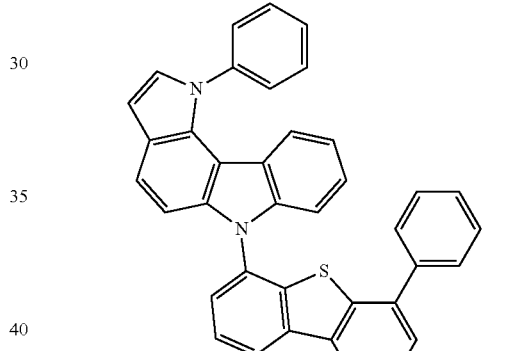
Inv445
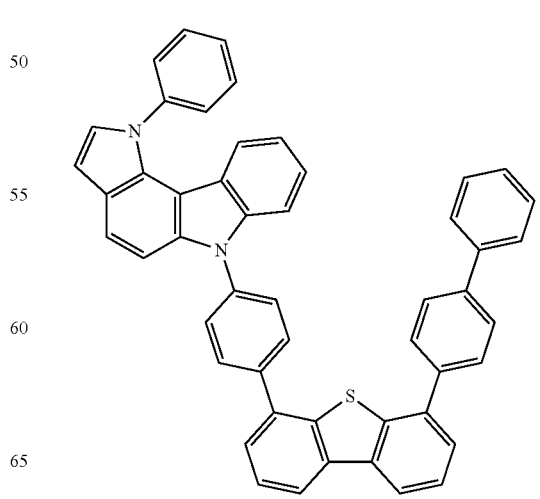

Inv446
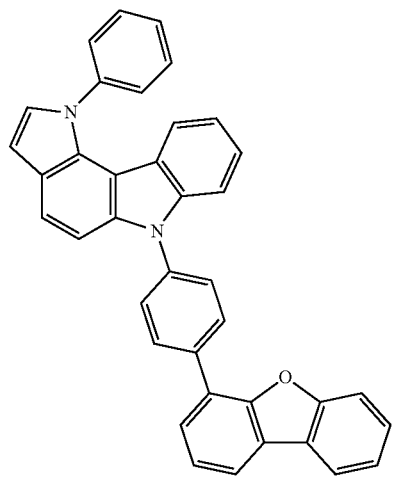
Inv449
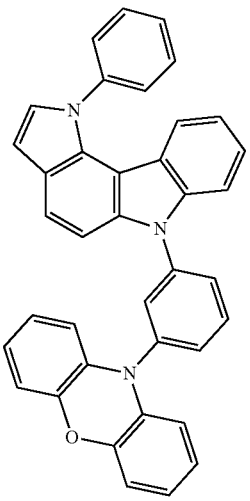
Inv447
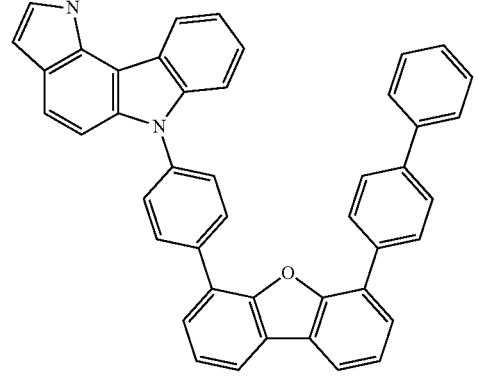
Inv450
Inv448
Inv451
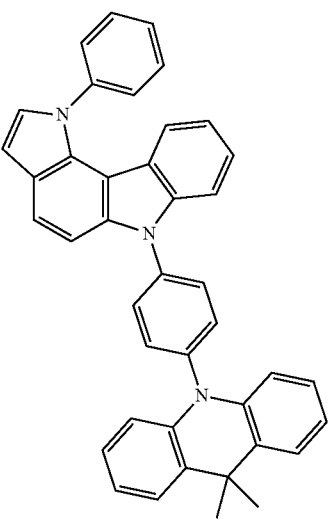

Inv452
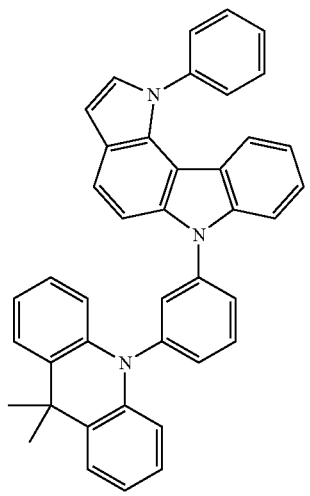
Inv453
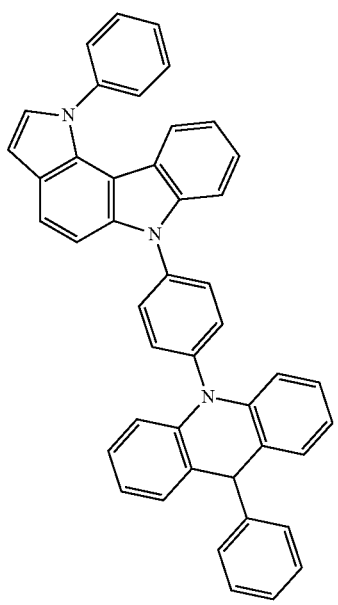
Inv454
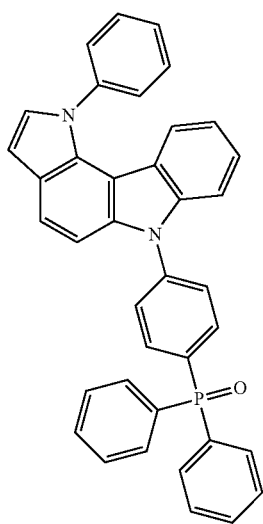
Inv455
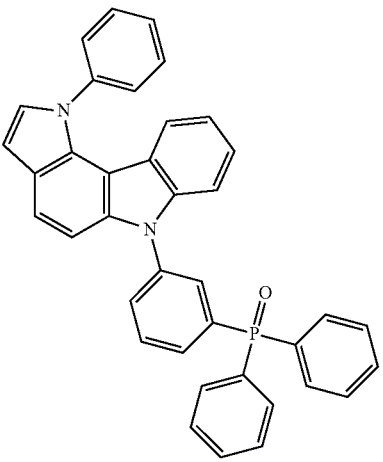
Inv456
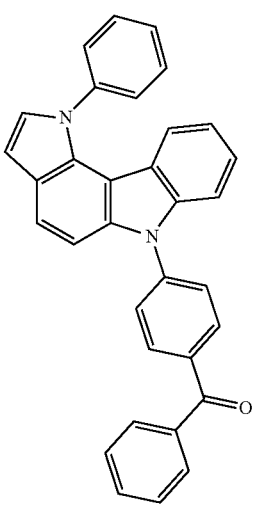
Inv457
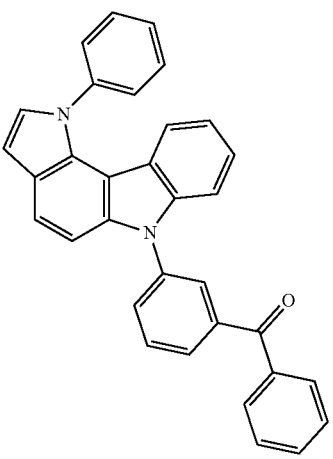

Inv458
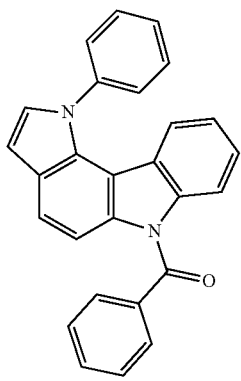
Inv459
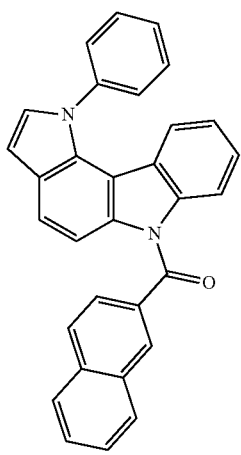
Inv460
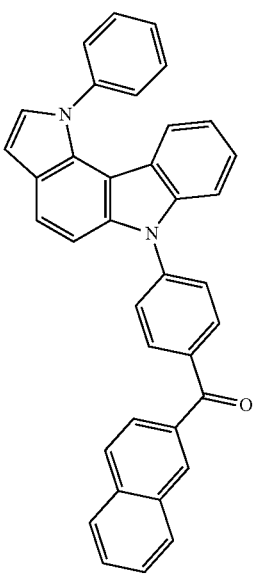
Inv461
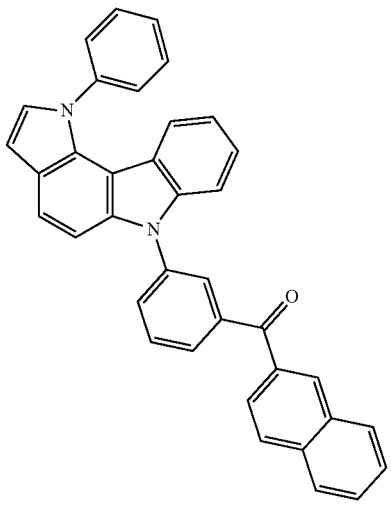
Inv462
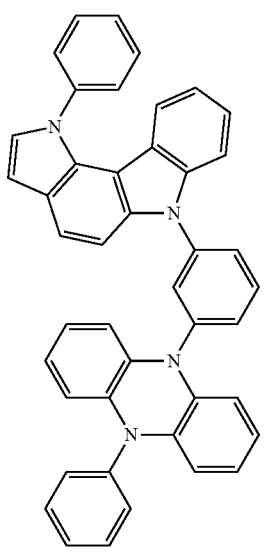
Inv463
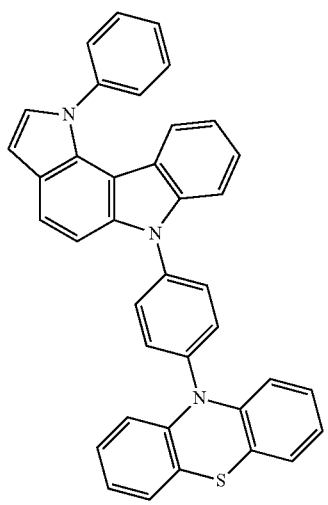

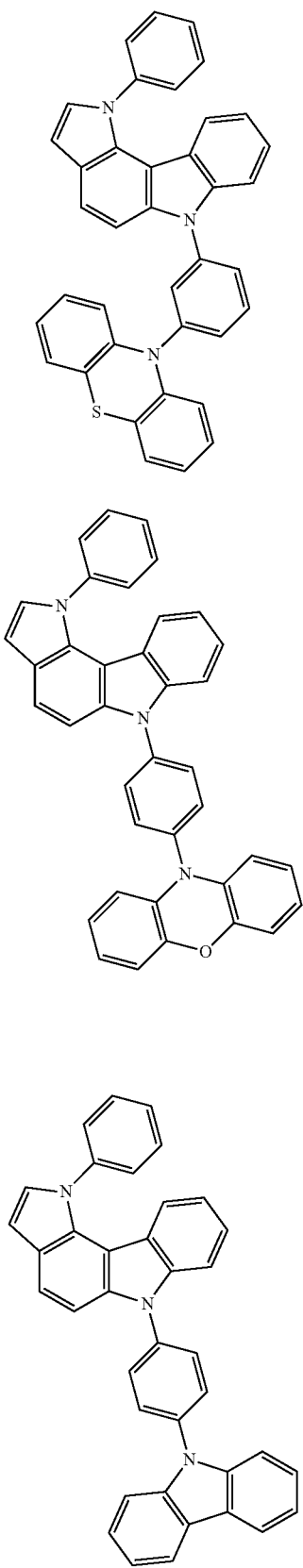
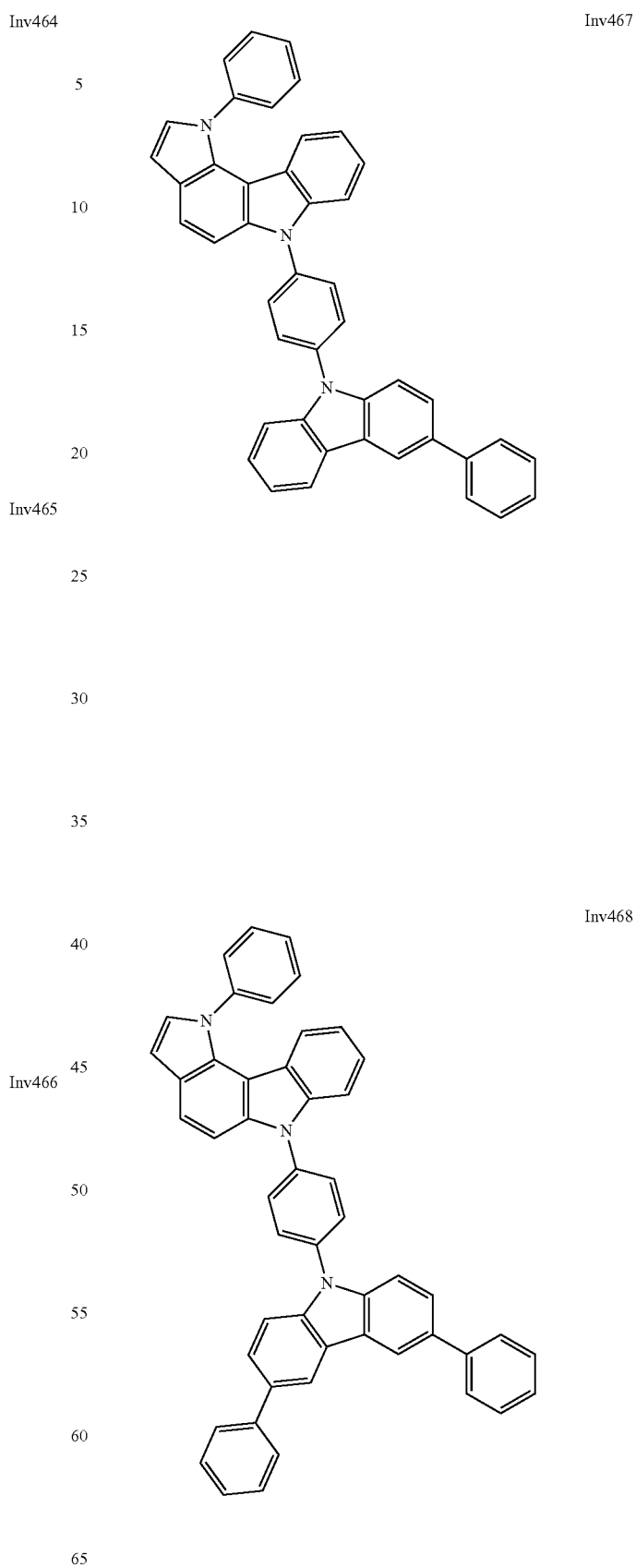

Inv469
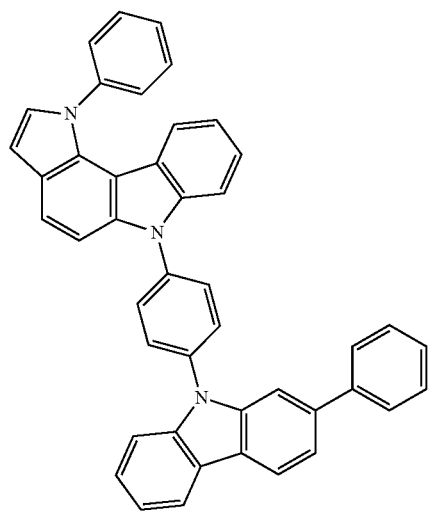
Inv470
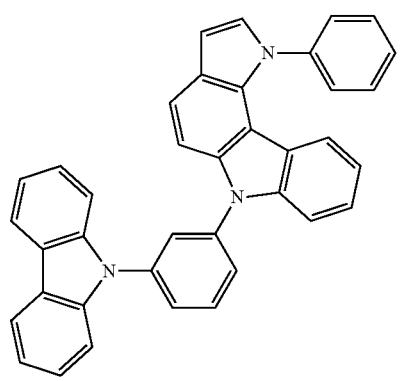
Inv471
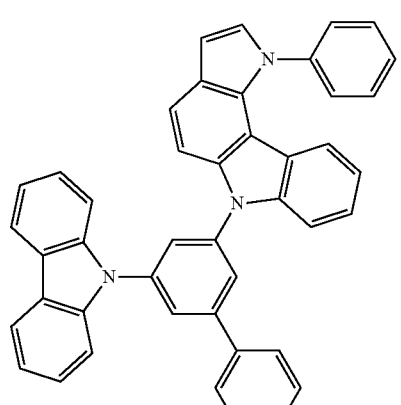
Inv472
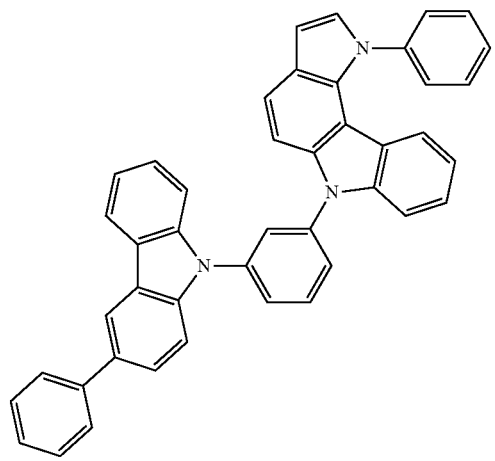
Inv473
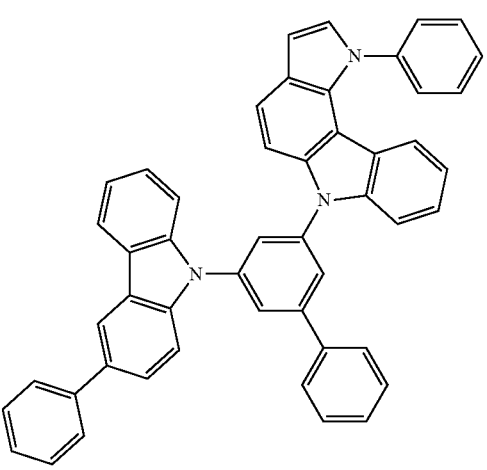
Inv474
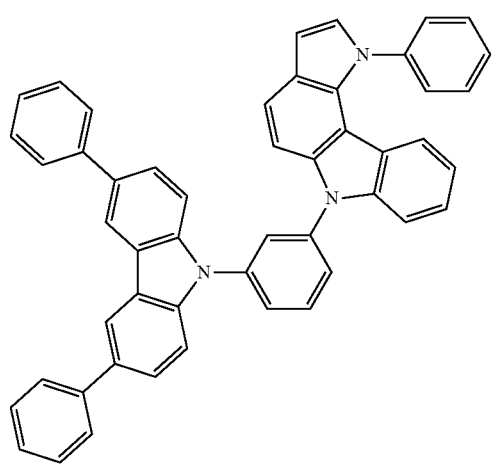

-continued
Inv475
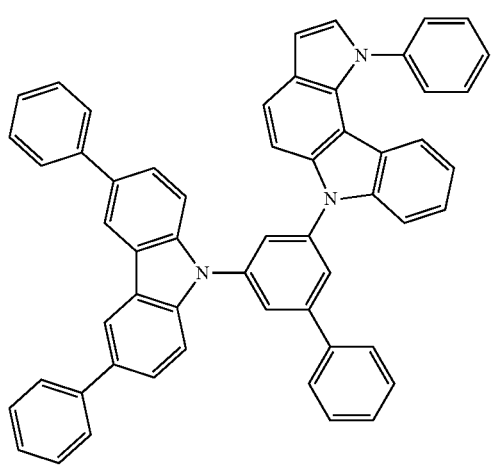
Inv476
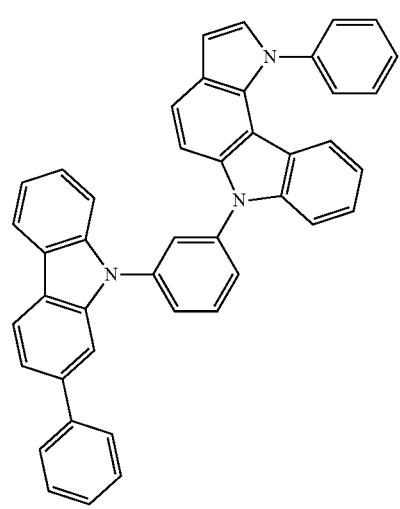
Inv477
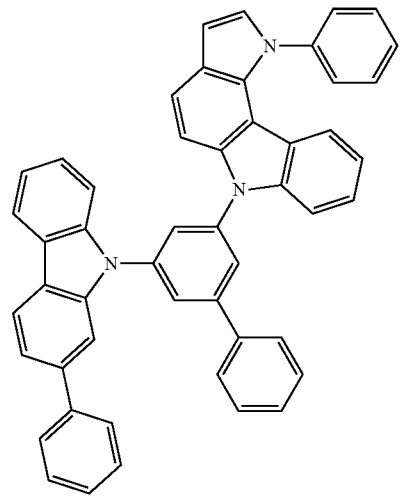
-continued
Inv478
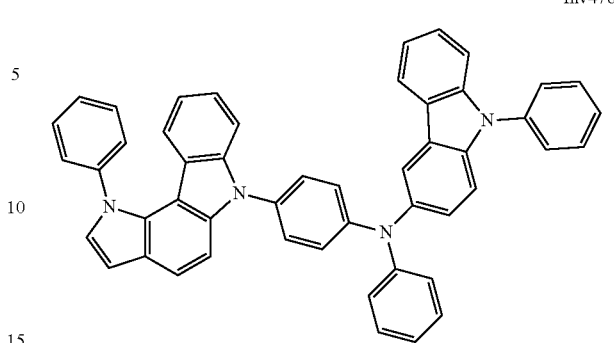
Inv479
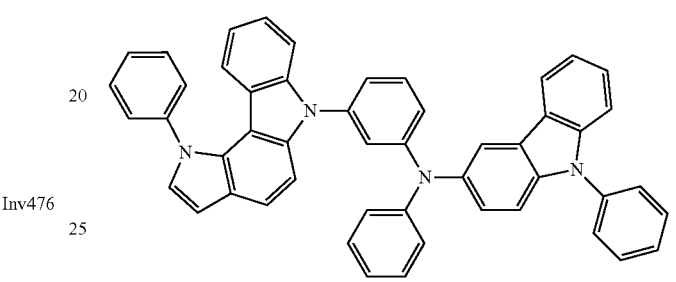
Inv480
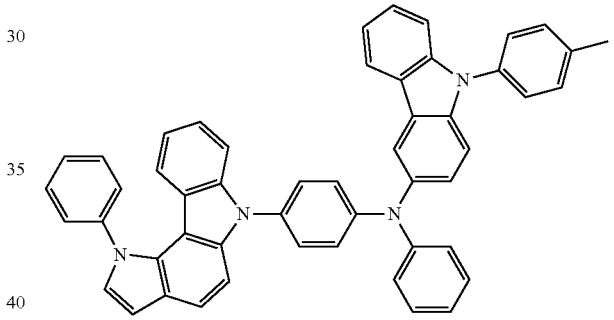
Inv481
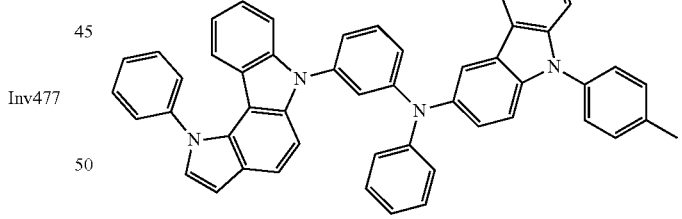
Inv482
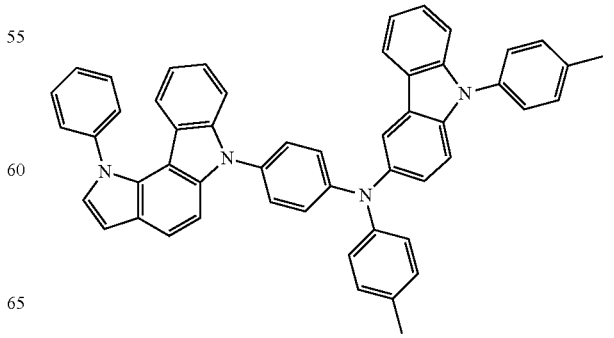

-continued
Inv483
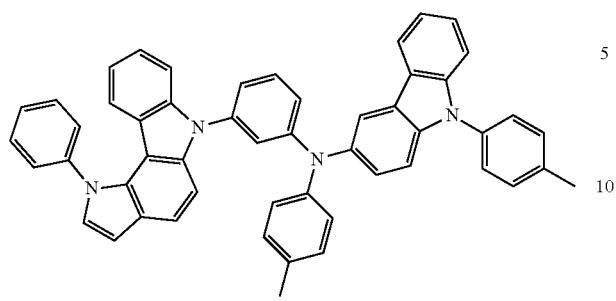
Inv484
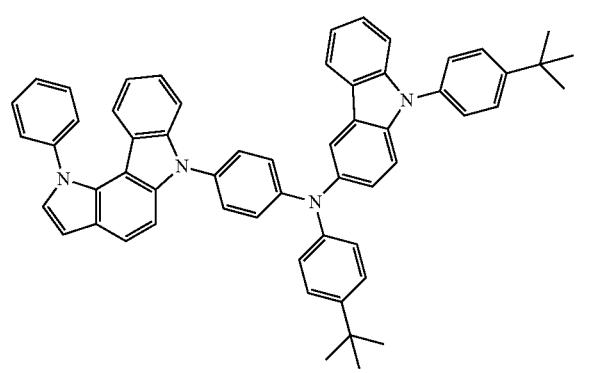
Inv485
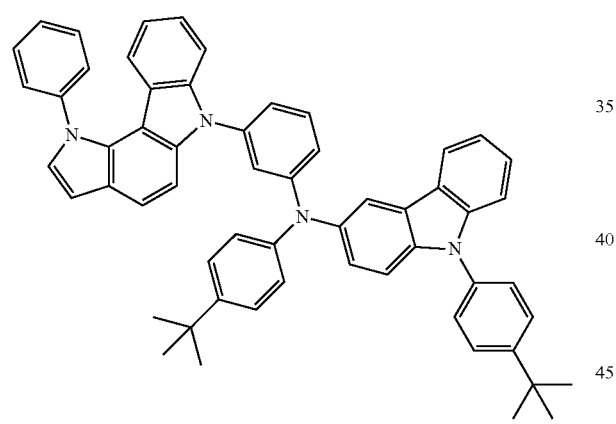
Inv486
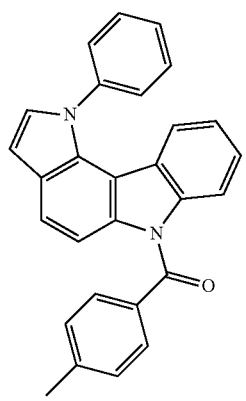
-continued
Inv487
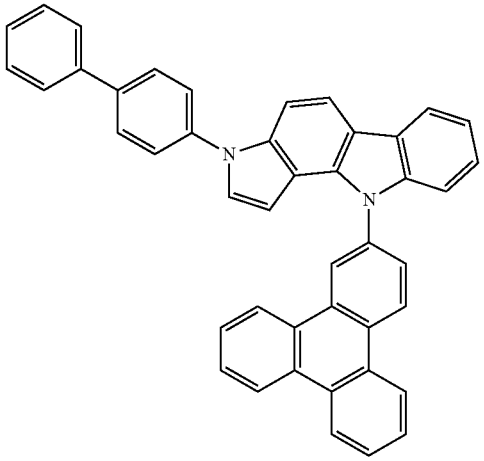
Inv488
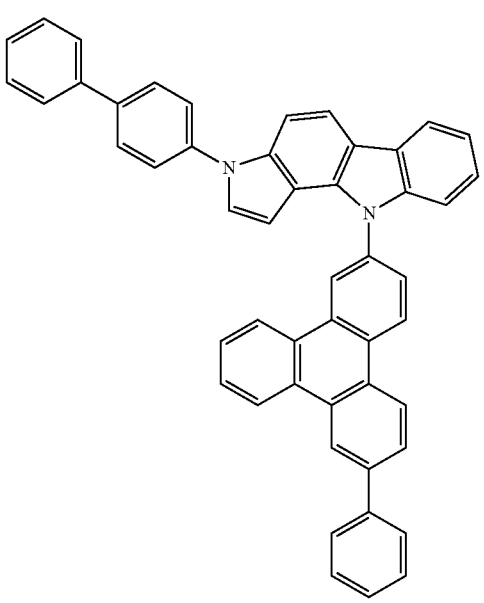
Inv489
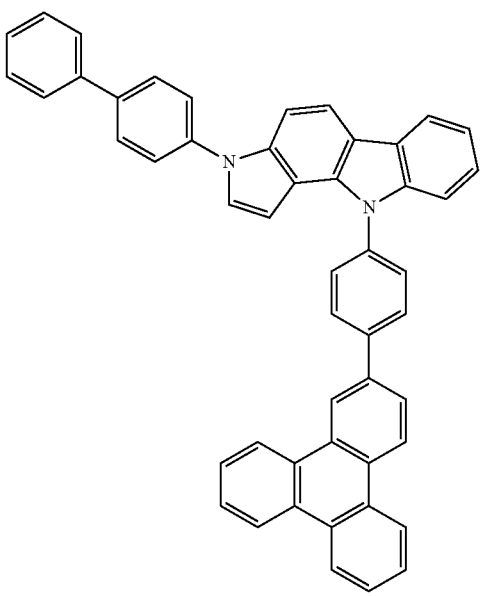

Inv490
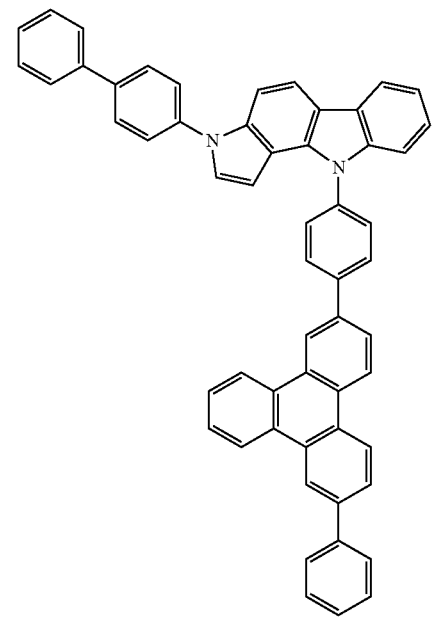
Inv491
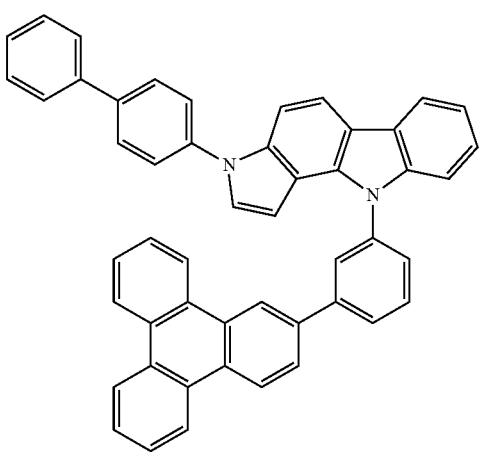
Inv492
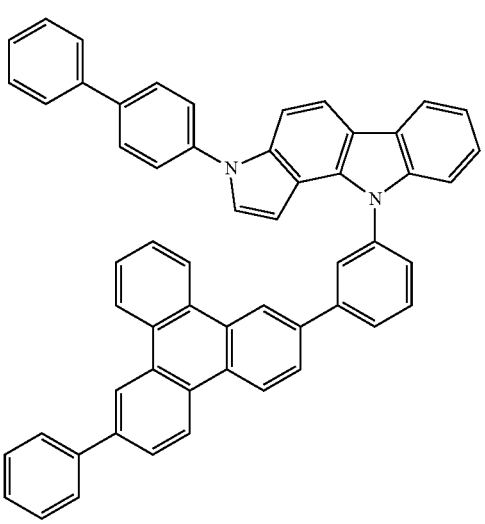
Inv493
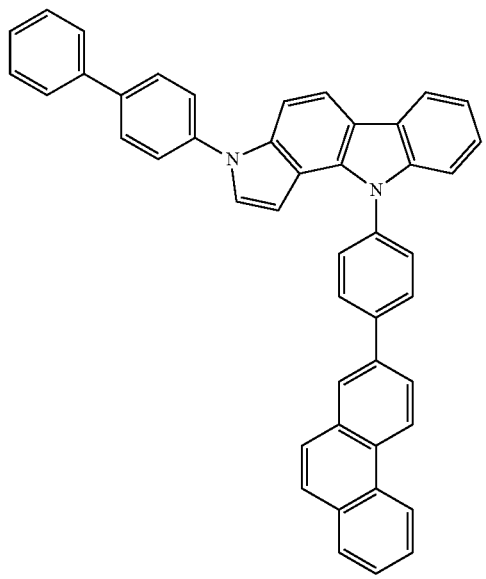
Inv494
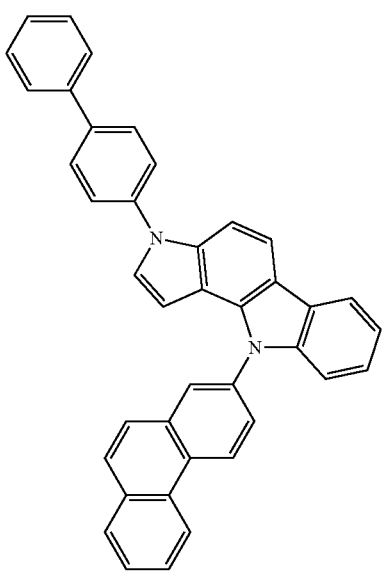
Inv495
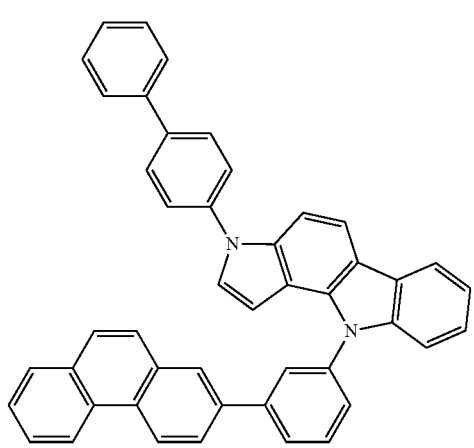

Inv496
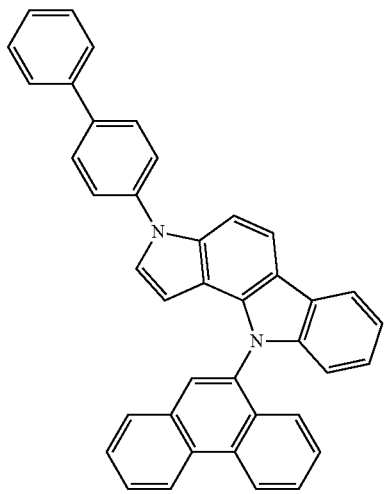
Inv497
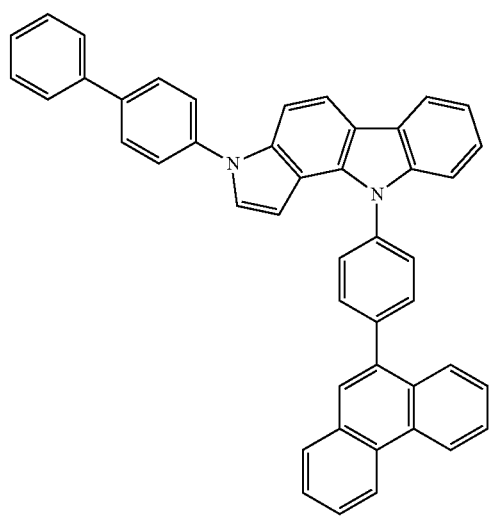
Inv498
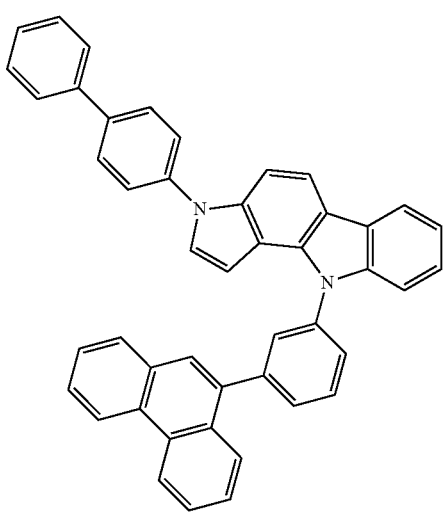
Inv499
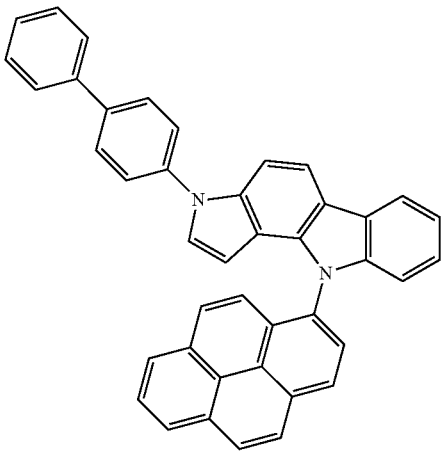
Inv500
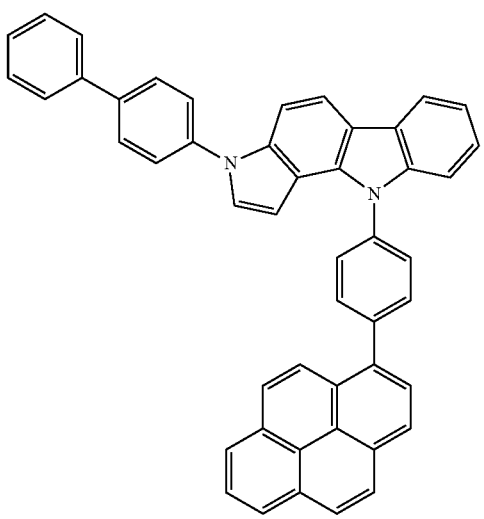
Inv501

-continued
Inv502
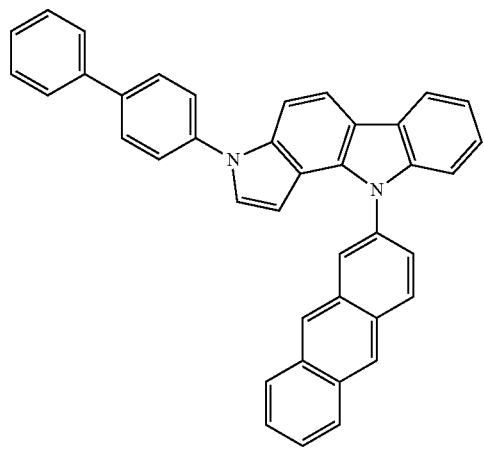
Inv503
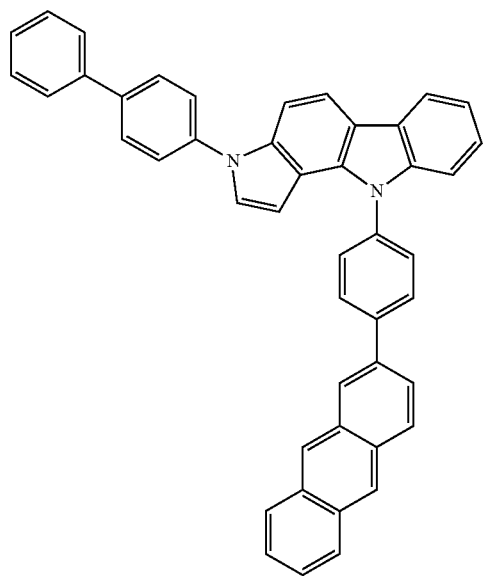
Inv504
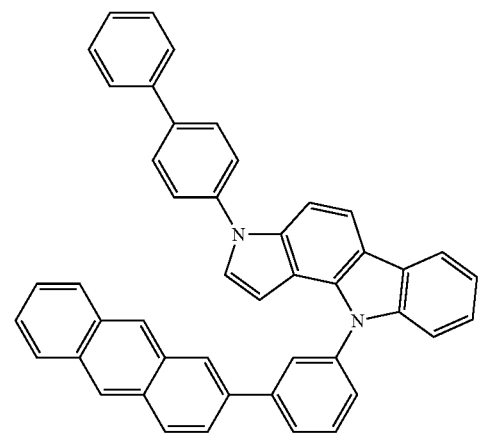
-continued
Inv505
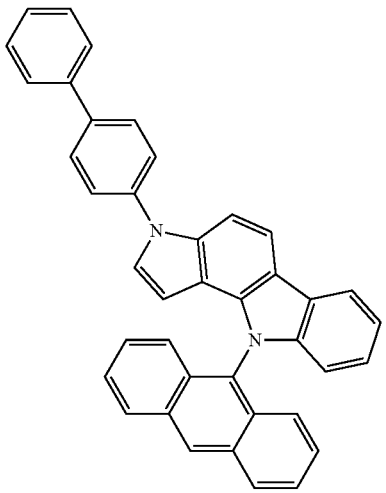
Inv506
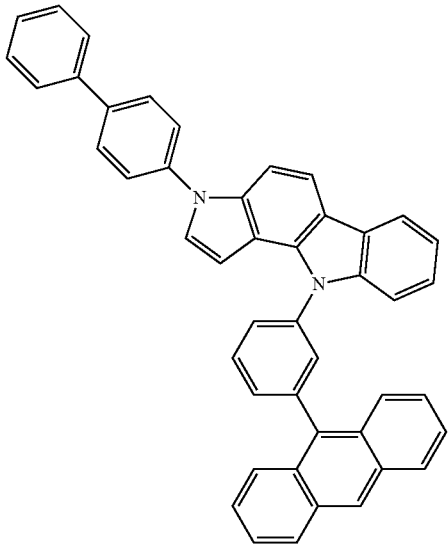
Inv507
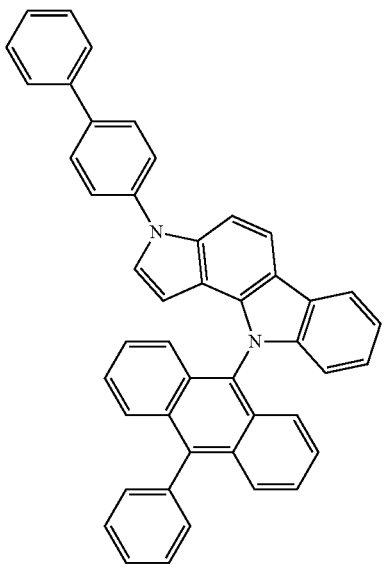

Inv508
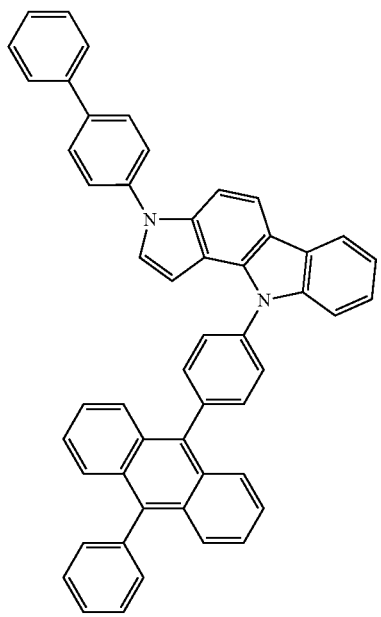
Inv510
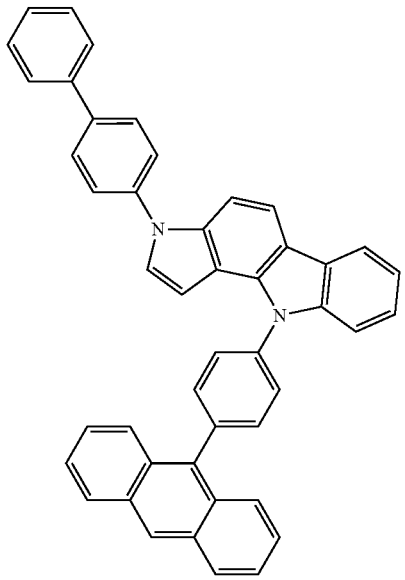
Inv509
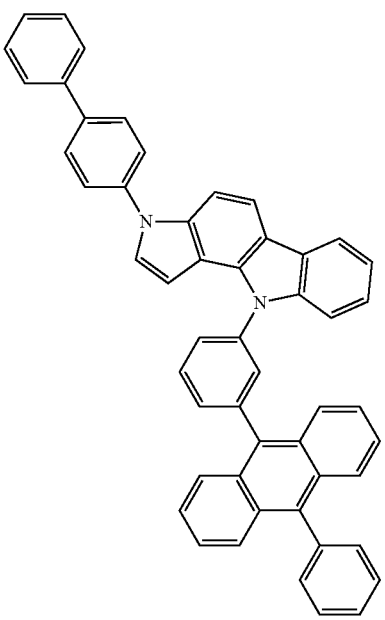
Inv511
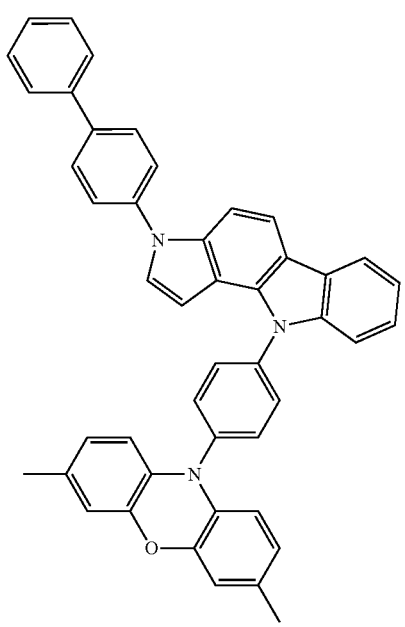

Inv512
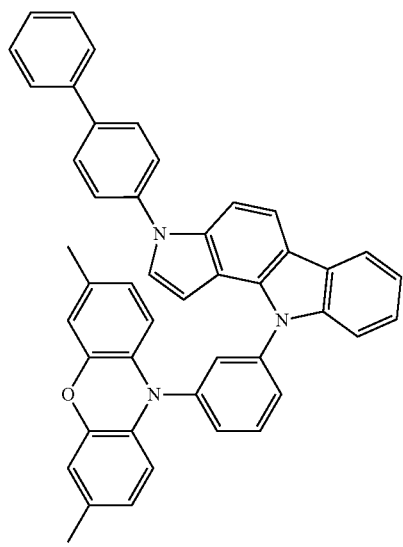
Inv514
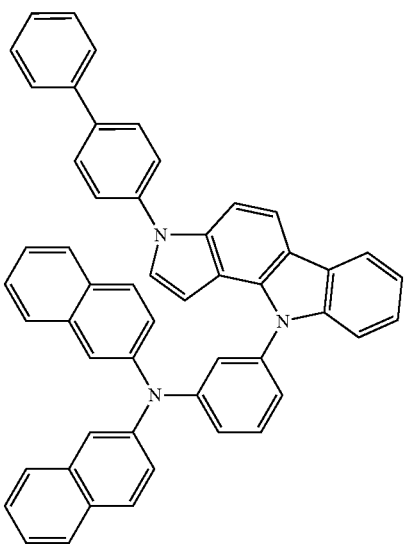
Inv513
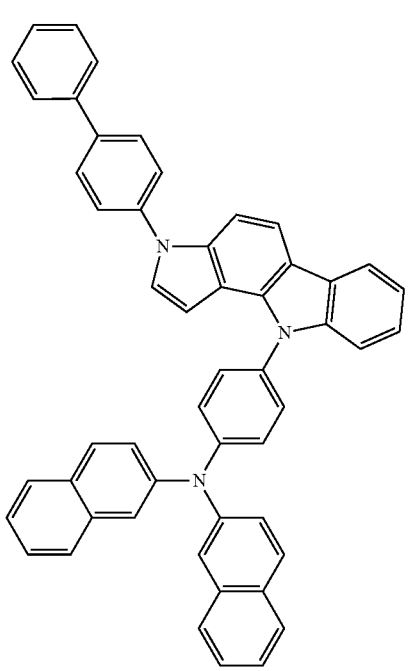
Inv515
Inv516
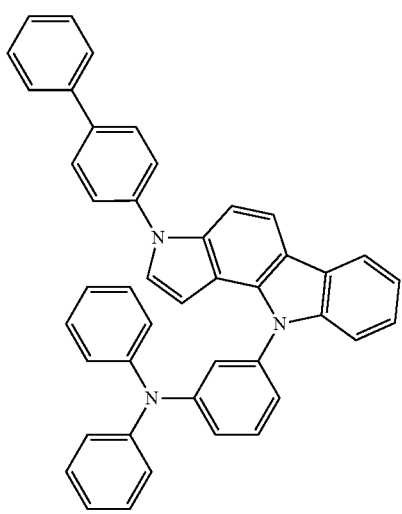

Inv517
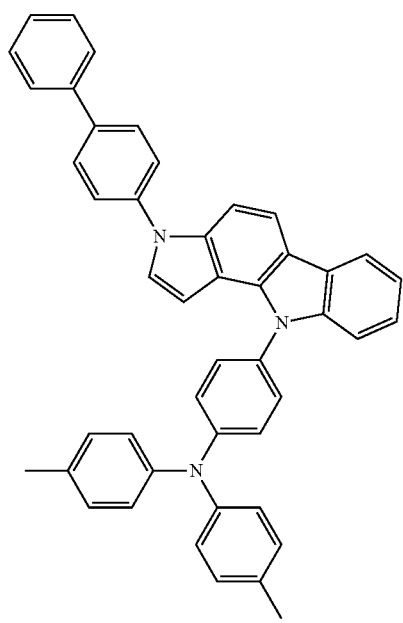
Inv519
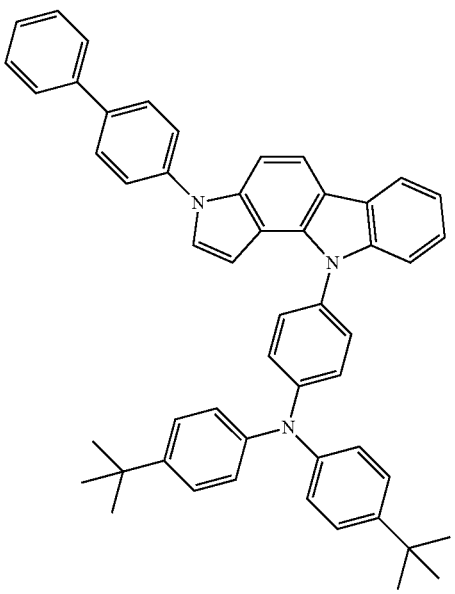
Inv520
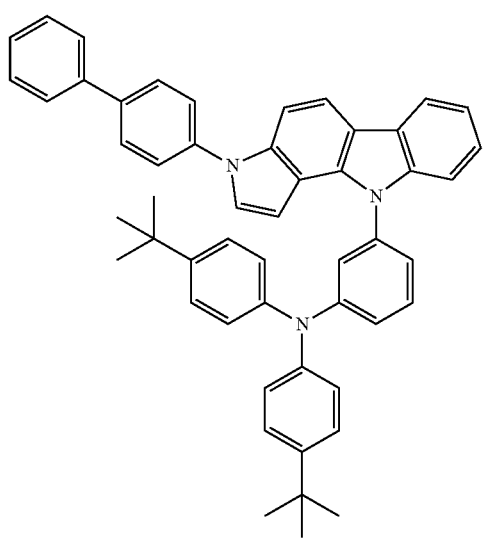
Inv518
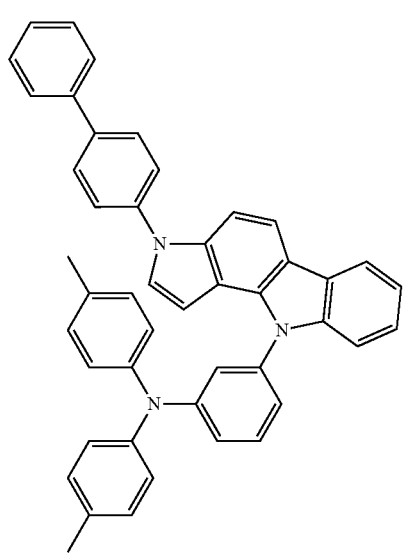
Inv521
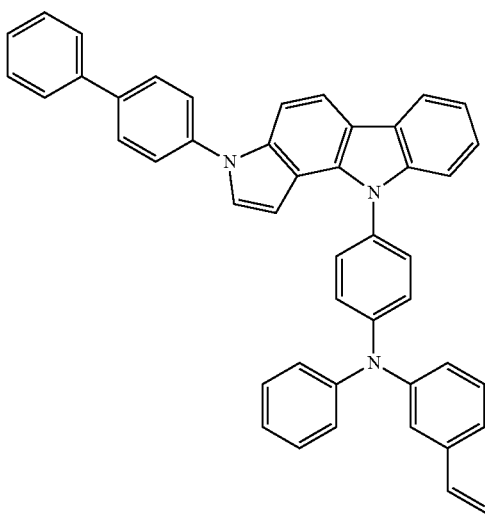

Inv522
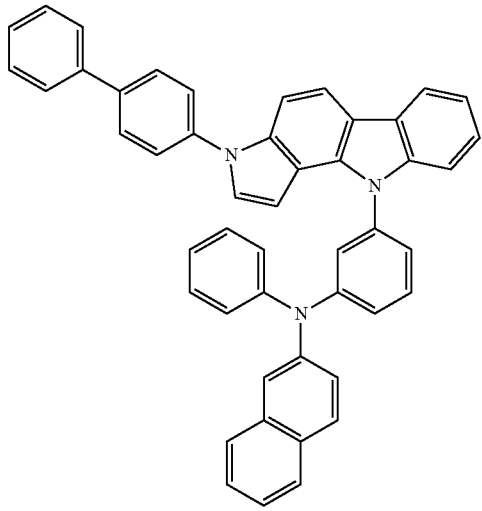
Inv523
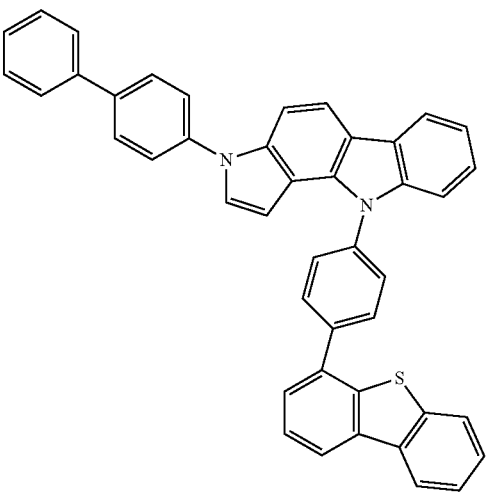
Inv524
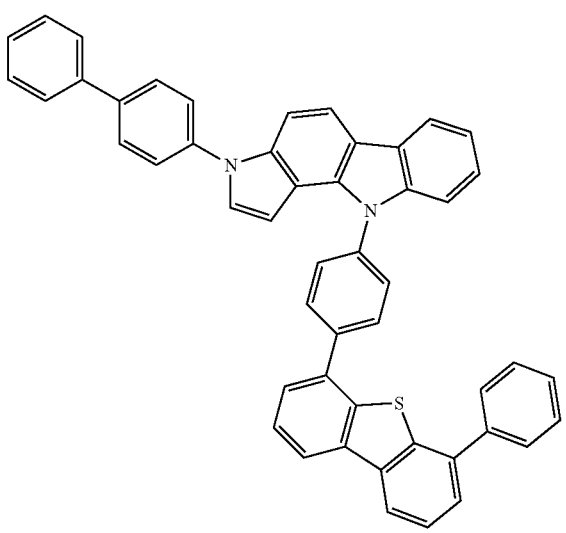
Inv525
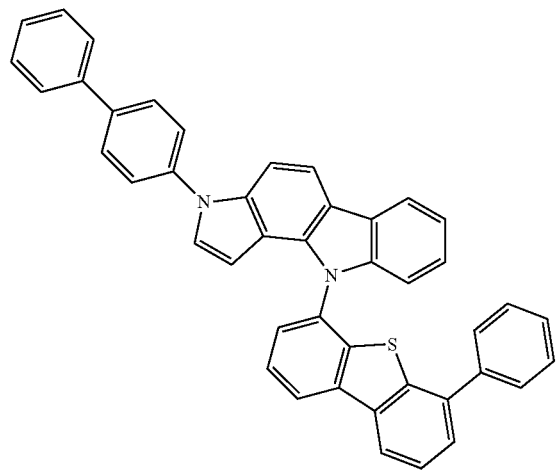
Inv526
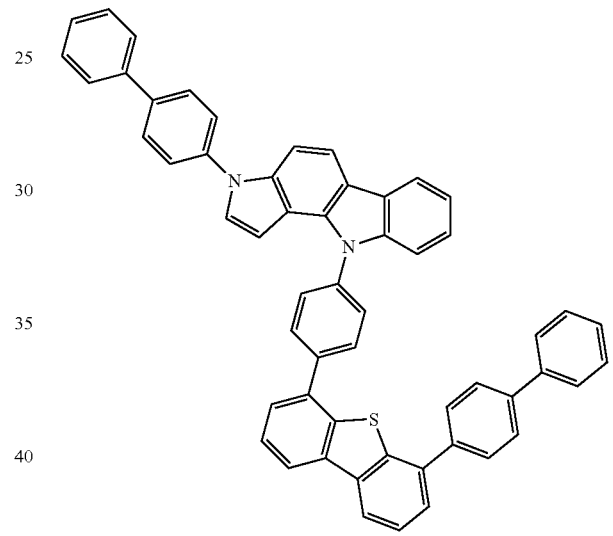
Inv527
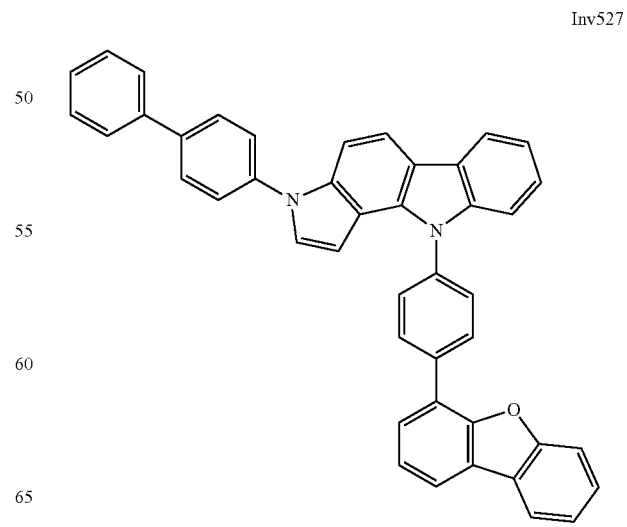

Inv528
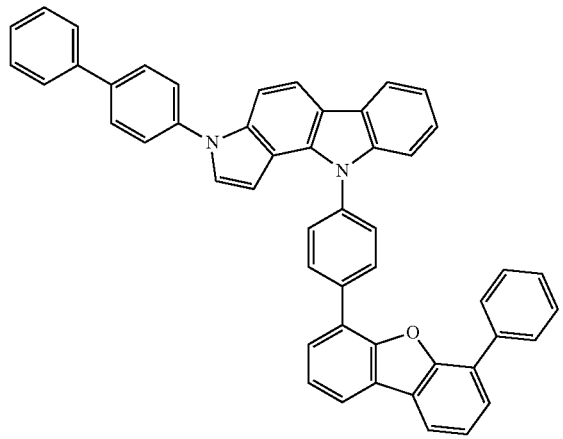
Inv531
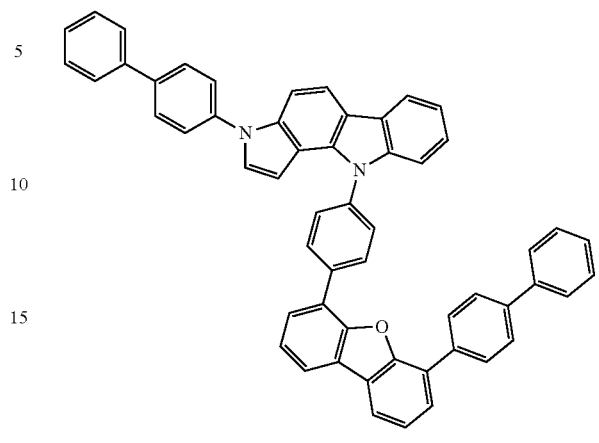
Inv529
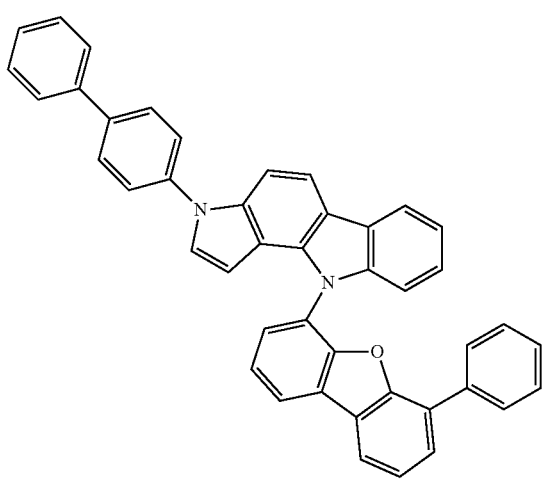
Inv532
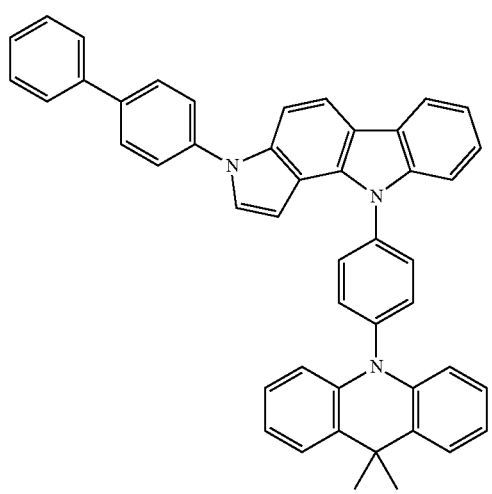
Inv530
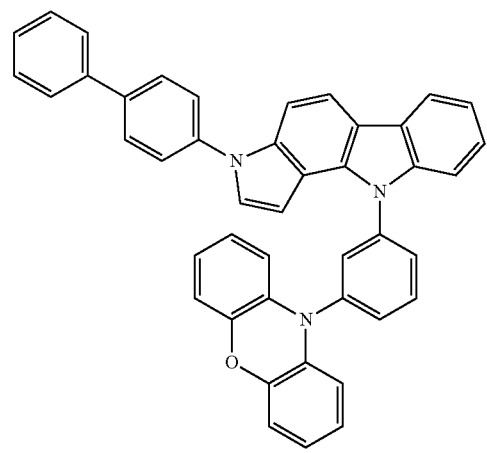
Inv533
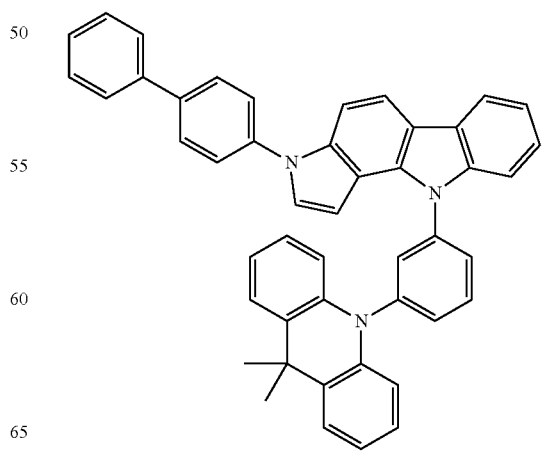

209
-continued
Inv534
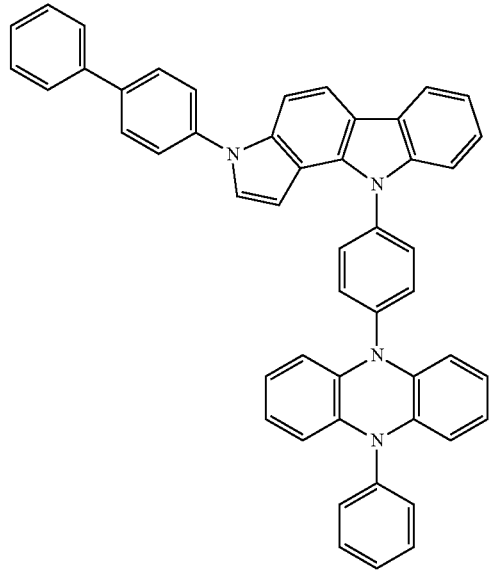
Inv535
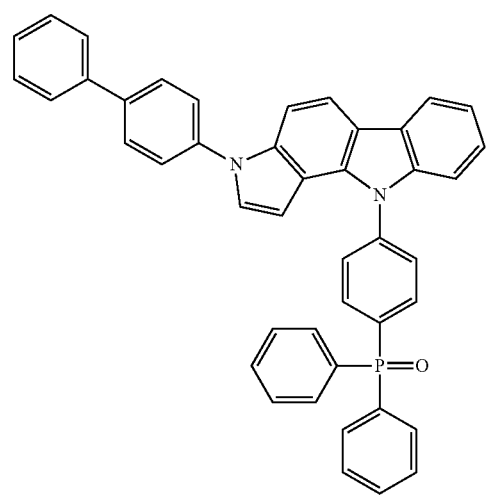
Inv536
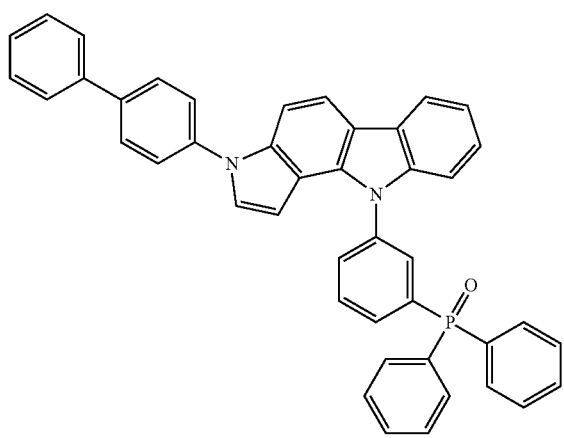
210
-continued
Inv537
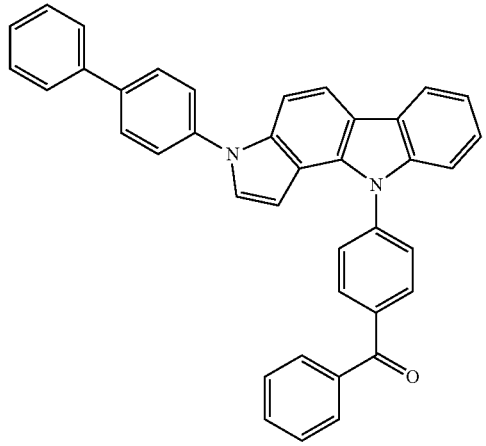
Inv538
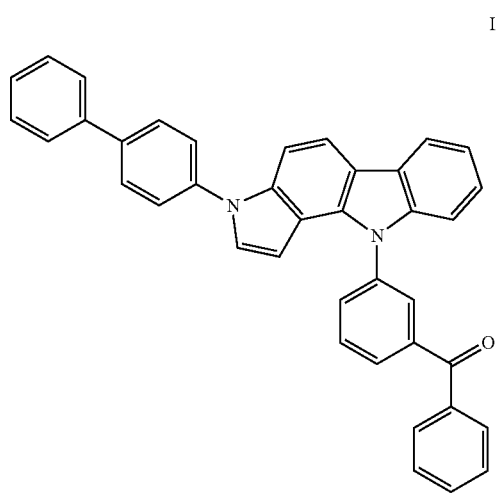
Inv539
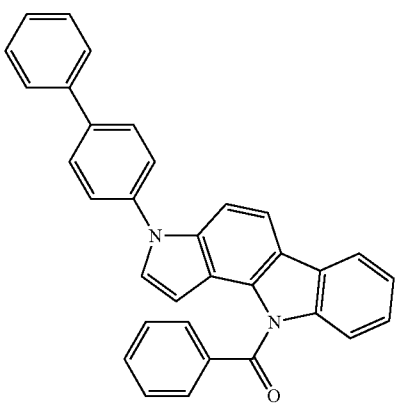

Inv540
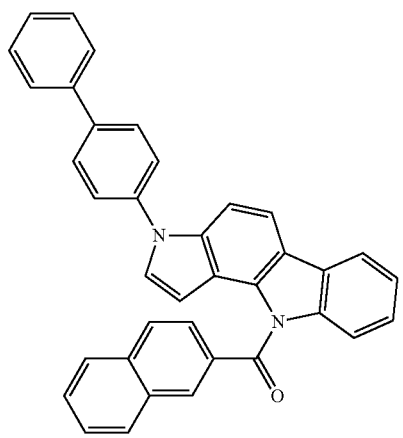
Inv541
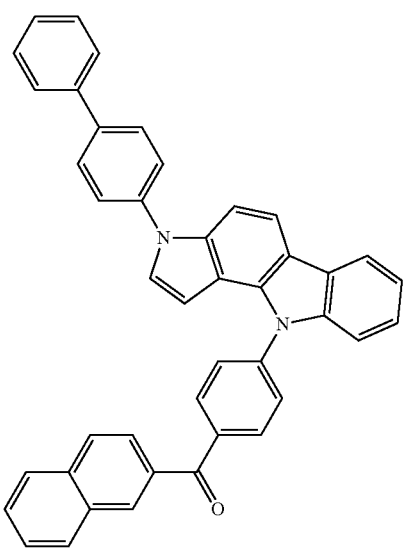
Inv542
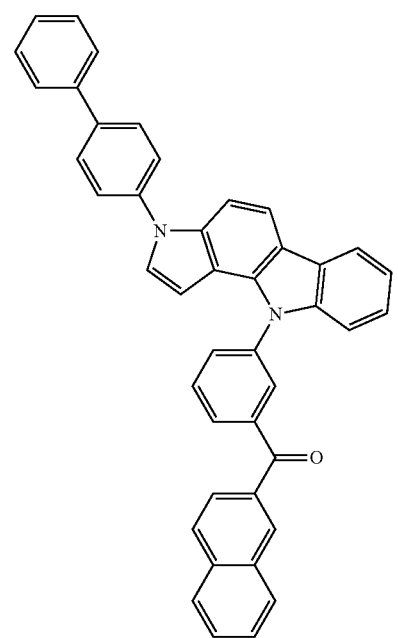
Inv543
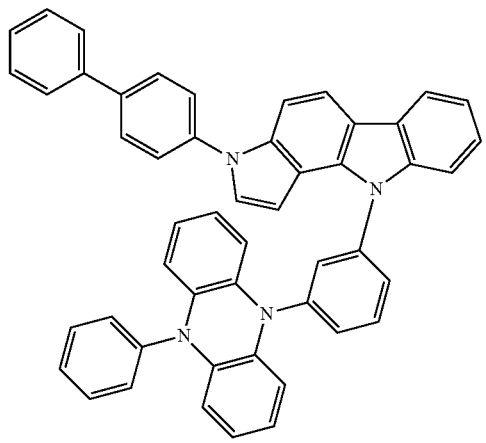
Inv544
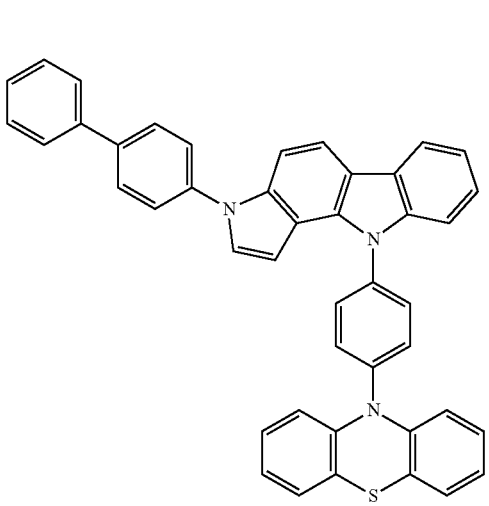
Inv545
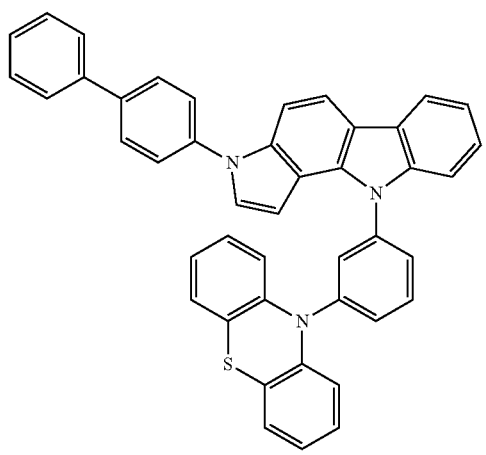

Inv546
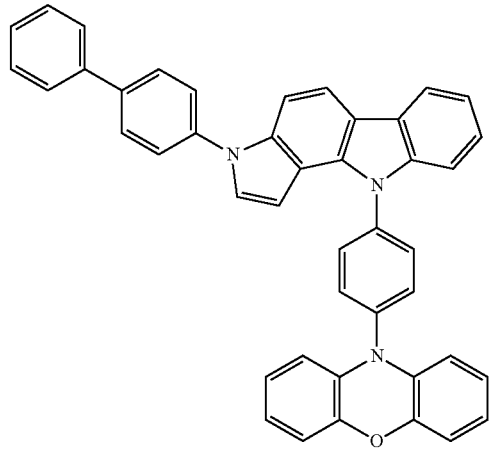
Inv549
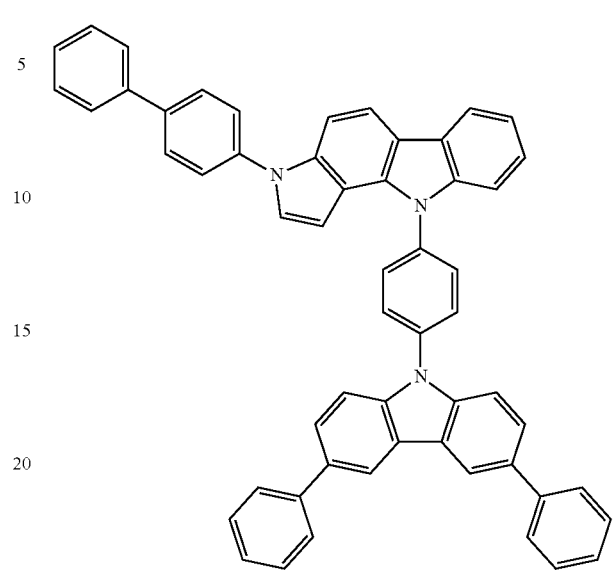
Inv547
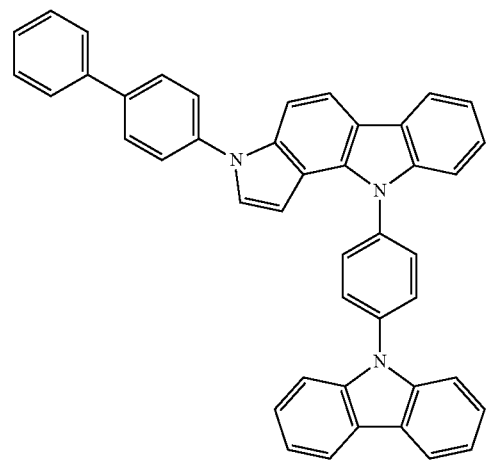
Inv550
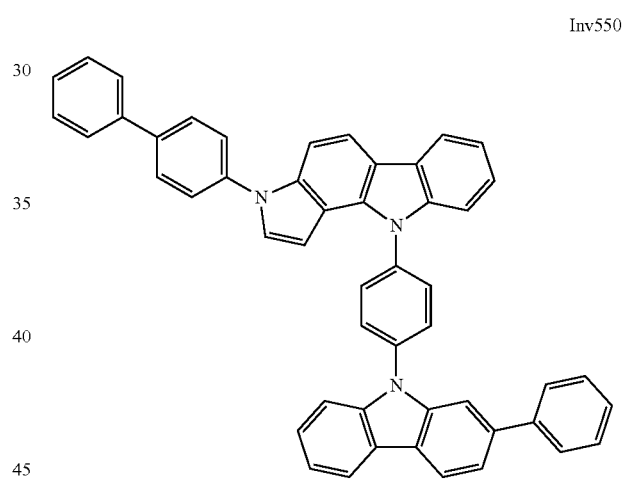
Inv548
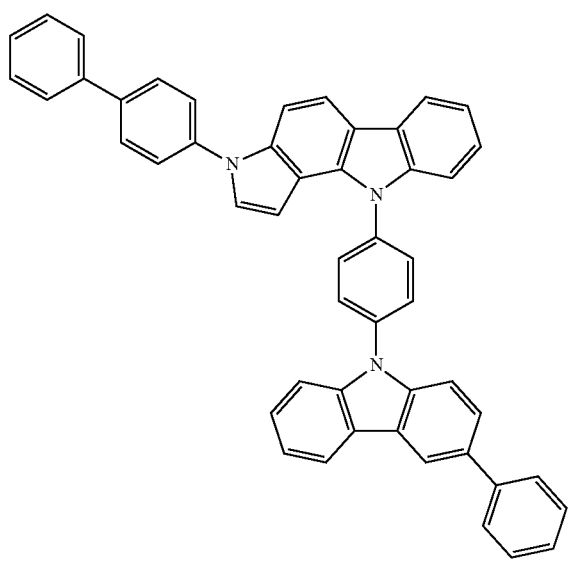
Inv551
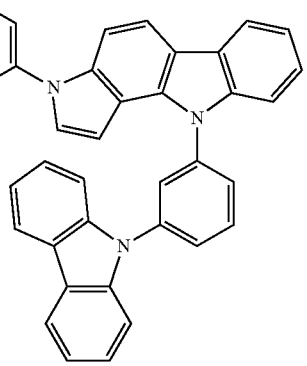

Inv552
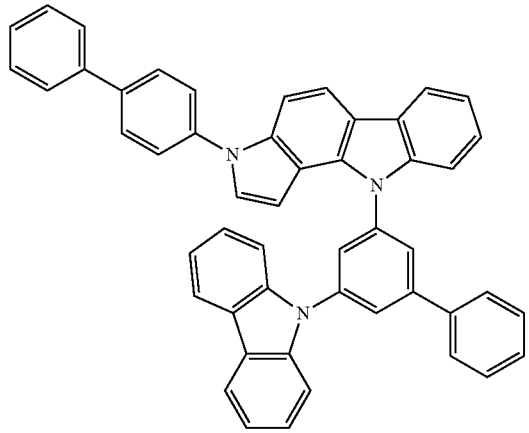
Inv553
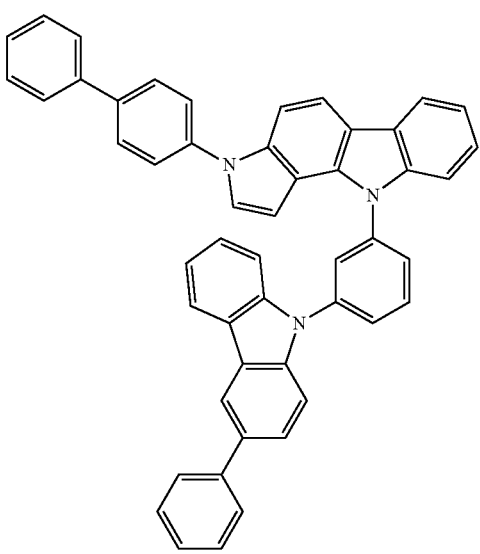
Inv554
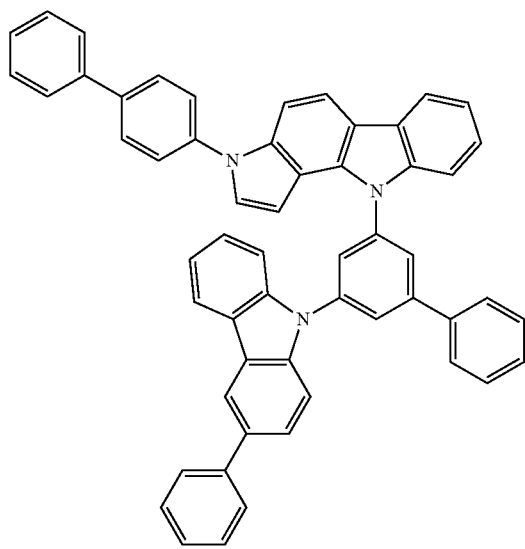
Inv555
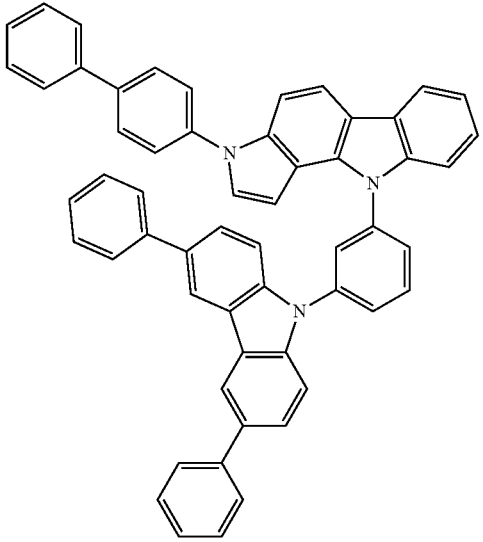
Inv556
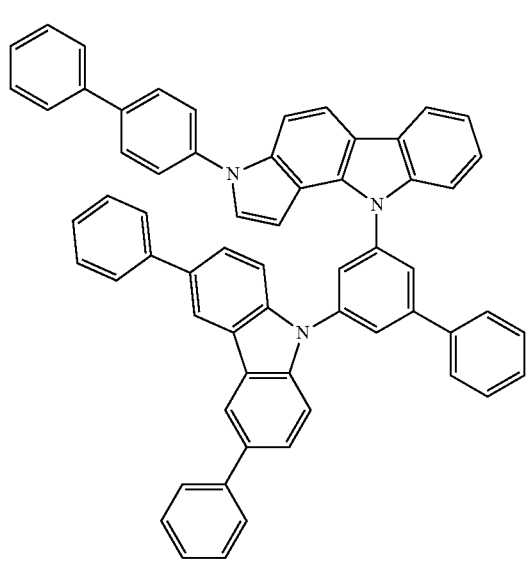
Inv557
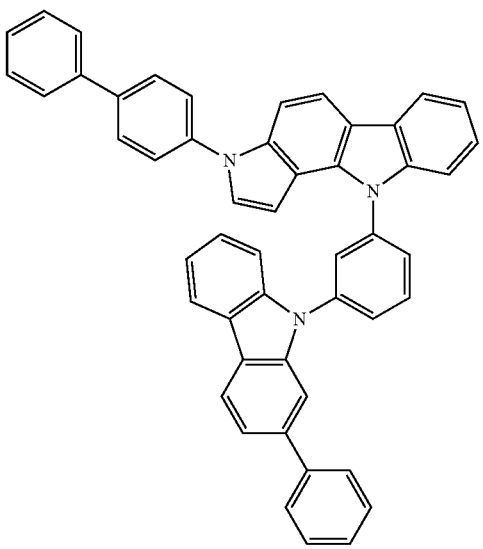

Inv558
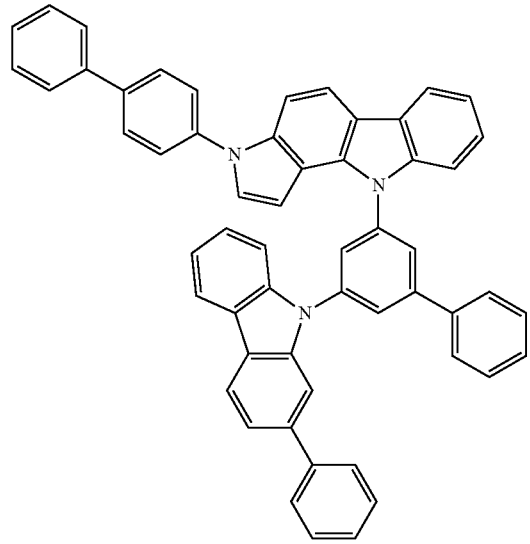
Inv560
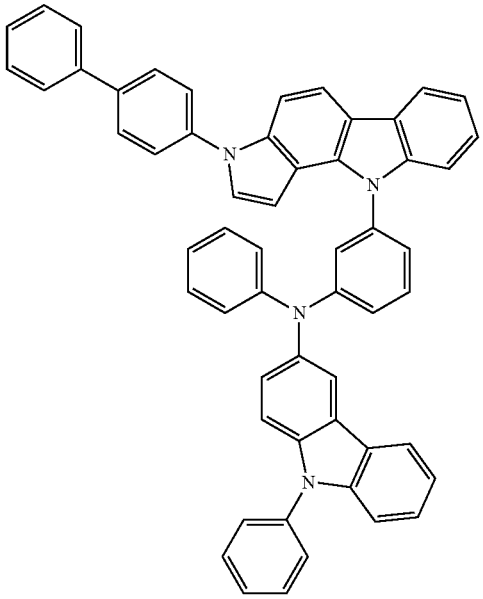
Inv559
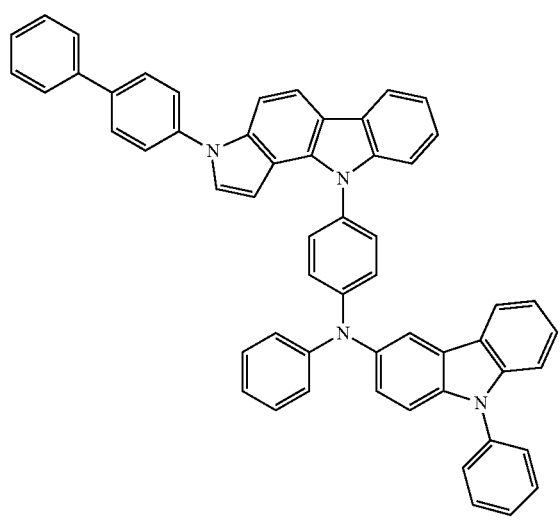
Inv561
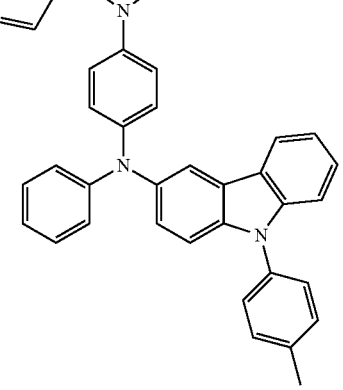

-continued
Inv562
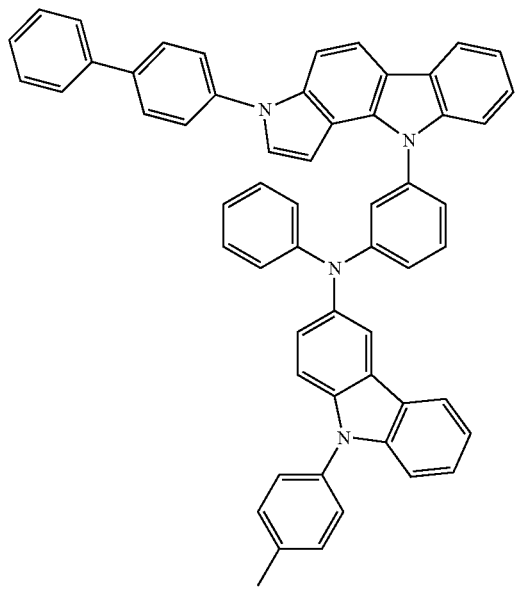
Inv563
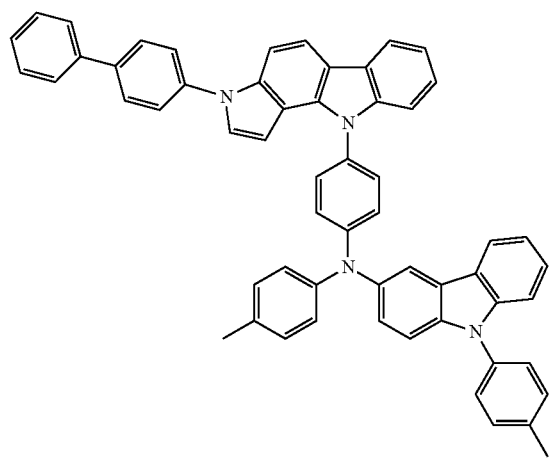
-continued
Inv564
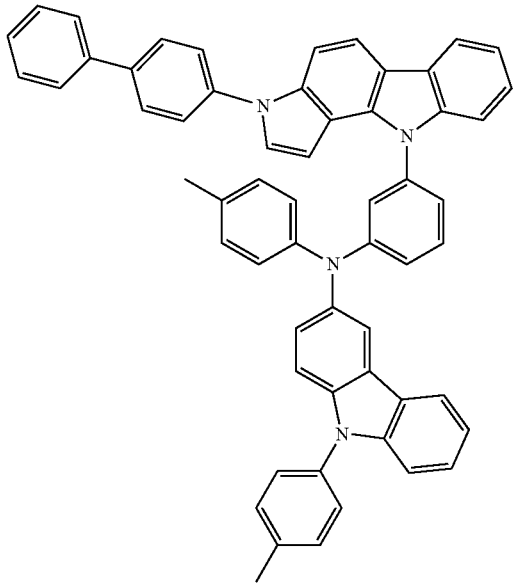
Inv565
Inv566
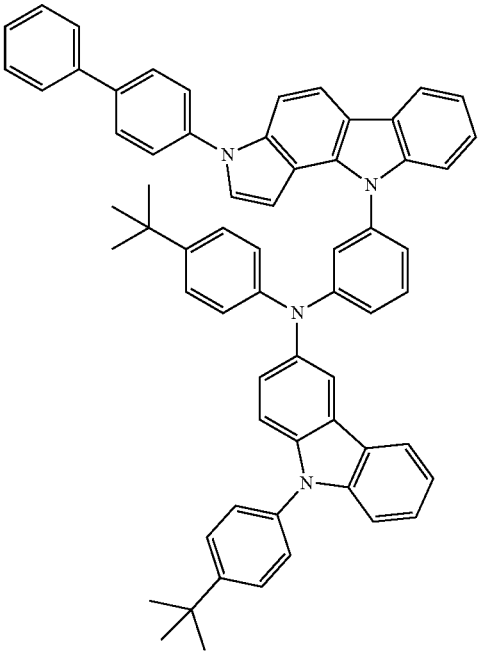

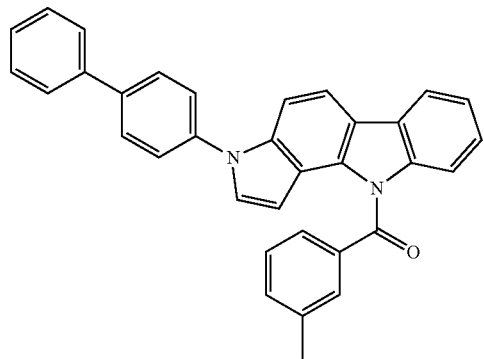
Inv567
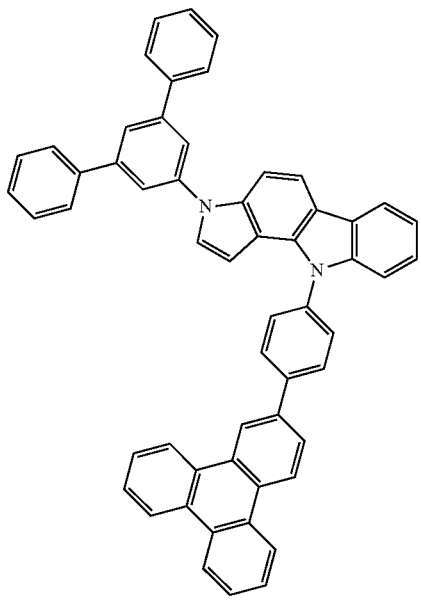
Inv570
Inv568
Inv569
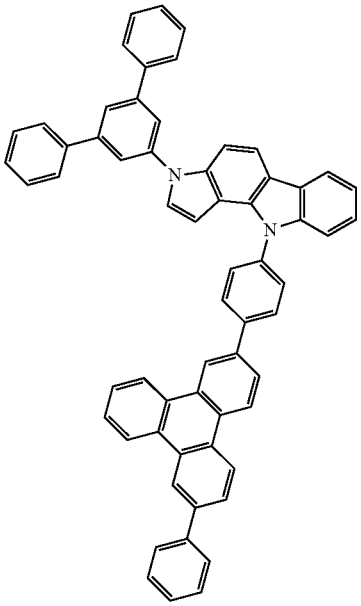
Inv571

Inv572
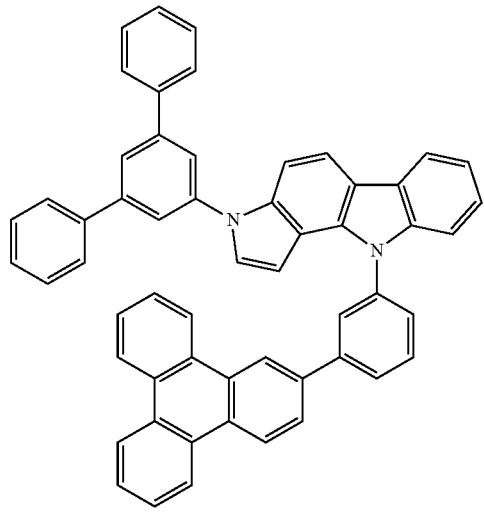
Inv573
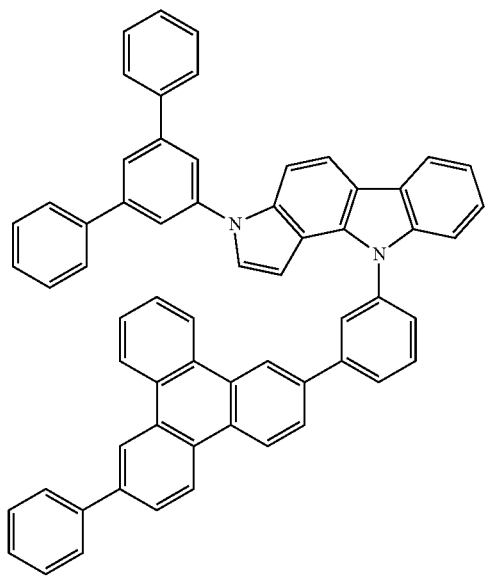
Inv574
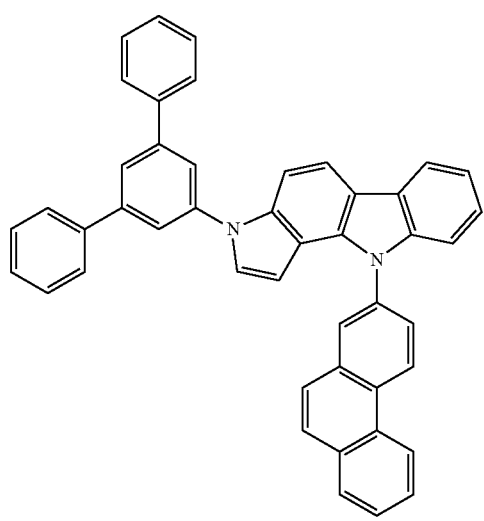
Inv575
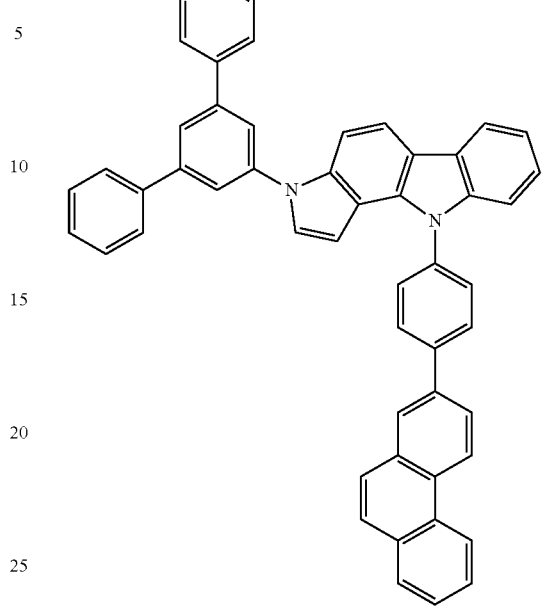
Inv576
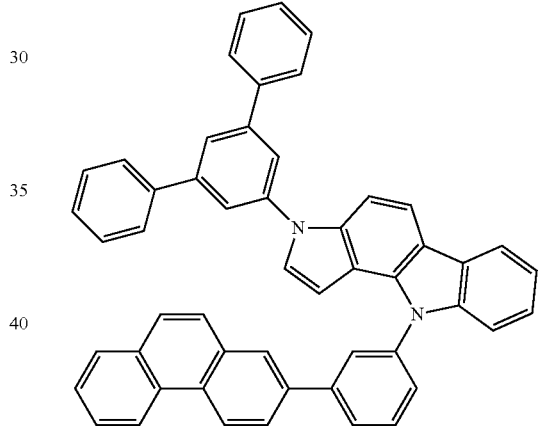
Inv577
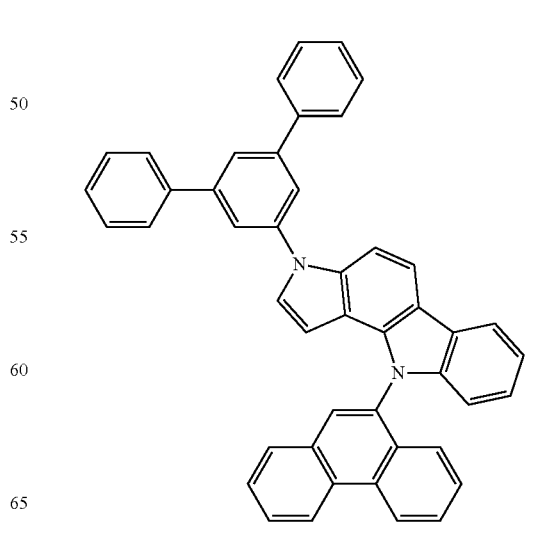

Inv578
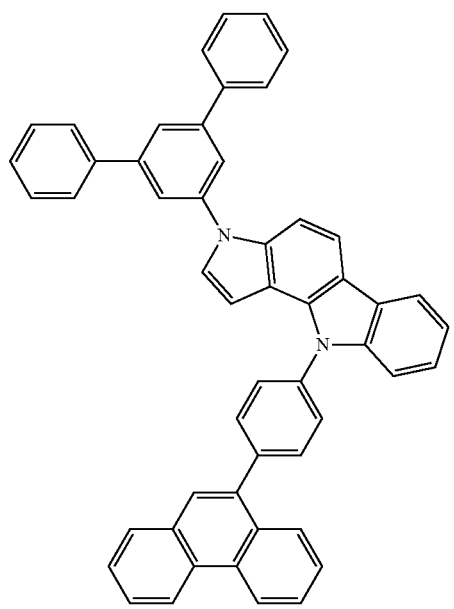
Inv579
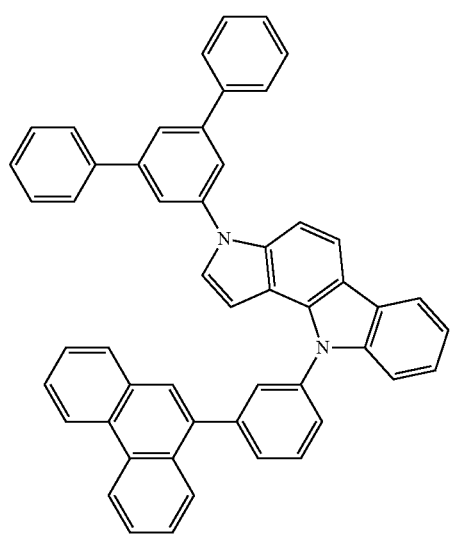
Inv580
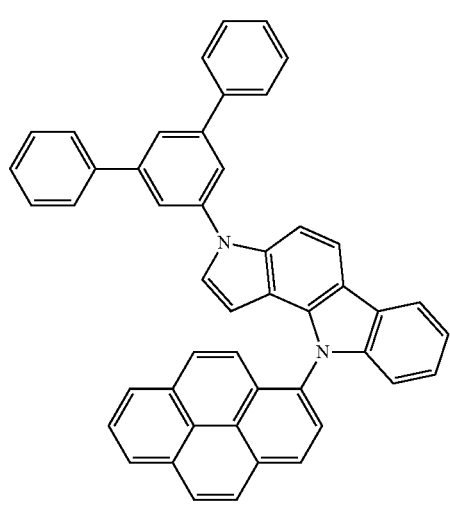
Inv581
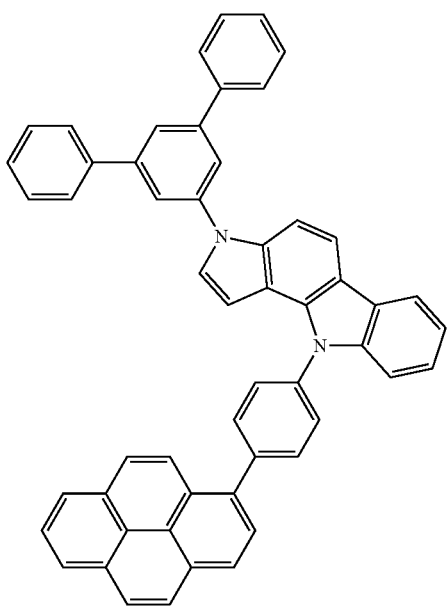
Inv582
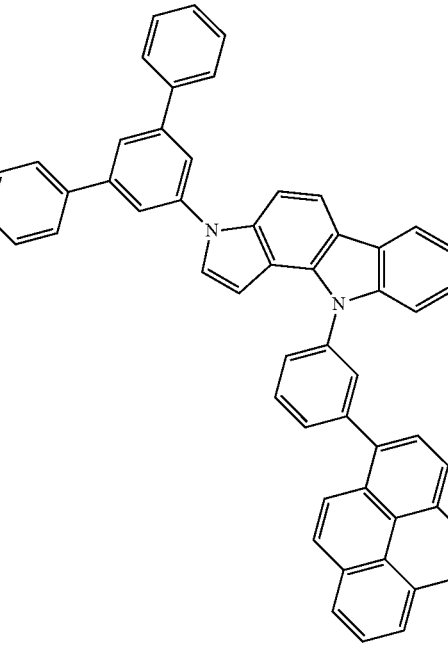

Inv583
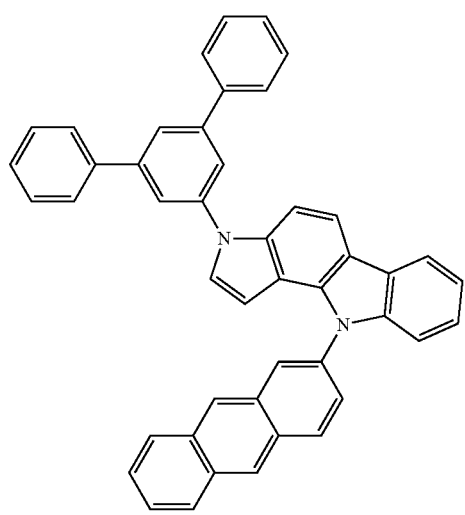
Inv584
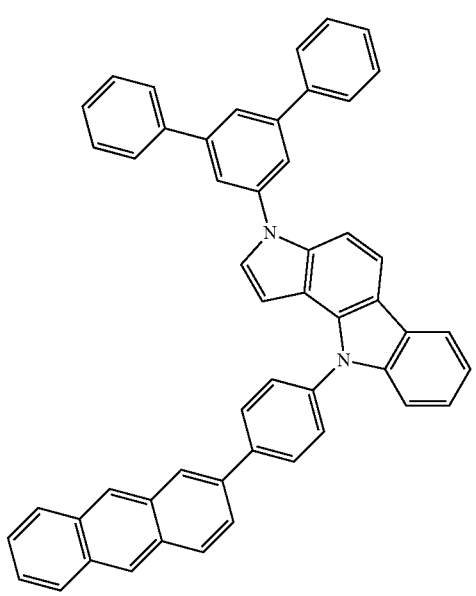
Inv585
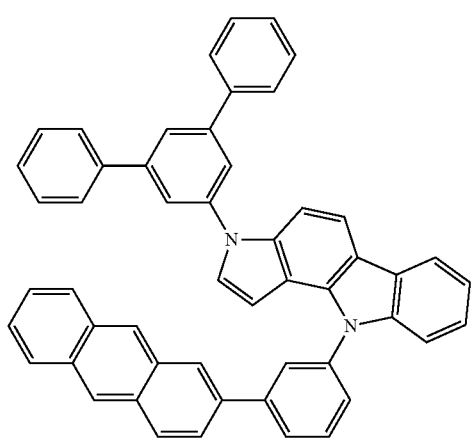
Inv586
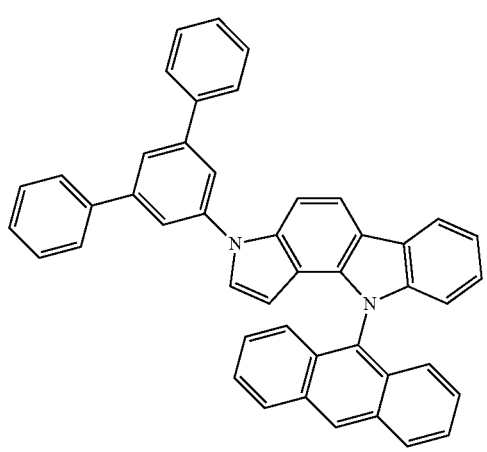
Inv587
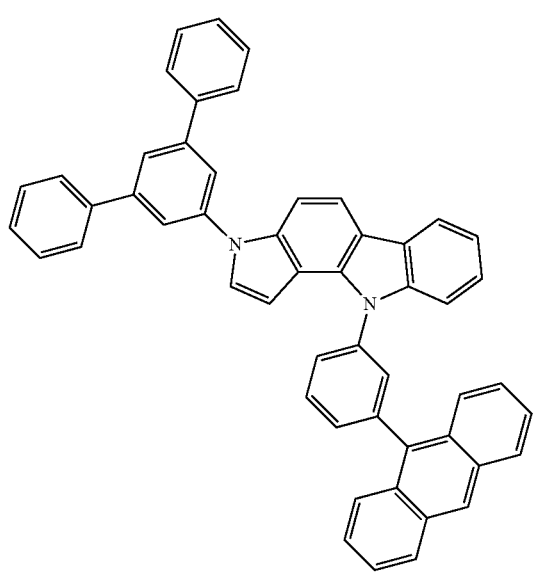
Inv588
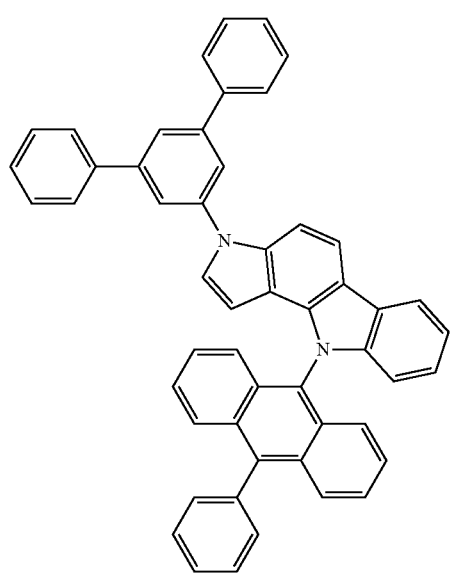

Inv589
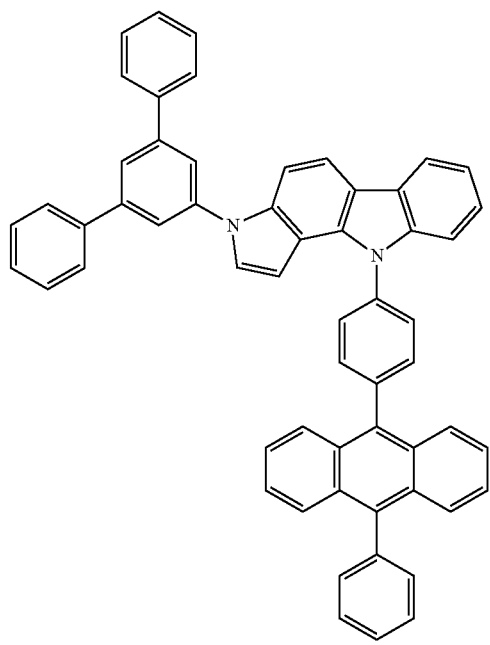
Inv591
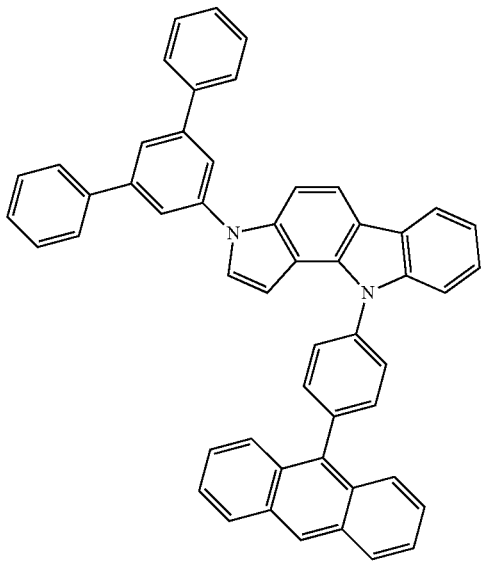
Inv590
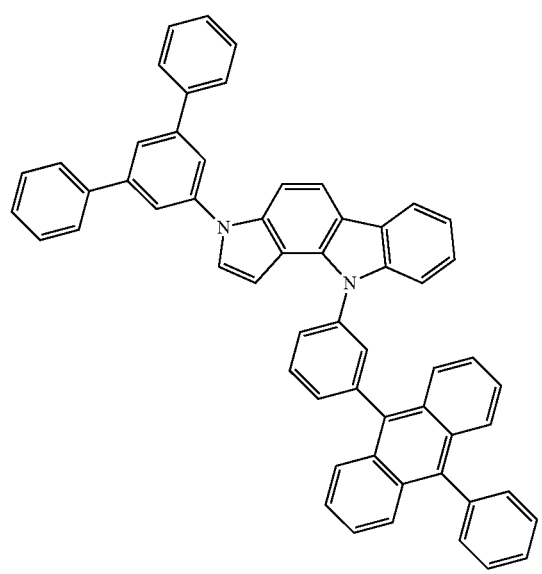
Inv592

-continued
Inv593
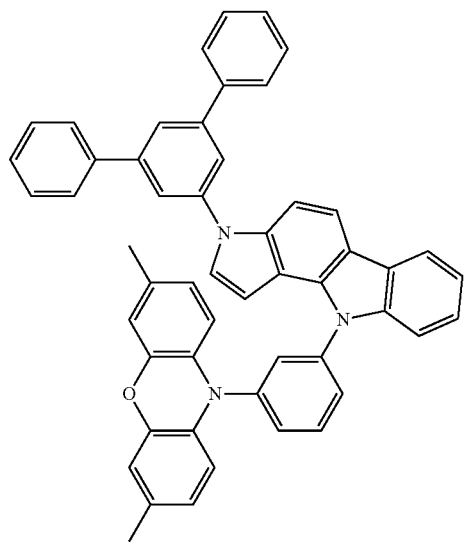
Inv594
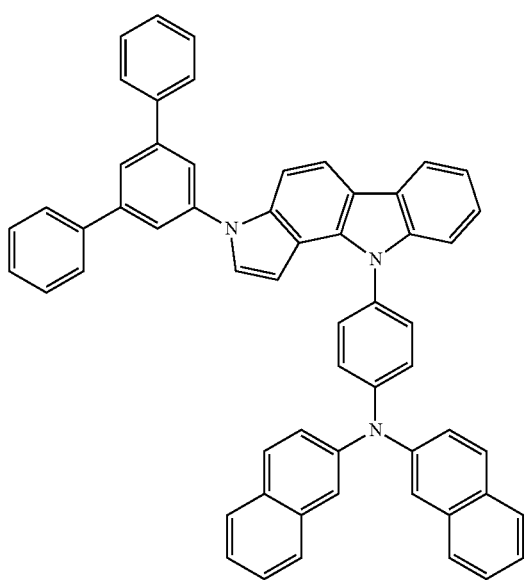
-continued
Inv595
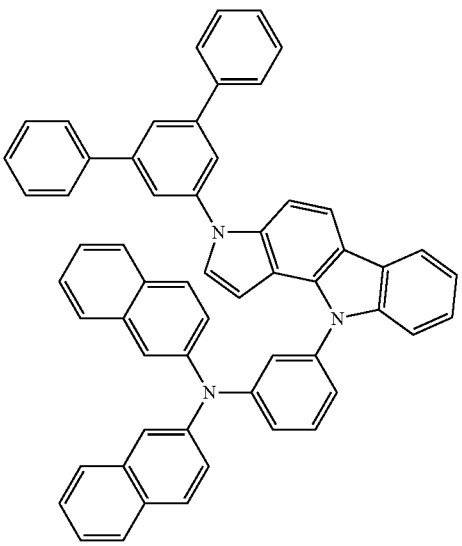
Inv596
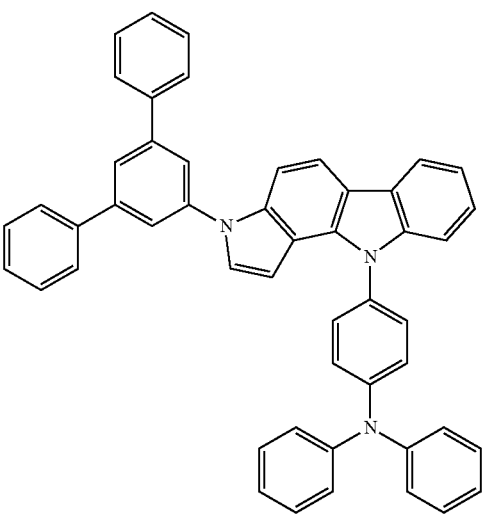
Inv597

Inv598
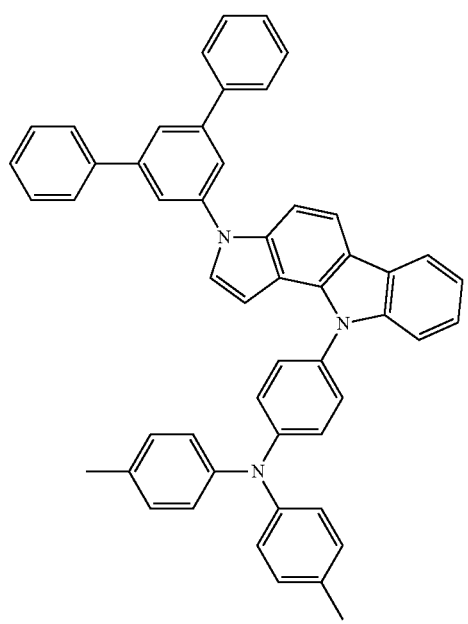
Inv600
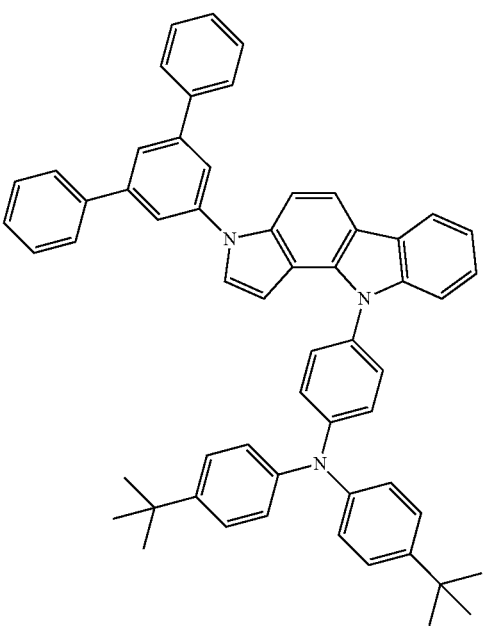
Inv599
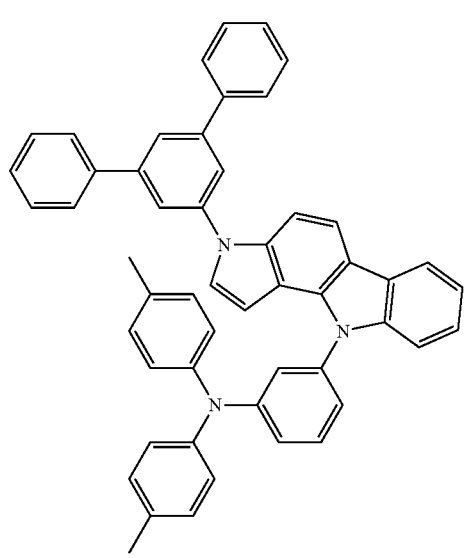
Inv601

-continued

Inv602

Inv605

Inv603

Inv606

Inv604

Inv607

-continued
Inv608
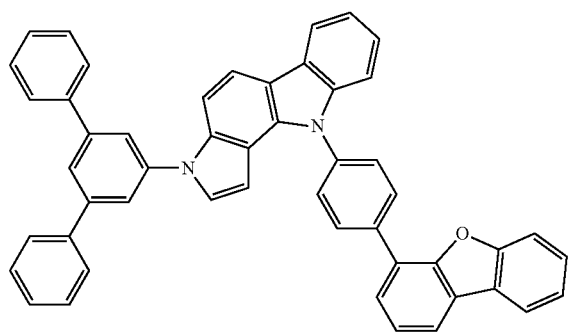
Inv609
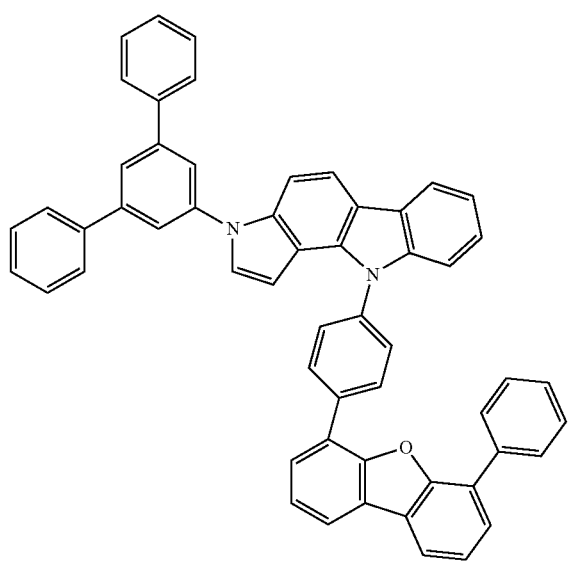
Inv610
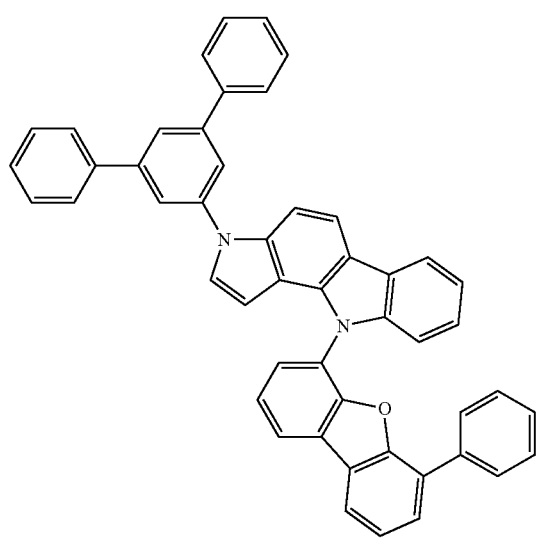
-continued
Inv611
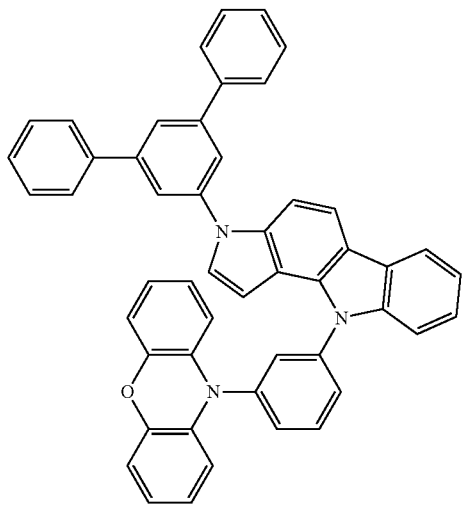
Inv612
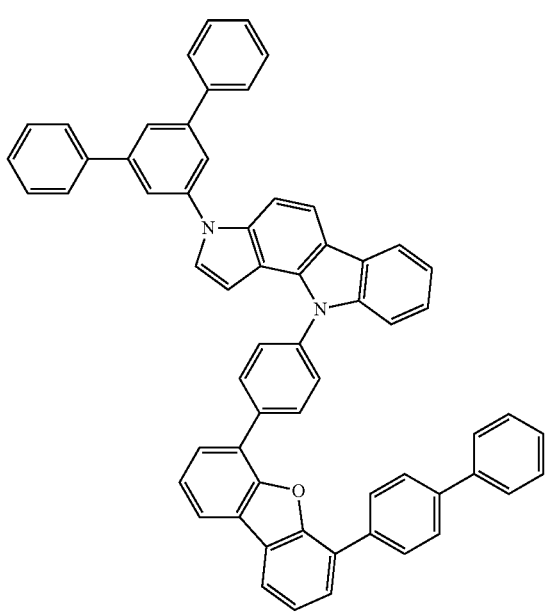

Inv613
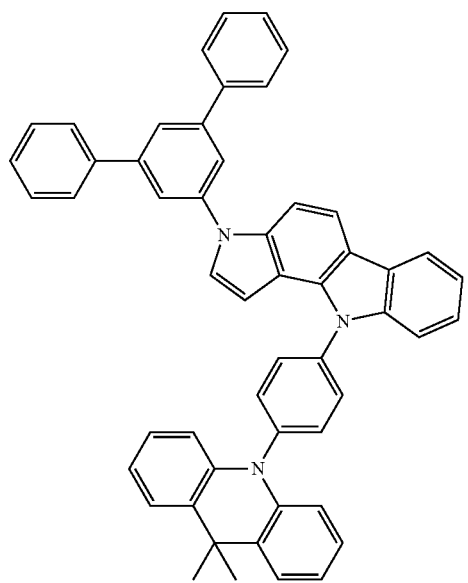
Inv614
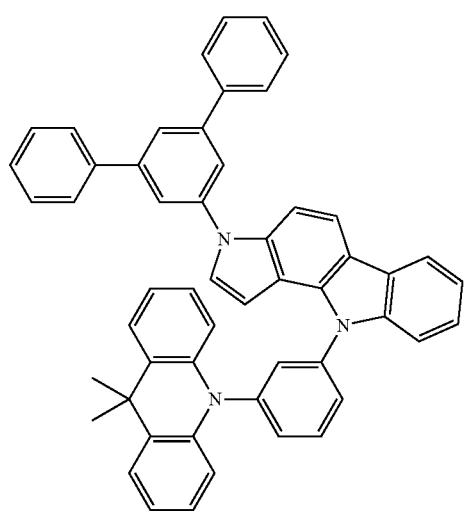
Inv615
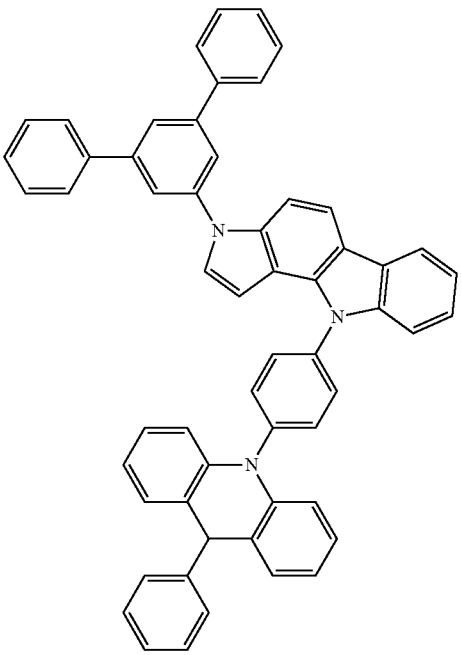
Inv616
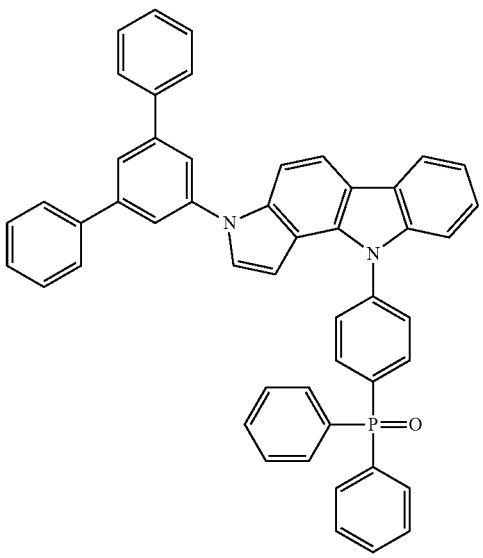

-continued
Inv617
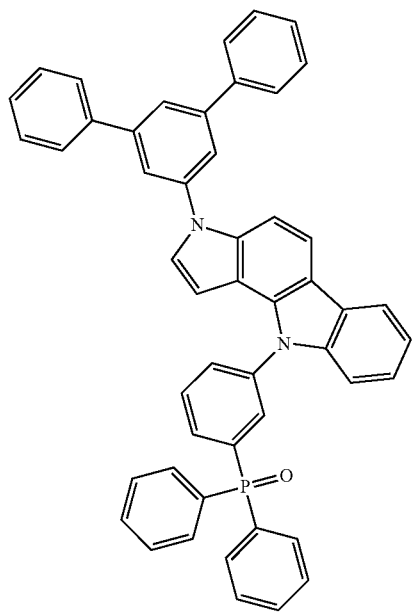
Inv618
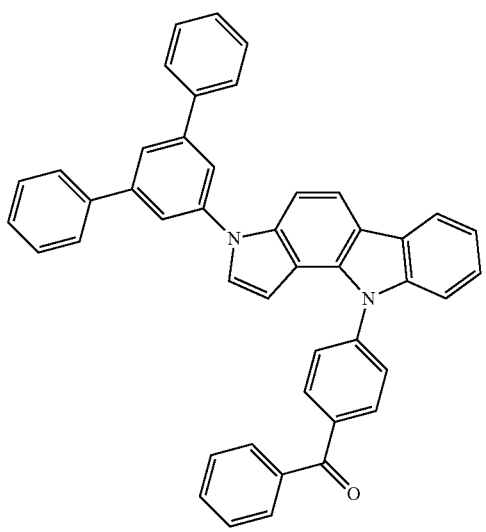
Inv619
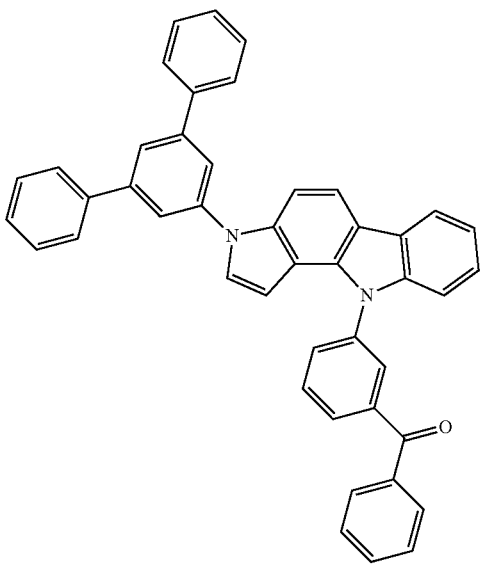
Inv620
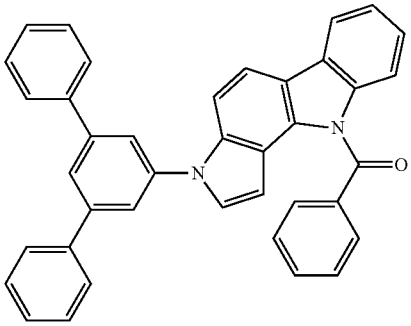
Inv621
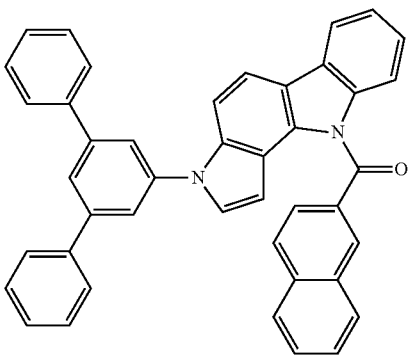

Inv622
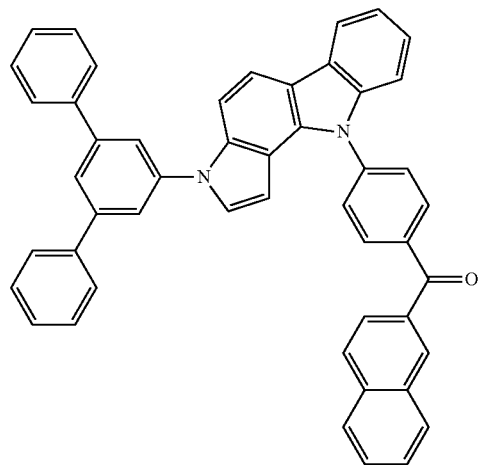
Inv623
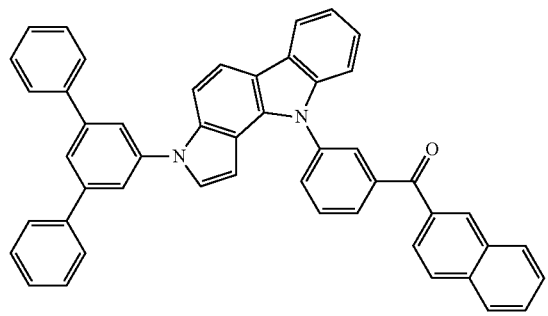
Inv624
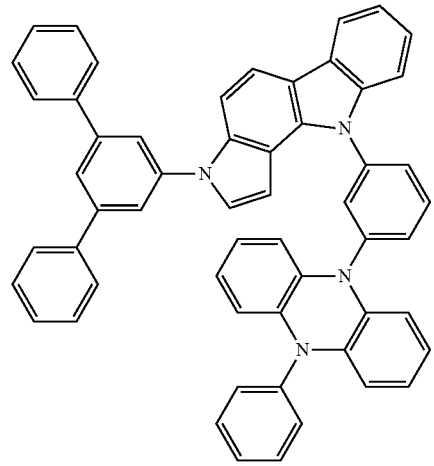
Inv625
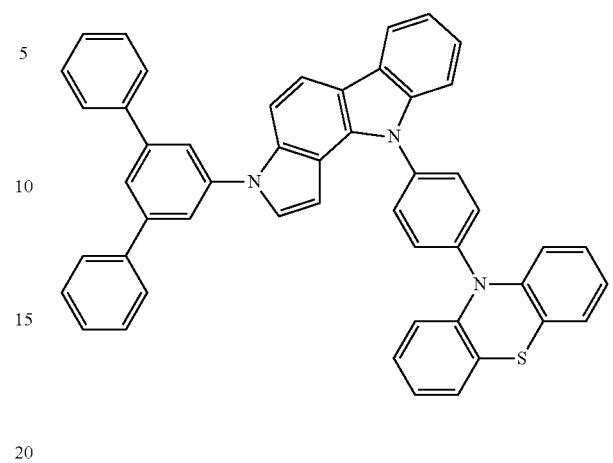
Inv626
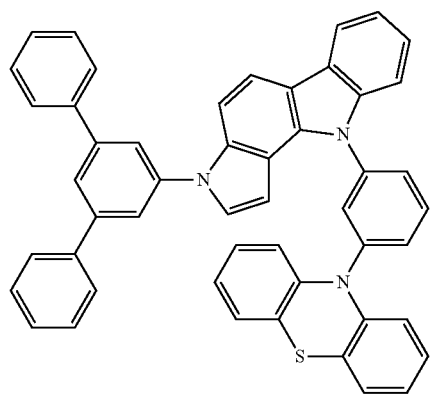
Inv627
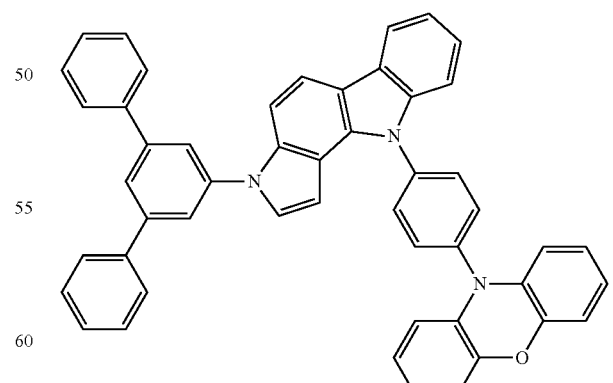

-continued
Inv628
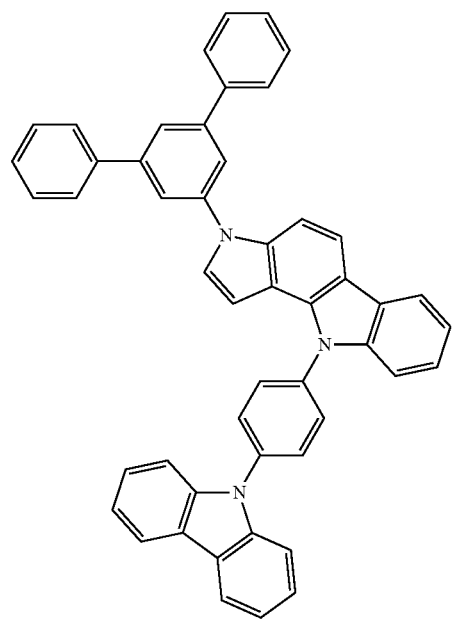
Inv629
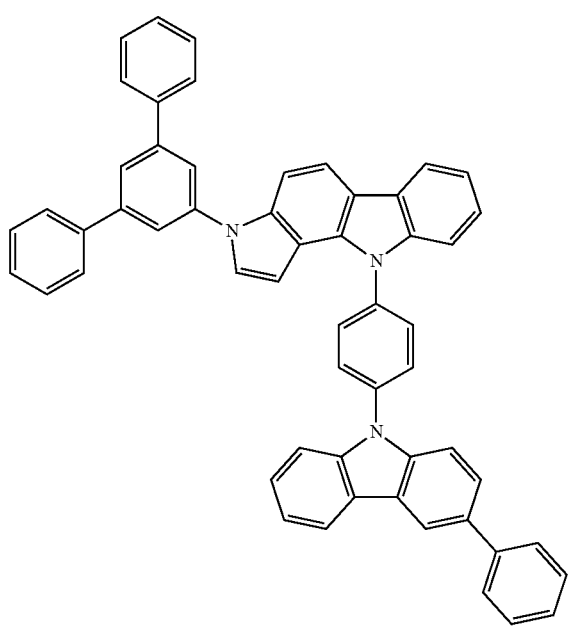
-continued
Inv630
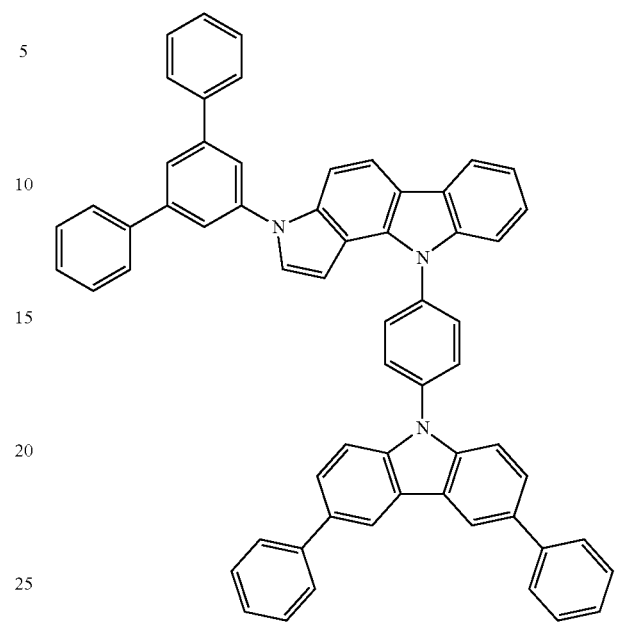
Inv631
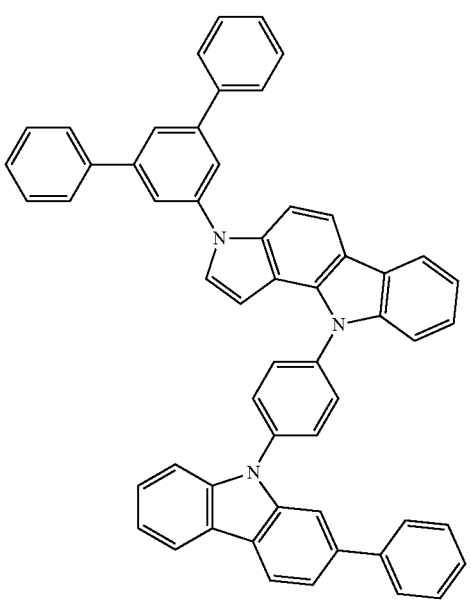

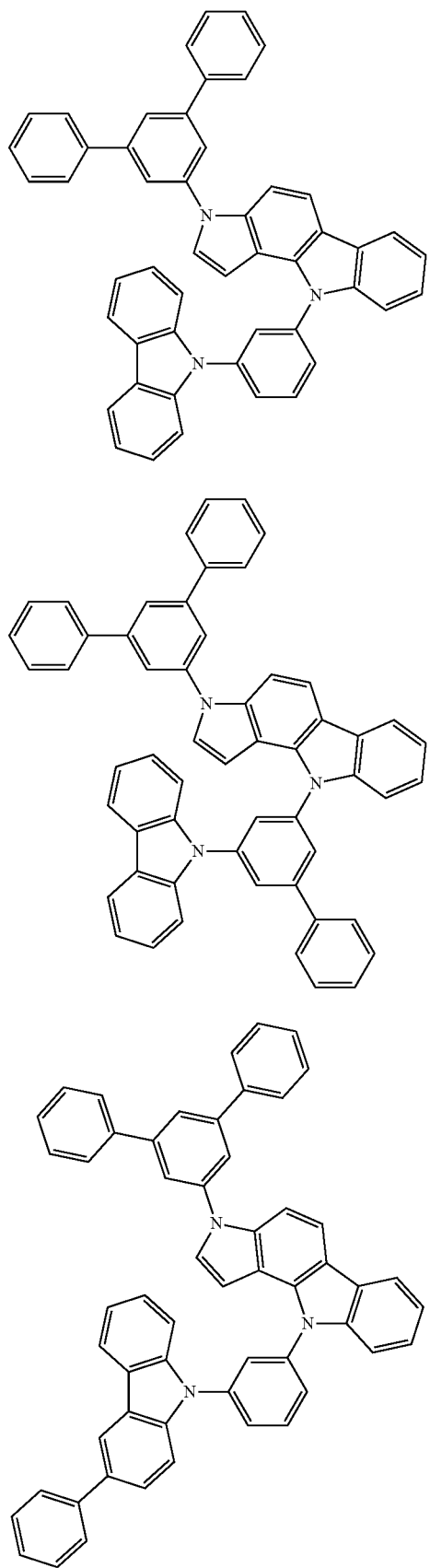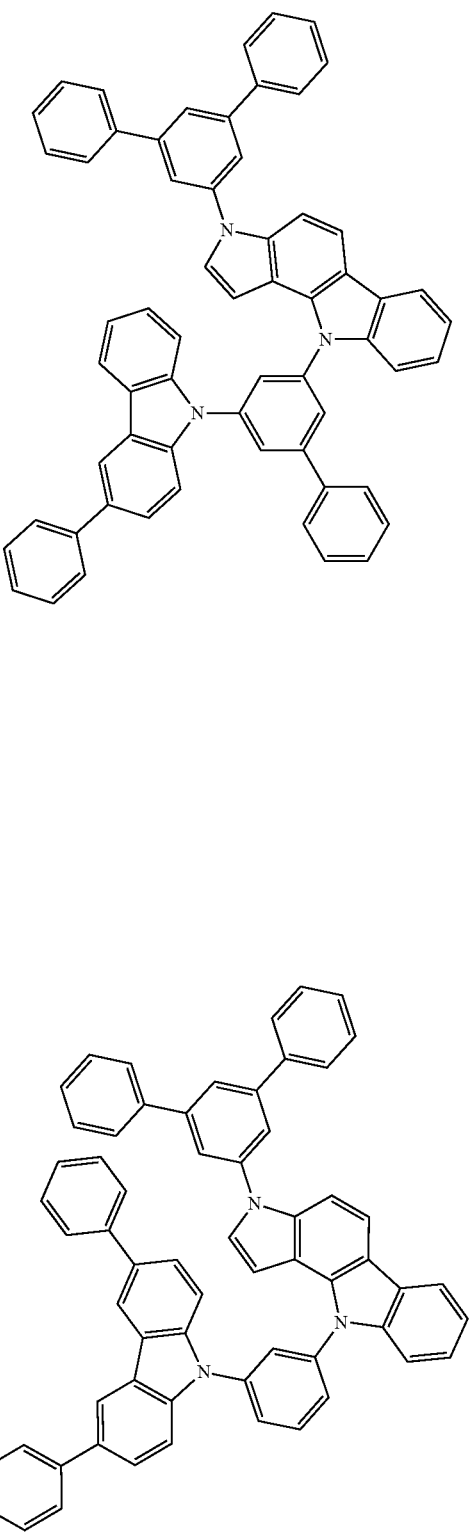

Inv637
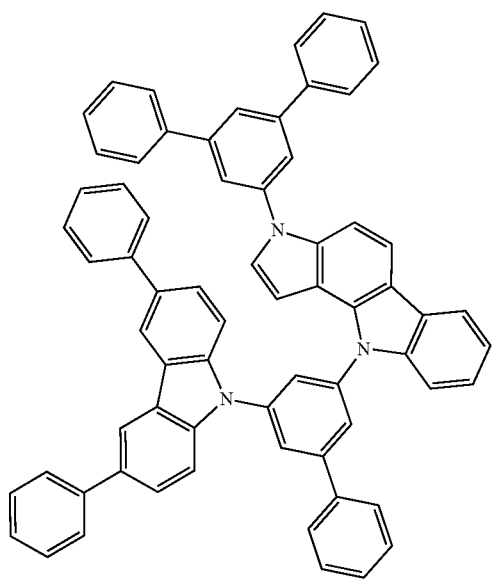
Inv638
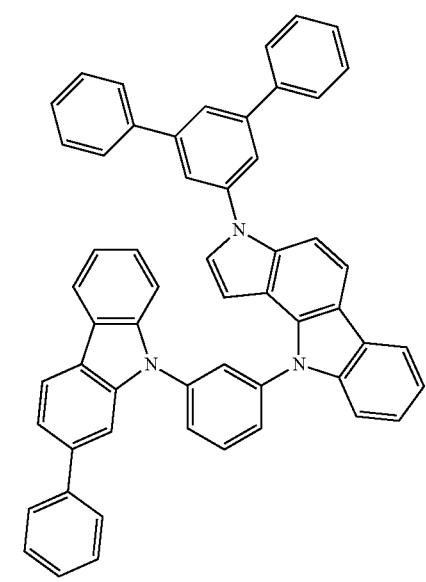
Inv639
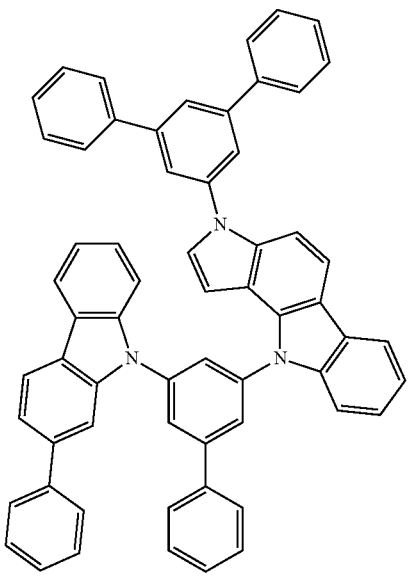
Inv640
Inv641
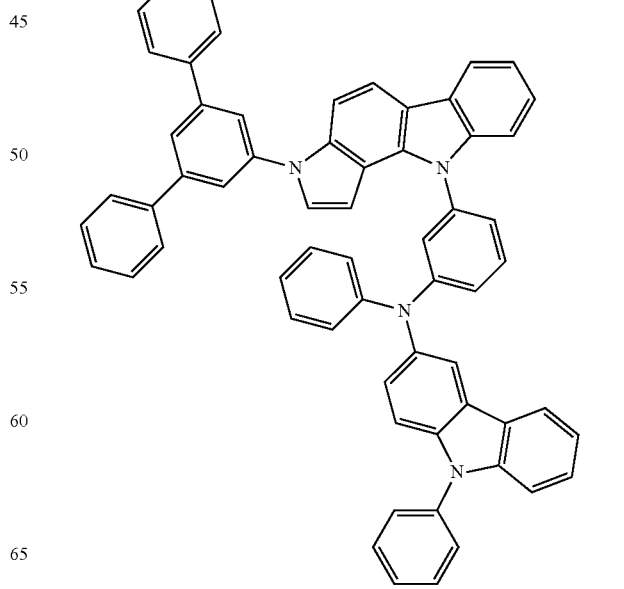

-continued
Inv642
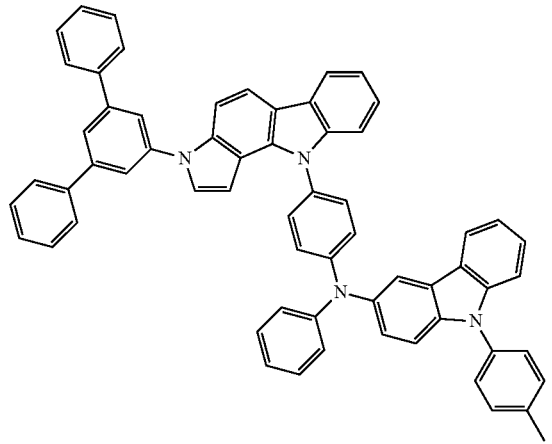
Inv645
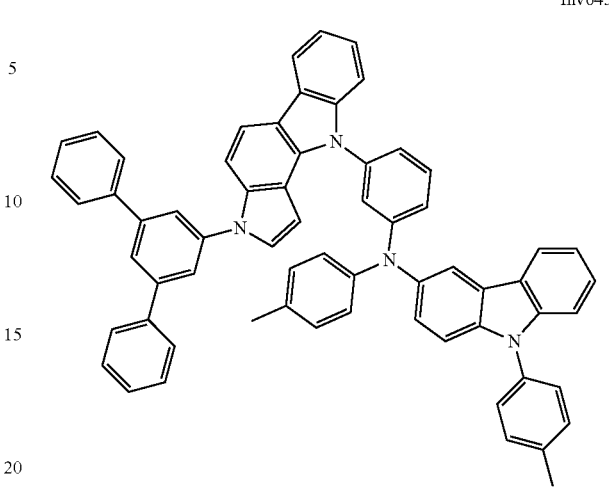
Inv643
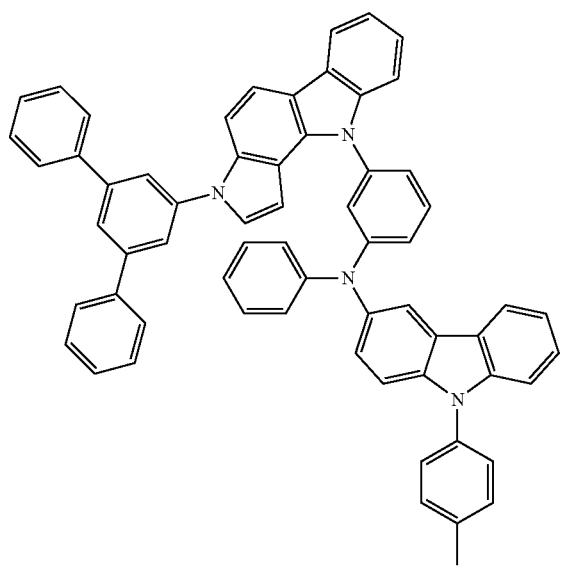
Inv646
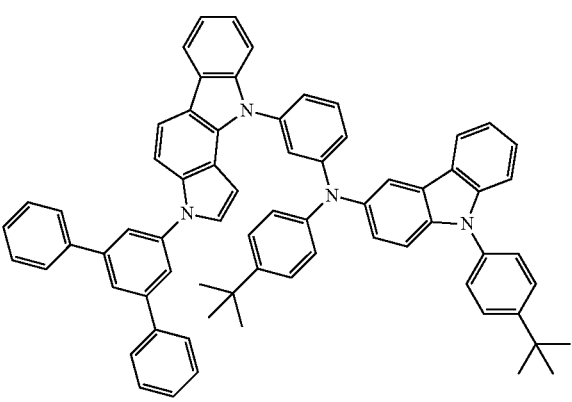
Inv644
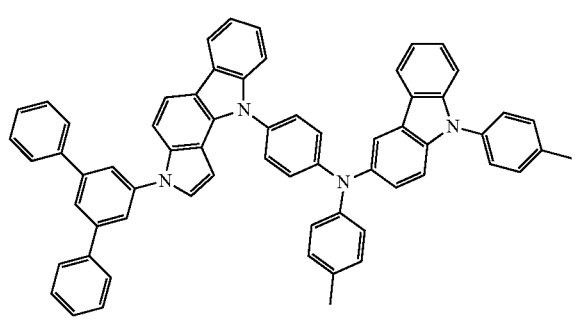
Inv647

Inv648
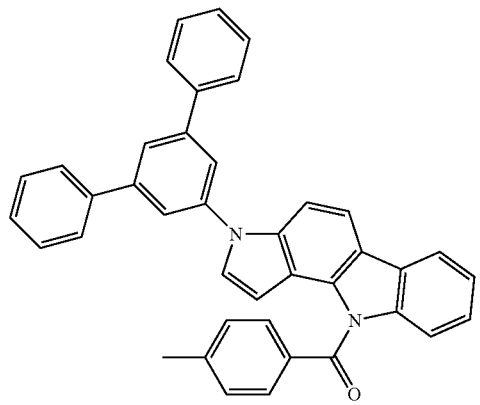
Inv651
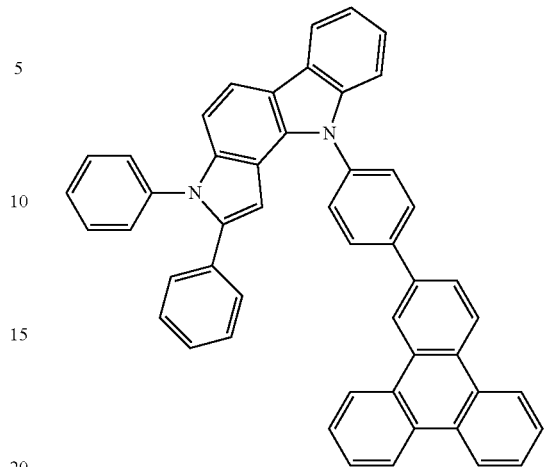
Inv649
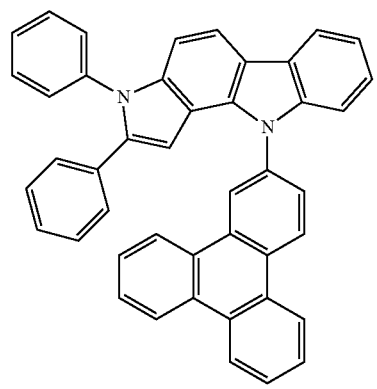
Inv652
Inv650
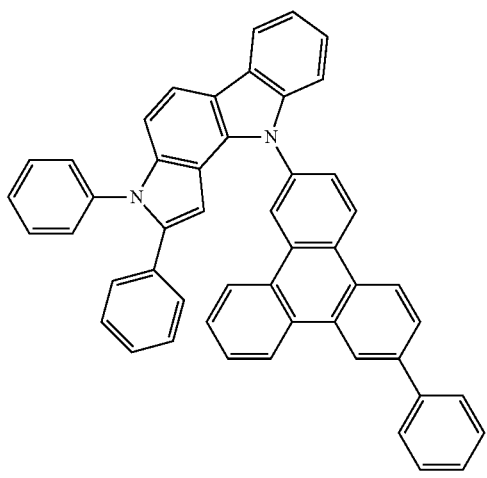
Inv653
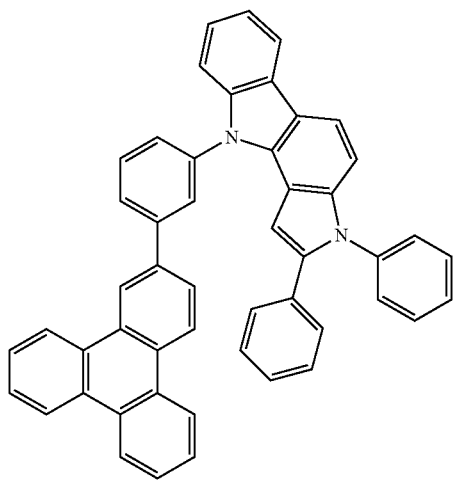

Inv654
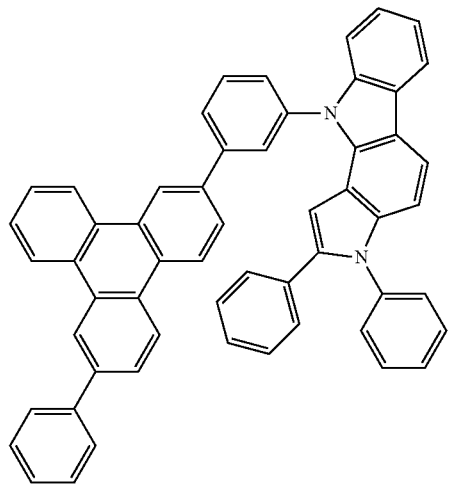
Inv655
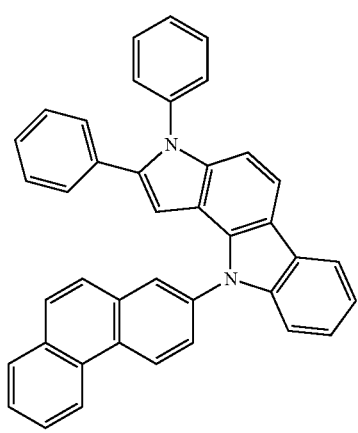
Inv656
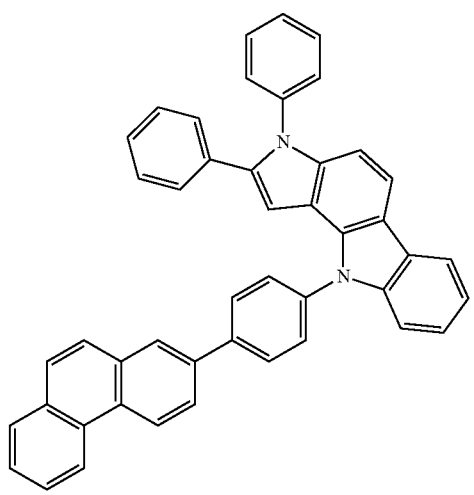
Inv657
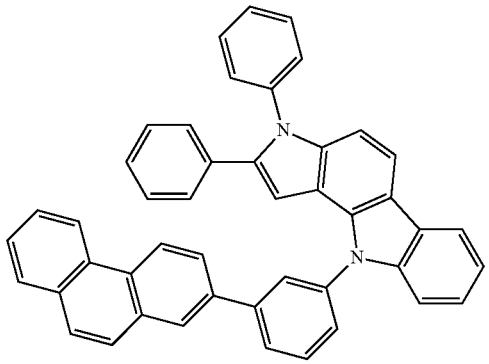
Inv658
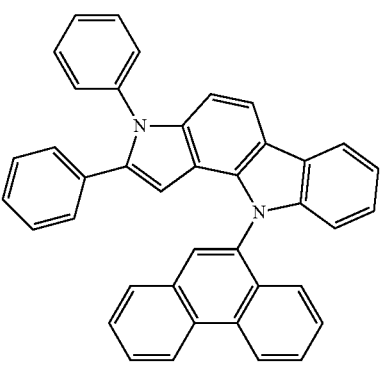
Inv659
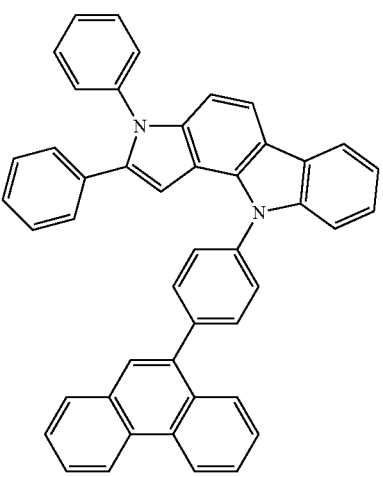

Inv660
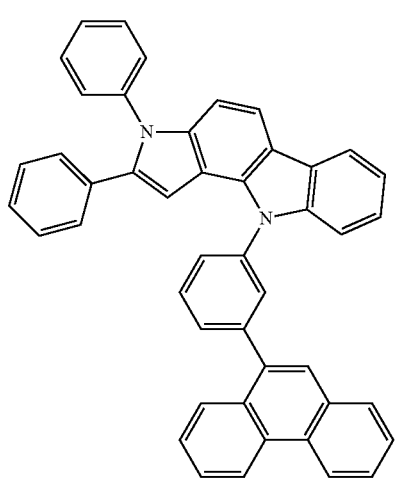
Inv661
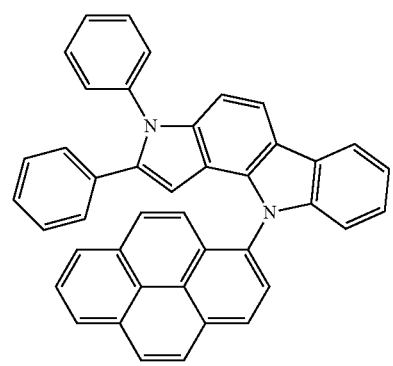
Inv662
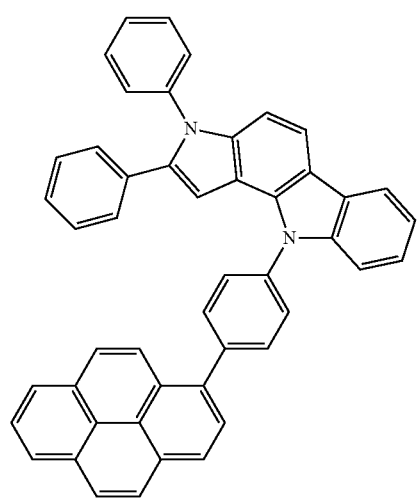
Inv663
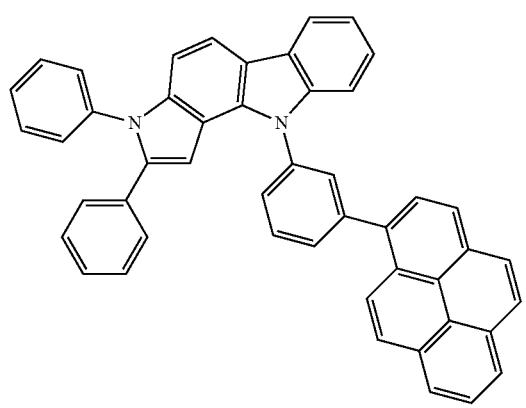
Inv664
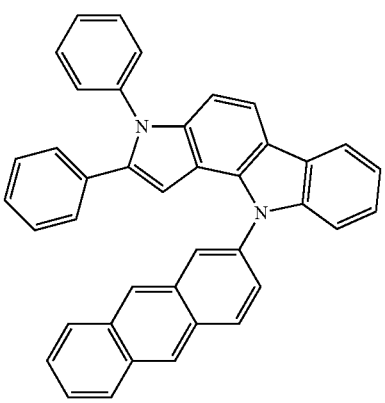
Inv665
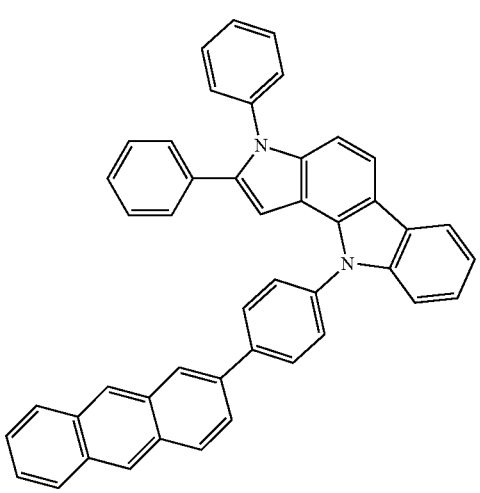

-continued
Inv666
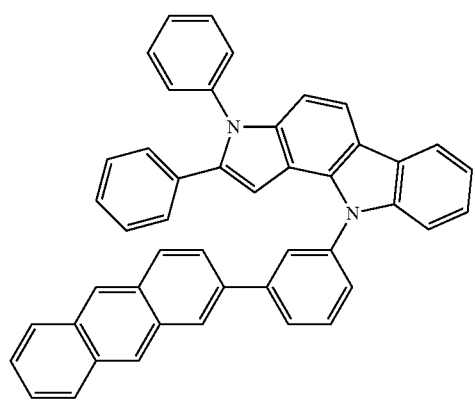
Inv667
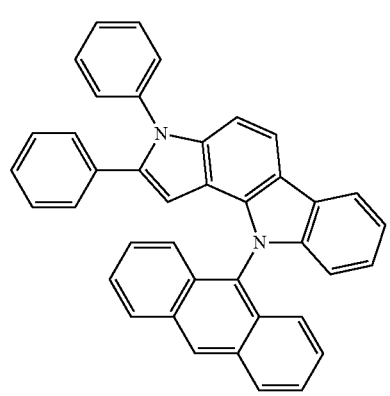
Inv668
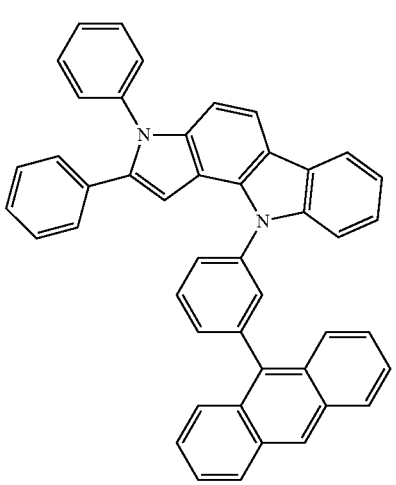
-continued
Inv669
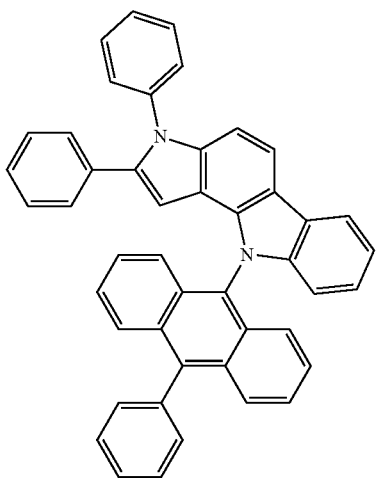
Inv670
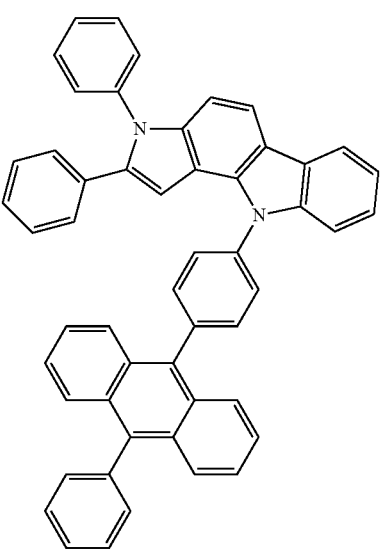
Inv671
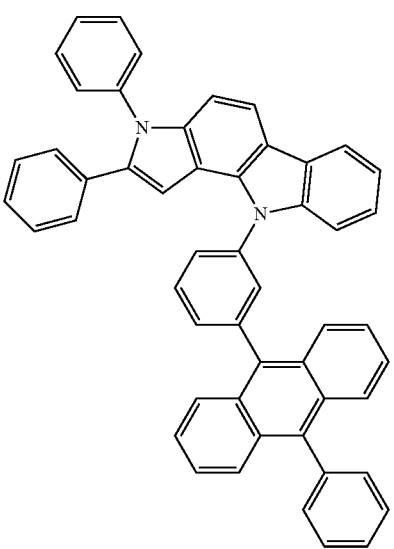

Inv672
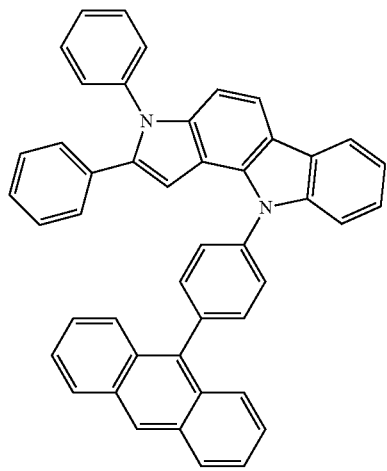
Inv675
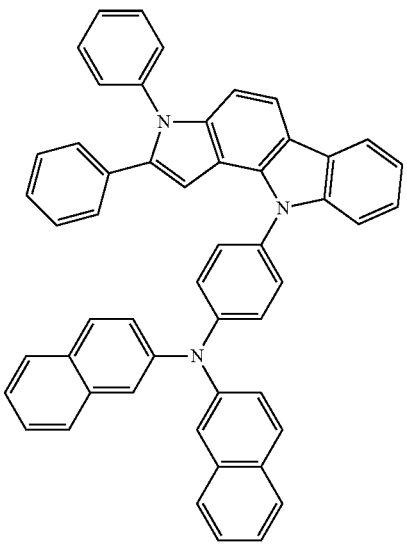
Inv673
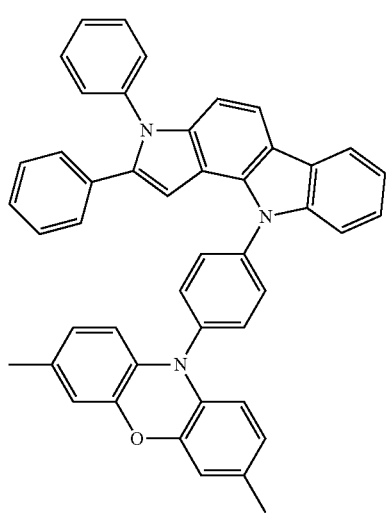
Inv676
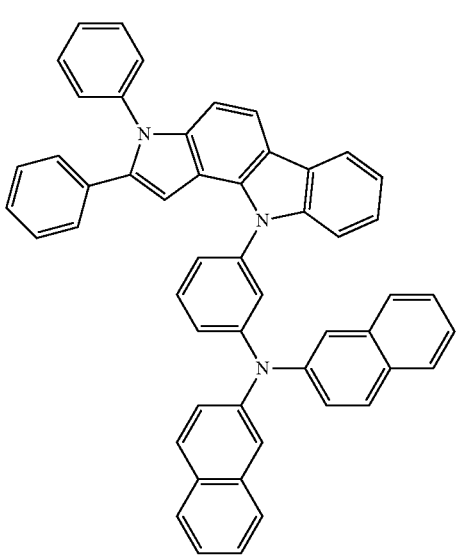
Inv674
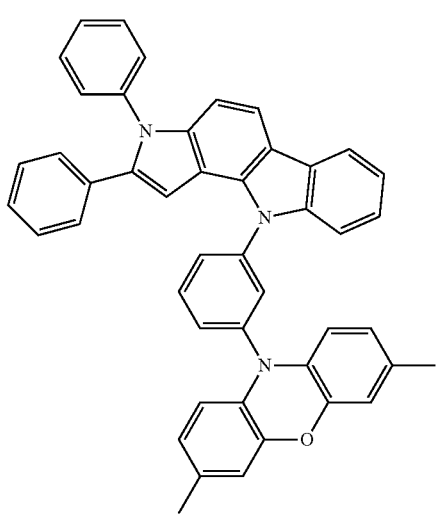
Inv677
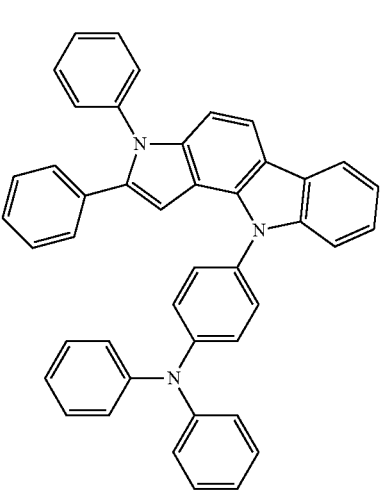

-continued
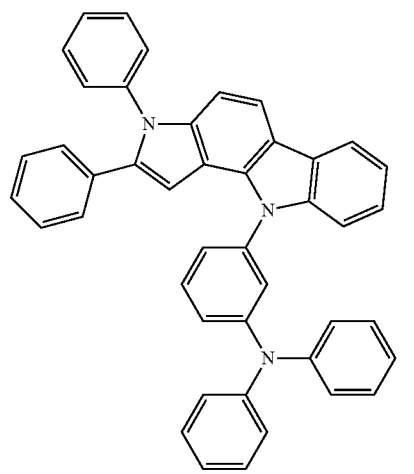
Inv678
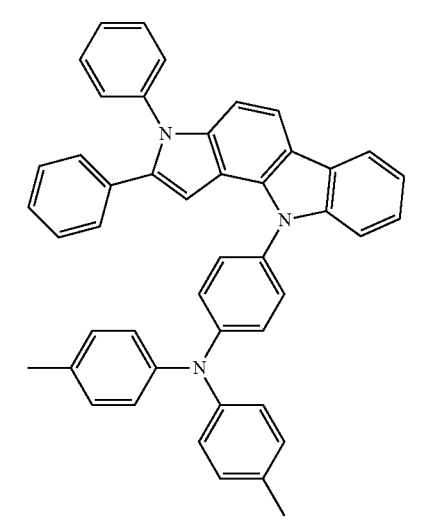
Inv679
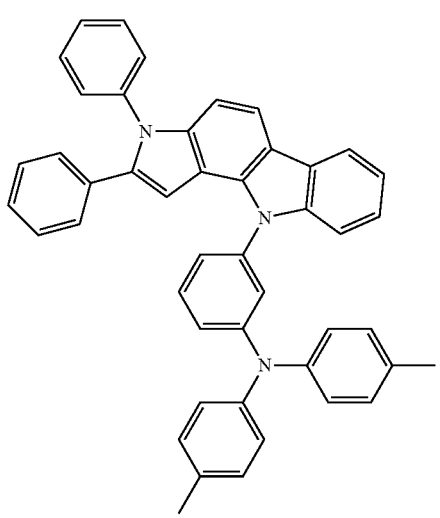
Inv680
-continued
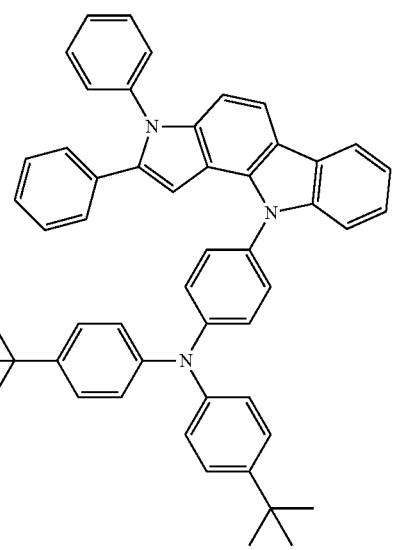
Inv681
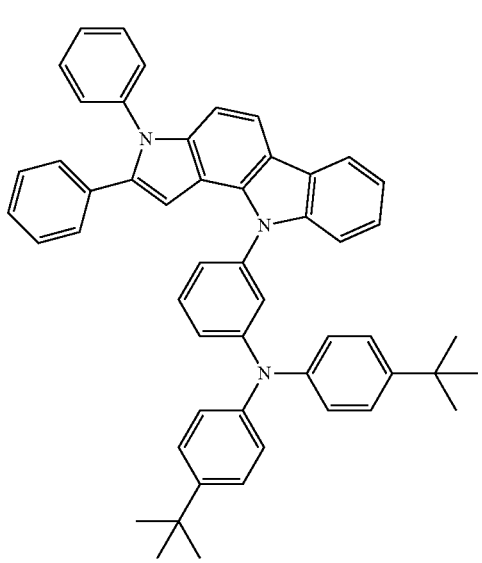
Inv682
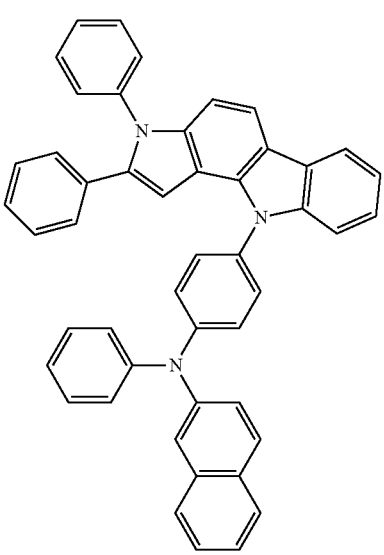
Inv683

Inv684
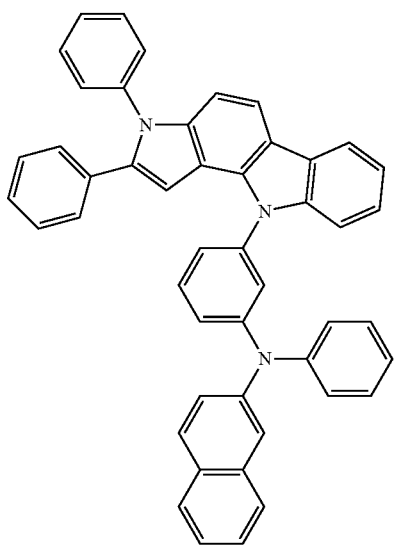
Inv685
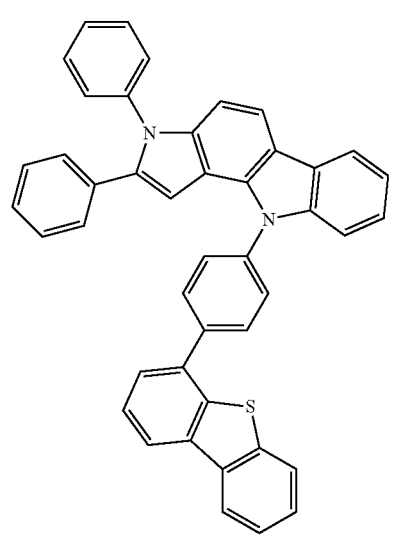
Inv686
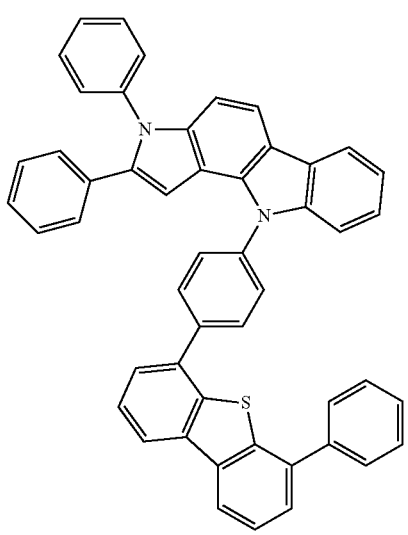
Inv687
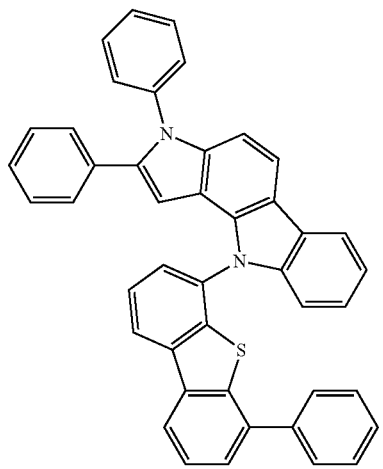
Inv688
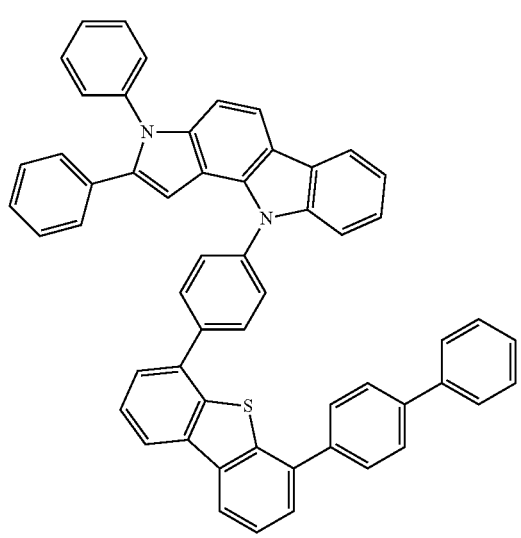
Inv689
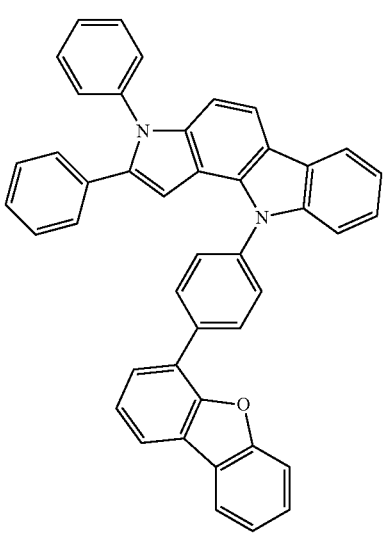

Inv690
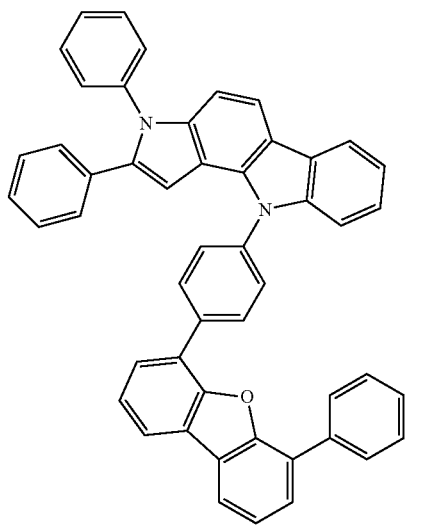
Inv691
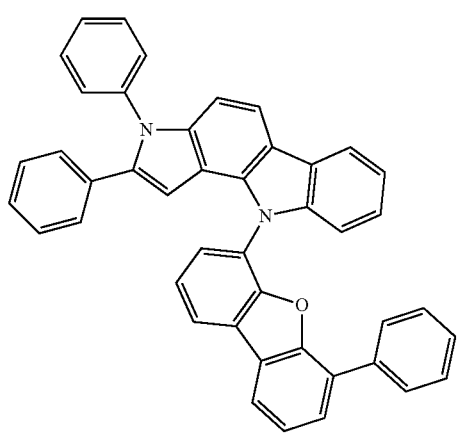
Inv692
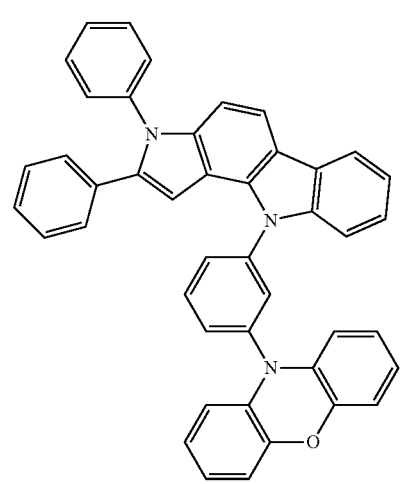
Inv693
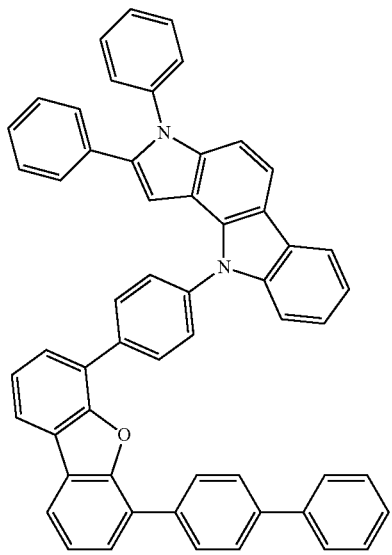
Inv694
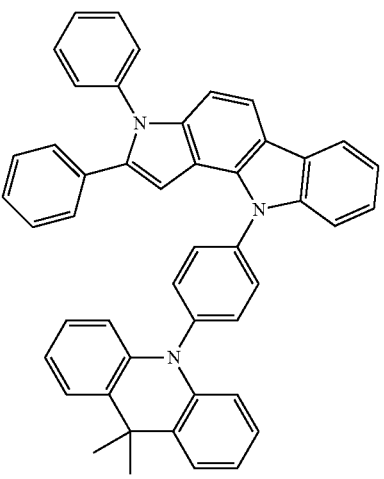
Inv695
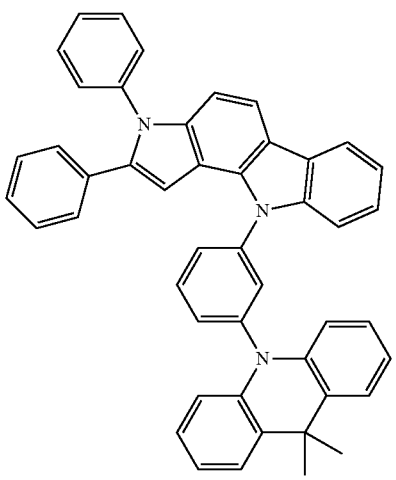

-continued
Inv696
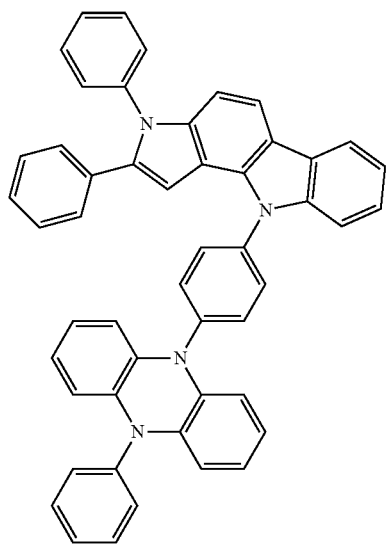
Inv697
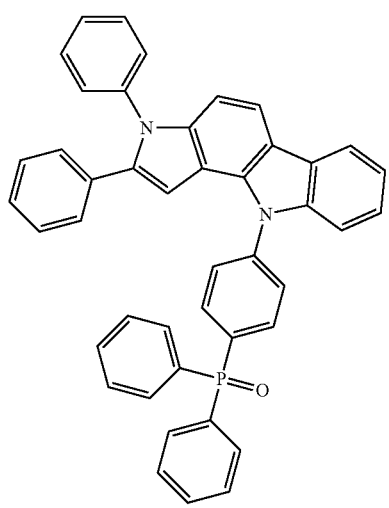
Inv698
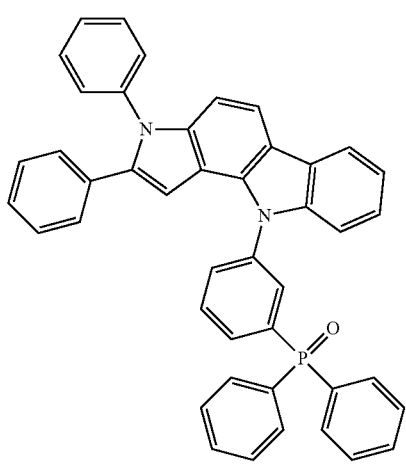
-continued
Inv699
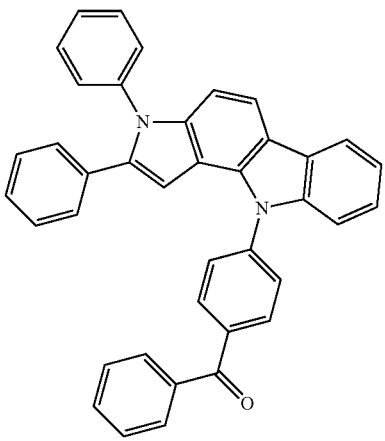
Inv700
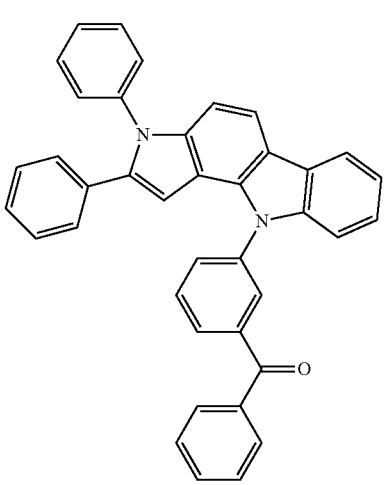
Inv701
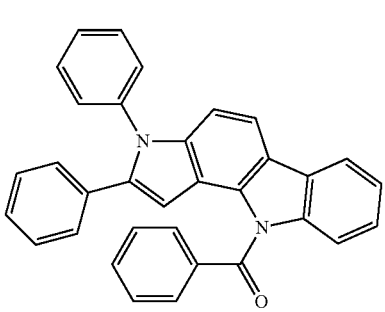
Inv702
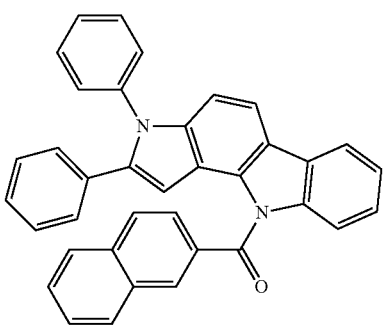

Inv703
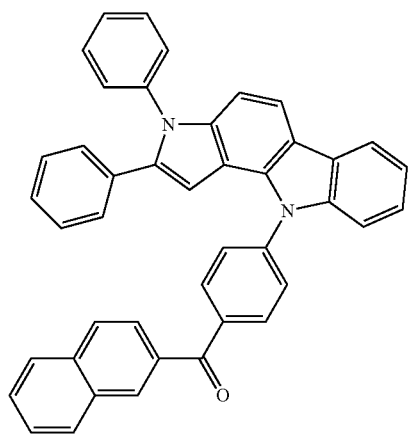
Inv704
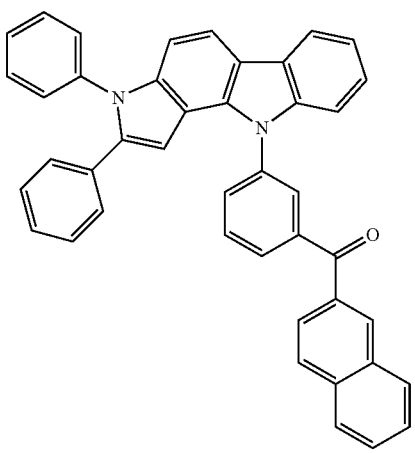
Inv705
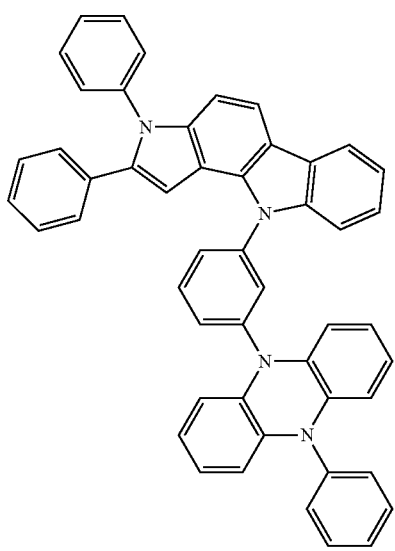
Inv706
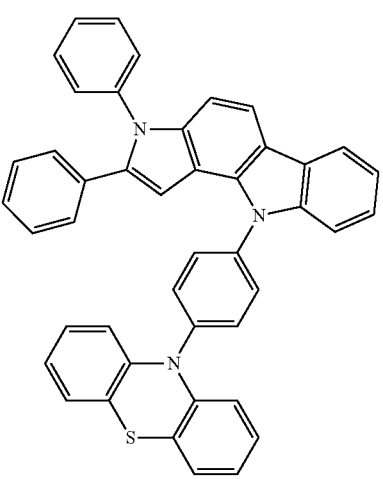
Inv707
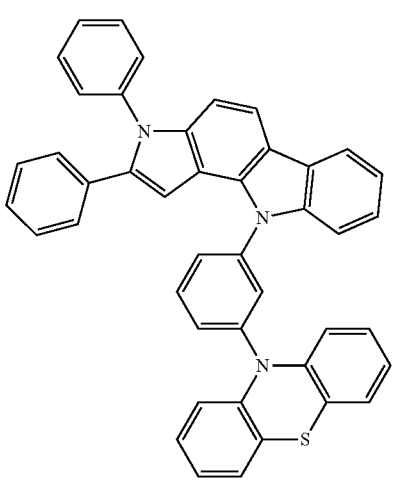
Inv708
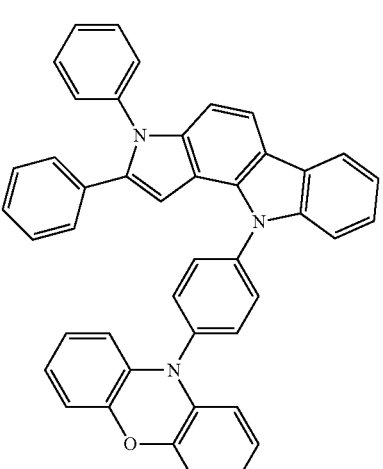

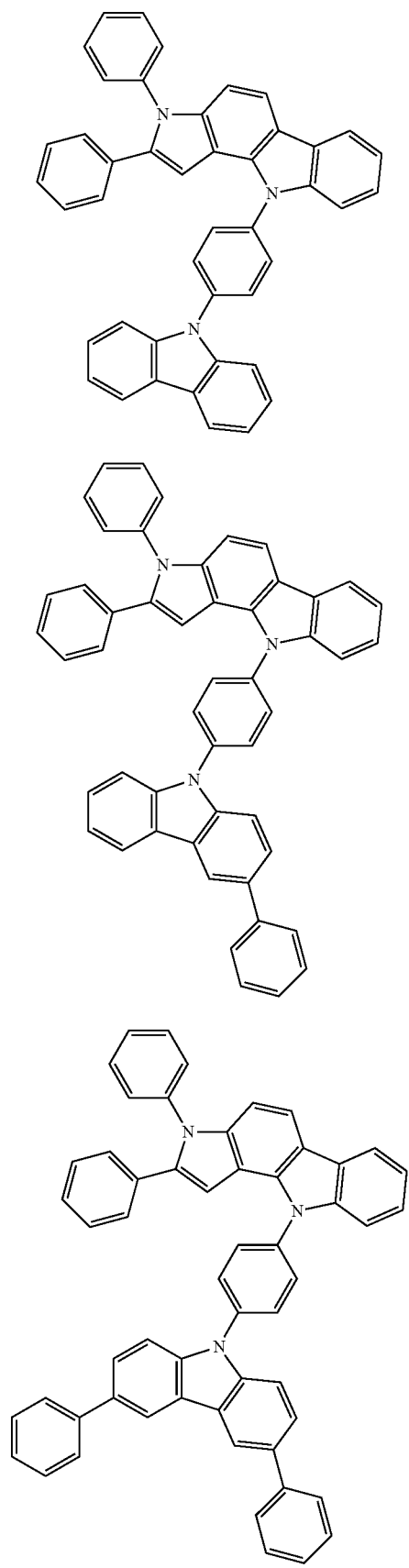
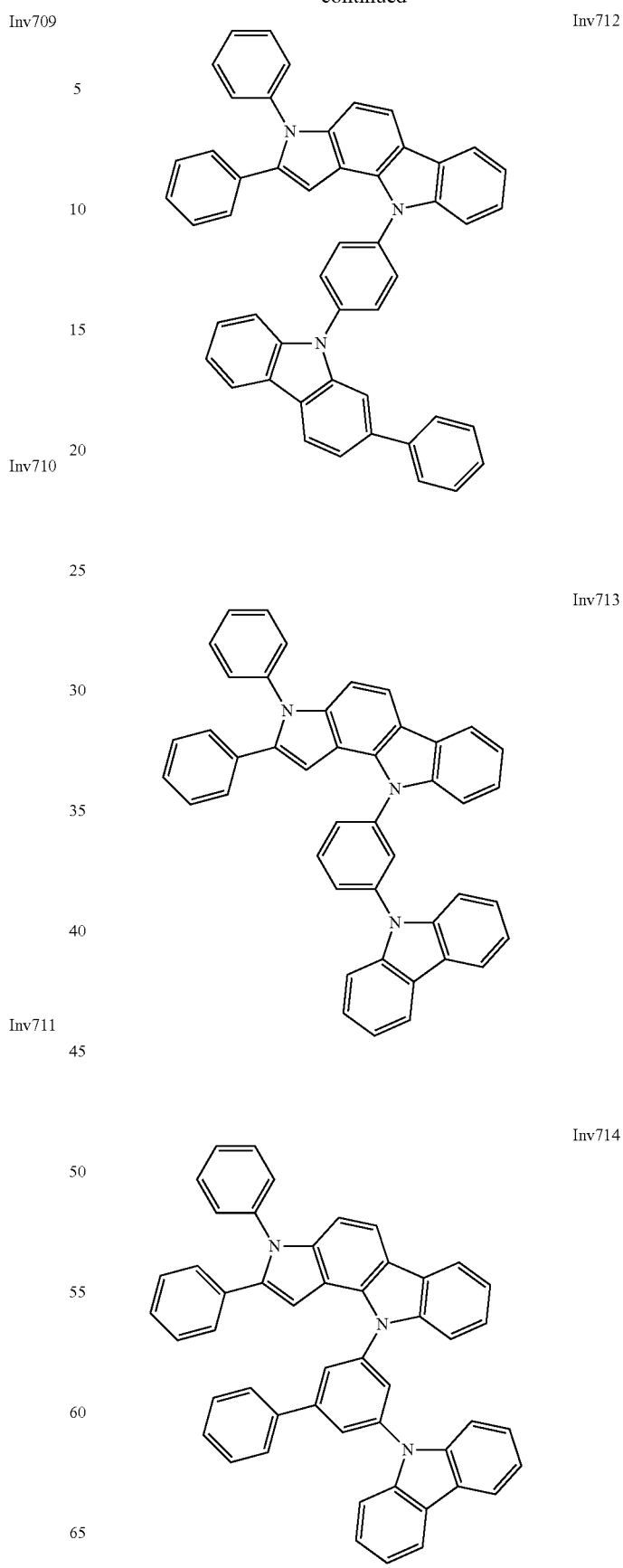

Inv715
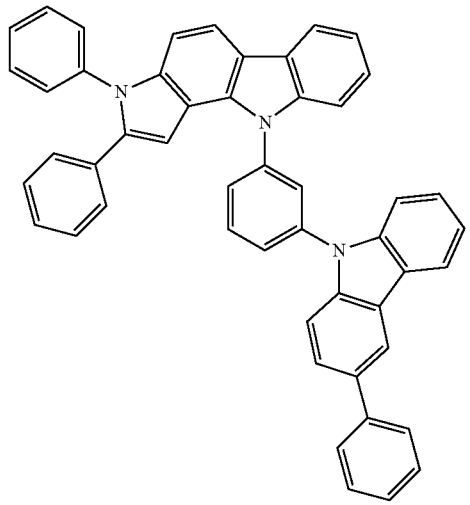
Inv716
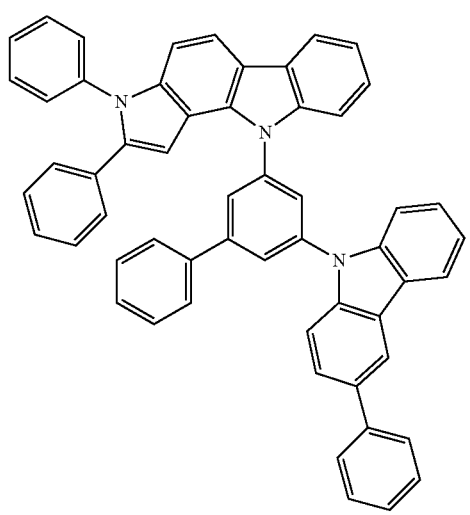
Inv717
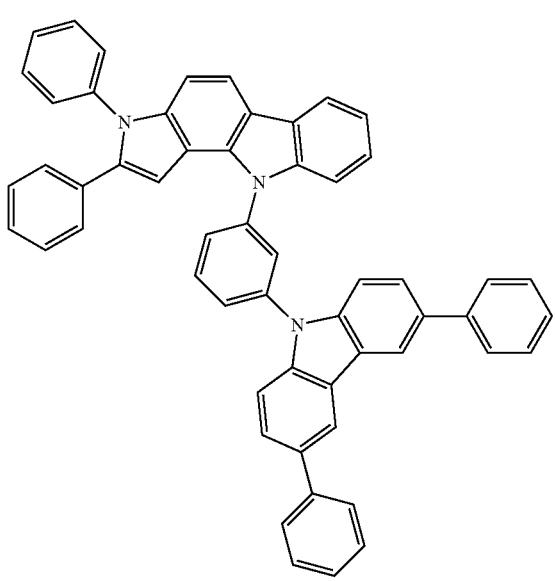
Inv718
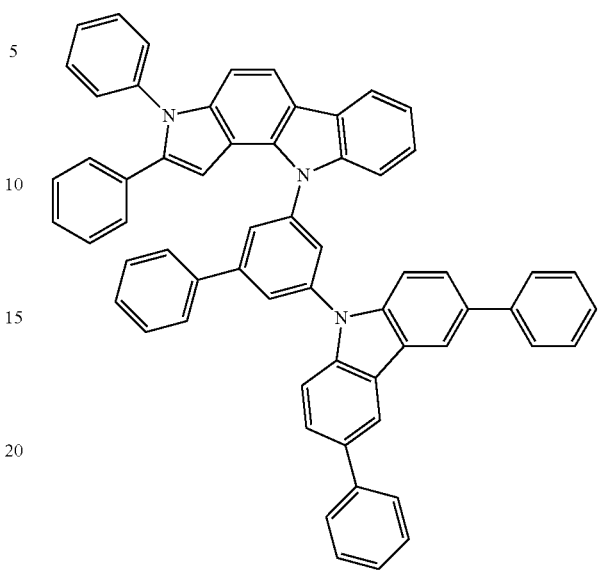
Inv719
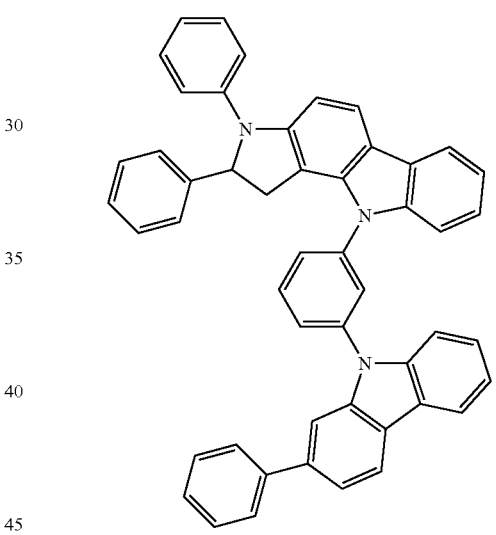
Inv720
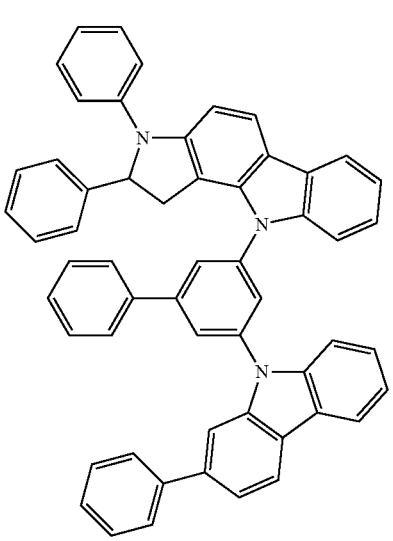

Inv721
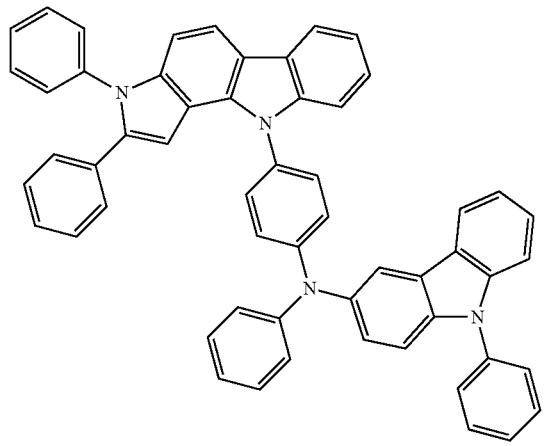
Inv724
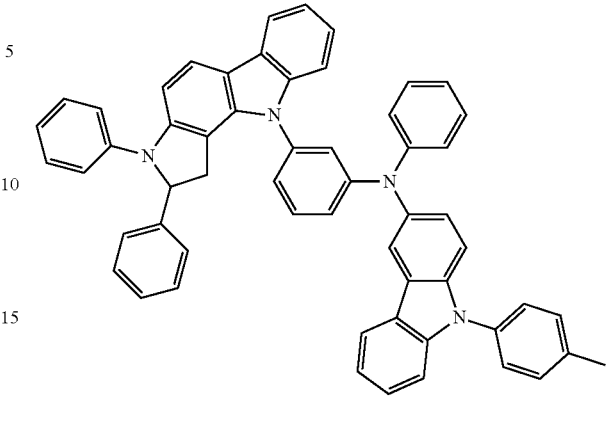
Inv722
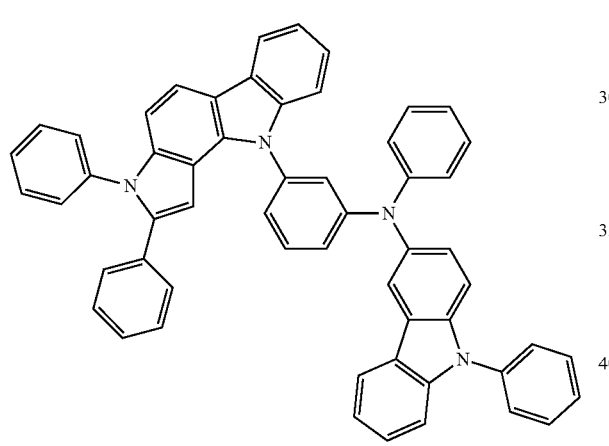
Inv725
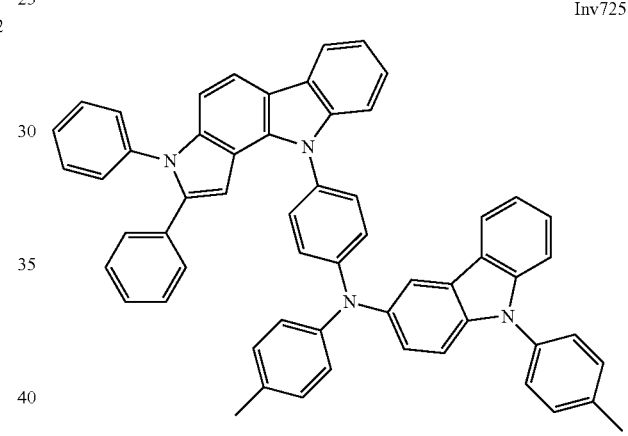
Inv723
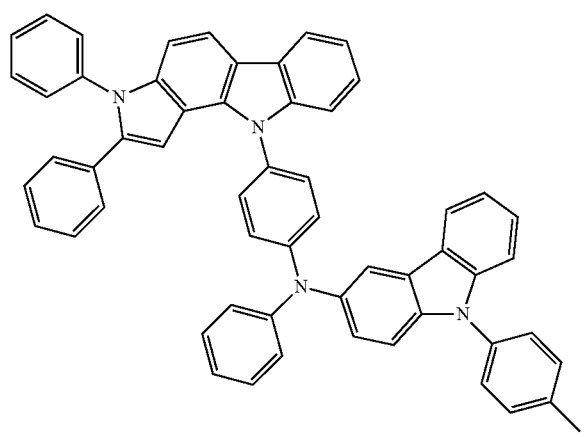
Inv726
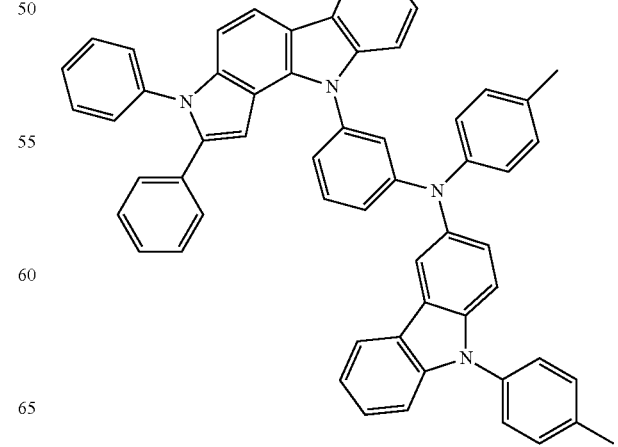

-continued
Inv727
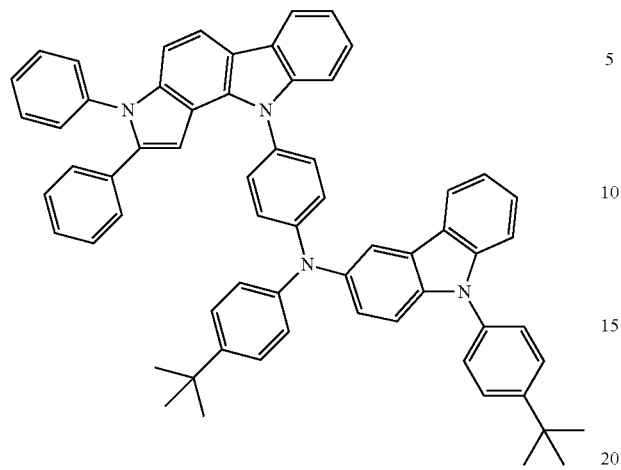
Inv728
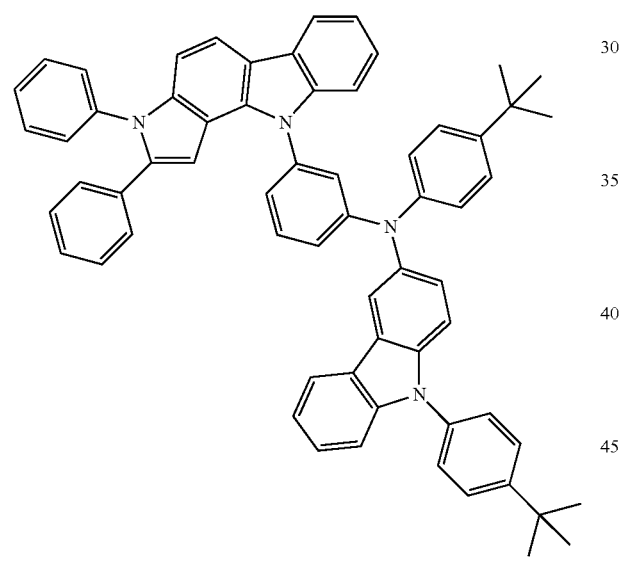
Inv729
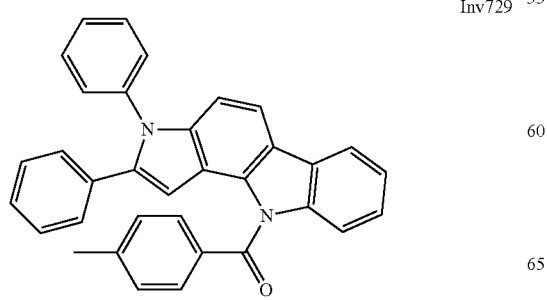
-continued
Inv730
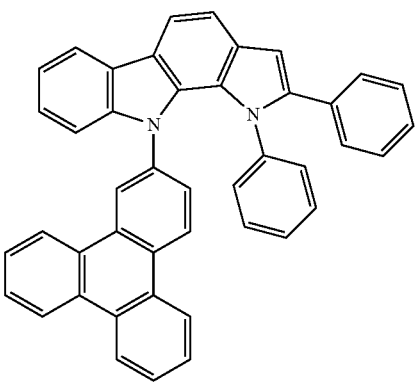
Inv731
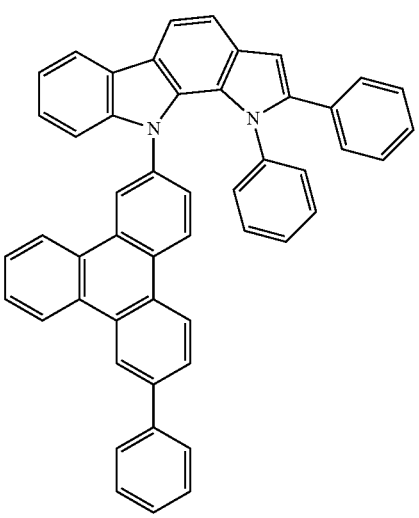
Inv732
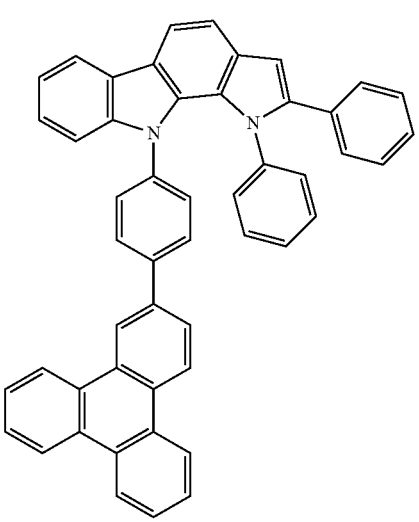

-continued
Inv733
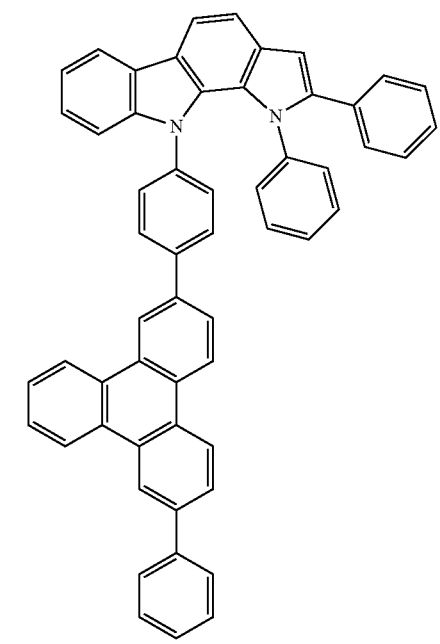
Inv734
Inv735
-continued
Inv736
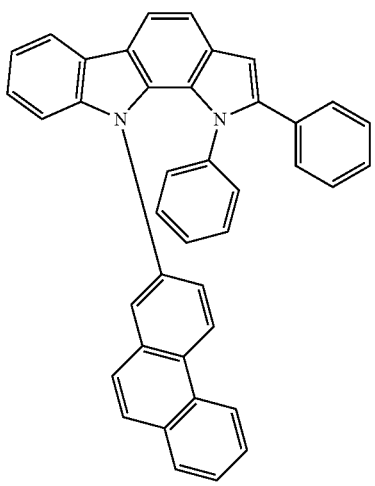
Inv737
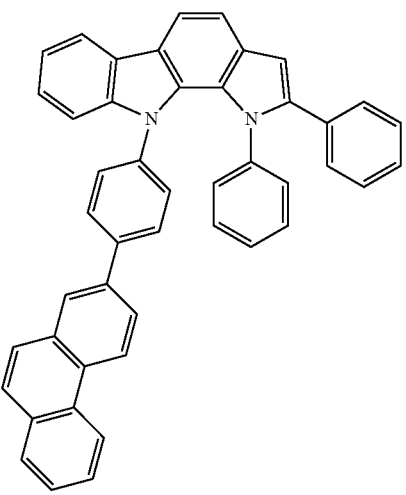
Inv738
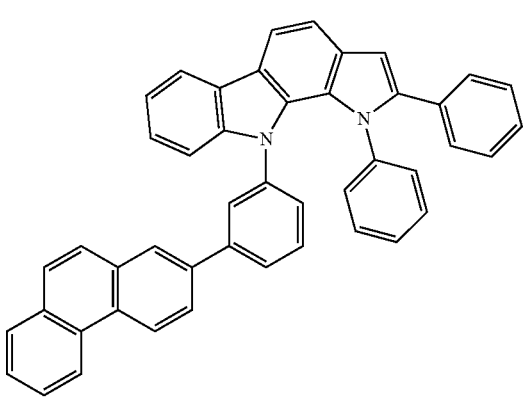

Inv739
Inv740
Inv741
Inv742
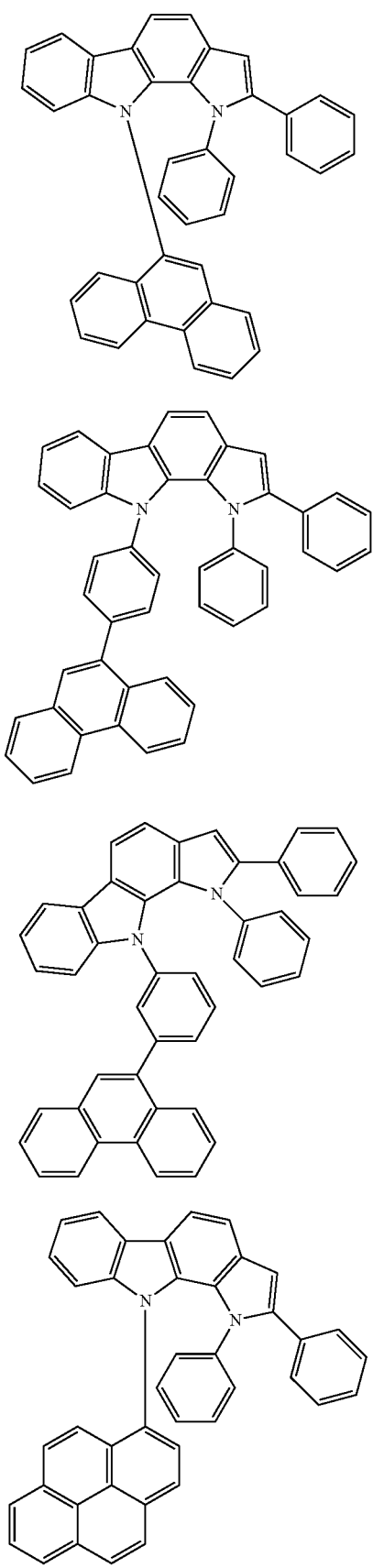
Inv743
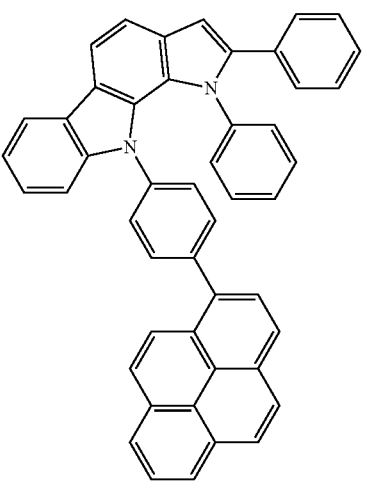
Inv744
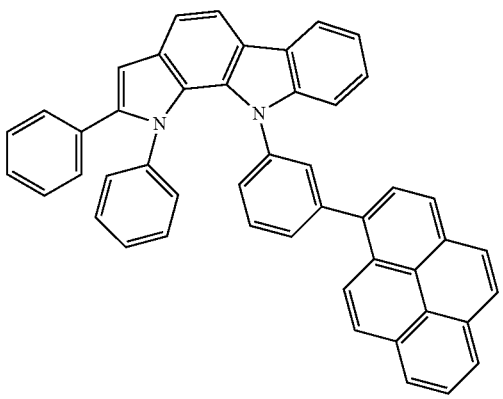
Inv745
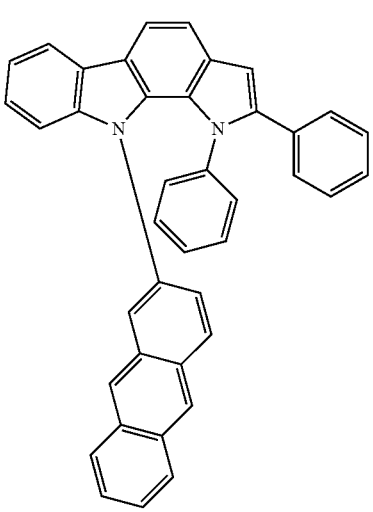

Inv746
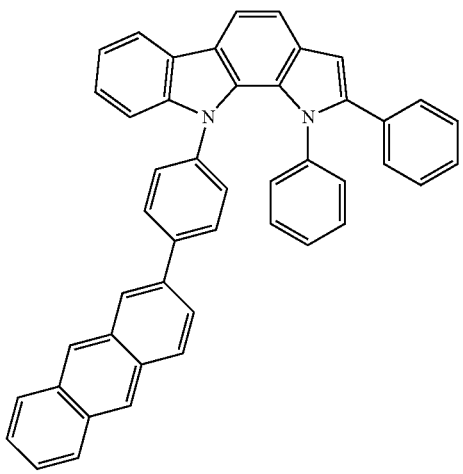
Inv747
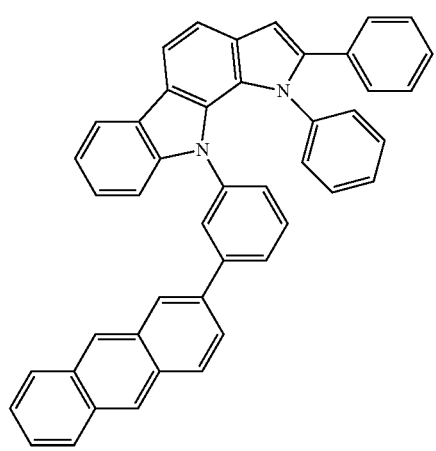
Inv748
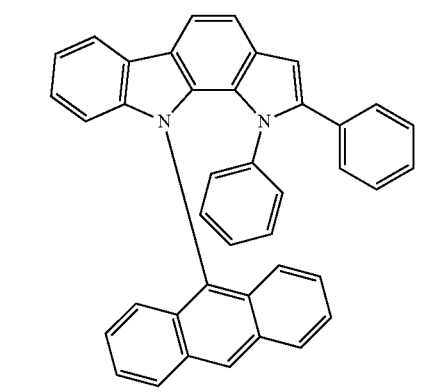
Inv749
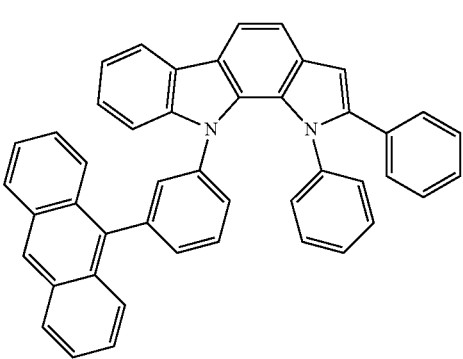
Inv750
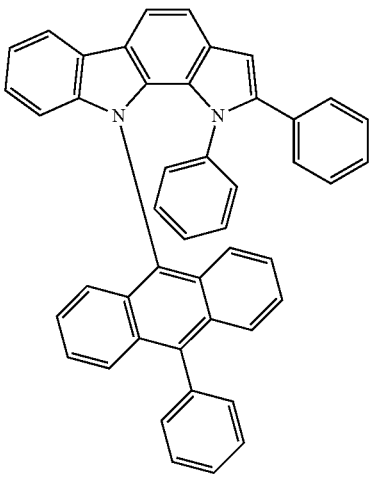
Inv751
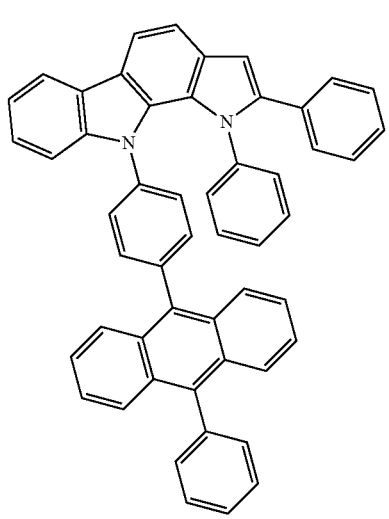
Inv752
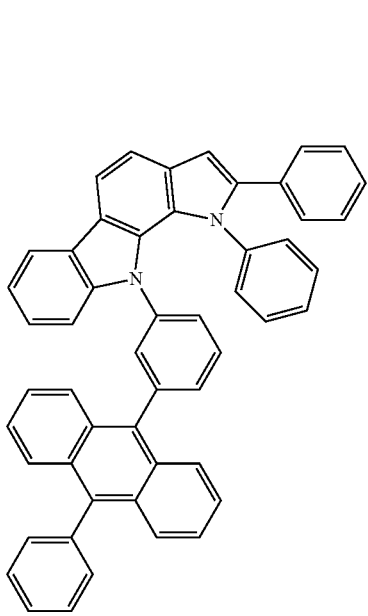

Inv753
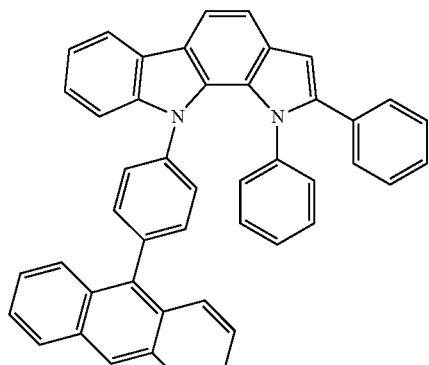
Inv754
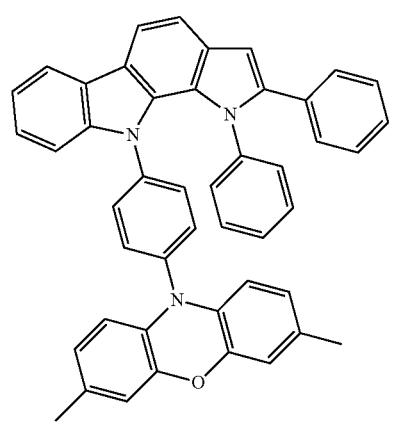
Inv755
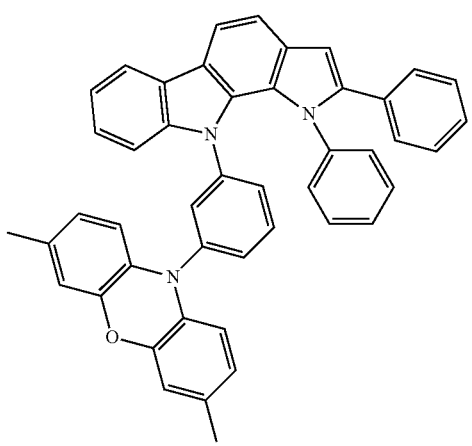
Inv756
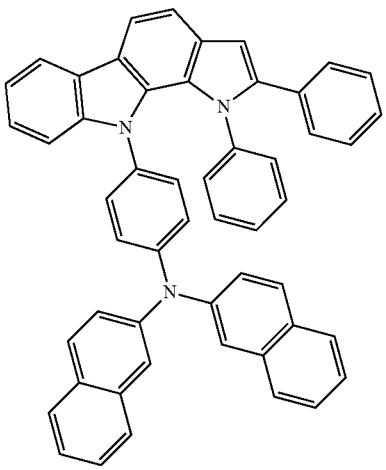
Inv757
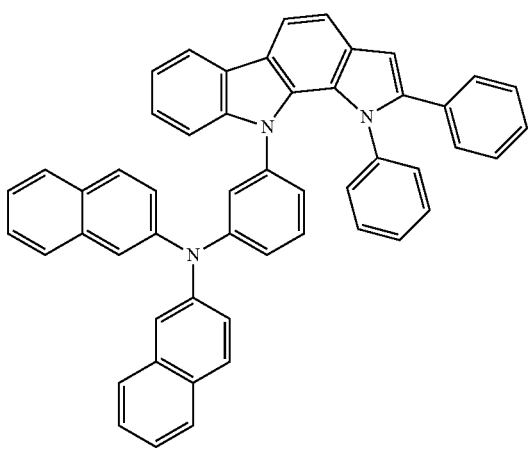
Inv758
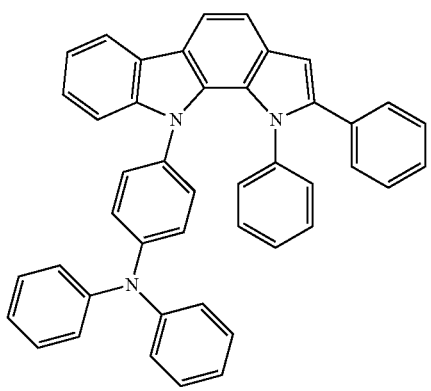

Inv759
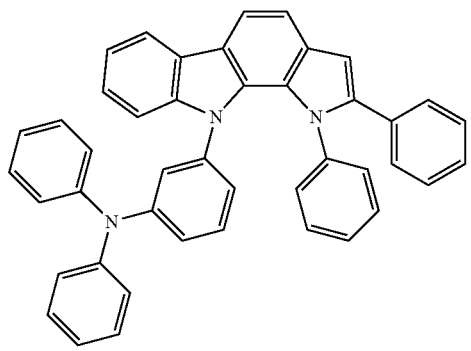
Inv760
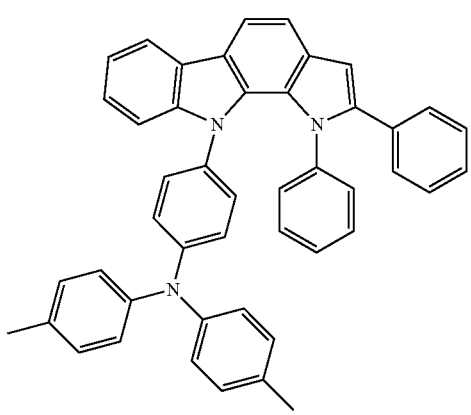
Inv761
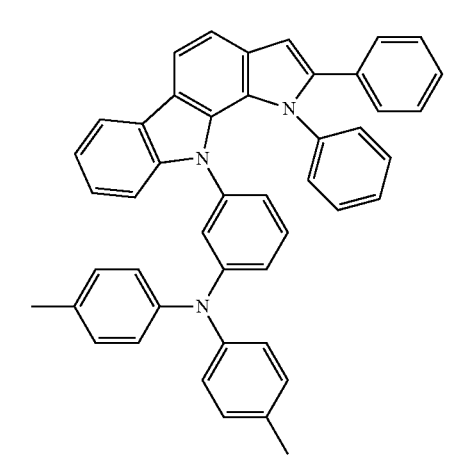
Inv762
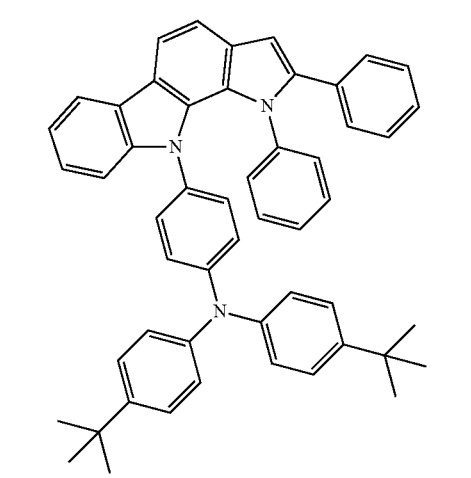
Inv763
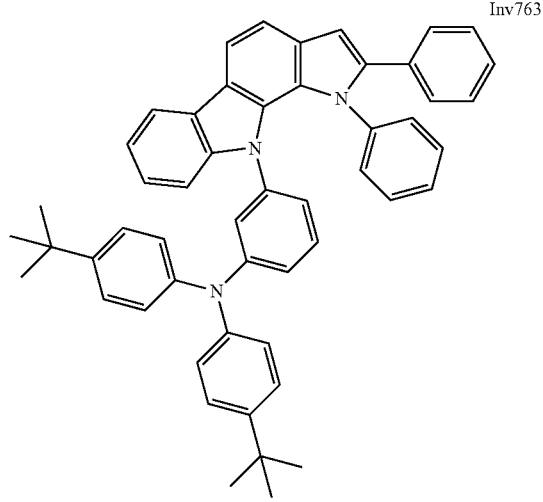
Inv764
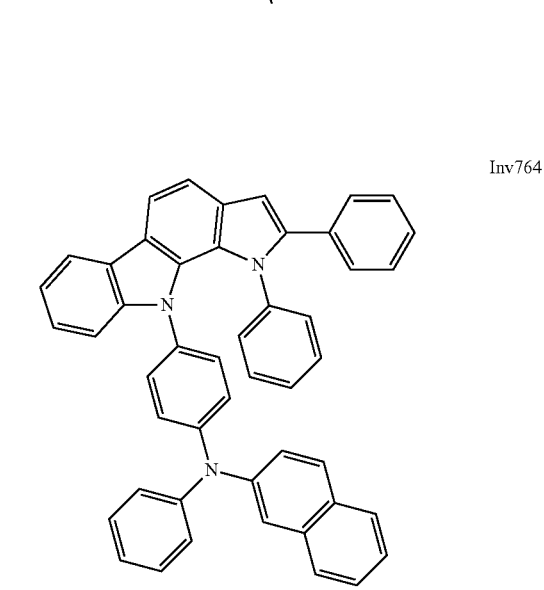
Inv 765
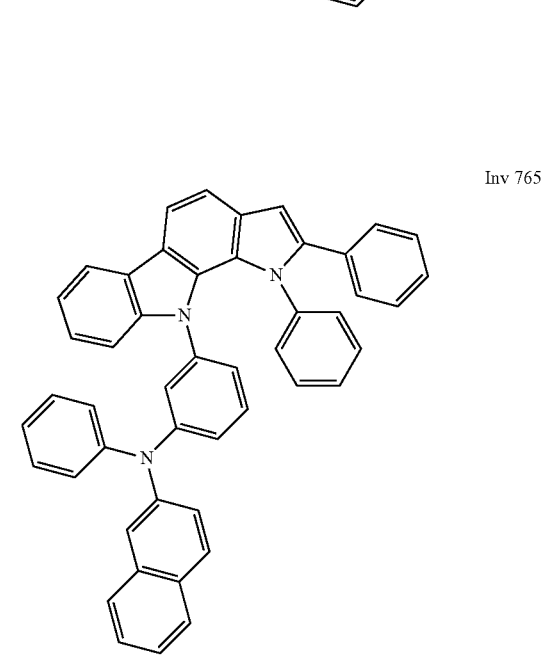

Inv766
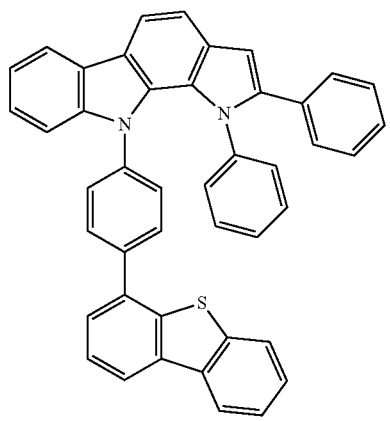
Inv767
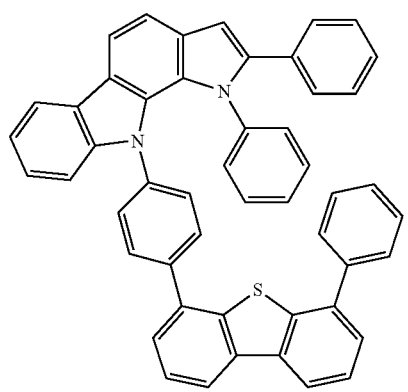
Inv768
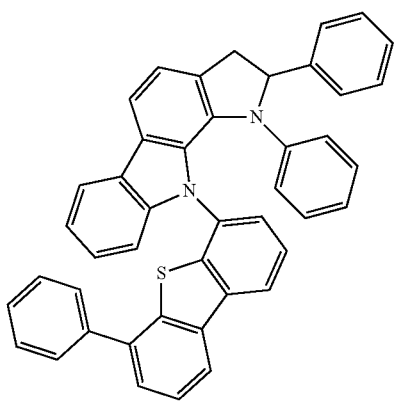
Inv769
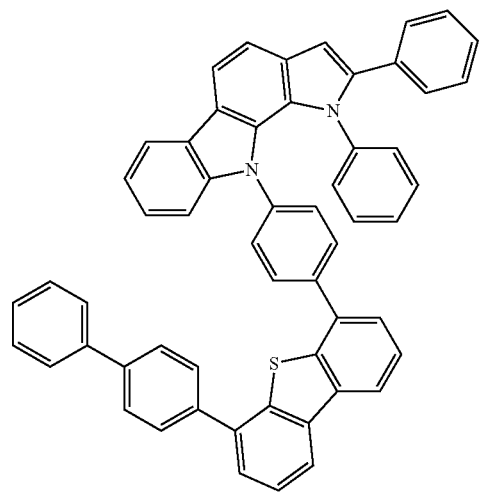
Inv770
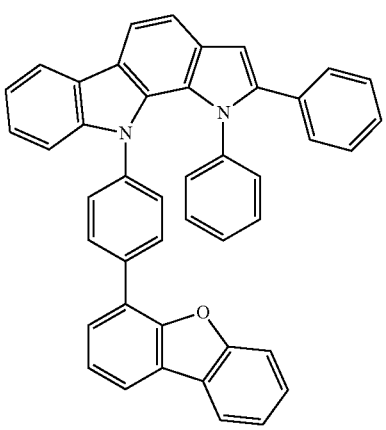
Inv771
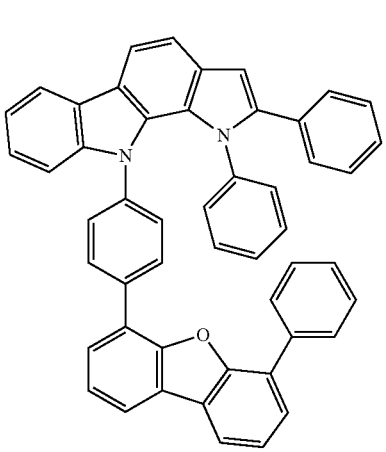

Inv772
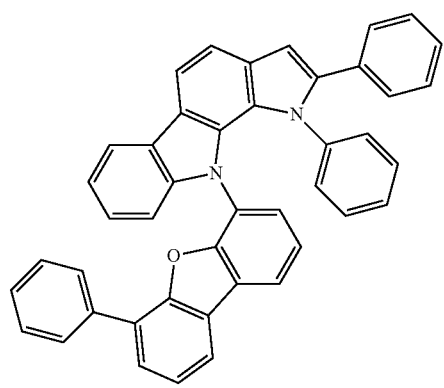
Inv773
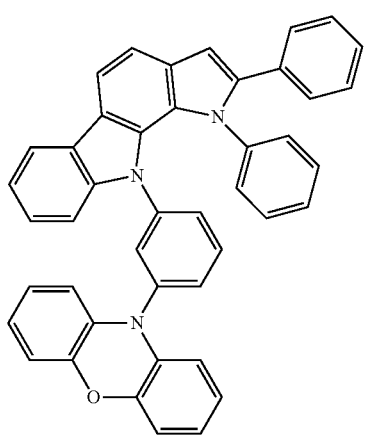
Inv774
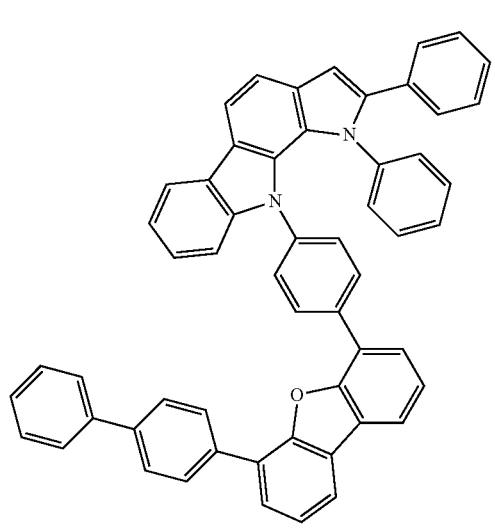
Inv775
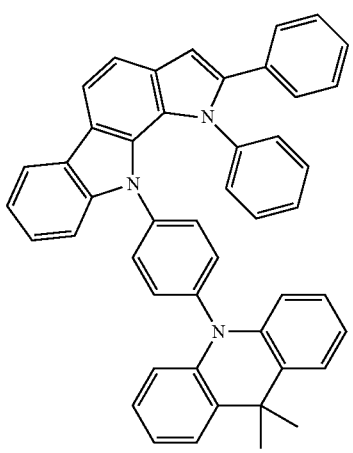
Inv776
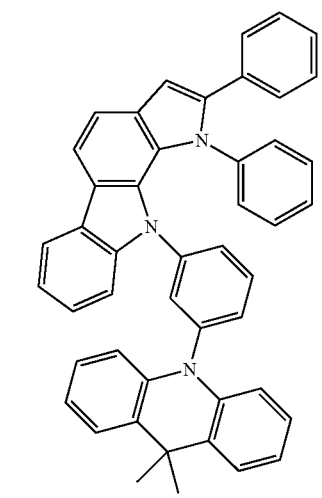
Inv777
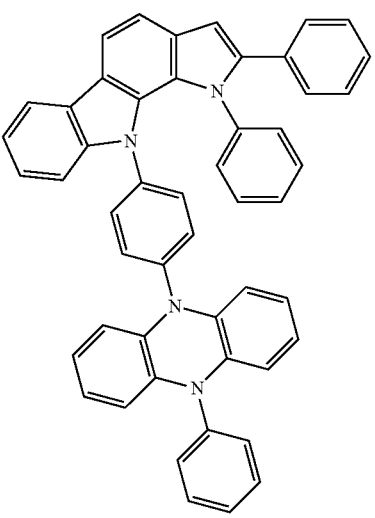

Inv778
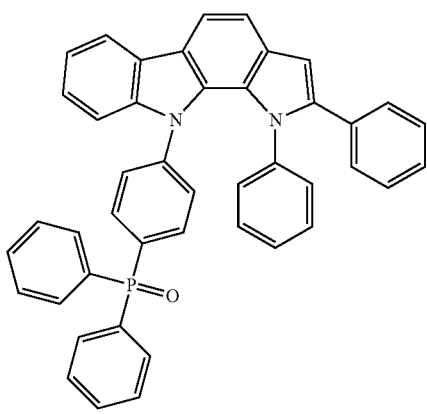
Inv779
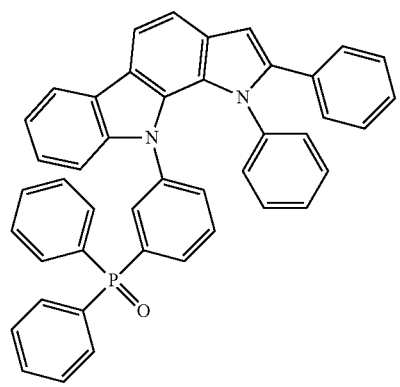
Inv780
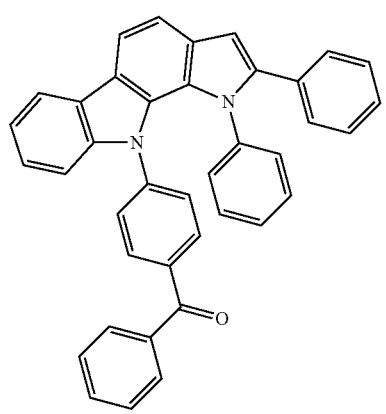
Inv781
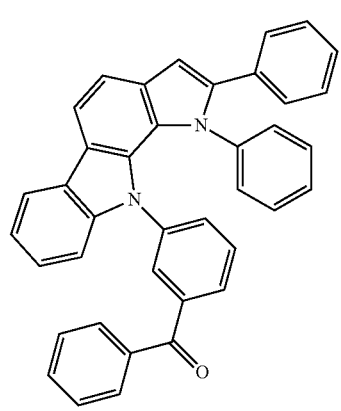
Inv782
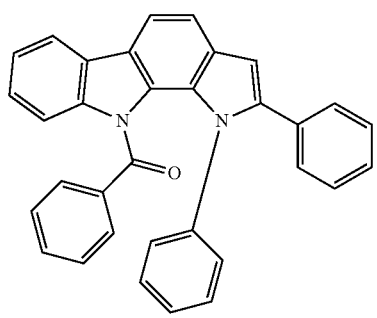
Inv783
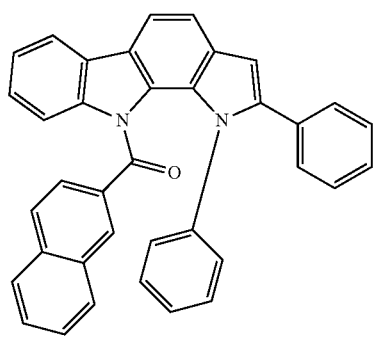
Inv784
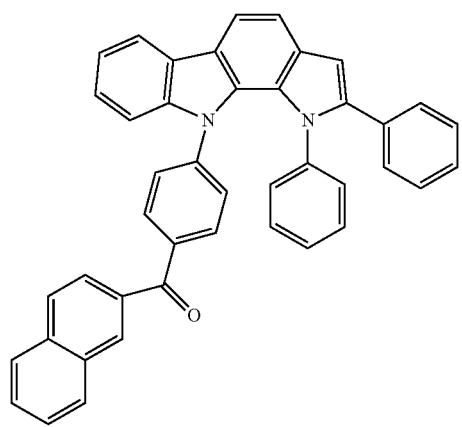
Inv785
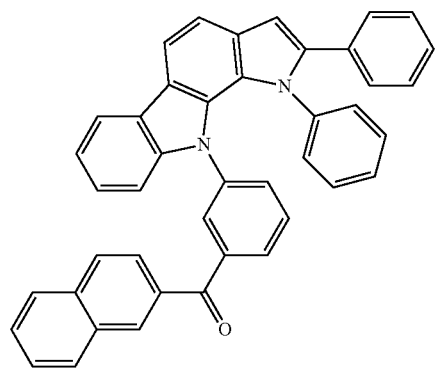

Inv786
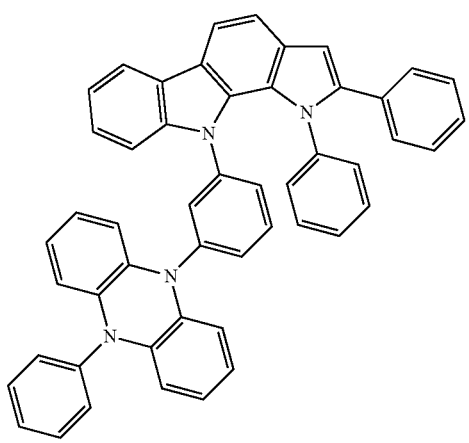
Inv787
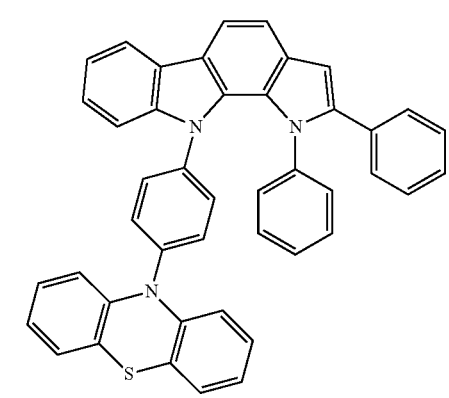
Inv788
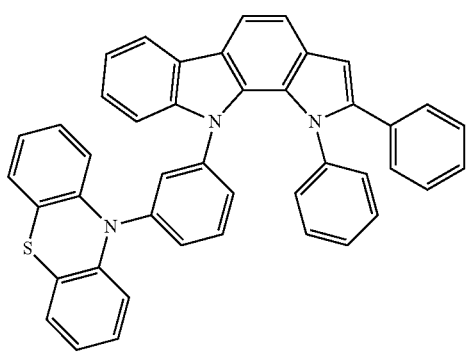
Inv789
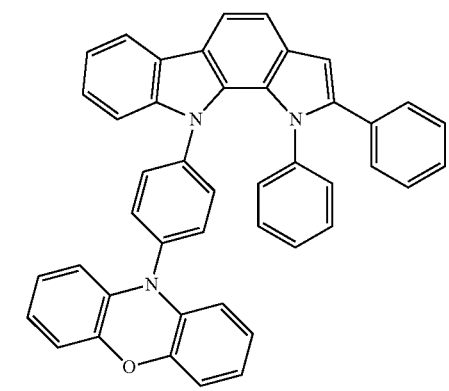
Inv790
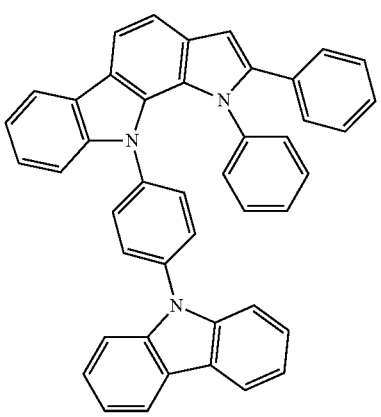
Inv791
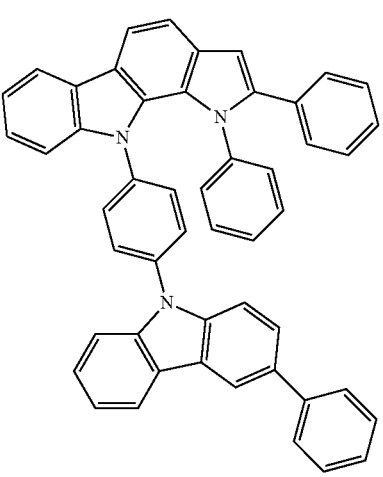
Inv792
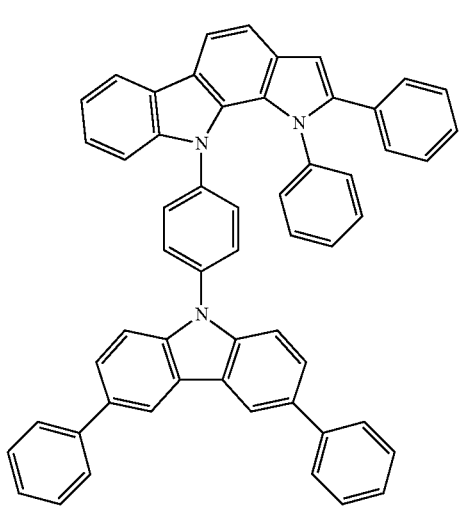

-continued
Inv793
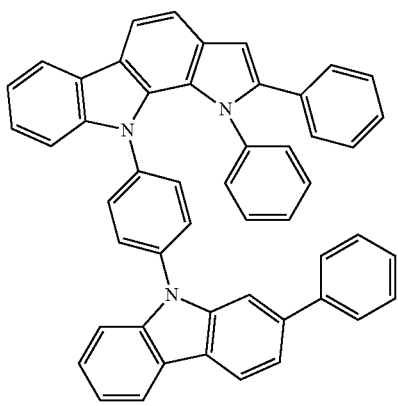
Inv794
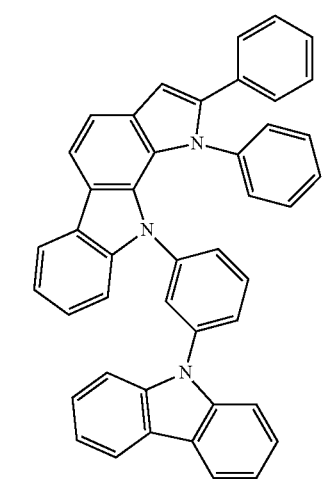
Inv795
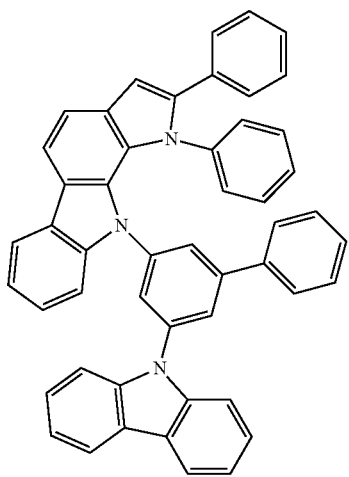
-continued
Inv796
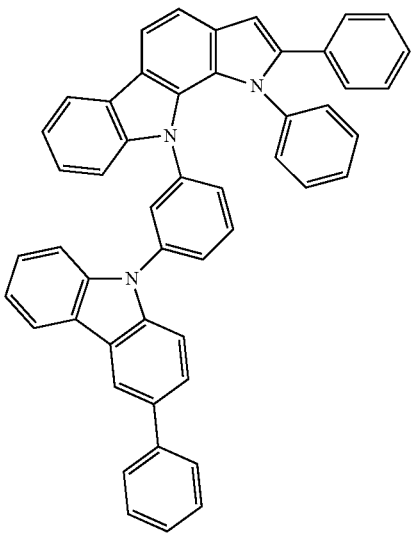
Inv797
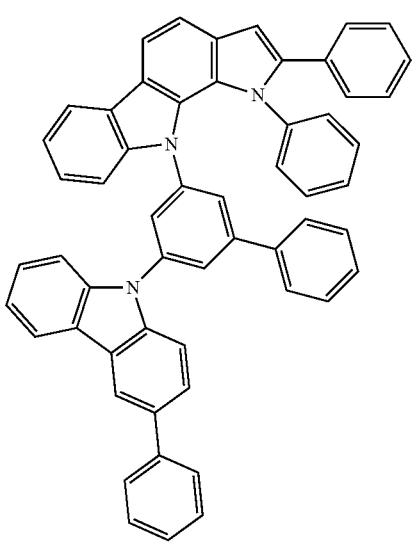
Inv798
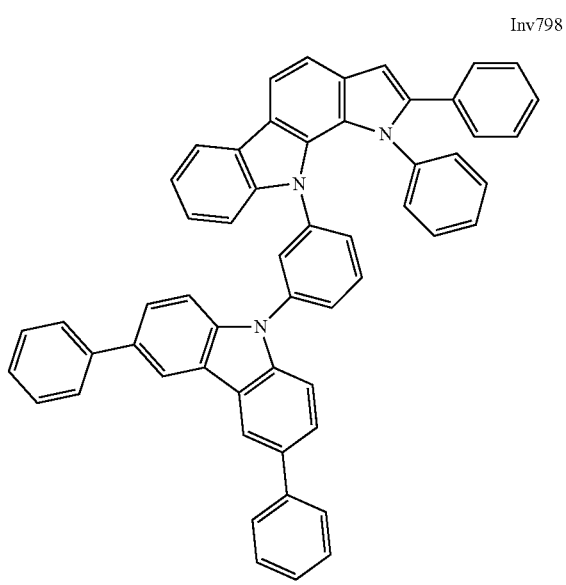

-continued
Inv799
Inv802
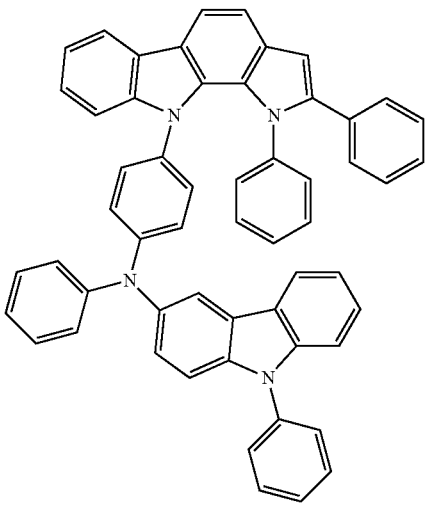
Inv800
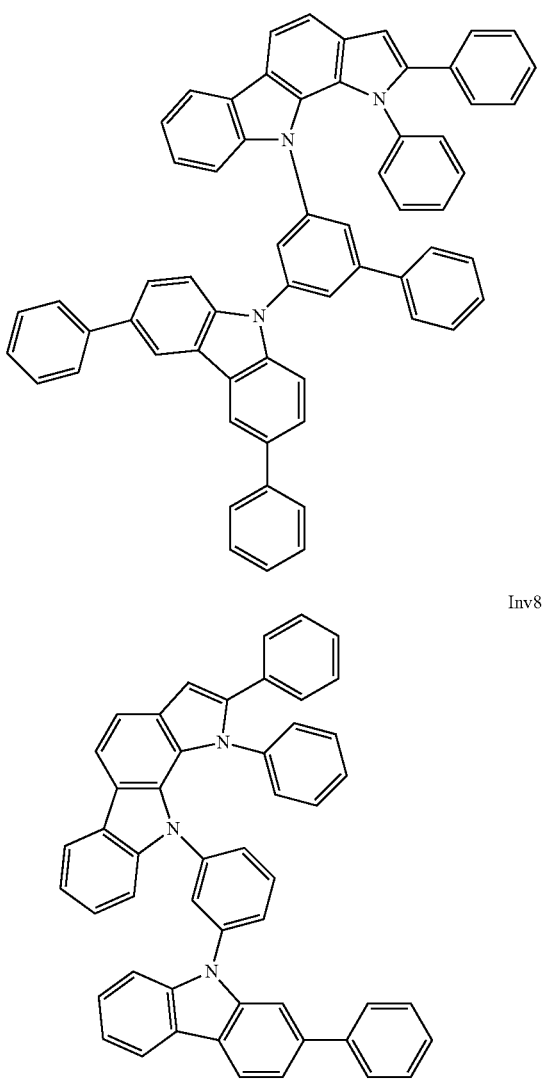
Inv803
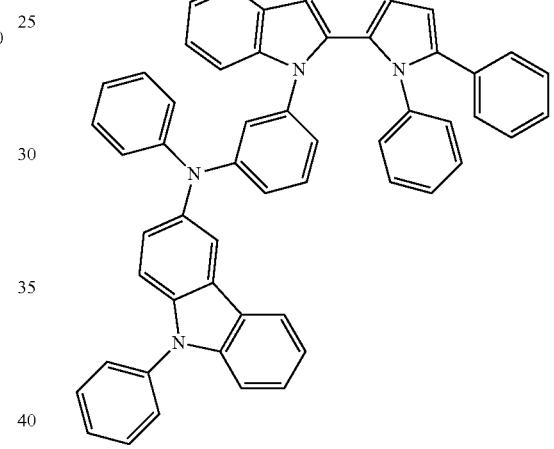
Inv801
Inv804
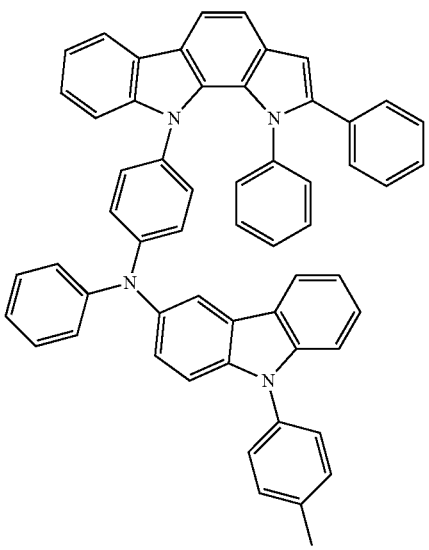

Inv805
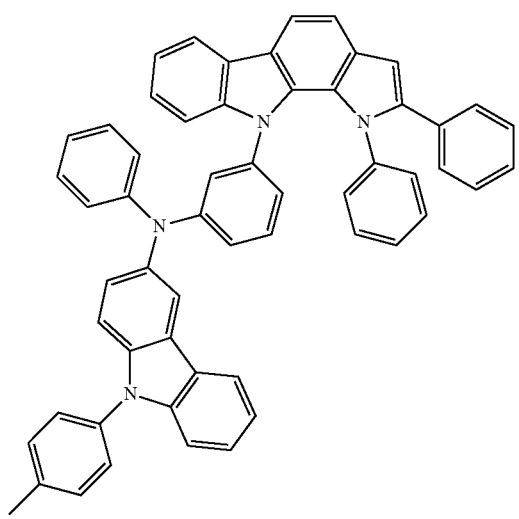
Inv806
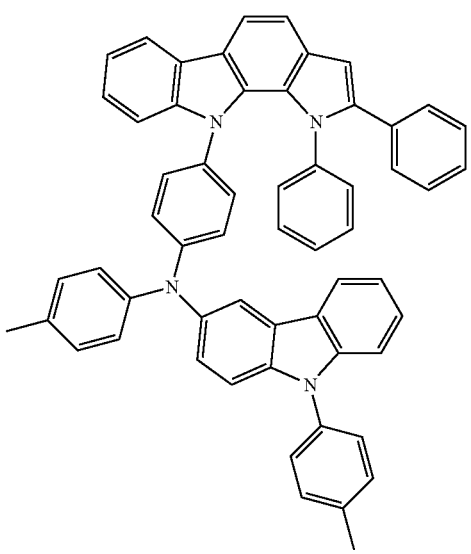
Inv807
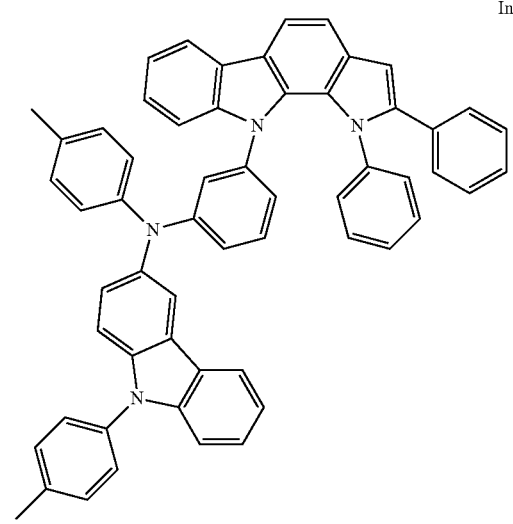
Inv808
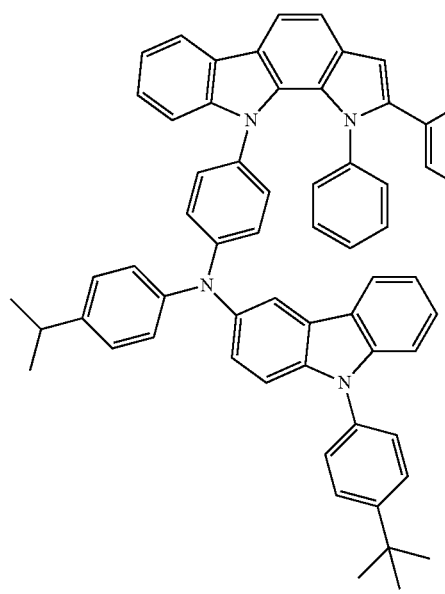
Inv809
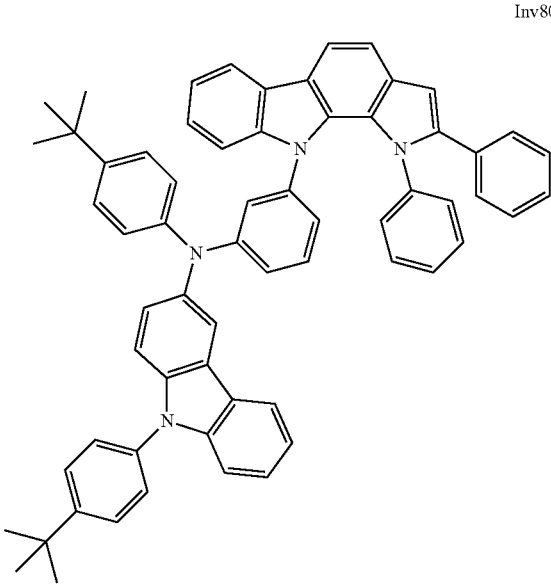
Inv810
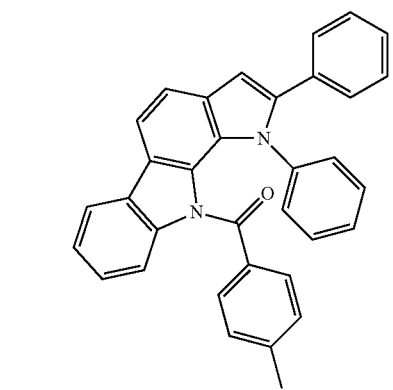

305
-continued
Inv811
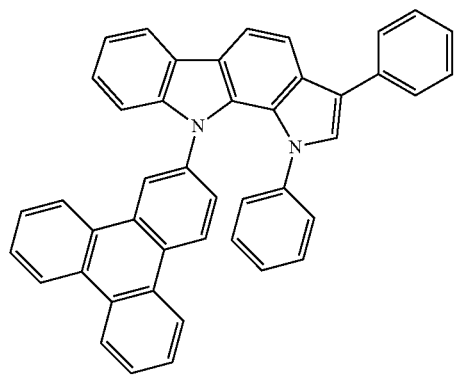
Inv812
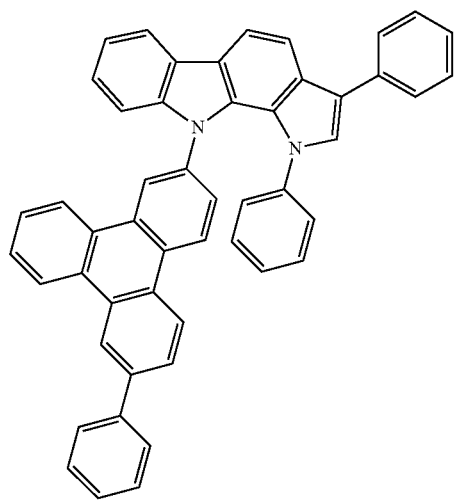
Inv813
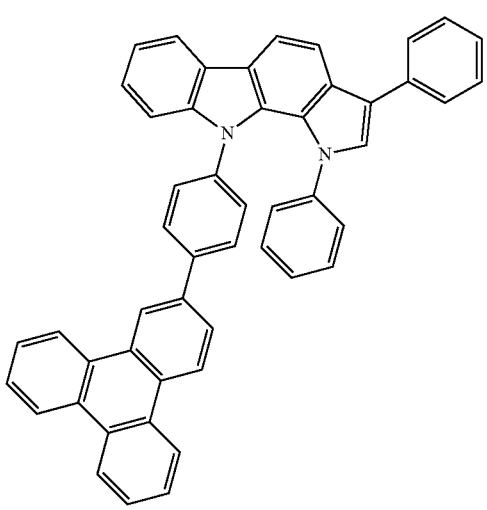
306
-continued
Inv814
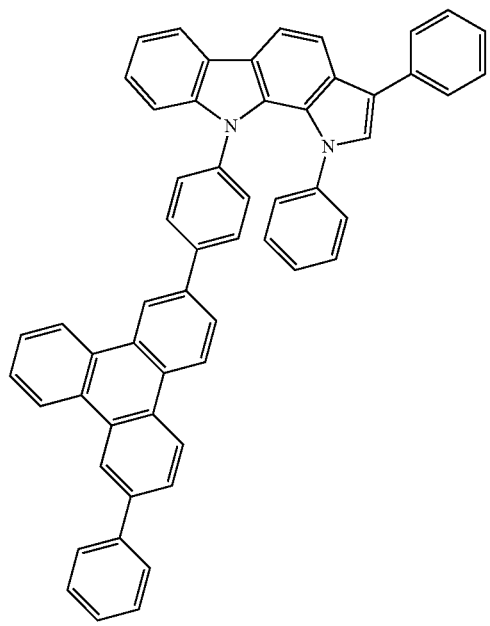
Inv815
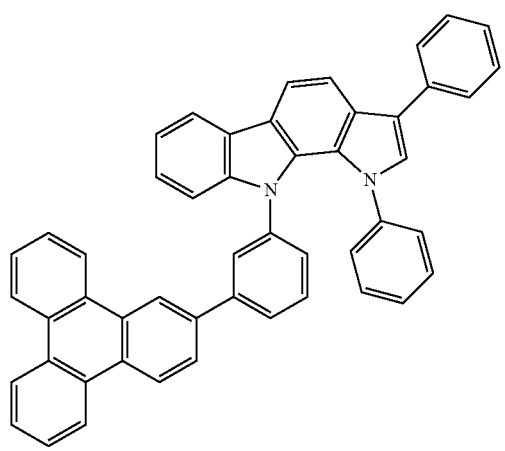
Inv816
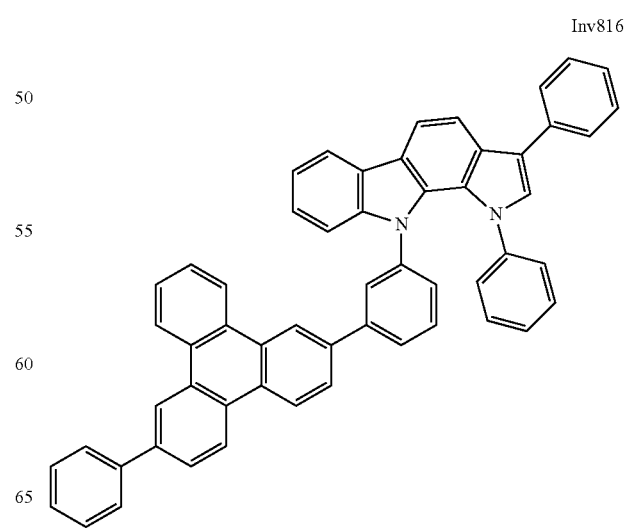

Inv817
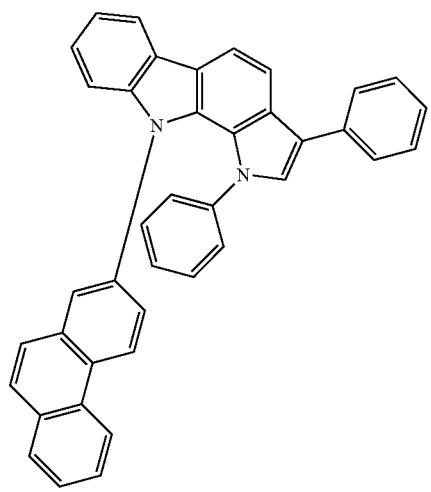
Inv818
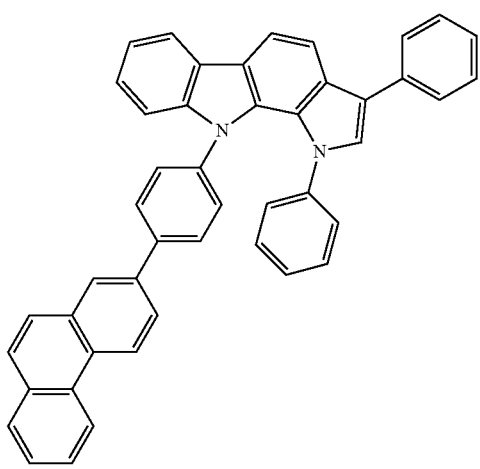
Inv819
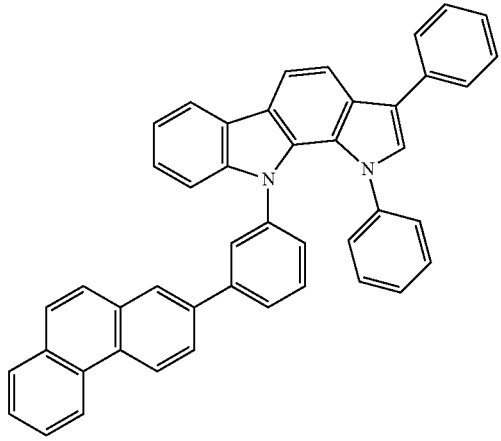
Inv820
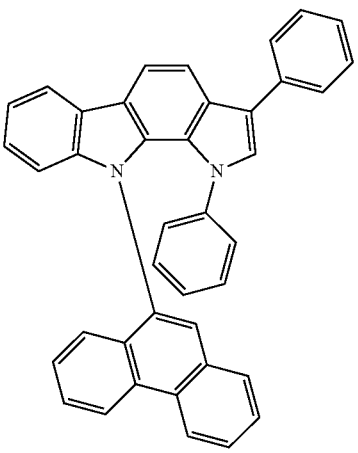
Inv821
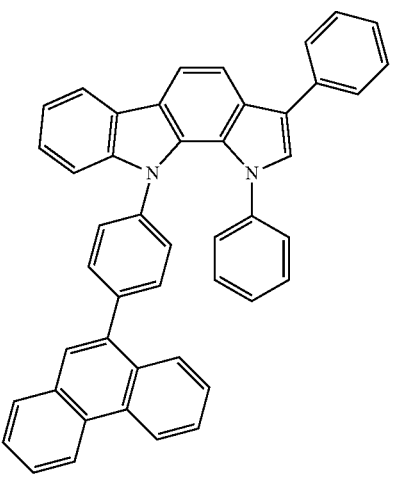
Inv822
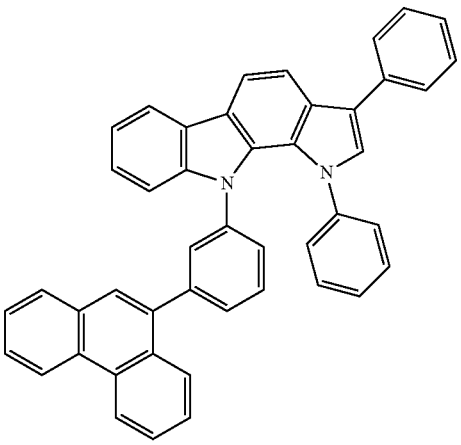

Inv823
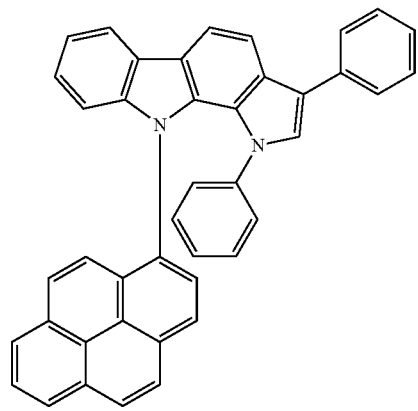
Inv824
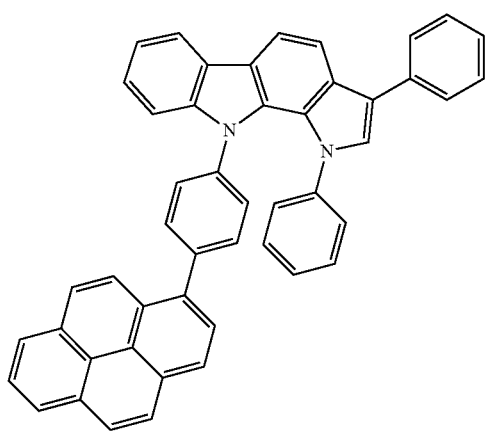
Inv825
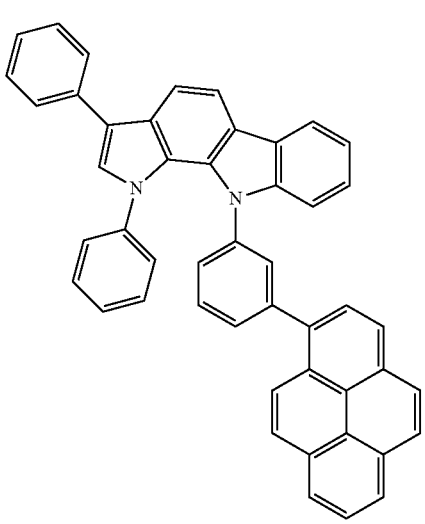
Inv826
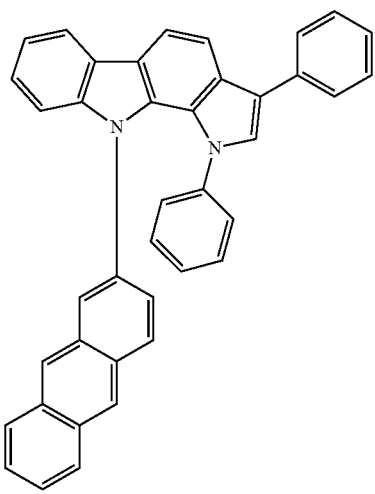
Inv827
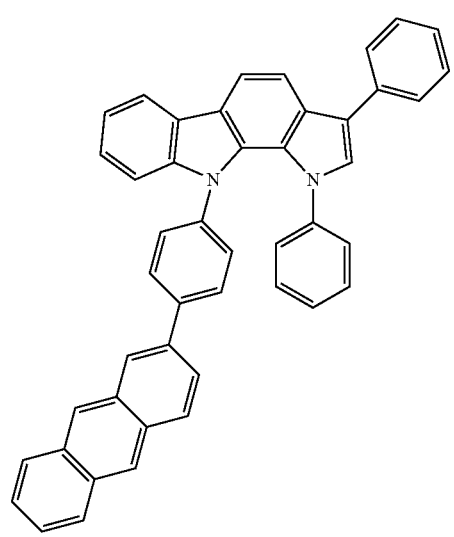
Inv828
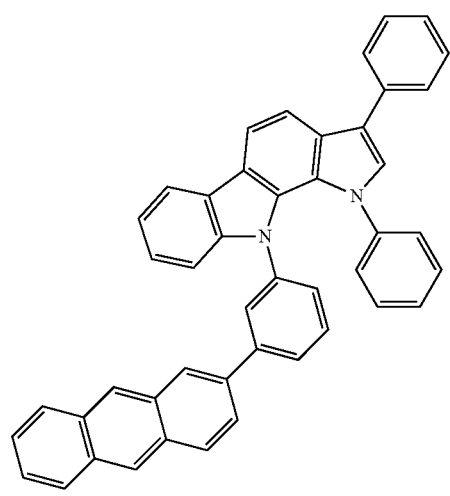

-continued
Inv829
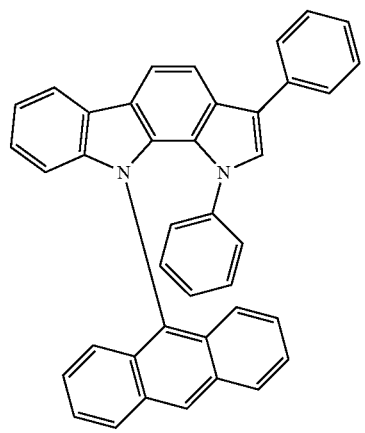
Inv830
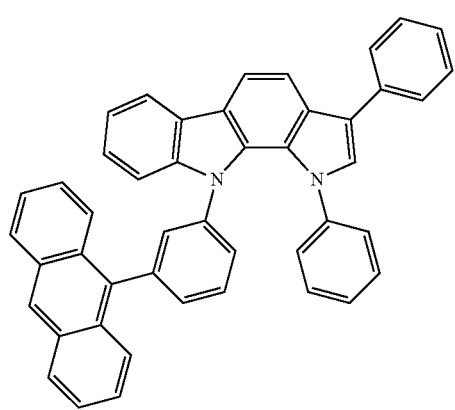
Inv831
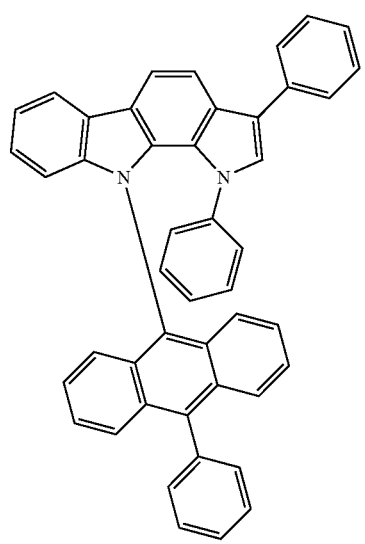
-continued
Inv832
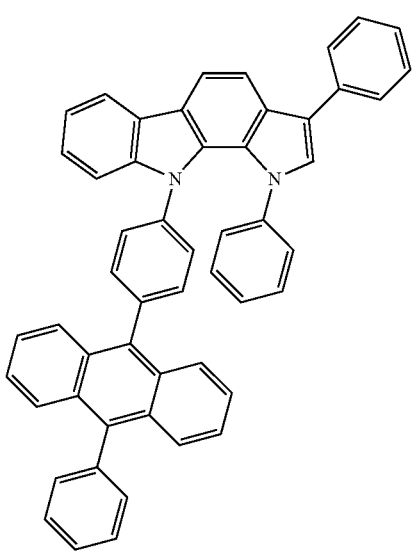
Inv833
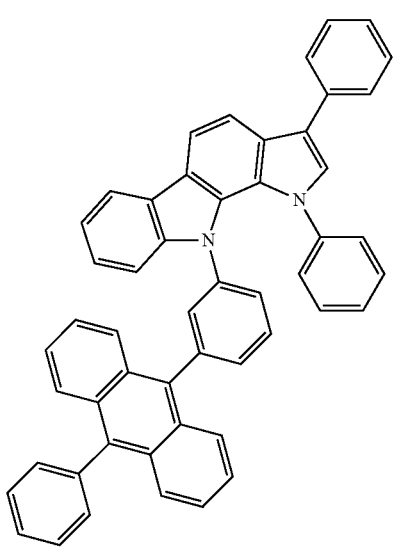
Inv834
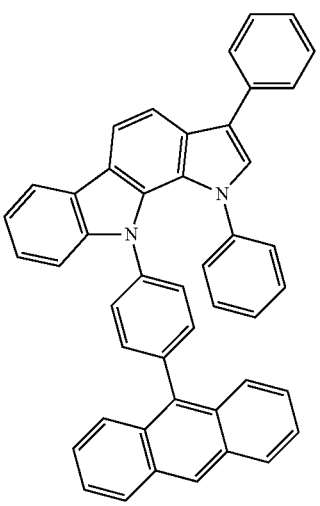

Inv835
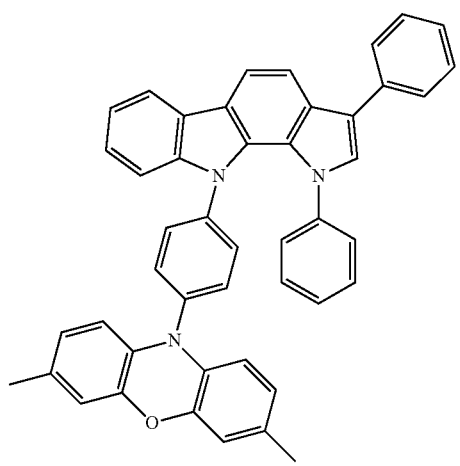
Inv836
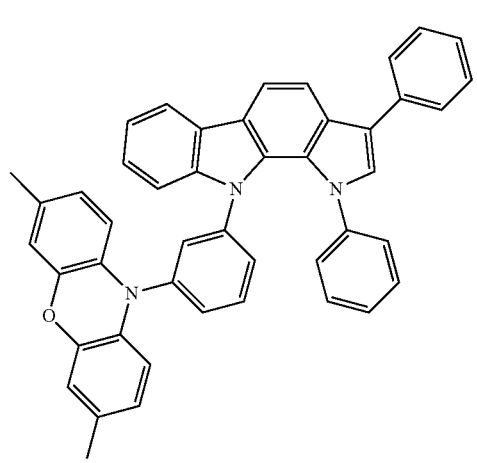
Inv837
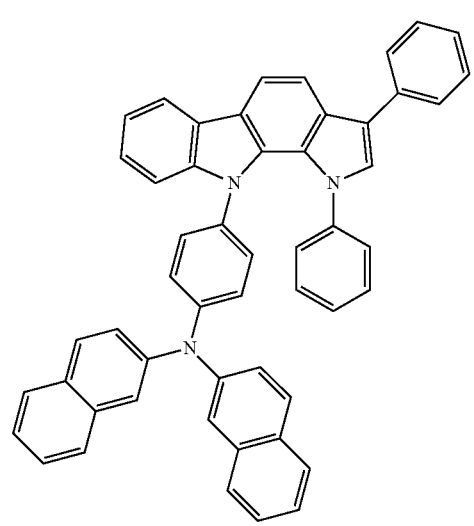
Inv838
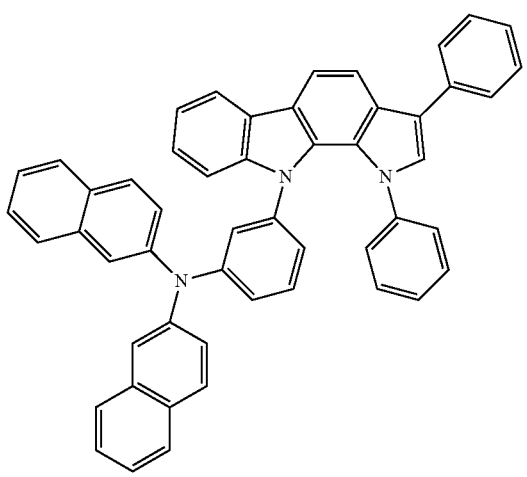
Inv839
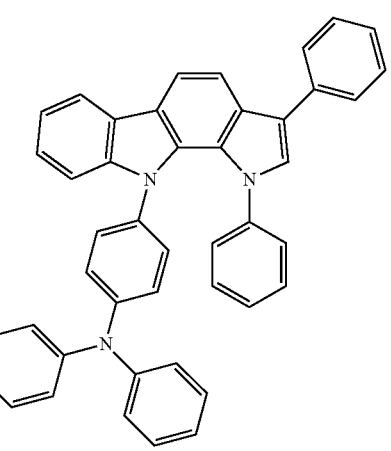
Inv840
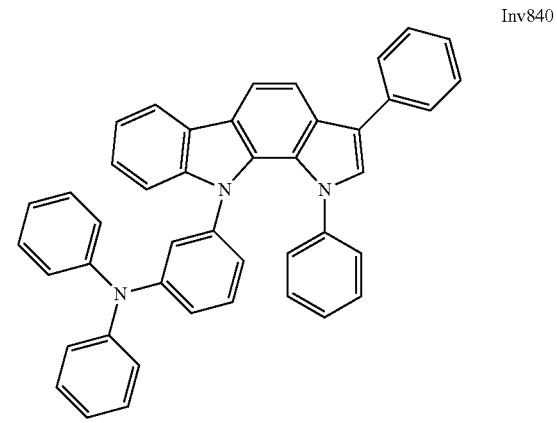

Inv841
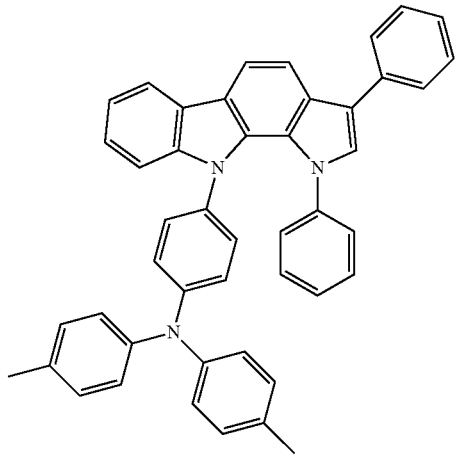
Inv844
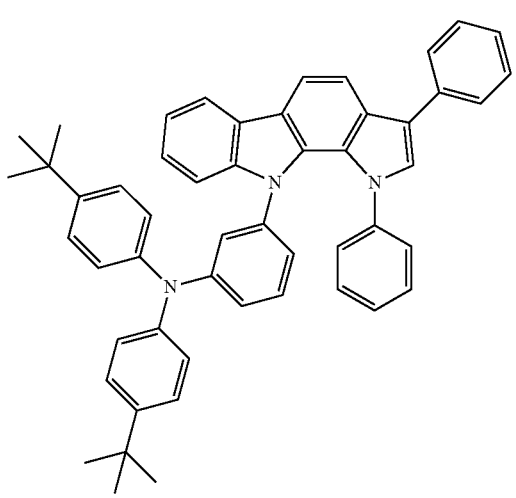
Inv842
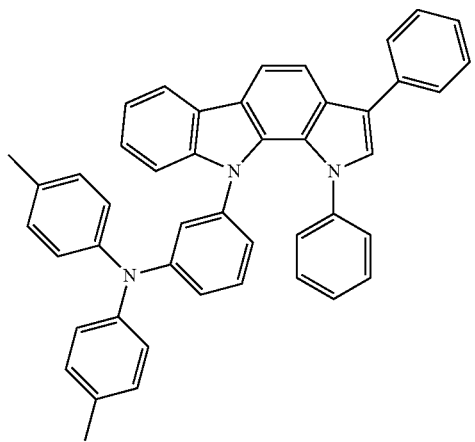
Inv845
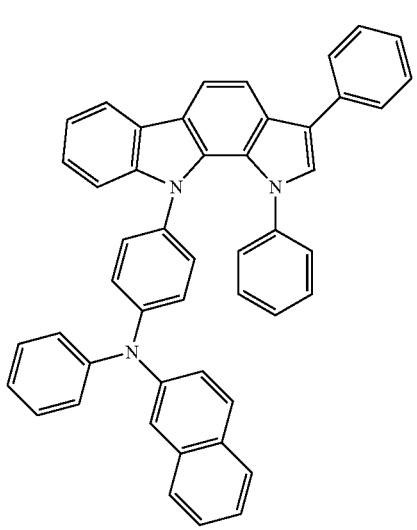
Inv843
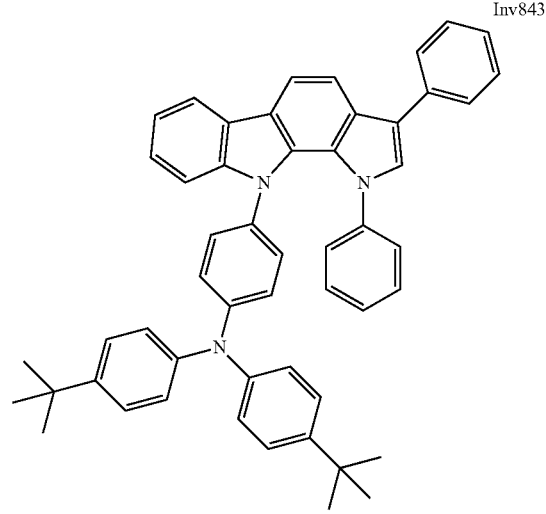
Inv846
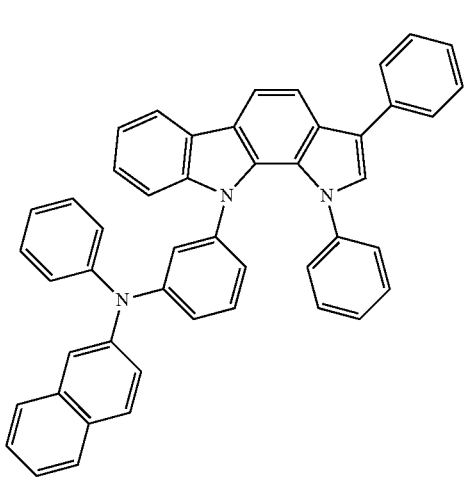

-continued
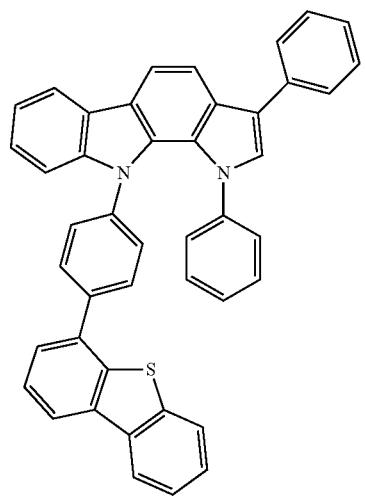
Inv847
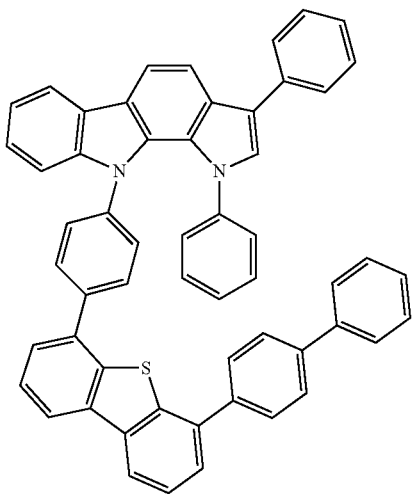
Inv850
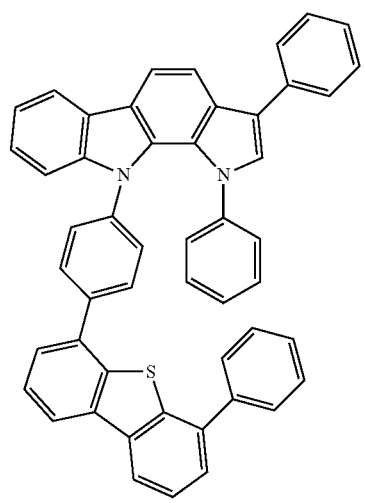
Inv848
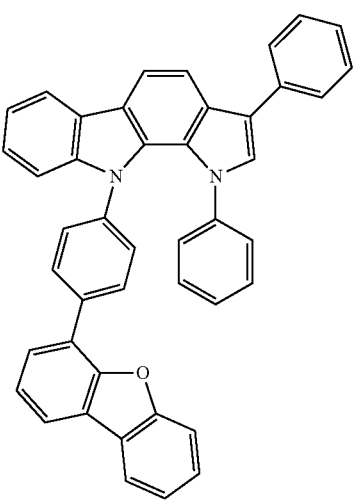
Inv851
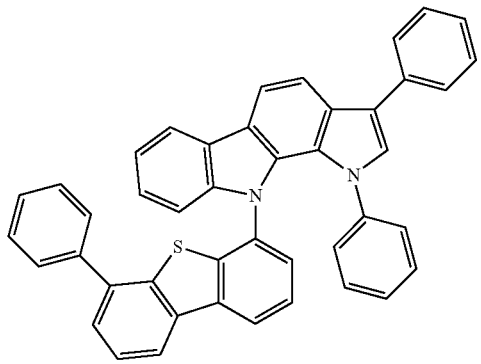
Inv849
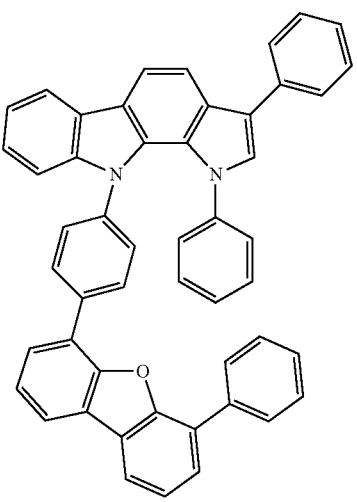
Inv852

Inv853
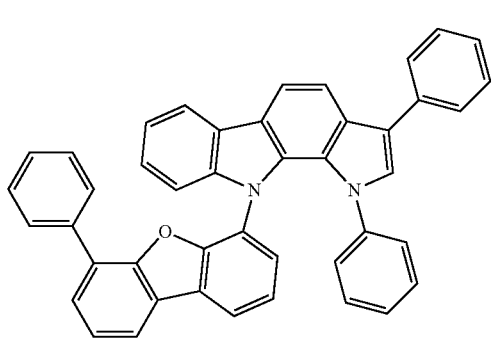
Inv854
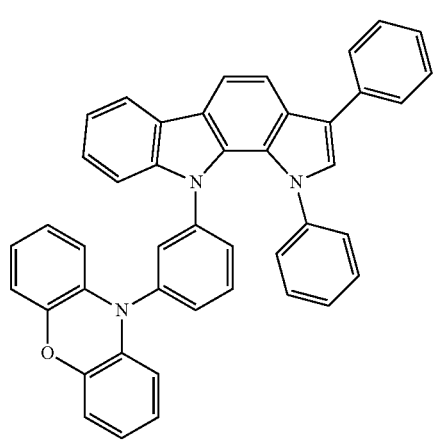
Inv855
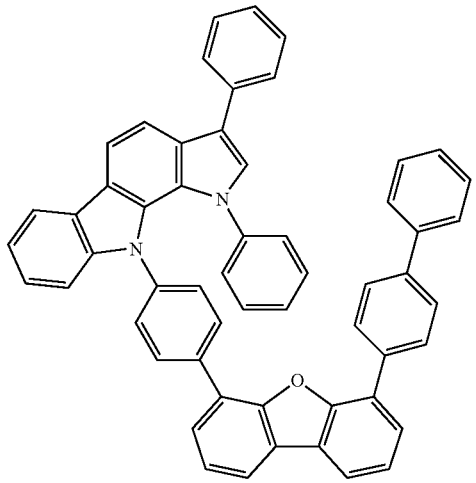
Inv856
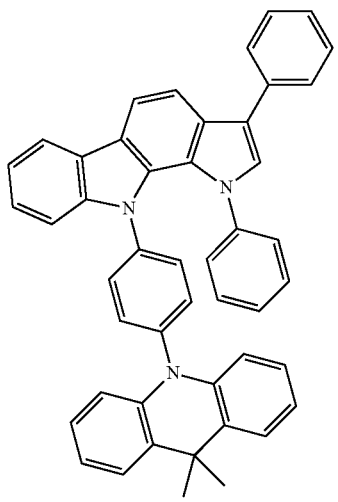
Inv857
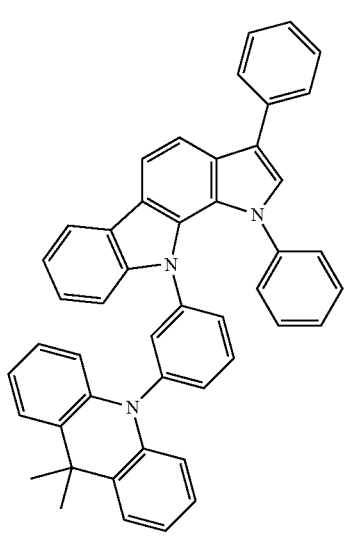
Inv858
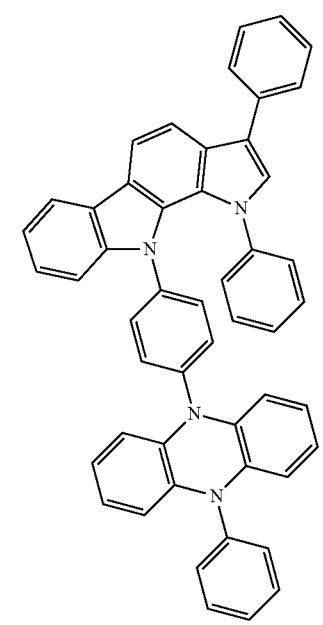

-continued
Inv859
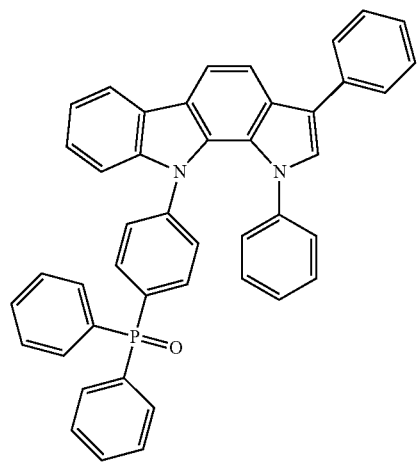
Inv860
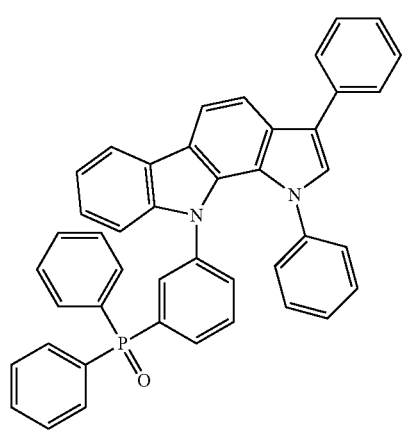
Inv861
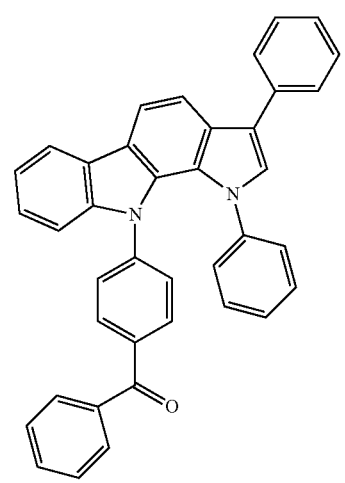
-continued
Inv862
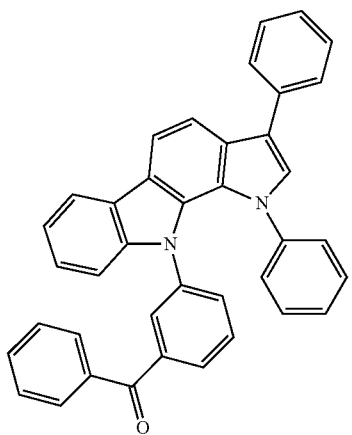
Inv863
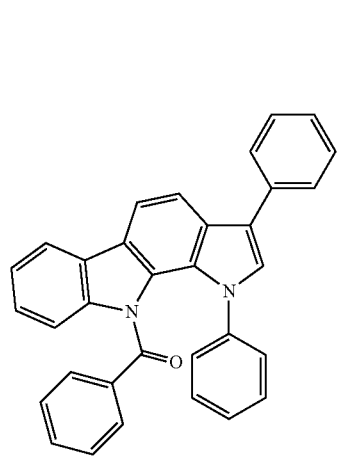
Inv864
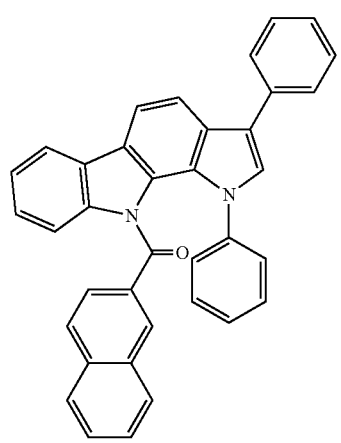

-continued
Inv865
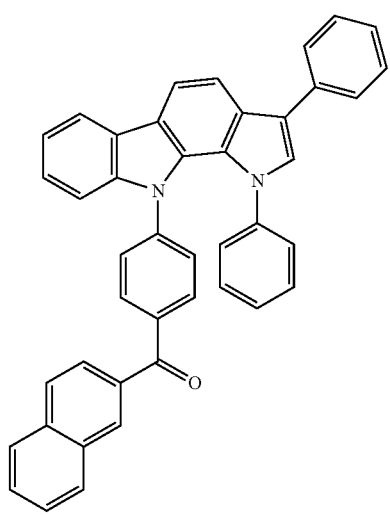
Inv866
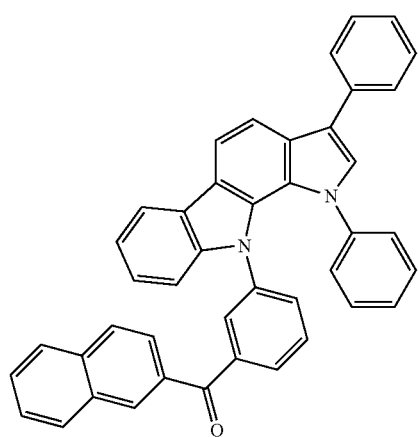
Inv867
-continued
Inv868
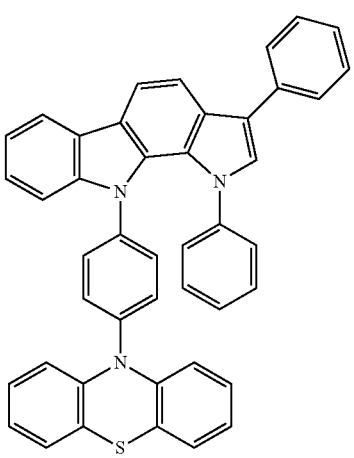
Inv869
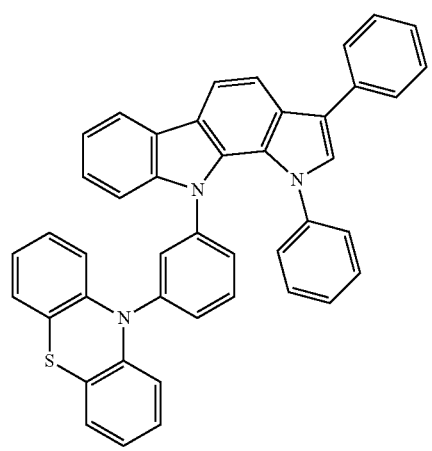
Inv870
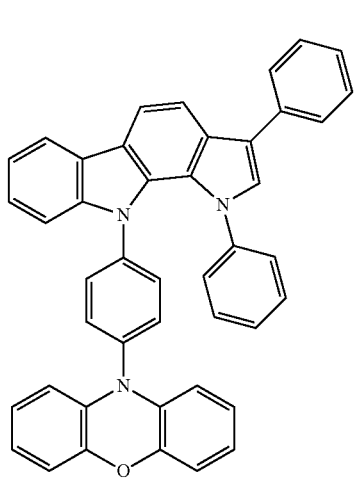

Inv871
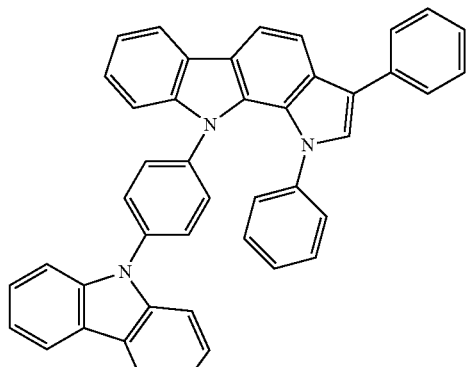
Inv874
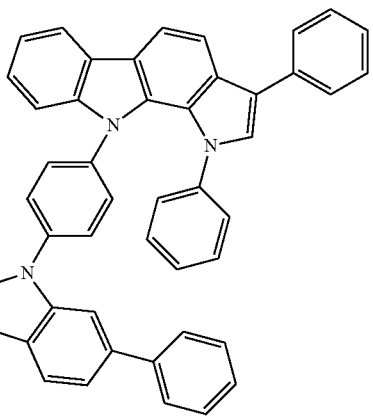
Inv872
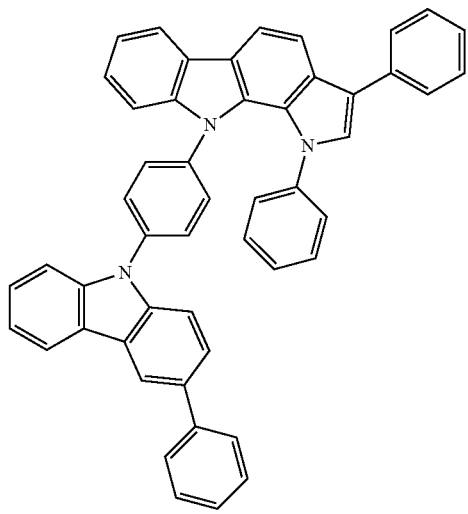
Inv875
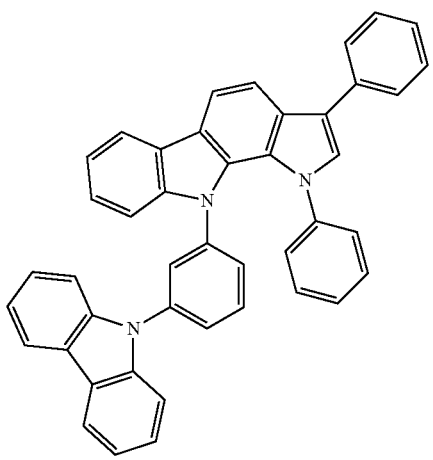
Inv873
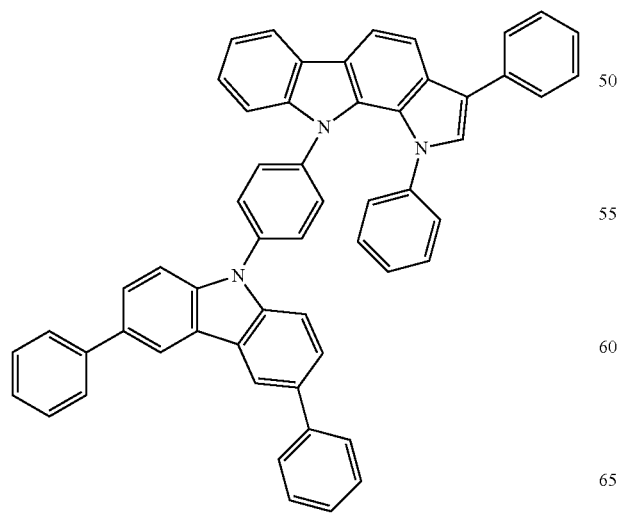
Inv876
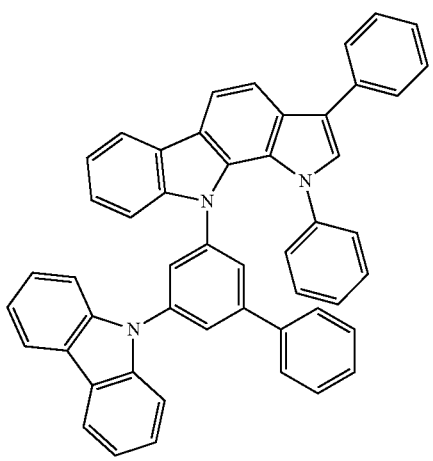

Inv877
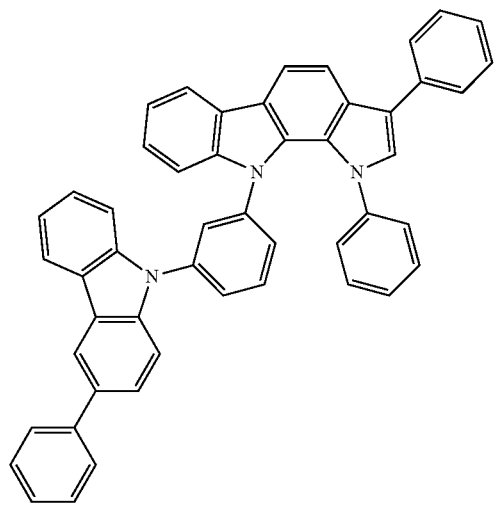
Inv878
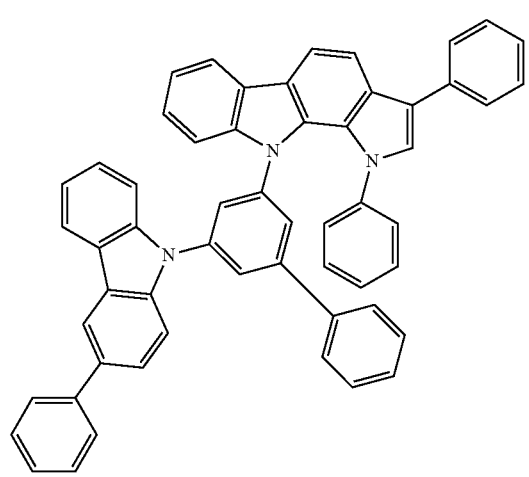
Inv879
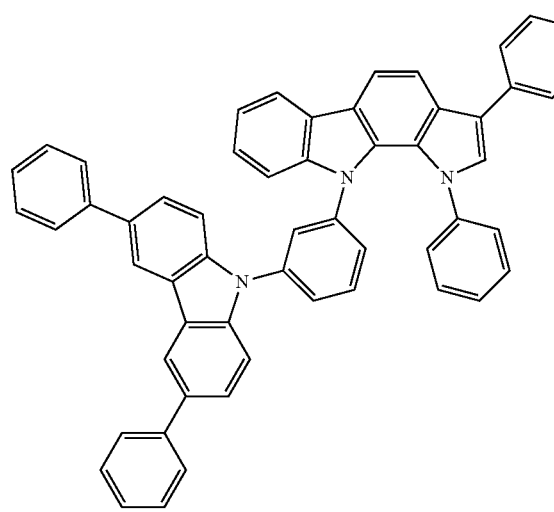
Inv880
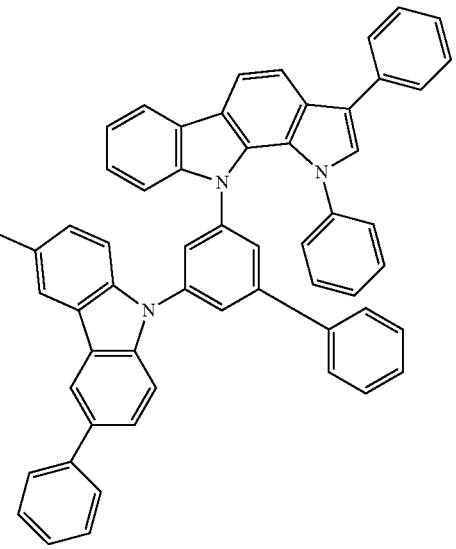
Inv881
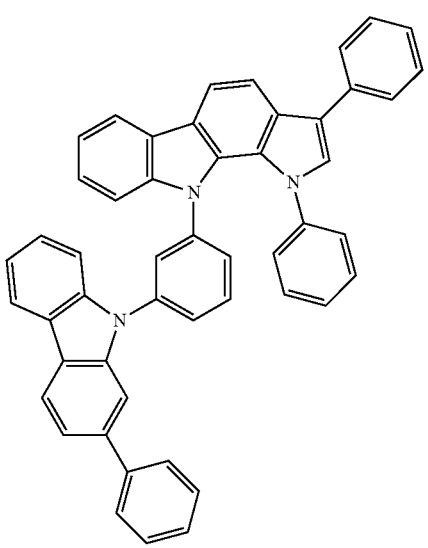
Inv882
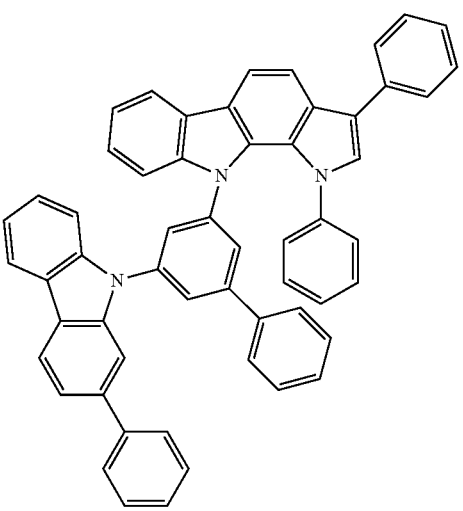

Inv883
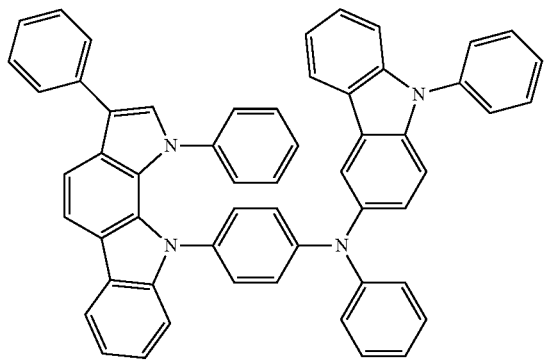
Inv886
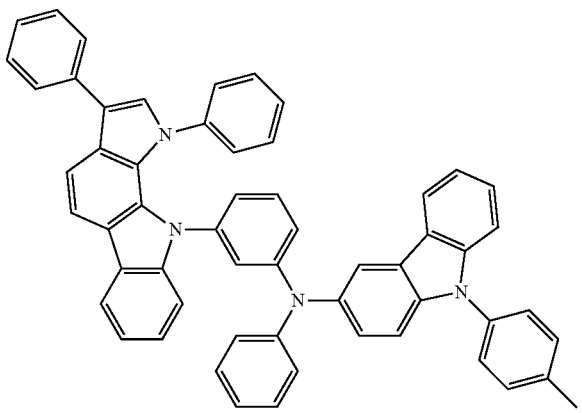
Inv884
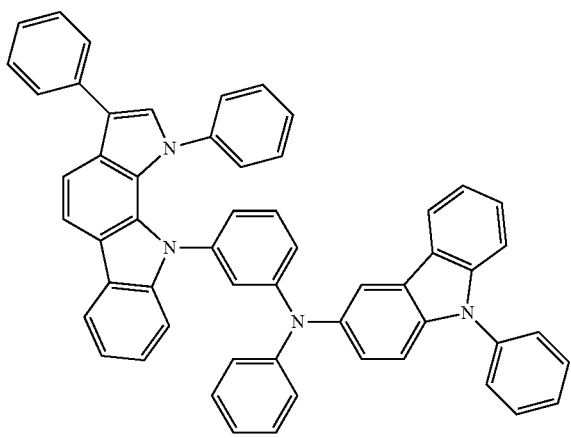
Inv887
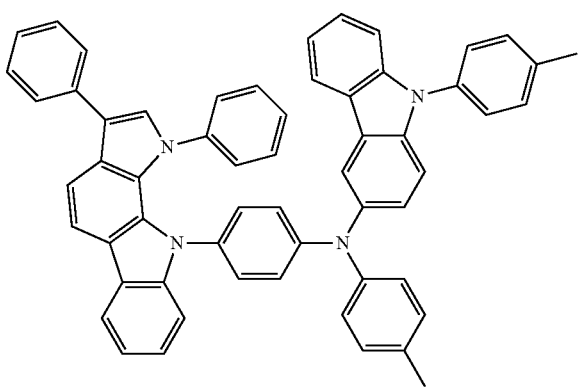
Inv885
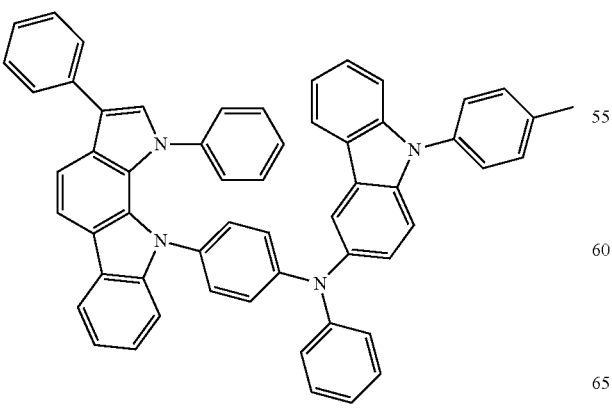
Inv888
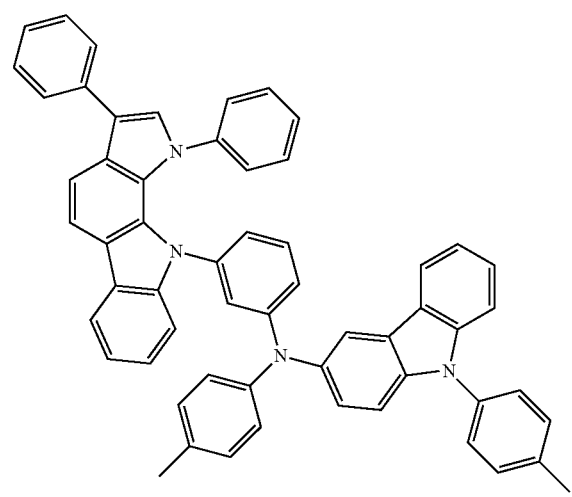

-continued
Inv889
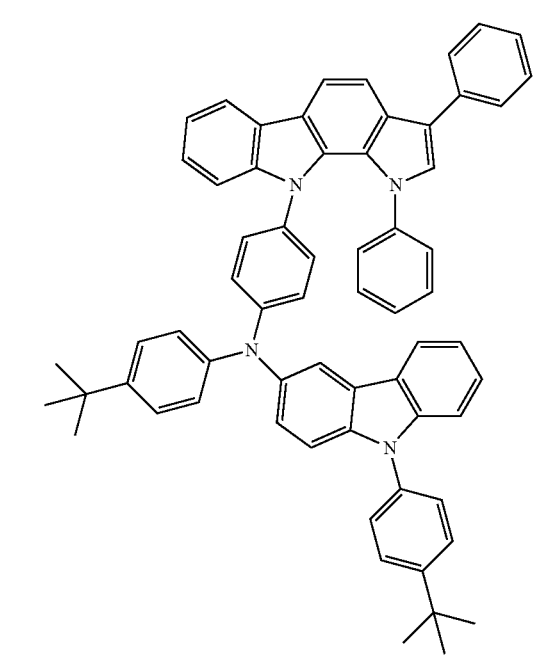
Inv890
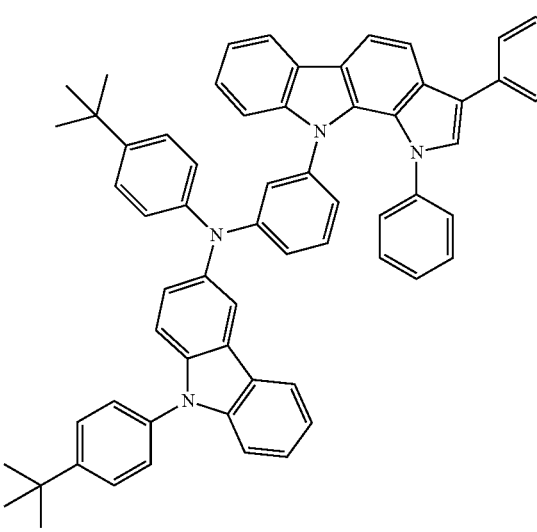
Inv891
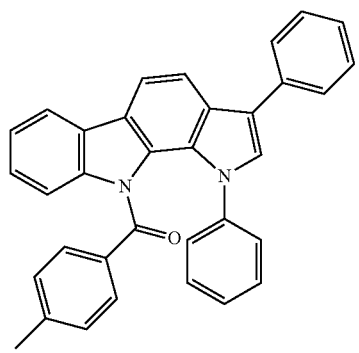
-continued
Inv892
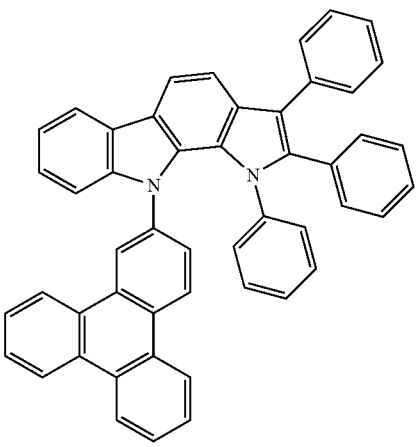
Inv893
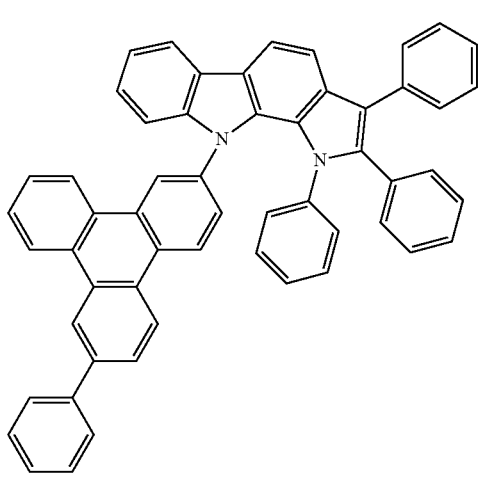
Inv894
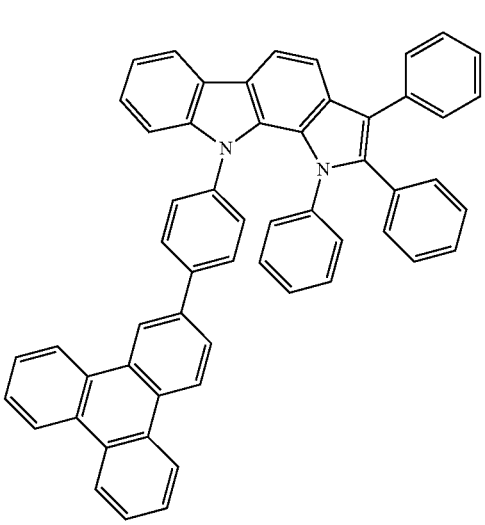

Inv895
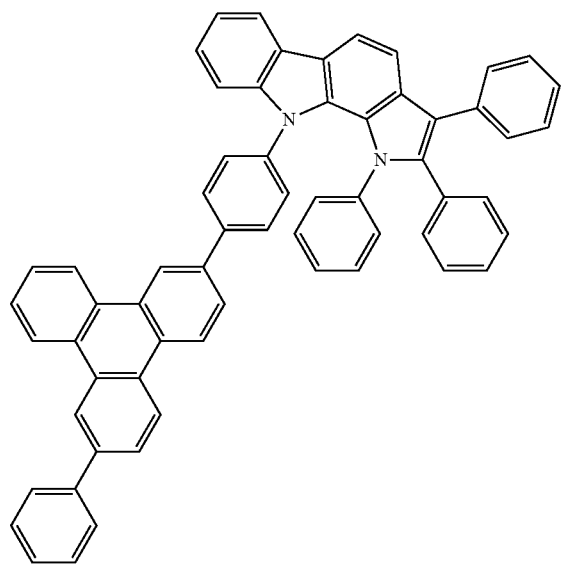
Inv897
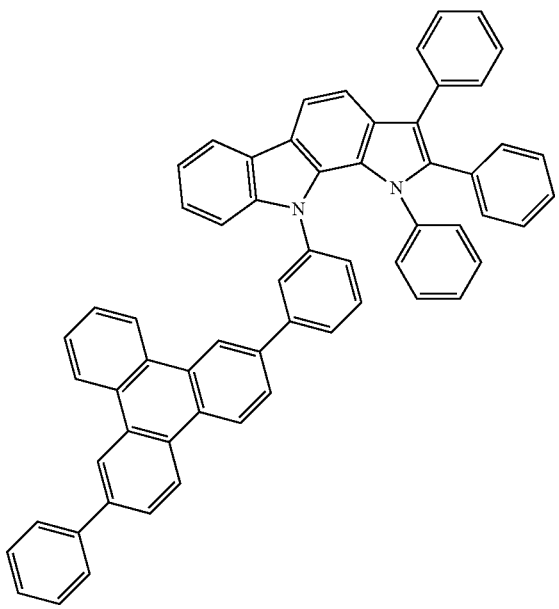
Inv898
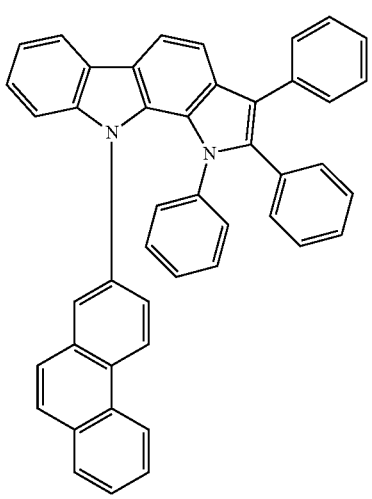
Inv896
Inv899
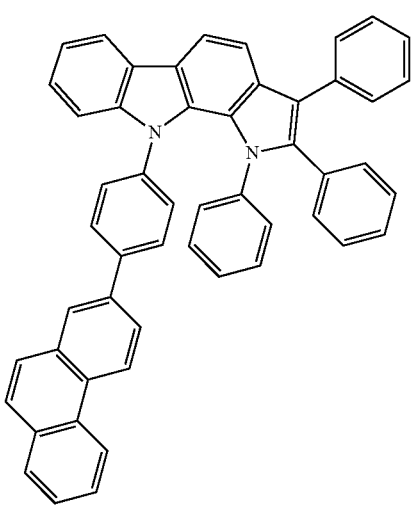

-continued
Inv900
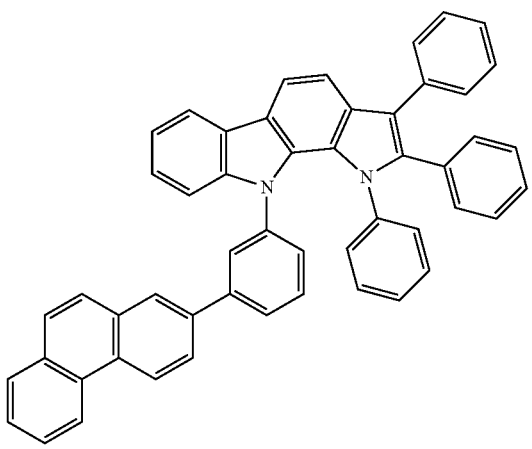
Inv903
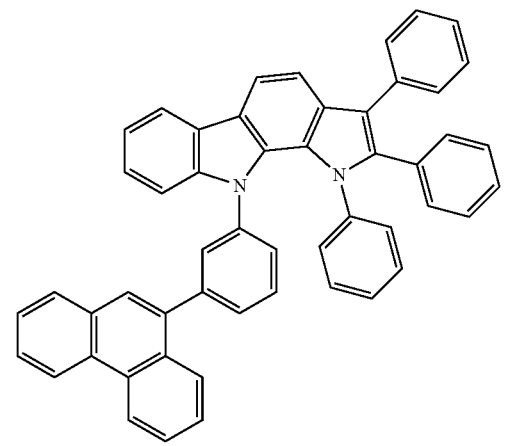
Inv901
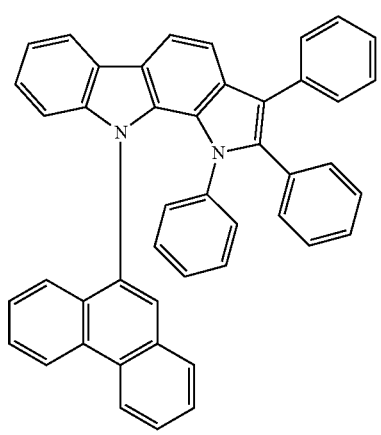
Inv904
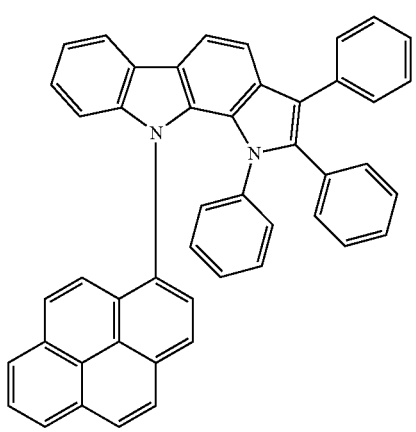
Inv902
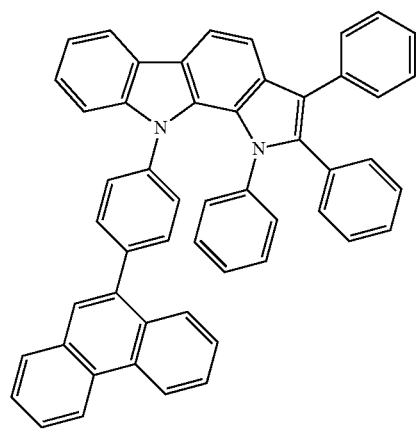
Inv905
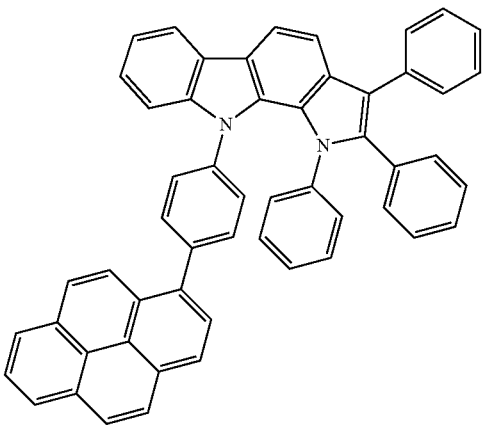

-continued
Inv906
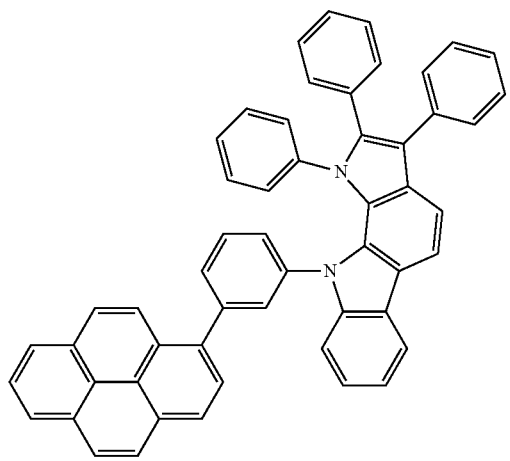
Inv907
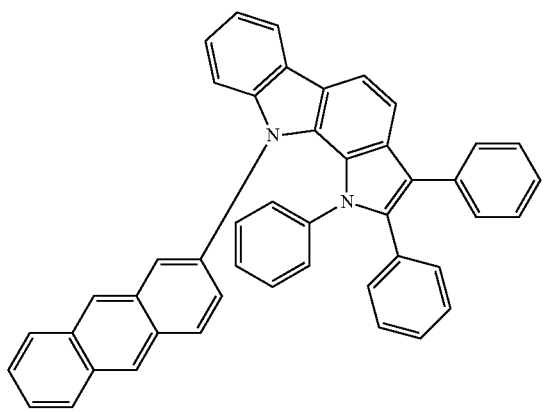
Inv908
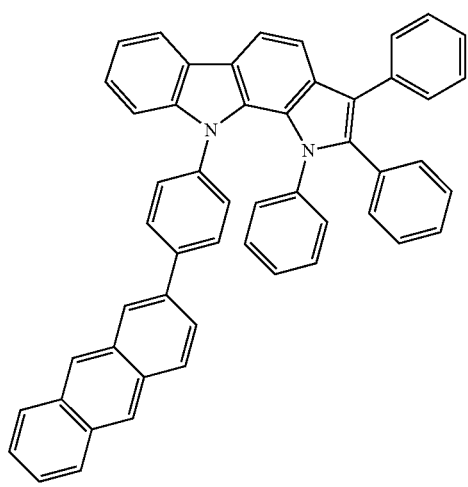
-continued
Inv909
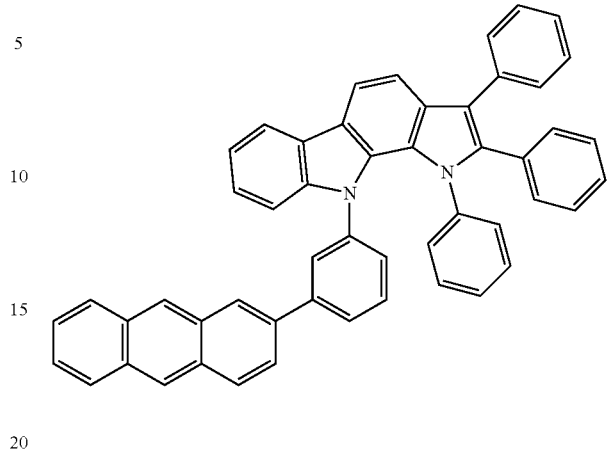
Inv910
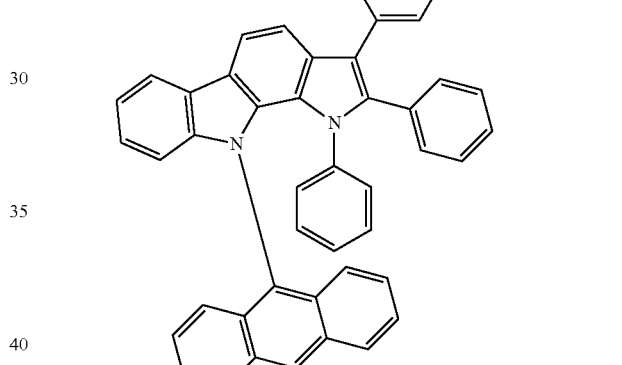
Inv911
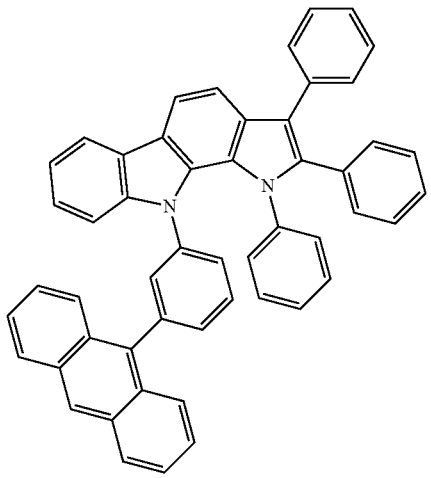

-continued
Inv912
Inv913
Inv914
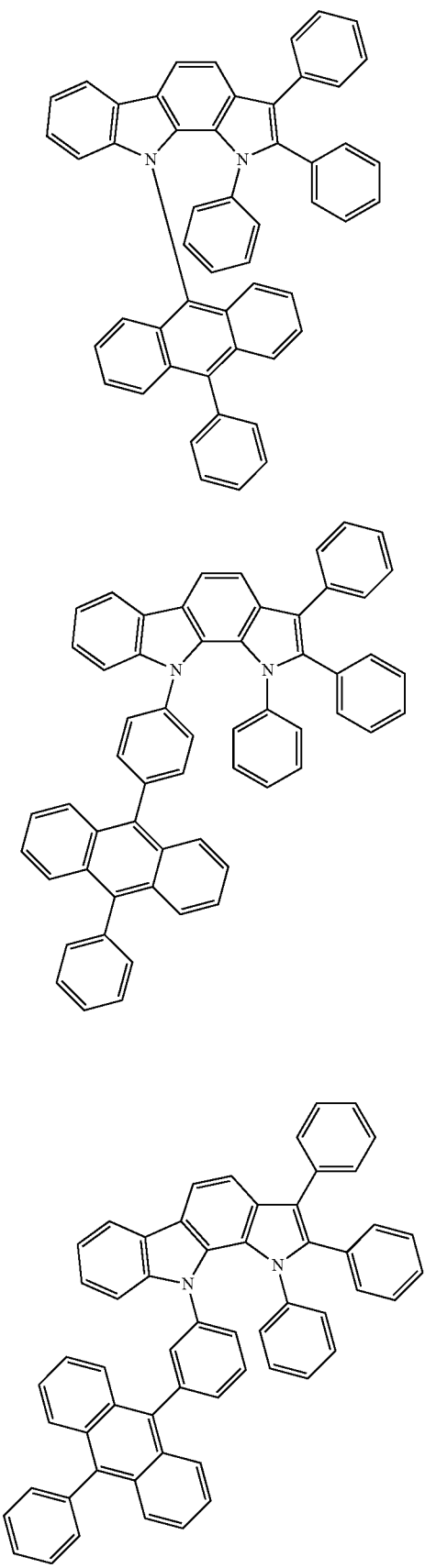
-continued
Inv915
Inv916
Inv917
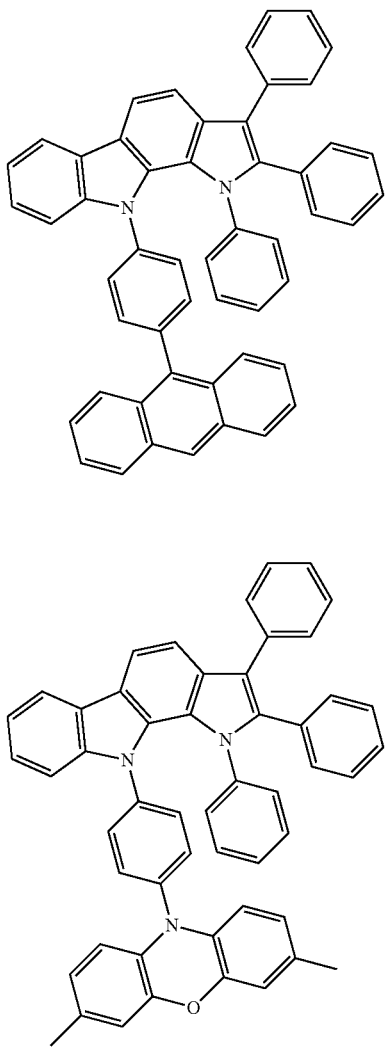
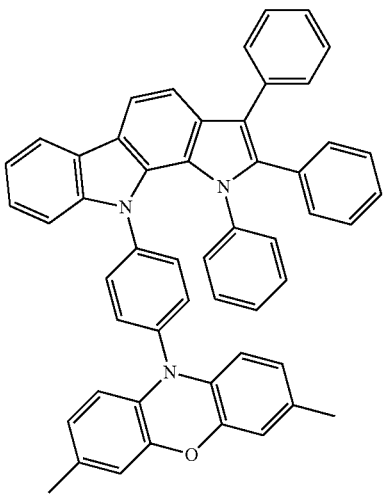
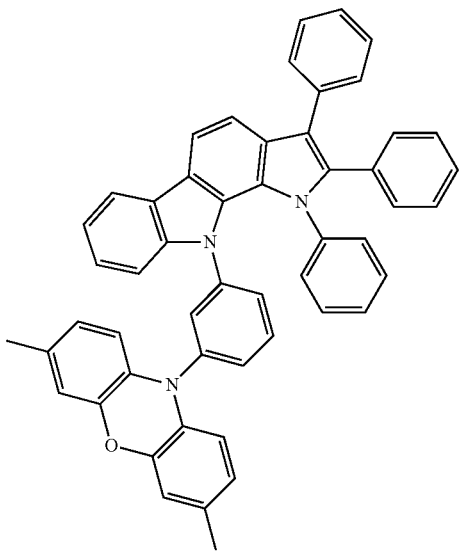

Inv918
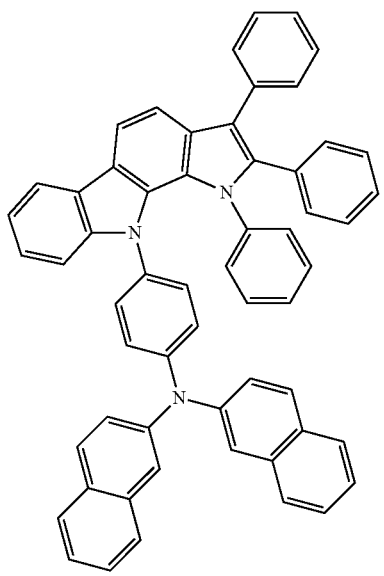
Inv919
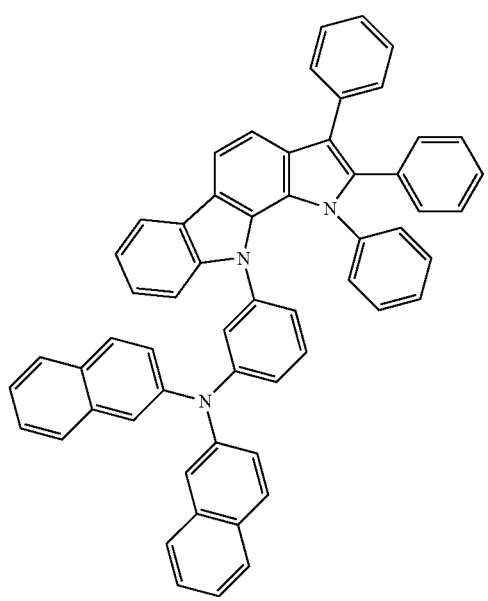
Inv920
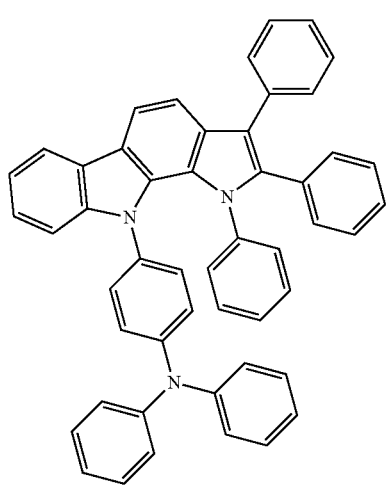
Inv921
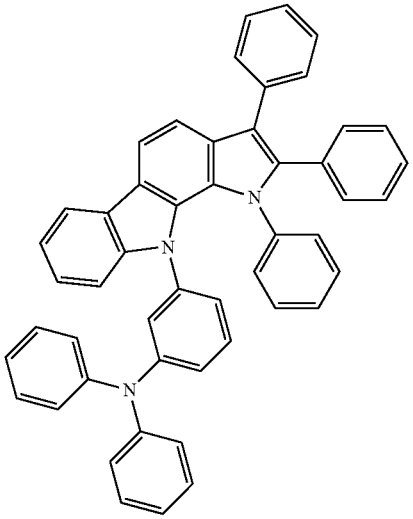
Inv922
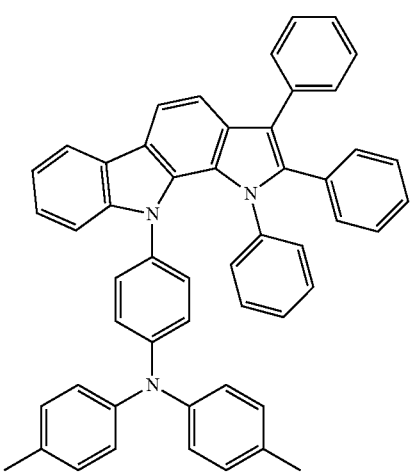
Inv923
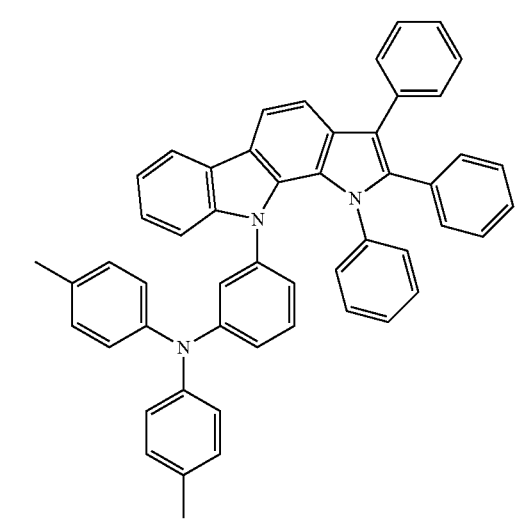

Inv924
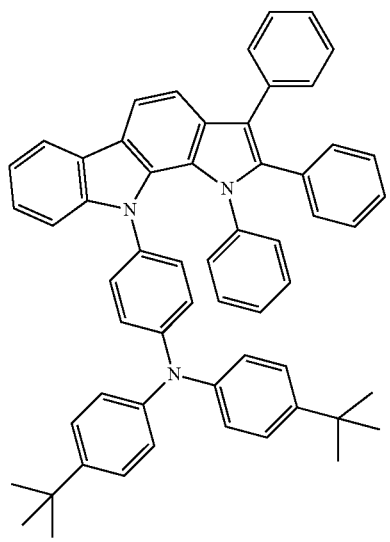
Inv925
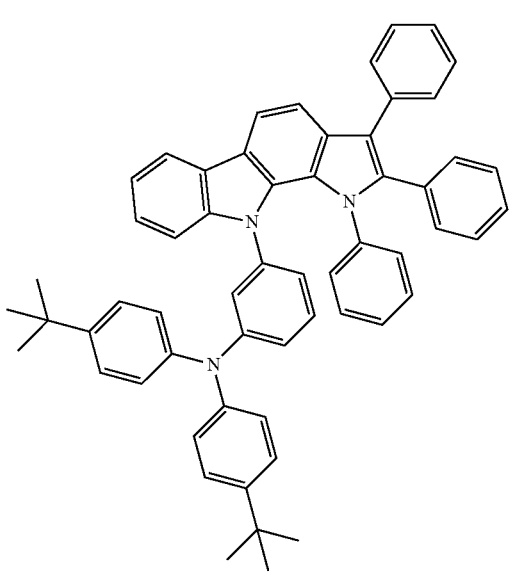
Inv926
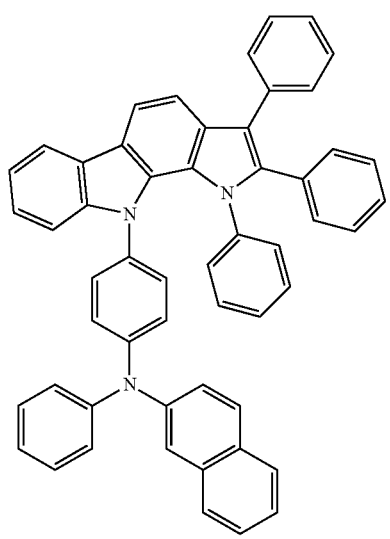
Inv927
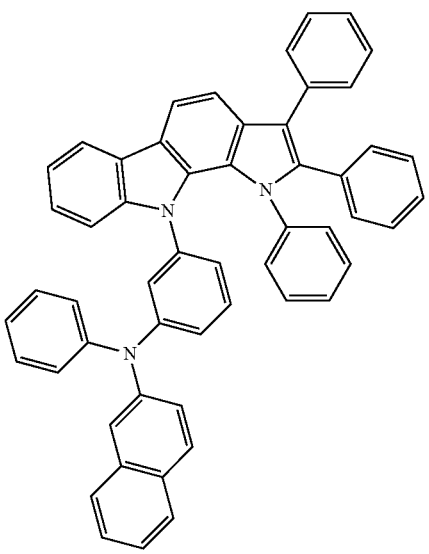
Inv928
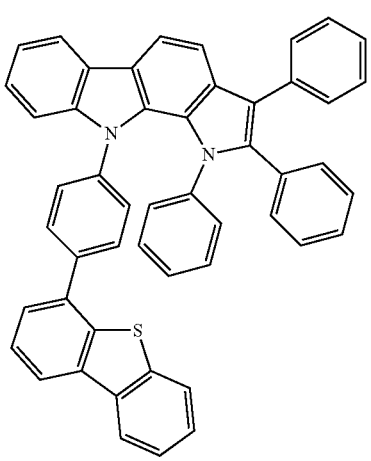
Inv929
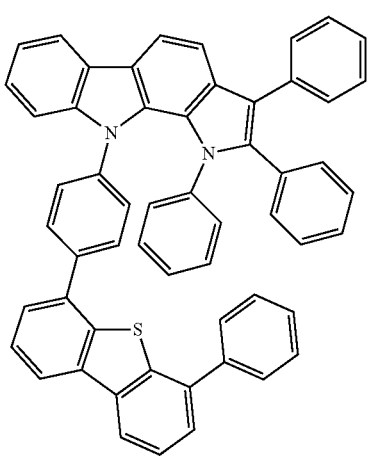

Inv930
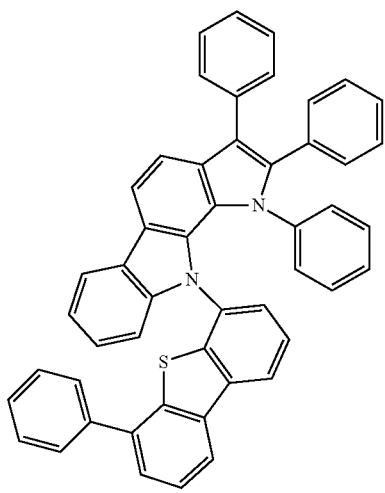
Inv933
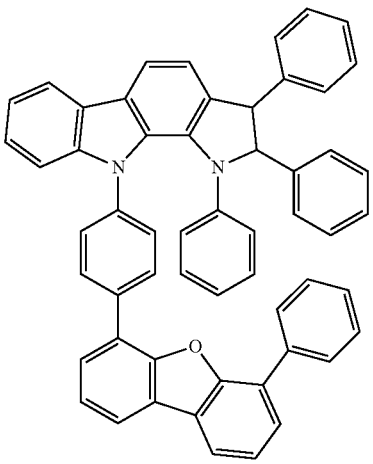
Inv931
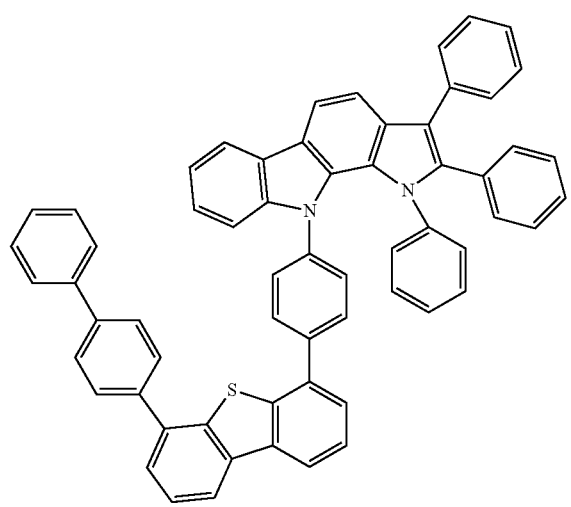
Inv934
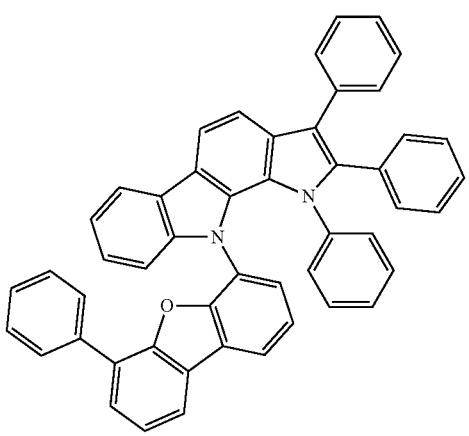
Inv932
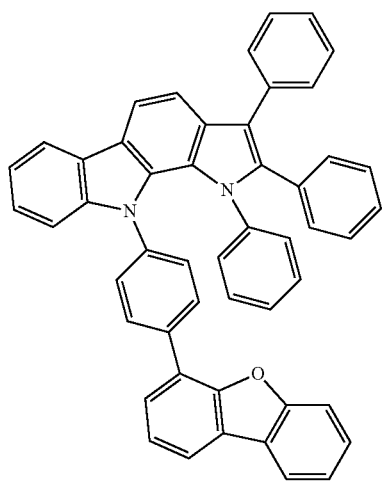
Inv935
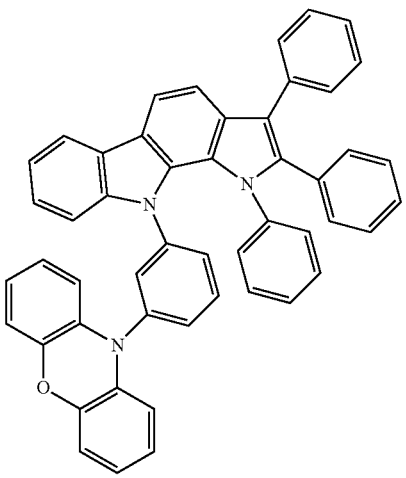

Inv936
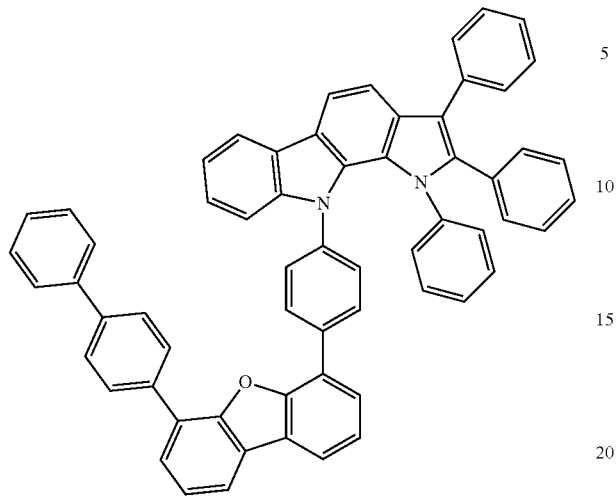
Inv937
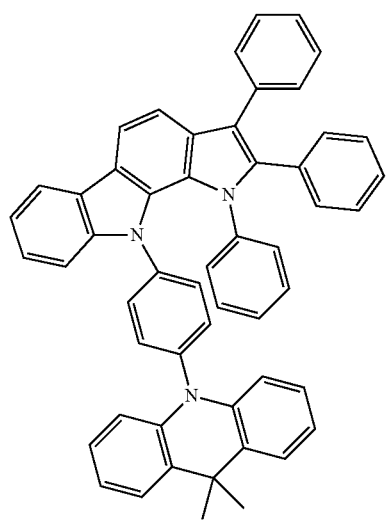
Inv938
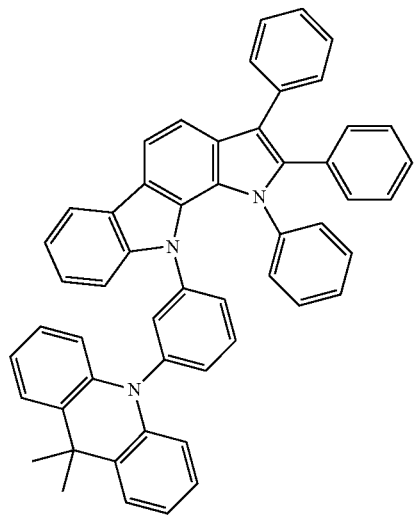
Inv939
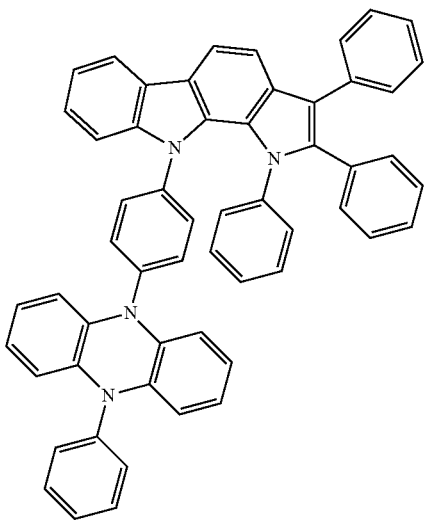
Inv940
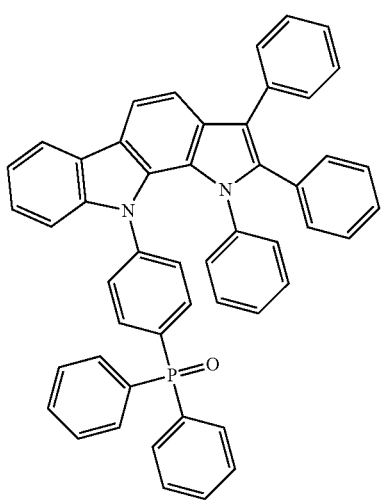
Inv941
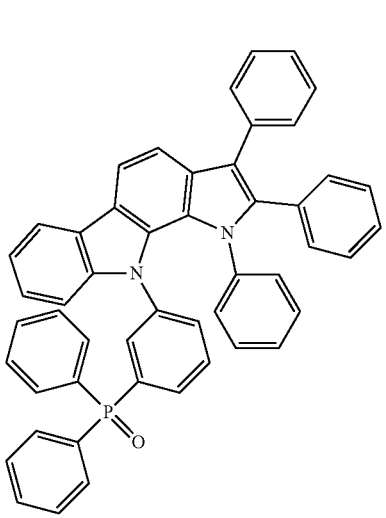

Inv942
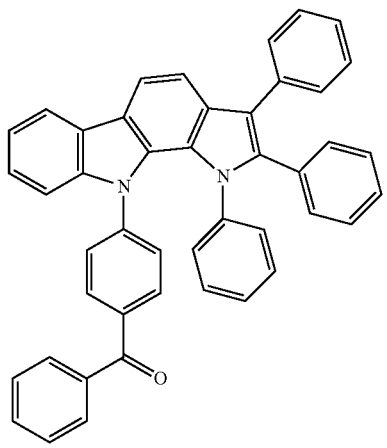
Inv943
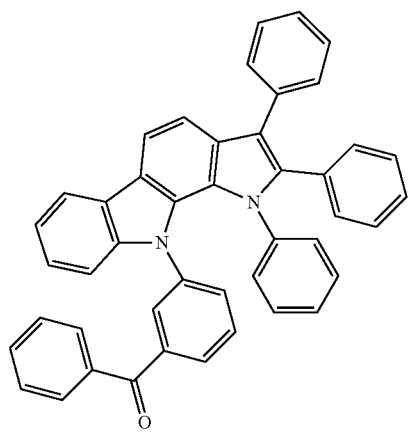
Inv944
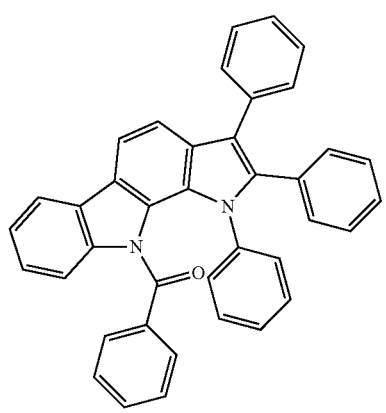
Inv945
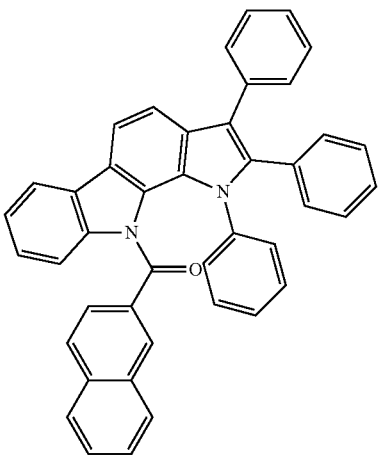
Inv946
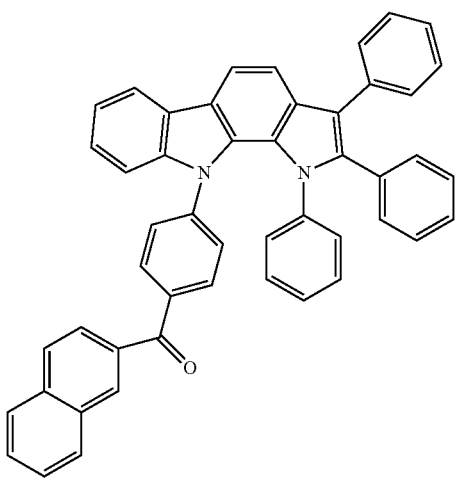
Inv947
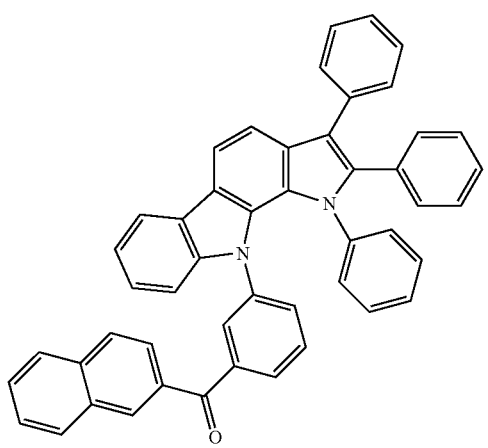

-continued
Inv948
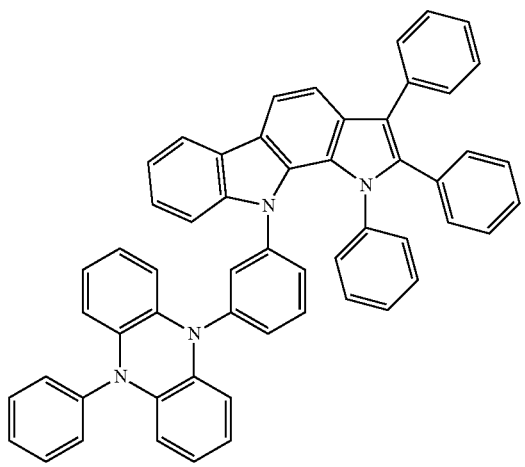
Inv949
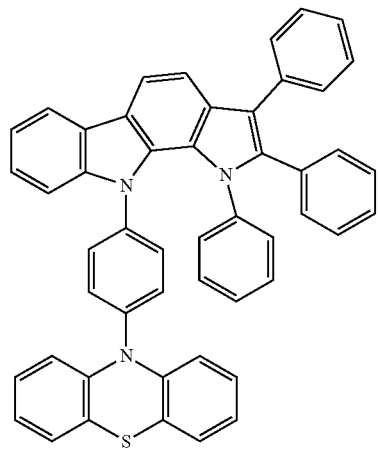
Inv950
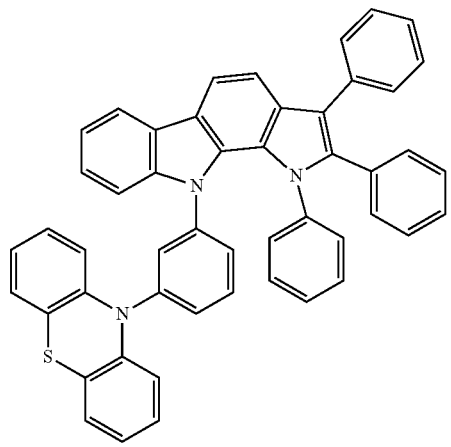
-continued
Inv951
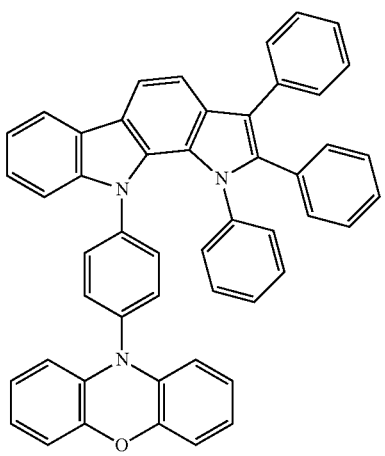
Inv952
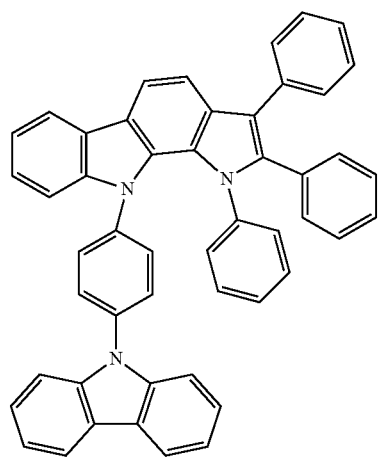
Inv953
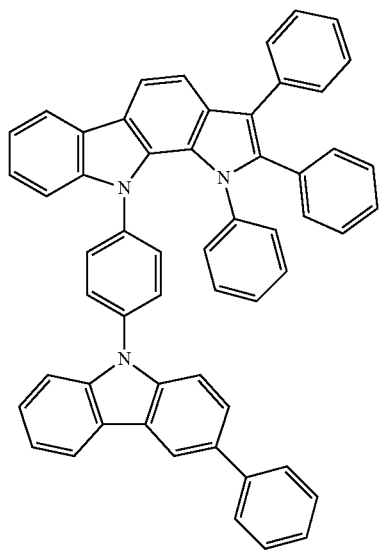

Inv954
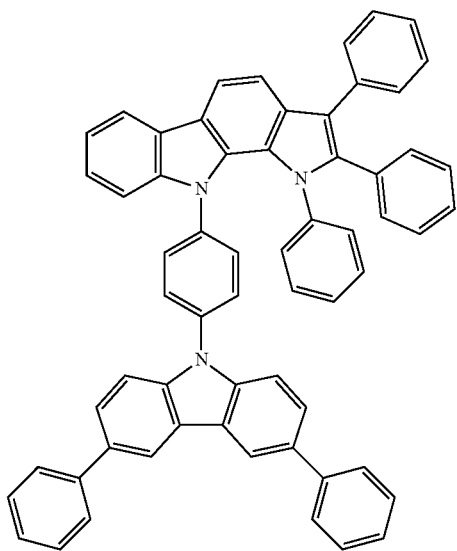
Inv955
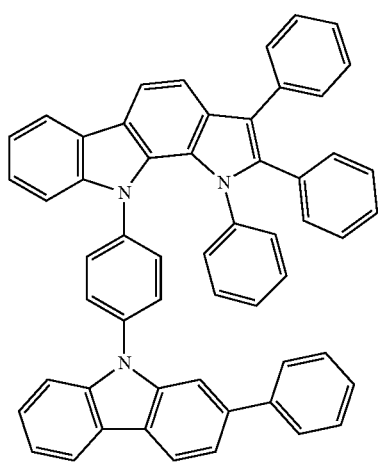
Inv956
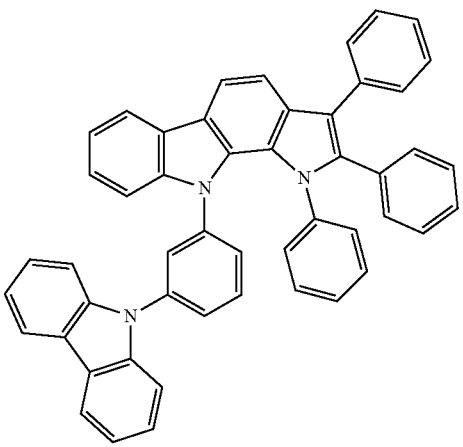
Inv957
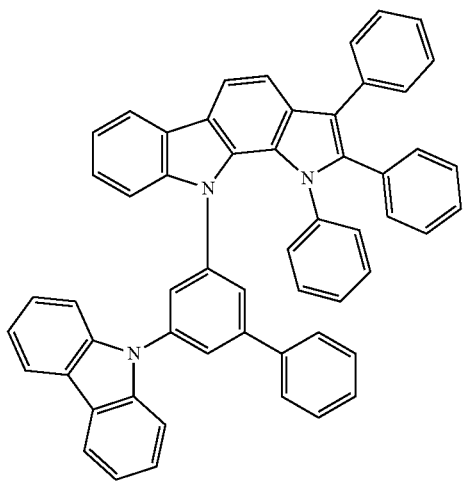
Inv958
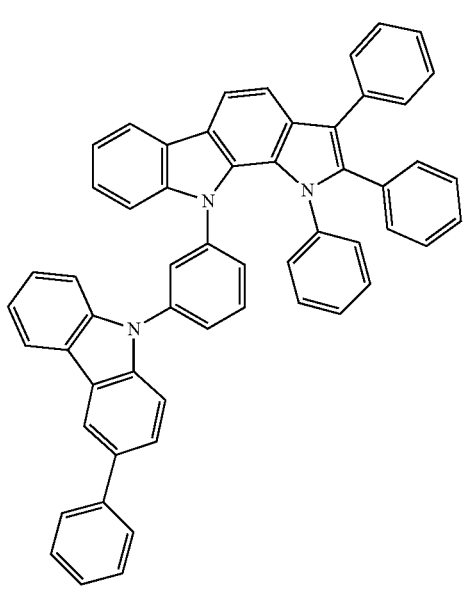
Inv959
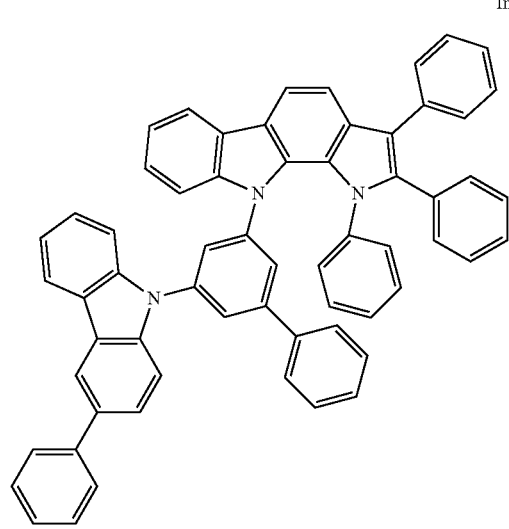

Inv960
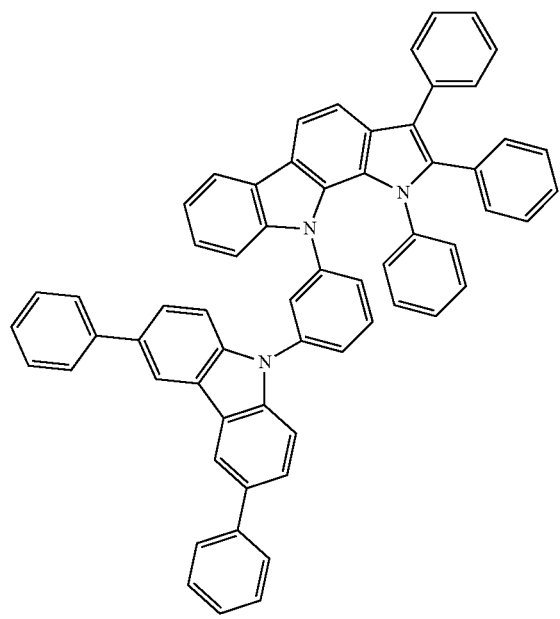
Inv961
Inv962
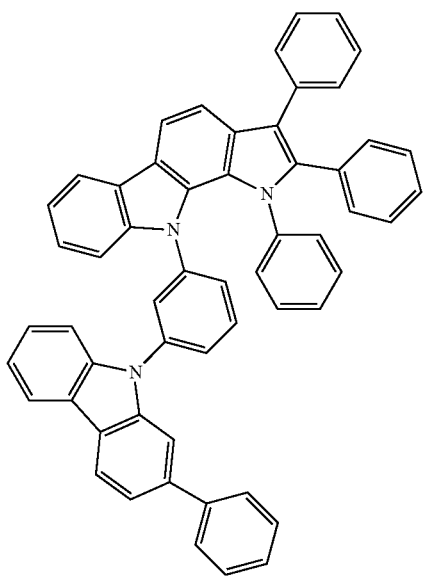
Inv963
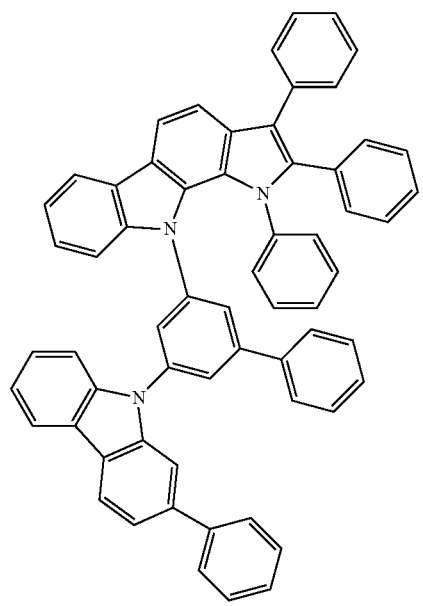
Inv964
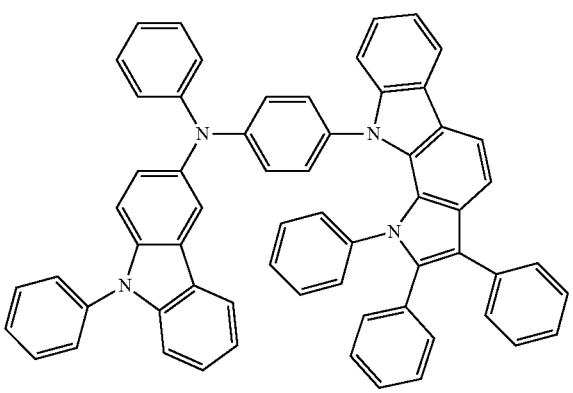

Inv965
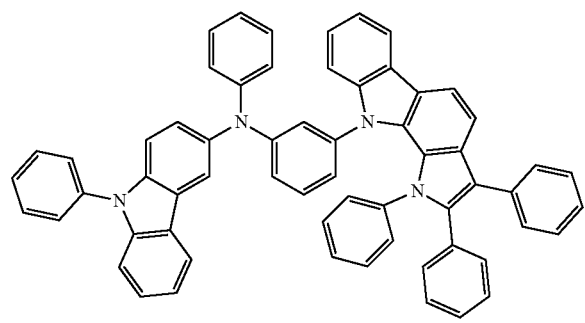
Inv968
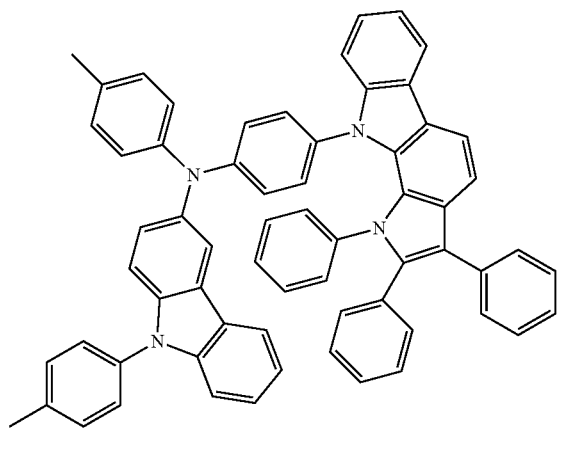
Inv966
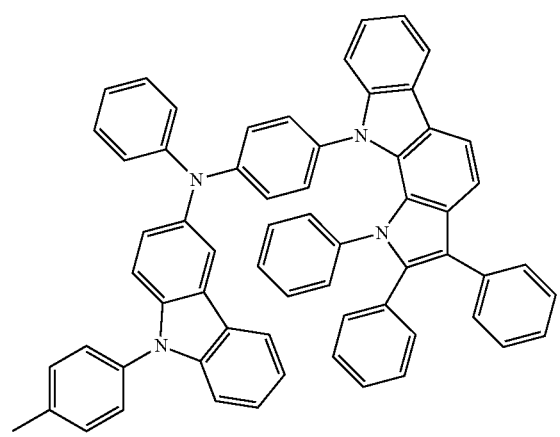
Inv969
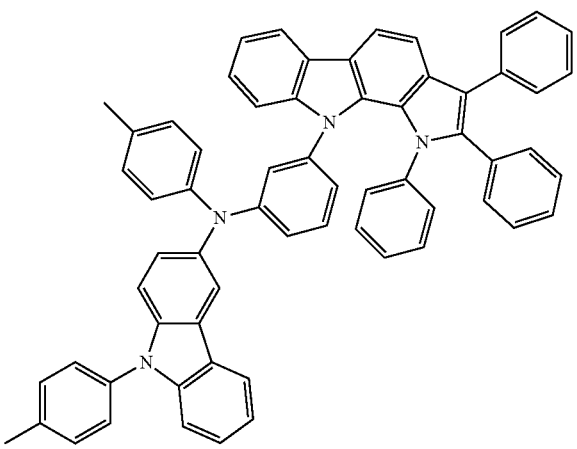
Inv967
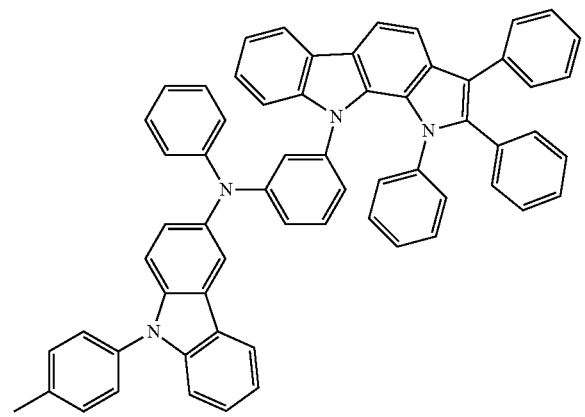
Inv970
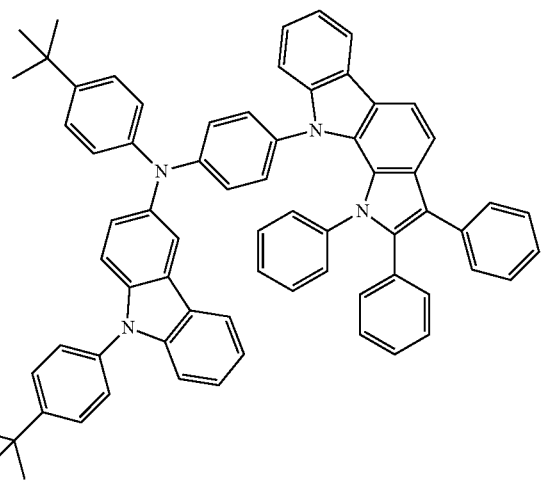

| 359 -continued | 360 -continued |
|---|---|
| Inv971 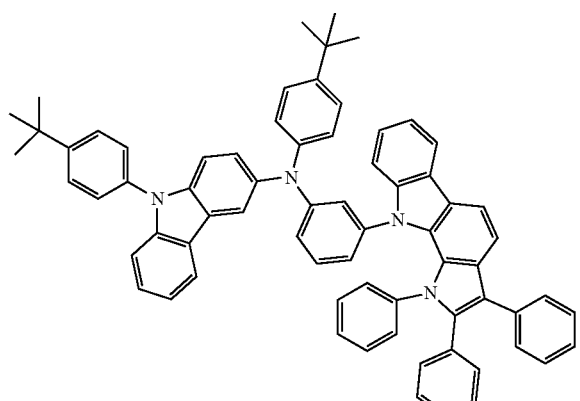 | Inv974 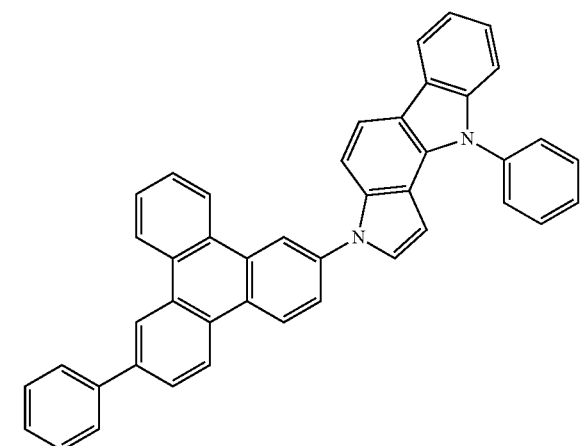 |
| Inv972 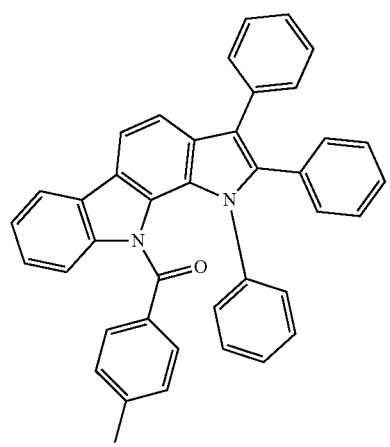 | Inv975 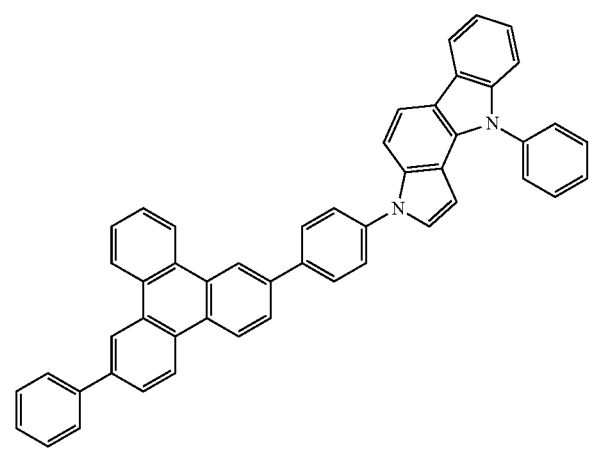 |
| Inv973 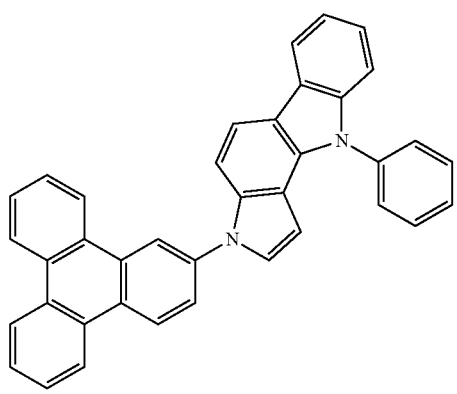 | Inv976 |

Inv977
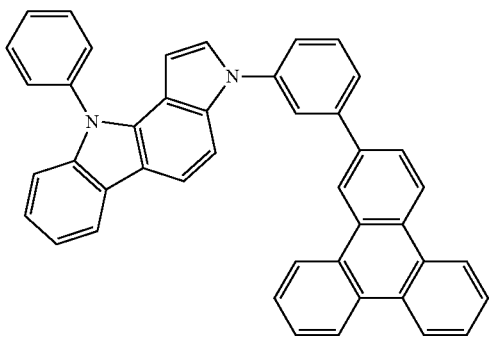
Inv978
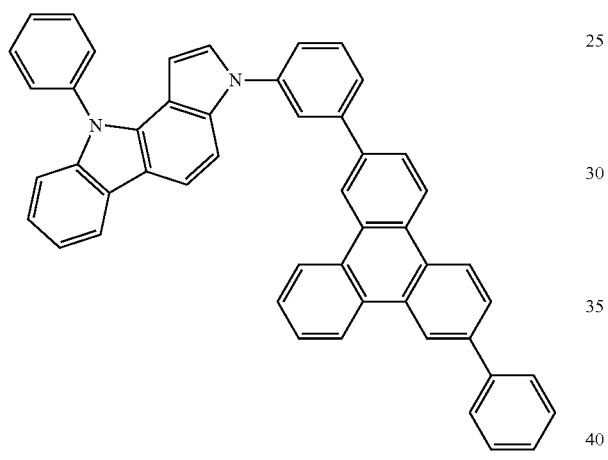
Inv979
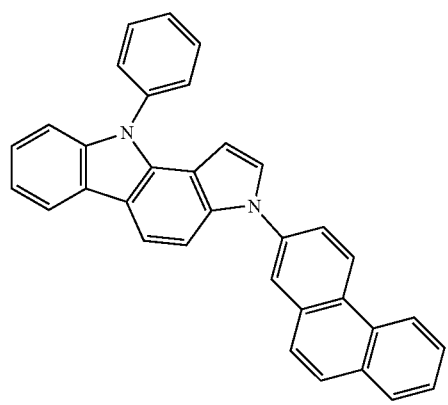
Inv980
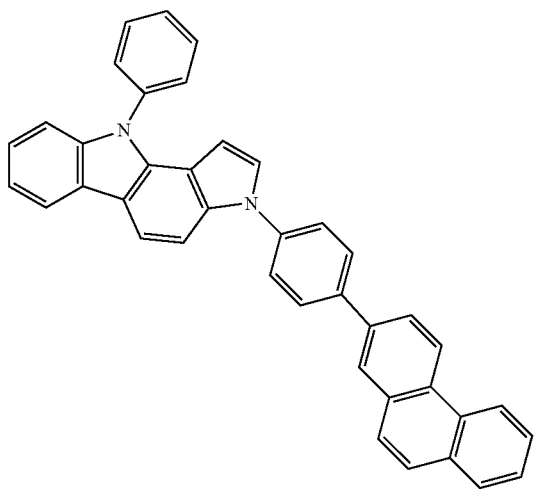
Inv981
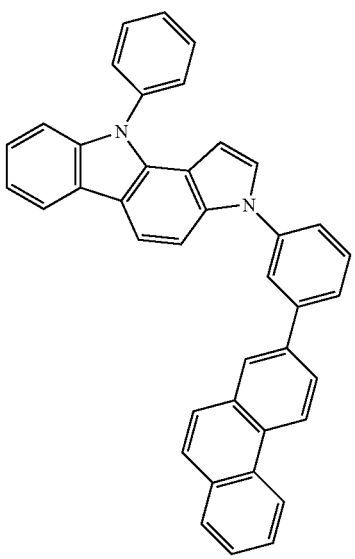
Inv982
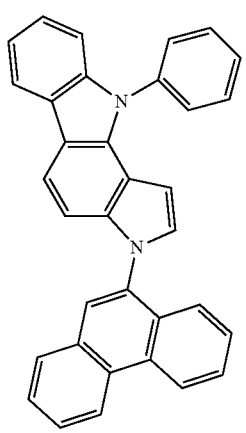

Inv983
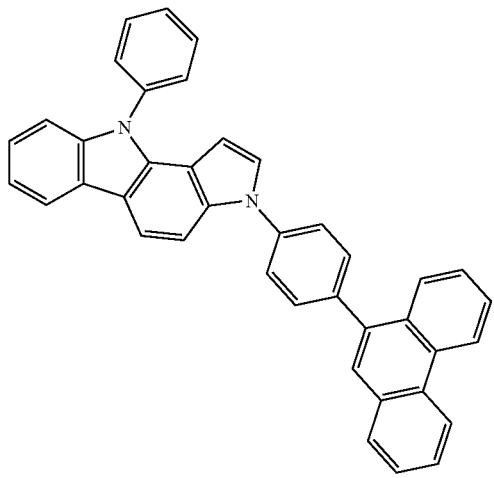
Inv984
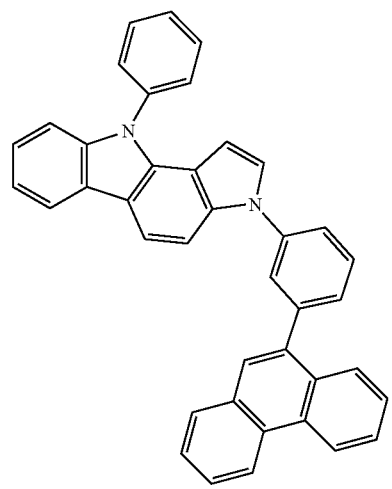
Inv985
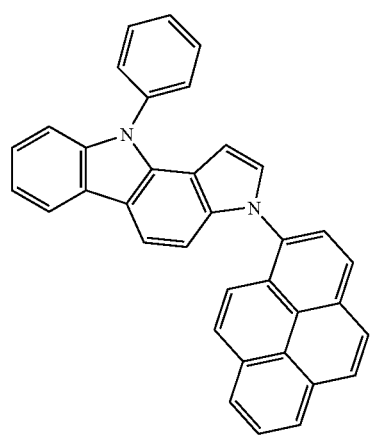
Inv986
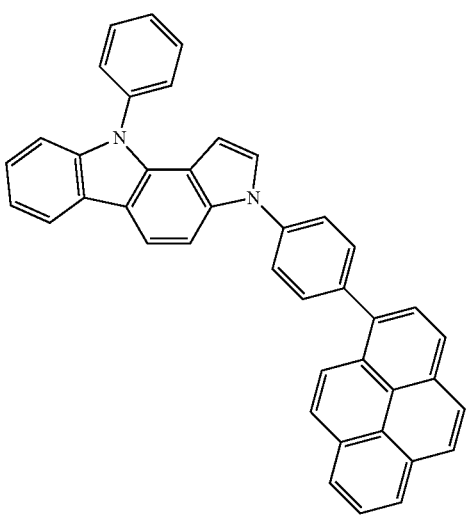
Inv986
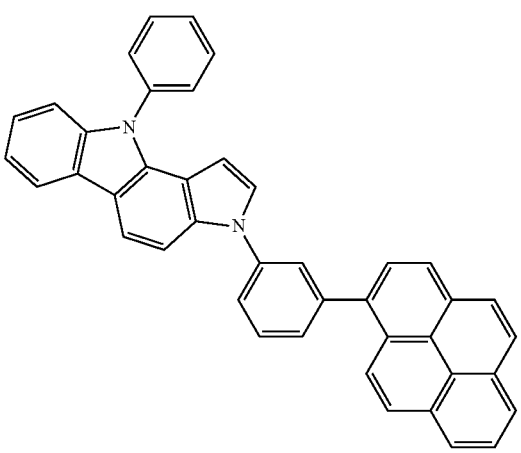
Inv988
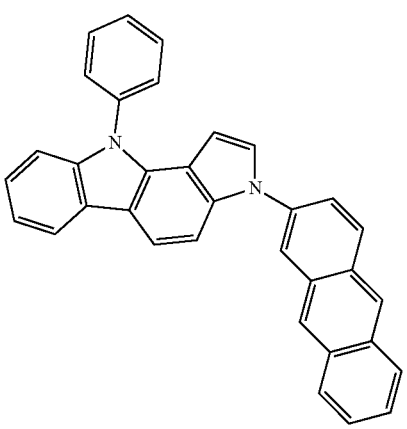

-continued
Inv989
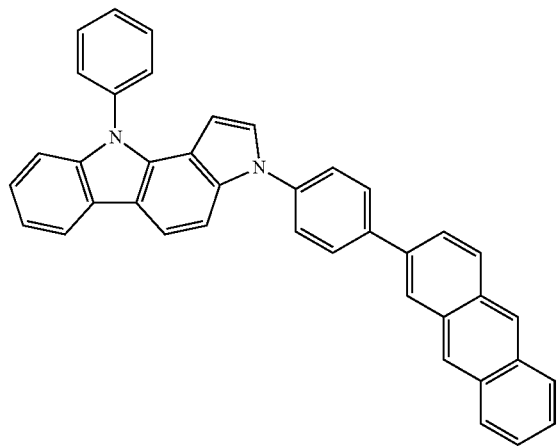
Inv992
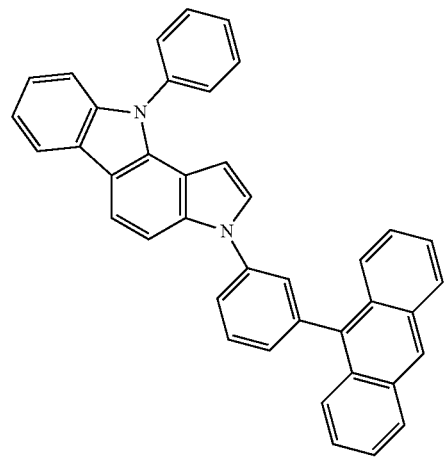
Inv990
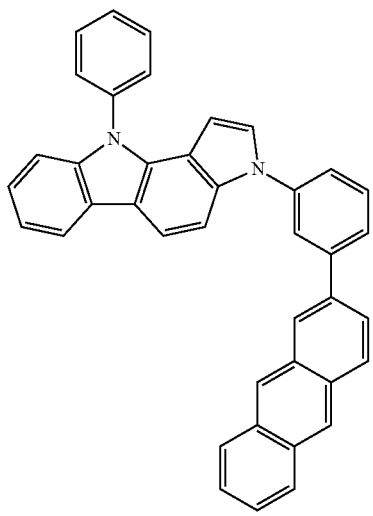
Inv993
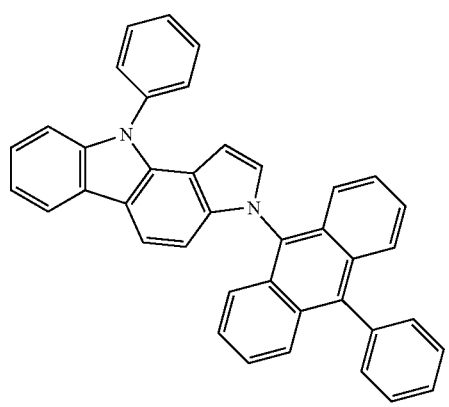
Inv991
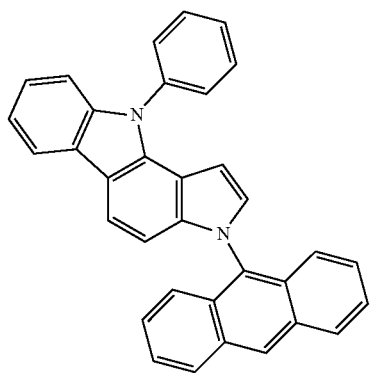
Inv994
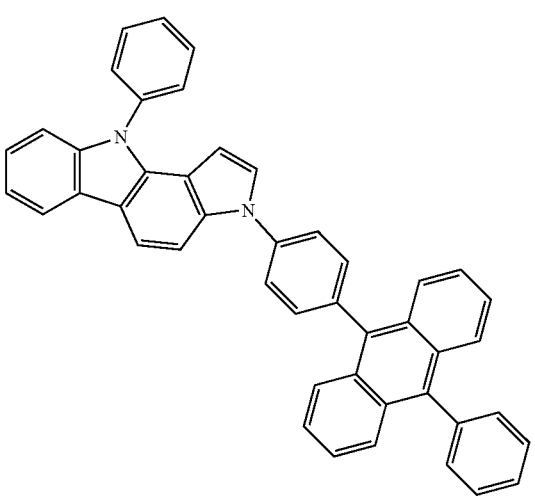

Inv995
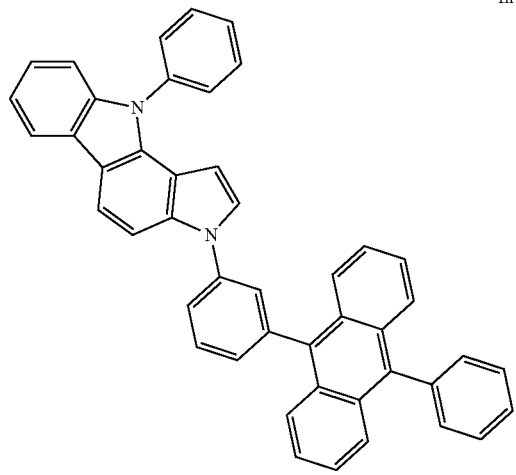
Inv996
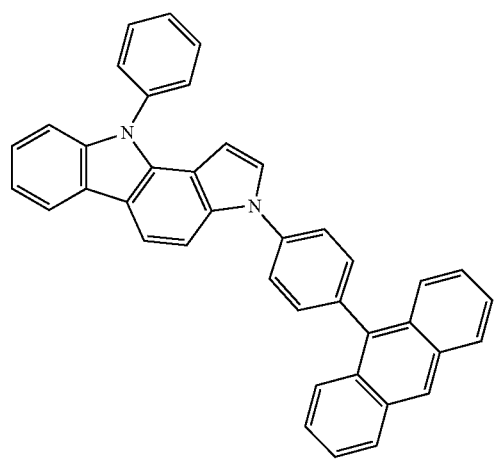
Inv997
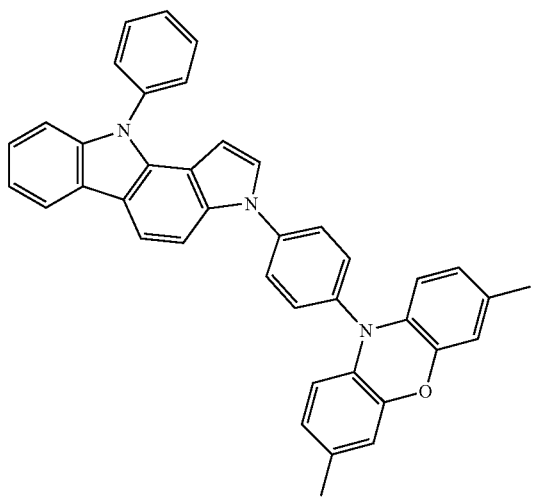
Inv998
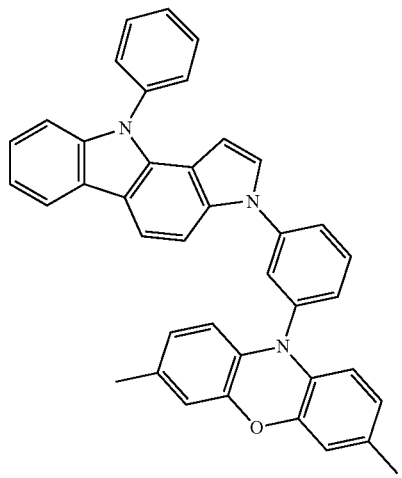
Inv999
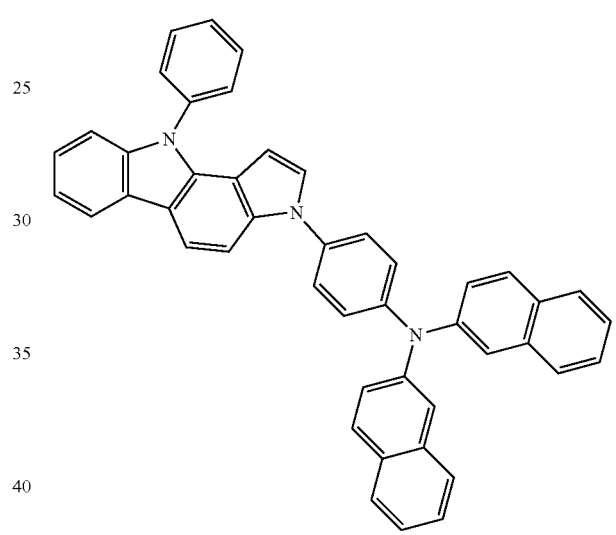
Inv1000
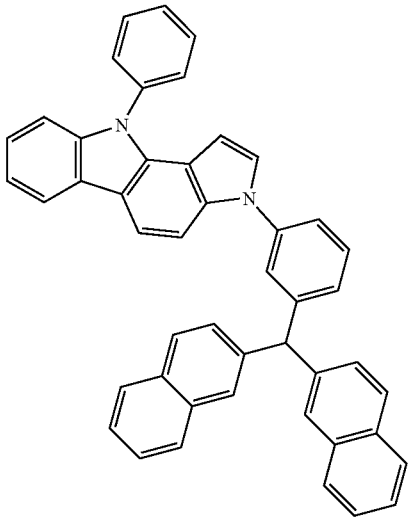

Inv1001
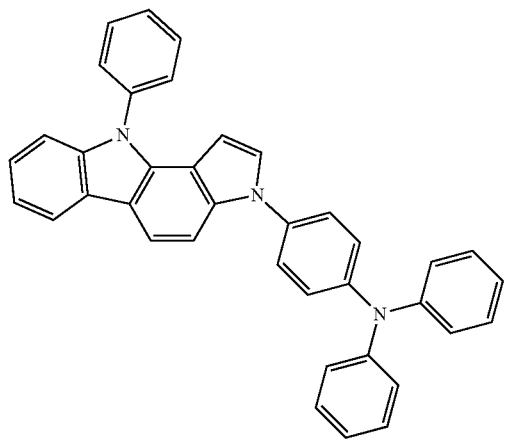
Inv1002
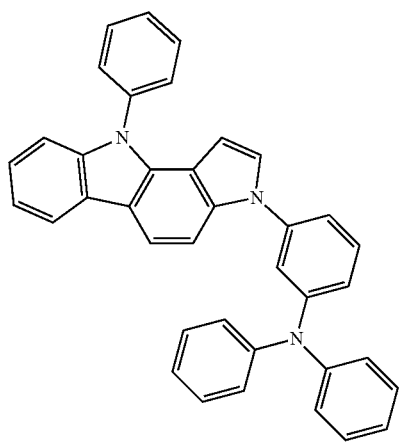
Inv1003
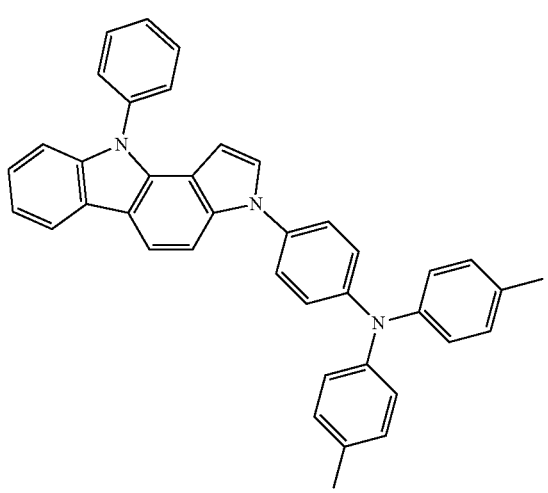
Inv1004
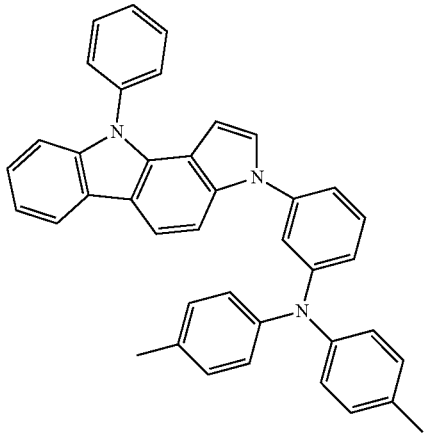
Inv1005
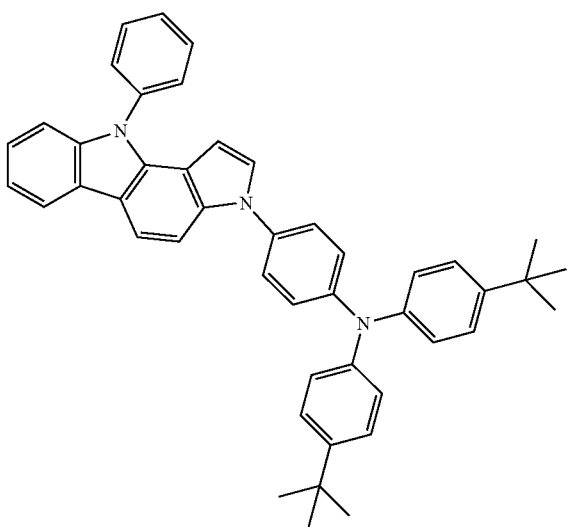
Inv1006
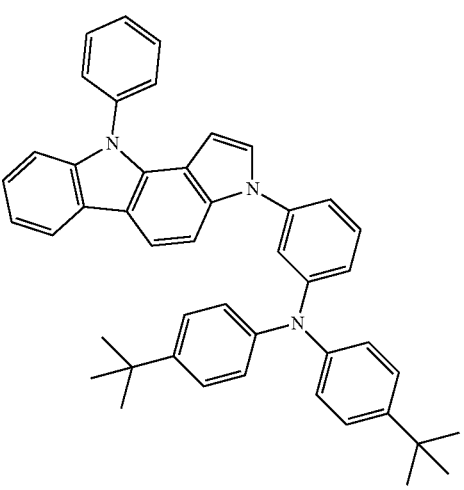

Inv1007
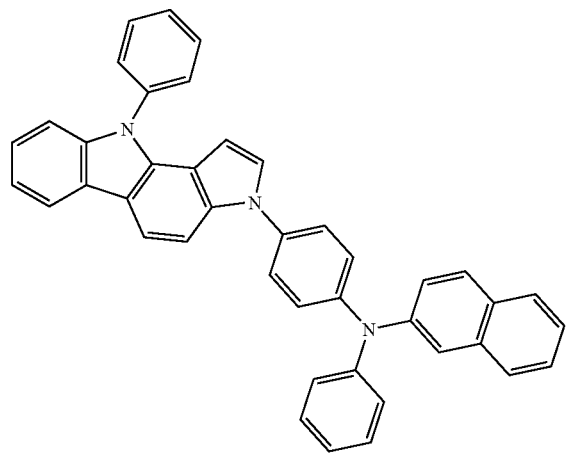
Inv1008
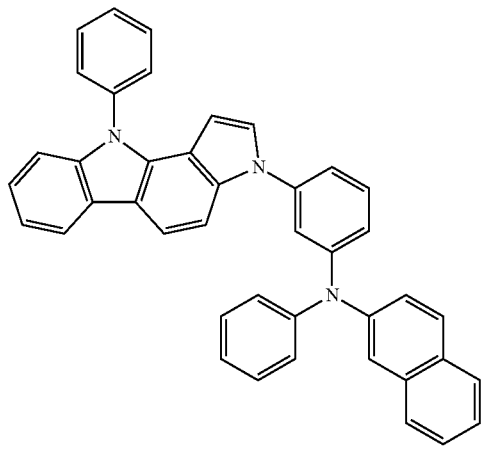
Inv1009
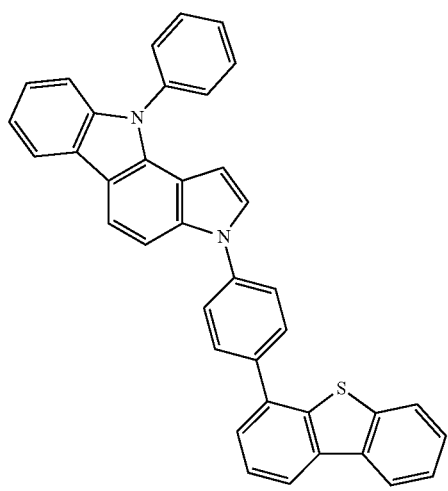
Inv1010
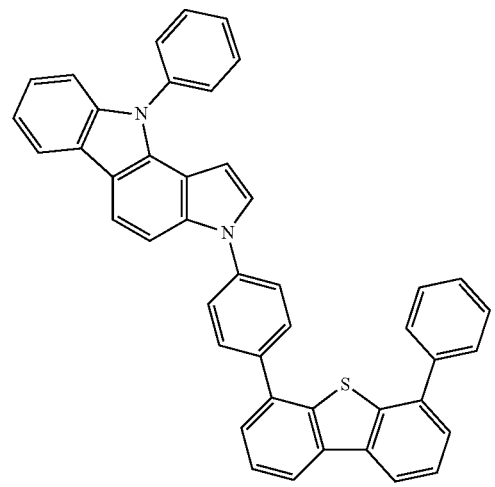
Inv1011
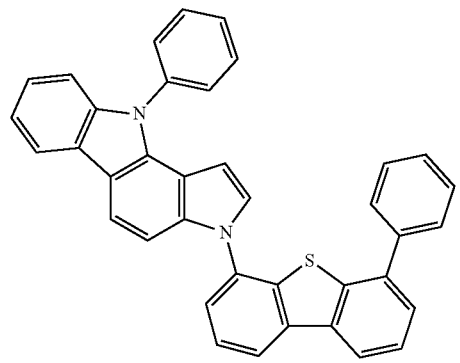
Inv1012
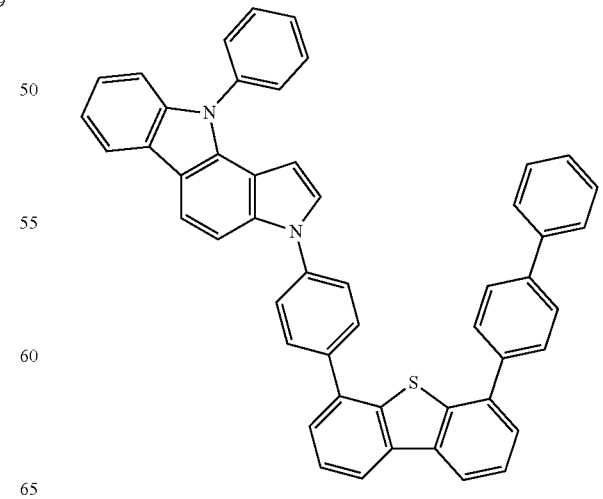

-continued
Inv1013
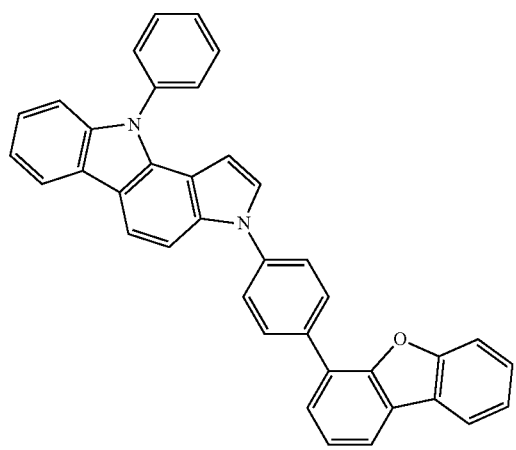
Inv1014
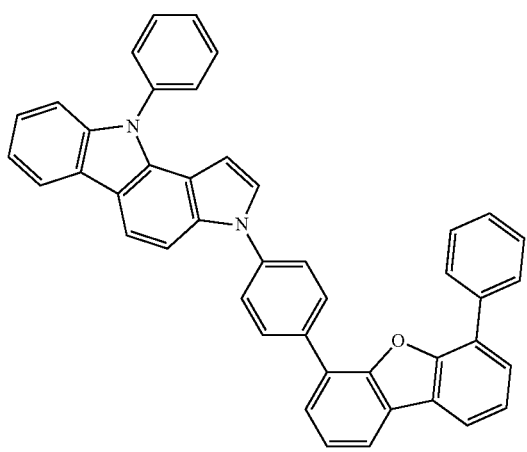
Inv1015
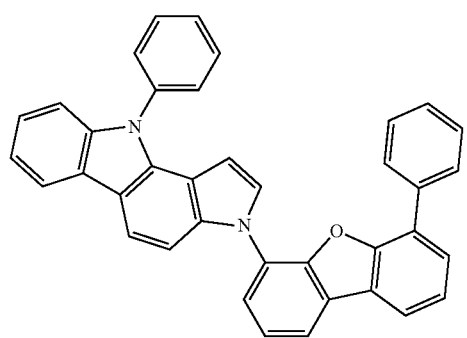
-continued
Inv1016
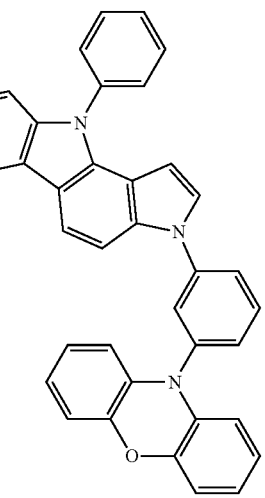
Inv1017
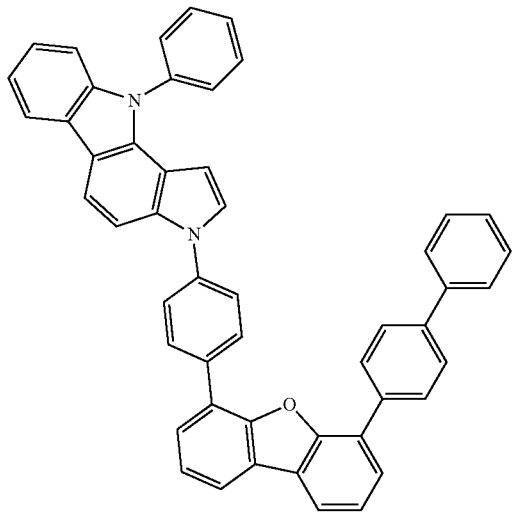
Inv1018
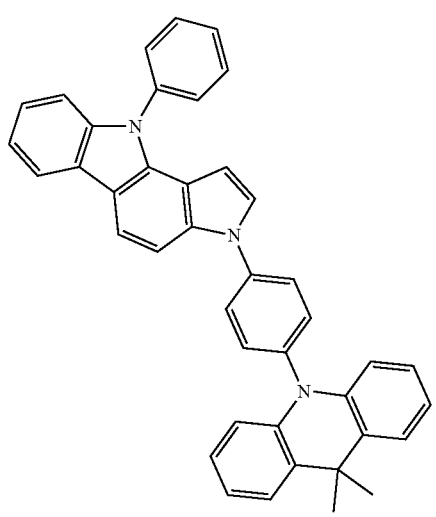

-continued
Inv1019
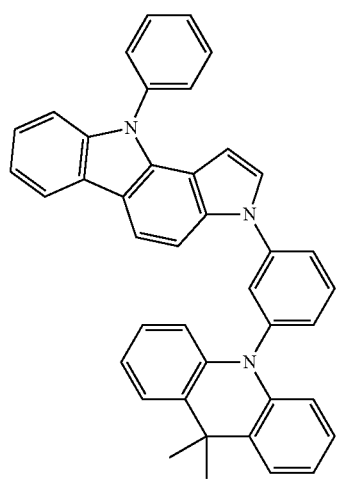
Inv1022
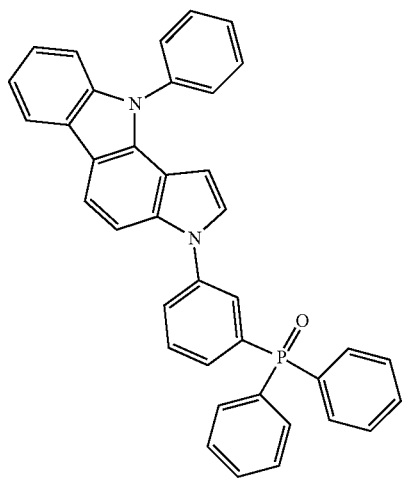
Inv1020
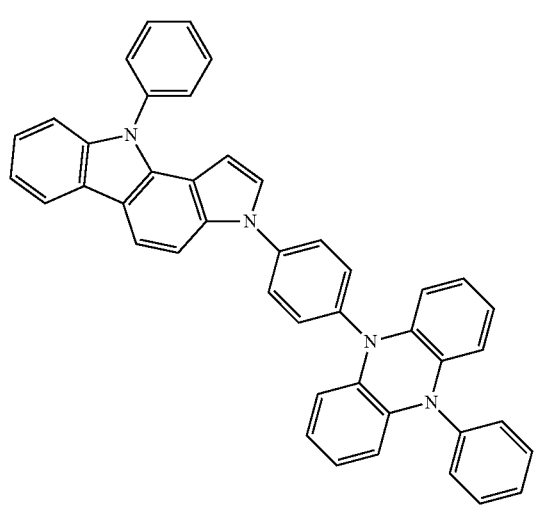
Inv1023
Inv1021
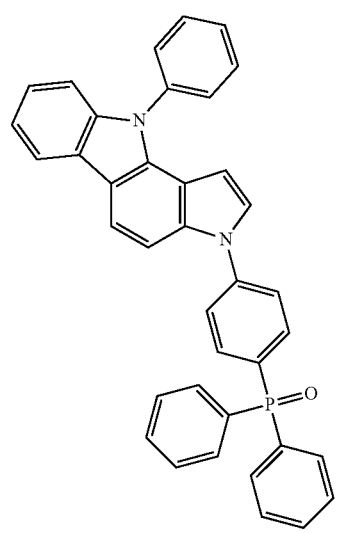
Inv1024
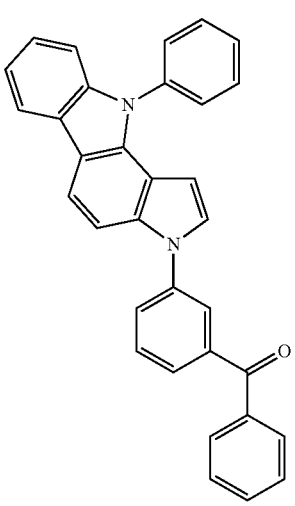

-continued
Inv1025
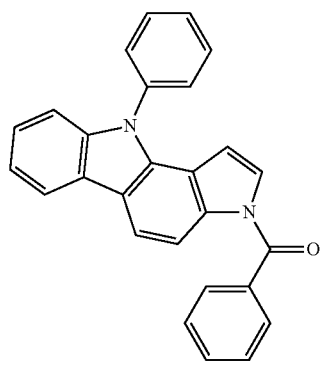
Inv1026
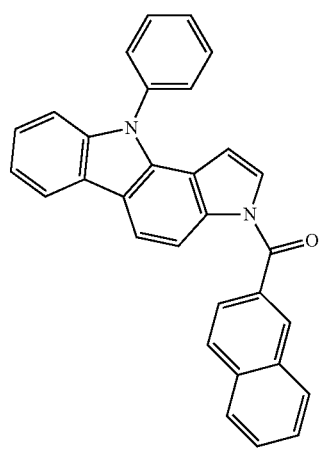
Inv1027
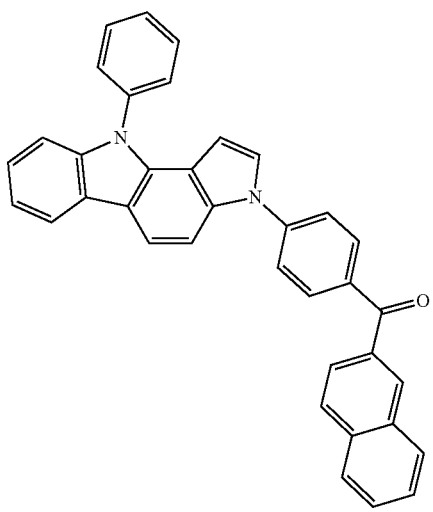
-continued
Inv1028
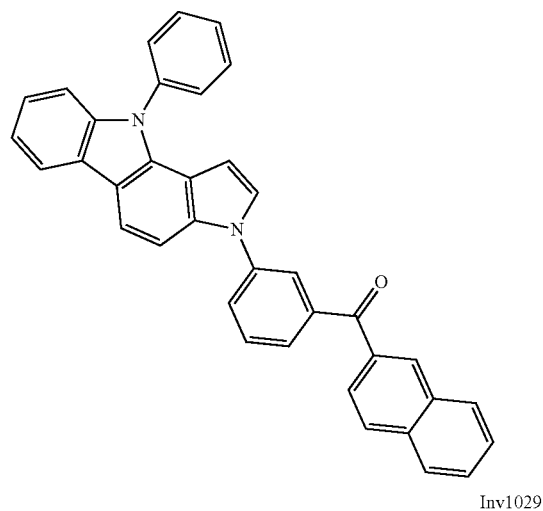
Inv1029
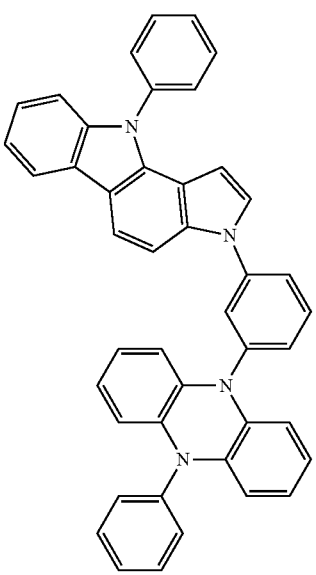
Inv1030
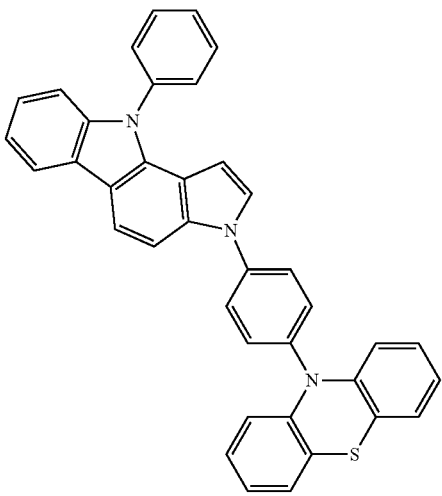

-continued
Inv1031
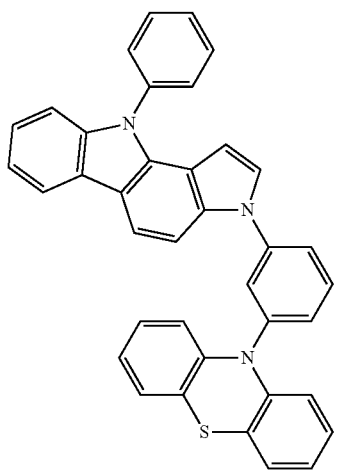
Inv1034
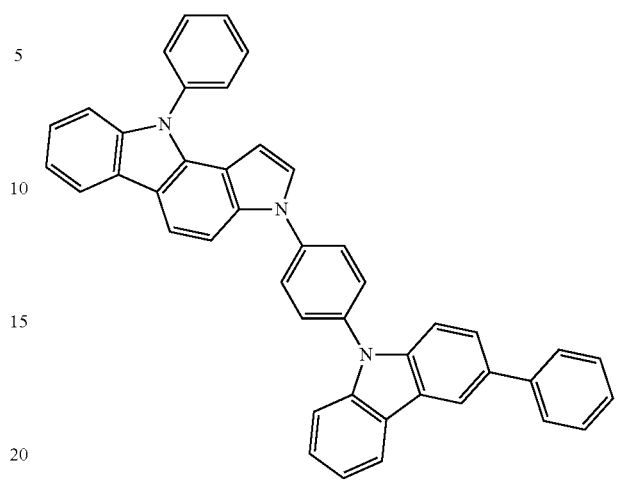
Inv1032
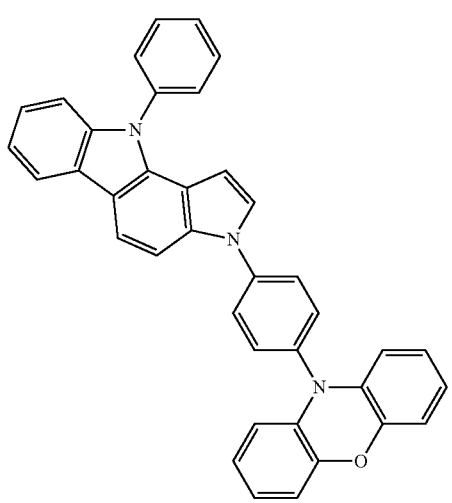
Inv1035
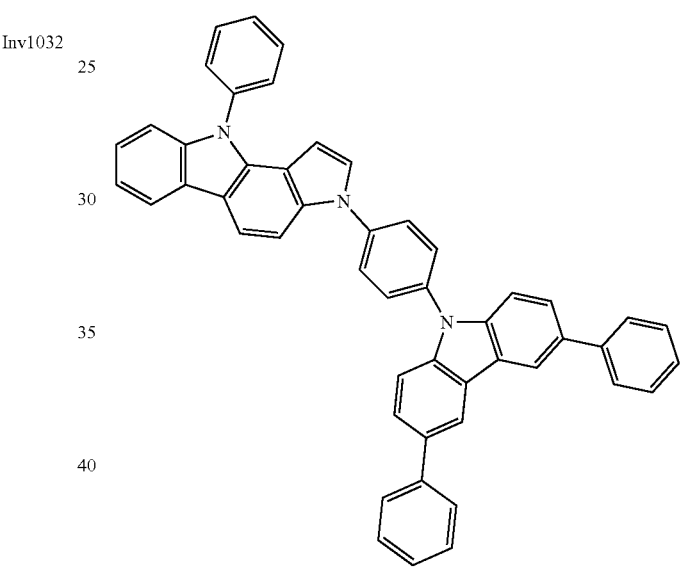
Inv1033
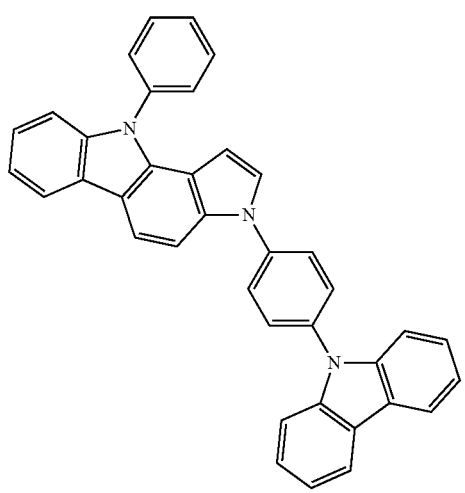
Inv1036
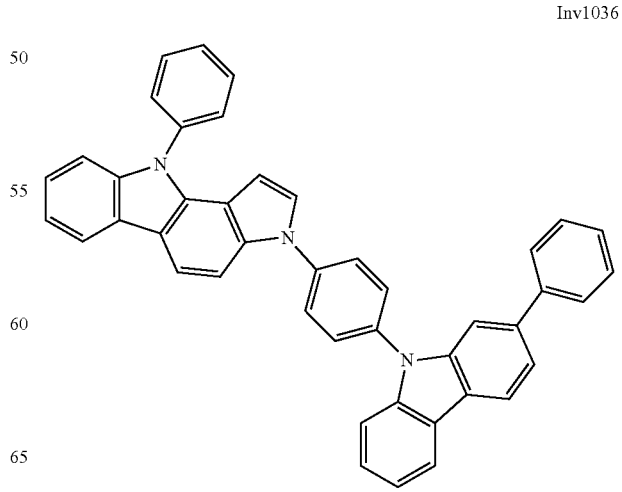

Inv1037
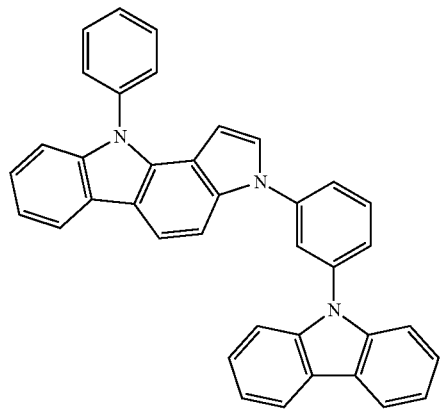
Inv1038
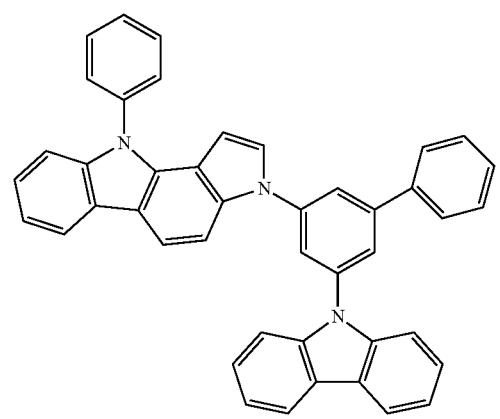
Inv1039
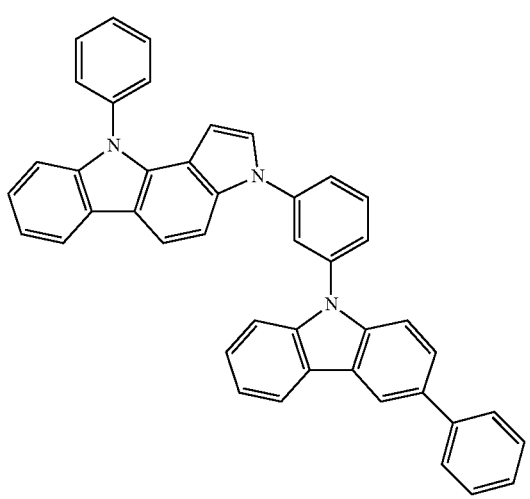
Inv1040
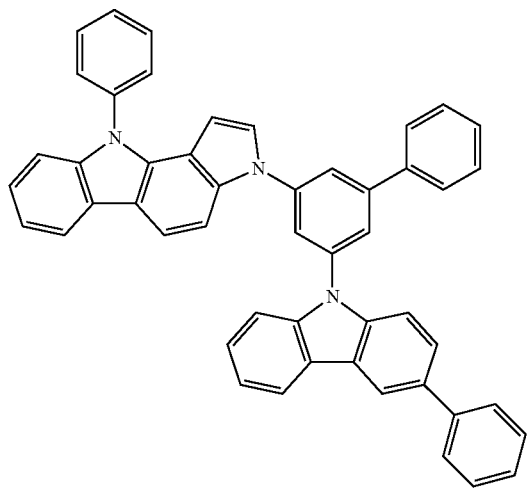
Inv1041
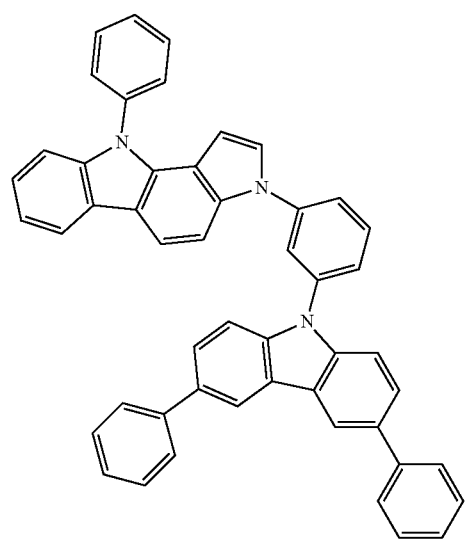
Inv1042
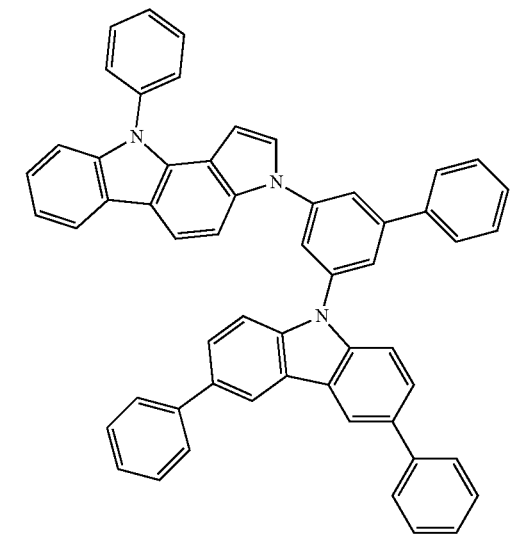

Inv1043
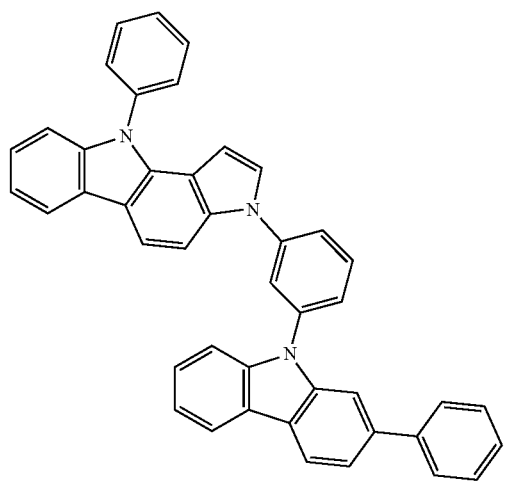
Inv1044
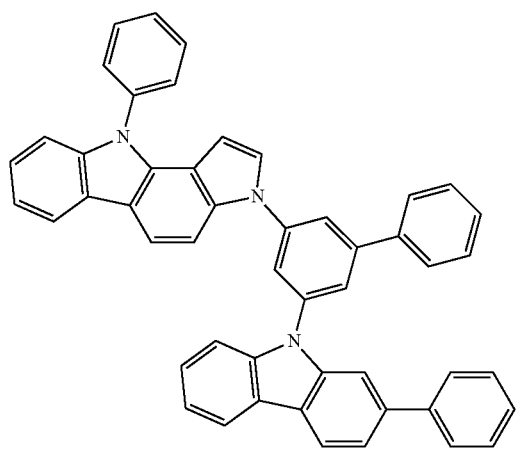
Inv1045
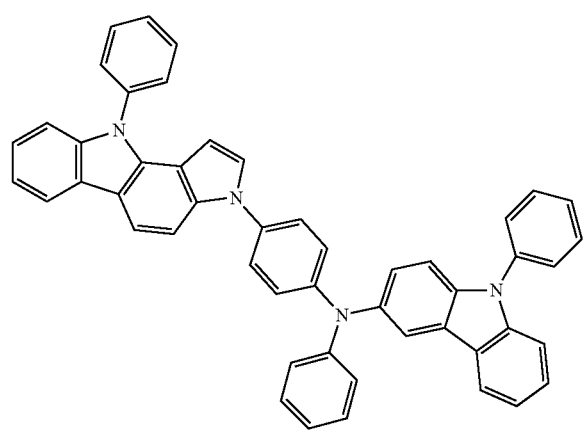
Inv1046
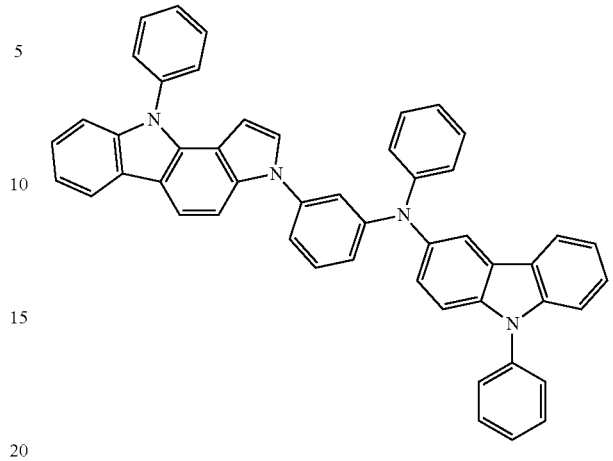
Inv1047
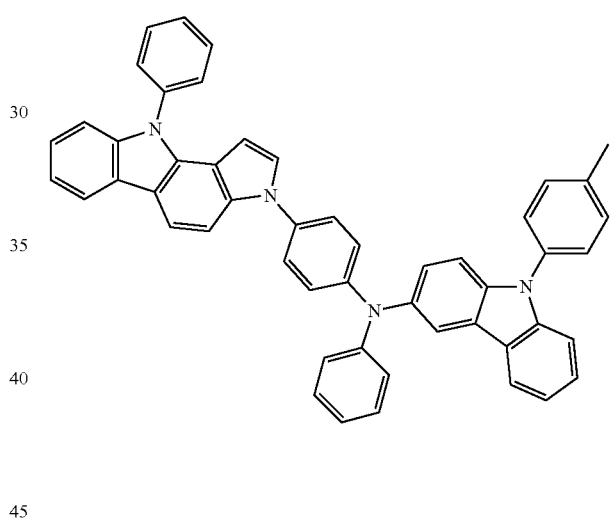
Inv1048
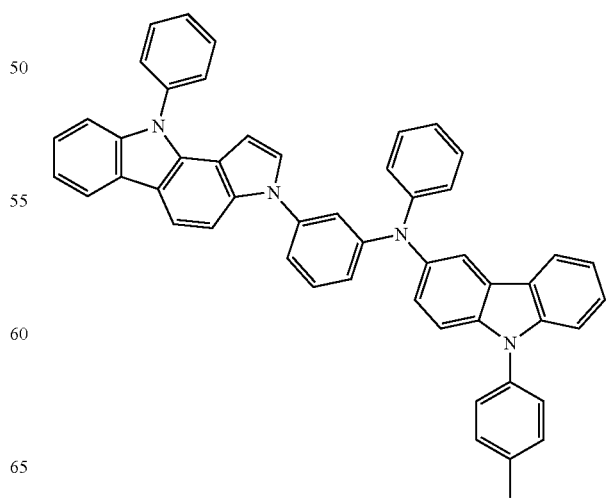

Inv1049
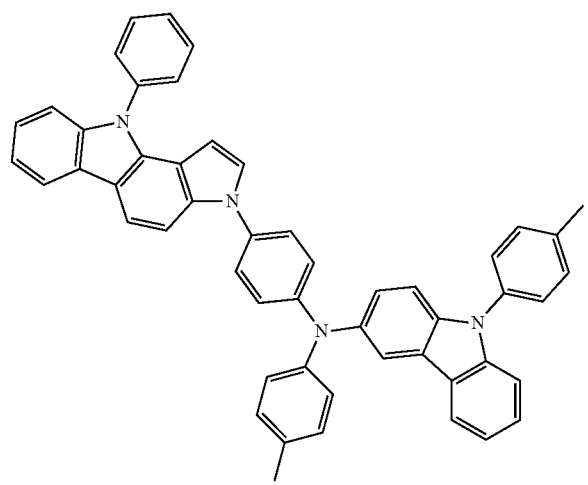
Inv1050
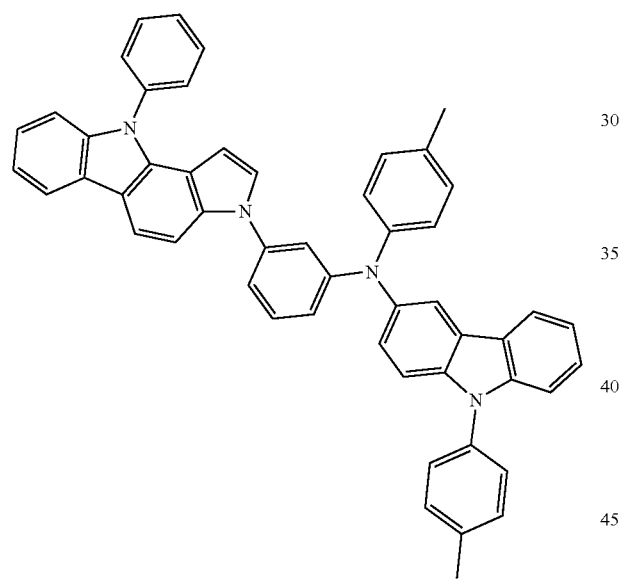
Inv1051
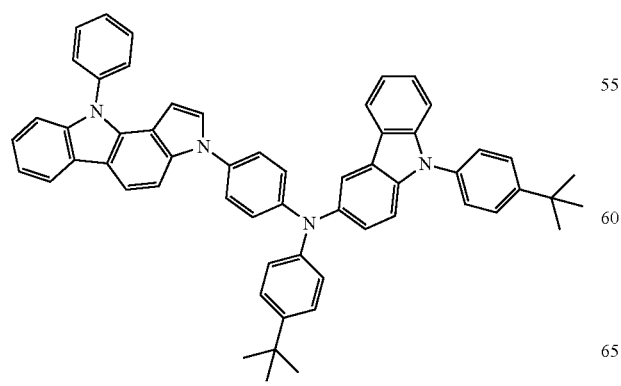
Inv1052
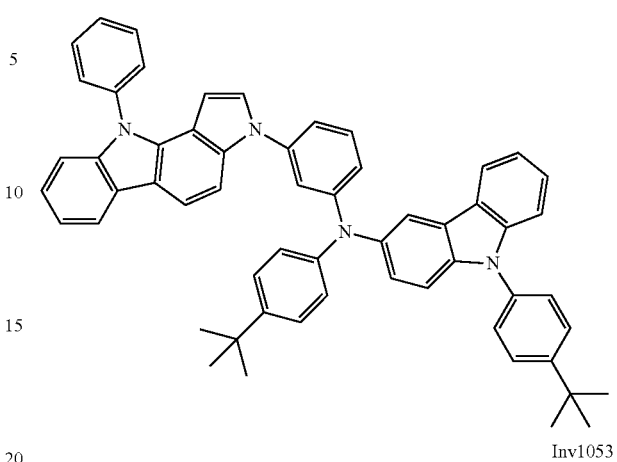
Inv1053
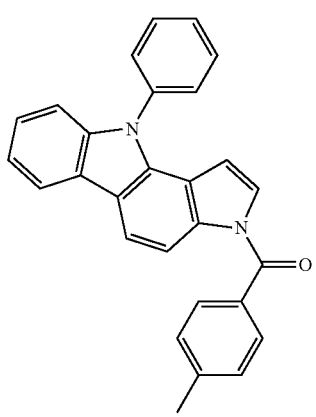
Inv1054
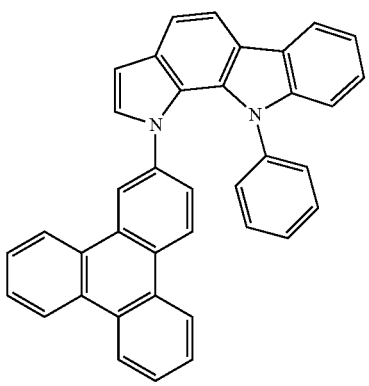
Inv1055
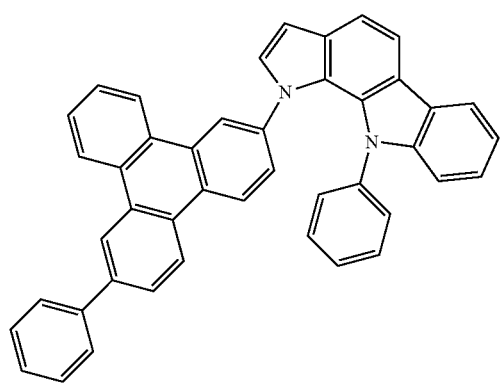

-continued
Inv1056
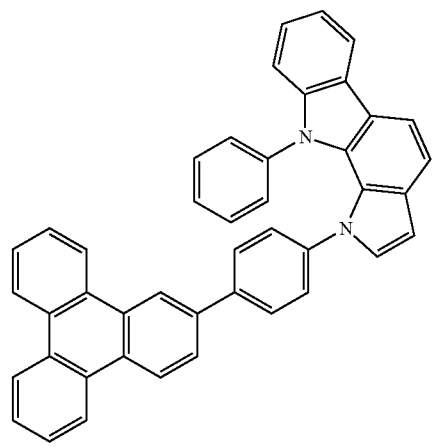
Inv1057
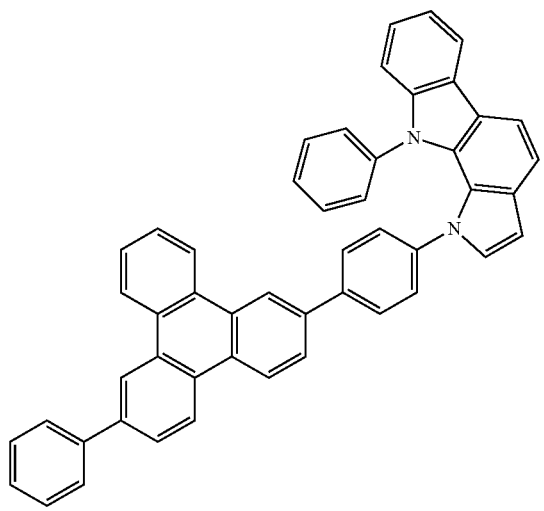
Inv1058
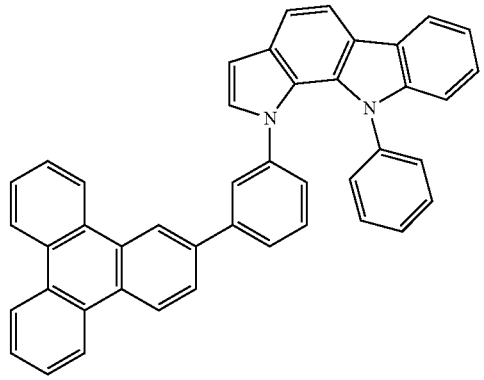
-continued
Inv1059
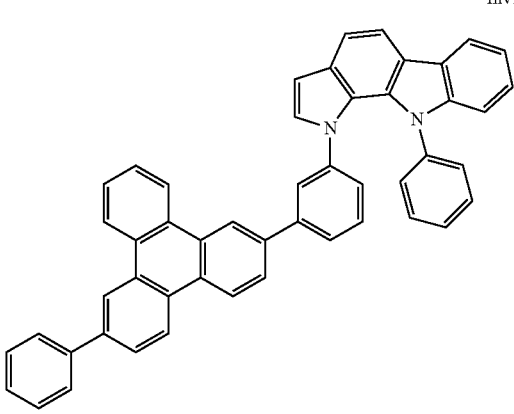
Inv1060
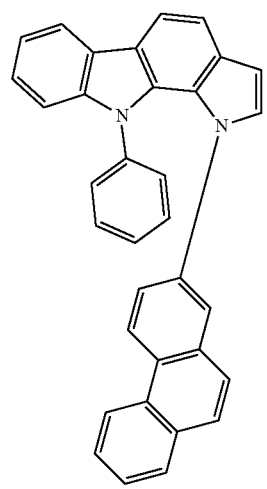
Inv1061
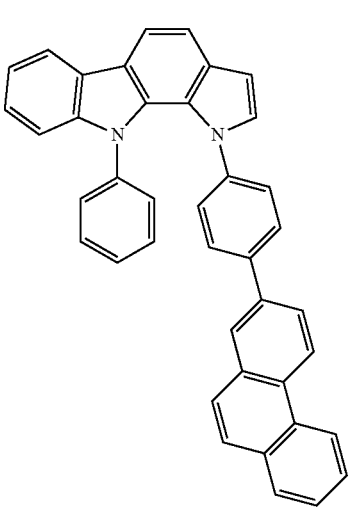

Inv1062
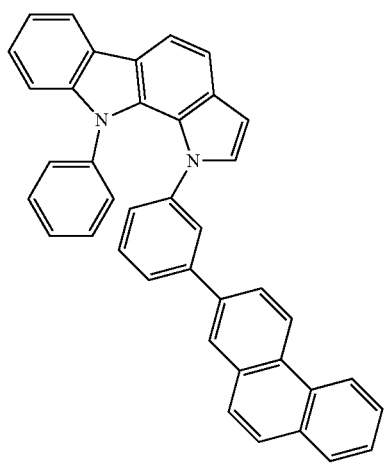
Inv1063
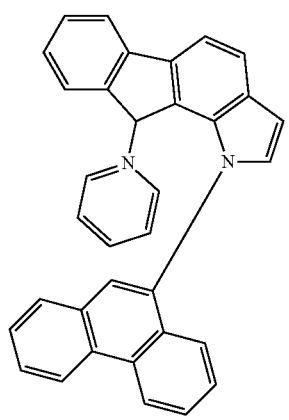
Inv1064
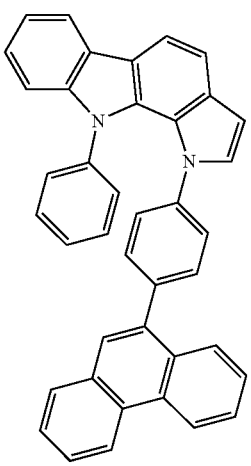
Inv1065
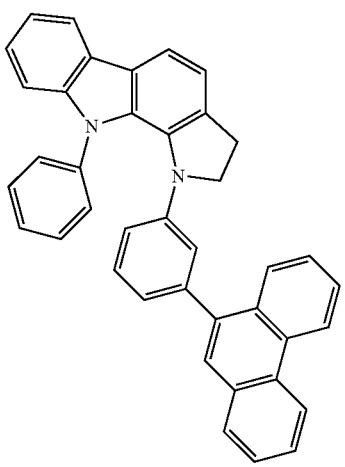
Inv1066
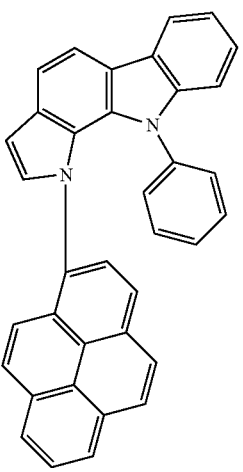
Inv1067
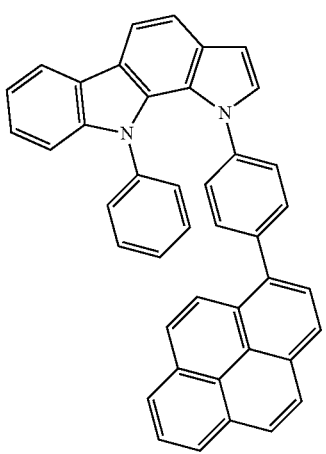

Inv1068
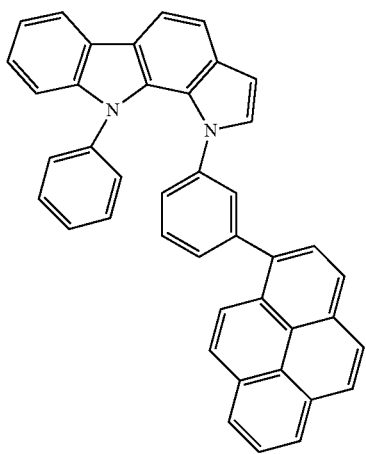
Inv1069
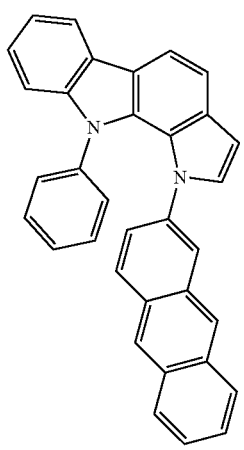
Inv1070
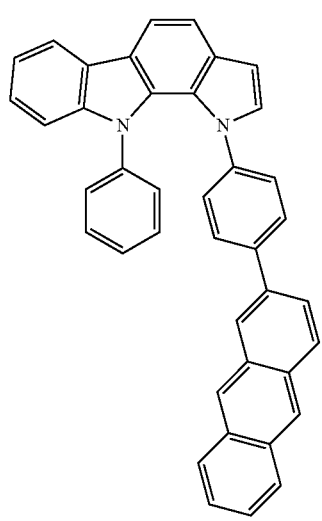
Inv1071
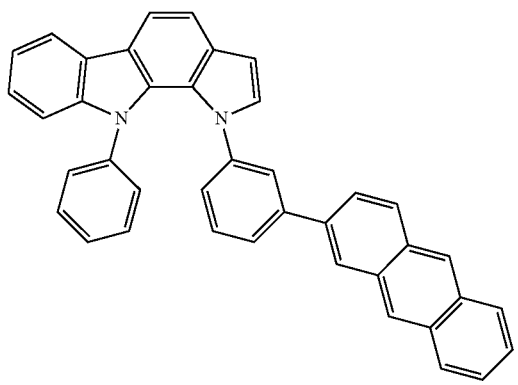
Inv1072
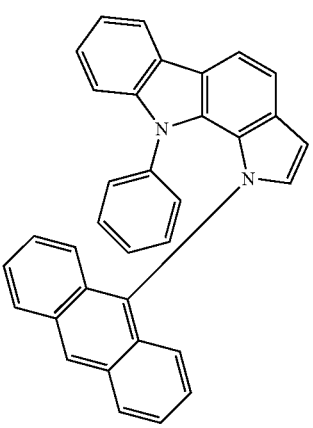
Inv1073
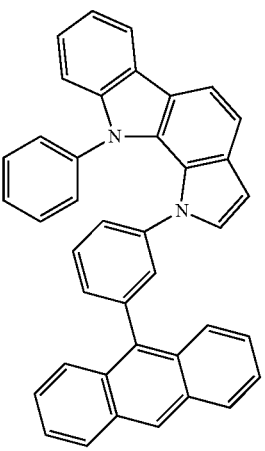

Inv1074
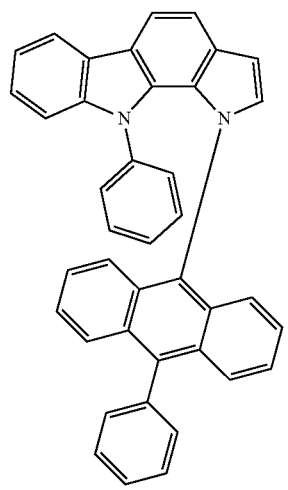
Inv1075
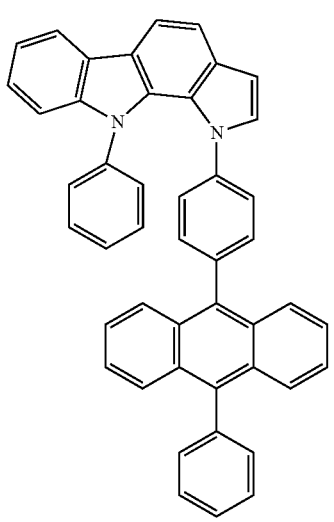
Inv1076
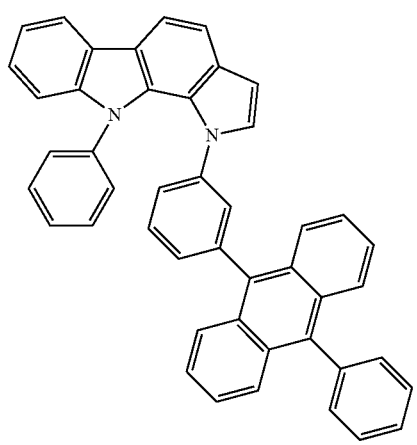
Inv1077
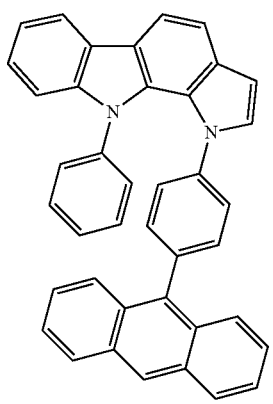
Inv1078
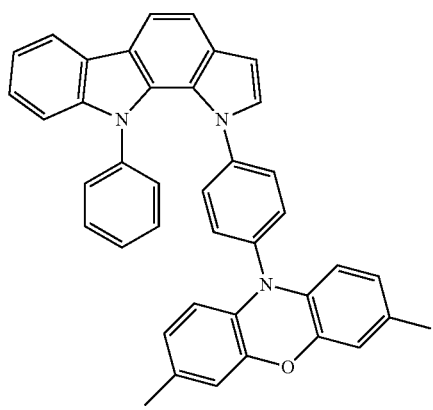
Inv1079
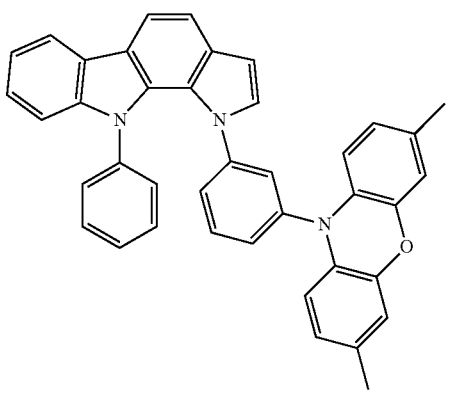
Inv1080
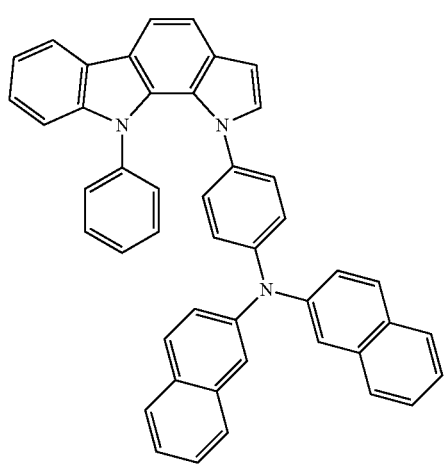

Inv1081
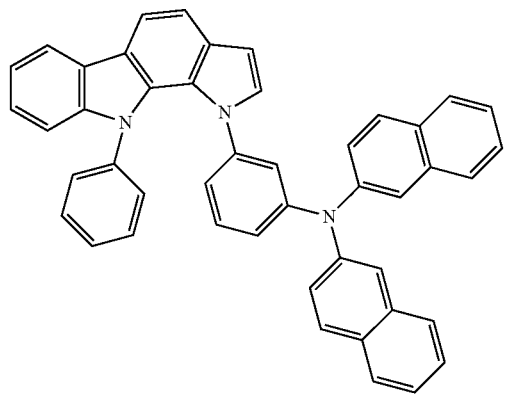
Inv1082
Inv1083
Inv1084
Inv1085
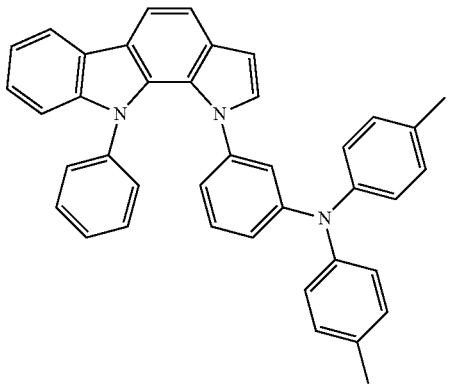
Inv1086
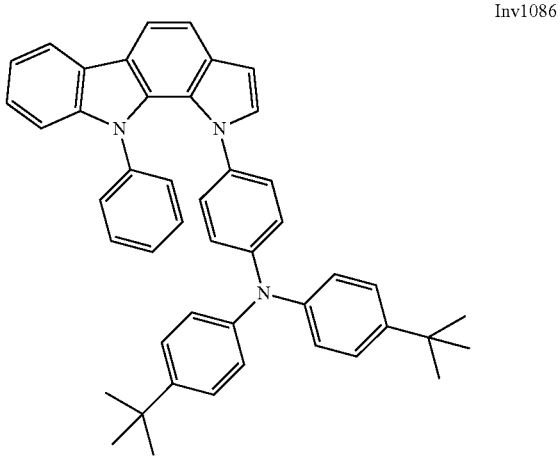
Inv1087
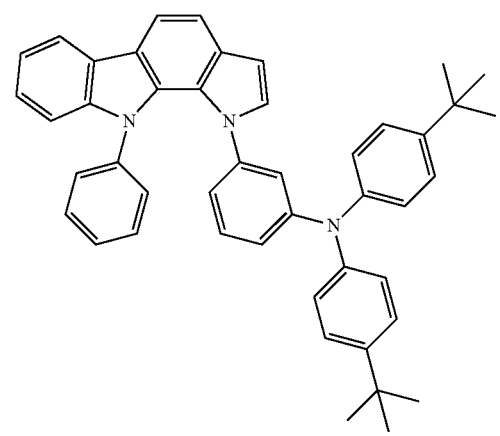

-continued
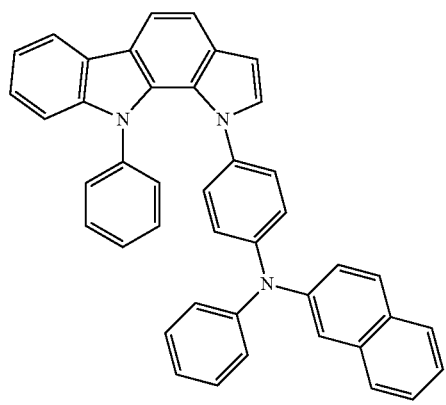
Inv1088
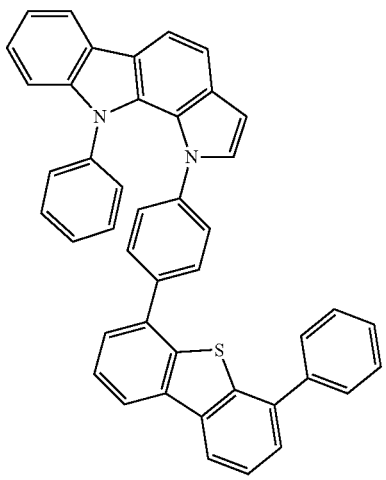
Inv1091
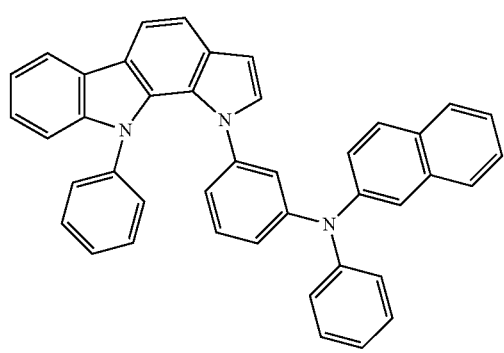
Inv1089
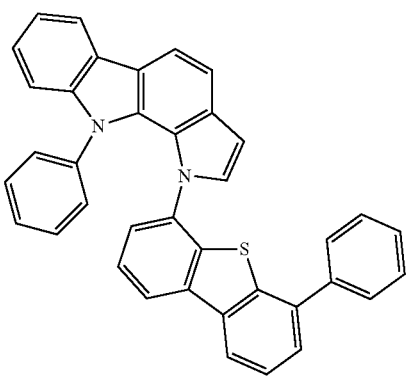
Inv1092
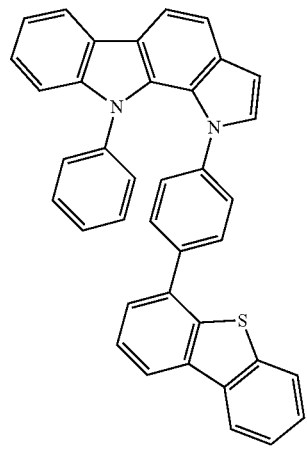
Inv1090
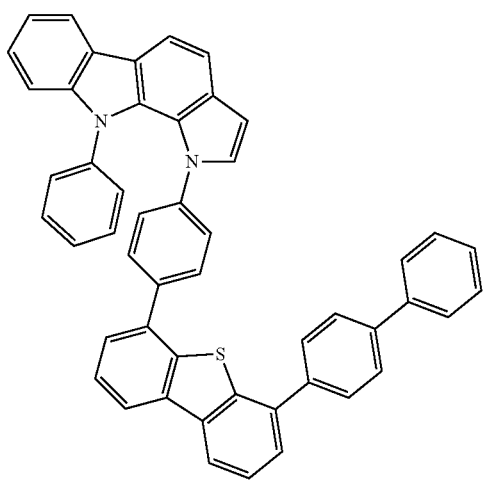
Inv1093

-continued
Inv1094
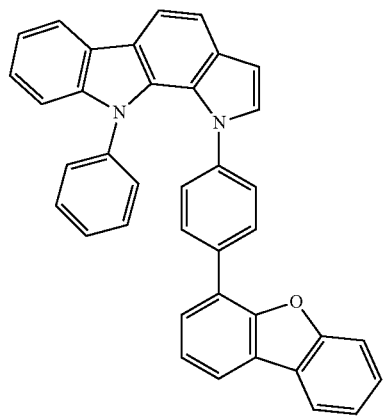
Inv1095
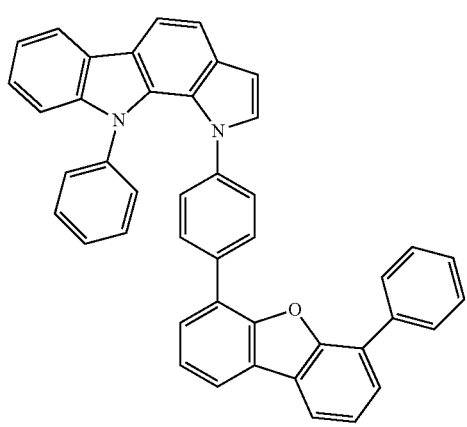
Inv1096
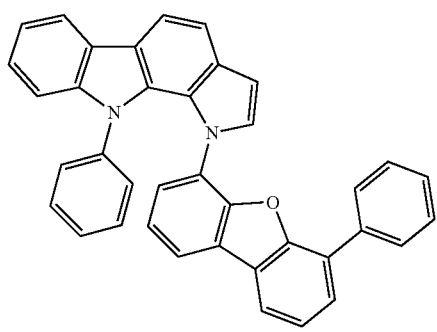
Inv1097
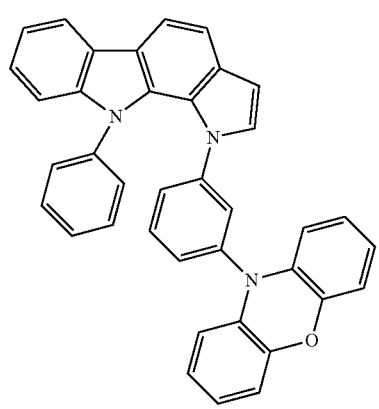
-continued
Inv1098
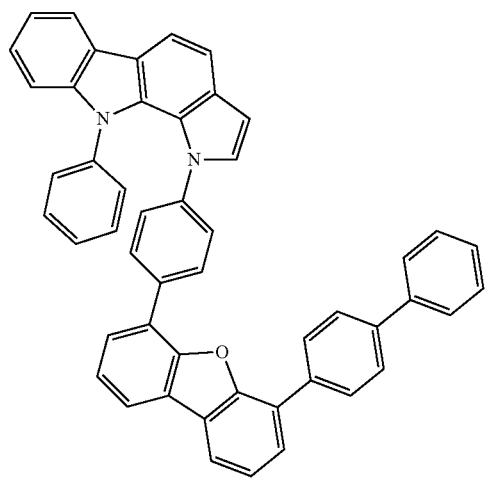
Inv1099
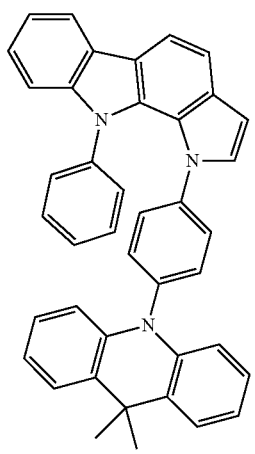
Inv1100
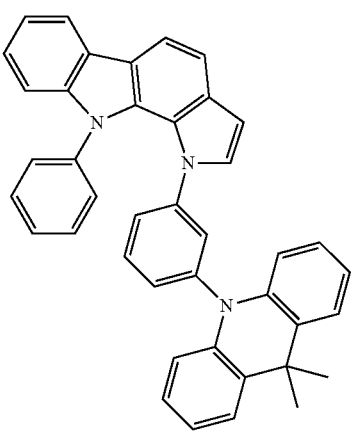

Inv1101
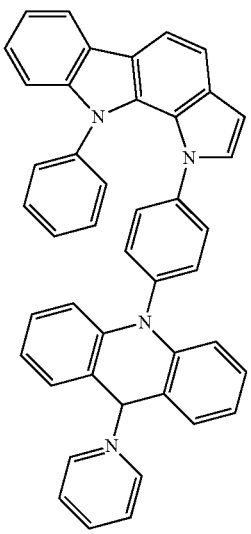
Inv1102
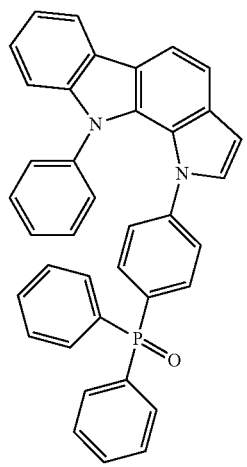
Inv1103
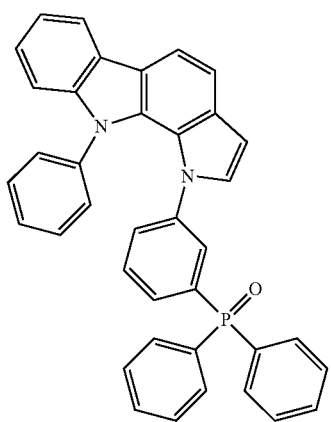
Inv1104
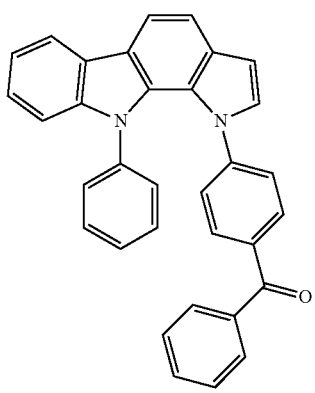
Inv1105
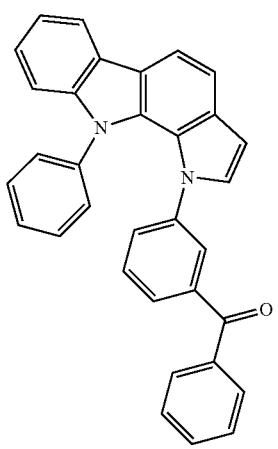
Inv1106
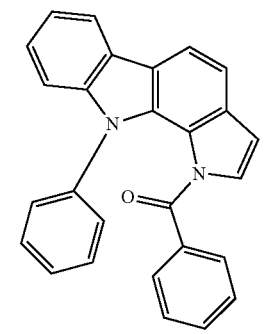
Inv1107
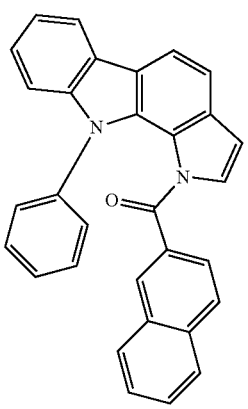

-continued
Inv1108
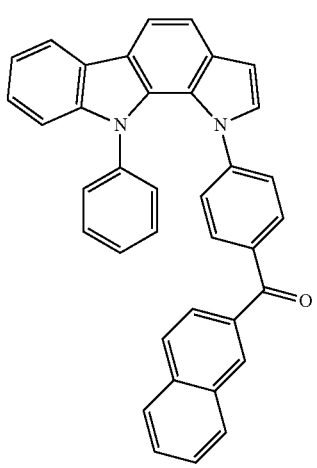
Inv1111
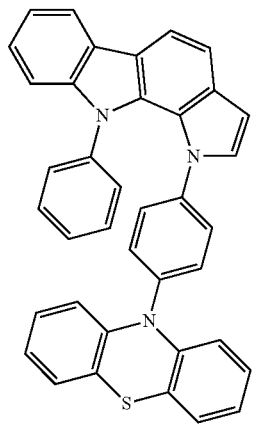
Inv1109
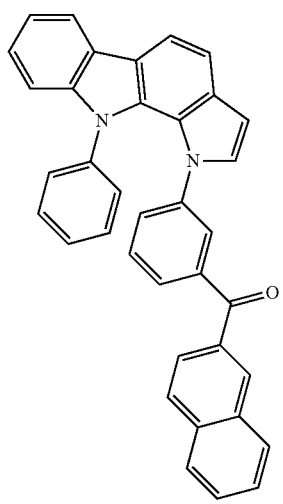
Inv1112
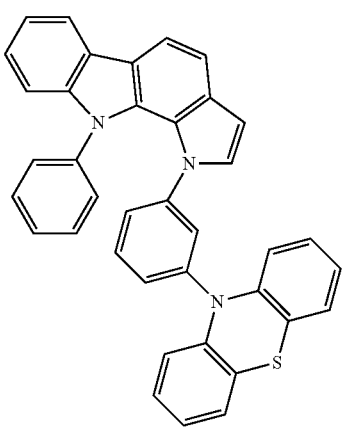
Inv1110
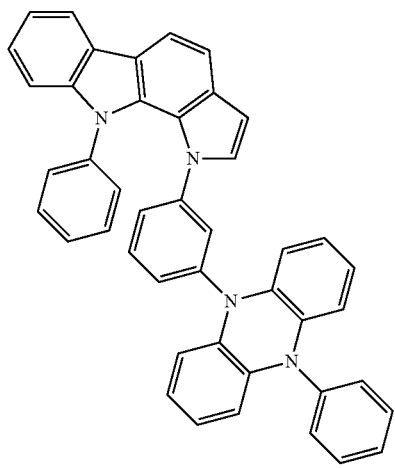
Inv1113
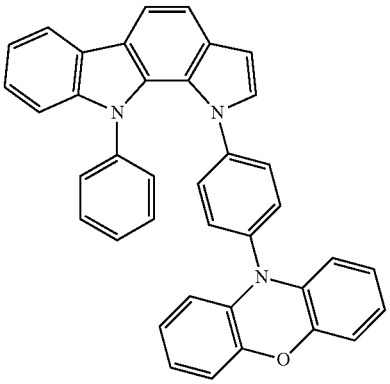

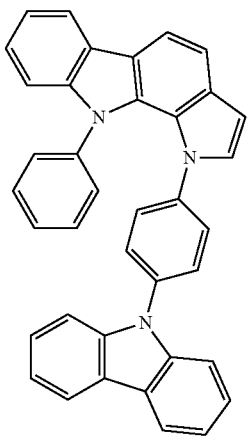
Inv1114
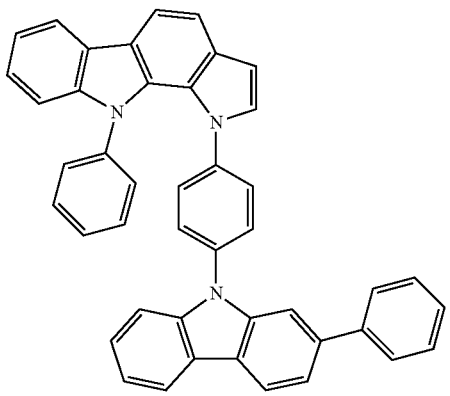
Inv1117
Inv1115
Inv1118
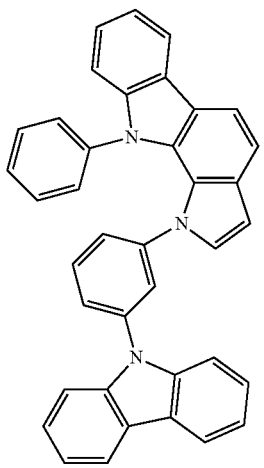
Inv1116
Inv1119
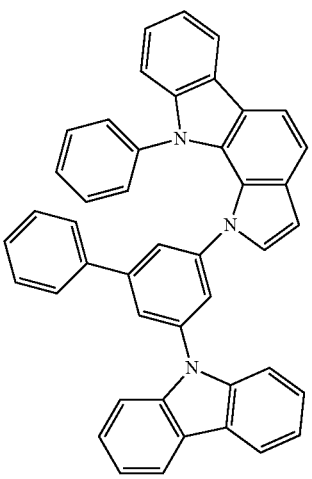

407
-continued
Inv1120
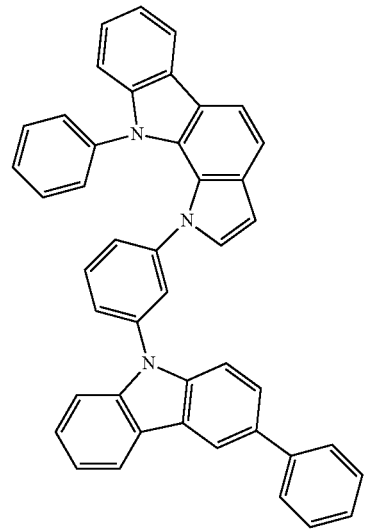
Inv1121
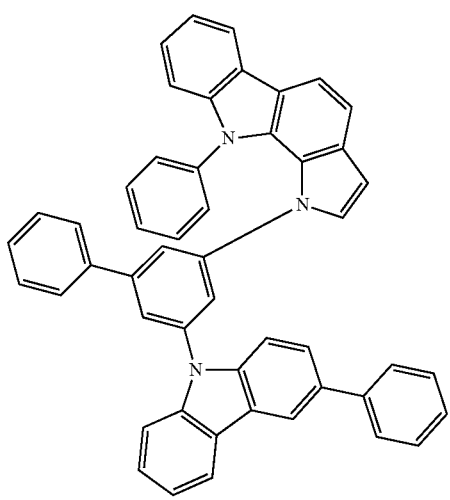
Inv1122
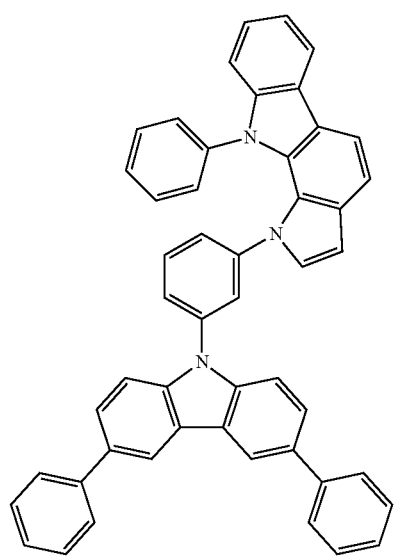
408
-continued
Inv1123
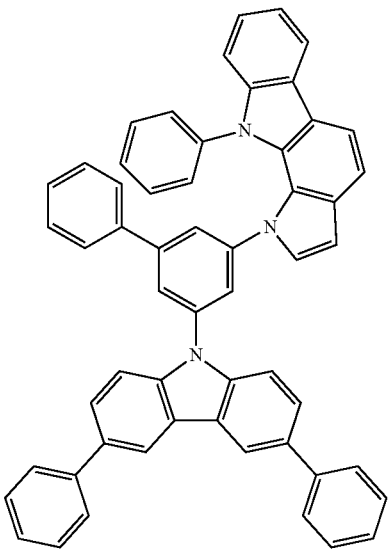
Inv1124
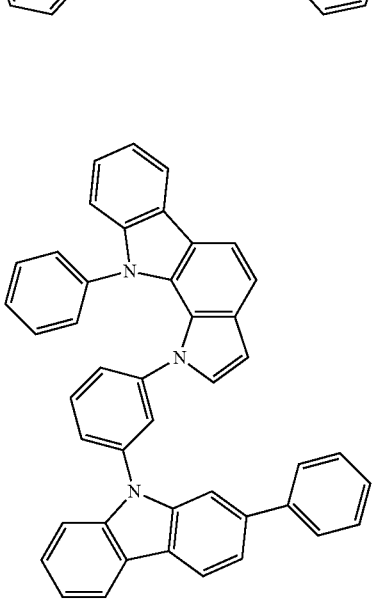
Inv1125
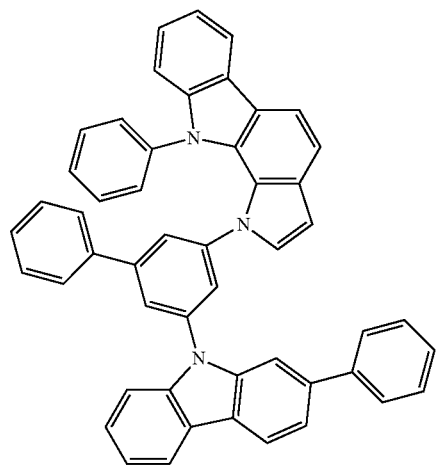

Inv1126
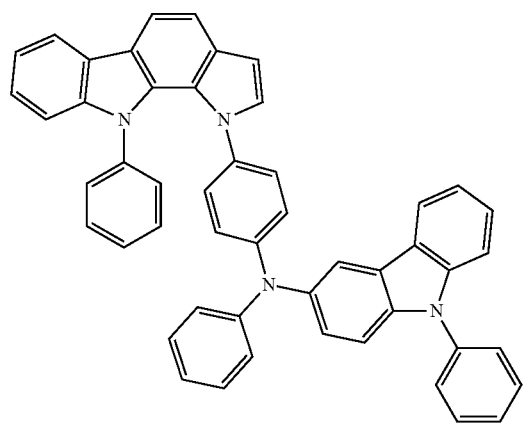
Inv1127
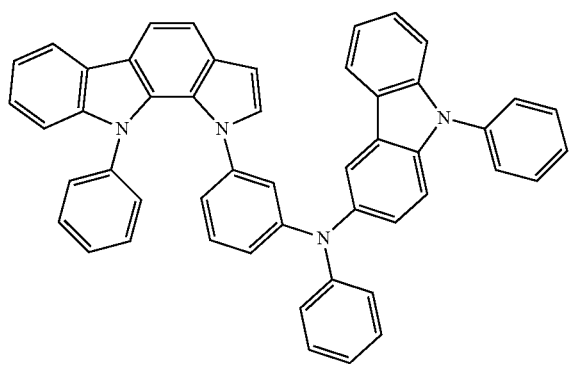
Inv1128
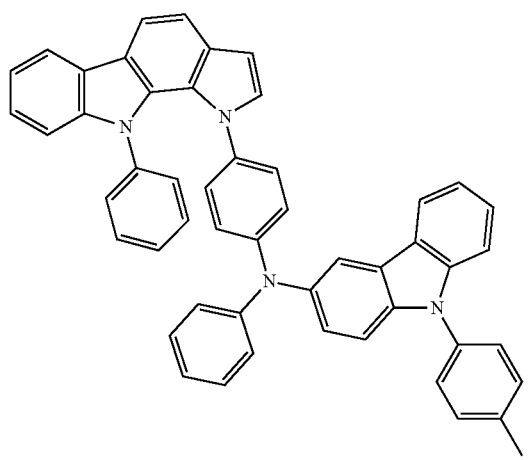
Inv1129
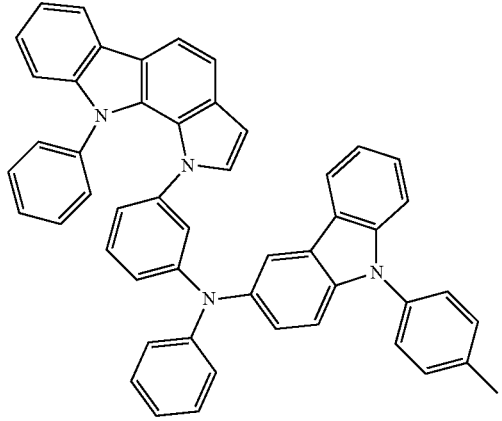
Inv1130
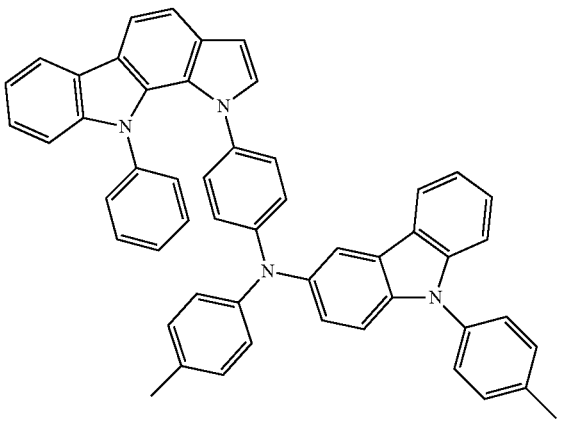
Inv1131
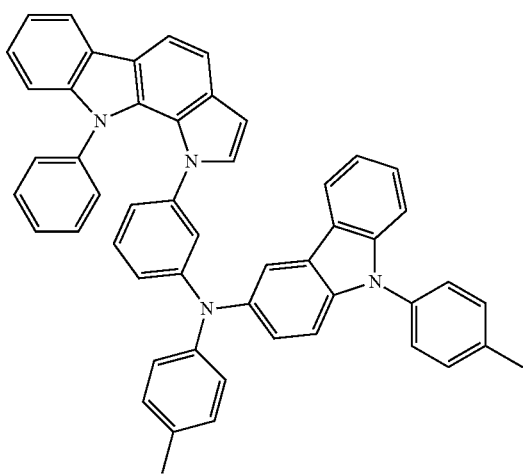

411
-continued
Inv1132
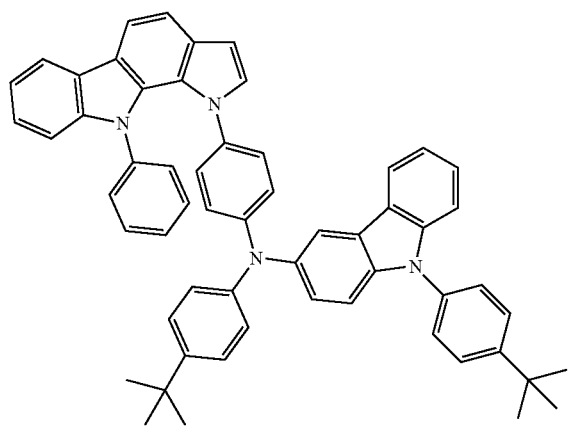
Inv1133
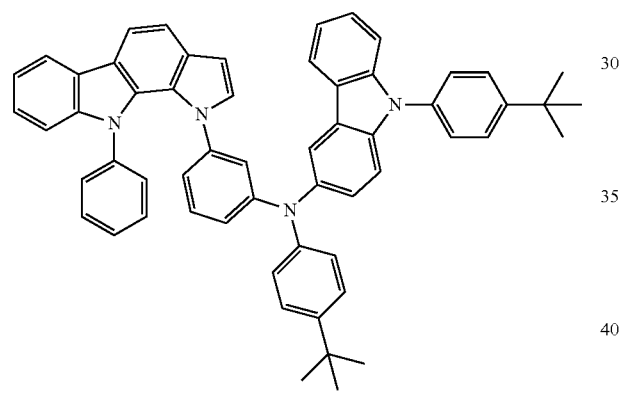
Inv1134
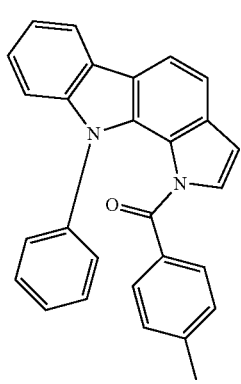
412
-continued
Inv1135
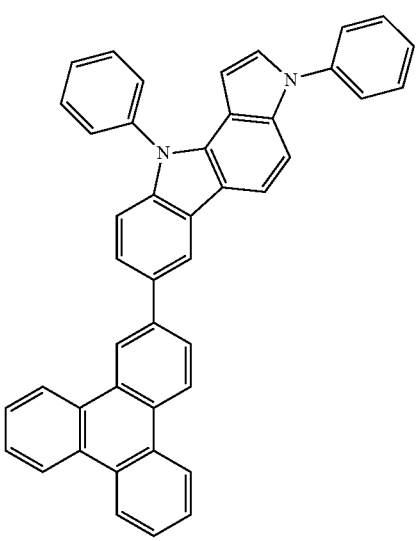
Inv1136
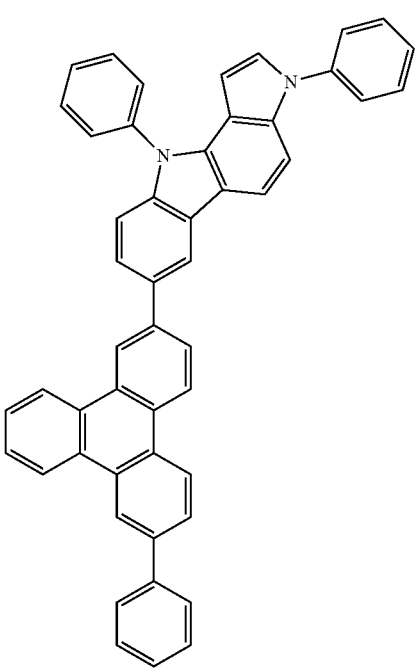

Inv1137
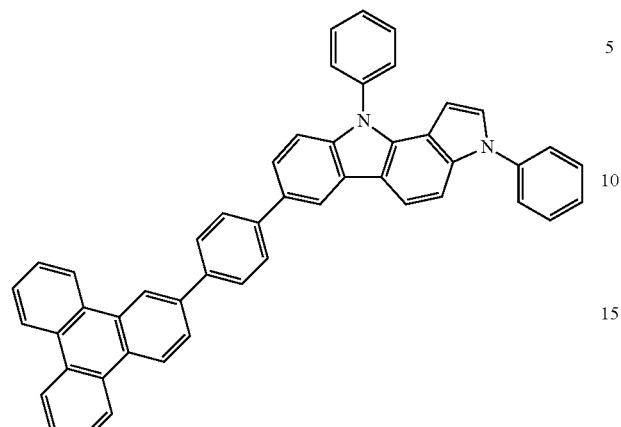
Inv1138
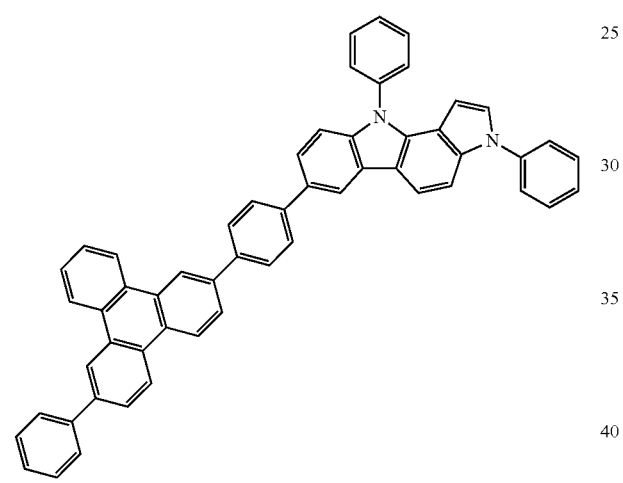
Inv1139
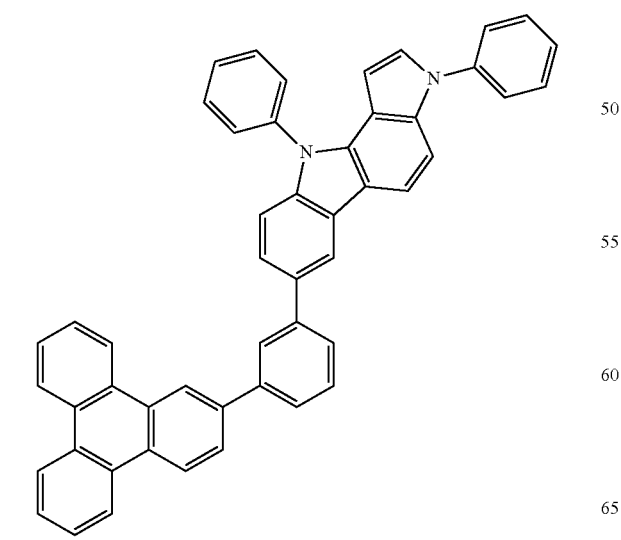
Inv1140
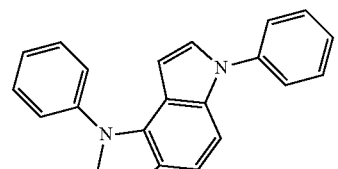
Inv1141
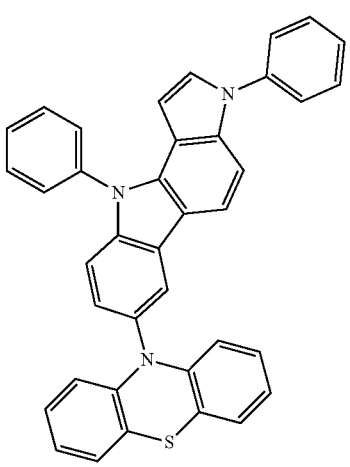
Inv1142
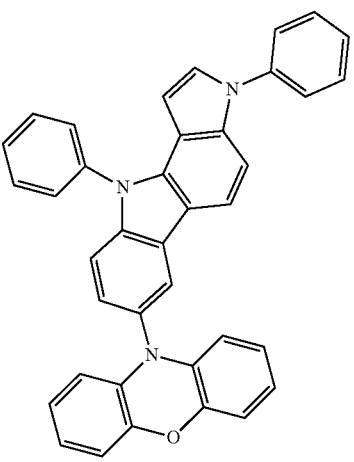

415
-continued
Inv1143
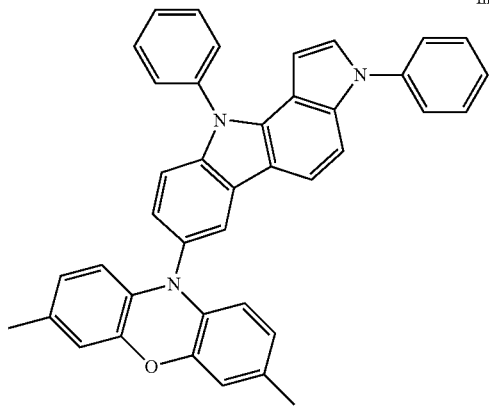
Inv1144
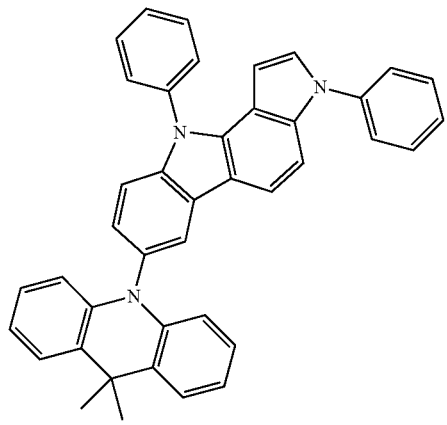
Inv1145
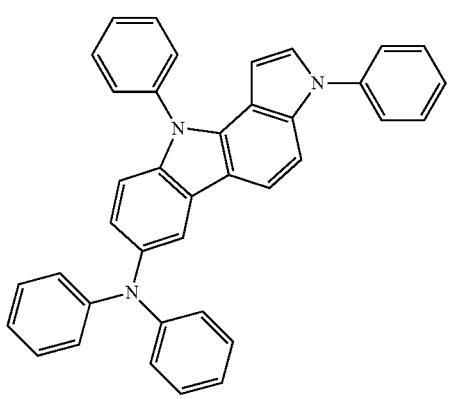
416
-continued
Inv1146
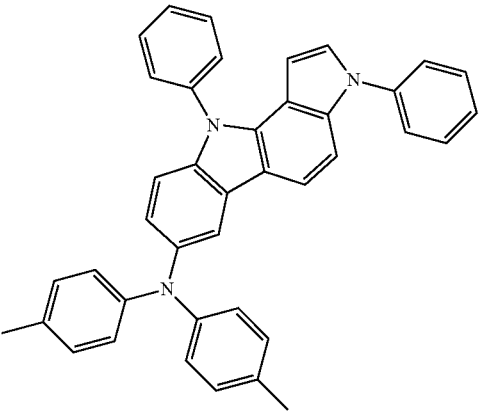
Inv1147
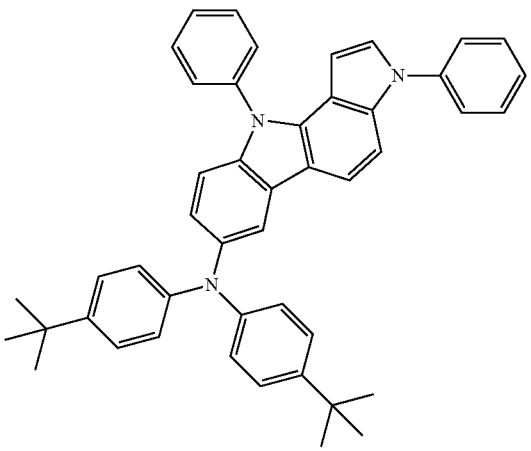
Inv1148
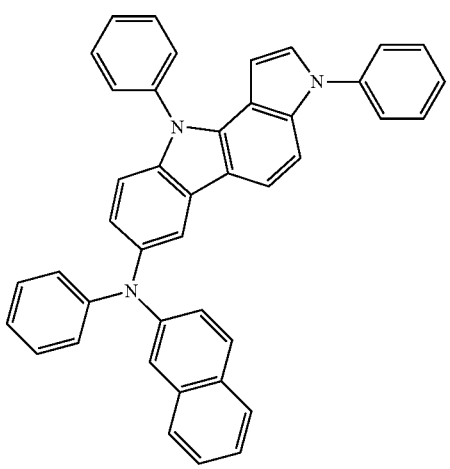

Inv1149
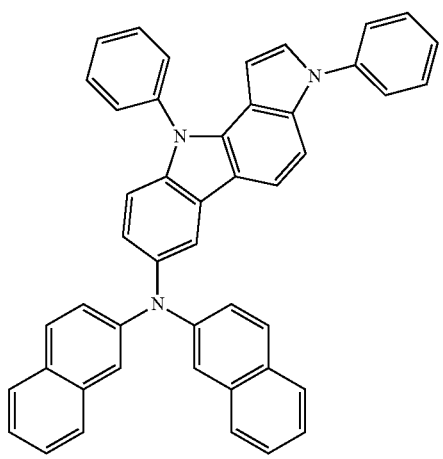
Inv1153
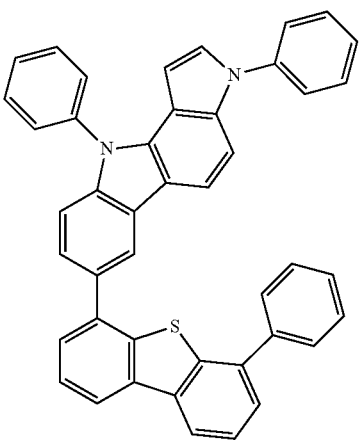
Inv1150
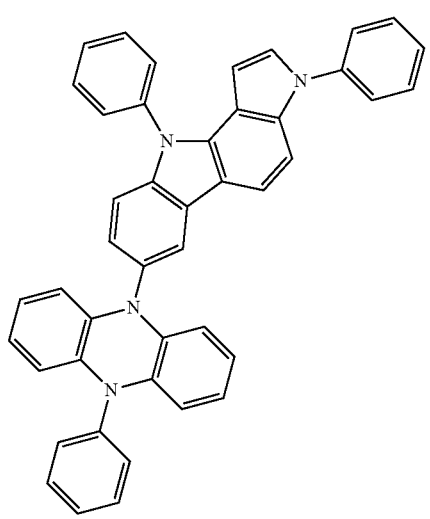
Inv1152
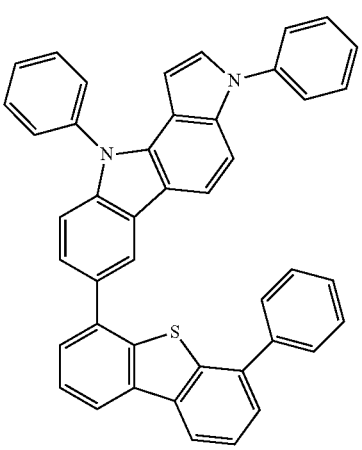
Inv1151
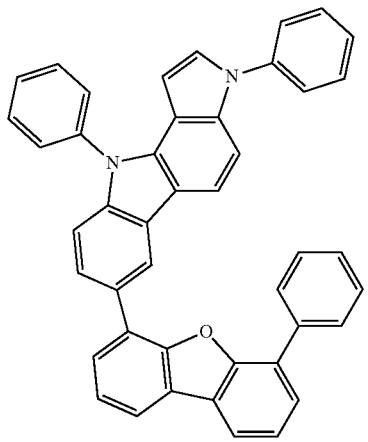
Inv1153
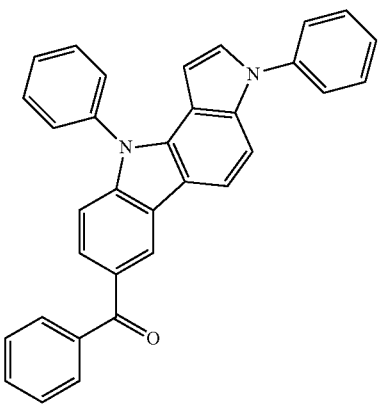

419
-continued
Inv1154
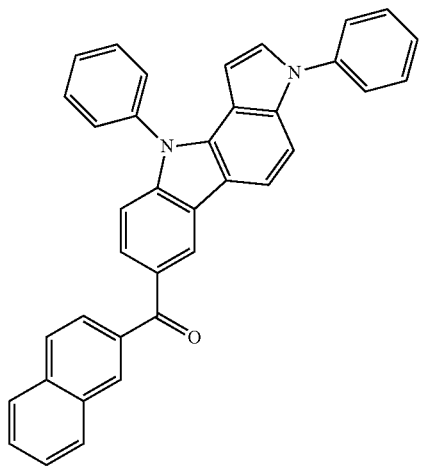
Inv1155
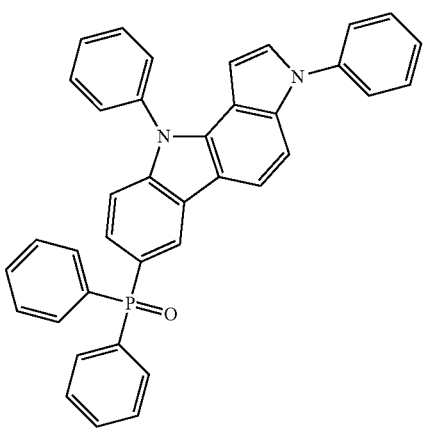
Inv1156
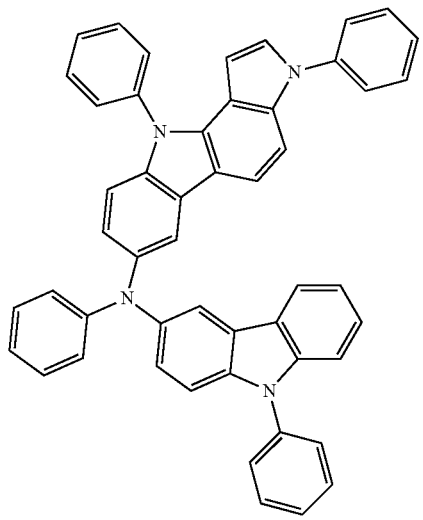
420
-continued
Inv1157
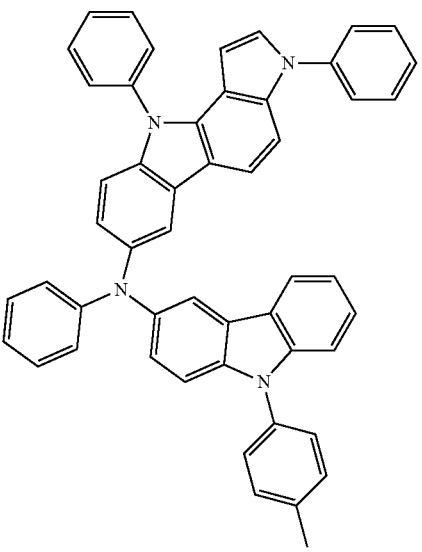
Inv1158
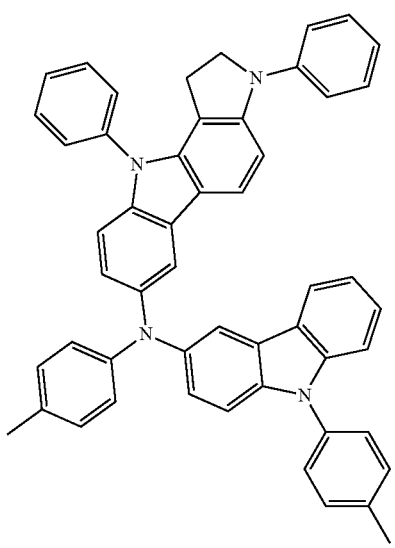

421
421
Inv1159
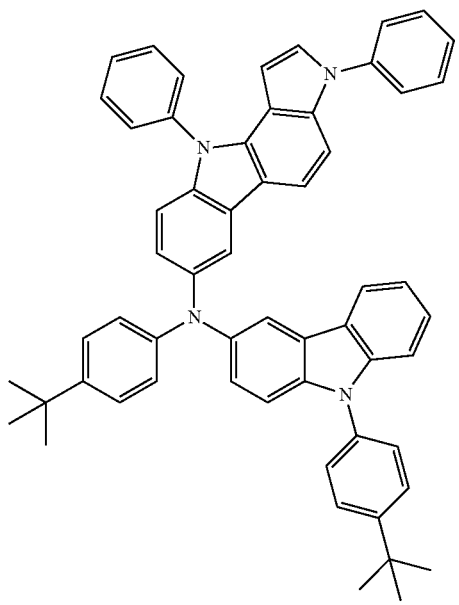
422
-continued
Inv1161
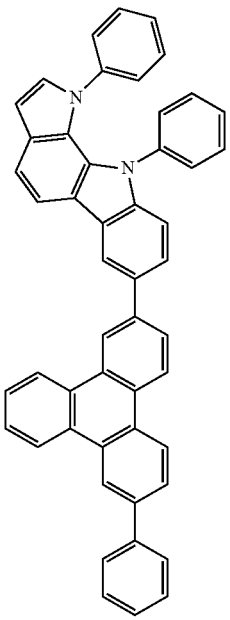
Inv1160
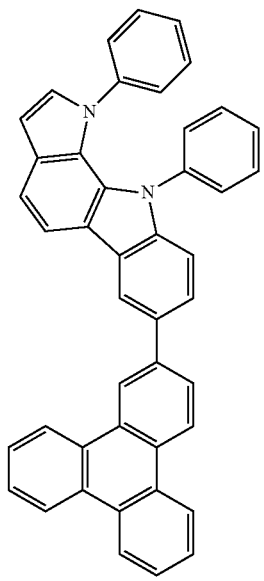
Inv1162
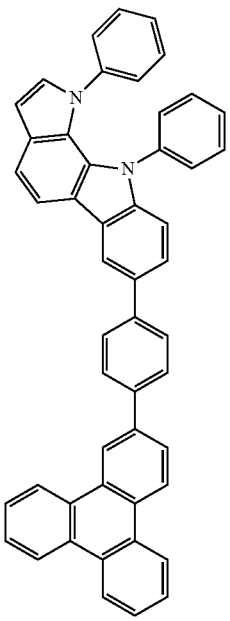

Inv1163
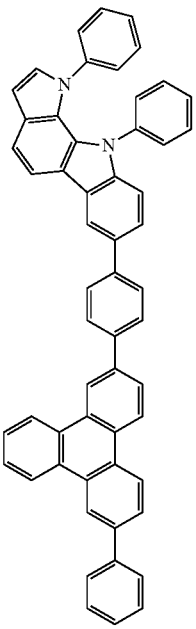
Inv1164
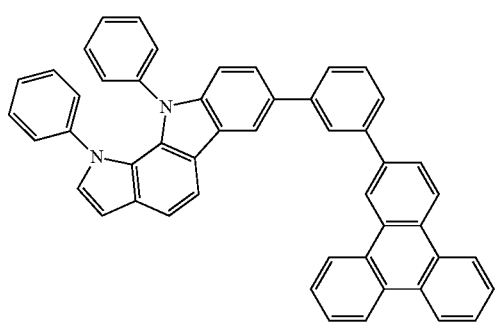
Inv1165
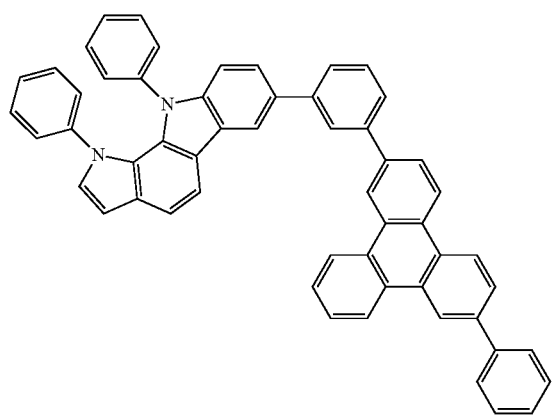
Inv1166
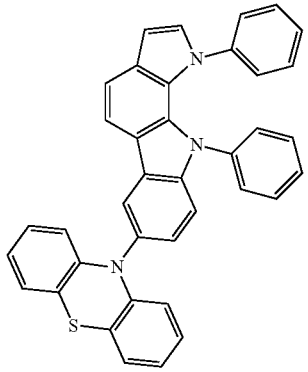
Inv1167
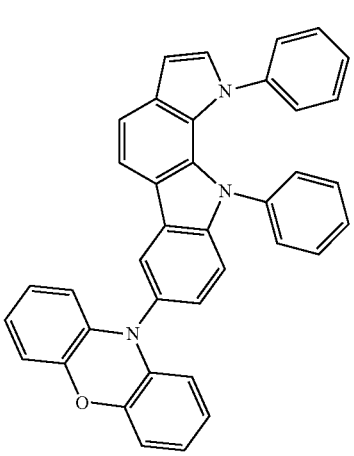
Inv1168
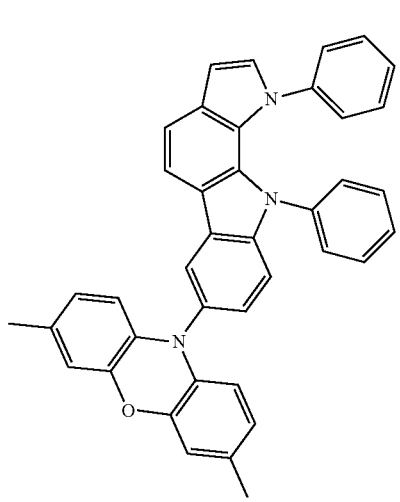

425
-continued
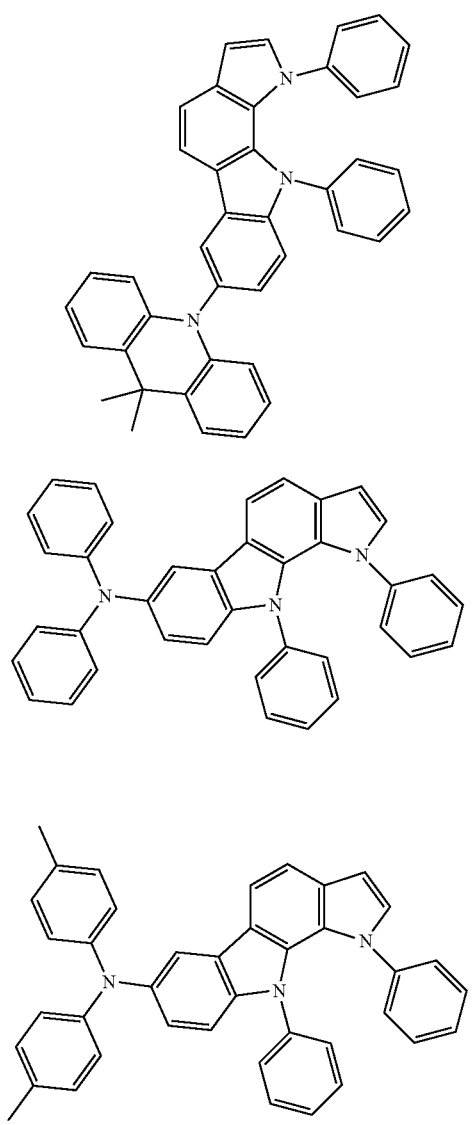
Inv1169
Inv1170
Inv1171
Inv1172
426
-continued
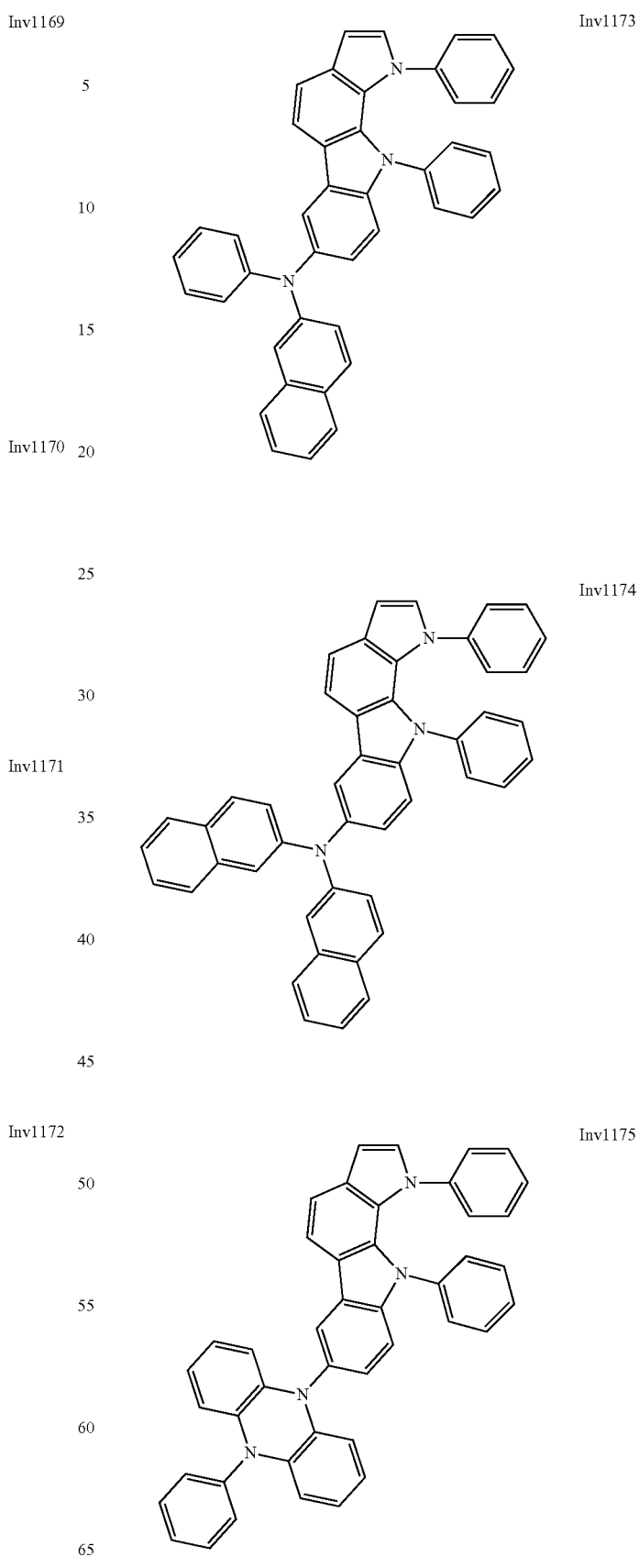
Inv1173
Inv1174
Inv1175

Inv1176
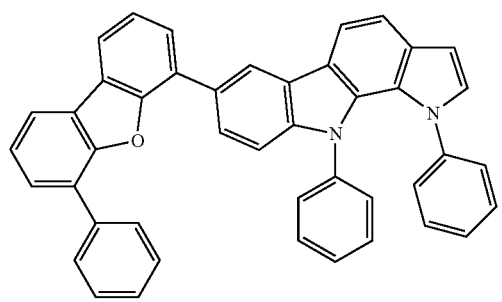
Inv1177
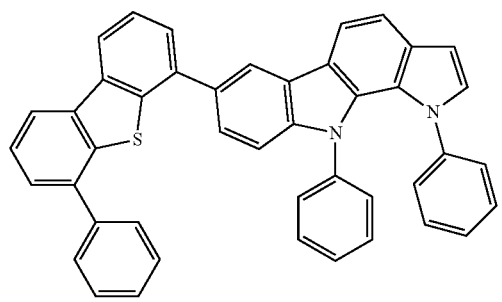
Inv1178
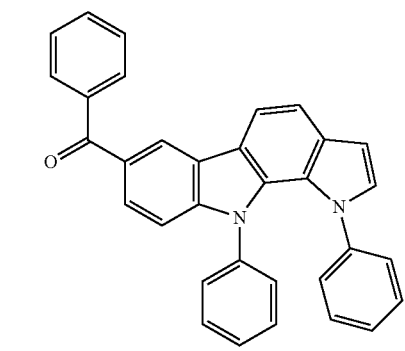
Inv1179
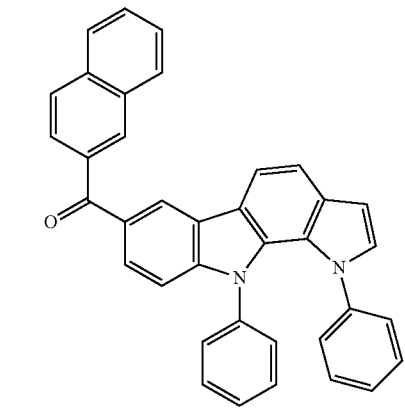
Inv1180
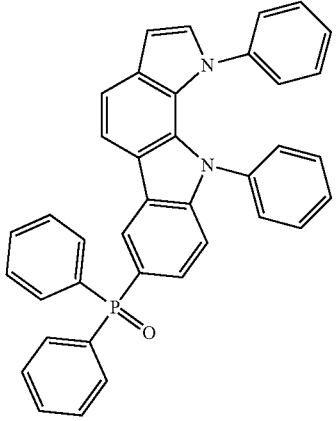
Inv1181
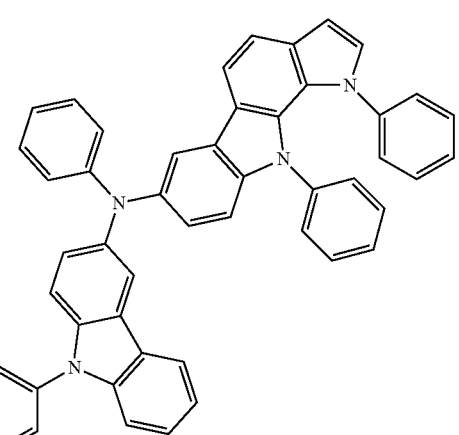
Inv1182
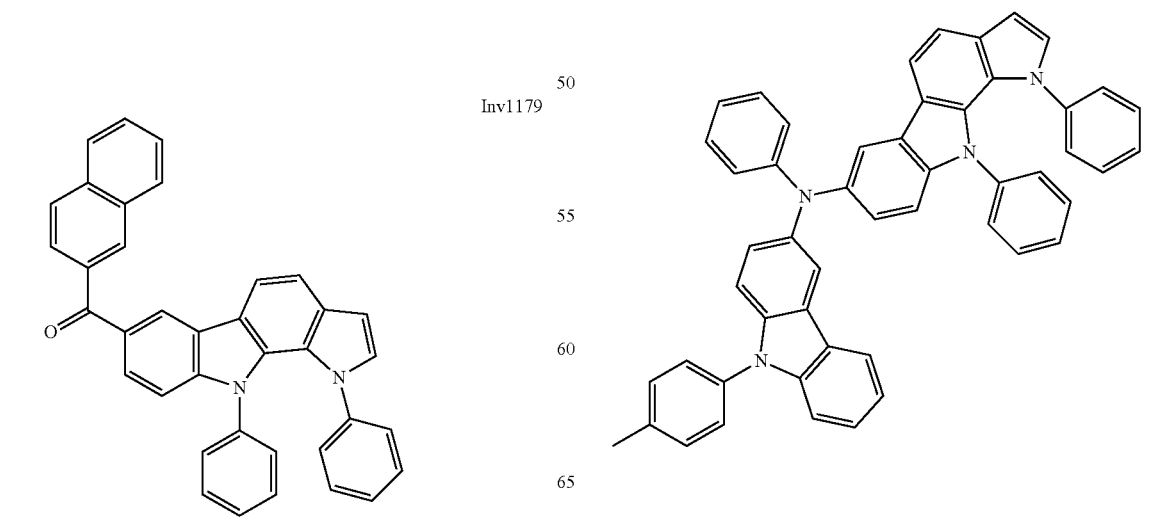

Inv1183
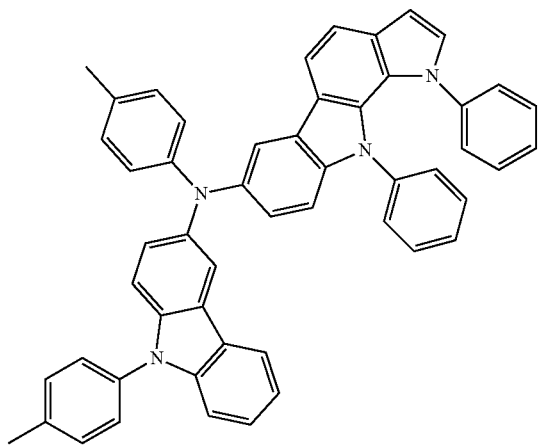
Inv1184
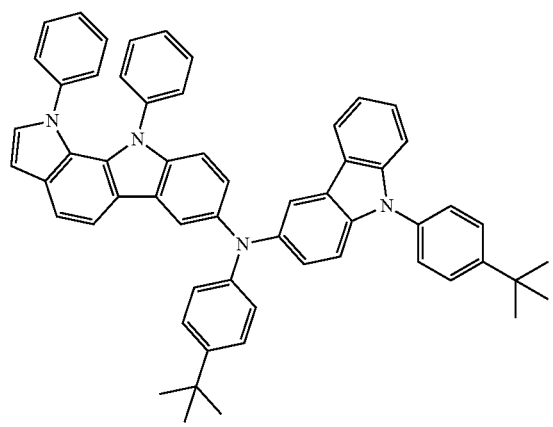
Inv1185
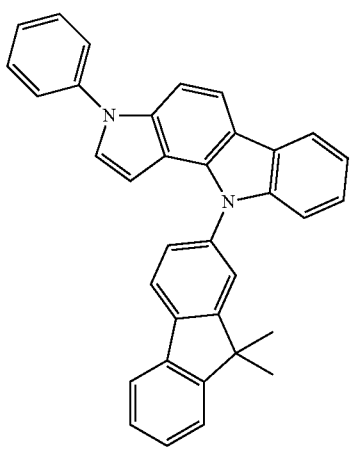
Inv1186
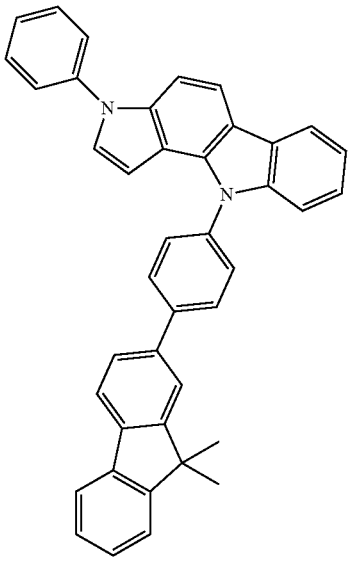
Inv1187
Inv1188
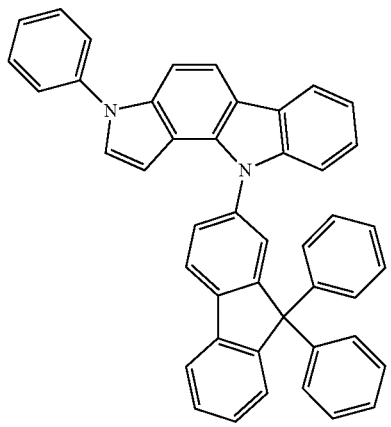

431
-continued
Inv1189
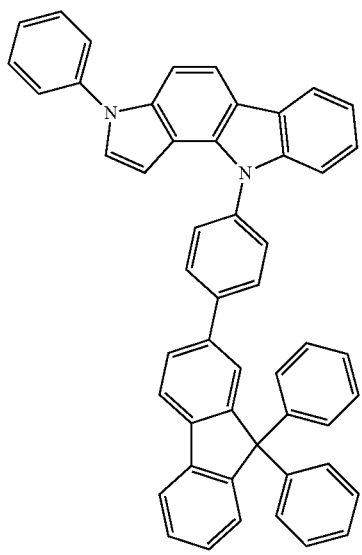
Inv1190
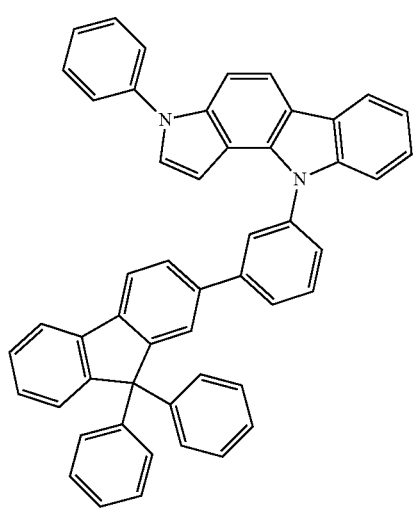
Inv1191
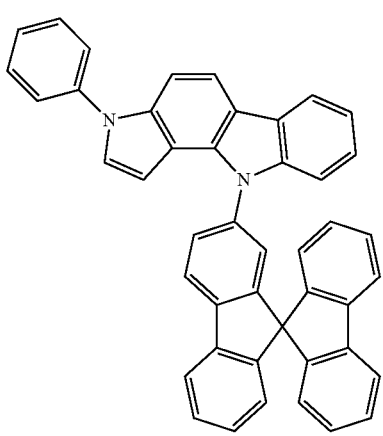
432
-continued
Inv1192
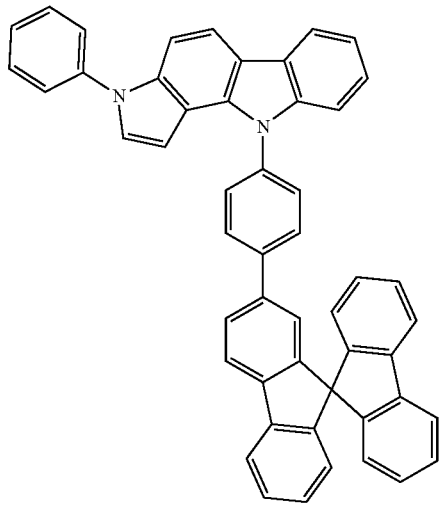
IInv1193
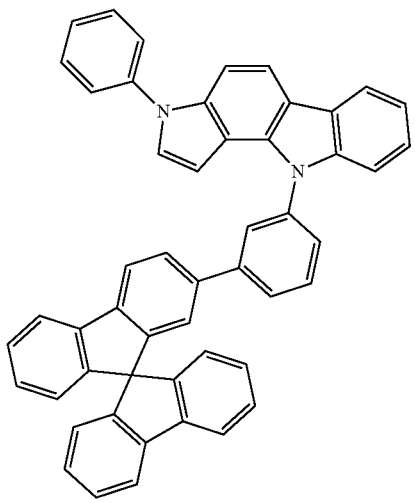
Inv1194
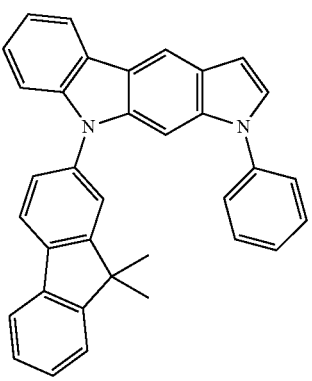

Inv1195
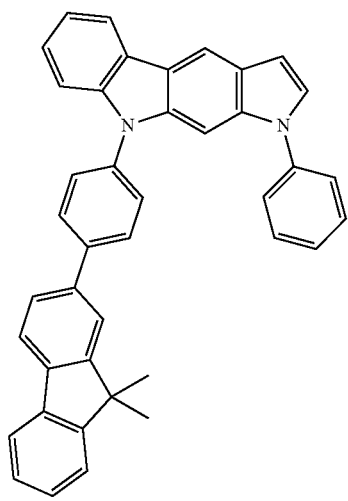
Inv1198
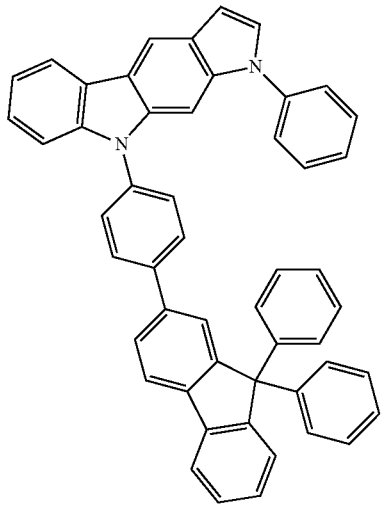
Inv1196
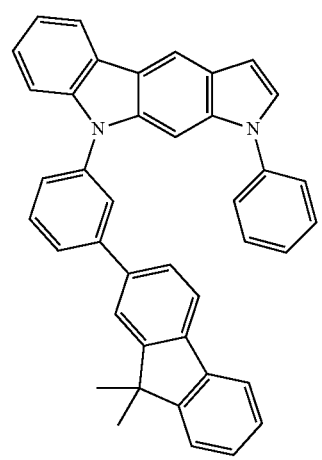
Inv1199
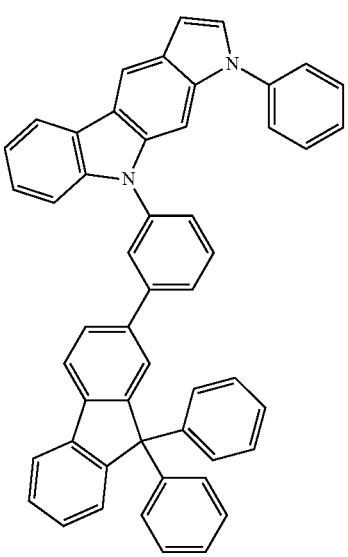
Inv1197
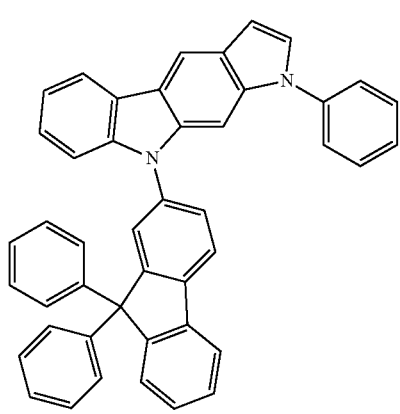
Inv1200
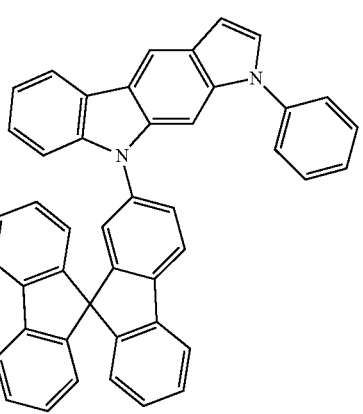

Inv1201
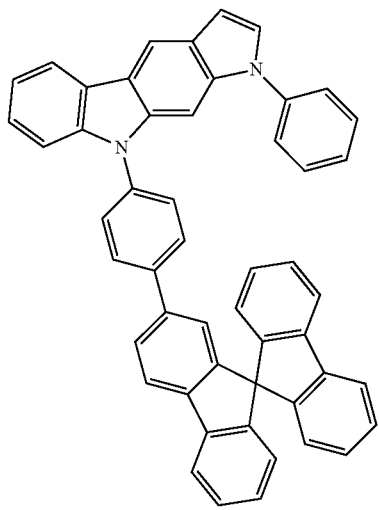
Inv1202
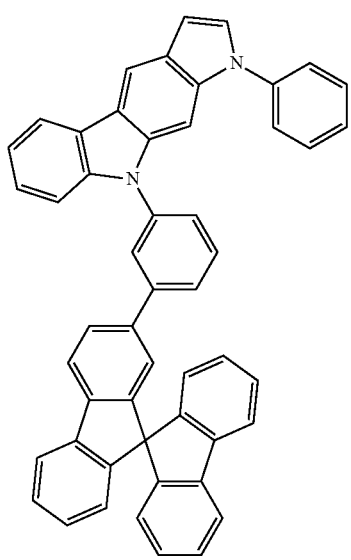
Inv1203
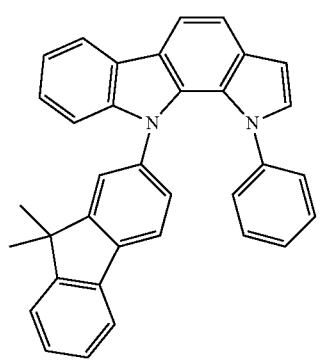
Inv1204
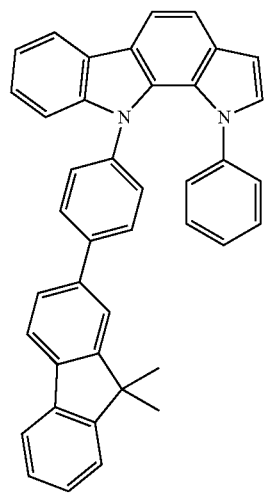
Inv1205
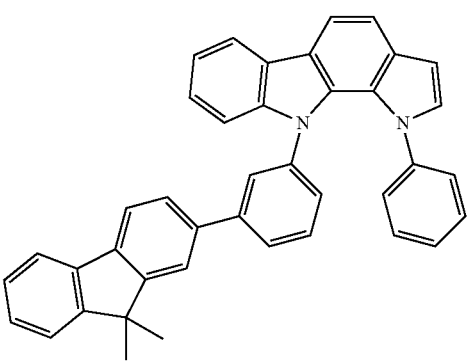
Inv1206
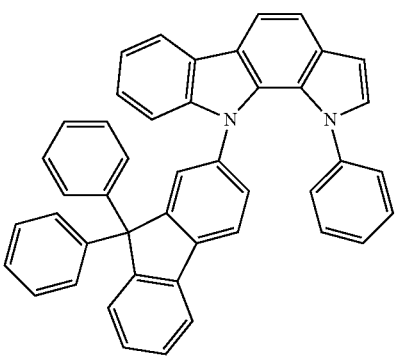

Inv1207
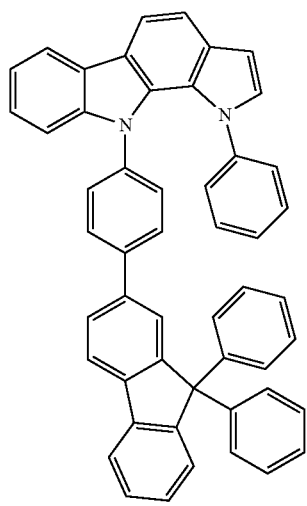
Inv1208
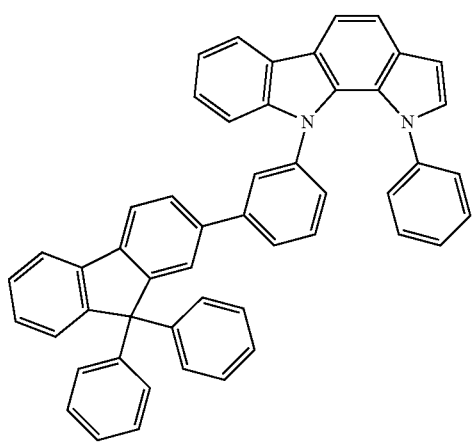
Inv1209
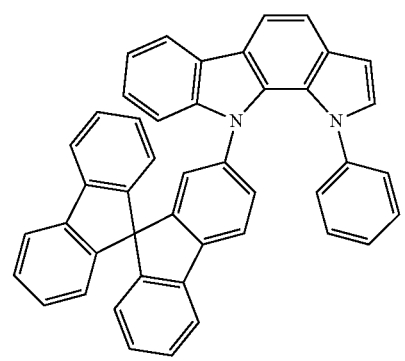
Inv1210
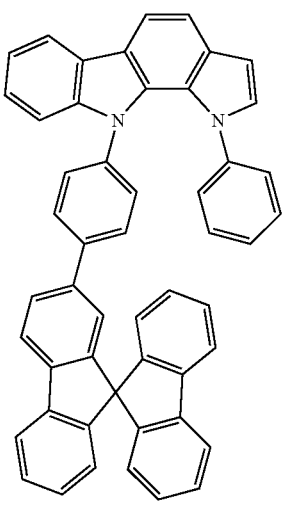
Inv1211
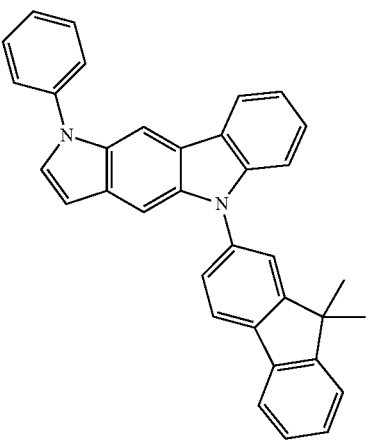
Inv1212

Inv1213
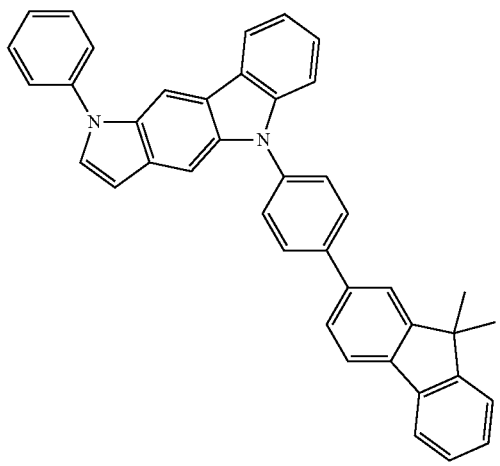
Inv1214
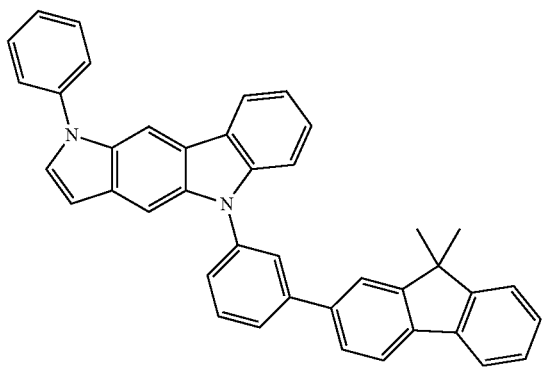
Inv1215
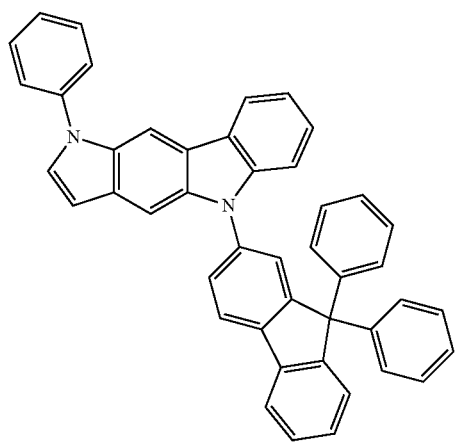
Inv1216
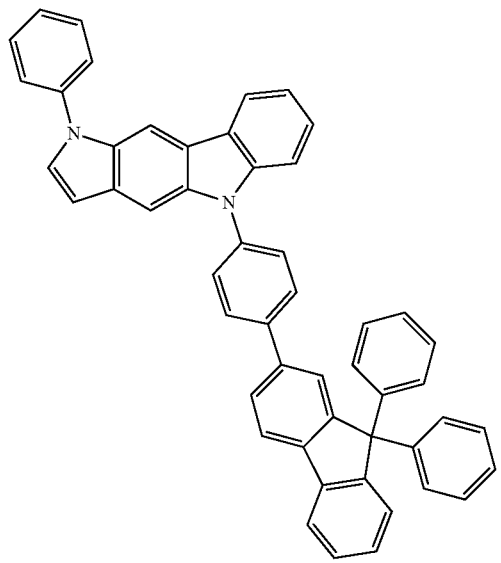
Inv1217
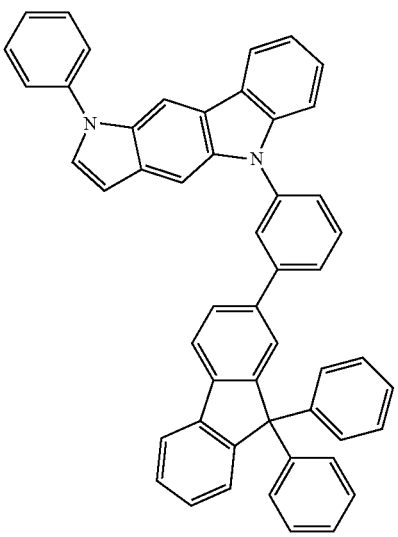
Inv1218
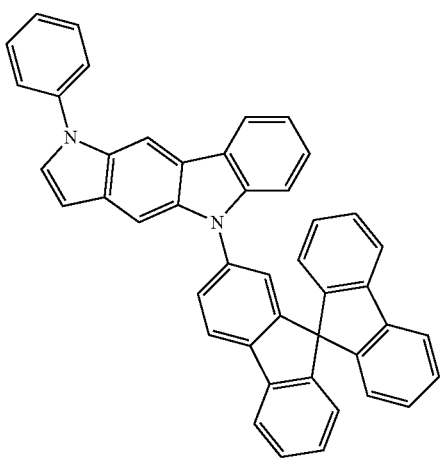

Inv1219
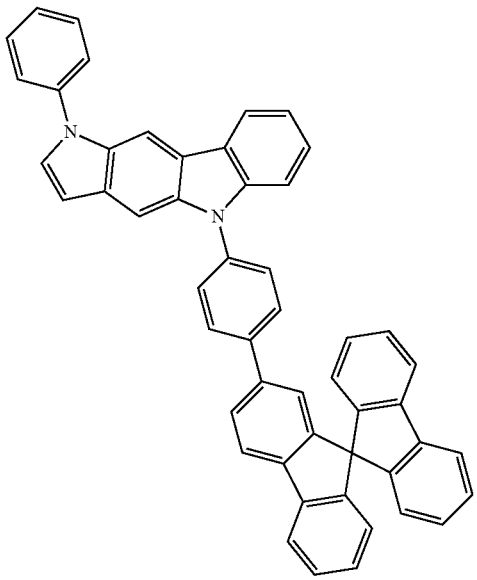
Inv1222
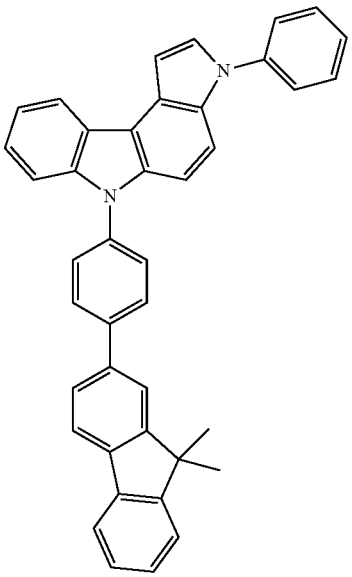
Inv1220
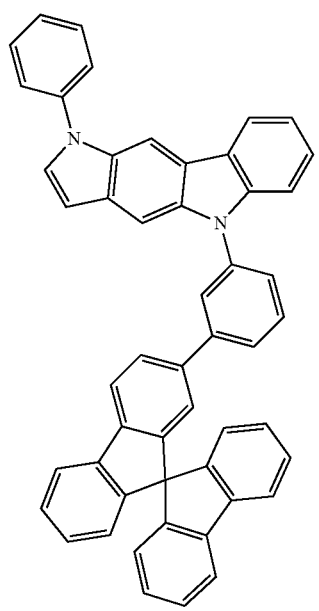
Inv1223
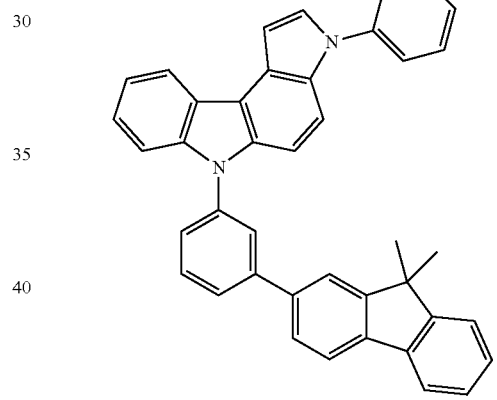
Inv1221
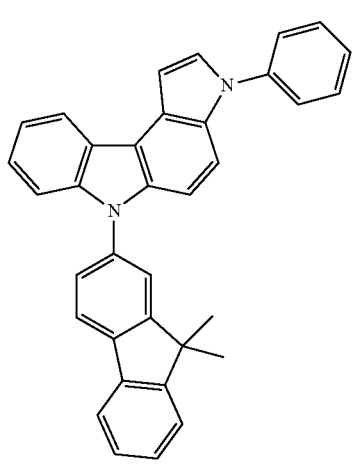
Inv1224
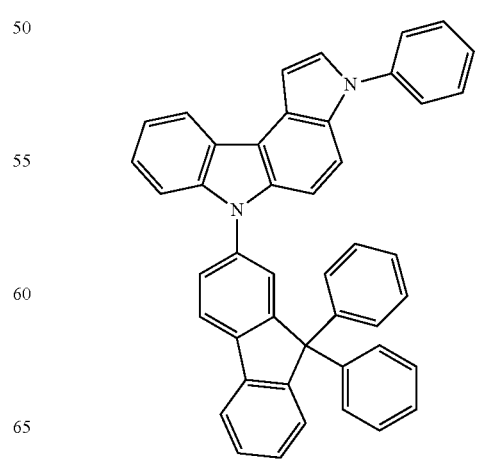

-continued
Inv1225
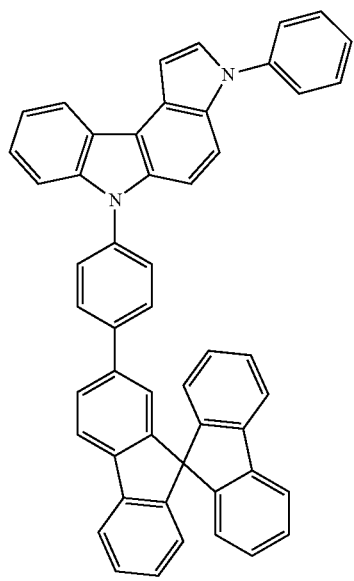
Inv1228
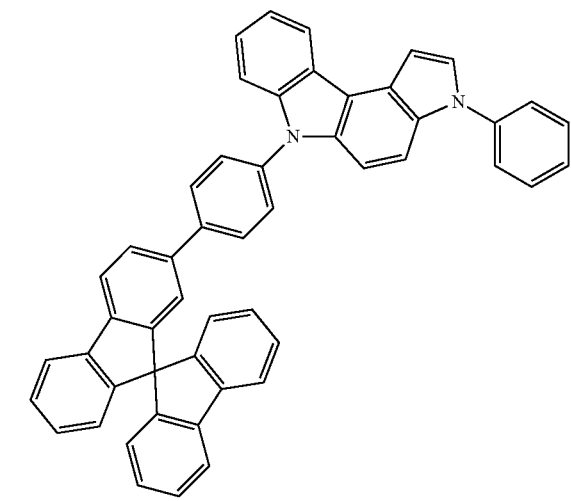
Inv1226
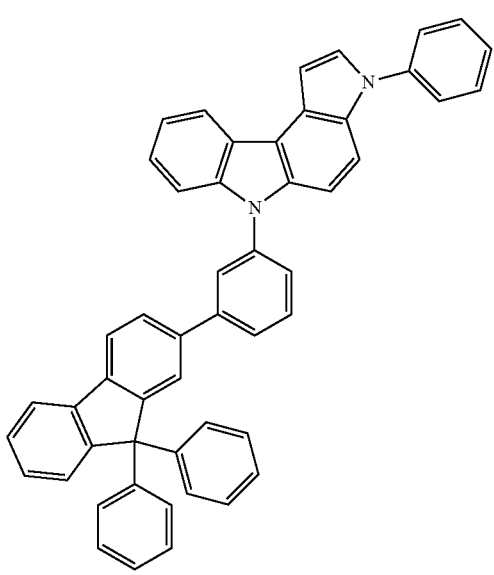
Inv1229
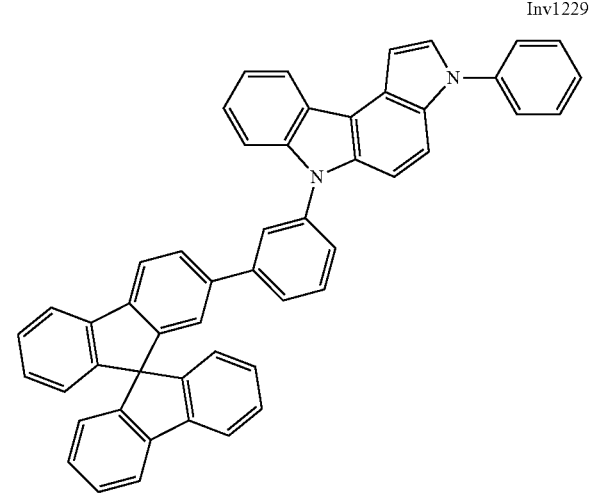
Inv1227
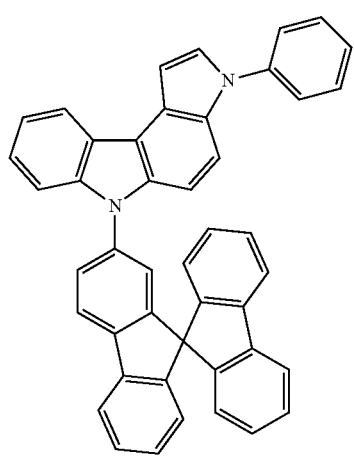
Inv1230
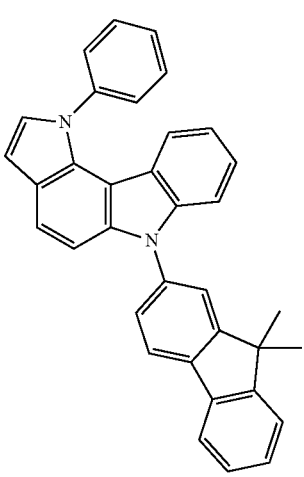

Inv1231
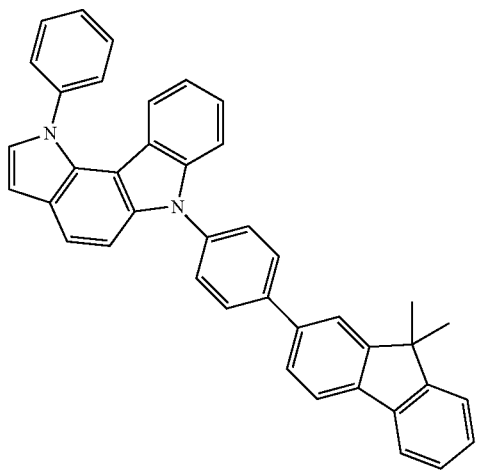
Inv1234
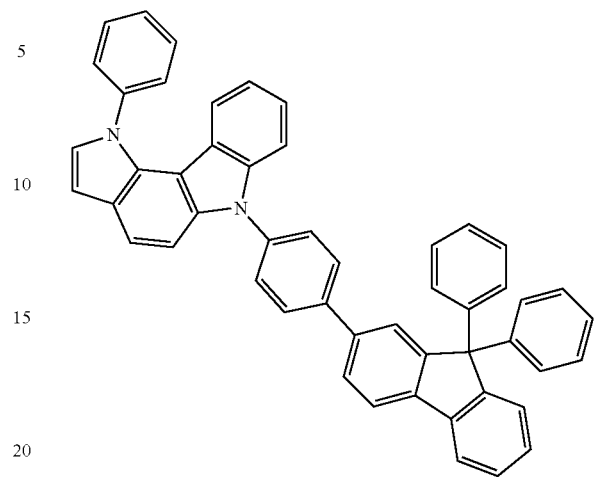
Inv1232
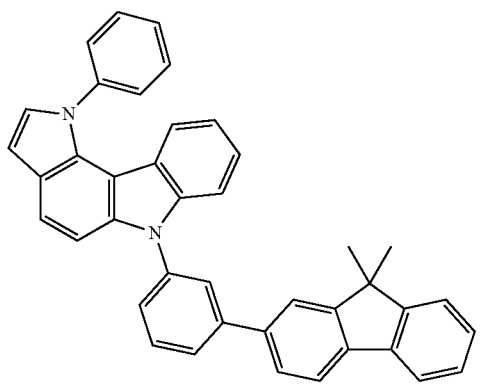
Inv1235
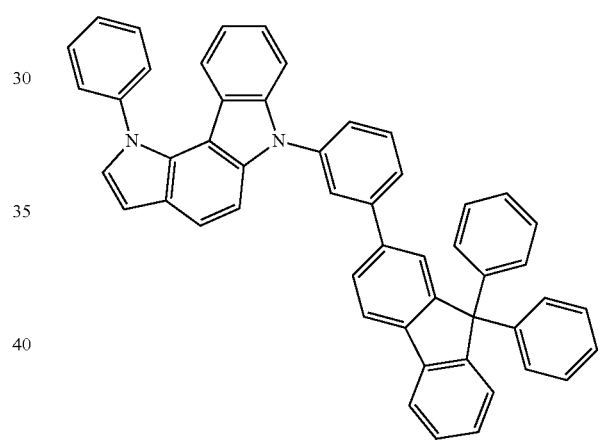
Inv1233
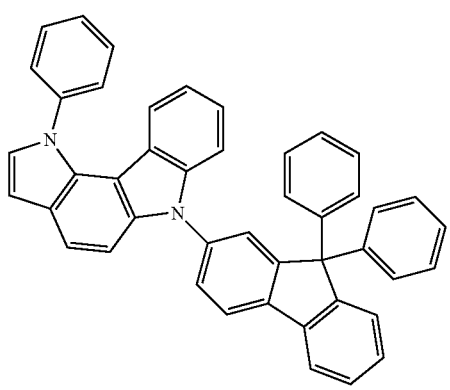
Inv1236
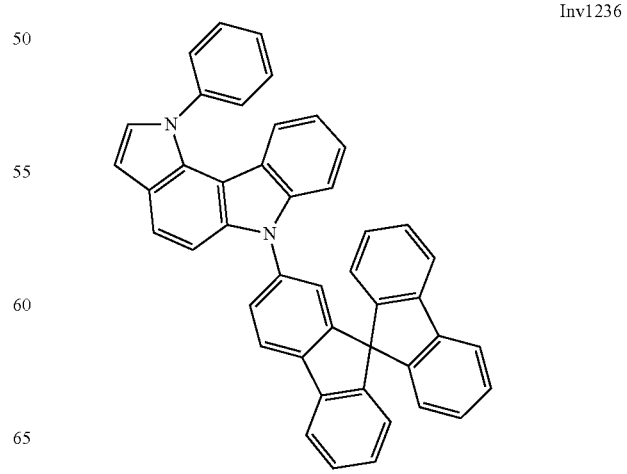

447
-continued
Inv1237
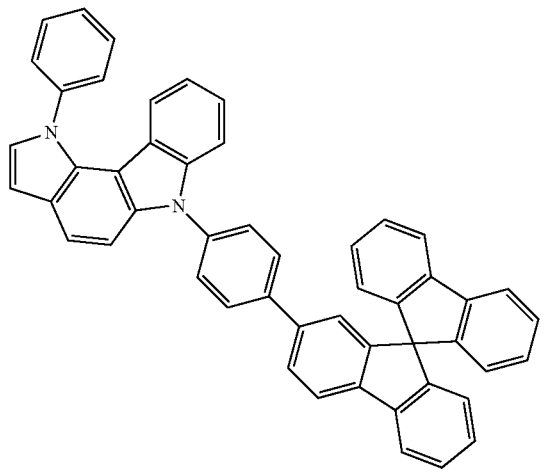
Inv1238
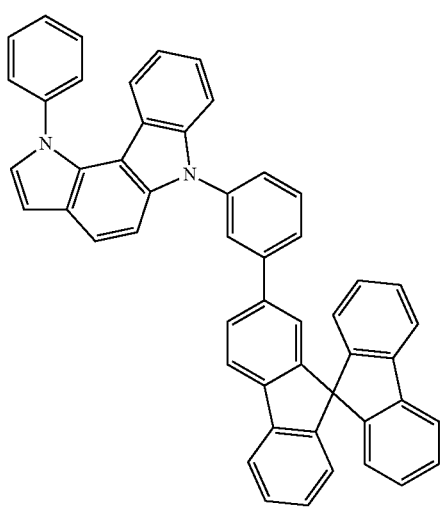
Inv1239
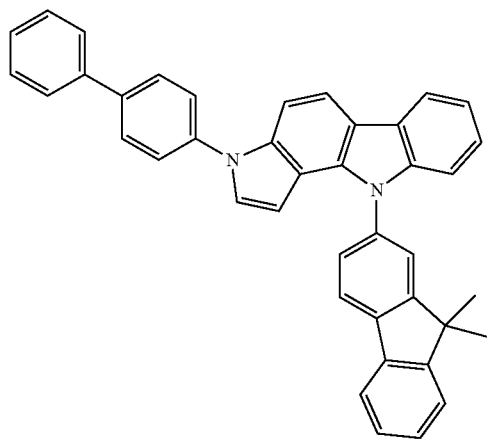
448
-continued
Inv1240
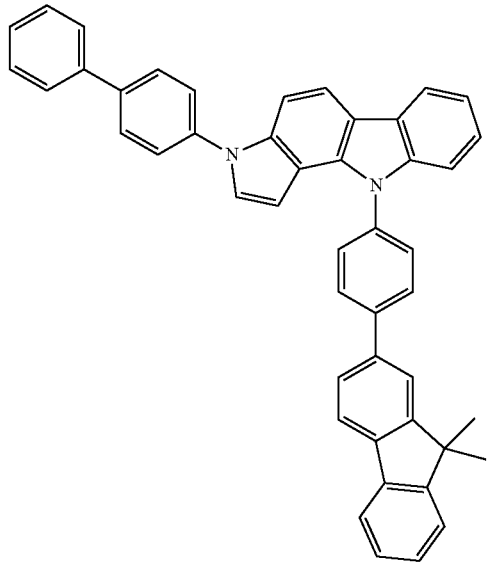
Inv1241
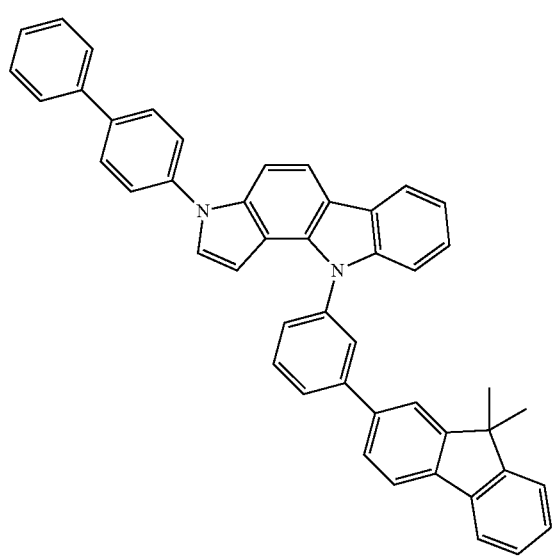
Inv1242
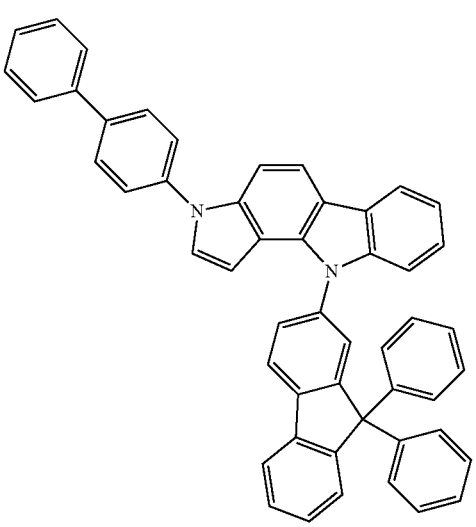

Inv1243
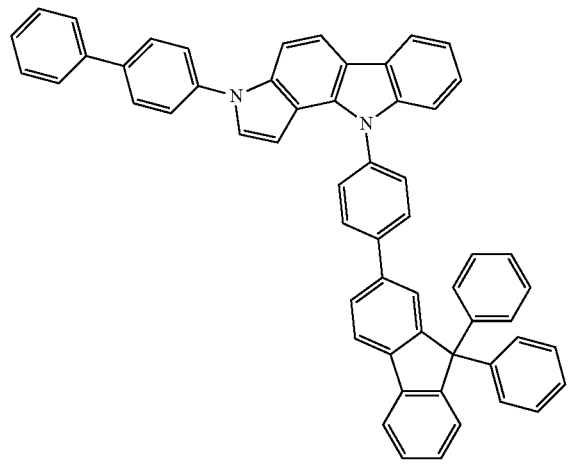
Inv1244
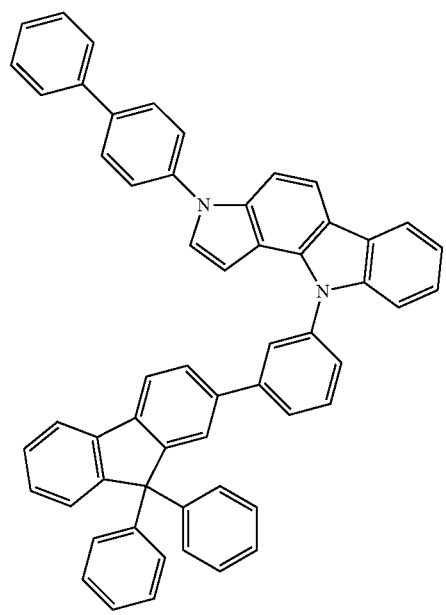
Inv1245
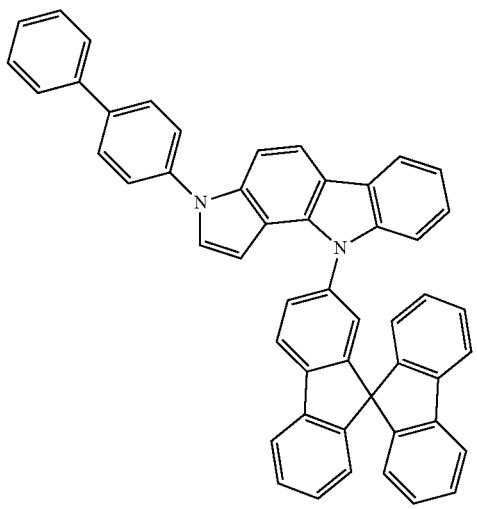
Inv1246
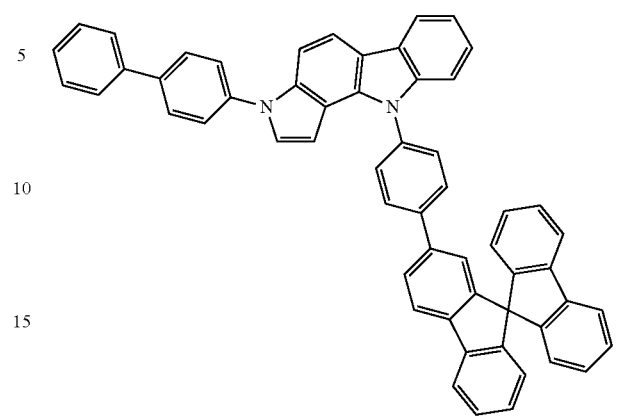
Inv1247
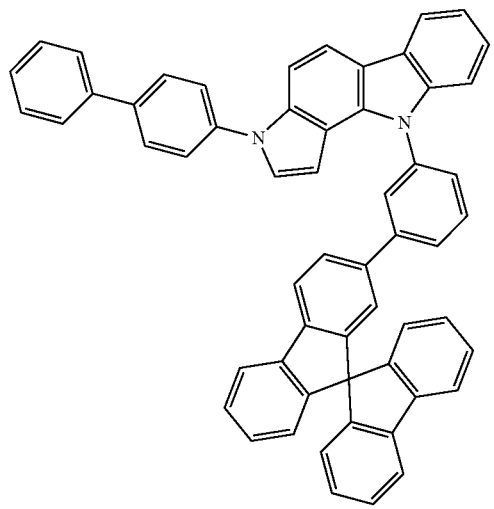
Inv1248
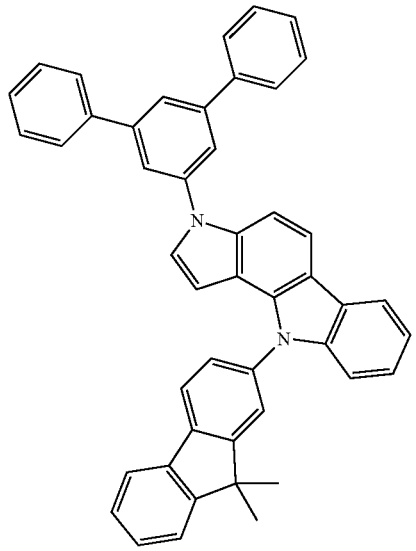

-continued
Inv1249
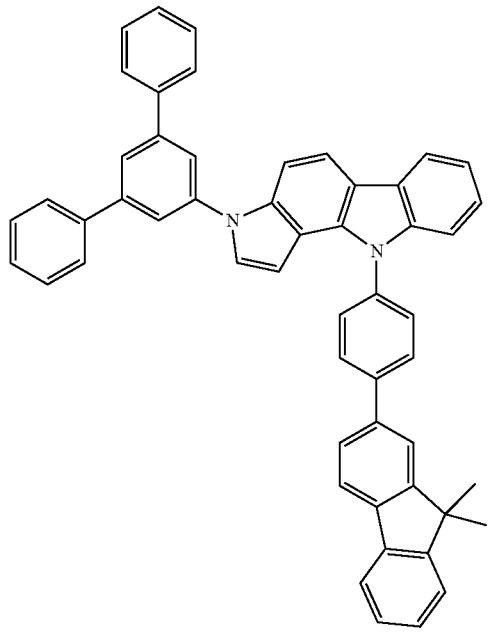
Inv1250
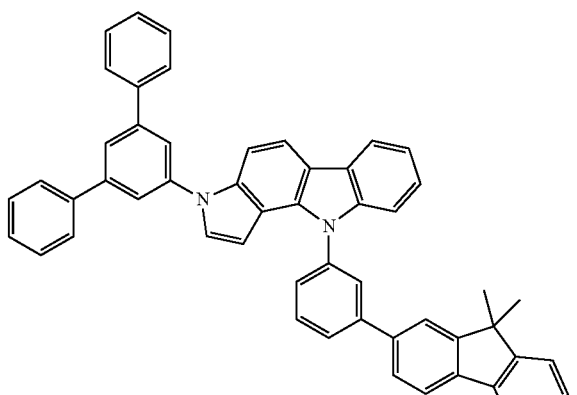
Inv1251
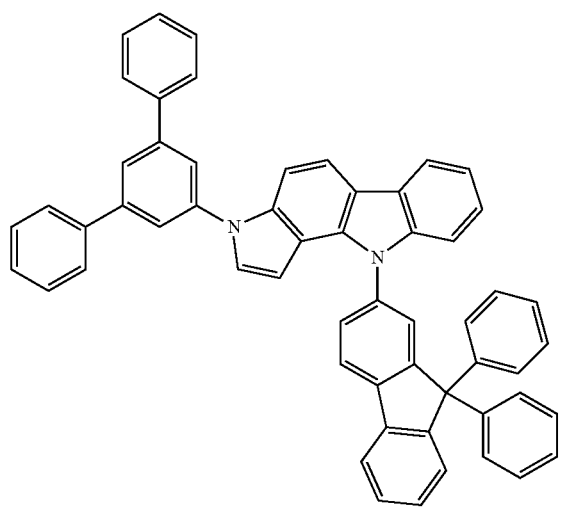
-continued
Inv1252
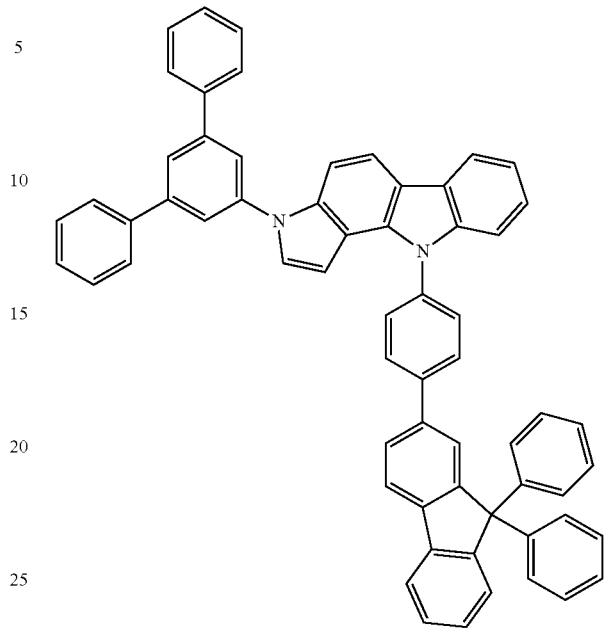
Inv1253

453
-continued
Inv1254
Inv1255
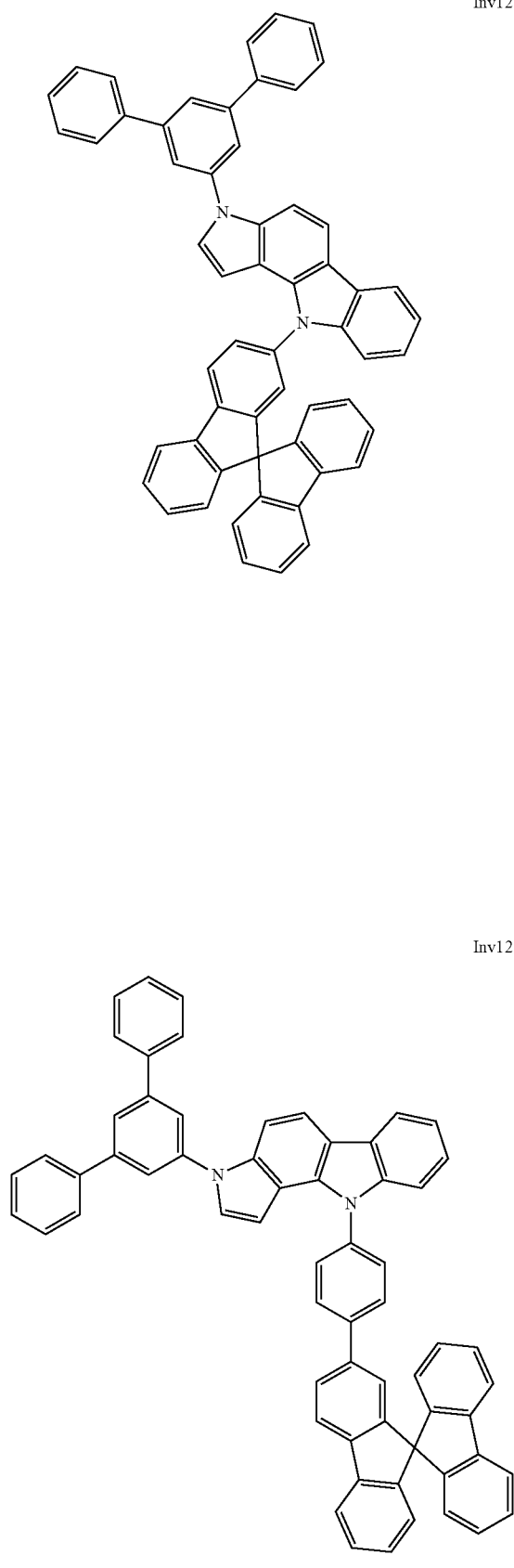
454
-continued
Inv1256
Inv1257
Inv1258
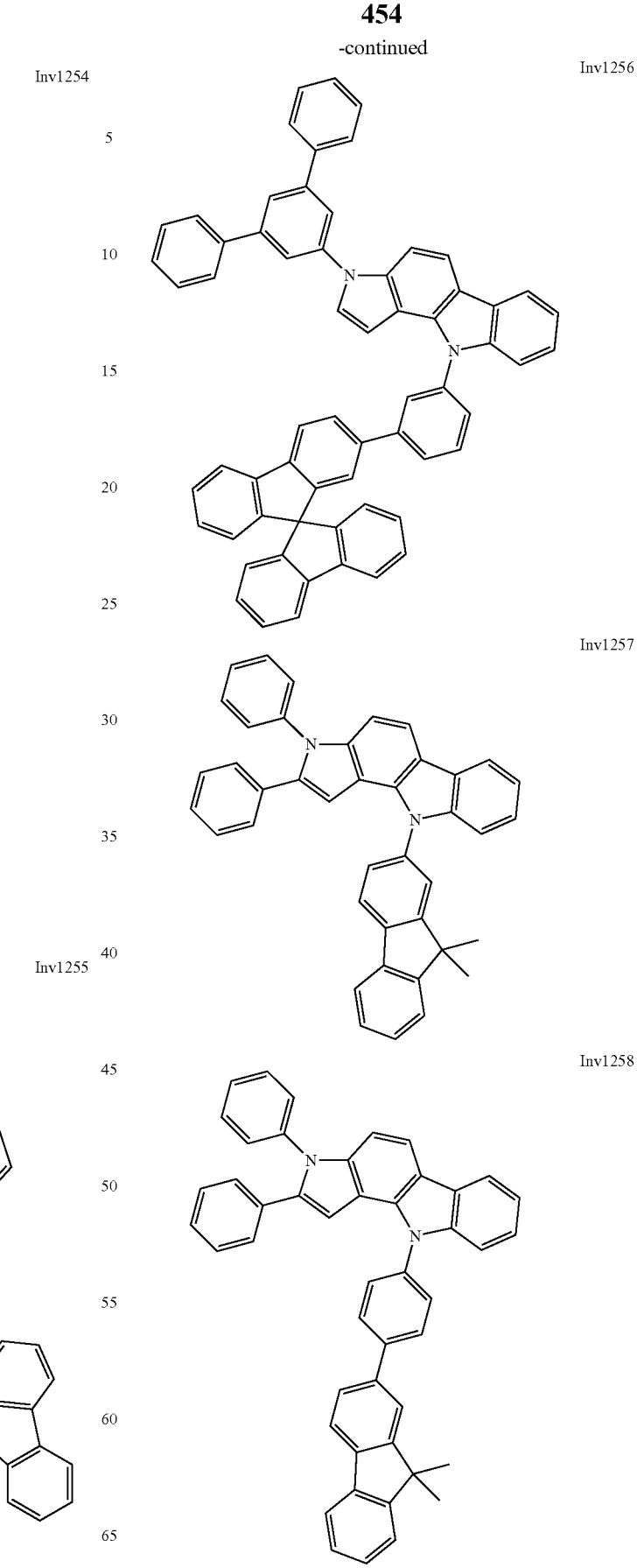

Inv1259
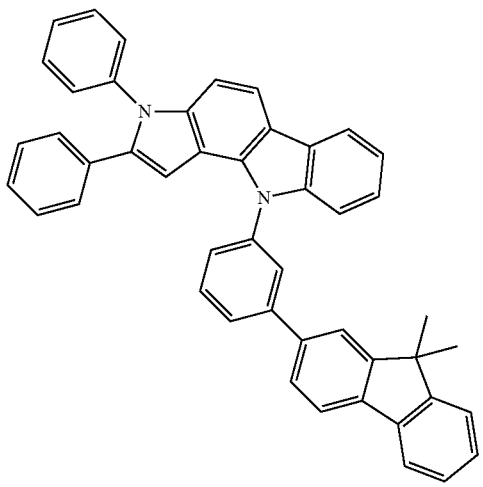
Inv1262
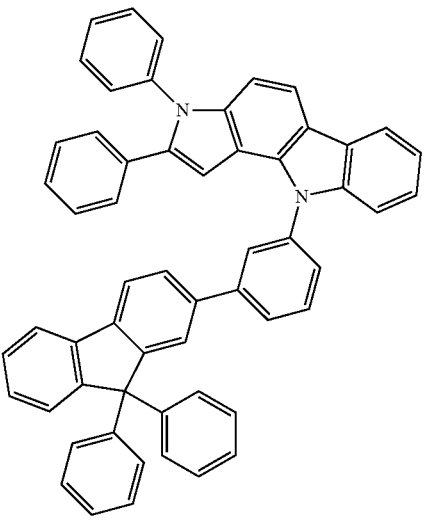
Inv1260
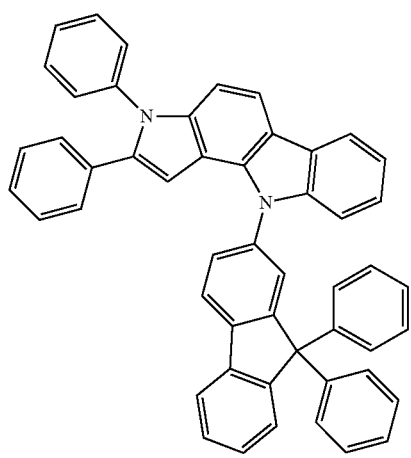
Inv1263
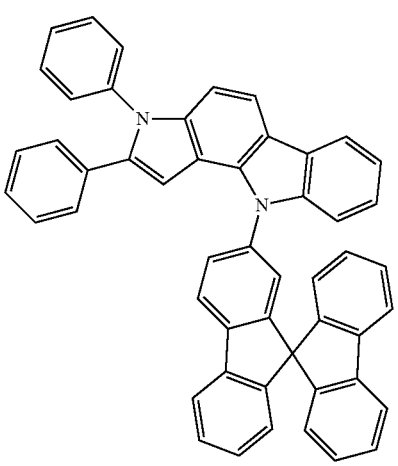
Inv1261
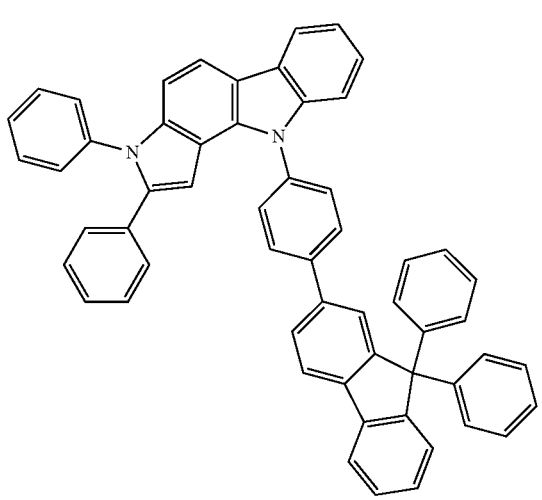
Inv1264
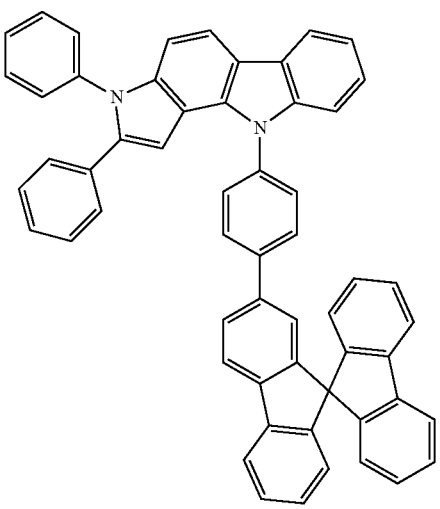

Inv1265
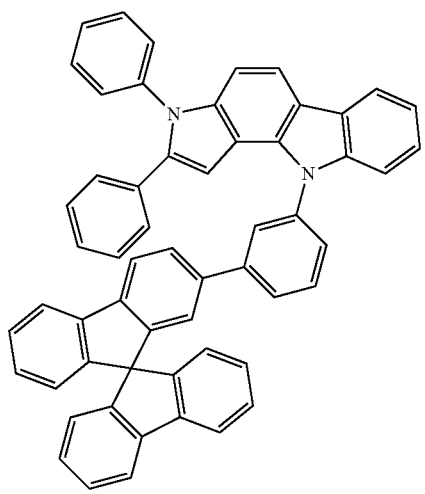
Inv1268
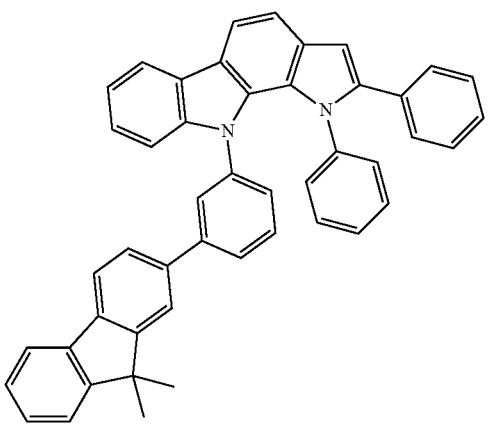
Inv1266
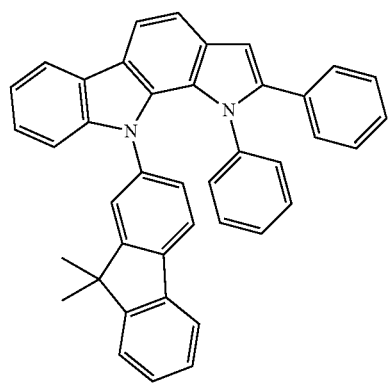
Inv1269
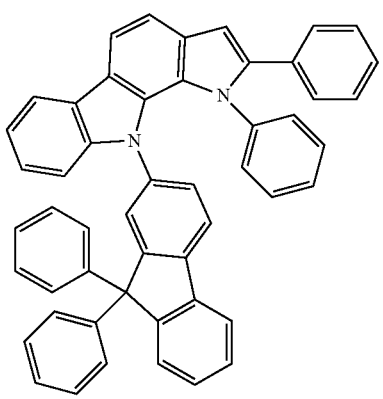
Inv1267
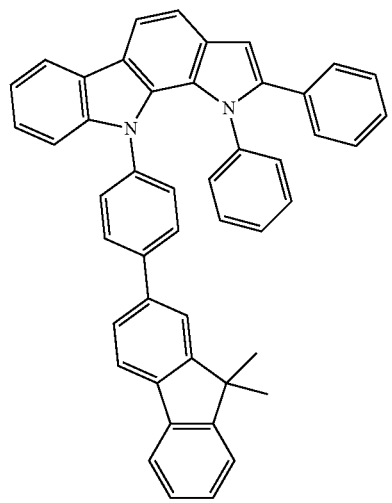
Inv1270
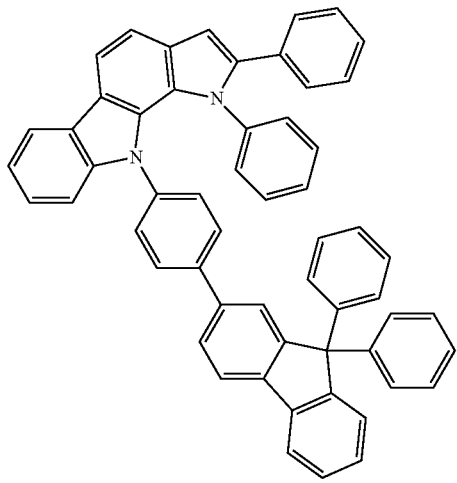

Inv1271
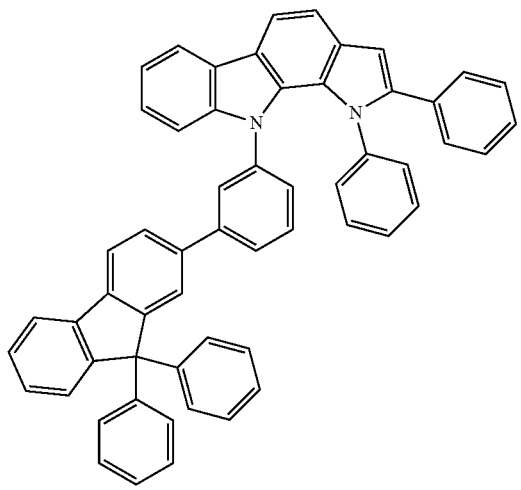
Inv1272
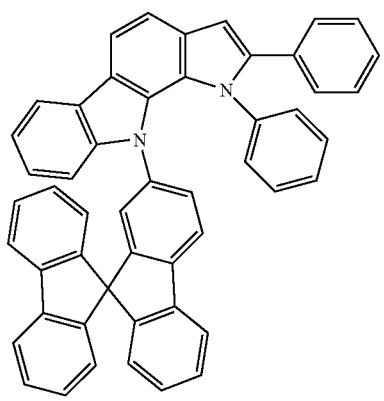
Inv1273
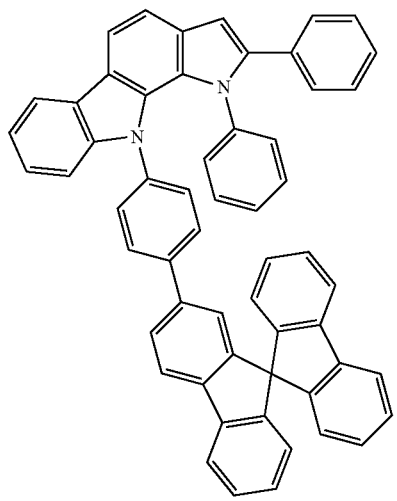
Inv1274
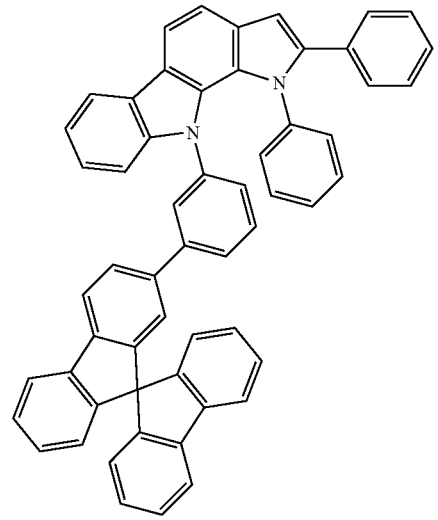
Inv1275
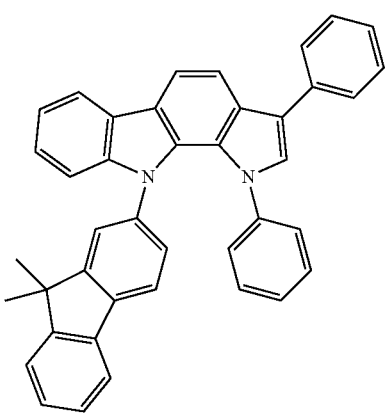
Inv1276
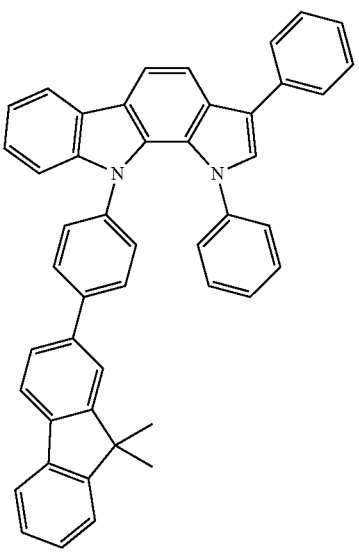

Inv1277
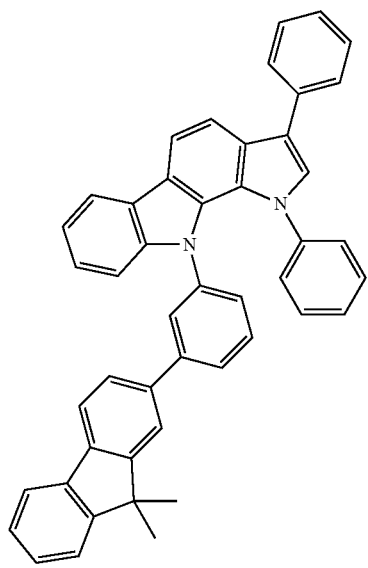
Inv1280
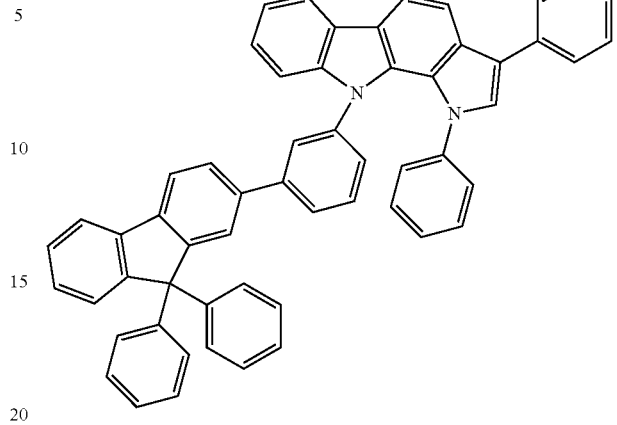
Inv1278
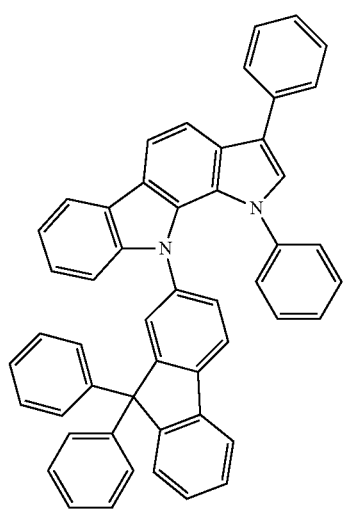
Inv1281
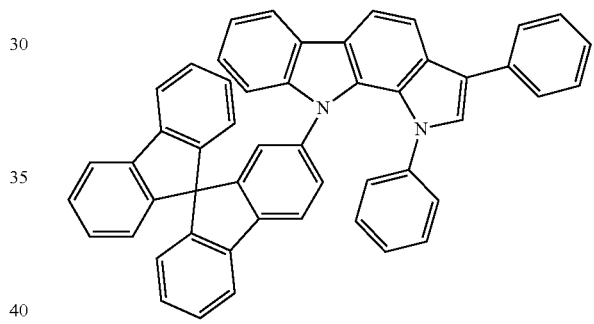
Inv1279
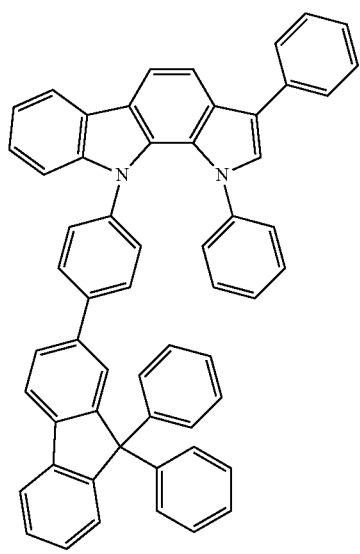
Inv1282
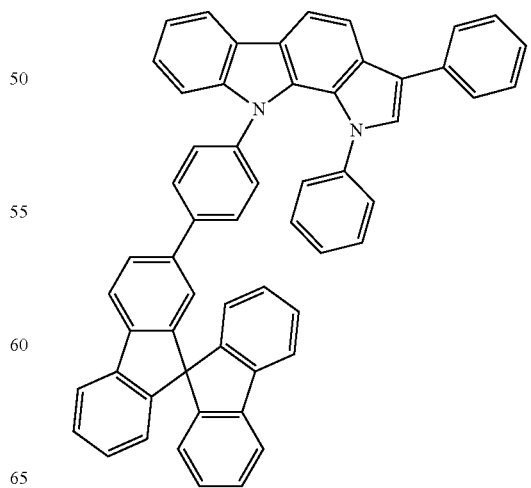

-continued
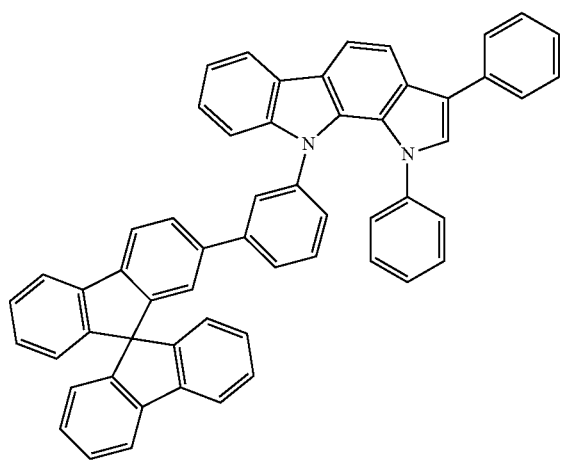
Inv1283
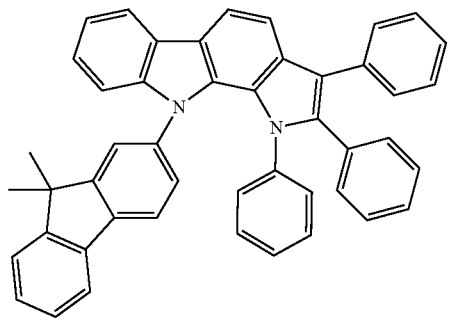
Inv1284
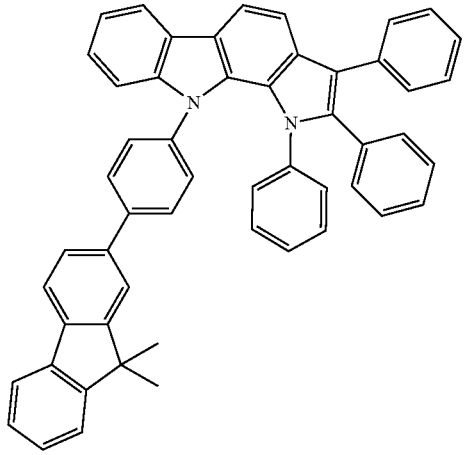
Inv1285
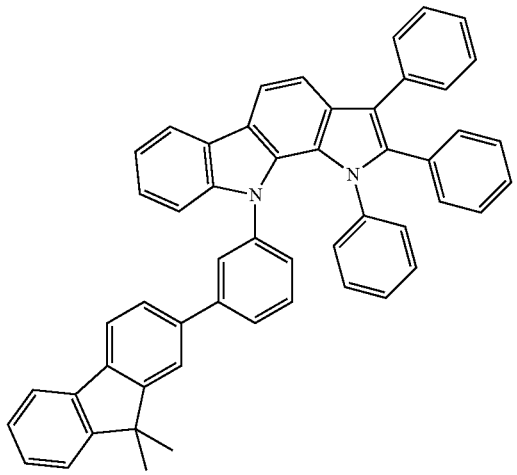
Inv1286
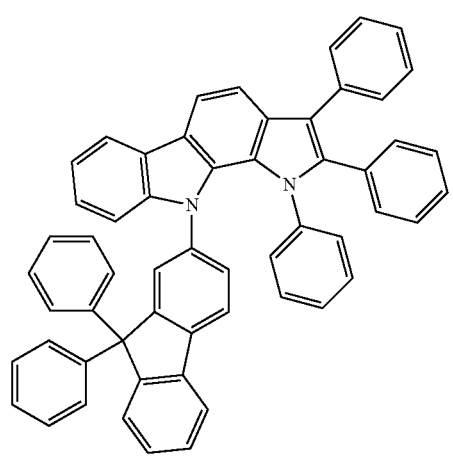
Inv1287
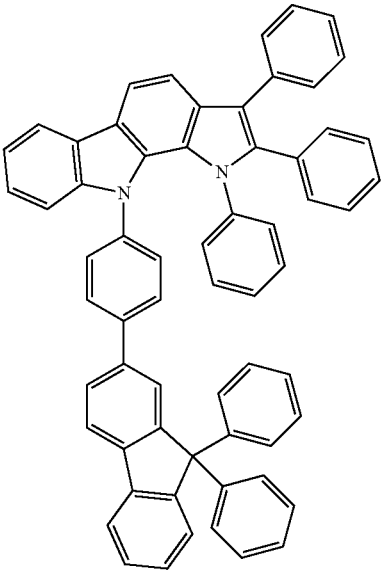
Inv1288

Inv1289
Inv1292
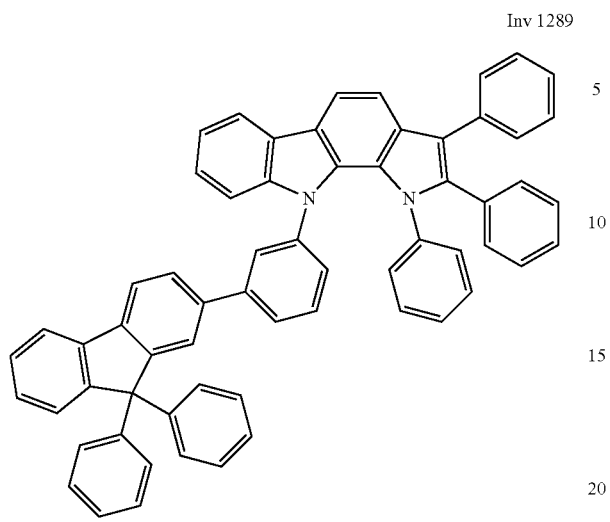
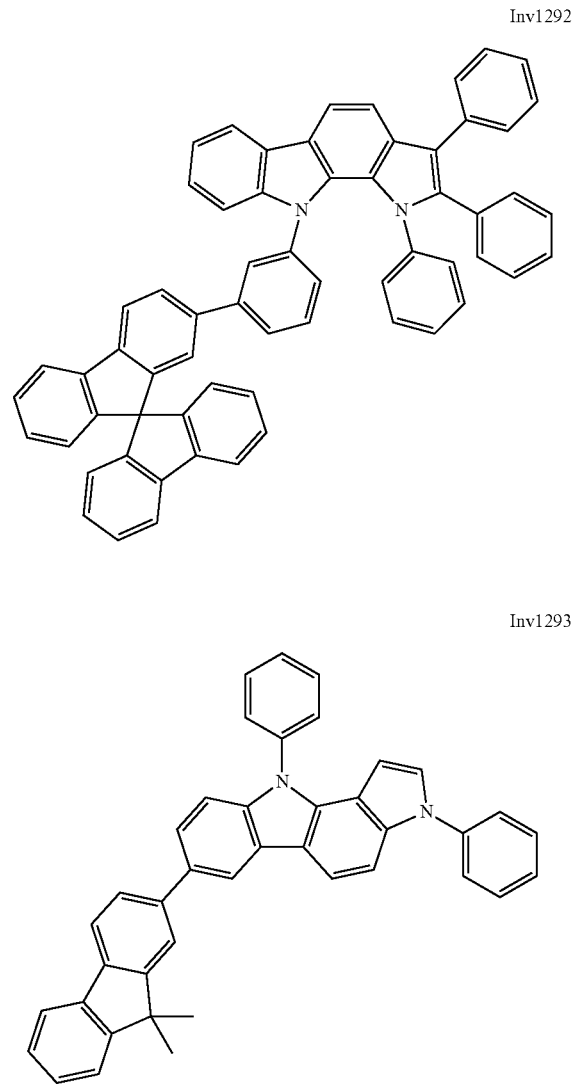
Inv1290
Inv1293
Inv1291
Inv1294
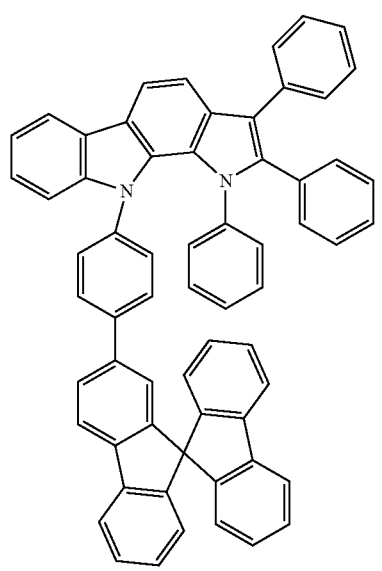
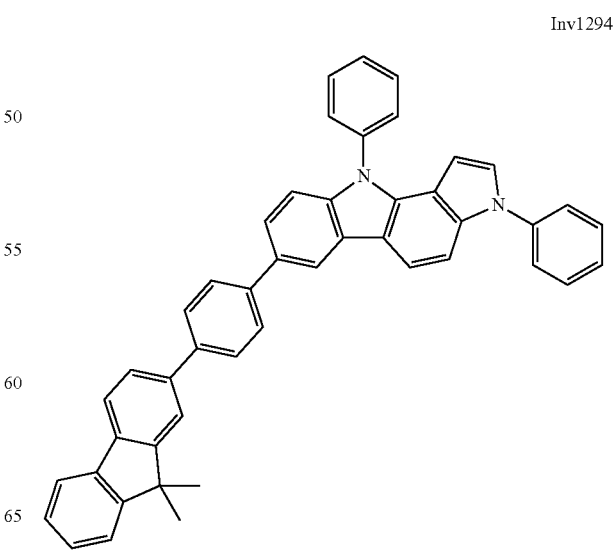

-continued
Inv1295
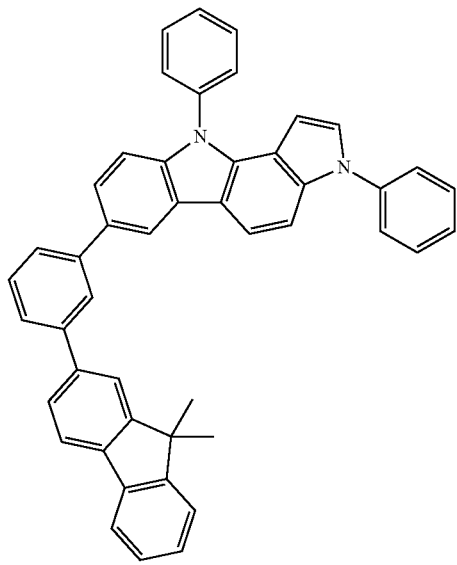
-continued
Inv1297
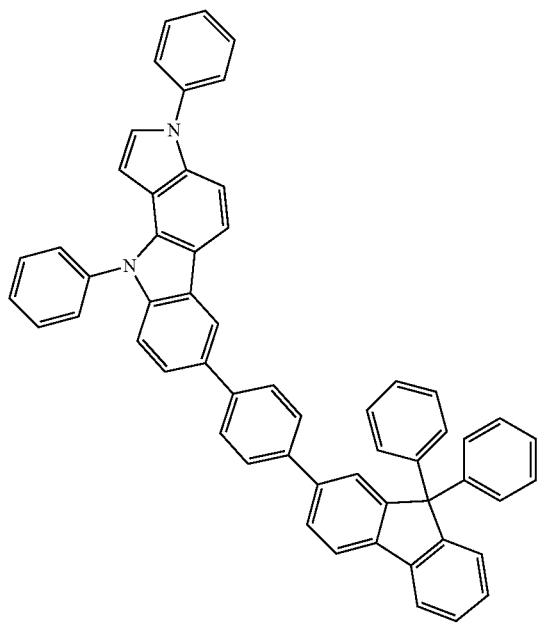
Inv1296
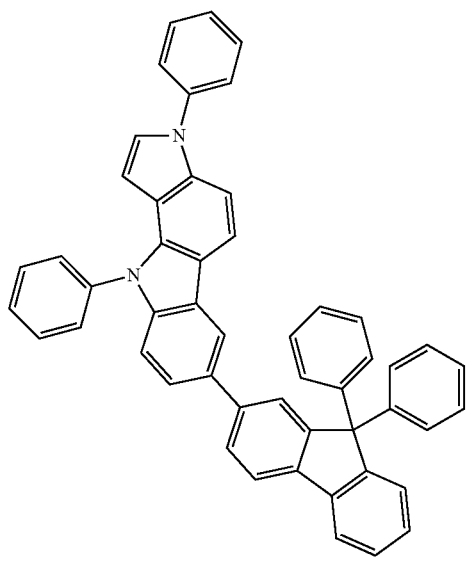
Inv1298
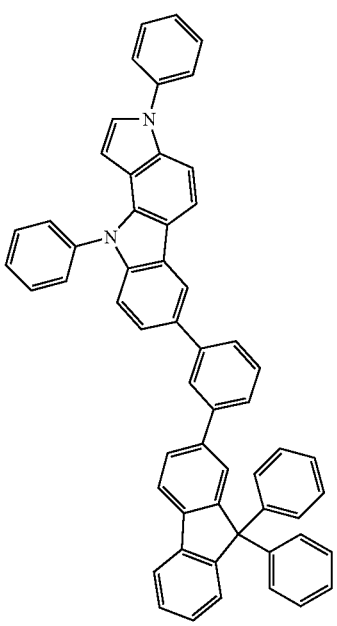

469
-continued
Inv1299
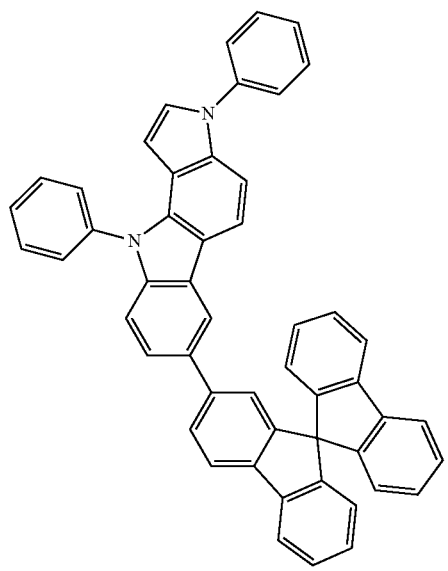
470
-continued
Inv1301
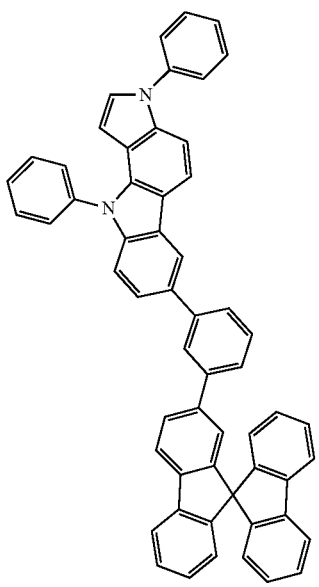
Inv1300
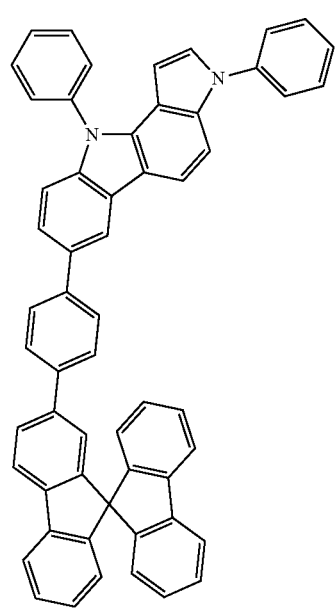
Inv1302
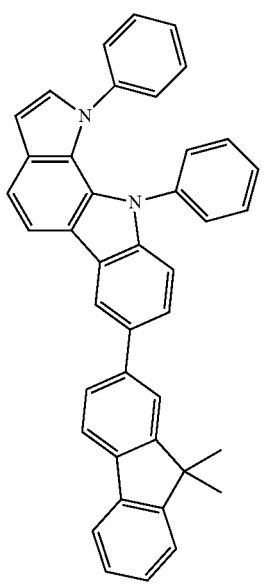

-continued
Inv1303
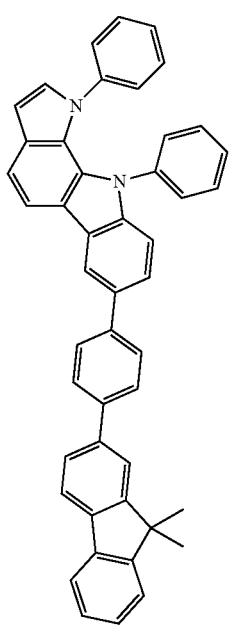
Inv1305
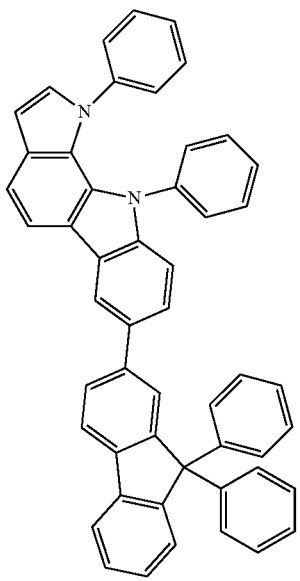
Inv1304
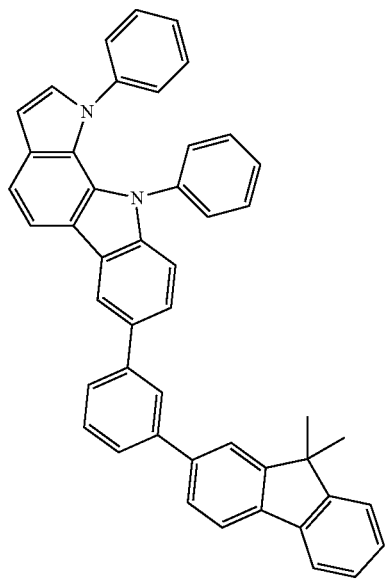
Inv1306
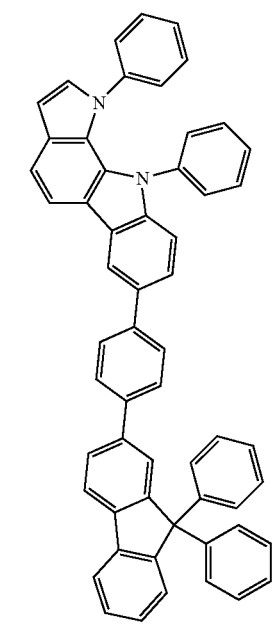

-continued
Inv1307
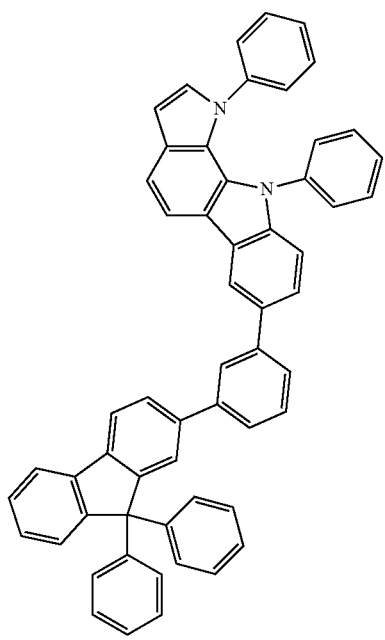
Inv1308
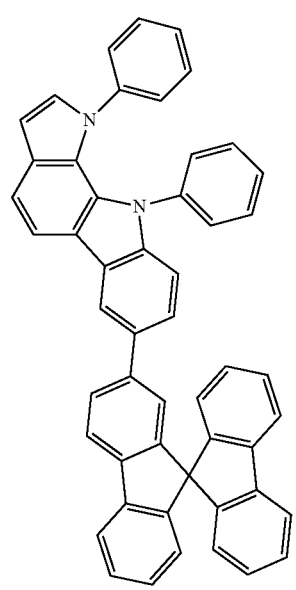
-continued
Inv1309
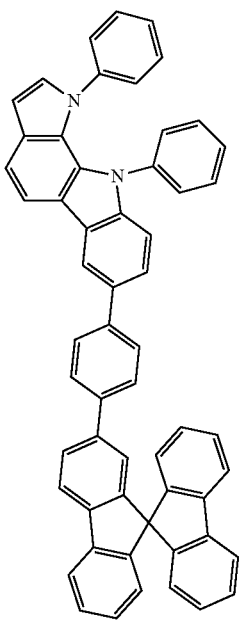
Inv1310
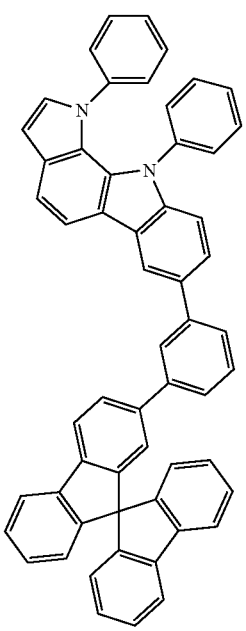

Inv1311
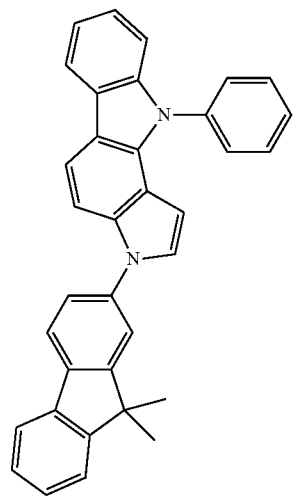
Inv1312
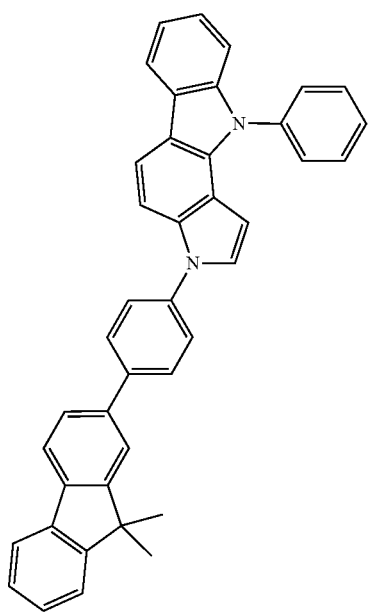
Inv1313
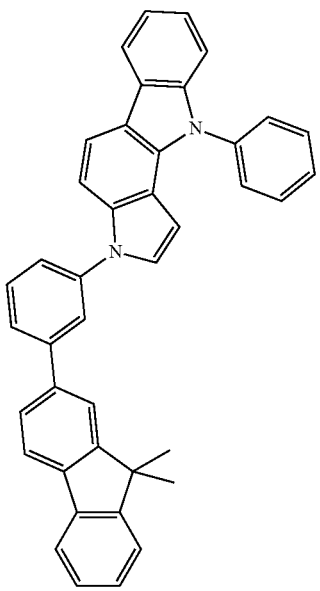
Inv1314
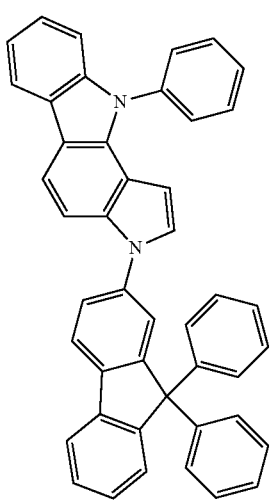

Inv1315
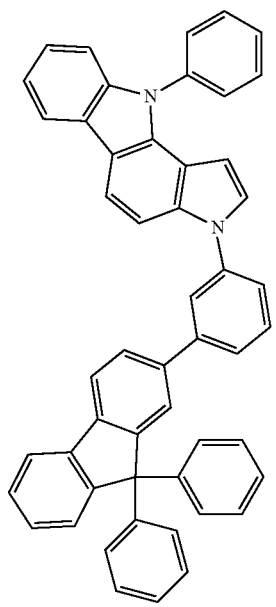
Inv1316
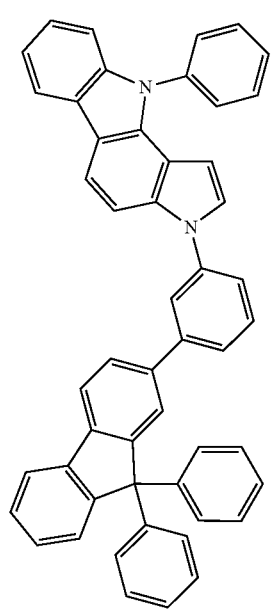
Inv1317
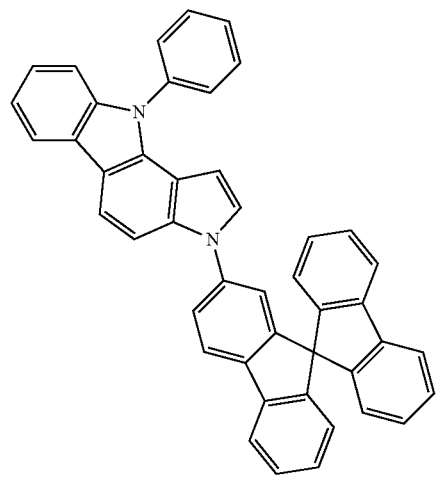
Inv1318
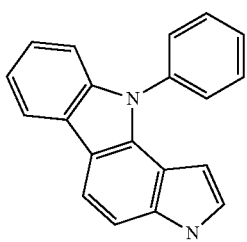
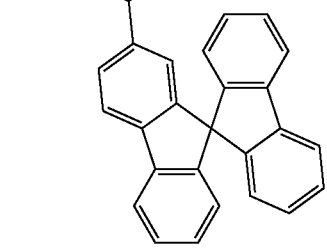
Inv1319
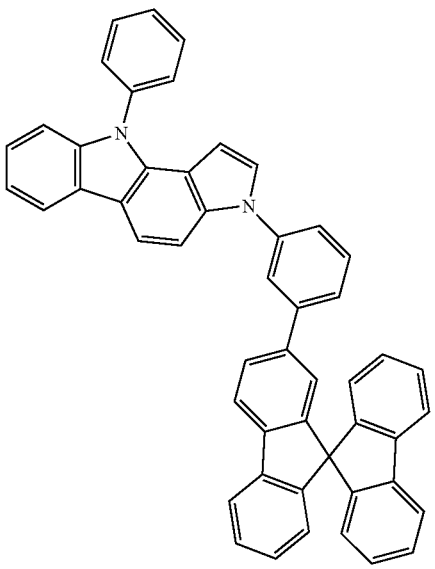

Inv1320
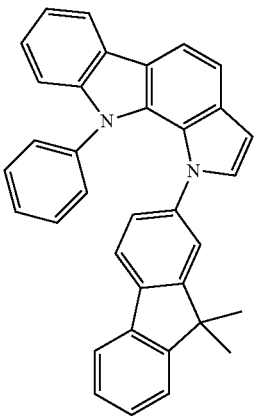
Inv1323
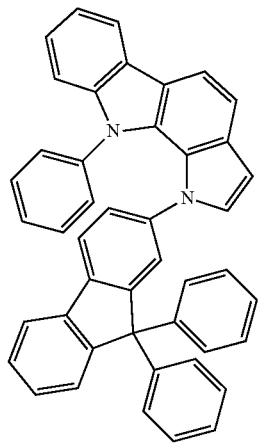
Inv1321
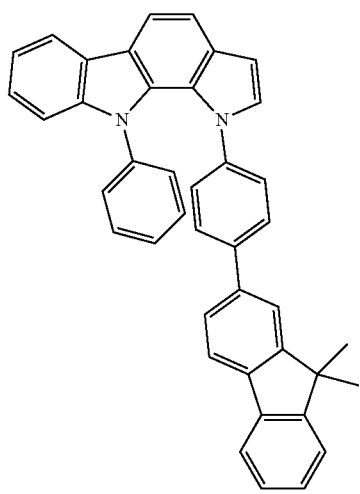
Inv1324
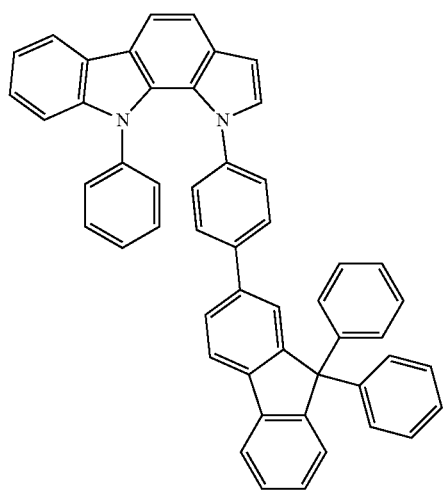
Inv1322
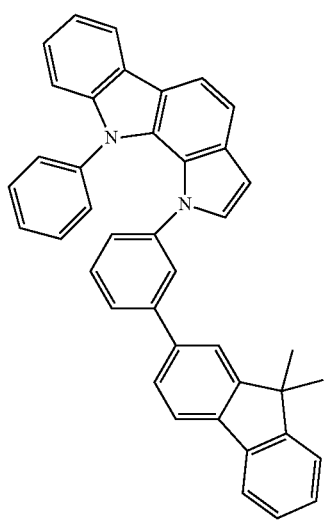
Inv1325
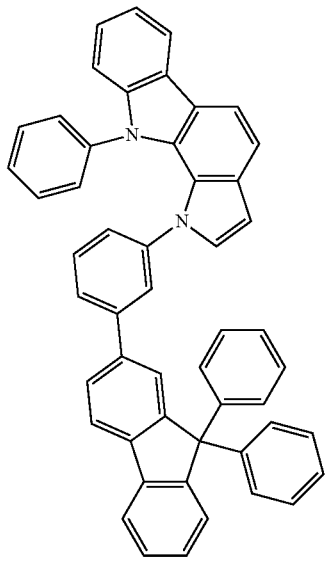

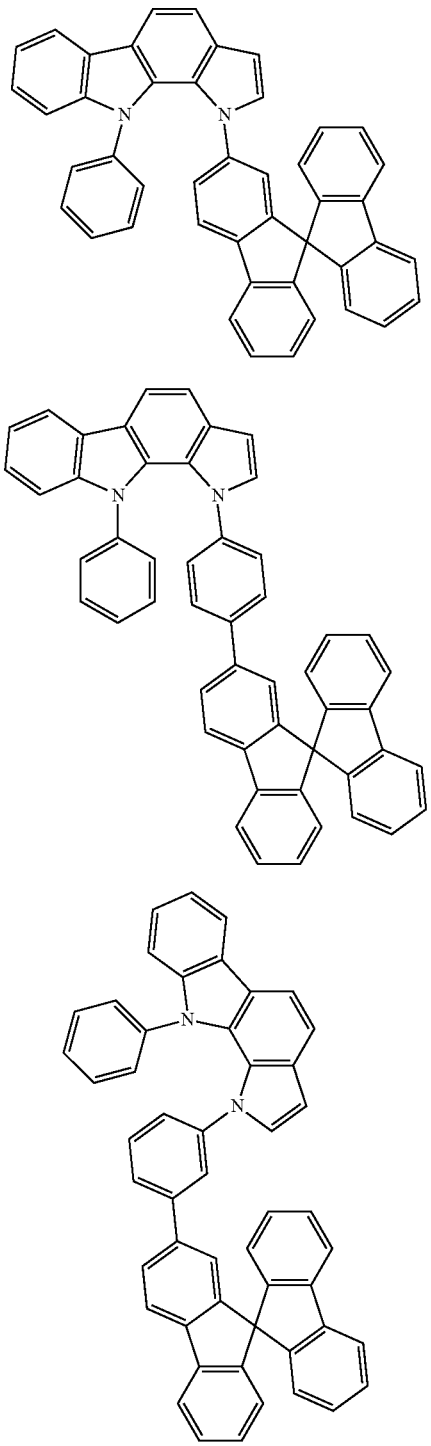

The compound of Formula 1 according to the present invention as described above may be variously synthesized by the following Synthesis Examples.

2. Organic Electroluminescence Device

The present invention provides an organic electroluminescence device including the compound represented by Formula 1 (preferably one compound of the compounds represented by Formulae 4 to 9).

Specifically, the organic electroluminescence device according to the present invention includes (i) an anode, (ii) a cathode, and (iii) an organic material layer including one or more layers interposed between the anode and the cathode, in which at least one of the organic material layers including one or more layers includes the compound represented by Formula 1 (preferably the compound represented by any one of Formulae 4 to 9).

Examples of the organic material layer including one or more layers include a hole injection layer, a hole transporting layer, a light-emitting layer, an electron transporting layer, an electron injection layer, and the like, and among them, at least one organic material layer may include the compound represented by Formula 1. Preferably, the organic material layer including one or more layers, which includes the compound of Formula 1, may be a hole transporting layer, a hole injection layer, or a light-emitting layer, and more preferably a light-emitting layer or a hole transporting layer.

The structure of the organic electroluminescence device according to the present invention is not particularly limited, but non-limiting examples thereof include a structure in which a substrate, an anode, a hole injection layer, a hole transporting layer, a light-emitting layer, an electron transporting layer, and a cathode are sequentially stacked. Here, an electron injection layer may also be additionally stacked on the electron transporting layer. Further, the organic electroluminescence device according to the present invention may also have a structure in which an insulating layer or an adhesive layer may be inserted into the interface between the electrode and the organic material layer.

The organic electroluminescence device according to the present invention may be manufactured by materials and methods publicly known in the art, except that one or more layers (specifically, a light-emitting layer, a hole transporting layer and/or an electron transporting layer) of the organic material layer are formed so as to include the compound represented by Formula 1.

The organic material layer may be formed by a vacuum deposition method or a solution application method. Examples of the solution application method include spin coating, dip coating, doctor blading, inkjet printing, or a thermal transfer method, but are not limited thereto.

As a substrate which is used when the organic electroluminescence device of the present invention is manufactured, a silicon wafer, a quartz or glass plate, a metal plate, a plastic film or sheet, and the like may be used, and examples of the substrate are not limited thereto.

Further, examples of an anode material include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; a conductive polymer, such as polythiophene, poly(3-methylthiophene), poly[3,4-(ethylene-1,2-dioxy)thiophene] (PEDT), polypyrrole, and polyaniline; or carbon black, and the like, but are not limited thereto.

As a cathode material, it is possible to use a metal, such as magnesium, calcium, sodium, potassium, titanium, indium, yttrium, lithium, gadolinium, aluminum, silver, tin, or lead, or alloys thereof; a multi-layer structured material, such as LiF/Al or $LiO_2$/Al, and the like, but examples thereof are not limited thereto.

Furthermore, the hole injection layer, the hole transporting layer, the electron injection layer, and the electron transporting layer are also not particularly limited, and materials publicly known in the art may be used.

Hereinafter, the present invention will be described in detail as follows through the Examples. However, the fol-

Preparation Example 1

Synthesis of IC-1

<Step 1> Synthesis of 5-(4,4,5,5-tetramethyl-1,3,2-dioxaborolan-2-yl)-1H-indole

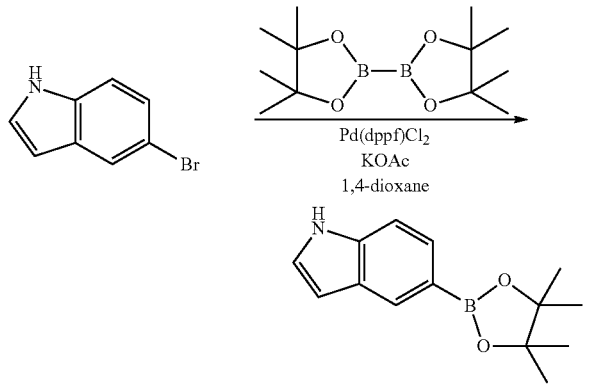

5-bromo-1H-indole (25 g, 0.128 mol), 4,4,4',4',5,5,5',5'-octamethyl-2,2'-bi(1,3,2-dioxaborolane) (48.58 g, 0.191 mol), Pd(dppf)Cl$_2$ (5.2 g, 5 mol), KOAc (37.55 g, 0.383 mol), and 1,4-dioxane (500 ml) were mixed under nitrogen flow, and the resulting mixture was stirred at 130° C. for 12 hours.

After the reaction was terminated, 5-(4,4,5,5-tetramethyl-1,3,2-dioxaborolan-2-yl)-1H-indole (22.32 g, yield 72%) was obtained by performing extraction with ethyl acetate, removing moisture over MgSO$_4$, and purifying the residue with column chromatography (Hexane:EA=10:1 (v/v)).

$^1$H-NMR: δ 1.24 (s, 12H), 6.45 (d, 1H), 7.27 (d, 1H), 7.42 (d, 1H), 7.52 (d, 1H), 7.95 (s, 1H), 8.21 (s, 1H)

<Step 2> Synthesis of 5-(2-nitrophenyl)-1H-indole

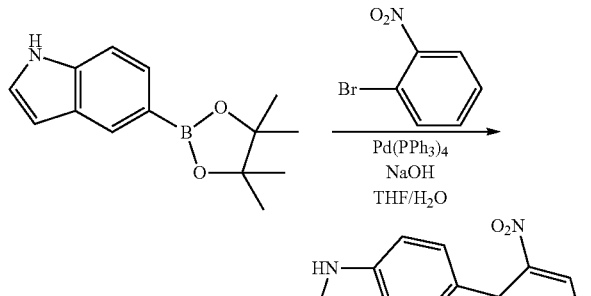

1-bromo-2-nitrobenzene (15.23 g, 75.41 mmol), the 5-(4,4,5,5-tetramethyl-1,3,2-dioxaborolan-2-yl)-1H-indole (22 g, 90.49 mmol) obtained in <Step 1>, NaOH (9.05 g, 226.24 mmol), and THF/H$_2$O (400 ml/200 ml) were mixed under nitrogen flow, Pd(PPh$_3$)$_4$ (4.36 g, 5 mol %) was added thereto at 40° C., and the resulting mixture was stirred at 80° C. for 12 hours.

After the reaction was terminated, extraction was performed with methylene chloride, MgSO$_4$ was added thereto, and the resulting product was filtered. 5-(2-nitrophenyl)-1H-indole (11.32 g, yield 63%) was obtained by removing the solvent from the obtained organic layer, and then purifying the residue with column chromatography (Hexane:EA=3:1 (v/v)).

$^1$H-NMR: δ 6.47 (d, 1H), 7.25 (d, 1H), 7.44 (d, 1H), 7.53 (d, 1H), 7.65 (t, 1H), 7.86 (t, 1H), 7.95 (s, 1H), 8.00 (d, 1H), 8.09 (t, 1H), 8.20 (s, 1H)

<Step 3> Synthesis of 5-(2-nitrophenyl)-1-phenyl-1H-indole

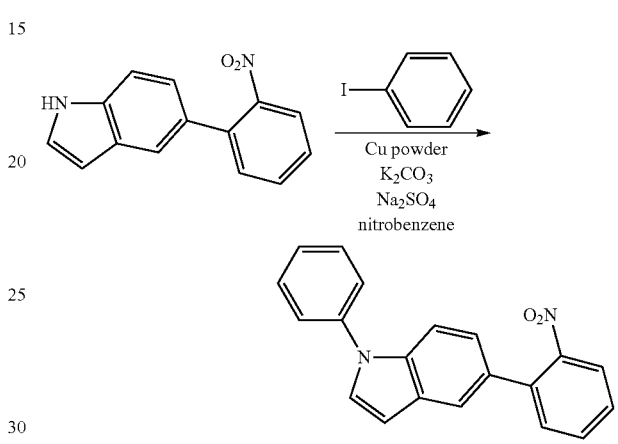

The 5-(2-nitrophenyl)-1H-indole (11 g, 46.17 mmol) obtained in <Step 2>, iodobenzene (14.13 g, 69.26 mmol), Cu powder (0.29 g, 4.62 mmol), K$_2$CO$_3$ (6.38 g, 46.17 mmol), Na$_2$SO$_4$ (6.56 g, 46.17 mmol), and nitrobenzene (200 ml) were mixed under nitrogen flow, and the resulting mixture was stirred at 190° C. for 12 hours.

After the reaction was terminated, nitrobenzene was removed, the organic layer was separated by methylene chloride, and water was removed by using MgSO$_4$. 5-(2-nitrophenyl)-1-phenyl-1H-indole (10.30 g, yield 71%) was obtained by removing the solvent from the organic layer from which water had been removed, and then purifying the residue with column chromatography (Hexane:MC=3:1 (v/v)).

$^1$H-NMR: δ 6.48 (d, 1H), 7.26 (d, 1H), 7.45 (m, 3H), 7.55 (m, 4H), 7.63 (t, 1H), 7.84 (t, 1H), 7.93 (s, 1H), 8.01 (d, 1H), 8.11 (t, 1H)

<Step 4> Synthesis of IC-1

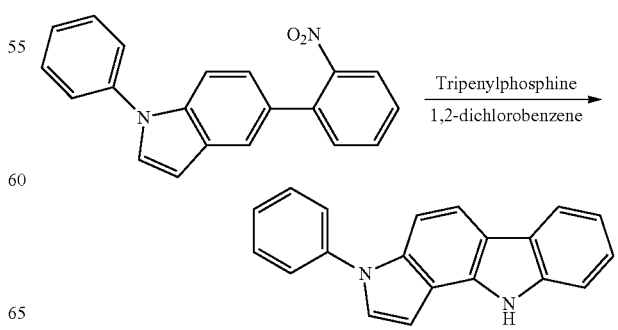

The 5-(2-nitrophenyl)-1-phenyl-1H-indole (5 g, 15.91 mmol) obtained in <Step 3>, triphenylphosphine (10.43 g, 39.77 mmol), and 1,2-dichlorobenzene (50 ml) were mixed under nitrogen flow, and the resulting mixture was stirred for 12 hours.

After the reaction was terminated, 1,2-dichlorobenzene was removed, and extraction was performed with dichloromethane. IC-1 (2.38 g, yield 53%) was obtained by removing water from the obtained organic layer over MgSO₄, and purifying the residue with column chromatography (Hexane:MC=3:1 (v/v)).

¹H-NMR: δ 6.99 (d, 1H), 7.12 (t, 1H), 7.27 (t, 1H), 7.32 (d, 1H), 7.41 (t, 1H), 7.50 (d, 1H), 7.60 (m, 5H), 7.85 (d, 1H), 8.02 (d, 1H), 10.59 (s, 1H)

Preparation Example 2

Synthesis of IC-2

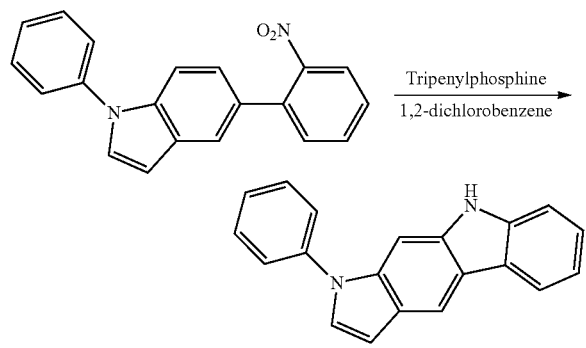

IC-2 was obtained by performing the same procedure as in <Step 4> of Preparation Example 1 using 5-(2-nitrophenyl)-1-phenyl-1H-indole, triphenylphosphine, and 1,2-dichlorobenzene.

¹H-NMR: δ 6.98 (d, 1H), 7.13 (t, 1H), 7.26 (t, 1H), 7.33 (d, 1H), 7.42 (t, 1H), 7.51 (s, 1H), 7.61 (m, 5H), 7.84 (d, 1H), 8.03 (s, 1H), 10.58 (s, 1H)

Preparation Example 3

Synthesis of IC-3

<Step 1> Synthesis of 6-(4,4,5,5-tetramethyl-1,3,2-dioxaborolan-2-yl)-1H-indole

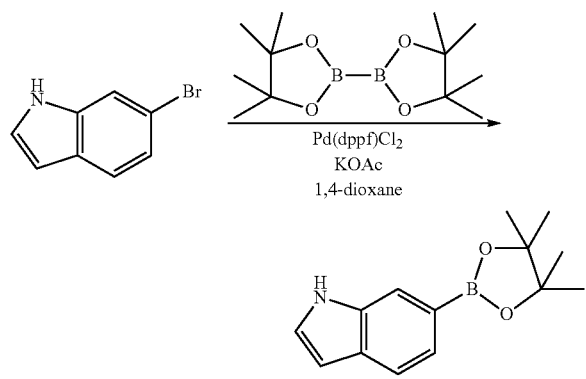

6-(4,4,5,5-tetramethyl-1,3,2-dioxaborolan-2-yl)-1H-indole was obtained by performing the same procedure as in <Step 1> of Preparation Example 1, except that 6-bromo-1H-indole was used instead of 5-bromo-1H-indole.

¹H-NMR: δ 1.25 (s, 12H), 6.52 (d, 1H), 7.16 (d, 1H), 7.21 (d, 1H), 7.49 (d, 1H), 7.53 (s, 1H), 8.15 (s, 1H)

<Step 2> Synthesis of 6-(2-nitrophenyl)-1H-indole

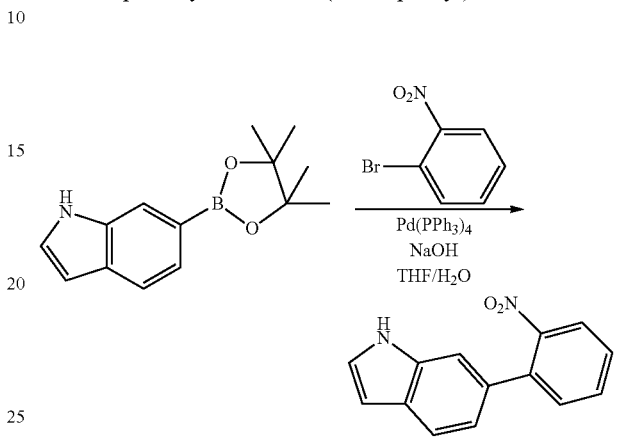

6-(2-nitrophenyl)-1H-indole was obtained by performing the same procedure as in <Step 2> of Preparation Example 1, except that 6-(4,4,5,5-tetramethyl-1,3,2-dioxaborolan-2-yl)-1H-indole was used instead of 5-(4,4,5,5-tetramethyl-1,3,2-dioxaborolan-2-yl)-1H-indole.

¹H-NMR: δ 6.57 (d, 1H), 7.07 (d, 1H), 7.24 (d, 1H), 7.35 (s, 1H), 7.43 (t, 1H), 7.50 (d, 1H), 7.58 (t, 1H), 7.66 (d, 1H), 7.78 (d, 1H), 8.19 (s, 1H)

<Step 3> Synthesis of 6-(2-nitrophenyl)-1-phenyl-1H-indole

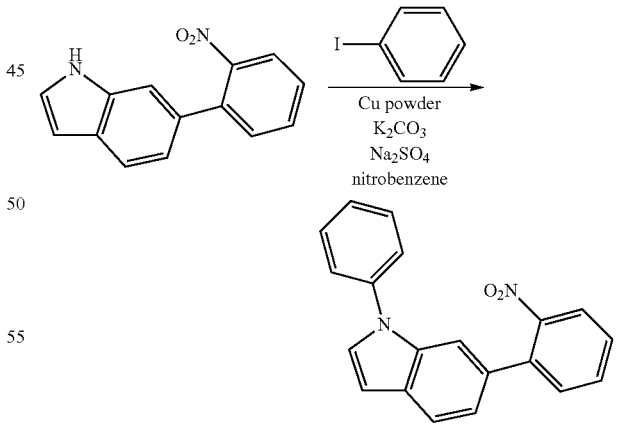

6-(2-nitrophenyl)-1-phenyl-1H-indole was obtained by performing the same procedure as in <Step 3> of Preparation Example 1, except that 6-(2-nitrophenyl)-1H-indole was used instead of 5-(2-nitrophenyl)-1H-indole.

¹H-NMR: δ 6.81 (d, 1H), 7.12 (t, 1H), 7.22 (t, 1H), 7.35 (s, 1H), 7.43 (d, 1H), 7.51 (m, 3H), 7.56 (m, 2H), 7.62 (m, 2H), 7.85 (d, 1H), 8.02 (d, 1H)

<Step 4> Synthesis of IC-3

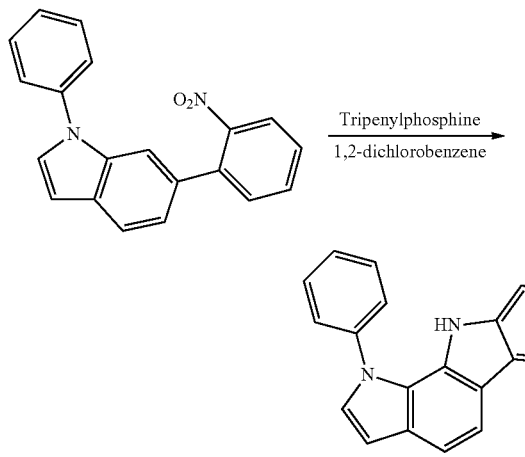

IC-3 was obtained by performing the same procedure as in <Step 4> of Preparation Example 1, except that 6-(2-nitrophenyl)-1-phenyl-1H-indole was used instead of 5-(2-nitrophenyl)-1-phenyl-1H-indole.

$^1$H-NMR: δ 6.80 (d, 1H), 7.11 (t, 1H), 7.23 (t, 1H), 7.42 (d, 1H), 7.50 (m, 3H), 7.57 (m, 2H), 7.63 (m, 2H), 7.86 (d, 1H), 8.03 (d, 1H), 9.81 (s, 1H)

Preparation Example 4

Synthesis of IC-4

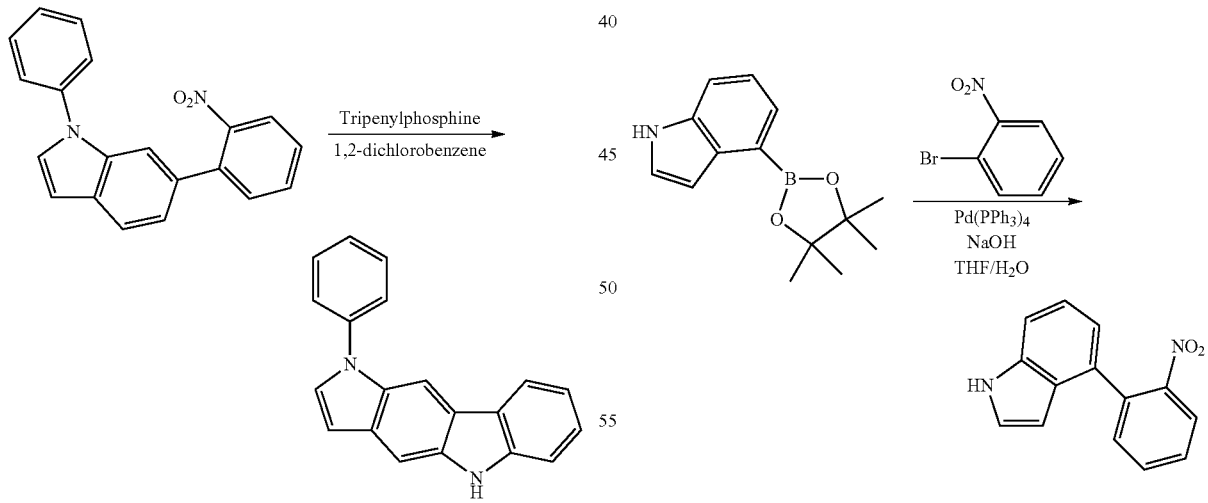

IC-4 was obtained by performing the same procedure as in <Step 4> of Preparation example 1, except that 6-(2-nitrophenyl)-1-phenyl-1H-indole was used instead of 5-(2-nitrophenyl)-1-phenyl-1H-indole.

$^1$H-NMR: δ 6.81 (d, 1H), 7.12 (t, 1H), 7.22 (t, 1H), 7.43 (s, 1H), 7.51 (m, 3H), 7.58 (m, 2H), 7.64 (m, 2H), 7.85 (d, 1H), 8.02 (s, 1H), 9.82 (s, 1H)

Preparation Example 5

Synthesis of IC-5

<Step 1> Synthesis of 4-(4,4,5,5-tetramethyl-1,3,2-dioxaborolan-2-yl)-1H-indole

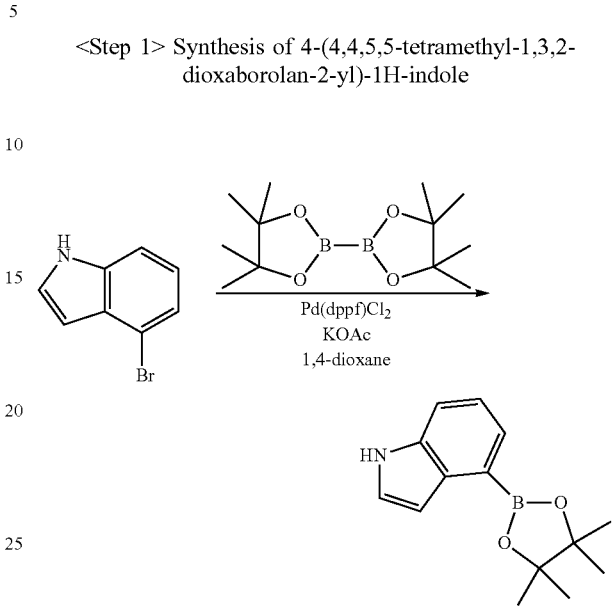

4-(4,4,5,5-tetramethyl-1,3,2-dioxaborolan-2-yl)-1H-indole was obtained by performing the same procedure as in <Step 1> of Preparation Example 1, except that 4-bromo-1H-indole was used instead of 5-bromo-1H-indole.

$^1$H-NMR: δ 1.26 (s, 12H), 6.43 (d, 1H), 7.26 (t, 1H), 7.48 (d, 1H), 7.74 (d, 1H), 7.85 (d, 1H), 8.23 (s, 1H)

<Step 2> Synthesis of 4-(2-nitrophenyl)-1H-indole 4-(2-nitrophenyl)-1H-indole was obtained by performing the same procedure as in <Step 2> of Preparation Example 1, except that the 4-(4,4,5,5-tetramethyl-1,3,2-dioxaborolan-2-yl)-1H-indole obtained in <Step 1> was used instead of 5-(4,4,5,5-tetramethyl-1,3,2-dioxaborolan-2-yl)-1H-indole.

$^1$H-NMR: δ 6.45 (d, 1H), 7.27 (t, 1H), 7.50 (d, 1H), 7.66 (t, 1H), 7.75 (d, 1H), 7.89 (m, 2H), 7.99 (d, 1H), 8.04 (d, 1H), 8.24 (s, 1H)

<Step 3> Synthesis of 4-(2-nitrophenyl)-1-phenyl-1H-indole

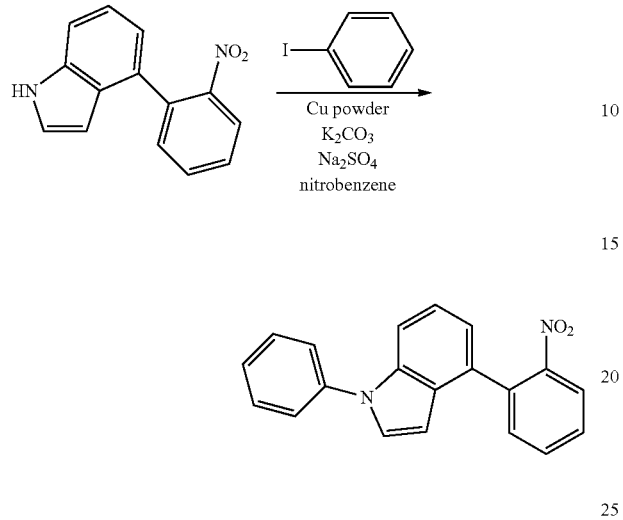

4-(2-nitrophenyl)-1-phenyl-1H-indole was obtained by performing the same procedure as in <Step 3> of Preparation Example 1, except that the 4-(2-nitrophenyl)-1H-indole obtained in <Step 2> was used instead of 5-(2-nitrophenyl)-1H-indole.

$^1$H-NMR: δ 6.47 (d, 1H), 7.28 (t, 1H), 7.47 (m, 2H), 7.52 (m, 2H), 7.60 (m, 2H), 7.67 (t, 1H), 7.75 (d, 1H), 7.89 (m, 2H), 8.00 (d, 1H), 8.06 (d, 1H)

<Step 4> Synthesis of IC-5

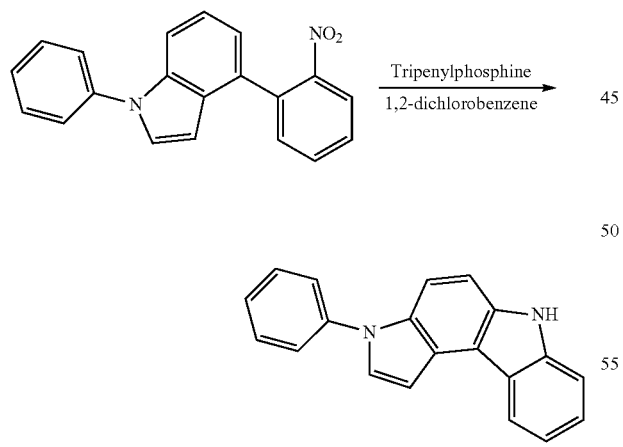

IC-5 was obtained by performing the same procedure as in <Step 4> of Preparation Example 1, except that the 4-(2-nitrophenyl)-1-phenyl-1H-indole obtained in <Step 3> was used instead of 5-(2-nitrophenyl)-1-phenyl-1H-indole.

$^1$H-NMR: δ 6.49 (d, 1H), 7.29 (t, 1H), 7.46 (m, 2H), 7.54 (m, 2H), 7.61 (d, 1H), 7.69 (t, 1H), 7.74 (d, 1H), 7.88 (m, 2H), 8.01 (d, 1H), 8.04 (d, 1H), 8.23 (s, 1H)

Preparation Example 6

Synthesis of IC-6

<Step 1> Synthesis of 7-(4,4,5,5-tetramethyl-1,3,2-dioxaborolan-2-yl)-1H-indole

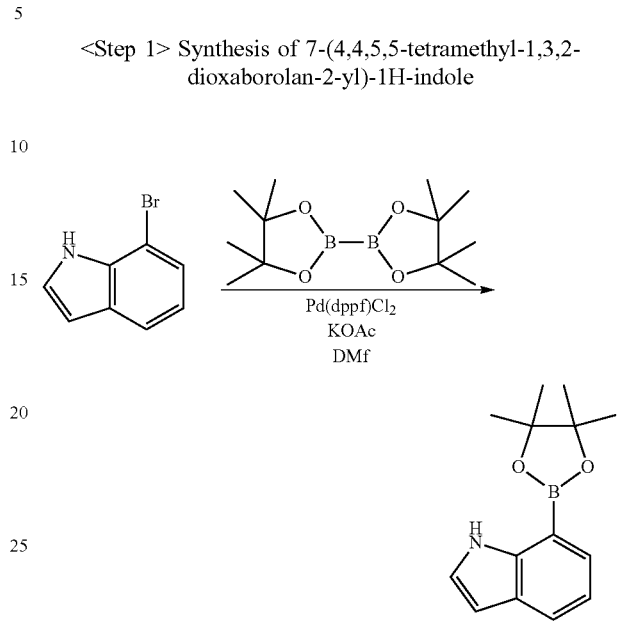

7-(4,4,5,5-tetramethyl-1,3,2-dioxaborolan-2-yl)-1H-indole was obtained by performing the same procedure as in <Step 1> of Preparation Example 1, except that 7-bromo-1H-indole was used instead of 5-bromo-1H-indole.

$^1$H-NMR: δ 1.25 (s, 12H), 6.43 (d, 1H), 7.25 (d, 1H), 7.45 (t, 1H), 7.56 (d, 1H), 7.71 (d, 1H), 8.22 (s, 1H)

<Step 2> Synthesis of 7-(2-nitrophenyl)-1H-indole

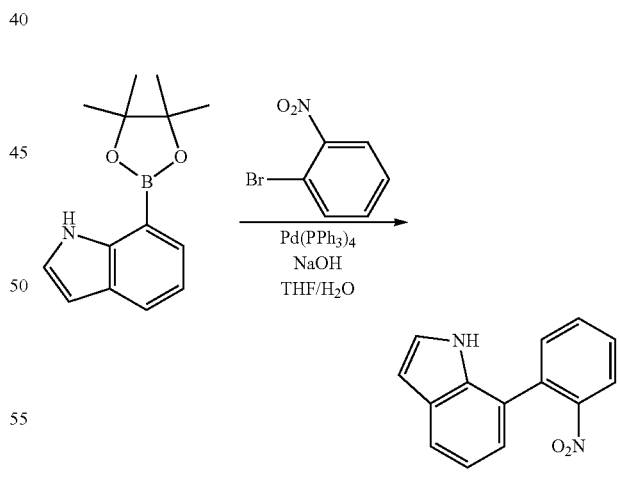

7-(2-nitrophenyl)-1H-indole was obtained by performing the same procedure as in <Step 2> of Preparation Example 1, except that the 7-(4,4,5,5-tetramethyl-1,3,2-dioxaborolan-2-yl)-1H-indole obtained in <Step 1> was used instead of 5-(4,4,5,5-tetramethyl-1,3,2-dioxaborolan-2-yl)-1H-indole.

$^1$H-NMR: δ 6.42 (d, 1H), 7.24 (d, 1H), 7.43 (t, 1H), 7.55 (d, 1H), 7.70 (m, 2H), 7.88 (t, 1H), 8.01 (d, 1H), 8.11 (d, 1H), 8.23 (s, 1H)

<Step 3> Synthesis of 7-(2-nitrophenyl)-1-phenyl-1H-indole

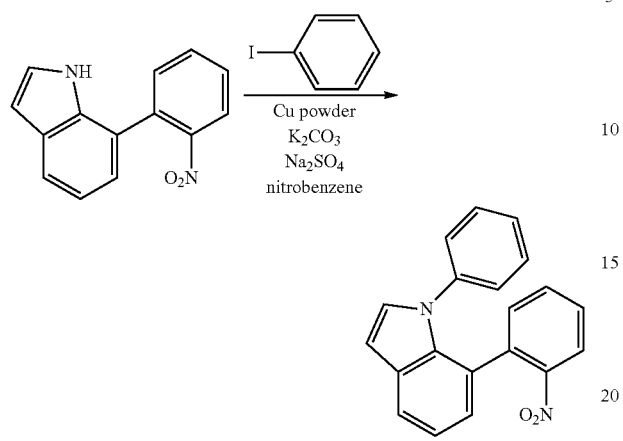

7-(2-nitrophenyl)-1-phenyl-1H-indole was obtained by performing the same procedure as in <Step 3> of Preparation Example 1, except that the 7-(2-nitrophenyl)-1H-indole obtained in <Step 2> was used instead of 5-(2-nitrophenyl)-1H-indole.

$^1$H-NMR: δ 6.43 (d, 1H), 7.26 (d, 1H), 7.44 (m, 3H), 7.56 (m, 4H), 7.71 (m, 2H), 7.89 (t, 1H), 8.02 (d, 1H), 8.10 (d, 1H)

<Step 4> Synthesis of IC-6

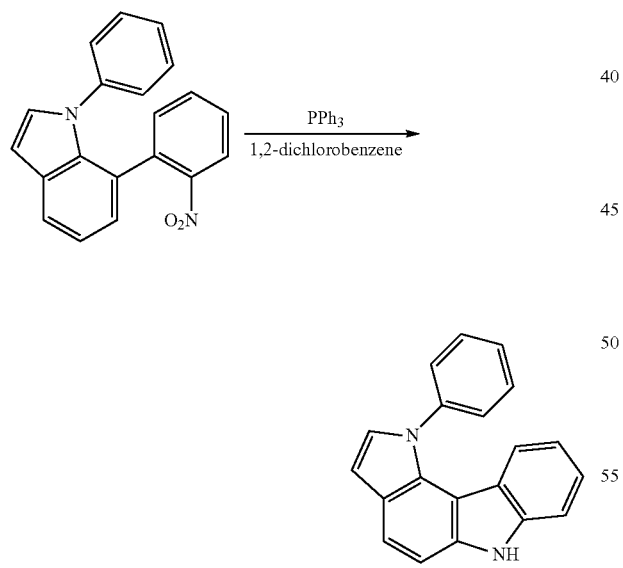

IC-6 was obtained by performing the same procedure as in <Step 4> of Preparation Example 1, except that the 7-(2-nitrophenyl)-1-phenyl-1H-indole obtained in <Step 3> was used instead of 5-(2-nitrophenyl)-1-phenyl-1H-indole.

$^1$H-NMR: δ 6.45 (d, 1H), 7.24 (d, 1H), 7.45 (m, 3H), 7.57 (m, 3H), 7.63 (d, 1H), 7.70 (d, 1H), 7.88 (t, 1H), 8.00 (d, 1H), 8.09 (d, 1H), 8.22 (s, 1H)

Preparation Example 7

Synthesis of IC-7

<Step 1> Synthesis of 5-(5-bromo-2-nitrophenyl)-1H-indole

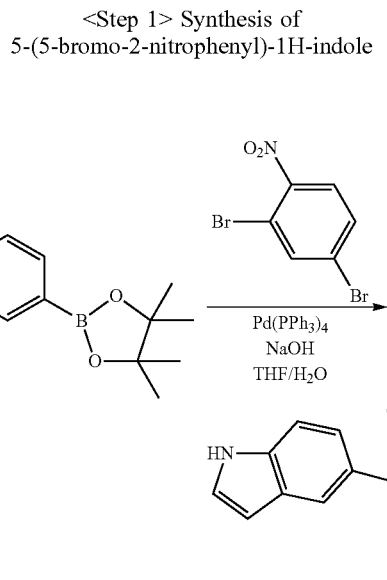

5-(5-bromo-2-nitrophenyl)-1H-indole was obtained by performing the same procedure as in <Step 2> of Preparation Example 1, except that 2,4-dibromo-1-nitrobenzene was used instead of 1-bromo-2-nitrobenzene.

$^1$H-NMR: δ 6.45 (d, 1H), 7.26 (d, 1H), 7.45 (d, 1H), 7.55 (d, 1H), 7.64 (d, 1H), 7.85 (d, 1H), 7.96 (s, 1H), 8.13 (s, 1H), 8.21 (s, 1H)

<Step 2> Synthesis of 5-(5-bromo-2-nitrophenyl)-1-phenyl-1H-indole

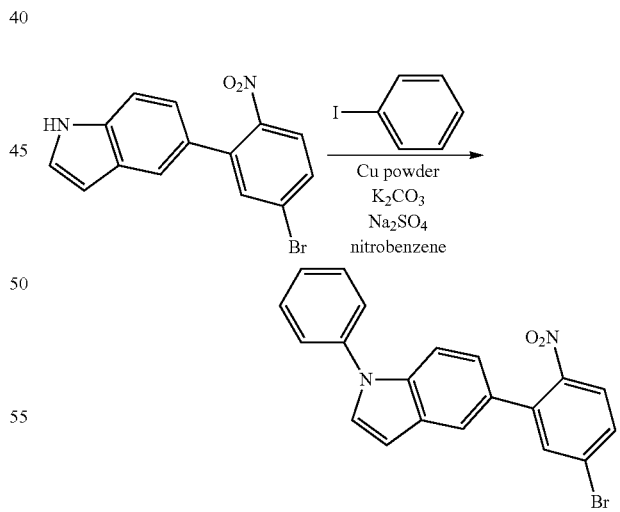

5-(5-bromo-2-nitrophenyl)-1-phenyl-1H-indole was obtained by performing the same procedure as in <Step 3> of Preparation Example 1, except that the 5-(5-bromo-2-nitrophenyl)-1H-indole obtained in <Step 1> was used instead of 5-(2-nitrophenyl)-1H-indole.

$^1$H-NMR: δ 6.44 (d, 1H), 7.25 (d, 1H), 7.46 (m, 3H), 7.56 (m, 4H), 7.65 (d, 1H), 7.86 (d, 1H), 7.95 (s, 1H), 8.11 (s, 1H)

\<Step 3\> Synthesis of 7-bromo-3-phenyl-3,10-dihydropyrrolo[3,2-a]carbazole

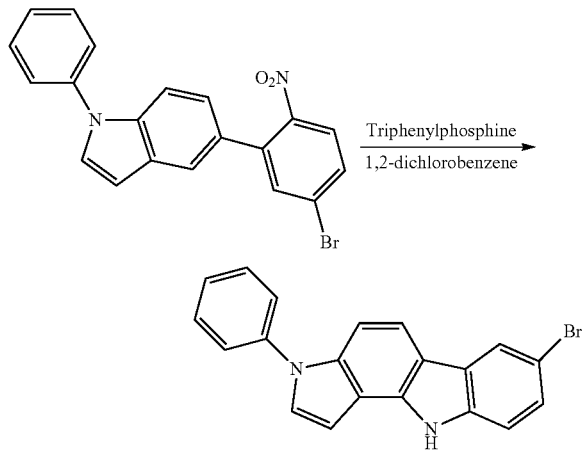

7-bromo-3-phenyl-3,10-dihydropyrrolo[3,2-a]carbazole was obtained by performing the same procedure as in \<Step 4\> of Preparation Example 1, except that the 5-(5-bromo-2-nitrophenyl)-1-phenyl-1H-indole obtained in \<Step 2\> was used instead of 5-(2-nitrophenyl)-1-phenyl-1H-indole.

$^1$H-NMR: δ 6.45 (d, 1H), 7.26 (d, 1H), 7.38 (m, 2H), 7.45 (d, 1H), 7.51 (d, 1H), 7.57 (m, 3H), 7.64 (d, 1H), 7.85 (d, 1H), 8.10 (s, 1H), 8.23 (s, 1H)

\<Step 4\> Synthesis of IC-7

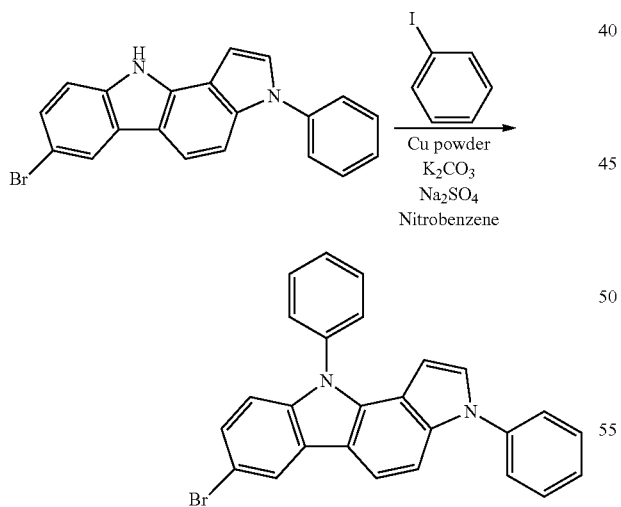

IC-7 was obtained by performing the same procedure as in \<Step 3\> of Preparation Example 1, except that the 7-bromo-3-phenyl-3,10-dihydropyrrolo[3,2-a]carbazole obtained in \<Step 3\> was used instead of 5-(2-nitrophenyl)-1H-indole.

$^1$H-NMR: δ 6.58 (d, 1H), 7.32 (d, 1H), 7.59 (m, 10H), 7.76 (s, 1H), 7.88 (d, 1H), 8.02 (m, 2H)

Preparation Example 8

Synthesis of IC-8

\<Step 1\> Synthesis of 6-(5-bromo-2-nitrophenyl)-1H-indole

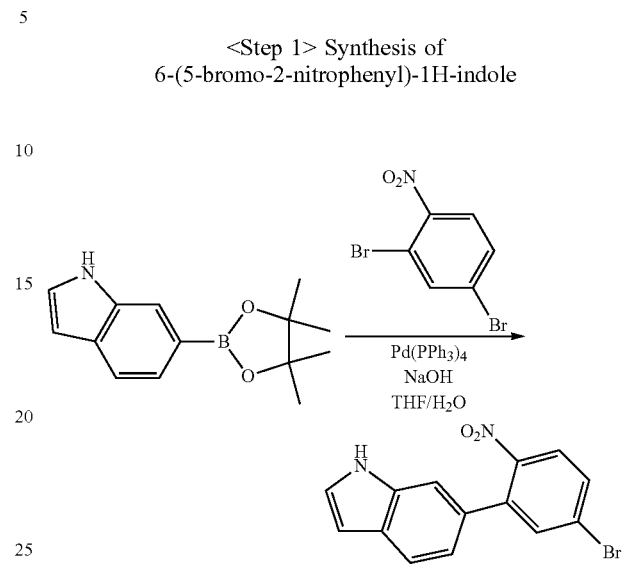

6-(5-bromo-2-nitrophenyl)-1H-indole was obtained by performing the same procedure as in \<Step 2\> of Preparation Example 1, except that 2,4-dibromo-1-nitrobenzene and 6-(4,4,5,5-tetramethyl-1,3,2-dioxaborolan-2-yl)-1H-indole were used instead of 1-bromo-2-nitrobenzene and 5-(4,4,5,5-tetramethyl-1,3,2-dioxaborolan-2-yl)-1H-indole.

$^1$H-NMR: δ 6.51 (d, 1H), 7.31 (d, 1H), 7.50 (d, 1H), 7.60 (d, 1H), 7.69 (d, 1H), 7.90 (d, 1H), 8.01 (s, 1H), 8.14 (s, 1H), 8.25 (s, 1H)

\<Step 2\> Synthesis of 6-(5-bromo-2-nitrophenyl)-1-phenyl-1H-indole

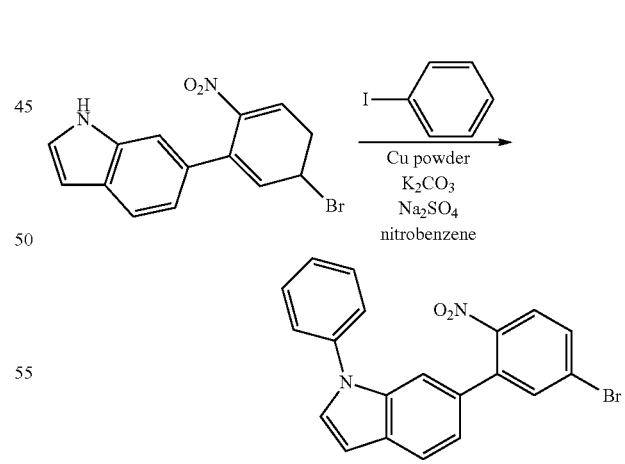

6-(5-bromo-2-nitrophenyl)-1-phenyl-1H-indole was obtained by performing the same procedure as in \<Step 3\> of Preparation Example 1, except that the 6-(5-bromo-2-nitrophenyl)-1H-indole obtained in \<Step 1\> was used instead of 5-(2-nitrophenyl)-1H-indole.

$^1$H-NMR: δ 6.49 (d, 1H), 7.30 (d, 1H), 7.51 (m, 3H), 7.61 (m, 4H), 7.70 (d, 1H), 7.91 (d, 1H), 8.00 (s, 1H), 8.16 (s, 1H)

<Step 3> Synthesis of 7-bromo-1-phenyl-1,10-dihydropyrrolo[2,3-a]carbazole

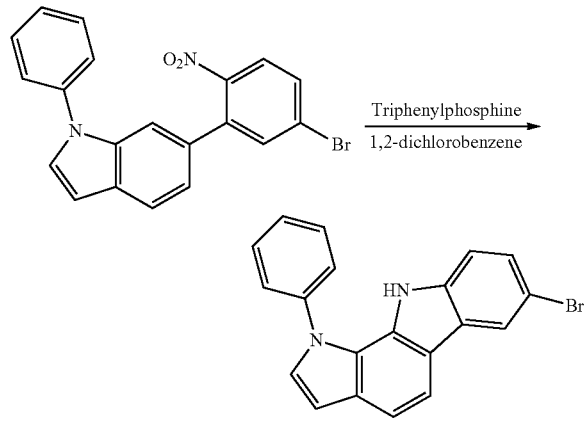

7-bromo-1-phenyl-1,10-dihydropyrrolo[2,3-a]carbazole was obtained by performing the same procedure as in <Step 4> of Preparation Example 1, except that the 6-(5-bromo-2-nitrophenyl)-1-phenyl-1H-indole obtained in <Step 2> was used instead of 5-(2-nitrophenyl)-1-phenyl-1H-indole.

$^1$H-NMR: δ 6.47 (d, 1H), 7.28 (d, 1H), 7.40 (m, 2H), 7.47 (d, 1H), 7.53 (d, 1H), 7.59 (m, 3H), 7.66 (d, 1H), 7.87 (d, 1H), 8.12 (s, 1H), 8.25 (s, 1H)

<Step 4> Synthesis of IC-8

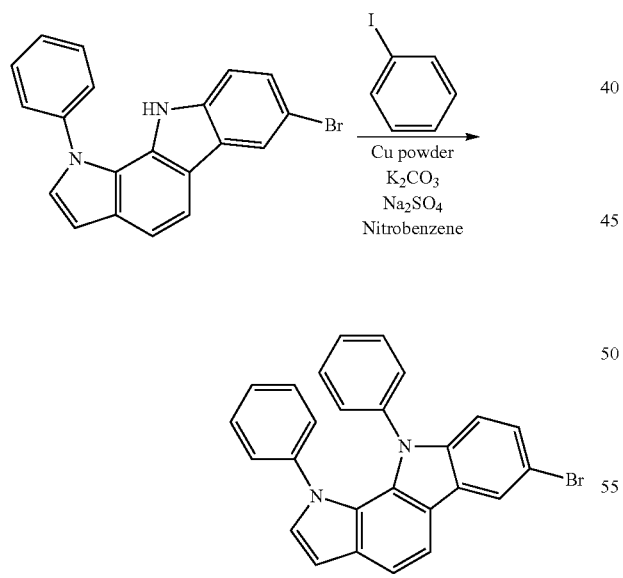

IC-8 was obtained by performing the same procedure as in <Step 3> of Preparation Example 1, except that the 7-bromo-1-phenyl-1,10-dihydropyrrolo[2,3-a]carbazole obtained in <Step 3> was used instead of 5-(2-nitrophenyl)-1H-indole.

$^1$H-NMR: δ 6.57 (d, 1H), 7.32 (d, 1H), 7.60 (m, 11H), 7.76 (s, 1H), 7.88 (m, 2H), 8.47 (d, 1H)

Preparation Example 9

Synthesis of IC-9

<Step 1> Synthesis of 5-(2-nitrophenyl)-1-o-tolyl-1H-indole

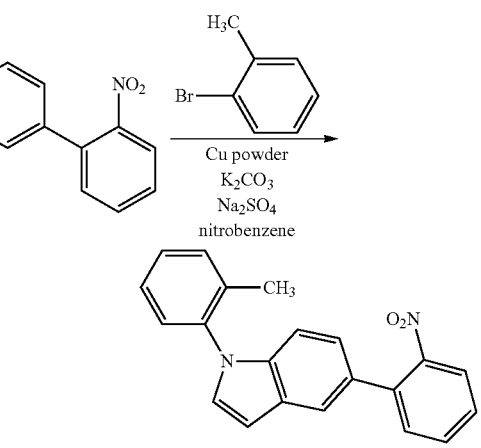

5-(2-nitrophenyl)-1-o-tolyl-1H-indole was obtained by performing the same procedure as in <Step 3> of Preparation Example 1, except that 1-bromo-2-methylbenzene was used instead of iodobenzene.

$^1$H-NMR: δ 1.92 (s, 3H), 6.47 (d, 1H), 7.25 (d, 1H), 7.46 (m, 3H), 7.56 (m, 3H), 7.64 (t, 1H), 7.85 (t, 1H), 7.94 (s, 1H), 8.00 (d, 1H), 8.12 (t, 1H)

<Step 2> Synthesis of IC-9

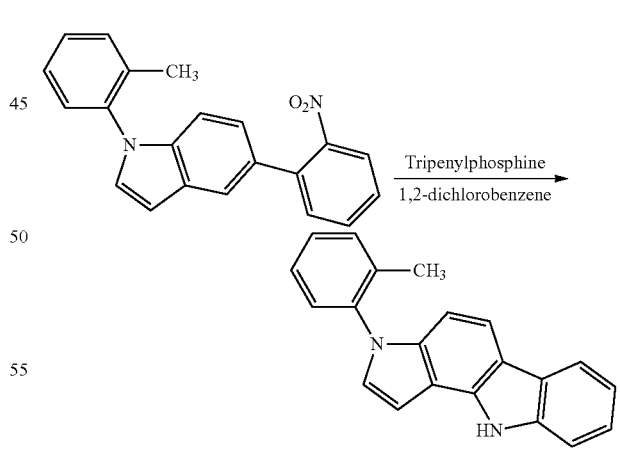

IC-9 was obtained by performing the same procedure as in <Step 4> of Preparation Example 1, except that the 5-(2-nitrophenyl)-1-o-tolyl-1H-indole obtained in <Step 1> was used instead of 5-(2-nitrophenyl)-1-phenyl-1H-indole.

$^1$H-NMR: δ 1.93 (s, 3H), 6.98 (d, 1H), 7.11 (t, 1H), 7.28 (t, 1H), 7.31 (d, 1H), 7.42 (t, 1H), 7.51 (d, 1H), 7.61 (m, 4H), 7.86 (d, 1H), 8.01 (d, 1H), 10.58 (s, 1H)

Preparation Example 10

Synthesis of IC-10

<Step 1> Synthesis of 1-(biphenyl-4-yl)-5-(2-nitrophenyl)-1H-indole

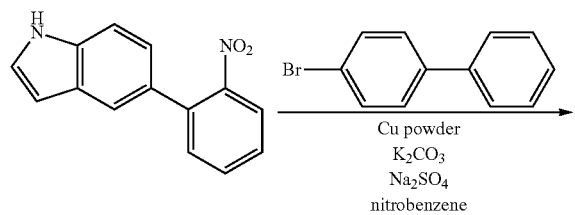

1-(biphenyl-4-yl)-5-(2-nitrophenyl)-1H-indole was obtained by performing the same procedure as in <Step 3> of Preparation Example 1, except that 4-bromobiphenyl was used instead of iodobenzene.

$^1$H-NMR: δ 6.73 (d, 1H), 7.18 (d, 1H), 7.39 (m, 2H), 7.47 (m, 3H), 7.54 (d, 1H), 7.59 (m, 3H), 7.64 (m, 4H), 7.75 (d, 2H), 7.82 (d, 1H)

<Step 2> Synthesis of IC-10

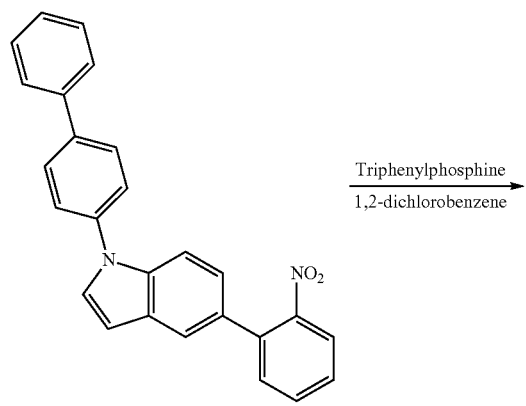

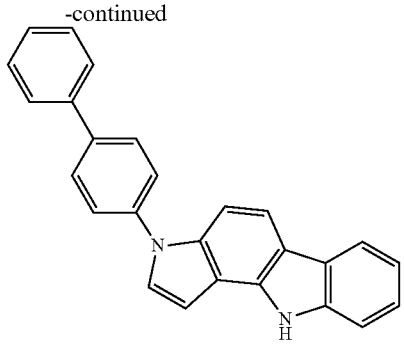

IC-10 was obtained by performing the same procedure as in <Step 4> of Preparation Example 1, except that the 1-(biphenyl-4-yl)-5-(2-nitrophenyl)-1H-indole obtained in <Step 1> was used instead of 5-(2-nitrophenyl)-1-phenyl-1H-indole.

$^1$H-NMR: δ 6.75 (d, 1H), 7.20 (d, 1H), 7.42 (m, 2H), 7.51 (m, 3H), 7.56 (d, 1H), 7.62 (m, 3H), 7.68 (m, 3H), 7.76 (d, 2H), 7.85 (d, 1H), 10.45 (s, 1H)

Preparation Example 11

Synthesis of IC-11

<Step 1> Synthesis of IC-11-1

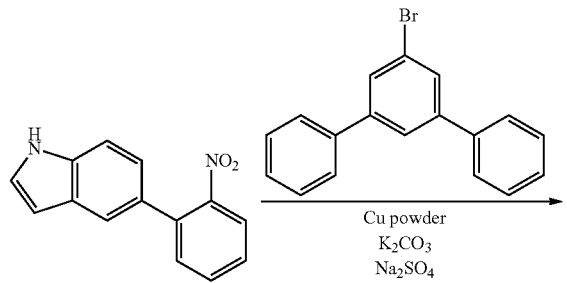

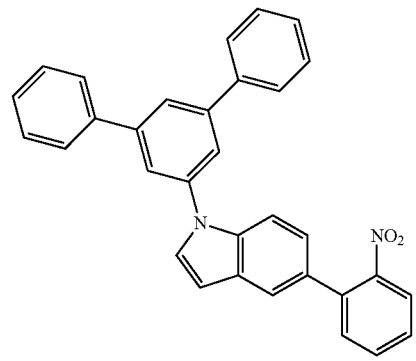

IC-11-1 was obtained by performing the same procedure as in <Step 3> of Preparation Example 1, except that 1-bromo-3,5-diphenyl benzene was used instead of iodobenzene.

$^1$H-NMR: δ 6.98 (d, 1H), 7.11 (t, 1H), 7.24 (t, 1H), 7.38 (t, 2H), 7.46 (m, 6H), 7.58 (d, 1H), 7.81 (d, 4H), 7.87 (m, 4H), 7.93 (d, 1H), 7.99 (d, 1H)

<Step 2> Synthesis of IC-11

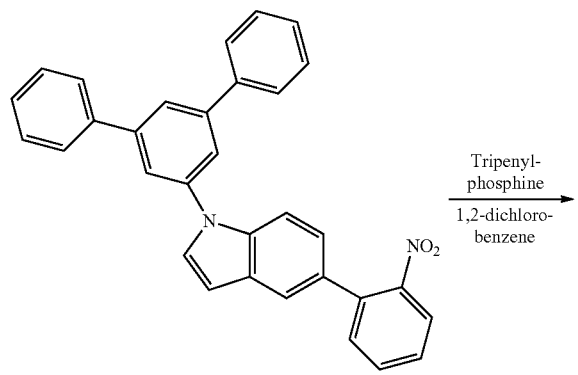

IC-11 was obtained by performing the same procedure as in <Step 4> of Preparation Example 1, except that the IC-11-1 obtained in <Step 1> was used instead of 5-(2-nitrophenyl)-1-phenyl-1H-indole.

$^1$H-NMR: δ 6.97 (d, 1H), 7.10 (t, 1H), 7.23 (t, 1H), 7.37 (t, 2H), 7.45 (m, 6H), 7.58 (d, 1H), 7.80 (d, 4H), 7.86 (m, 3H), 7.92 (d, 1H), 7.98 (d, 1H), 10.60 (s, 1H)

Preparation Example 12

Synthesis of IC-12

<Step 1> Synthesis of 5-(2-nitrophenyl)-1-(2-(trifluoromethyl)phenyl)-1H-indole

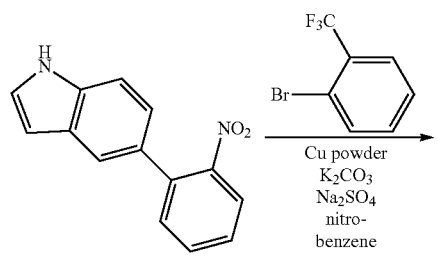

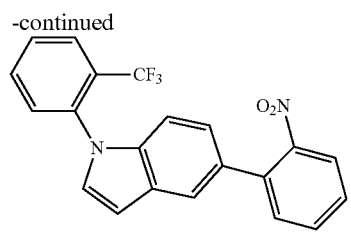

5-(2-nitrophenyl)-1-(2-(trifluoromethyl)phenyl)-1H-indole was obtained by performing the same procedure as in <Step 3> of Preparation Example 1, except that 1-bromo-2-(trifluoromethyl)benzene was used instead of iodobenzene.

$^1$H-NMR: δ 6.48 (d, 1H), 7.26 (d, 1H), 7.47 (m, 3H), 7.57 (m, 3H), 7.63 (t, 1H), 7.84 (t, 1H), 7.95 (s, 1H), 8.01 (d, 1H), 8.13 (t, 1H)

<Step 2> Synthesis of IC-12

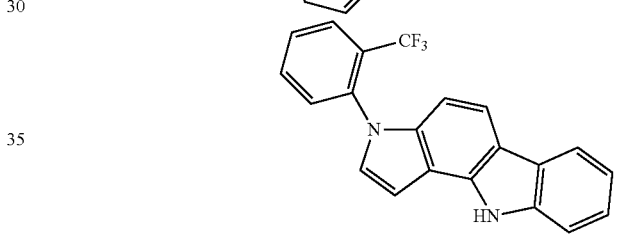

IC-12 was obtained by performing the same procedure as in <Step 4> of Preparation Example 1, except that the 5-(2-nitrophenyl)-1-(2-(trifluoromethyl)phenyl)-1H-indole obtained in <Step 1> was used instead of 5-(2-nitrophenyl)-1-phenyl-1H-indole.

$^1$H-NMR: δ 6.97 (d, 1H), 7.12 (t, 1H), 7.29 (t, 1H), 7.32 (d, 1H), 7.41 (t, 1H), 7.52 (d, 1H), 7.60 (m, 4H), 7.85 (d, 1H), 8.01 (d, 1H), 10.57 (s, 1H)

Preparation Example 13

Synthesis of IC-13

<Step 1> Synthesis of 1-(biphenyl-3-yl)-5-(2-nitrophenyl)-1H-indole

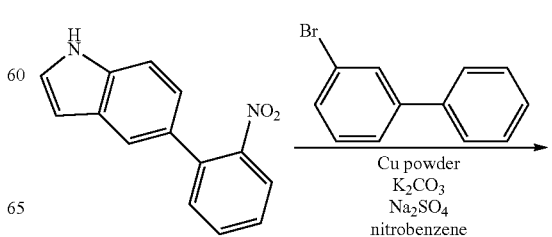

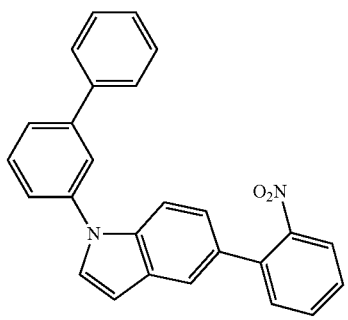

1-(biphenyl-3-yl)-5-(2-nitrophenyl)-1H-indole was obtained by performing the same procedure as in <Step 3> of Preparation Example 1, except that 3-bromobiphenyl was used instead of iodobenzene.

¹H-NMR: δ 6.75 (d, 1H), 7.19 (d, 1H), 7.38 (m, 2H), 7.48 (m, 3H), 7.52 (d, 1H), 7.58 (m, 3H), 7.65 (m, 4H), 7.76 (m, 2H), 7.85 (d, 1H)

<Step 2> Synthesis of IC-13

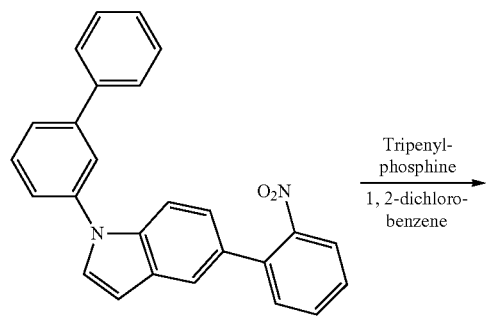

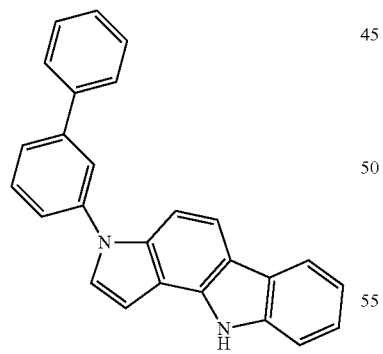

IC-13 was obtained by performing the same procedure as in <Step 4> of Preparation Example 1, except that the 1-(biphenyl-3-yl)-5-(2-nitrophenyl)-1H-indole obtained in <Step 1> was used instead of 5-(2-nitrophenyl)-1-phenyl-1H-indole.

¹H-NMR: δ 6.74 (d, 1H), 7.21 (d, 1H), 7.41 (m, 2H), 7.52 (m, 3H), 7.56 (d, 1H), 7.61 (m, 3H), 7.69 (m, 3H), 7.77 (m, 2H), 7.86 (d, 1H), 10.44 (s, 1H)

Preparation Example 14

Synthesis of IC-14

<Step 1> Synthesis of 1-(biphenyl-3-yl)-6-(2-nitrophenyl)-1H-indole

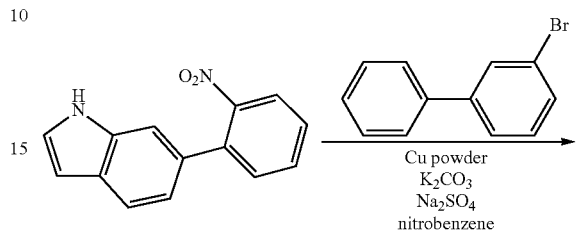

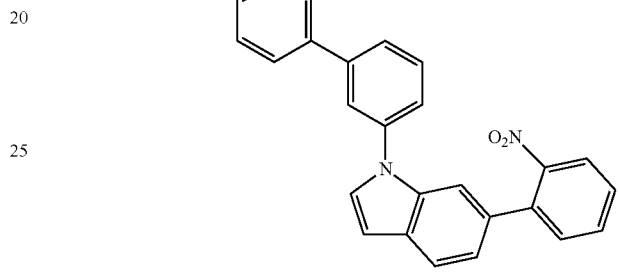

1-(biphenyl-3-yl)-6-(2-nitrophenyl)-1H-indole was obtained by performing the same procedure as in <Step 3> of Preparation Example 1, except that 6-(2-nitrophenyl)-1H-indole and 3-bromobiphenyl were used instead of 5-(2-nitrophenyl)-1H-indole and iodobenzene.

¹H-NMR: δ 6.76 (d, 1H), 7.18 (d, 1H), 7.37 (m, 2H), 7.47 (m, 3H), 7.51 (d, 1H), 7.57 (m, 3H), 7.64 (m, 4H), 7.75 (m, 2H), 7.86 (d, 1H)

<Step 2> Synthesis of IC-14

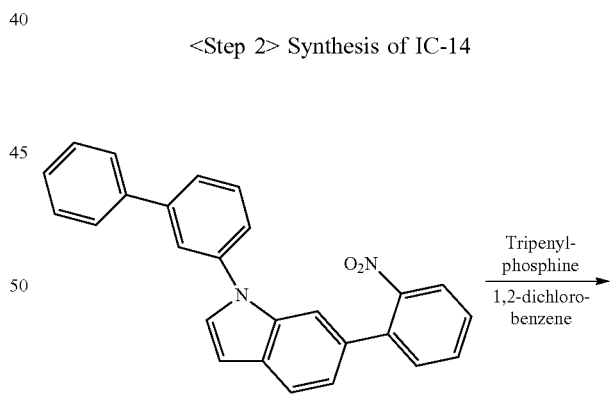

IC-14 was obtained by performing the same procedure as in <Step 4> of Preparation example 1, except that the 1-(biphenyl-3-yl)-6-(2-nitrophenyl)-1H-indole obtained in <Step 1> was used instead of 5-(2-nitrophenyl)-1-phenyl-1H-indole.

¹H-NMR: δ 6.75 (d, 1H), 7.20 (d, 1H), 7.40 (m, 2H), 7.51 (m, 3H), 7.57 (d, 1H), 7.62 (m, 3H), 7.70 (m, 3H), 7.76 (m, 2H), 7.85 (d, 1H), 10.43 (s, 1H)

Preparation Example 15

Synthesis of IC-15

<Step 1> Synthesis of 1-(biphenyl-4-yl)-6-(2-nitrophenyl)-1H-indole

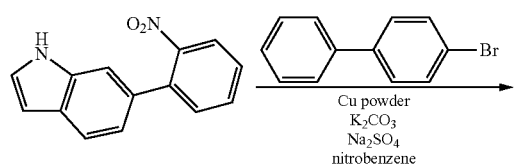

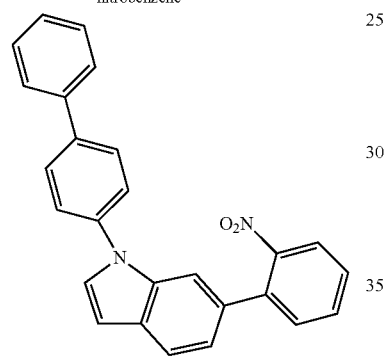

1-(biphenyl-4-yl)-6-(2-nitrophenyl)-1H-indole was obtained by performing the same procedure as in <Step 3> of Preparation Example 1, except that 6-(2-nitrophenyl)-1H-indole and 4-bromobiphenyl were used instead of 5-(2-nitrophenyl)-1H-indole and iodobenzene.

¹H-NMR: δ 6.74 (d, 1H), 7.19 (d, 1H), 7.40 (m, 2H), 7.46 (m, 3H), 7.55 (d, 1H), 7.58 (m, 3H), 7.63 (m, 4H), 7.75 (d, 2H), 7.83 (d, 1H)

<Step 2> Synthesis of IC-15

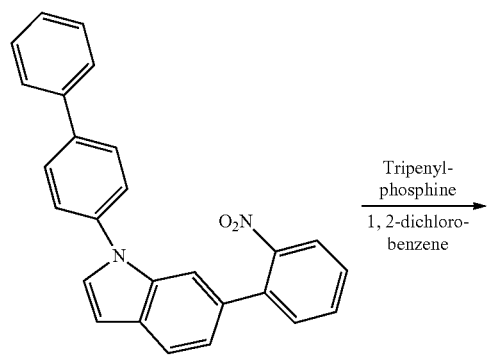

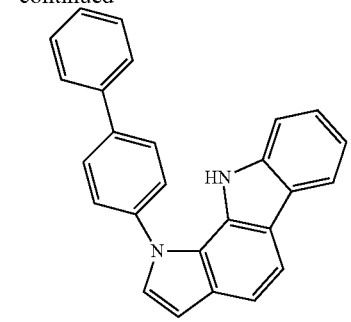

IC-15 was obtained by performing the same procedure as in <Step 4> of Preparation Example 1, except that the 1-(biphenyl-4-yl)-6-(2-nitrophenyl)-1H-indole obtained in <Step 1> was used instead of 5-(2-nitrophenyl)-1-phenyl-1H-indole.

¹H-NMR: δ 6.74 (d, 1H), 7.19 (d, 1H), 7.43 (m, 2H), 7.52 (m, 3H), 7.57 (d, 1H), 7.63 (m, 3H), 7.69 (m, 3H), 7.75 (d, 2H), 7.86 (d, 1H), 10.46 (s, 1H)

Preparation Example 16

Synthesis of IC-16

<Step 1> Synthesis of IC-16-1

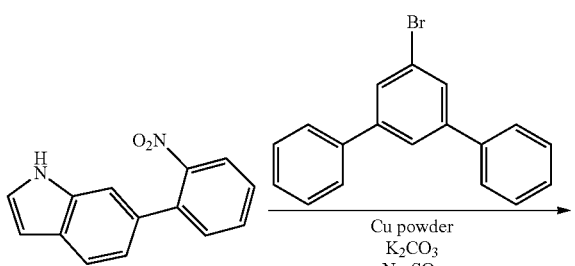

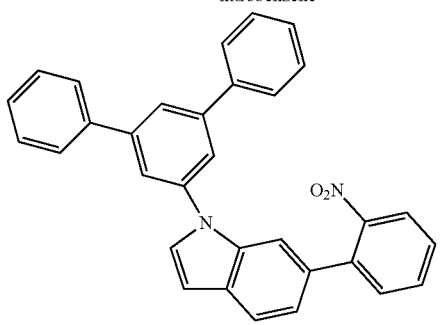

IC-16-1 was obtained by performing the same procedure as in <Step 3> of Preparation Example 1, except that 6-(2-nitrophenyl)-1H-indole and 1-bromo-3,5-diphenyl benzene were used instead of 5-(2-nitrophenyl)-1H-indole and iodobenzene.

¹H-NMR: δ 6.98 (d, 1H), 7.11 (t, 1H), 7.24 (t, 1H), 7.38 (m, 2H), 7.45 (m, 6H), 7.57 (d, 1H), 7.80 (d, 4H), 7.86 (m, 4H), 7.92 (d, 1H), 7.98 (d, 1H)

<Step 2> Synthesis of IC-16

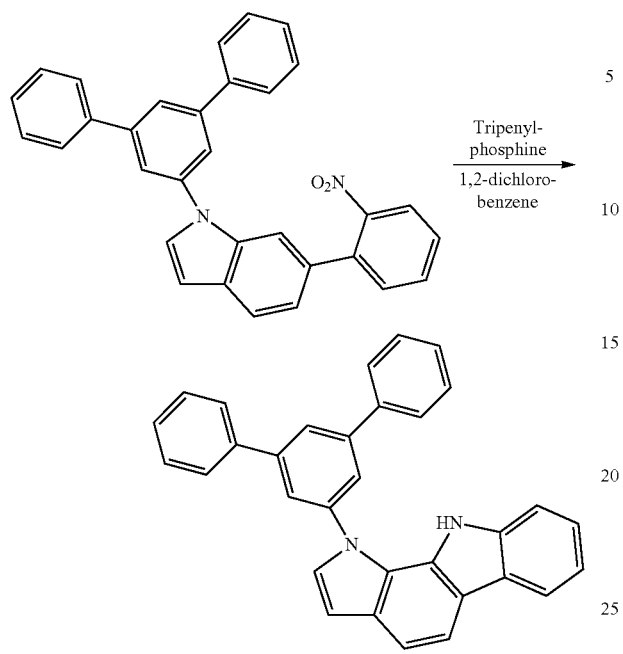

IC-16 was obtained by performing the same procedure as in <Step 4> of Preparation Example 1, except that the IC-16-1 obtained in <Step 1> was used instead of 5-(2-nitrophenyl)-1-phenyl-1H-indole.

$^1$H-NMR: δ 6.97 (d, 1H), 7.10 (t, 1H), 7.23 (t, 1H), 7.37 (t, 2H), 7.45 (m, 6H), 7.58 (d, 1H), 7.80 (d, 4H), 7.86 (m, 3H), 7.92 (d, 1H), 7.98 (d, 1H), 10.59 (s, 1H)

Preparation Example 17

Synthesis of IC-17

<Step 1> Synthesis of 6-(2-nitrophenyl)-1-(3-(trifluoromethyl)phenyl)-1H-indole

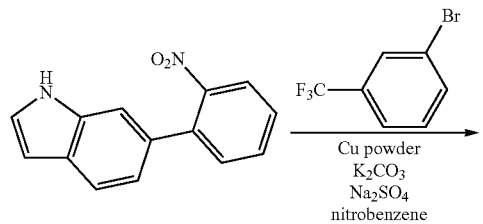

6-(2-nitrophenyl)-1-(3-(trifluoromethyl)phenyl)-1H-indole was obtained by performing the same procedure as in <Step 3> of Preparation Example 1, except that 6-(2-nitrophenyl)-1H-indole and 1-bromo-3-(trifluoromethyl)benzene were used instead of 5-(2-nitrophenyl)-1H-indole and iodobenzene.

$^1$H-NMR: δ 6.80 (d, 1H), 7.11 (t, 1H), 7.21 (t, 1H), 7.36 (s, 1H), 7.42 (s, 1H), 7.50 (m, 2H), 7.55 (m, 2H), 7.63 (m, 2H), 7.86 (d, 1H), 8.01 (d, 1H)

<Step 2> Synthesis of IC-17

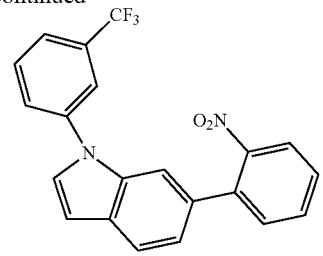

IC-17 was obtained by performing the same procedure as in <Step 4> of Preparation Example 1, except that the 6-(2-nitrophenyl)-1-(3-(trifluoromethyl)phenyl)-1H-indole obtained in <Step 1> was used instead of 5-(2-nitrophenyl)-1-phenyl-1H-indole.

$^1$H-NMR: δ 6.81 (d, 1H), 7.12 (t, 1H), 7.24 (t, 1H), 7.43 (d, 1H), 7.51 (m, 2H), 7.58 (m, 2H), 7.64 (m, 2H), 7.85 (d, 1H), 8.02 (d, 1H), 9.82 (s, 1H)

Preparation Example 18

Synthesis of IC-18

<Step 1> Synthesis of 3-(5-(2-nitrophenyl)-1H-indol-1-yl)-9-phenyl-9H-carbazole

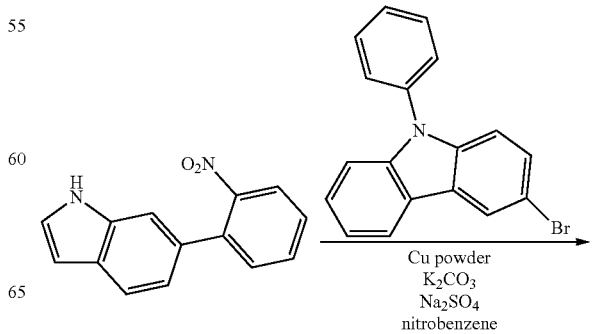

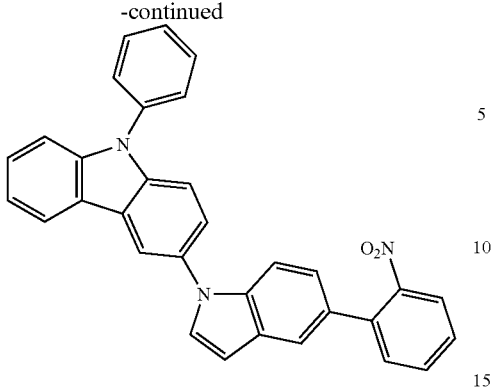

3-(5-(2-nitrophenyl)-1H-indol-1-yl)-9-phenyl-9H-carbazole was obtained by performing the same procedure as in <Step 3> of Preparation Example 1, except that 6-(2-nitrophenyl)-1H-indole and 3-bromo-9-phenyl-9H-carbazole were used instead of 5-(2-nitrophenyl)-1H-indole and iodobenzene.

GC-Mass (theoretical value: 479.16 g/mol, measured value: 479 g/mol)

<Step 2> Synthesis of IC-18

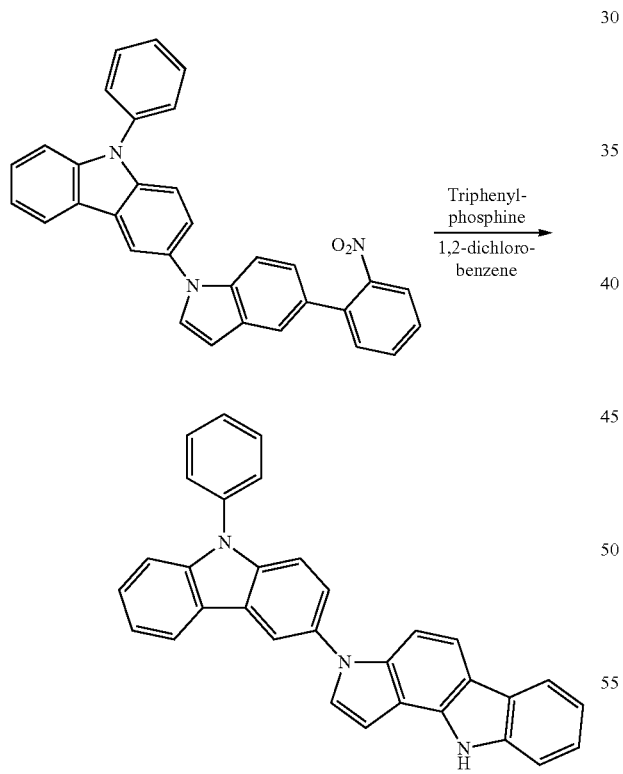

IC-18 was obtained by performing the same procedure as in <Step 4> of Preparation example 1, except that the 3-(5-(2-nitrophenyl)-1H-indol-1-yl)-9-phenyl-9H-carbazole obtained in <Step 1> was used instead of 5-(2-nitrophenyl)-1-phenyl-1H-indole.

GC-Mass (theoretical value: 447.17 g/mol, measured value: 447 g/mol)

Preparation Example 19

Synthesis of IC-19

<Step 1> Synthesis of 9-(4,6-diphenyl-1,3,5-triazin-2-yl)-3-(5-(2-nitrophenyl)-1H-indol-1-yl)-9H-carbazole

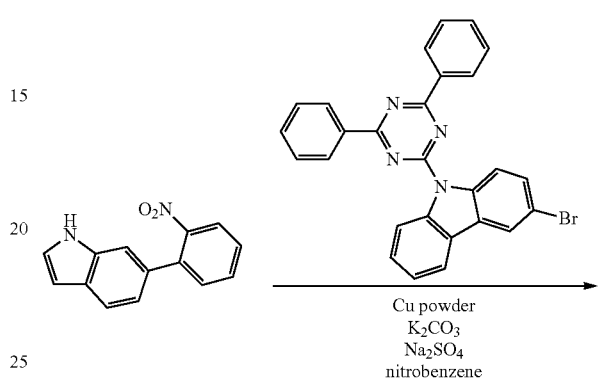

9-(4,6-diphenyl-1,3,5-triazin-2-yl)-3-(5-(2-nitrophenyl)-1H-indol-1-yl)-9H-carbazole was obtained by performing the same procedure as in <Step 3> of Preparation Example 1, except that 6-(2-nitrophenyl)-1H-indole and 3-bromo-9-(4,6-diphenyl-1,3,5-triazin-2-yl)-9H-carbazole were used instead of 5-(2-nitrophenyl)-1H-indole and iodobenzene.

GC-Mass (theoretical value: 634.21 g/mol, measured value: 634 g/mol)

<Step 2> Synthesis of 3-(9-(4,6-diphenyl-1,3,5-triazin-2-yl)-9H-carbazol-3-yl)-3,10-dihydropyrrolo[3,2-a]carbazole

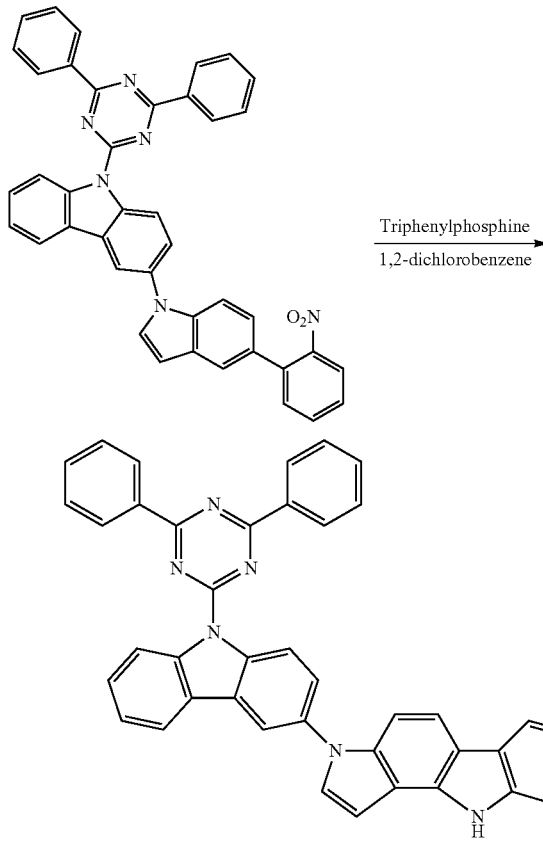

IC-19 was obtained by performing the same procedure as in <Step 4> of Preparation Example 1, except that the 9-(4,6-diphenyl-1,3,5-triazin-2-yl)-3-(5-(2-nitrophenyl)-1H-indol-1-yl)-9H-carbazole obtained in <Step 1> was used instead of 5-(2-nitrophenyl)-1-phenyl-1H-indole.

GC-Mass (theoretical value: 602.22 g/mol, measured value: 602 g/mol)

Preparation Example 20

Synthesis of IC-20

<Step 1> Synthesis of 5-bromo-2-phenyl-1H-indole

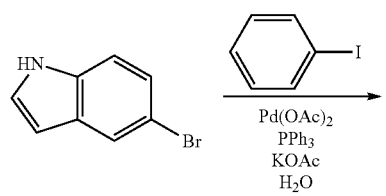

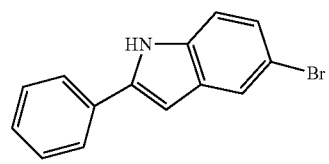

5-bromo-1H-indole (25 g, 0.13 mol), iodobenzene (31.22 g, 0.15 mol), Pd(OAc)$_2$ (1.43 g, 5 mol %), triphenylphosphine (1.67 g, 5 mol %), KOAc (37.55 g, 0.38 mol), and H$_2$O (300 ml) were mixed under nitrogen flow, and the resulting mixture was stirred at 110° C. for 24 hours.

After the reaction was terminated, 5-bromo-2-phenyl-1H-indole (16.66 g, yield 48%) was obtained by performing extraction with ethyl acetate, removing moisture over MgSO$_4$, and purifying the residue with column chromatography (Hexane:EA=10:1 (v/v)).

$^1$H-NMR: δ 6.89 (dd, 1H), 7.20 (dd, 1H), 7.34 (m, 1H), 7.36 (d, 1H), 7.47 (t, 2H), 7.71 (d, 1H), 7.86 (dd, 2H), 11.74 (s, 1H)

<Step 2> Synthesis of 5-(2-nitrophenyl)-2-phenyl-1H-indole

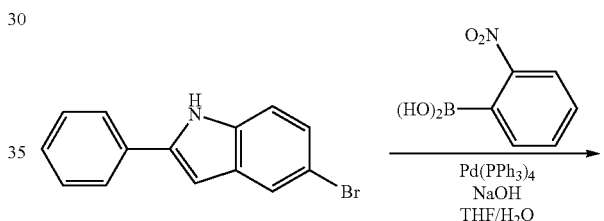

2-nitrophenylboronic acid (11.04 g, 66.14 mmol), the 5-bromo-2-phenyl-1H-indole (15 g, 55.12 mmol) obtained in <Step 1>, NaOH (6.61 g, 165.36 mmol), and THF/H$_2$O (200 ml/100 ml) were mixed under nitrogen flow, Pd(PPh$_3$)$_4$ (3.18 g, 5 mol) was added thereto at 40° C., and the resulting mixture was stirred at 80° C. for 12 hours.

After the reaction was terminated, extraction was performed with methylene chloride, MgSO$_4$ was added thereto, and the resulting product was filtered. 5-(2-nitrophenyl)-2-phenyl-1H-indole (10.74 g, yield 62%) was obtained by removing the solvent from the obtained organic layer, and then purifying the residue with column chromatography (Hexane:EA=5:1 (v/v)).

$^1$H-NMR: δ 6.88 (dd, 1H), 7.21 (d, 1H), 7.32 (m, 1H), 7.34 (d, 1H), 7.46 (m, 3H), 7.64 (m, 2H), 7.77 (d, 2H), 8.02 (d, 2H), 11.73 (s, 1H)

<Step 3> Synthesis of 5-(2-nitrophenyl)-1,2-diphenyl-1H-indole

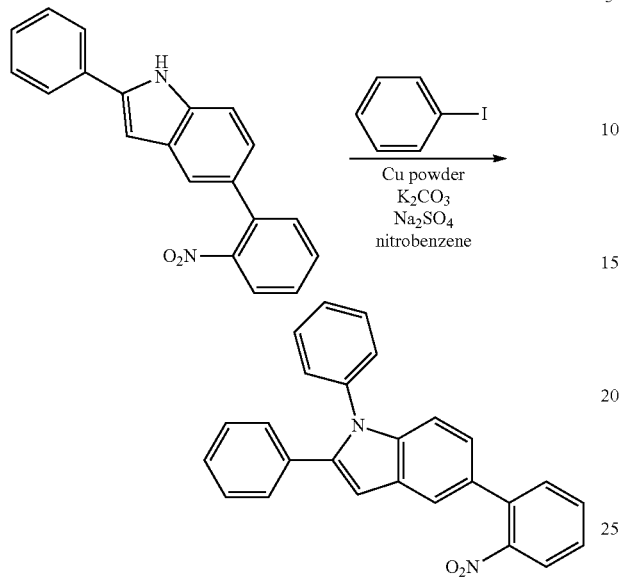

5-(2-nitrophenyl)-1,2-diphenyl-1H-indole was obtained by performing the same procedure as in <Step 3> of Preparation Example 1, except that the 5-(2-nitrophenyl)-2-phenyl-1H-indole obtained in <Step 2> was used instead of 5-(2-nitrophenyl)-1H-indole.

GC-Mass (theoretical value: 390.14 g/mol, measured value: 390 g/mol)

<Step 4> Synthesis of IC-20

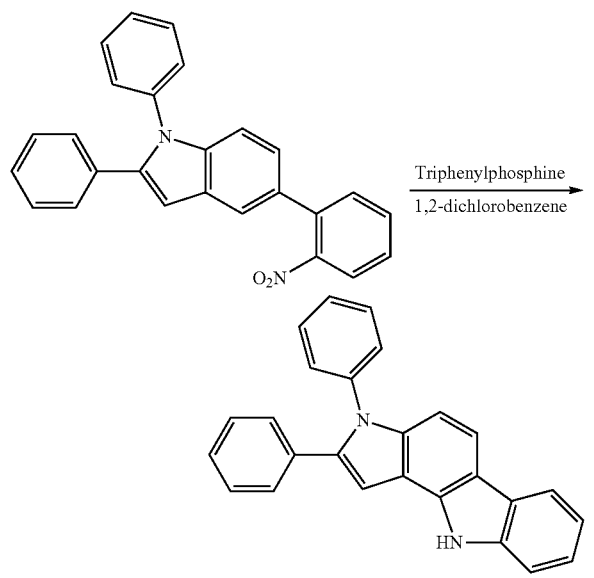

IC-20 was obtained by performing the same procedure as in <Step 4> of Preparation Example 1, except that the 5-(2-nitrophenyl)-1,2-diphenyl-1H-indole obtained in <Step 3> was used instead of 5-(2-nitrophenyl)-1-phenyl-1H-indole.

GC-Mass (theoretical value: 358.15 g/mol, measured value: 358 g/mol)

Preparation Example 21

Synthesis of IC-21

<Step 1> Synthesis of 6-chloro-2-phenyl-1H-indole

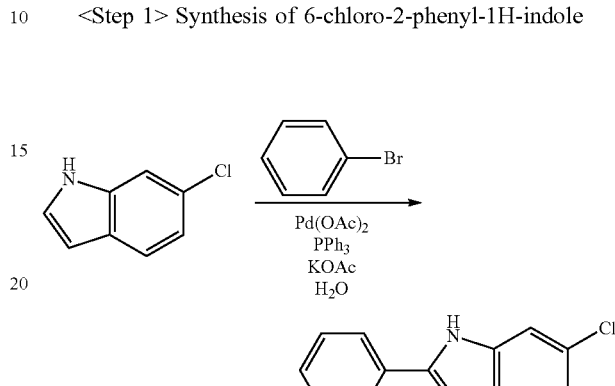

6-chloro-2-phenyl-1H-indole was obtained by performing the same procedure as in <Step 1> of Preparation Example 20, except that 6-chloro-1H-indole and bromobenzene were used instead of 5-bromo-1H-indole and iodobenzene.

$^1$H-NMR: δ 6.92 (d, 1H), 7.02 (dd, 1H), 7.33 (t, 1H), 7.41 (s, 1H), 7.47 (t, 2H), 7.54 (d, 1H), 7.85 (d, 2H), 11.68 (s, 1H)

<Step 2> Synthesis of 6-(2-nitrophenyl)-2-phenyl-1H-indole

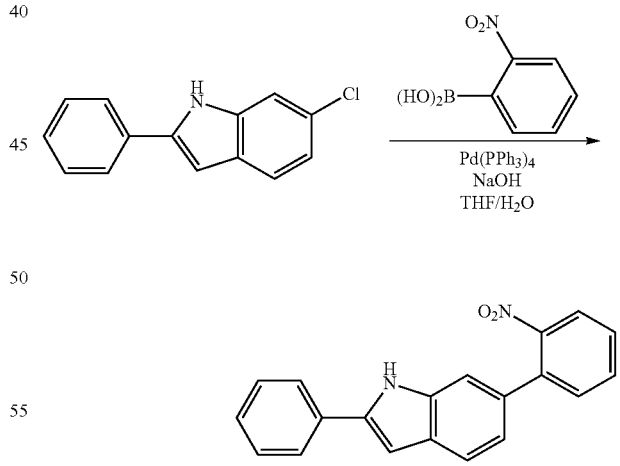

6-(2-nitrophenyl)-2-phenyl-1H-indole was obtained by performing the same procedure as in <Step 2> of Preparation Example 20, except that the 6-chloro-2-phenyl-1H-indole obtained in <Step 1> was used instead of 5-bromo-2-phenyl-1H-indole.

$^1$H-NMR: δ 6.91 (d, 1H), 7.03 (d, 1H), 7.31 (t, 1H), 7.42 (s, 1H), 7.48 (m, 3H), 7.53 (d, 1H), 7.76 (m, 3H), 8.01 (d, 2H), 11.66 (s, 1H)

<Step 3> Synthesis of 6-(2-nitrophenyl)-1,2-diphenyl-1H-indole

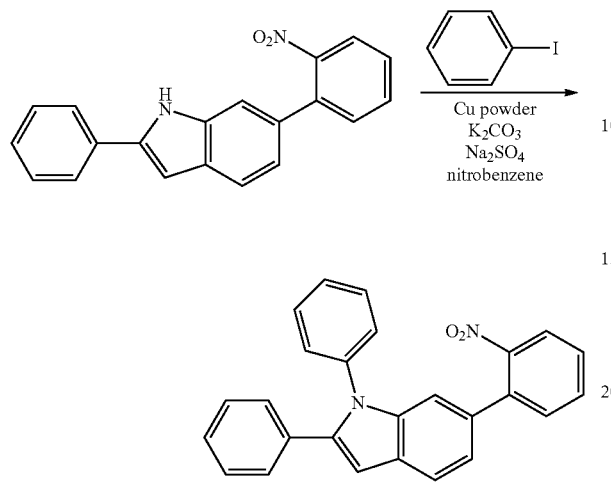

6-(2-nitrophenyl)-1,2-diphenyl-1H-indole was obtained by performing the same procedure as in <Step 3> of Preparation Example 1, except that the 6-(2-nitrophenyl)-2-phenyl-1H-indole obtained in <Step 2> was used instead of 5-(2-nitrophenyl)-1H-indole.

GC-Mass (theoretical value: 390.14 g/mol, measured value: 390 g/mol)

<Step 4> Synthesis of 6-(2-nitrophenyl)-1,2-diphenyl-1H-indole

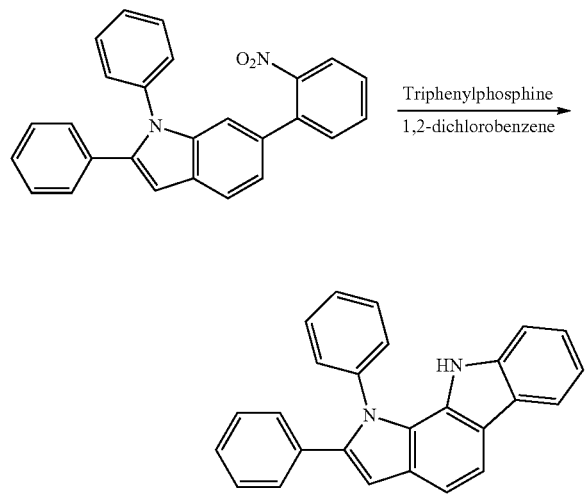

IC-21 was obtained by performing the same procedure as in <Step 4> of Preparation Example 1, except that the 6-(2-nitrophenyl)-1,2-diphenyl-1H-indole obtained in <Step 3> was used instead of 5-(2-nitrophenyl)-1-phenyl-1H-indole.

GC-Mass (theoretical value: 358.15 g/mol, measured value: 358 g/mol)

Preparation Example 22

Synthesis of IC-22

<Step 1> Synthesis of 6-chloro-3-phenyl-1H-indole

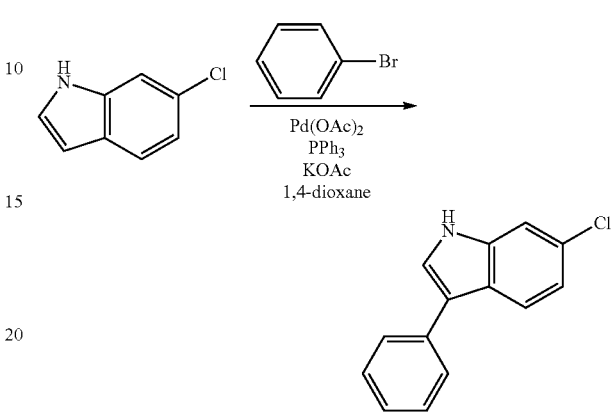

6-bromo-1H-indole (25 g, 0.17 mol), bromobenzene (31.19 g, 0.20 mol), Pd(OAc)$_2$ (1.86 g, 5 mol), triphenylphosphine (2.17 g, 5 mol %), K$_2$CO$_3$ (68.64 g, 0.50 mol), and 1,4-dioxane (300 ml) were mixed under nitrogen flow, and the resulting mixture was stirred at 130° C. for 18 hours.

After the reaction was terminated, 6-chloro-3-phenyl-1H-indole (24.5 g, yield 65%) was obtained by performing extraction with ethyl acetate, removing moisture over MgSO$_4$, and purifying the residue with column chromatography (Hexane:EA=10:1 (v/v)).

$^1$H-NMR: δ 7.10 (dd, 1H), 7.25 (m, 1H), 7.43 (t, 2H), 7.49 (d, 1H), 7.67 (dd, 2H), 7.73 (d, 1H), 7.85 (d, 1H), 11.49 (s, 1H)

<Step 2> Synthesis of 6-(2-nitrophenyl)-3-phenyl-1H-indole

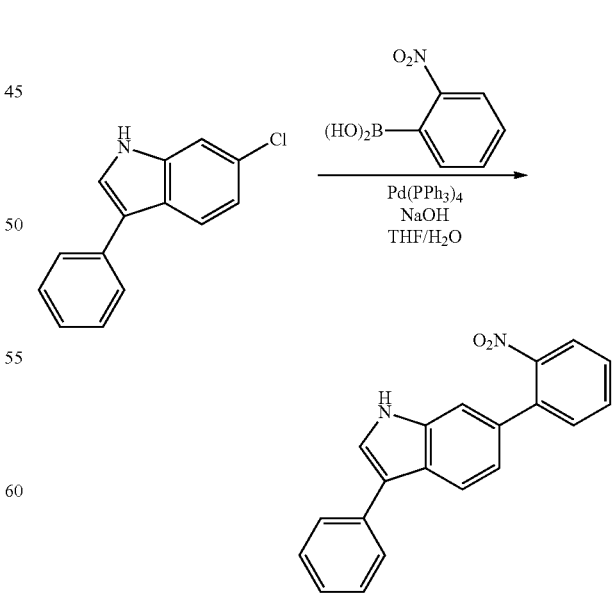

6-(2-nitrophenyl)-3-phenyl-1H-indole was obtained by performing the same procedure as in <Step 2> of Preparation Example 20, except that the 6-chloro-3-phenyl-1H-indole obtained in <Step 1> was used instead of 5-bromo-2-phenyl-1H-indole.

¹H-NMR: δ 7.11 (d, 1H), 7.26 (m, 1H), 7.44 (t, 2H), 7.48 (m, 2H), 7.55 (m, 3H), 7.61 (d, 1H), 7.73 (d, 1H), 8.00 (d, 2H), 11.48 (s, 1H)

<Step 3> Synthesis of
6-(2-nitrophenyl)-1,3-diphenyl-1H-indole

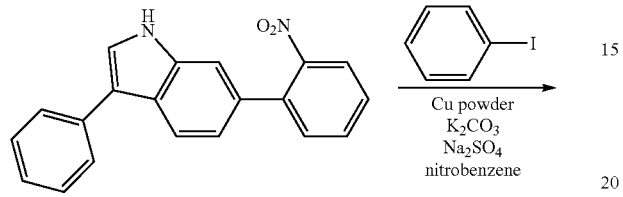

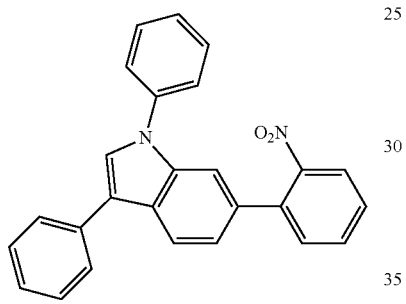

6-(2-nitrophenyl)-1,3-diphenyl-1H-indole was obtained by performing the same procedure as in <Step 3> of Preparation Example 1, except that the 6-(2-nitrophenyl)-3-phenyl-1H-indole obtained in <Step 2> was used instead of 5-(2-nitrophenyl)-1H-indole.

GC-Mass (theoretical value: 390.14 g/mol, measured value: 390 g/mol)

<Step 4> Synthesis of
6-(2-nitrophenyl)-1,3-diphenyl-1H-indole

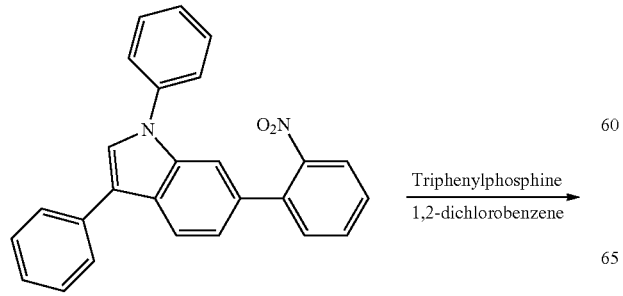

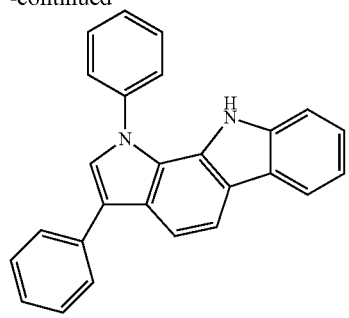

IC-22 was obtained by performing the same procedure as in <Step 4> of Preparation Example 1, except that the 6-(2-nitrophenyl)-1,3-diphenyl-1H-indole obtained in <Step 3> was used instead of 5-(2-nitrophenyl)-1-phenyl-1H-indole.

GC-Mass (theoretical value: 358.15 g/mol, measured value: 358 g/mol)

Preparation Example 23

Synthesis of IC-23

<Step 1> Synthesis of
5-bromo-2,3-diphenyl-1H-indole

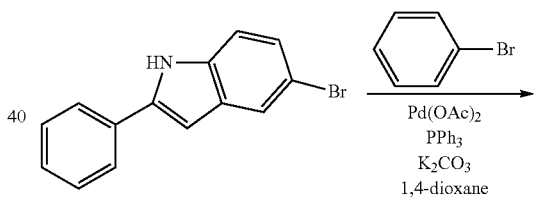

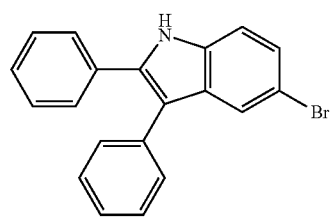

5-bromo-2,3-diphenyl-1H-indole was obtained by performing the same procedure as in <Step 1> of Preparation Example 22, except that 5-bromo-2-phenyl-1H-indole was used instead of 6-chloro-1H-indole.

¹H-NMR: δ 7.23 (d, 1H), 7.31 (t, 2H), 7.43 (m, 6H), 7.67 (d, 1H), 7.71 (d, 1H), 7.84 (d, 2H), 11.34 (s, 1H)

<Step 2> Synthesis of 5-(2-nitrophenyl)-2,3-diphenyl-1H-indole

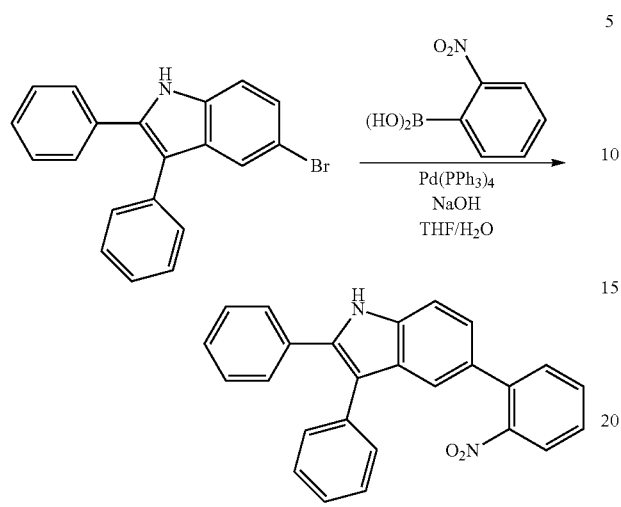

5-(2-nitrophenyl)-2,3-diphenyl-1H-indole was obtained by performing the same procedure as in <Step 2> of Preparation Example 20, except that the 5-bromo-2,3-diphenyl-1H-indole obtained in <Step 1> was used instead of 5-bromo-2-phenyl-1H-indole.

GC-Mass (theoretical value: 390.14 g/mol, measured value: 390 g/mol)

<Step 3> Synthesis of 5-(2-nitrophenyl)-1,2,3-triphenyl-1H-indole

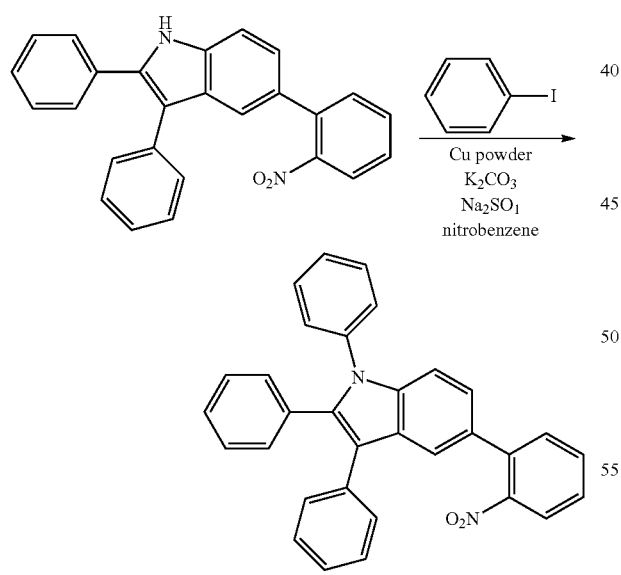

5-(2-nitrophenyl)-1,2,3-triphenyl-1H-indole was obtained by performing the same procedure as in <Step 3> of Preparation Example 1, except that the 5-(2-nitrophenyl)-2,3-diphenyl-1H-indole obtained in <Step 2> was used instead of 5-(2-nitrophenyl)-1H-indole.

GC-Mass (theoretical value: 466.17 g/mol, measured value: 466 g/mol)

<Step 4> Synthesis of IC-23

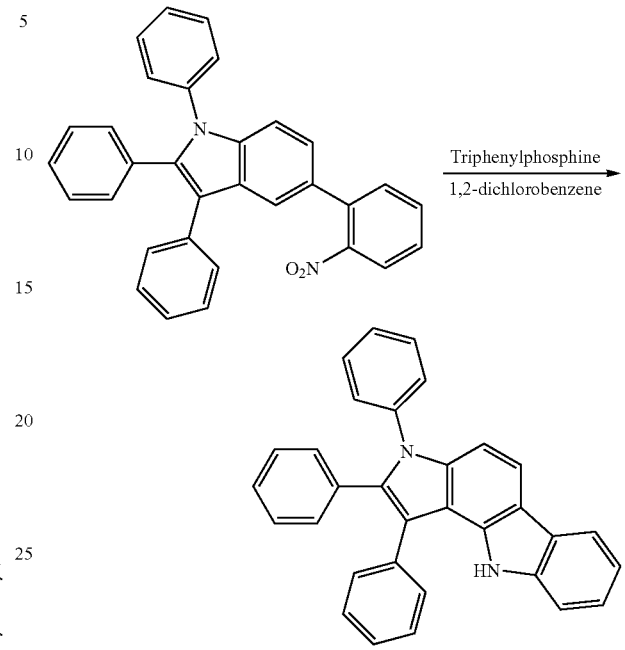

IC-23 was obtained by performing the same procedure as in <Step 4> of Preparation Example 1, except that the 5-(2-nitrophenyl)-1,2,3-triphenyl-1H-indole obtained in <Step 3> was used instead of 5-(2-nitrophenyl)-1-phenyl-1H-indole.

GC-Mass (theoretical value: 434.18 g/mol, measured value: 434 g/mol)

Preparation Example 24

Synthesis of IC-24

<Step 1> Synthesis of 6-chloro-2,3-diphenyl-1H-indole

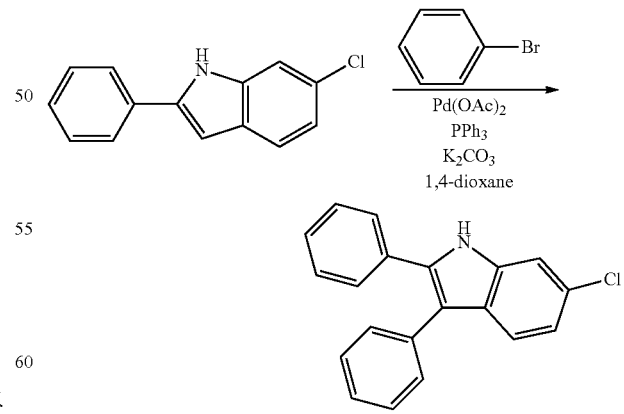

6-chloro-2,3-diphenyl-1H-indole was obtained by performing the same procedure as in <Step 1> of Preparation Example 22, except that 6-chloro-2-phenyl-1H-indole was used instead of 6-chloro-1H-indole.

¹H-NMR: δ 7.18 (d, 1H), 7.29 (t, 2H), 7.50 (m, 6H), 7.62 (d, 1H), 7.75 (d, 1H), 7.89 (d, 2H), 11.35 (s, 1H)

<Step 2> Synthesis of 6-(2-nitrophenyl)-2,3-diphenyl-1H-indole

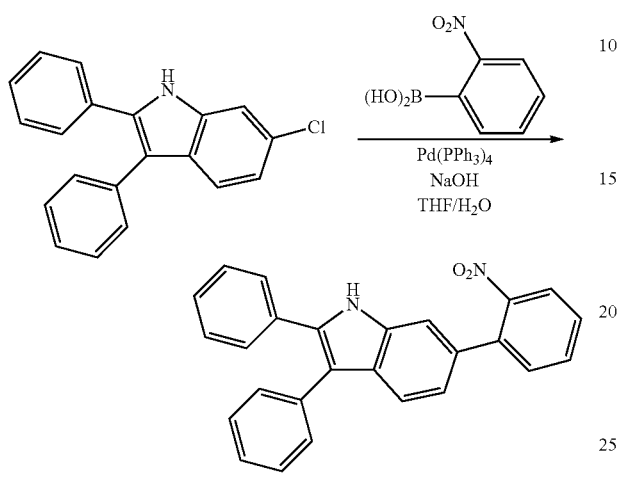

6-(2-nitrophenyl)-2,3-diphenyl-1H-indole was obtained by performing the same procedure as in <Step 2> of Preparation Example 20, except that the 6-chloro-2,3-diphenyl-1H-indole obtained in <Step 1> was used instead of 5-bromo-2-phenyl-1H-indole.

GC-Mass (theoretical value: 390.14 g/mol, measured value: 390 g/mol)

<Step 3> Synthesis of 6-(2-nitrophenyl)-1,2,3-triphenyl-1H-indole

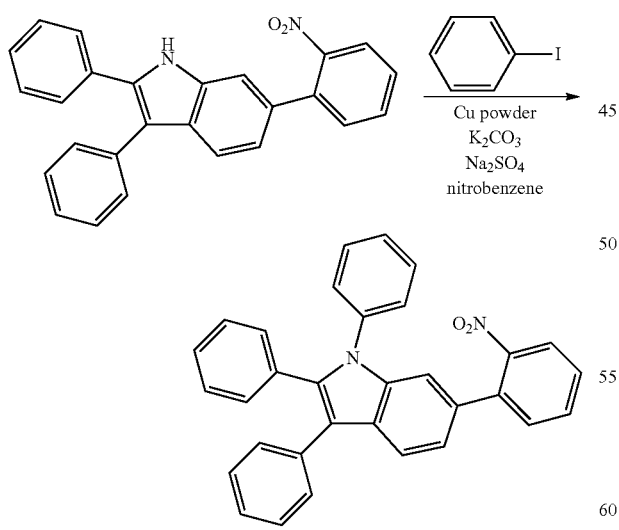

6-(2-nitrophenyl)-1,2,3-triphenyl-1H-indole was obtained by performing the same procedure as in <Step 3> of Preparation Example 1, except that the 6-(2-nitrophenyl)-2,3-diphenyl-1H-indole obtained in <Step 2> was used instead of 5-(2-nitrophenyl)-1H-indole.

GC-Mass (theoretical value: 466.17 g/mol, measured value: 466 g/mol)

<Step 4> Synthesis of IC-24

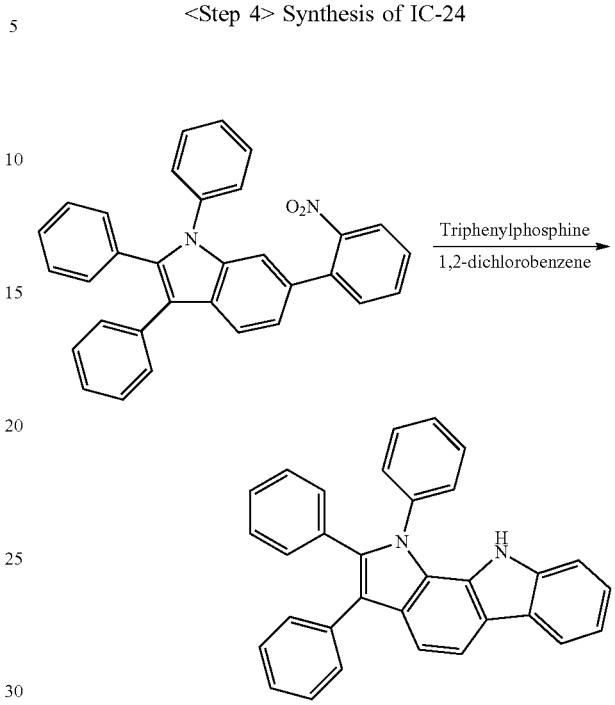

IC-24 was obtained by performing the same procedure as in <Step 4> of Preparation Example 1, except that the 6-(2-nitrophenyl)-1,2,3-triphenyl-1H-indole obtained in <Step 3> was used instead of 5-(2-nitrophenyl)-1-phenyl-1H-indole.

GC-Mass (theoretical value: 434.18 g/mol, measured value: 434 g/mol)

Preparation Example 25

Synthesis of IC-25

<Step 1> Synthesis of 1-(3-(4,6-diphenyl-1,3,5-triazin-2-yl)phenyl)-6-(2-nitrophenyl)-1H-indole

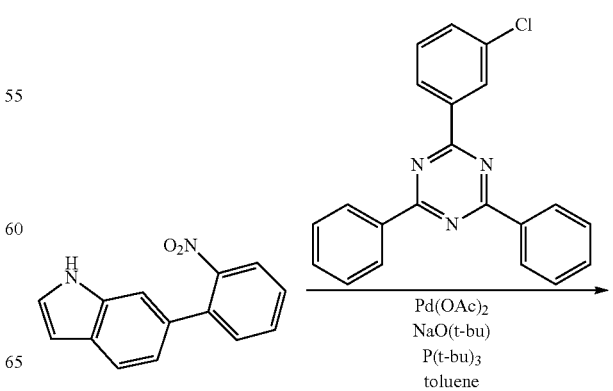

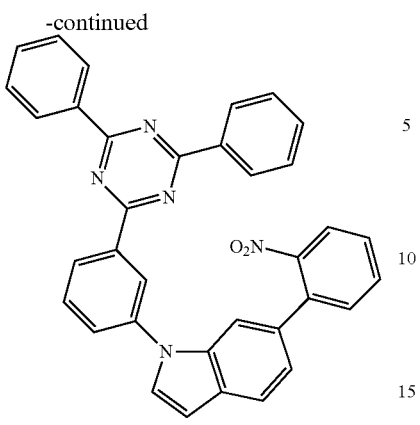

6-(2-nitrophenyl)-1H-indole (10 g, 41.97 mmol), 2-(3-chlorophenyl)-4,6-diphenyl-1,3,5-triazine (17.32 g, 50.37 mmol), Pd(OAc)$_2$ (0.47 g, 5 mol %), NaO(t-bu) (8.07 g, 83.95 mmol), P(t-bu)$_3$ (0.85 g, 4.19 mmol), and toluene (100 ml) were mixed under nitrogen flow, and the resulting mixture was stirred at 110° C. for 12 hours.

After the reaction was terminated, 1-(3-(4,6-diphenyl-1,3,5-triazin-2-yl)phenyl)-6-(2-nitrophenyl)-1H-indole (15.8 g, yield 69%) was obtained by performing extraction with ethyl acetate, removing moisture over MgSO$_4$, and purifying the residue with column chromatography (Hexane:EA=3:1 (v/v)).

GC-Mass (theoretical value: 545.19 g/mol, measured value: 545 g/mol)

<Step 2> Synthesis of IC-25

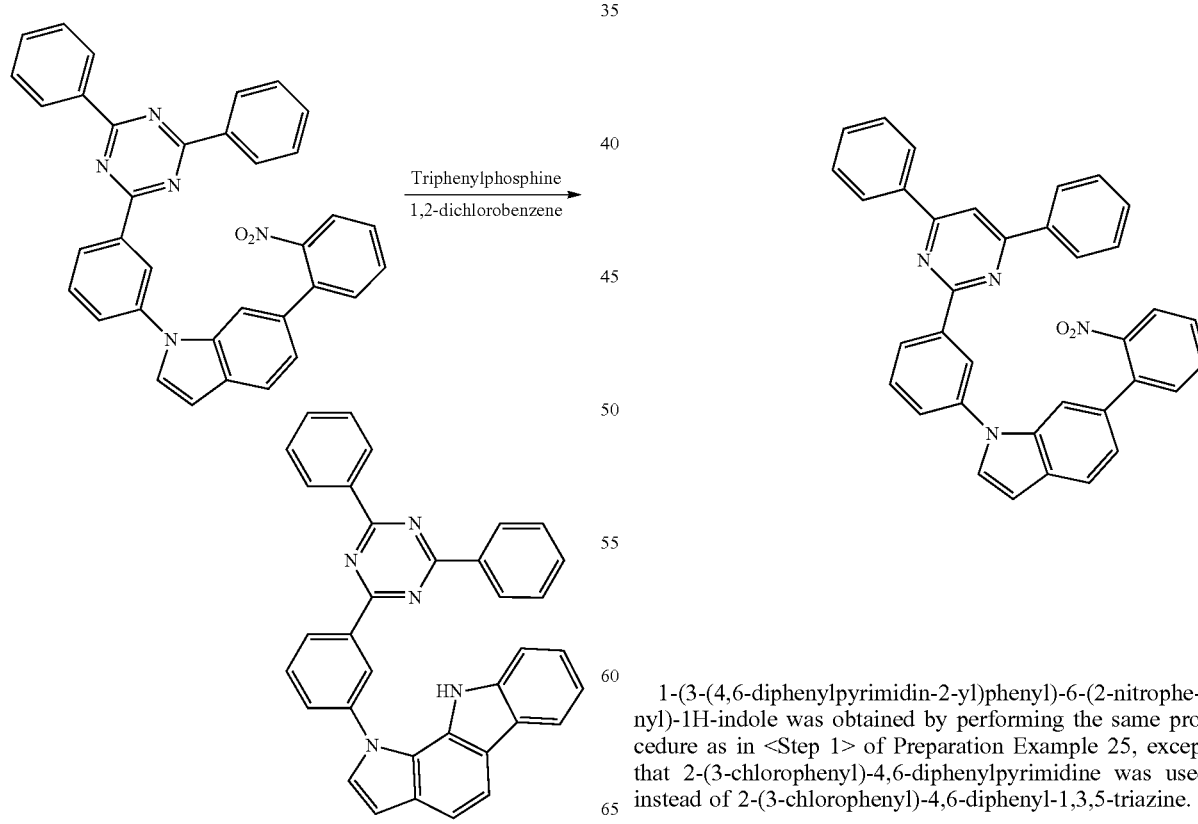

IC-25 was obtained by performing the same procedure as in <Step 4> of Preparation Example 1, except that the 1-(3-(4,6-diphenyl-1,3,5-triazin-2-yl)phenyl)-6-(2-nitrophenyl)-1H-indole obtained in <Step 1> was used instead of 5-(2-nitrophenyl)-1-phenyl-1H-indole.

GC-Mass (theoretical value: 513.20 g/mol, measured value: 513 g/mol)

Preparation Example 26

Synthesis of IC-26

<Step 1> Synthesis of 1-(3-(4,6-diphenylpyrimidin-2-yl)phenyl)-6-(2-nitrophenyl)-1H-indole

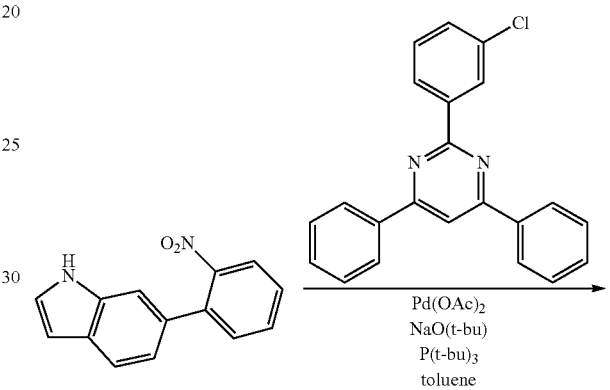

1-(3-(4,6-diphenylpyrimidin-2-yl)phenyl)-6-(2-nitrophenyl)-1H-indole was obtained by performing the same procedure as in <Step 1> of Preparation Example 25, except that 2-(3-chlorophenyl)-4,6-diphenylpyrimidine was used instead of 2-(3-chlorophenyl)-4,6-diphenyl-1,3,5-triazine.

GC-Mass (theoretical value: 544.19 g/mol, measured value: 544 g/mol)

523

<Step 2> Synthesis of IC-26

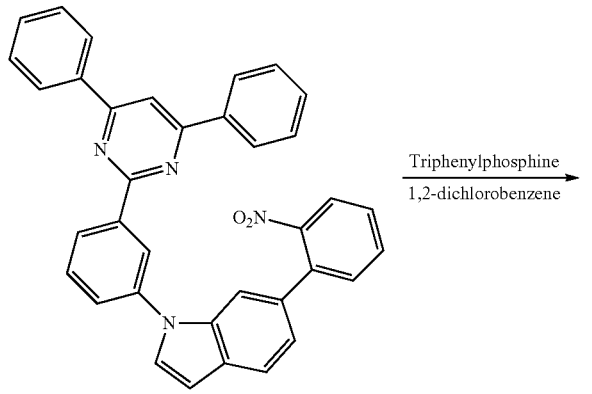

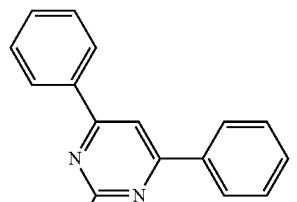

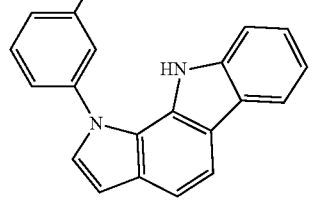

IC-26 was obtained by performing the same procedure as in <Step 4> of Preparation Example 1, except that the 1-(3-(4,6-diphenylpyrimidin-2-yl)phenyl)-6-(2-nitrophenyl)-1H-indole obtained in <Step 1> was used instead of 5-(2-nitrophenyl)-1-phenyl-1H-indole.

GC-Mass (theoretical value: 512.20 g/mol, measured value: 512 g/mol)

Preparation Example 27

Synthesis of IC-27

<Step 1> Synthesis of 1-(3-(4,6-diphenyl-1,3,5-triazin-2-yl)phenyl)-5-(2-nitrophenyl)-1H-indole

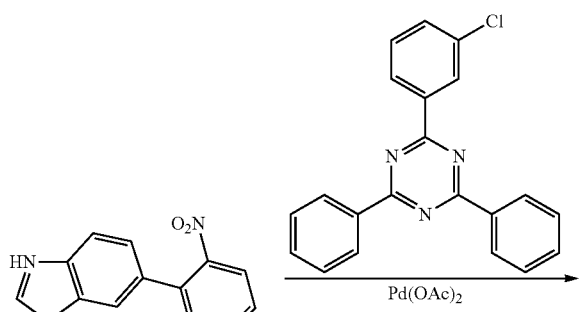

524

-continued

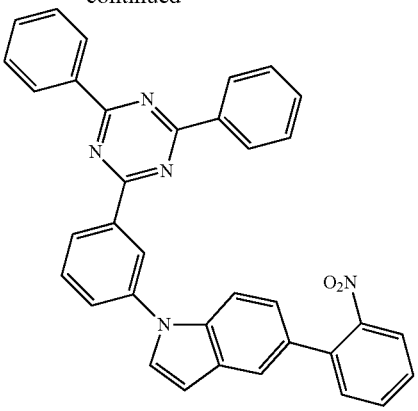

1-(3-(4,6-diphenyl-1,3,5-triazin-2-yl)phenyl)-5-(2-nitrophenyl)-1H-indole was obtained by performing the same procedure as in <Step 1> of Preparation Example 25, except that 5-(2-nitrophenyl)-1H-indole was used instead of 6-(2-nitrophenyl)-1H-indole.

GC-Mass (theoretical value: 545.19 g/mol, measured value: 545 g/mol)

<Step 2> Synthesis of IC-27

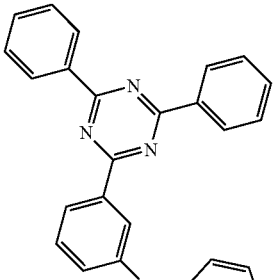

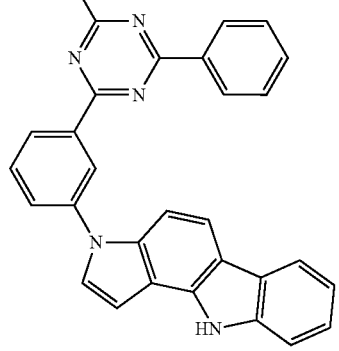

IC-27 was obtained by performing the same procedure as in <Step 4> of Preparation Example 1, except that the 1-(3-(4,6-diphenyl-1,3,5-triazin-2-yl)phenyl)-5-(2-nitrophenyl)-1H-indole obtained in <Step 1> was used instead of 5-(2-nitrophenyl)-1-phenyl-1H-indole.

GC-Mass (theoretical value: 513.20 g/mol, measured value: 513 g/mol)

Preparation Example 28

Synthesis of IC-28

<Step 1> Synthesis of 1-(3-(4,6-diphenylpyrimidin-2-yl)phenyl)-5-(2-nitrophenyl)-1H-indole

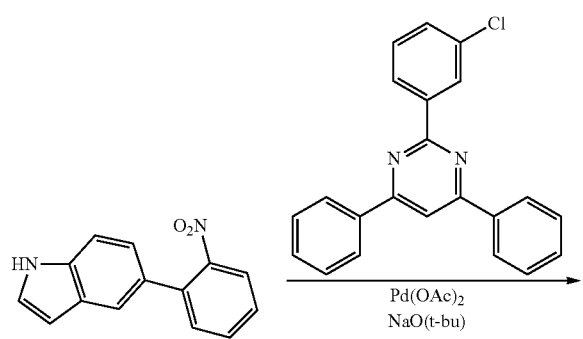

1-(3-(4,6-diphenylpyrimidin-2-yl)phenyl)-5-(2-nitrophenyl)-1H-indole was obtained by performing the same procedure as in <Step 1> of Preparation Example 25, except that 5-(2-nitrophenyl)-1H-indole and 2-(3-chlorophenyl)-4,6-diphenylpyrimidine were used instead of 6-(2-nitrophenyl)-1H-indole and 2-(3-chlorophenyl)-4,6-diphenyl-1,3,5-triazine.

GC-Mass (theoretical value: 544.19 g/mol, measured value: 544 g/mol)

<Step 2> Synthesis of IC-28

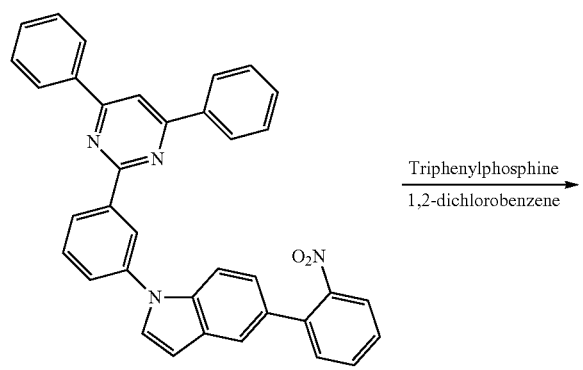

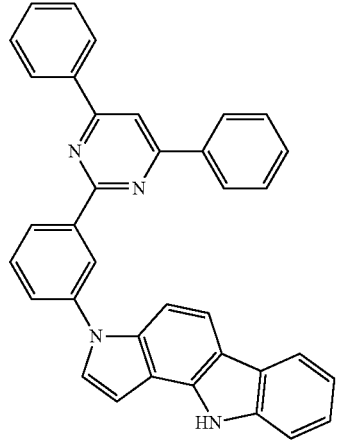

IC-28 was obtained by performing the same procedure as in <Step 4> of Preparation Example 1, except that the 1-(3-(4,6-diphenylpyrimidin-2-yl)phenyl)-5-(2-nitrophenyl)-1H-indole obtained in <Step 1> was used instead of 5-(2-nitrophenyl)-1-phenyl-1H-indole.

GC-Mass (theoretical value: 512.20 g/mol, measured value: 512 g/mol)

Preparation Example 29

Synthesis of IC-29

<Step 1> Synthesis of 9-phenyl-9H-carbazol-2-amine

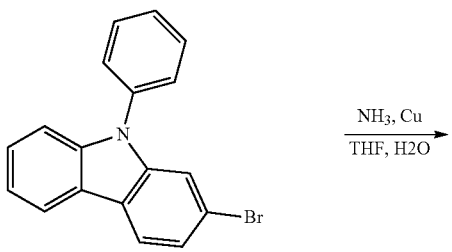

After 9.66 g (30.0 mmol) of 2-bromo-9-phenyl-9H-carbazole was dissolved in 100 ml of toluene under nitrogen flow, 10.2 ml (150 mmol) of 28% aqueous ammonia and 0.10 g (5 mol %) of Cu were added thereto, and the resulting mixture was stirred at 110° C. for 12 hours. After the reaction was terminated, extraction was performed with methylene chloride, MgSO$_4$ was added thereto, and the resulting product was filtered. 6.5 g (yield: 83%) of the target compound 9-phenyl-9H-carbazol-2-amine was obtained by removing the solvent from the filtered organic layer, and then using column chromatography.

¹H-NMR: δ 6.51 (s, 2H), 6.72 (m, 2H), 7.53 (m, 2H), 7.55 (m, 5H), 7.98 (d, 1H), 8.05 (d, 1H), 8.62 (d, 1H)

<Step 2> Synthesis of IC-29

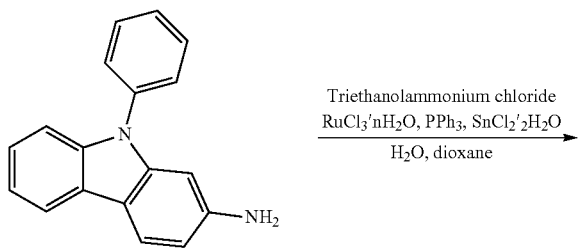

5.16 g (20.0 mmol) of 9-phenyl-9H-carbazol-2-amine was dissolved in H₂O/dioxane (10 ml/90 ml) under nitrogen flow, and then 0.372 g (2 mmol) of triethanolammonium chloride, 0.052 g (0.2 mmol) of RuCln-H₂O, 0.158 g (0.6 mmol) of PPh₃, and 0.452 g (2 mmol) of SnCl₂.2H₂O were added thereto, and the resulting mixture was stirred at 180° C. for 20 hours. After the reaction was terminated, the reactant was poured into aqueous 5% HCl, extraction was performed with methylene chloride, MgSO₄ was added thereto, and the resulting product was filtered. 2.8 g (yield: 54%) of the target compound IC-29 was obtained by removing the solvent from the filtered organic layer, and then using column chromatography.

¹H-NMR: δ 6.48 (d, 1H), 7.35 (m, 4H), 7.58 (m, 5H), 7.98 (d, 1H), 8.15 (d, 1H), 8.59 (d, 1H), 10.12 (s, 1H)

Preparation Example 30

Synthesis of IC-30

<Step 1> Synthesis of 9-phenyl-9H-carbazol-1-amine

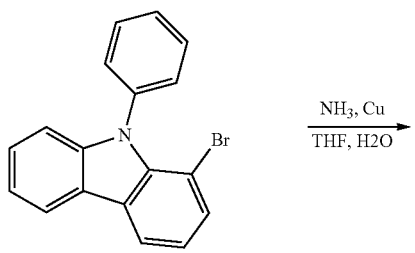

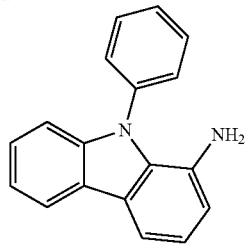

6.2 g (yield: 80%) of the target compound 9-phenyl-9H-carbazol-1-amine was obtained in the same manner as in <Step 1> of Preparation Example 29, except that 1-bromo-9-phenyl-9H-carbazole was used instead of 2-bromo-9-phenyl-9H-carbazole.

¹H-NMR: δ 6.37 (s, 2H), 6.82 (d, 1H), 7.15 (t, 1H), 7.36 (m, 2H), 7.62 (m, 5H), 8.02 (d, 1H), 8.63 (d, 1H)

<Step 2> Synthesis of IC-30

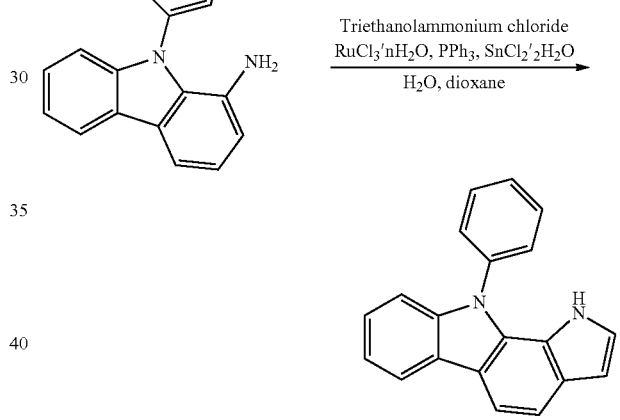

2.4 g (yield: 42%) of the target compound IC-30 was obtained in the same manner as in <Step 2> of Preparation Example 29, except that 9-phenyl-9H-carbazol-1-amine was used instead of 9-phenyl-9H-carbazol-2-amine.

¹H-NMR: δ 6.52 (d, 1H), 7.41 (m, 3H), 7.58 (m, 5H), 8.01 (d, 1H), 8.18 (d, 1H), 8.62 (d, 1H), 10.22 (s, 1H)

Synthesis Example 1

Synthesis of Inv5

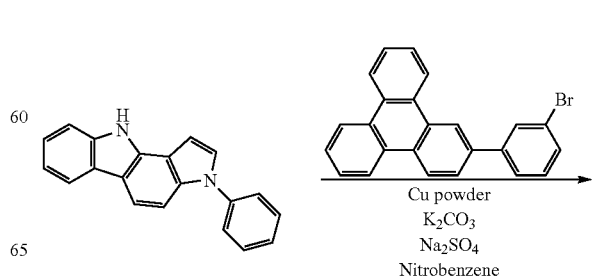

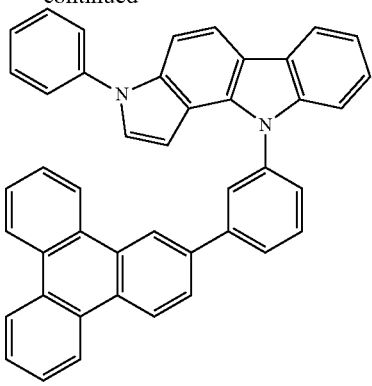

IC-1 (2.5 g, 8.85 mmol), 2-(3-bromophenyl)triphenylene (4.07 g, 10.62 mmol), Cu powder (0.05 g, 0.88 mmol), K₂CO₃ (1.22 g, 8.85 mmol), Na₂SO₄ (2.51 g, 17.7 mmol), and nitrobenzene (30 ml) were mixed under nitrogen flow, and the resulting mixture was stirred at 190° C. for 12 hours. After the reaction was terminated, nitrobenzene was removed and the organic layer was extracted with methylene chloride, and then dried over MgSO₄. Inv5 (3.6 g, yield: 69%) was obtained by removing the solvent from the organic layer, and then purifying the residue with column chromatography.

GC-Mass (theoretical value: 584.71 g/mol, measured value: 584 g/mol)

Synthesis Example 2

Synthesis of Inv29

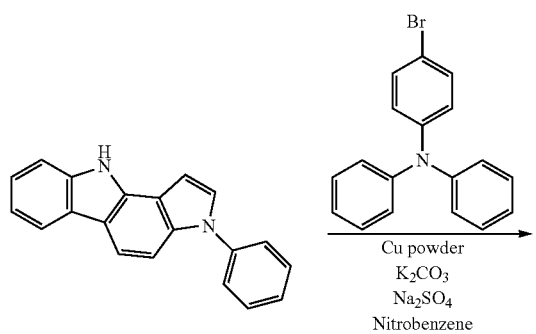

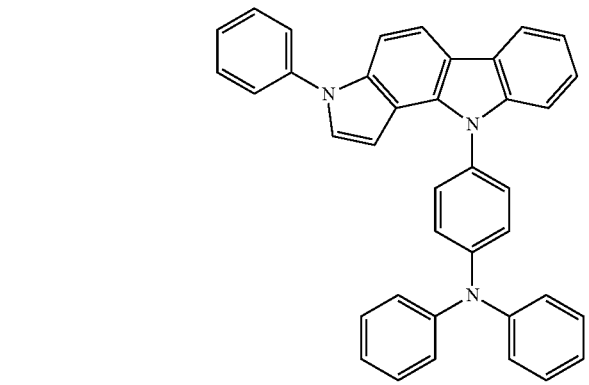

The target compound Inv29 (3.1 g, yield: 66%) was obtained in the same manner as in Synthesis Example 1, except that 4-bromo-N,N-diphenylaniline was used instead of 2-(3-bromophenyl)triphenylene.

GC-Mass (theoretical value: 525.64 g/mol, measured value: 525 g/mol)

Synthesis Example 3

Synthesis of Inv38

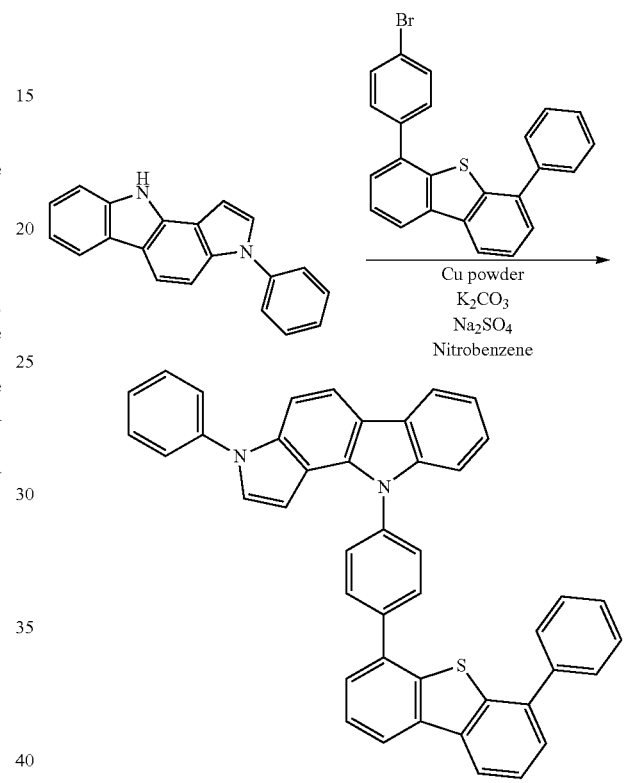

The target compound Inv38 (3.3 g, yield: 61%) was obtained in the same manner as in Synthesis Example 1, except that 4-(4-bromophenyl)-6-phenyldibenzo[b,d]thiophene was used instead of 2-(3-bromophenyl)triphenylene.

GC-Mass (theoretical value: 616.77 g/mol, measured value: 616 g/mol)

Synthesis Example 4

Synthesis of Inv39

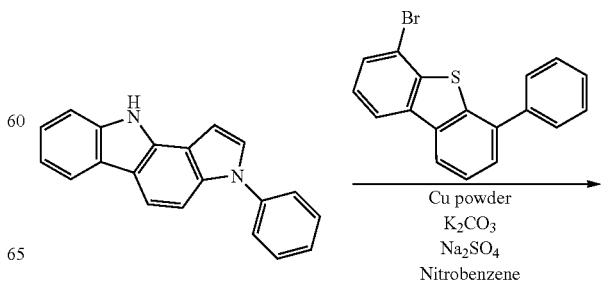

-continued

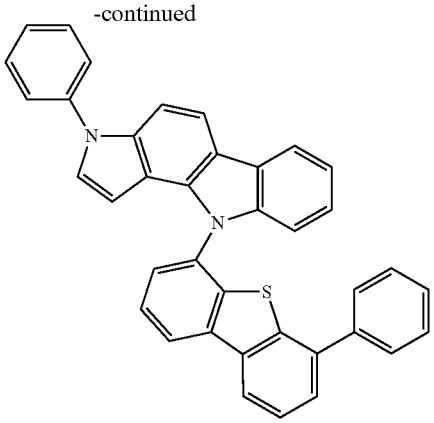

The target compound Inv39 (2.8 g, yield: 59%) was obtained in the same manner as in Synthesis Example 1, except that 4-bromo-6-phenyldibenzo[b,d]thiophene was used instead of 2-(3-bromophenyl)triphenylene.

GC-Mass (theoretical value: 540.68 g/mol, measured value: 541 g/mol)

Synthesis Example 5

Synthesis of Inv42

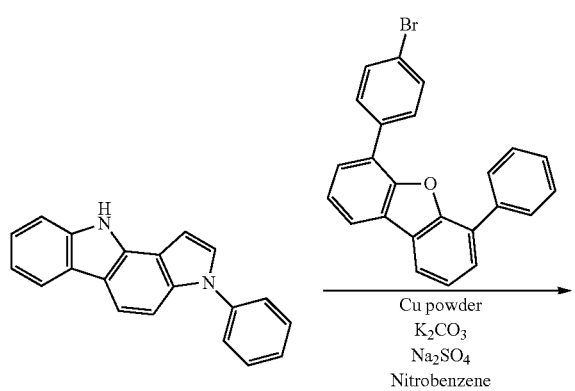

The target compound Inv42 (3.2 g, yield: 60%) was obtained in the same manner as in Synthesis Example 1, except that 4-(4-bromophenyl)-6-phenyldibenzo[b,d]furan was used instead of 2-(3-bromophenyl)triphenylene.

GC-Mass (theoretical value: 600.71 g/mol, measured value: 600 g/mol)

Synthesis Example 6

Synthesis of Inv46

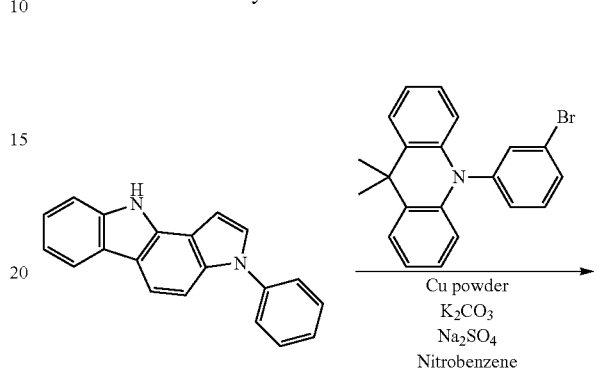

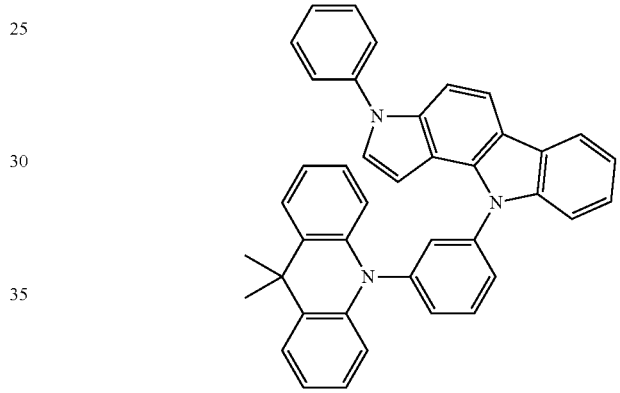

The target compound Inv46 (2.7 g, yield: 54%) was obtained in the same manner as in Synthesis Example 1, except that 10-(3-bromophenyl)-9,9-dimethyl-9,10-dihydroacridine was used instead of 2-(3-bromophenyl)triphenylene.

GC-Mass (theoretical value: 565.7 g/mol, measured value: 566 g/mol)

Synthesis Example 7

Synthesis of Inv47

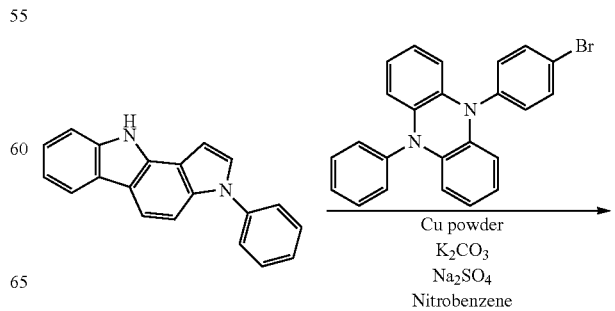

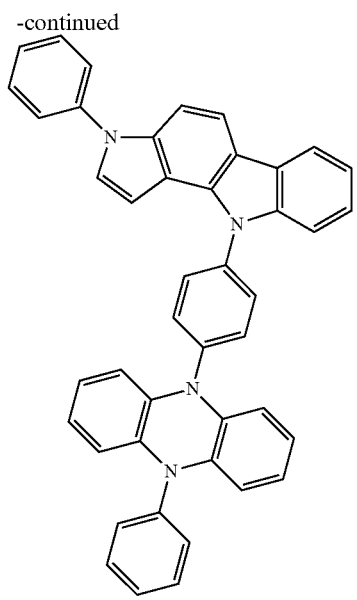

The target compound Inv47 (3.3 g, yield: 60%) was obtained in the same manner as in Synthesis Example 1, except that 5-(4-bromophenyl)-10-phenyl-5,10-dihydrophenazine was used instead of 2-(3-bromophenyl)triphenylene.

GC-Mass (theoretical value: 614.74 g/mol, measured value: 614 g/mol)

Synthesis Example 8

Synthesis of Inv48

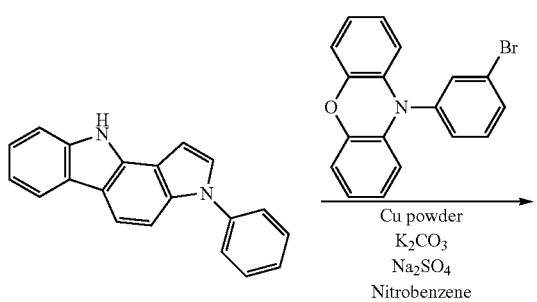

The target compound Inv48 (3.1 g, yield: 64%) was obtained in the same manner as in Synthesis Example 1, except that 10-(3-bromophenyl)-10H-phenoxazine was used instead of 2-(3-bromophenyl)triphenylene.

GC-Mass (theoretical value: 539.62 g/mol, measured value: 539 g/mol)

Synthesis Example 9

Synthesis of Inv58

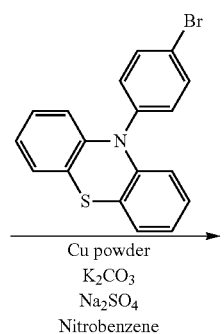

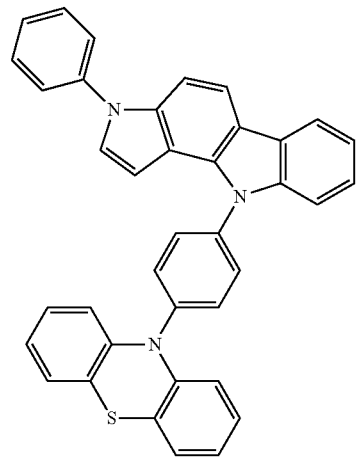

The target compound Inv58 (2.9 g, yield: 59%) was obtained in the same manner as in Synthesis Example 1, except that 10-(4-bromophenyl)-10H-phenothiazine was used instead of 2-(3-bromophenyl)triphenylene.

GC-Mass (theoretical value: 555.69 g/mol, measured value: 555 g/mol)

Synthesis Example 10

Synthesis of Inv65

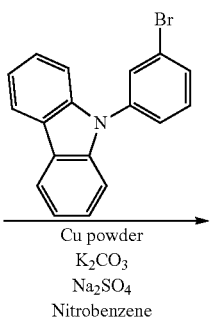

-continued

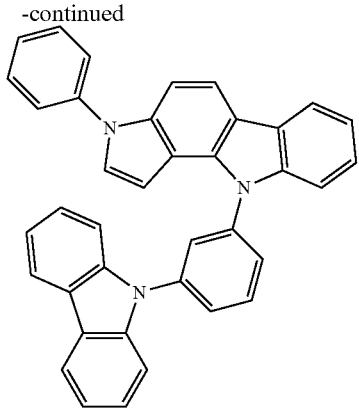

The target compound Inv65 (2.8 g, yield: 60%) was obtained in the same manner as in Synthesis Example 1, except that 9-(3-bromophenyl)-9H-carbazole was used instead of 2-(3-bromophenyl)triphenylene.

GC-Mass (theoretical value: 523.63 g/mol, measured value: 523 g/mol)

Synthesis Example 11

Synthesis of Inv167

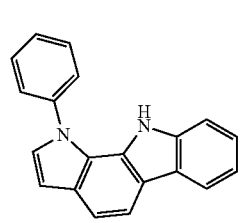 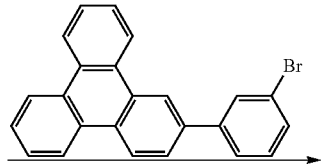

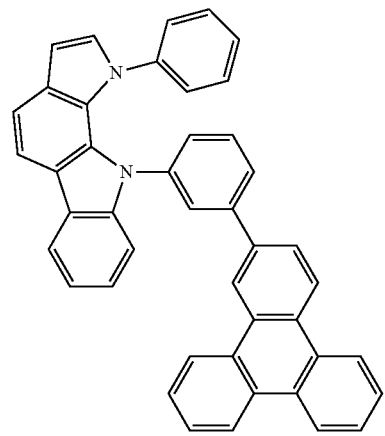

Inv167 (3.3 g, yield: 64%) was obtained in the same manner as in Synthesis Example 1, except that IC-3 was used instead of IC-1.

GC-Mass (theoretical value: 584.71 g/mol, measured value: 584 g/mol)

Synthesis Example 12

Synthesis of Inv192

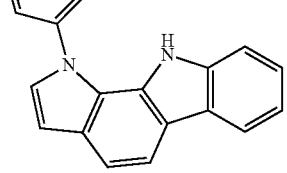 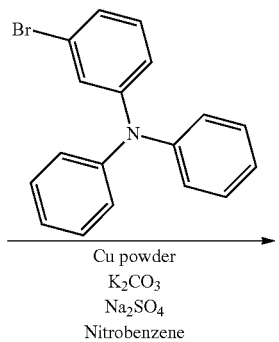

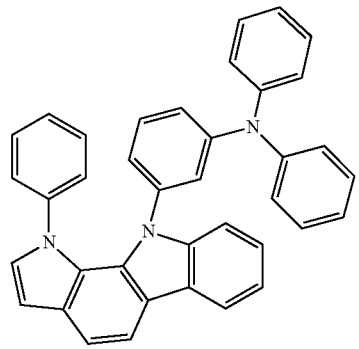

The target compound Inv129 (2.9 g, yield: 63%) was obtained in the same manner as in Synthesis Example 11, except that 3-bromo-N,N-diphenylaniline was used instead of 2-(3-bromophenyl)triphenylene.

GC-Mass (theoretical value: 525.64 g/mol, measured value: 525 g/mol)

Synthesis Example 13

Synthesis of Inv200

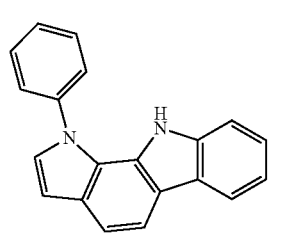 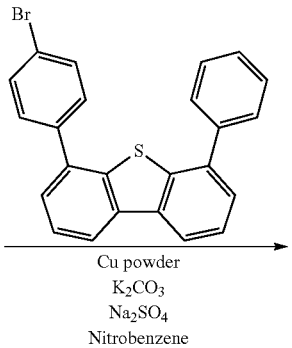

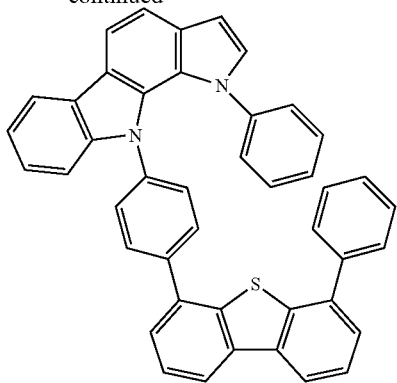

The target compound Inv200 (3.4 g, yield: 62%) was obtained in the same manner as in Synthesis Example 11, except that 4-(4-bromophenyl)-6-phenyldibenzo[b,d]thiophene was used instead of 2-(3-bromophenyl)triphenylene.

GC-Mass (theoretical value: 616.77 g/mol, measured value: 616 g/mol)

Synthesis Example 14

Synthesis of Inv205

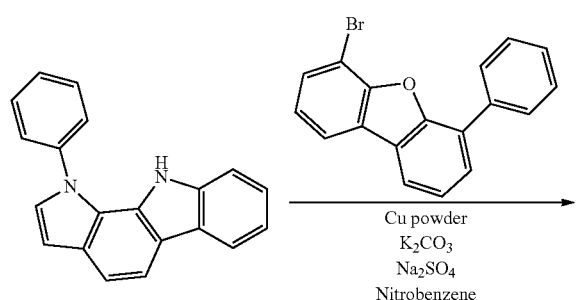

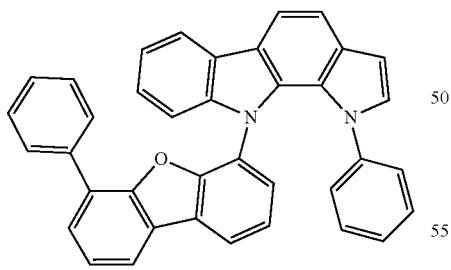

The target compound Inv205 (4.64 g, yield: 58%) was obtained in the same manner as in Synthesis Example 11, except that 4-bromo-6-phenyldibenzo[b,d]furan was used instead of 2-(3-bromophenyl)triphenylene.

GC-Mass (theoretical value: 524.61 g/mol, measured value: 524 g/mol)

Synthesis Example 15

Synthesis of Inv208

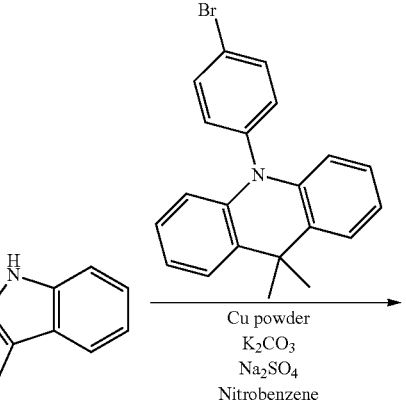

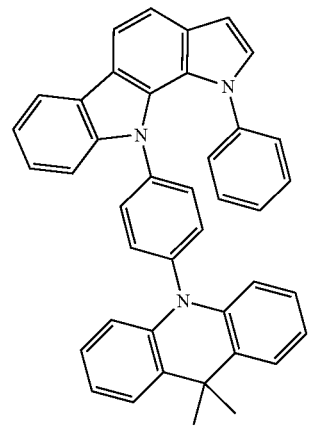

The target compound Inv208 (3.4 g, yield: 68%) was obtained in the same manner as in Synthesis Example 11, except that 10-(4-bromophenyl)-9,9-dimethyl-9,10-dihydroacridine was used instead of 2-(3-bromophenyl)triphenylene.

GC-Mass (theoretical value: 565.7 g/mol, measured value: 565 g/mol)

Synthesis Example 16

Synthesis of Inv222

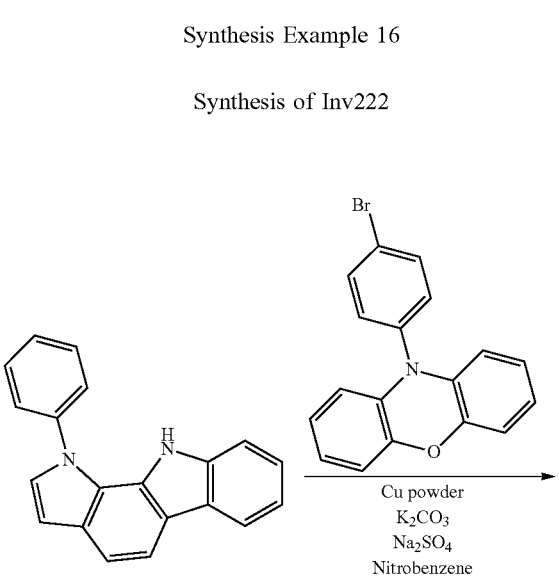

-continued

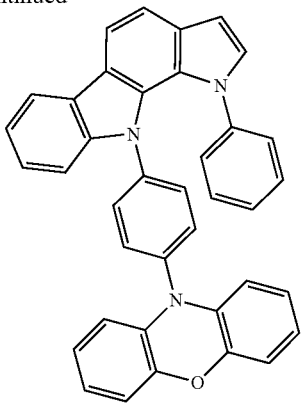

The target compound Inv222 (2.7 g, yield: 56%) was obtained in the same manner as in Synthesis Example 11, except that 10-(4-bromophenyl)-10H-phenoxazine was used instead of 2-(3-bromophenyl)triphenylene.

GC-Mass (theoretical value: 539.62 g/mol, measured value: 539 g/mol)

Synthesis Example 17

Synthesis of Inv219

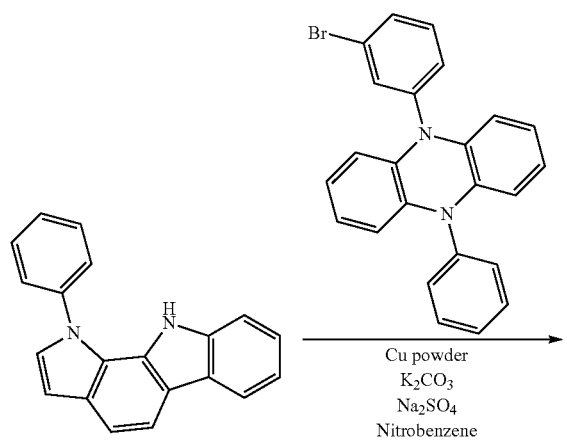

The target compound Inv219 (3.3 g, yield: 60%) was obtained in the same manner as in Synthesis Example 11, except that 5-(3-bromophenyl)-10-phenyl-5,10-dihydrophenazine was used instead of 2-(3-bromophenyl)triphenylene.

GC-Mass (theoretical value: 614.74 g/mol, measured value: 614 g/mol)

Synthesis Example 18

Synthesis of Inv224

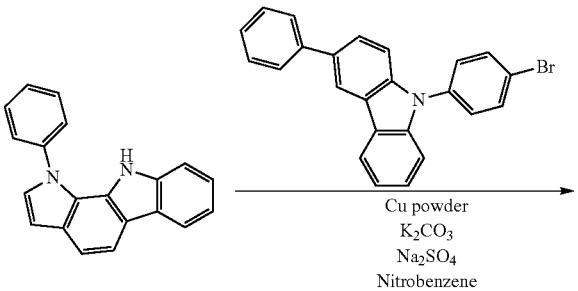

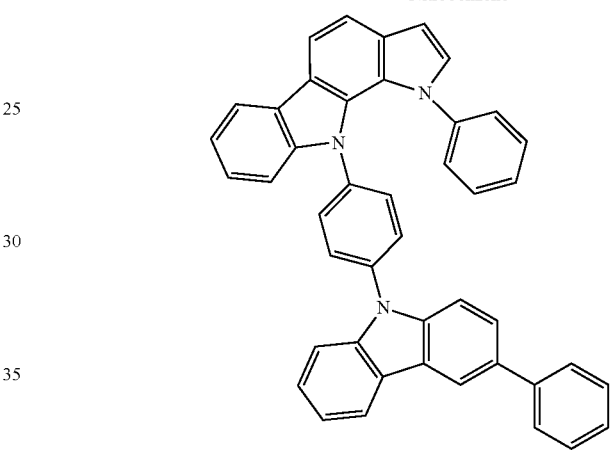

The target compound Inv224 (2.9 g, yield: 59%) was obtained in the same manner as in Synthesis Example 11, except that 9-(4-bromophenyl)-3-phenyl-9H-carbazole was used instead of 2-(3-bromophenyl)triphenylene.

GC-Mass (theoretical value: 599.72 g/mol, measured value: 599 g/mol)

Synthesis Example 19

Synthesis of Inv572

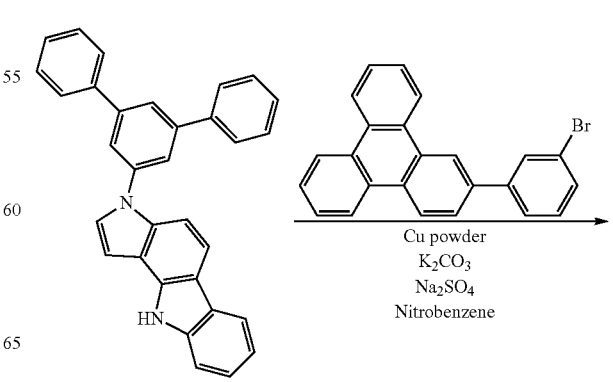

541

-continued

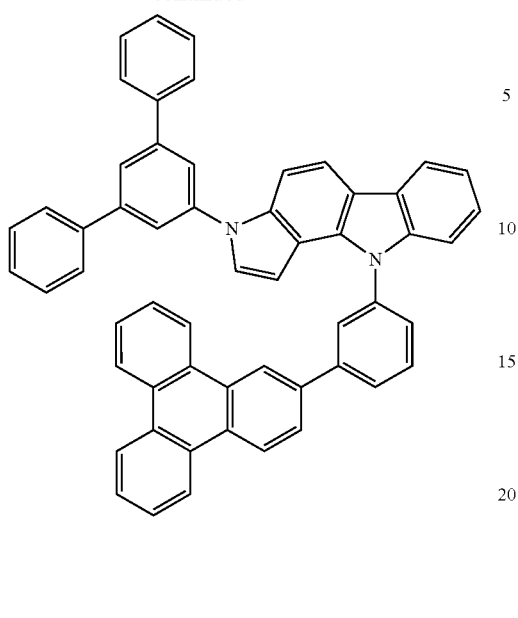

Inv572 (3.2 g, yield: 64%) was obtained in the same manner as in Synthesis Example 1, except that IC-11 was used instead of IC-1.

GC-Mass (theoretical value: 736.9 g/mol, measured value: 736 g/mol)

Synthesis Example 20

Synthesis of Inv596

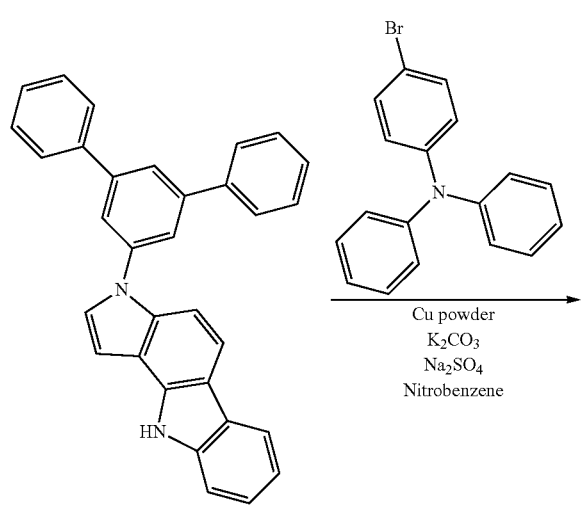

542

-continued

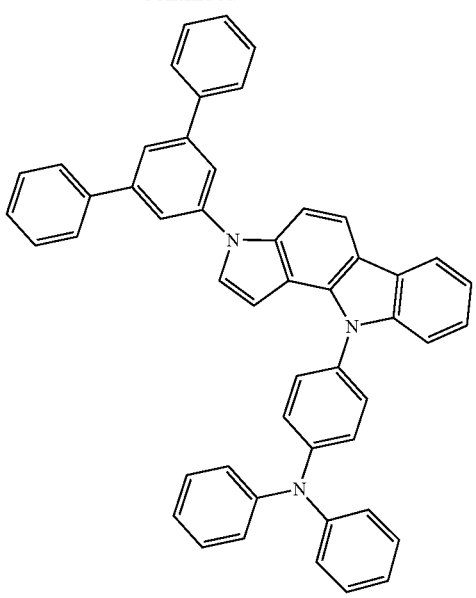

The target compound Inv596 (2.9 g, yield: 64%) was obtained in the same manner as in Synthesis Example 19, except that 4-bromo-N,N-diphenylaniline was used instead of 2-(3-bromophenyl)triphenylene.

GC-Mass (theoretical value: 677.83 g/mol, measured value: 677 g/mol)

Synthesis Example 21

Synthesis of Inv606

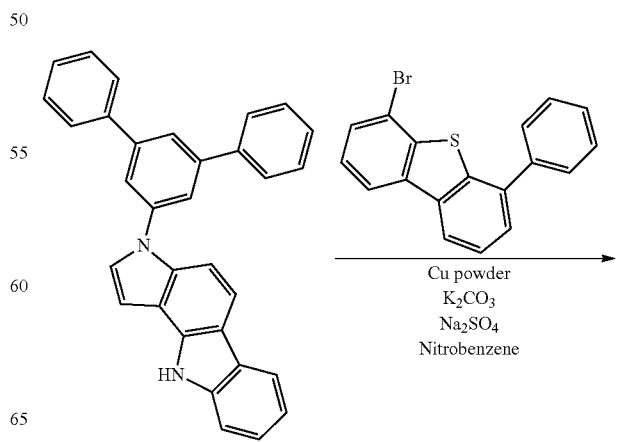

-continued

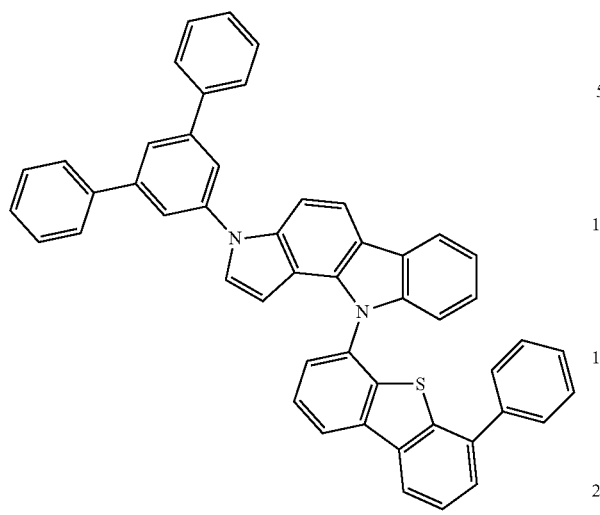

-continued

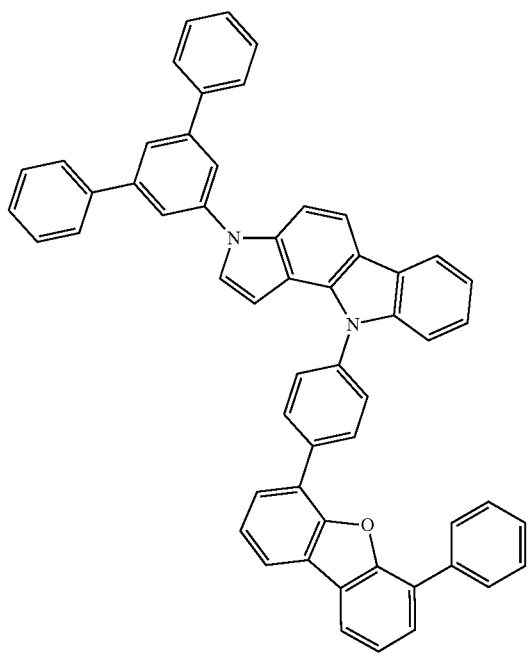

The target compound Inv606 (3 g, yield: 65%) was obtained in the same manner as in Synthesis Example 19, except that 4-bromo-6-phenyldibenzo[b,d]thiophene was used instead of 2-(3-bromophenyl)triphenylene.

GC-Mass (theoretical value: 692.87 g/mol, measured value: 692 g/mol)

Synthesis Example 22

Synthesis of Inv609

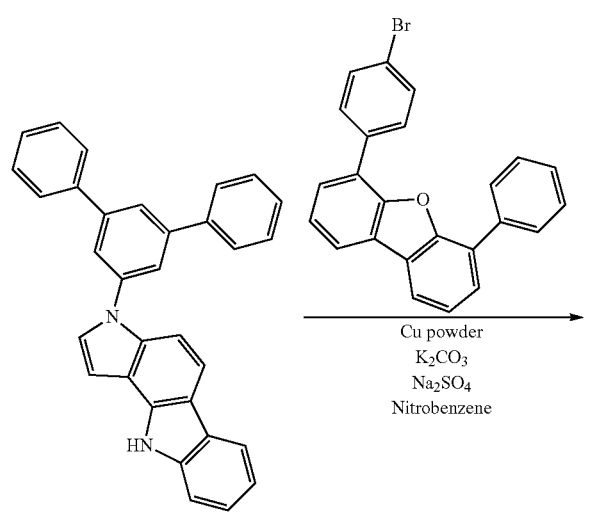

The target compound Inv609 (3.1 g, yield: 62%) was obtained in the same manner as in Synthesis Example 19, except that 4-(4-bromophenyl)-6-phenyldibenzo[b,d]furan was used instead of 2-(3-bromophenyl)triphenylene.

GC-Mass (theoretical value: 752.9 g/mol, measured value: 752 g/mol)

Synthesis Example 23

Synthesis of Inv611

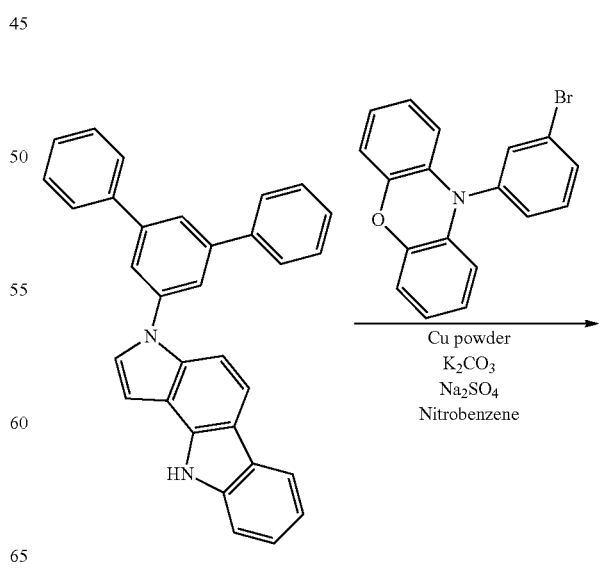

545
-continued

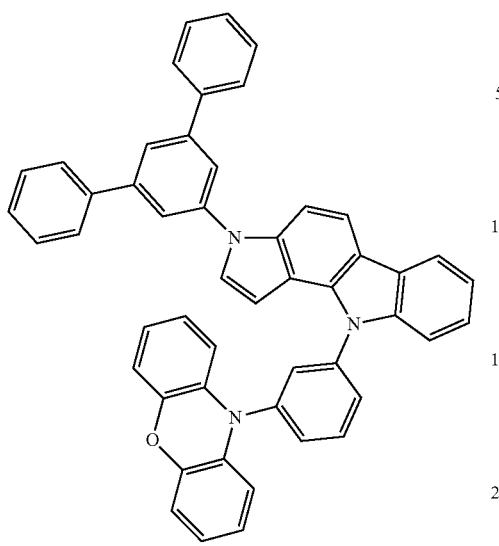

546
-continued

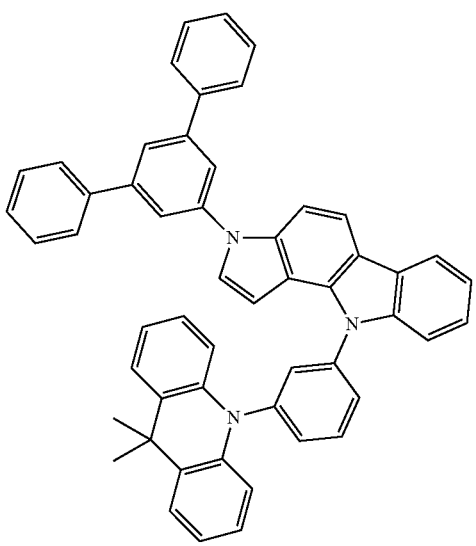

The target compound Inv611 (2.8 g, yield: 62%) was obtained in the same manner as in Synthesis Example 19, except that 10-(3-bromophenyl)-10H-phenoxazine was used instead of 2-(3-bromophenyl)triphenylene.

GC-Mass (theoretical value: 691.82 g/mol, measured value: 691 g/mol)

Synthesis Example 24

Synthesis of Inv614

The target compound Inv614 (2.5 g, yield: 53%) was obtained in the same manner as in Synthesis Example 19, except that 10-(3-bromophenyl)-9,9-dimethyl-9,10-dihydroacridine was used instead of 2-(3-bromophenyl)triphenylene.

GC-Mass (theoretical value: 717.9 g/mol, measured value: 717 g/mol)

Synthesis Example 25

Synthesis of Inv615

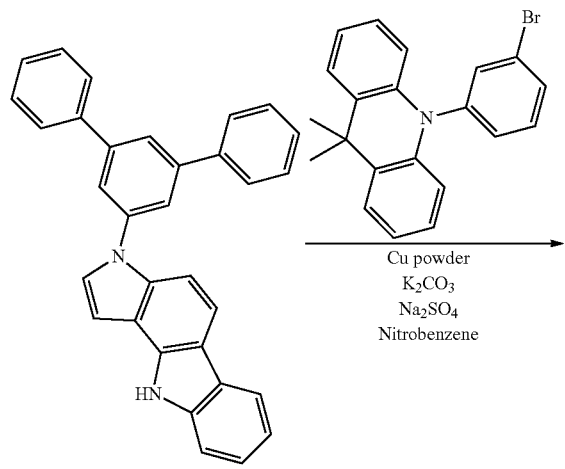

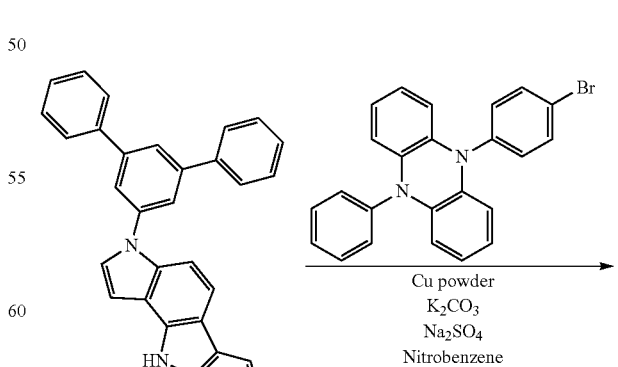

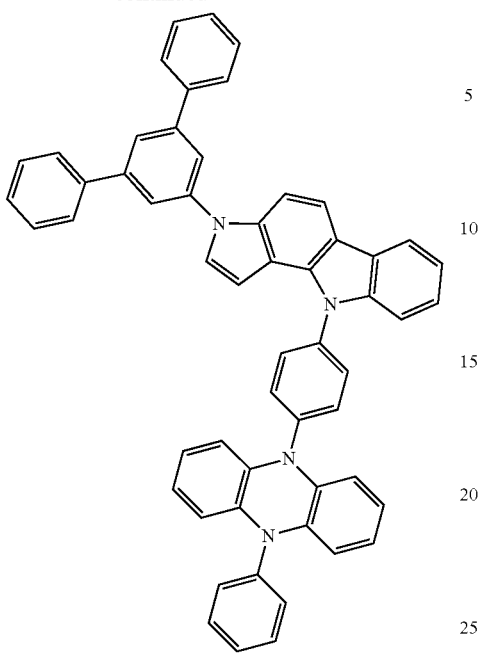

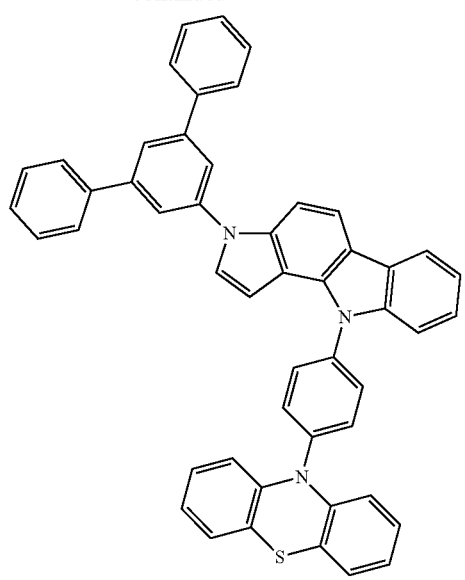

The target compound Inv615 (2.8 g, yield: 56%) was obtained in the same manner as in Synthesis Example 19, except that 5-(4-bromophenyl)-10-phenyl-5,10-dihydrophenazine was used instead of 2-(3-bromophenyl)triphenylene.

GC-Mass (theoretical value: 766.93 g/mol, measured value: 766 g/mol)

Synthesis Example 26

Synthesis of Inv625

The target compound Inv625 (2.7 g, yield: 58%) was obtained in the same manner as in Synthesis Example 19, except that 10-(4-bromophenyl)-10H-phenothiazine was used instead of 2-(3-bromophenyl)triphenylene.

GC-Mass (theoretical value: 707.88 g/mol, measured value: 707 g/mol)

Synthesis Example 27

Synthesis of Inv632

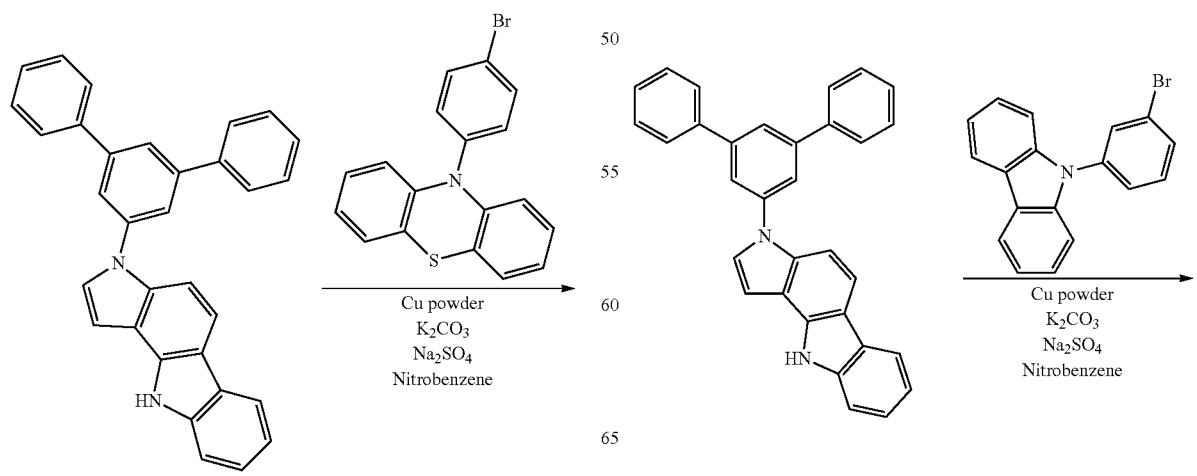

-continued

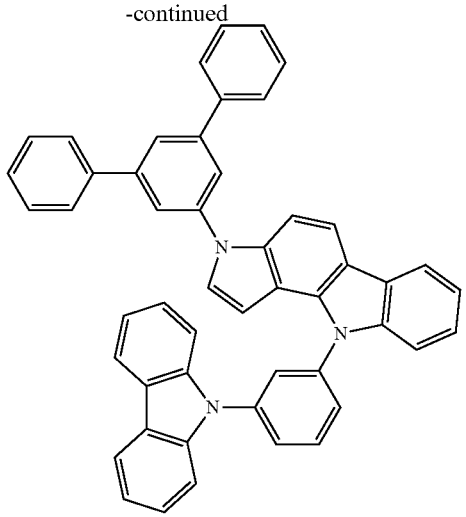

The target compound Inv632 (2.6 g, yield: 59%) was obtained in the same manner as in Synthesis Example 19, except that 9-(3-bromophenyl)-9H-carbazole was used instead of 2-(3-bromophenyl)triphenylene.

GC-Mass (theoretical value: 675.82 g/mol, measured value: 675 g/mol)

Synthesis Example 28

Synthesis of Inv653

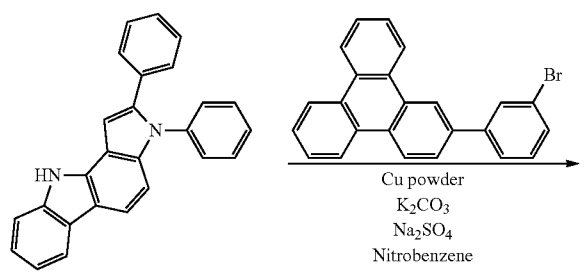

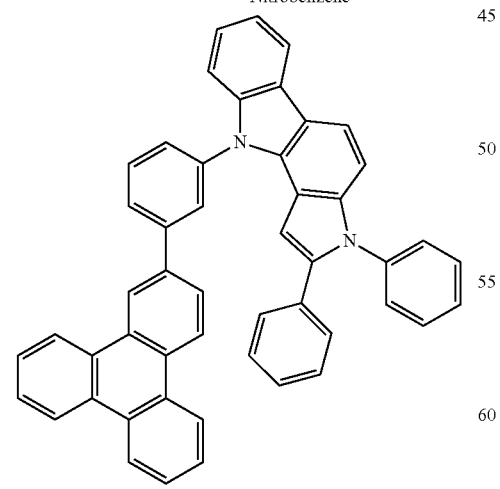

Inv653 (3.5 g, yield: 63%) was obtained in the same manner as in Synthesis Example 1, except that IC-20 was used instead of IC-1.

GC-Mass (theoretical value: 660.8 g/mol, measured value: 660 g/mol)

Synthesis Example 29

Synthesis of Inv678

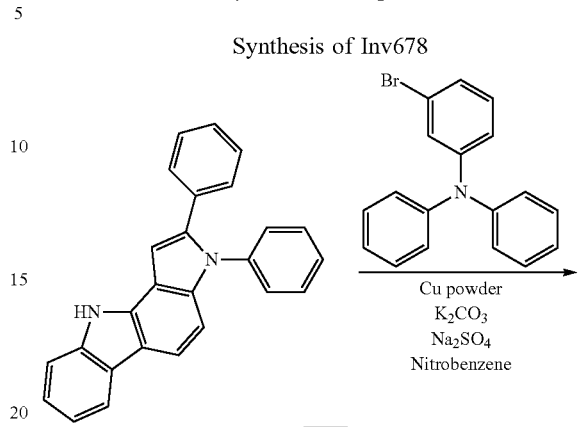

The target compound Inv678 (2.8 g, yield: 56%) was obtained in the same manner as in Synthesis Example 28, except that 3-bromo-N,N-diphenylaniline was used instead of 2-(3-bromophenyl)triphenylene.

GC-Mass (theoretical value: 601.74 g/mol, measured value: 601 g/mol)

Synthesis Example 30

Synthesis of Inv686

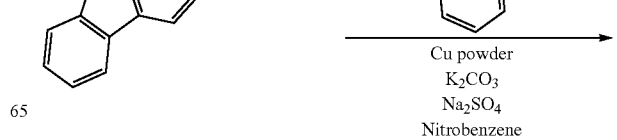

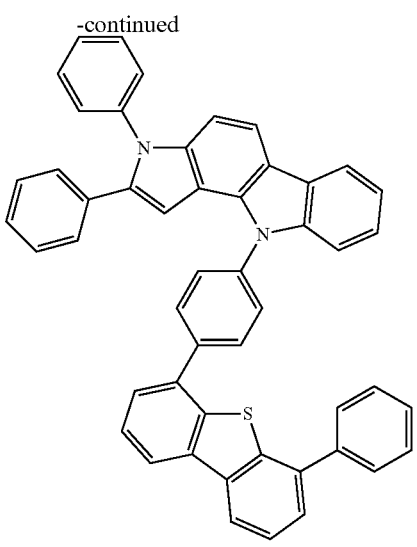

The target compound Inv686 (3.3 g, yield: 56%) was obtained in the same manner as in Synthesis Example 28, except that 4-(4-bromophenyl)-6-phenyldibenzo[b,d]thiophene was used instead of 2-(3-bromophenyl)triphenylene.

GC-Mass (theoretical value: 692.87 g/mol, measured value: 692 g/mol)

Synthesis Example 31

Synthesis of Inv691

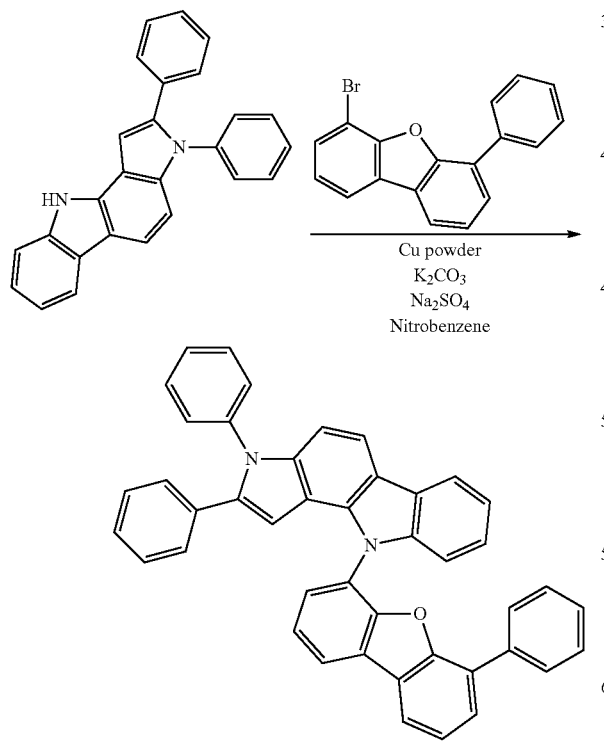

The target compound Inv691 (3 g, yield: 61%) was obtained in the same manner as in Synthesis Example 28, except that 4-bromo-6-phenyldibenzo[b,d]furan was used instead of 2-(3-bromophenyl)triphenylene.

GC-Mass (theoretical value: 600.71 g/mol, measured value: 600 g/mol)

Synthesis Example 32

Synthesis of Inv694

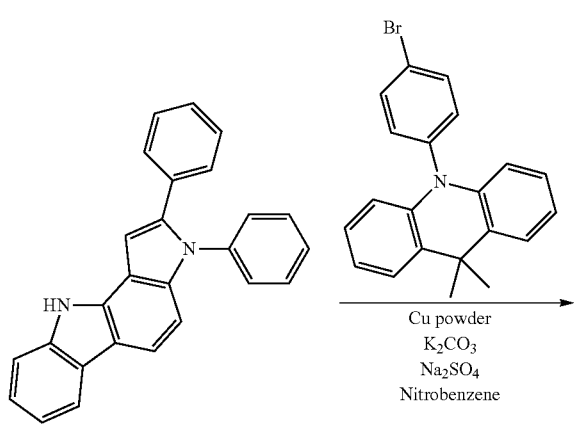

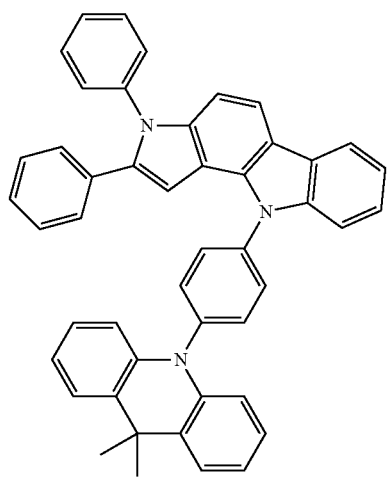

The target compound Inv694 (3.3 g, yield: 62%) was obtained in the same manner as in Synthesis Example 28, except that 10-(4-bromophenyl)-9,9-dimethyl-9,10-dihydroacridine was used instead of 2-(3-bromophenyl)triphenylene.

GC-Mass (theoretical value: 641.8 g/mol, measured value: 641 g/mol)

Synthesis Example 33

Synthesis of Inv705

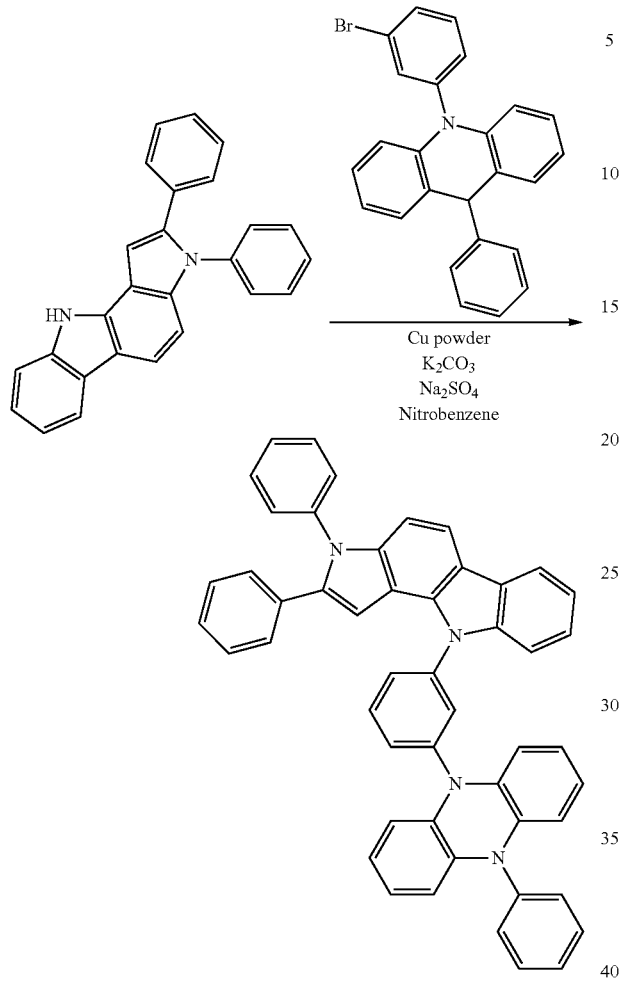

The target compound Inv705 (3.4 g, yield: 59%) was obtained in the same manner as in Synthesis Example 28, except that 5-(3-bromophenyl)-10-phenyl-5,10-dihydrophenazine was used instead of 2-(3-bromophenyl)triphenylene.

GC-Mass (theoretical value: 690.83 g/mol, measured value: 690 g/mol)

Synthesis Example 34

Synthesis of Inv707

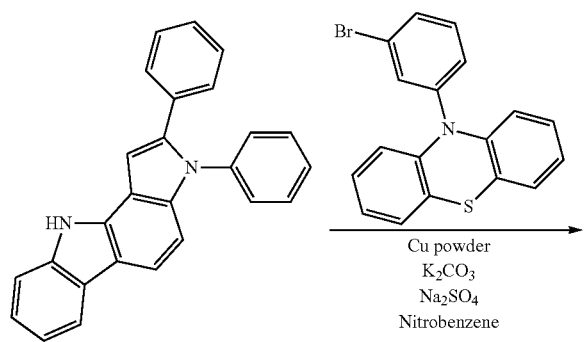

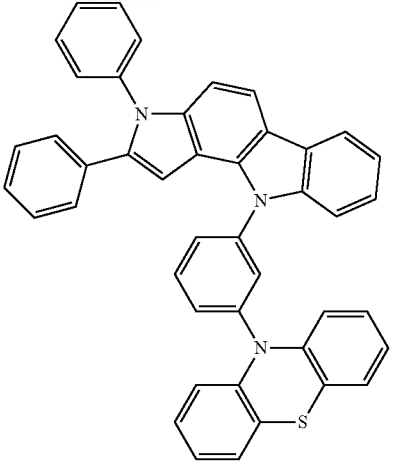

The target compound Inv707 (3.3 g, yield: 52%) was obtained in the same manner as in Synthesis Example 28, except that 10-(3-bromophenyl)-10H-phenothiazine was used instead of 2-(3-bromophenyl)triphenylene.

GC-Mass (theoretical value: 631.79 g/mol, measured value: 631 g/mol)

Synthesis Example 35

Synthesis of Inv708

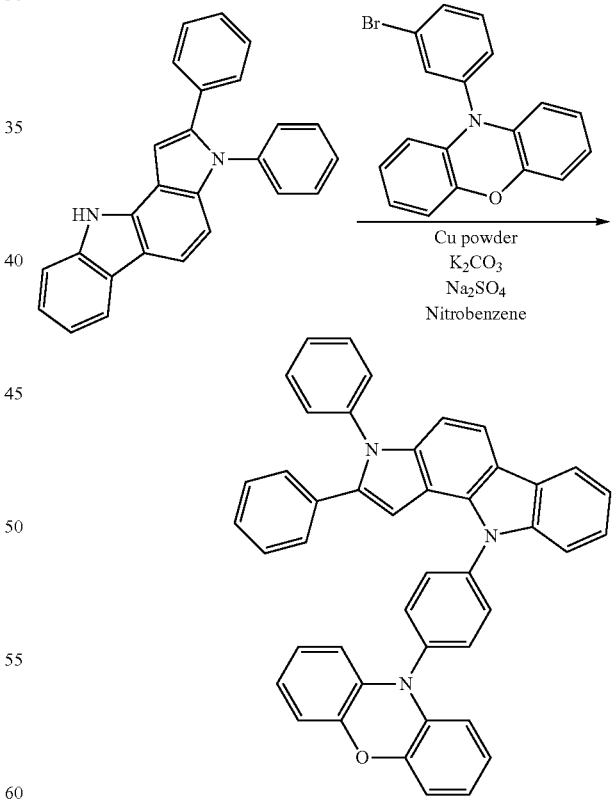

The target compound Inv708 (3.1 g, yield: 60%) was obtained in the same manner as in Synthesis Example 28, except that 10-(4-bromophenyl)-10H-phenoxazine was used instead of 2-(3-bromophenyl)triphenylene.

GC-Mass (theoretical value: 615.72 g/mol, measured value: 615 g/mol)

Synthesis Example 36

Synthesis of Inv710

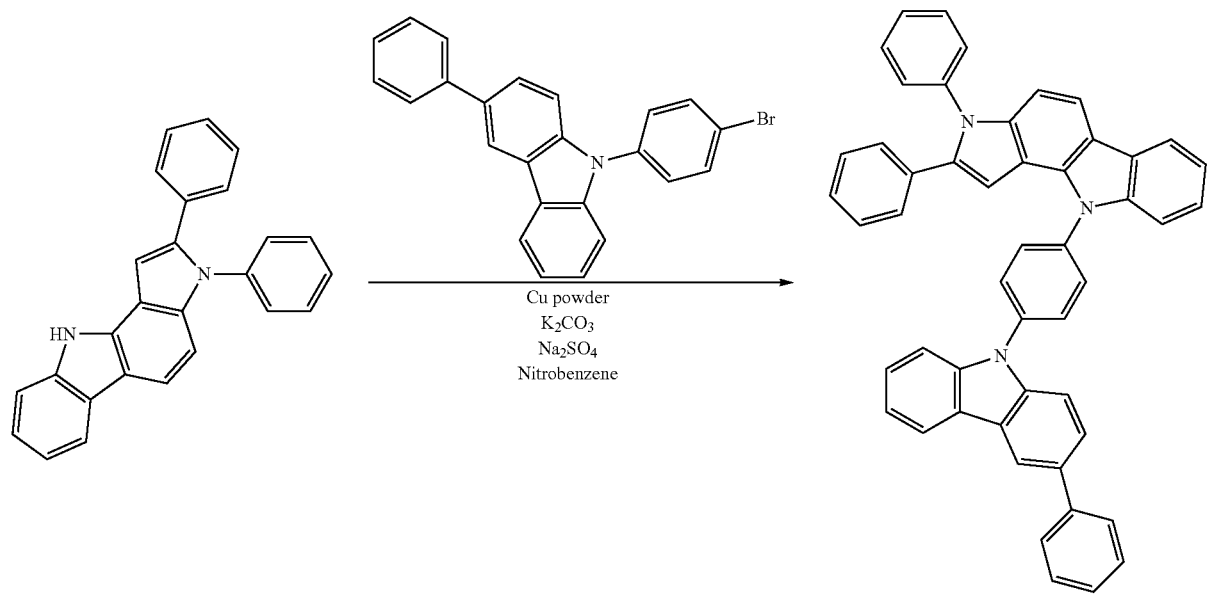 [SMILES: c1ccc(-c2cc3c4[nH]c5ccccc5c4ccc3n2-c2ccccc2)cc1 ; Brc1ccc(-n2c3ccccc3c3cc(-c4ccccc4)ccc32)cc1 ; c1ccc(-c2ccc3c(c2)c2ccccc2n3-c2ccc(-n3c4ccccc4c4ccc5c(cc(-c6ccccc6)n5-c5ccccc5)c43)cc2)cc1]

The target compound Inv710 (3.3 g, yield: 59%) was obtained in the same manner as in Synthesis Example 28, except that 9-(4-bromophenyl)-3-phenyl-9H-carbazole was used instead of 2-(3-bromophenyl)triphenylene.

GC-Mass (theoretical value: 675.82 g/mol, measured value: 675 g/mol)

Synthesis Example 37

Synthesis of Inv896

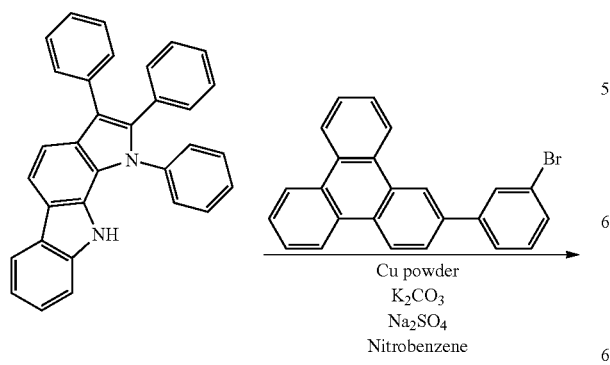

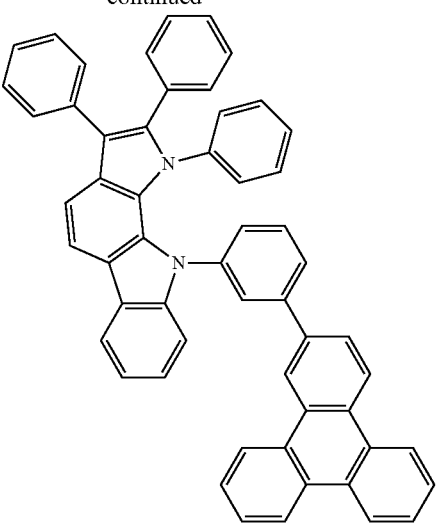

Inv896 (3 g, yield: 62%) was obtained in the same manner as in Synthesis Example 1, except that IC-24 was used instead of IC-1.

GC-Mass (theoretical value: 736.9 g/mol, measured value: 736 g/mol)

Synthesis Example 38

Synthesis of Inv920

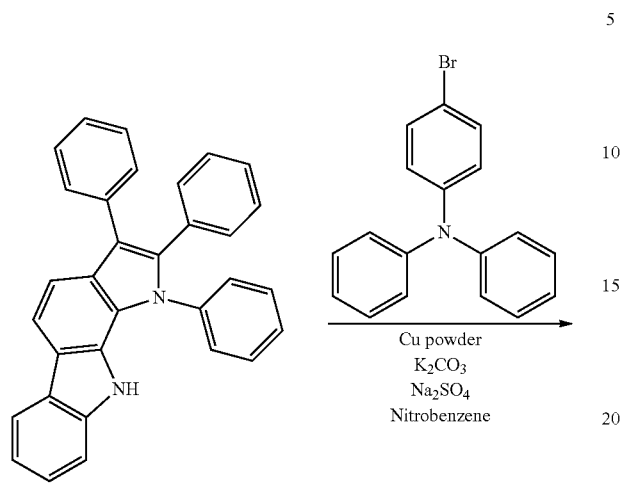

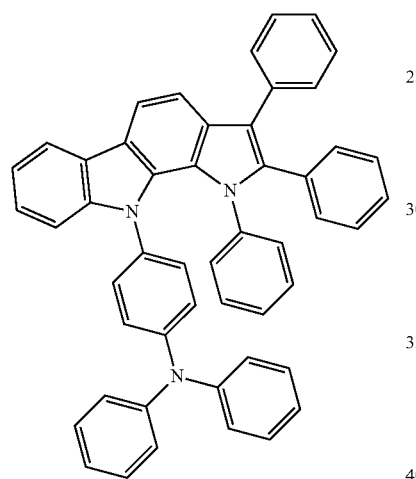

The target compound Inv920 (2.9 g, yield: 64%) was obtained in the same manner as in Synthesis Example 37, except that 4-bromo-N,N-diphenylaniline was used instead of 2-(3-bromophenyl)triphenylene.

GC-Mass (theoretical value: 677.83 g/mol, measured value: 677 g/mol)

Synthesis Example 39

Synthesis of Inv930

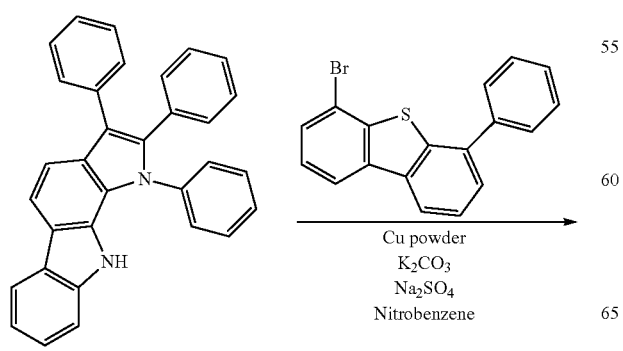

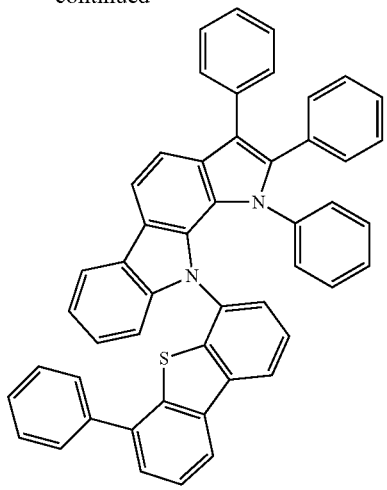

The target compound Inv930 (2.8 g, yield: 61%) was obtained in the same manner as in Synthesis Example 37, except that 4-bromo-6-phenyldibenzo[b,d]thiophene was used instead of 2-(3-bromophenyl)triphenylene.

GC-Mass (theoretical value: 692.87 g/mol, measured value: 692 g/mol)

Synthesis Example 40

Synthesis of Inv933

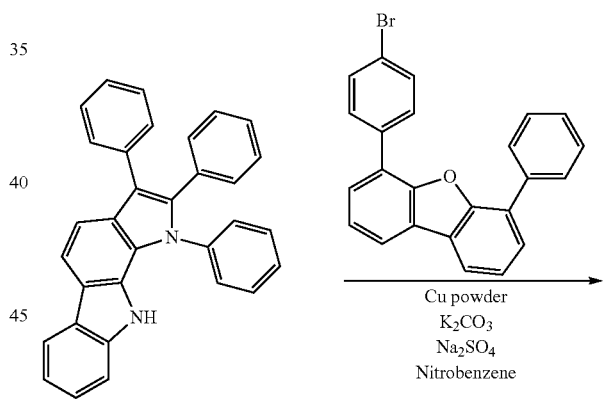

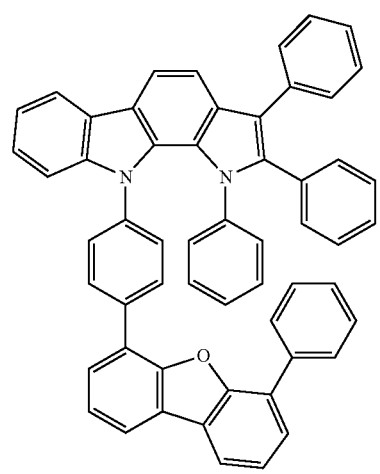

The target compound Inv933 (2.7 g, yield: 54%) was obtained in the same manner as in Synthesis Example 37, except that 4-(4-bromophenyl)-6-phenyldibenzo[b,d]furan was used instead of 2-(3-bromophenyl)triphenylene.

GC-Mass (theoretical value: 752.9 g/mol, measured value: 752 g/mol)

Synthesis Example 41

Synthesis of Inv935

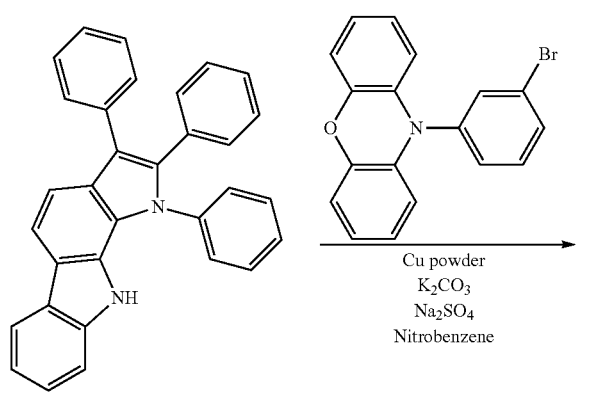

The target compound Inv935 (2.6 g, yield: 57%) was obtained in the same manner as in Synthesis Example 37, except that 10-(3-bromophenyl)-10H-phenoxazine was used instead of 2-(3-bromophenyl)triphenylene.

GC-Mass (theoretical value: 691.82 g/mol, measured value: 691 g/mol)

Synthesis Example 42

Synthesis of Inv938

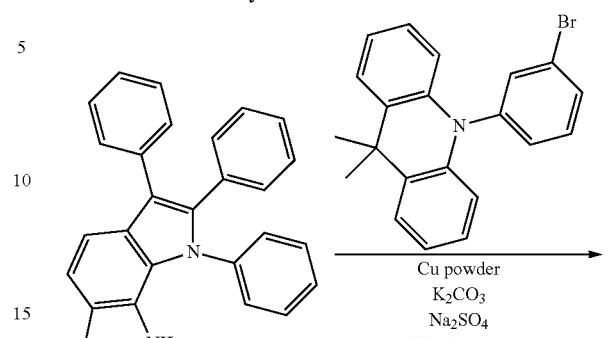

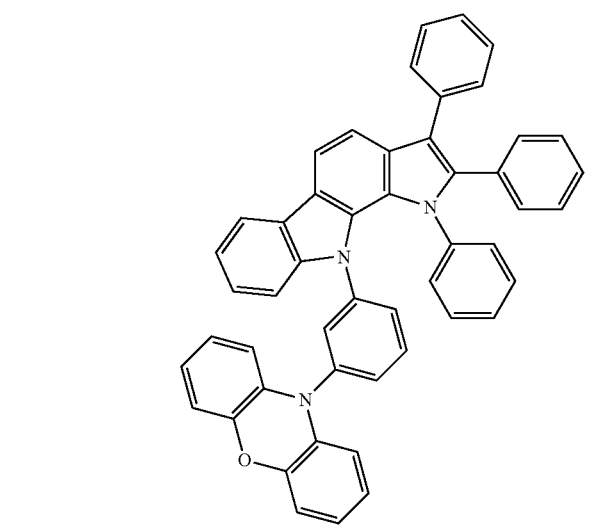

The target compound Inv938 (2.8 g, yield: 59%) was obtained in the same manner as in Synthesis Example 37, except that 10-(3-bromophenyl)-9,9-dimethyl-9,10-dihydroacridine was used instead of 2-(3-bromophenyl)triphenylene.

GC-Mass (theoretical value: 717.9 g/mol, measured value: 717 g/mol)

Synthesis Example 43

Synthesis of Inv939

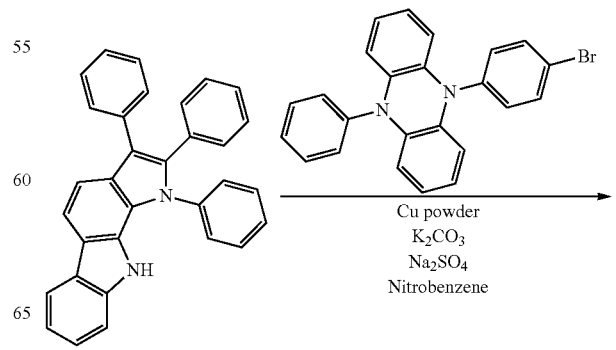

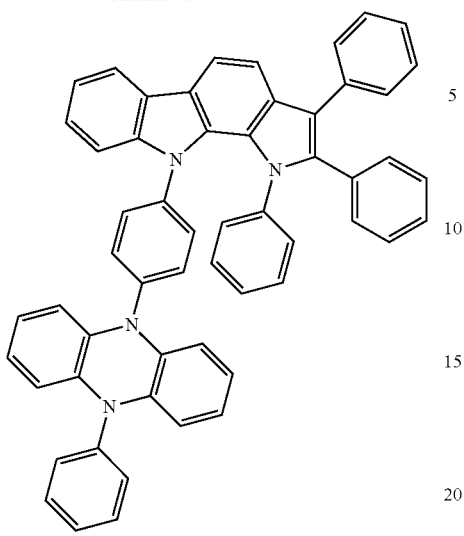

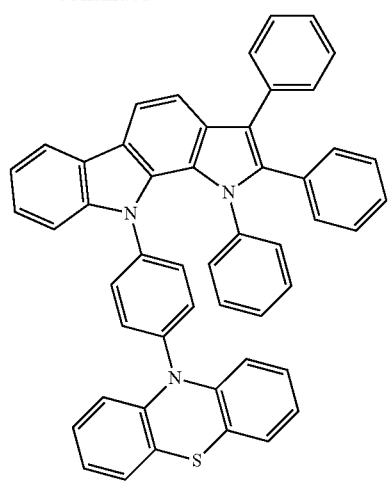

The target compound Inv939 (2.9 g, yield: 58%) was obtained in the same manner as in Synthesis Example 37, except that 5-(4-bromophenyl)-10-phenyl-5,10-dihydrophenazine was used instead of 2-(3-bromophenyl)triphenylene.

GC-Mass (theoretical value: 766.93 g/mol, measured value: 766 g/mol)

Synthesis Example 44

Synthesis of Inv949

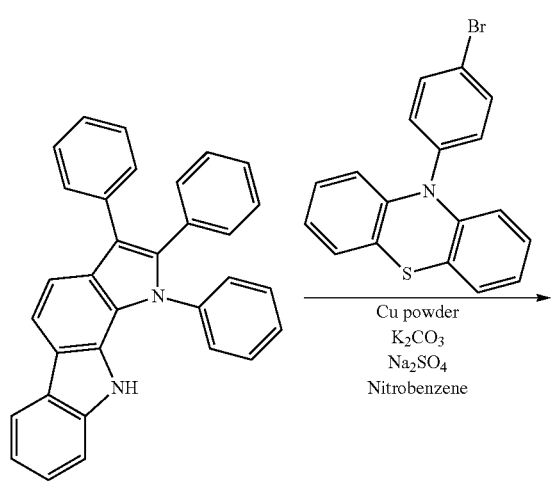

The target compound Inv949 (2.6 g, yield: 55%) was obtained in the same manner as in Synthesis Example 37, except that 10-(4-bromophenyl)-10H-phenothiazine was used instead of 2-(3-bromophenyl)triphenylene.

GC-Mass (theoretical value: 707.88 g/mol, measured value: 707 g/mol)

Synthesis Example 45

Synthesis of Inv956

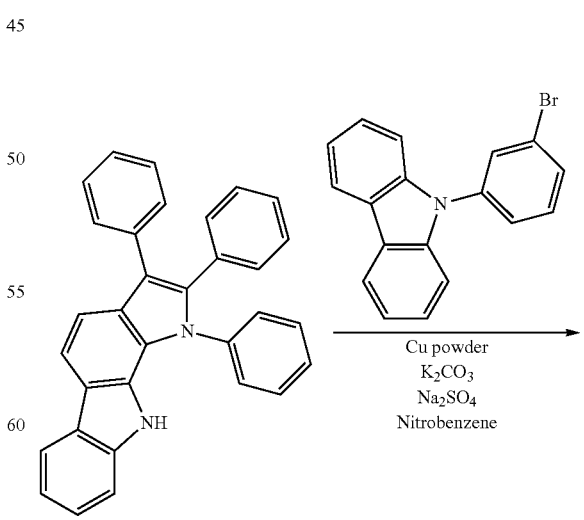

-continued

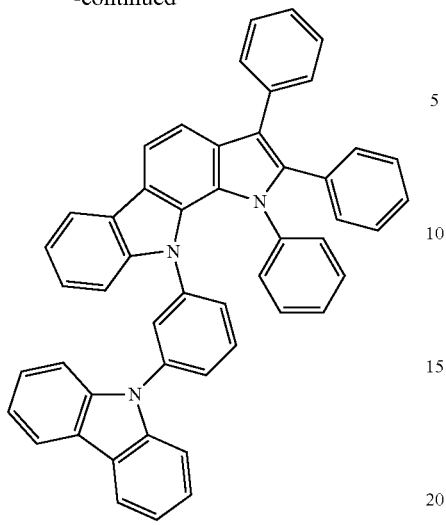

The target compound Inv956 (2.5 g, yield: 56%) was obtained in the same manner as in Synthesis Example 37, except that 9-(3-bromophenyl)-9H-carbazole was used instead of 2-(3-bromophenyl)triphenylene.

GC-Mass (theoretical value: 675.82 g/mol, measured value: 675 g/mol)

Synthesis Example 46

Synthesis of Inv977

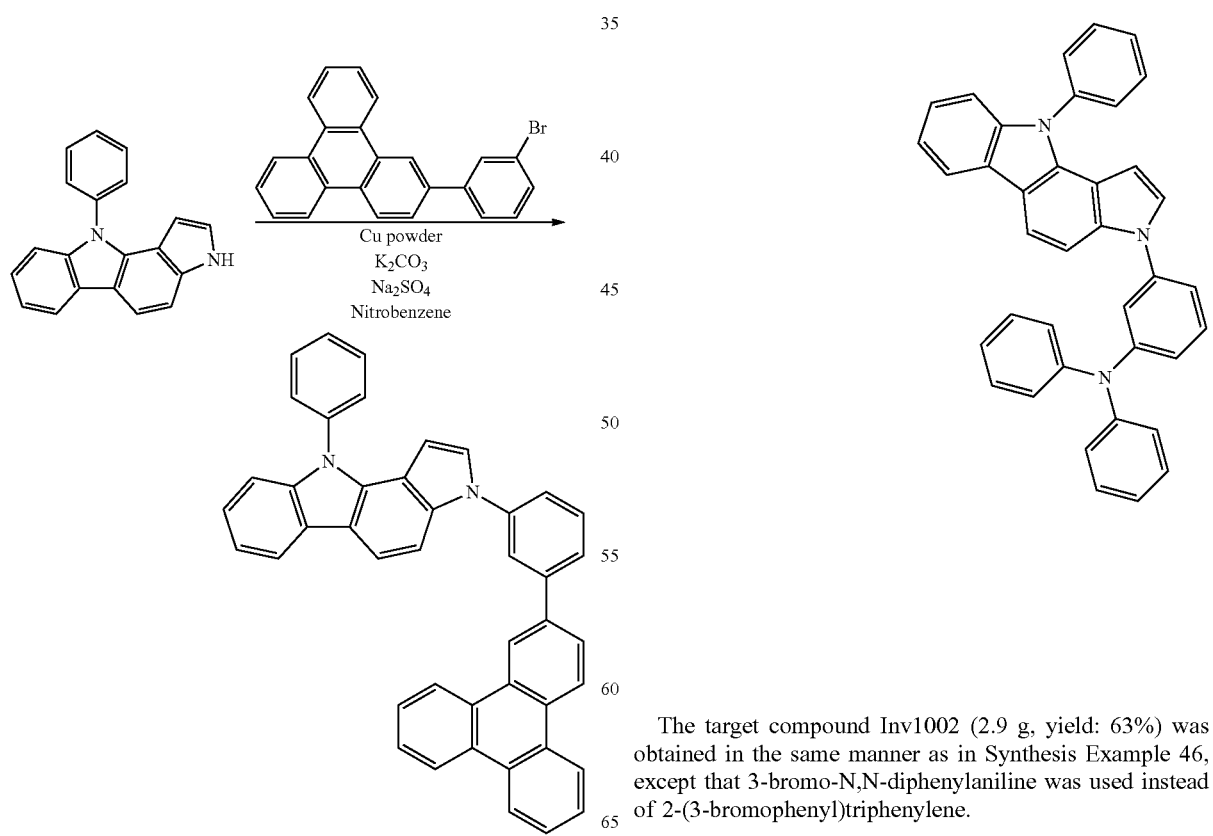

Inv977 (3.1 g, yield: 60%) was obtained in the same manner as in Synthesis Example 1, except that IC-29 was used instead of IC-1.

GC-Mass (theoretical value: 584.71 g/mol, measured value: 584 g/mol)

Synthesis Example 47

Synthesis of Inv1002

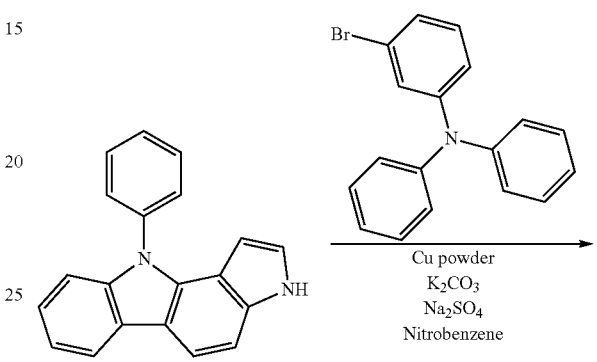

The target compound Inv1002 (2.9 g, yield: 63%) was obtained in the same manner as in Synthesis Example 46, except that 3-bromo-N,N-diphenylaniline was used instead of 2-(3-bromophenyl)triphenylene.

GC-Mass (theoretical value: 525.64 g/mol, measured value: 525 g/mol)

Synthesis Example 48

Synthesis of Inv1010

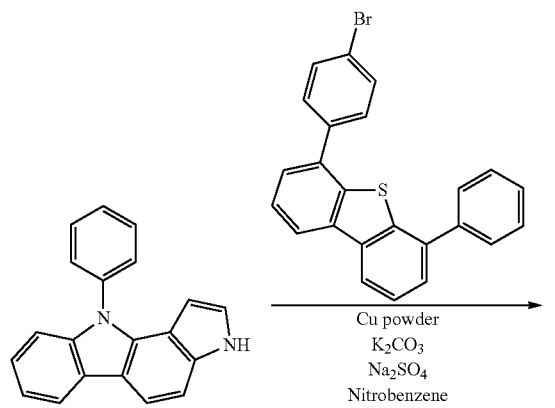

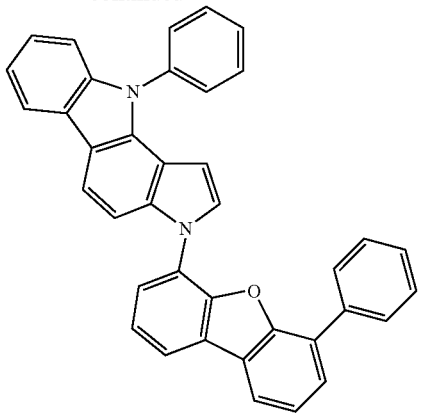

The target compound Inv1010 (3.4 g, yield: 62%) was obtained in the same manner as in Synthesis Example 46, except that 4-(4-bromophenyl)-6-phenyldibenzo[b,d]thiophene was used instead of 2-(3-bromophenyl)triphenylene.

GC-Mass (theoretical value: 616.77 g/mol, measured value: 616 g/mol)

Synthesis Example 49

Synthesis of Inv1015

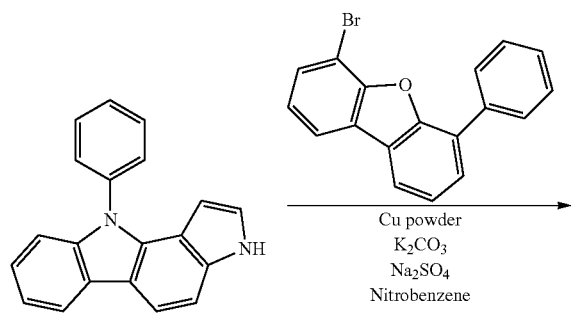

The target compound Inv1015 (4.64 g, yield: 58%) was obtained in the same manner as in Synthesis Example 46, except that 4-bromo-6-phenyldibenzo[b,d]furan was used instead of 2-(3-bromophenyl)triphenylene.

GC-Mass (theoretical value: 524.61 g/mol, measured value: 524 g/mol)

Synthesis Example 50

Synthesis of Inv1018

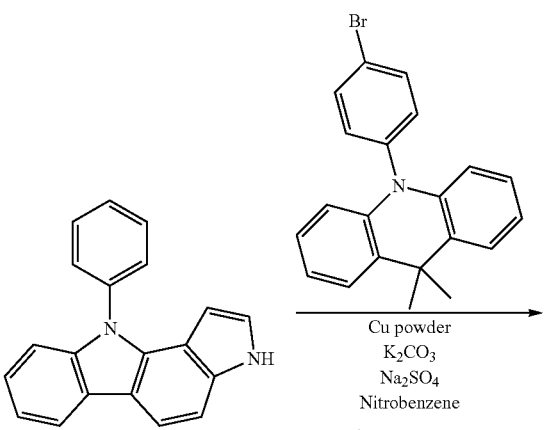

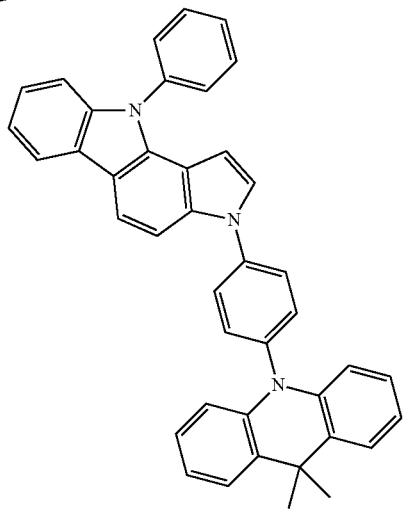

The target compound Inv1018 (3.4 g, yield: 68%) was obtained in the same manner as in Synthesis Example 46, except that 10-(4-bromophenyl)-9,9-dimethyl-9,10-dihydroacridine was used instead of 2-(3-bromophenyl)triphenylene.

GC-Mass (theoretical value: 565.7 g/mol, measured value: 565 g/mol)

Synthesis Example 51

Synthesis of Inv1029

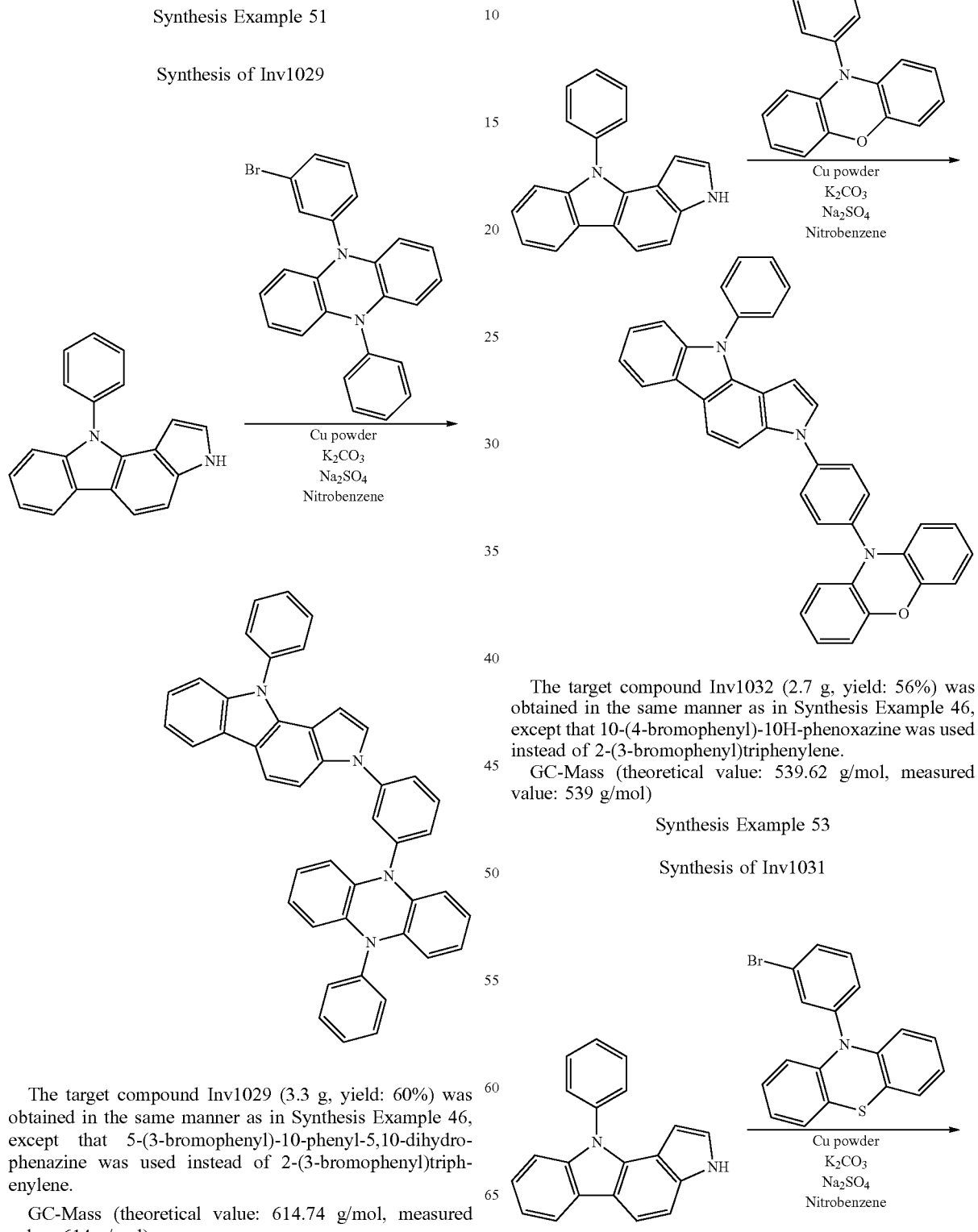

The target compound Inv1029 (3.3 g, yield: 60%) was obtained in the same manner as in Synthesis Example 46, except that 5-(3-bromophenyl)-10-phenyl-5,10-dihydrophenazine was used instead of 2-(3-bromophenyl)triphenylene.

GC-Mass (theoretical value: 614.74 g/mol, measured value: 614 g/mol)

Synthesis Example 52

Synthesis of Inv1032

The target compound Inv1032 (2.7 g, yield: 56%) was obtained in the same manner as in Synthesis Example 46, except that 10-(4-bromophenyl)-10H-phenoxazine was used instead of 2-(3-bromophenyl)triphenylene.

GC-Mass (theoretical value: 539.62 g/mol, measured value: 539 g/mol)

Synthesis Example 53

Synthesis of Inv1031

-continued

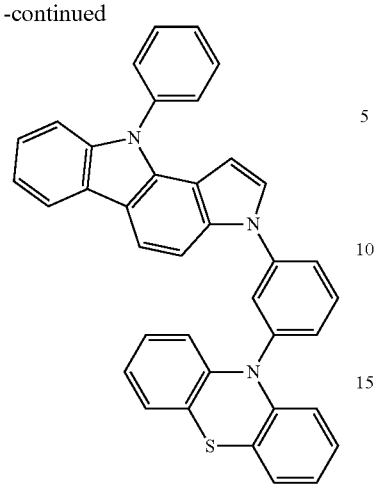

The target compound Inv1031 (2.6 g, yield: 53%) was obtained in the same manner as in Synthesis Example 46, except that 10-(3-bromophenyl)-10H-phenothiazine was used instead of 2-(3-bromophenyl)triphenylene.

GC-Mass (theoretical value: 555.69 g/mol, measured value: 555 g/mol)

Synthesis Example 54

Synthesis of Inv1034

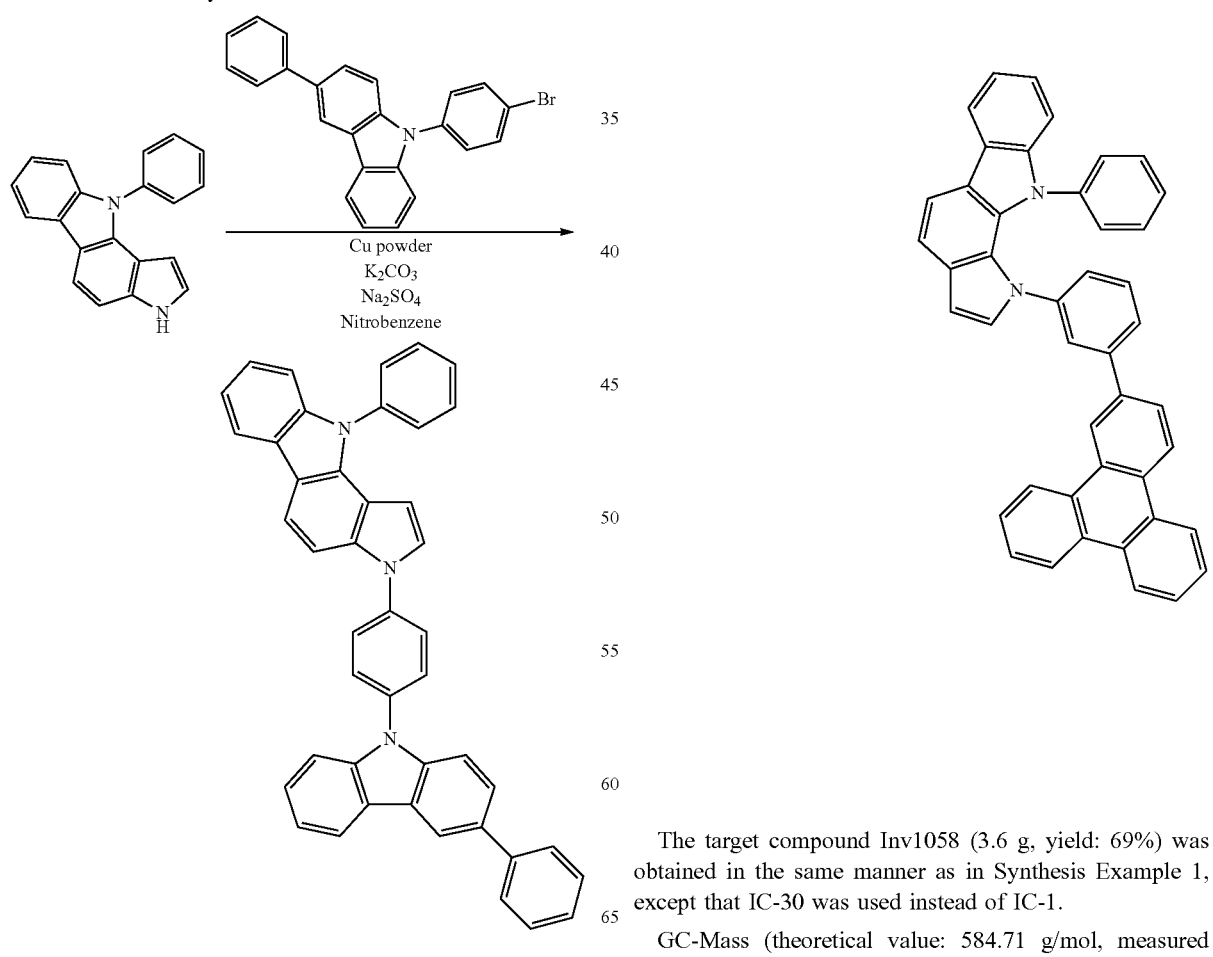

The target compound Inv1034 (2.9 g, yield: 59%) was obtained in the same manner as in Synthesis Example 46, except that 9-(4-bromophenyl)-3-phenyl-9H-carbazole was used instead of 2-(3-bromophenyl)triphenylene.

GC-Mass (theoretical value: 599.72 g/mol, measured value: 599 g/mol)

Synthesis Example 55

Synthesis of Inv1058

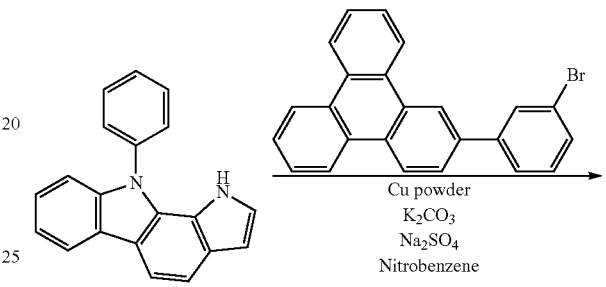

The target compound Inv1058 (3.6 g, yield: 69%) was obtained in the same manner as in Synthesis Example 1, except that IC-30 was used instead of IC-1.

GC-Mass (theoretical value: 584.71 g/mol, measured value: 584 g/mol)

Synthesis Example 56

Synthesis of Inv1082

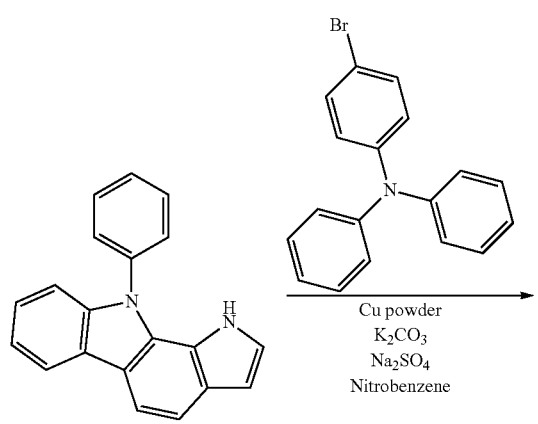

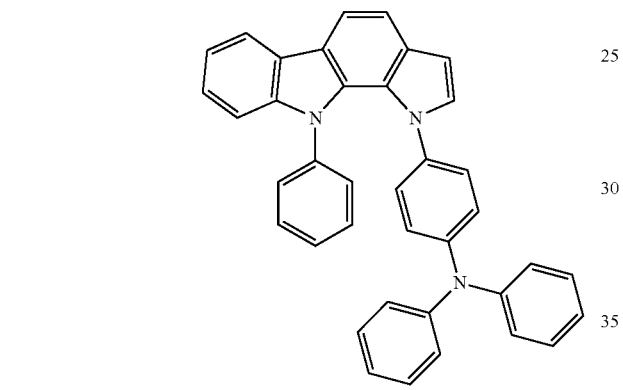

The target compound Inv1082 (3.1 g, yield: 66%) was obtained in the same manner as in Synthesis Example 55, except that 4-bromo-N,N-diphenylaniline was used instead of 2-(3-bromophenyl)triphenylene.

GC-Mass (theoretical value: 525.64 g/mol, measured value: 525 g/mol)

Synthesis Example 57

Synthesis of Inv1092

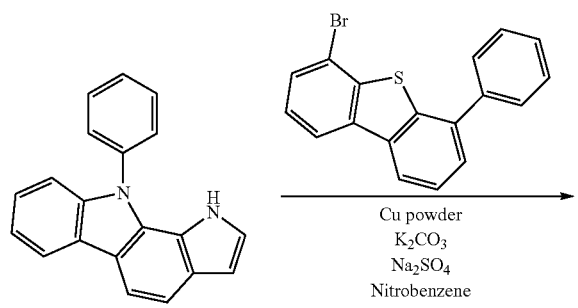

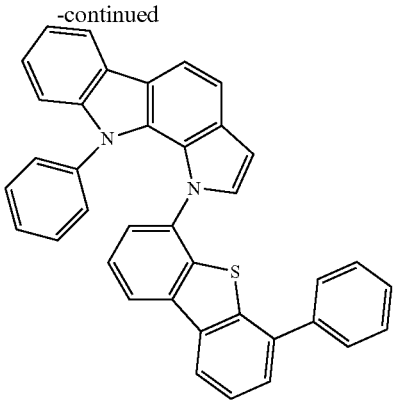

The target compound Inv1092 (2.8 g, yield: 59%) was obtained in the same manner as in Synthesis Example 55, except that 4-bromo-6-phenyldibenzo[b,d]thiophene was used instead of 2-(3-bromophenyl)triphenylene.

GC-Mass (theoretical value: 540.68 g/mol, measured value: 541 g/mol)

Synthesis Example 58

Synthesis of Inv1095

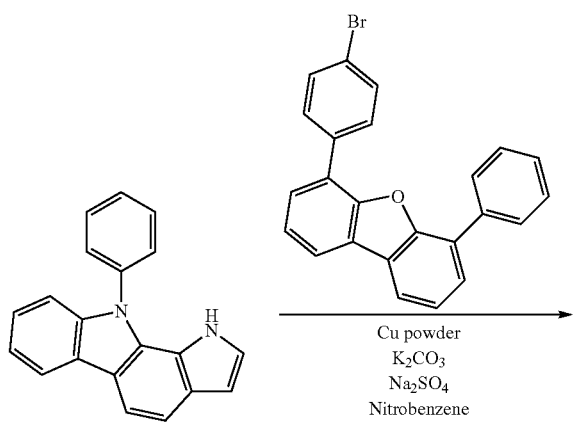

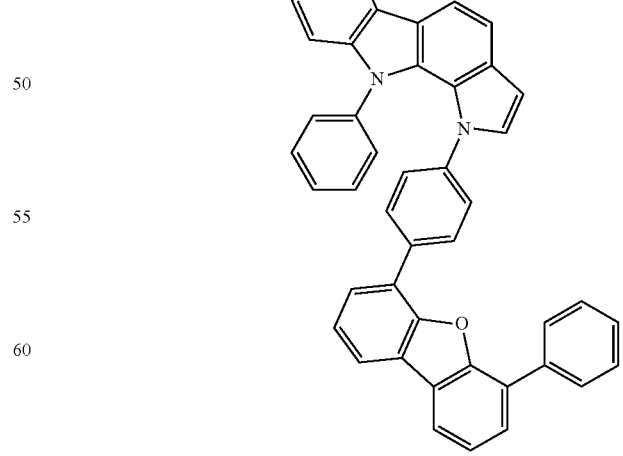

The target compound Inv1095 (3.2 g, yield: 60%) was obtained in the same manner as in Synthesis Example 55, except that 4-(4-bromophenyl)-6-phenyldibenzo[b,d]furan was used instead of 2-(3-bromophenyl)triphenylene.

GC-Mass (theoretical value: 600.71 g/mol, measured value: 600 g/mol)

Synthesis Example 59

Synthesis of Inv1097

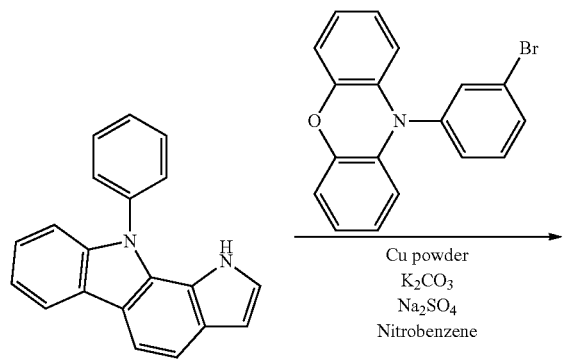

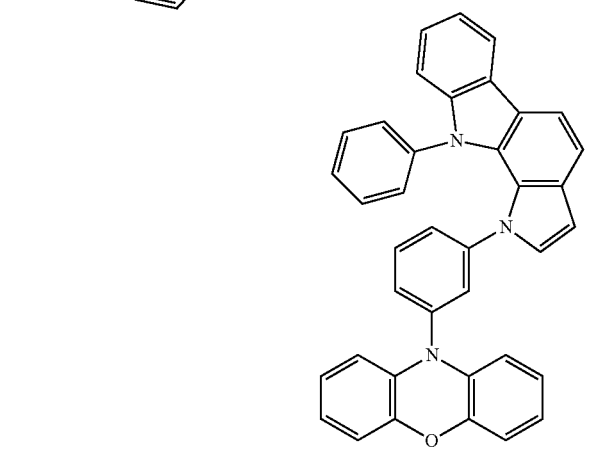

The target compound Inv1097 (3.1 g, yield: 64%) was obtained in the same manner as in Synthesis Example 55, except that 10-(3-bromophenyl)-10H-phenoxazine was used instead of 2-(3-bromophenyl)triphenylene.

GC-Mass (theoretical value: 539.62 g/mol, measured value: 539 g/mol)

Synthesis Example 60

Synthesis of Inv1100

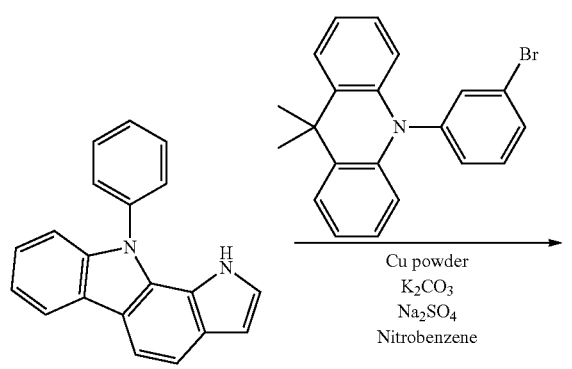
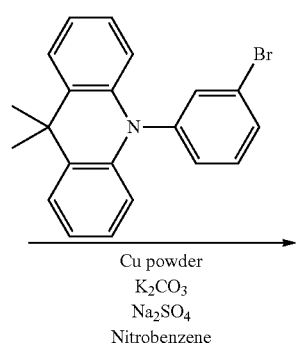

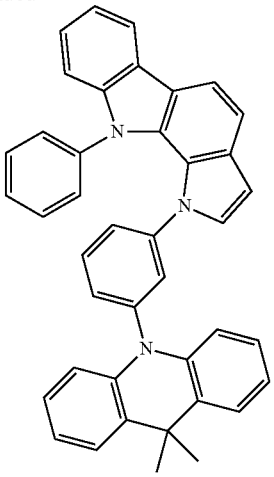

The target compound Inv1100 (2.7 g, yield: 54%) was obtained in the same manner as in Synthesis Example 55, except that 10-(3-bromophenyl)-9,9-dimethyl-9,10-dihydroacridine was used instead of 2-(3-bromophenyl)triphenylene.

GC-Mass (theoretical value: 565.7 g/mol, measured value: 566 g/mol)

Synthesis Example 61

Synthesis of Inv1101

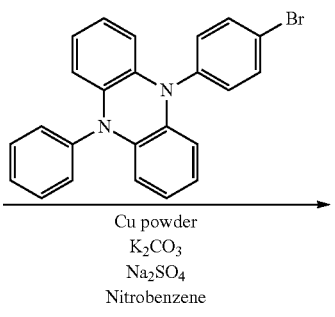

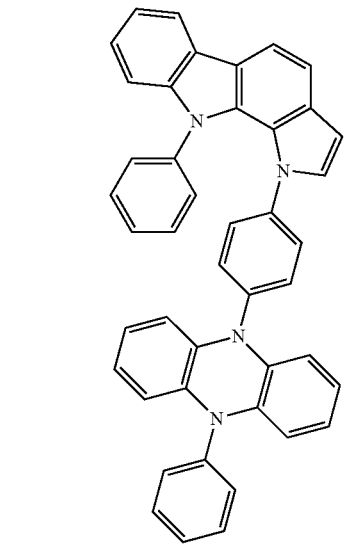

The target compound Inv1101 (3.3 g, yield: 60%) was obtained in the same manner as in Synthesis Example 55, except that 5-(4-bromophenyl)-10-phenyl-5,10-dihydrophenazine was used instead of 2-(3-bromophenyl)triphenylene.

GC-Mass (theoretical value: 614.74 g/mol, measured value: 614 g/mol)

Synthesis Example 62

Synthesis of Inv1111

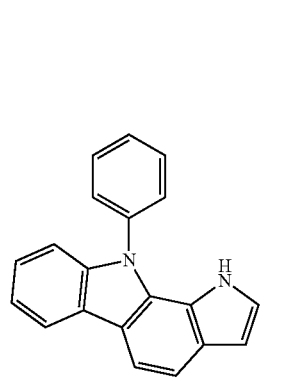
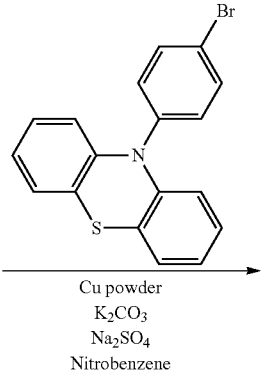

The target compound Inv1111 (2.9 g, yield: 59%) was obtained in the same manner as in Synthesis Example 55, except that 10-(4-bromophenyl)-10H-phenothiazine was used instead of 2-(3-bromophenyl)triphenylene.

GC-Mass (theoretical value: 555.69 g/mol, measured value: 555 g/mol)

Synthesis Example 63

Synthesis of Inv1118

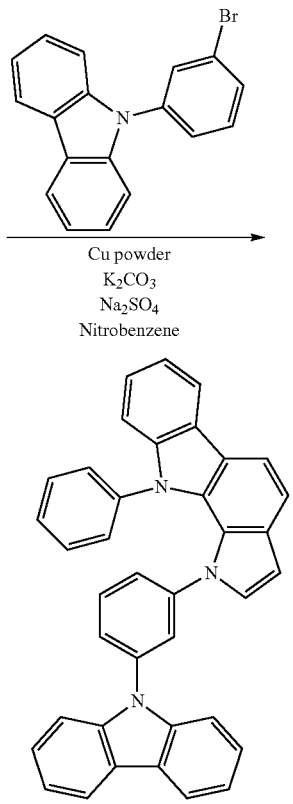

The target compound Inv1118 (2.8 g, yield: 60%) was obtained in the same manner as in Synthesis Example 55, except that 9-(3-bromophenyl)-9H-carbazole was used instead of 2-(3-bromophenyl)triphenylene.

GC-Mass (theoretical value: 523.63 g/mol, measured value: 523 g/mol)

Synthesis Example 64

Synthesis of Inv1139

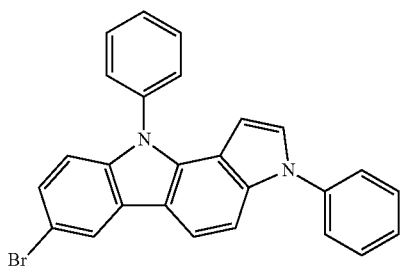
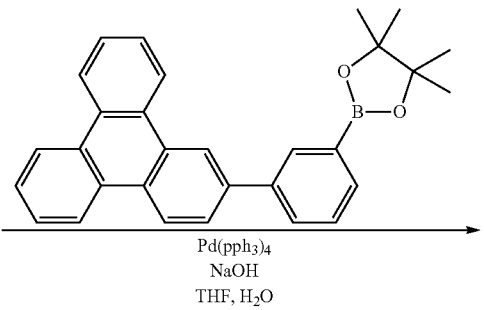

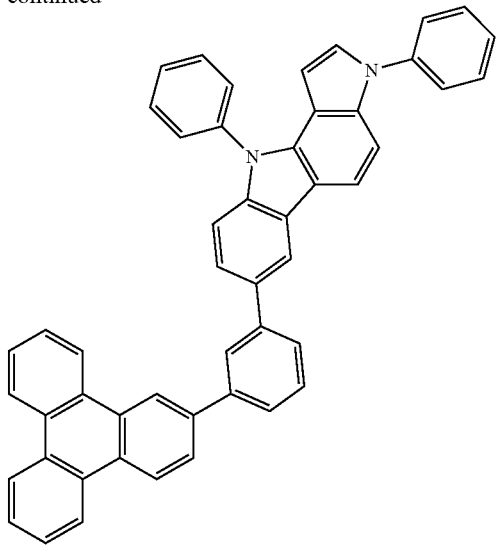

IC-7 (3 g, 6.85 mmol), 4,4,5,5-tetramethyl-2-(3-(triphenylen-2-yl)phenyl)-1,3,2-dioxaborolane (3.5 g, 8.23 mmol), NaOH (0.82 g, 20.57 mmol), and THF/H$_2$O (60 ml/20 ml) were mixed under nitrogen flow, Pd(PPh$_3$)$_4$ (0.23 g, 0.2 mmol) was added thereto at 40° C., and the resulting mixture was stirred at 80° C. for 12 hours.

After the reaction was terminated, extraction was performed with methylene chloride, MgSO$_4$ was added thereto, and the organic layer was dried. Inv1139 (3.8 g, yield: 84%) was obtained by removing the solvent from the organic layer, and then purifying the residue with column chromatography.

GC-Mass (theoretical value: 660.8 g/mol, measured value: 660 g/mol)

Synthesis Example 65

Synthesis of Inv1141

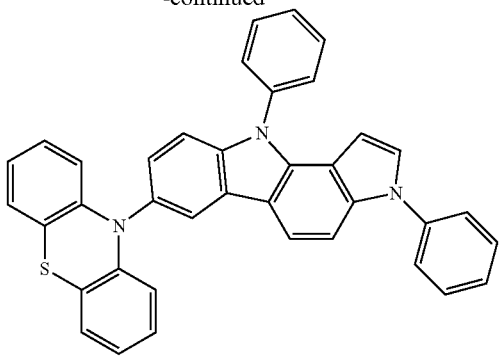

The target compound Inv1141 (2.9 g, yield: 59%) was obtained in the same manner as in Synthesis Example 1, except that IC-7 and 10H-phenothiazine were used instead of IC-1 and 2-(3-bromophenyl)triphenylene, respectively.

GC-Mass (theoretical value: 555.69 g/mol, measured value: 523 g/mol)

Synthesis Example 66

Synthesis of Inv1142

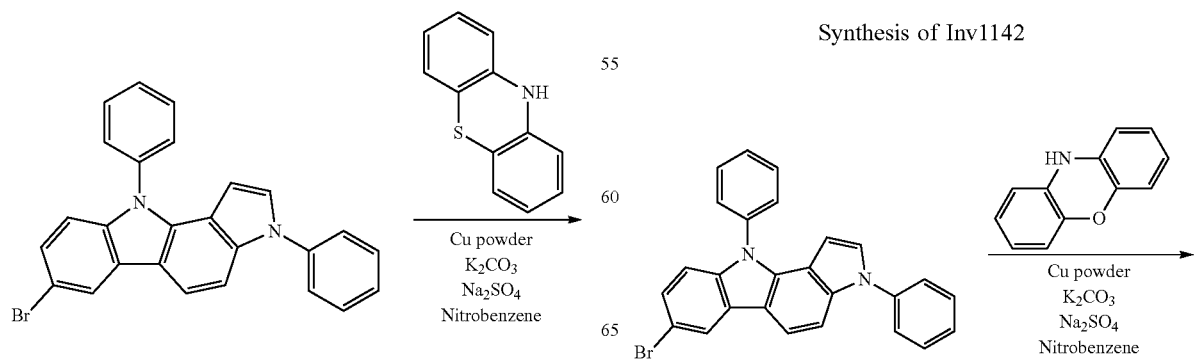

-continued

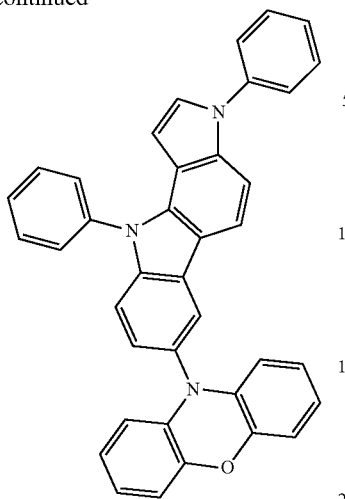

The target compound Inv1142 (3.1 g, yield: 64%) was obtained in the same manner as in Synthesis Example 65, except that 10H-phenoxazine was used instead of 10H-phenothiazine.

GC-Mass (theoretical value: 539.62 g/mol, measured value: 539 g/mol)

Synthesis Example 67

Synthesis of Inv1144

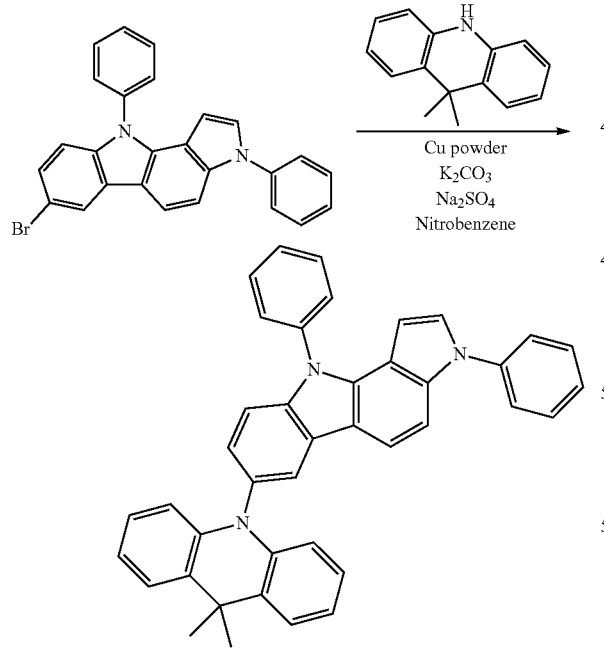

The target compound Inv1144 (2.7 g, yield: 54%) was obtained in the same manner as in Synthesis Example 65, except that 9,9-dimethyl-9,10-dihydroacridine was used instead of 10H-phenothiazine.

GC-Mass (theoretical value: 565.7 g/mol, measured value: 565 g/mol)

Synthesis Example 68

Synthesis of Inv1145

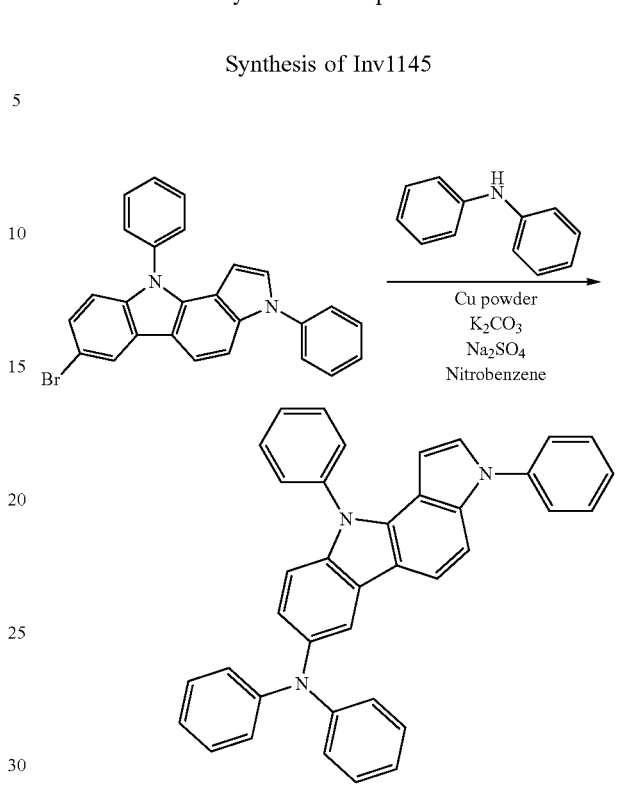

The target compound Inv1145 (3.1 g, yield: 66%) was obtained in the same manner as in Synthesis Example 65, except that diphenylamine was used instead of 10H-phenothiazine.

GC-Mass (theoretical value: 525.64 g/mol, measured value: 525 g/mol)

Synthesis Example 69

Synthesis of Inv1150

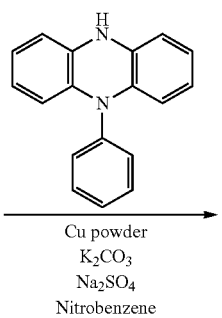

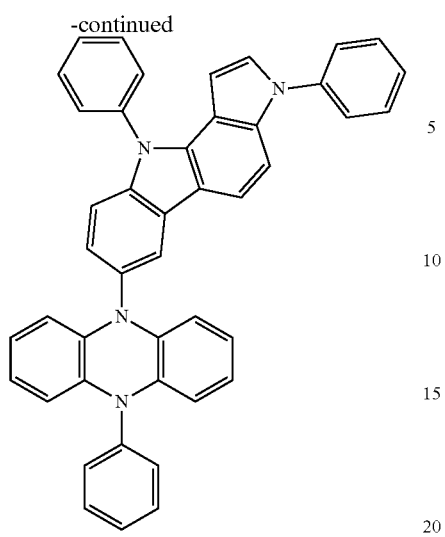

The target compound Inv1150 (2.7 g, yield: 64%) was obtained in the same manner as in Synthesis Example 65, except that 5-phenyl-5,10-dihydrophenazine was used instead of 10H-phenothiazine.

GC-Mass (theoretical value: 614.74 g/mol, measured value: 614 g/mol)

Synthesis Example 70

Synthesis of Inv1151

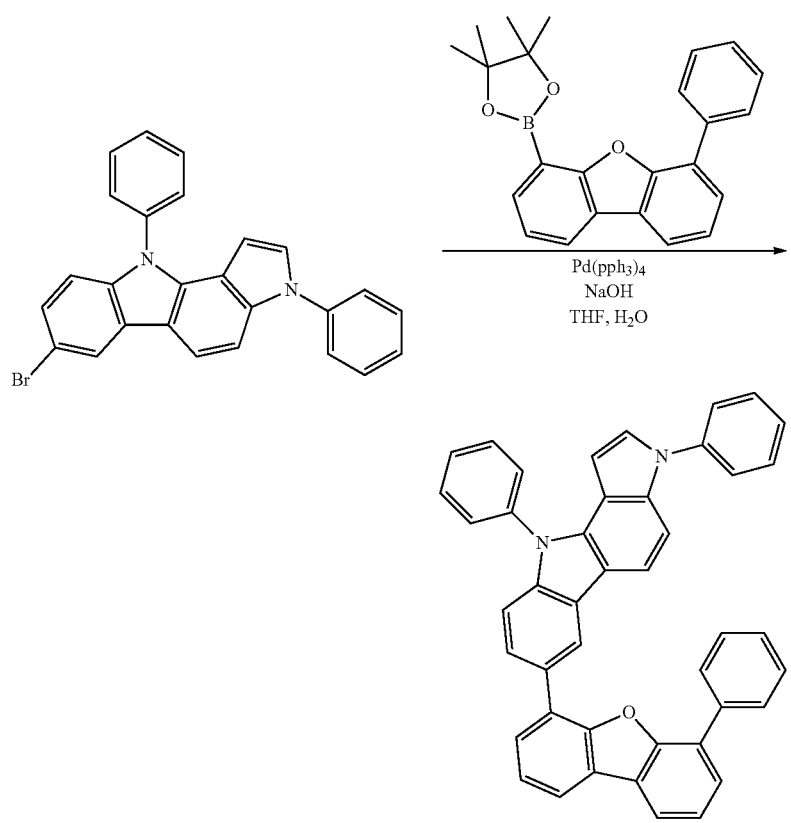

The target compound Inv1151 (3.5 g, yield: 85%) was obtained in the same manner as in Synthesis Example 64, except that 4,4,5,5-tetramethyl-2-(6-phenyldibenzo[b,d]furan-4-yl)-1,3,2-dioxaborolane was used instead of 4,4,5,5-tetramethyl-2-(3-(triphenylen-2-yl)phenyl)-1,3,2-dioxaborolane.

GC-Mass (theoretical value: 600.71 g/mol, measured value: 600 g/mol)

Synthesis Example 71

Synthesis of Inv1152

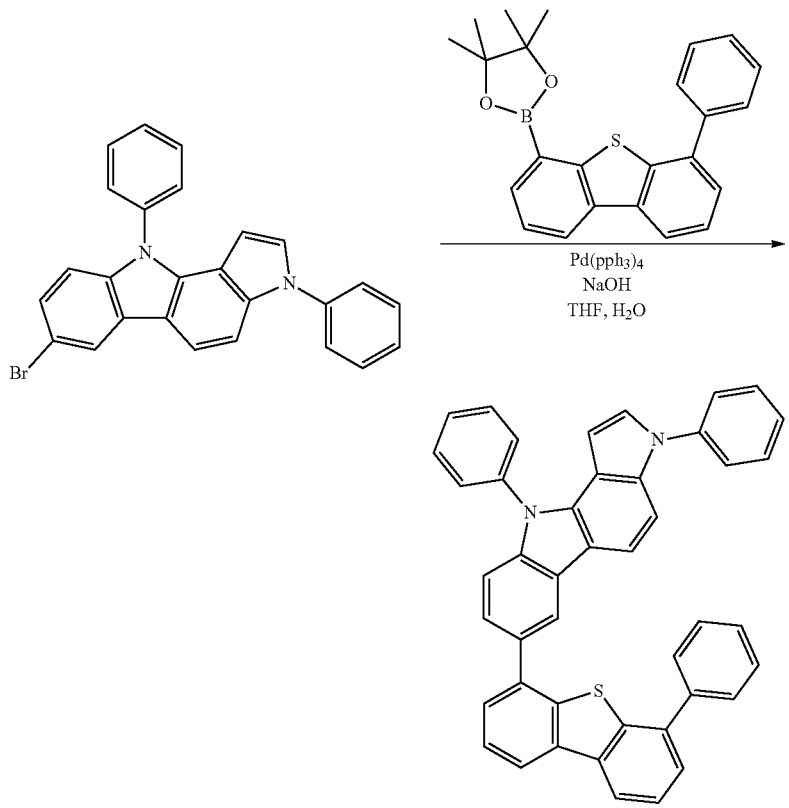

The target compound Inv1152 (3.6 g, yield: 85%) was obtained in the same manner as in Synthesis Example 64, except that 4,4,5,5-tetramethyl-2-(6-phenyldibenzo[b,d]thiophen-4-yl)-1,3,2-dioxaborolane was used instead of 4,4,5,5-tetramethyl-2-(3-(triphenylen-2-yl)phenyl)-1,3,2-dioxaborolane.

GC-Mass (theoretical value: 616.77 g/mol, measured value: 616 g/mol)

Synthesis Example 72

Synthesis of Inv1164

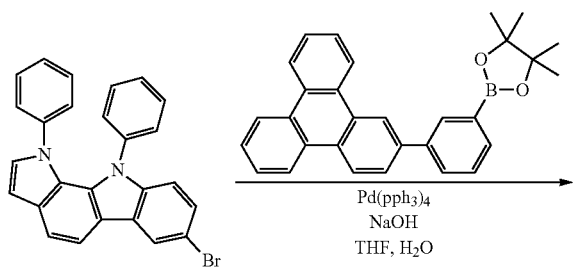

-continued

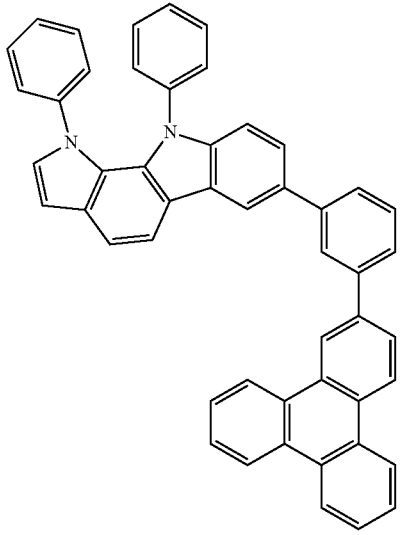

The target compound Inv1164 (3.7 g, yield: 82%) was obtained in the same manner as in Synthesis Example 64, except that IC-8 was used under nitrogen flow instead of IC-7.

GC-Mass (theoretical value: 660.8 g/mol, measured value: 660 g/mol)

Synthesis Example 73

Synthesis of Inv1166

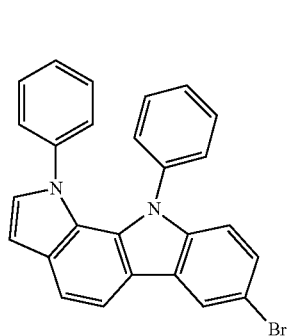 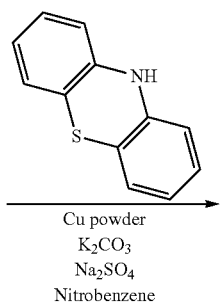

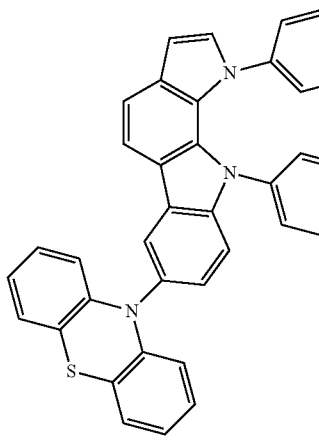

The target compound Inv1166 (2.6 g, yield: 53%) was obtained in the same manner as in Synthesis Example 1, except that IC-8 and 10H-phenothiazine were used instead of IC-1 and 2-(3-bromophenyl)triphenylene, respectively.

GC-Mass (theoretical value: 555.69 g/mol, measured value: 523 g/mol)

Synthesis Example 74

Synthesis of Inv1167

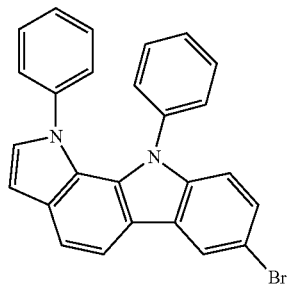 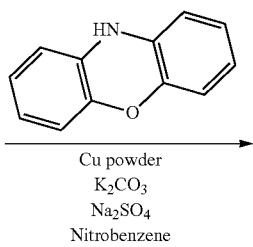

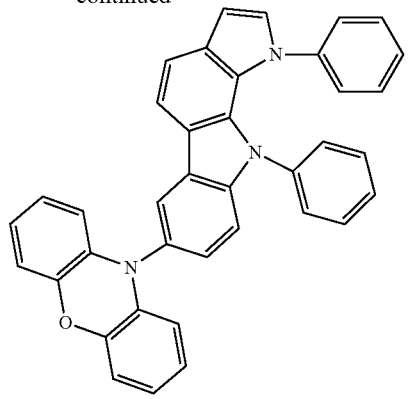

The target compound Inv1167 (2.7 g, yield: 56%) was obtained in the same manner as in Synthesis Example 73, except that 10H-phenoxazine was used instead of 10H-phenothiazine.

GC-Mass (theoretical value: 539.62 g/mol, measured value: 539 g/mol)

Synthesis Example 75

Synthesis of Inv1169

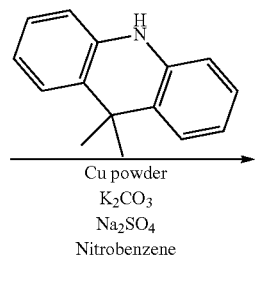

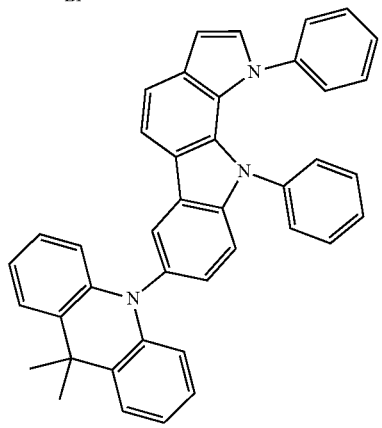

The target compound Inv1169 (3.4 g, yield: 68%) was obtained in the same manner as in Synthesis Example 73, except that 9,9-dimethyl-9,10-dihydroacridine was used instead of 10H-phenothiazine.

GC-Mass (theoretical value: 565.7 g/mol, measured value: 565 g/mol)

Synthesis Example 76

Synthesis of Inv1170

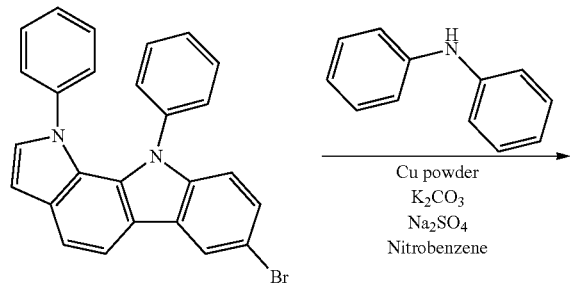

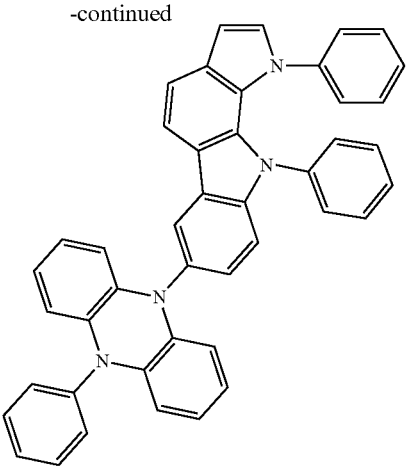

The target compound Inv1170 (2.9 g, yield: 63%) was obtained in the same manner as in Synthesis Example 73, except that diphenylamine was used instead of 10H-phenothiazine.

GC-Mass (theoretical value: 525.64 g/mol, measured value: 525 g/mol)

Synthesis Example 77

Synthesis of Inv1175

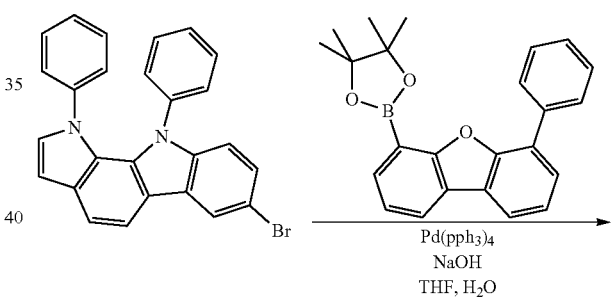

The target compound Inv1175 (2.8 g, yield: 66%) was obtained in the same manner as in Synthesis Example 73, except that 5-phenyl-5,10-dihydrophenazine was used instead of 10H-phenothiazine.

GC-Mass (theoretical value: 614.74 g/mol, measured value: 614 g/mol)

Synthesis Example 78

Synthesis of Inv1176

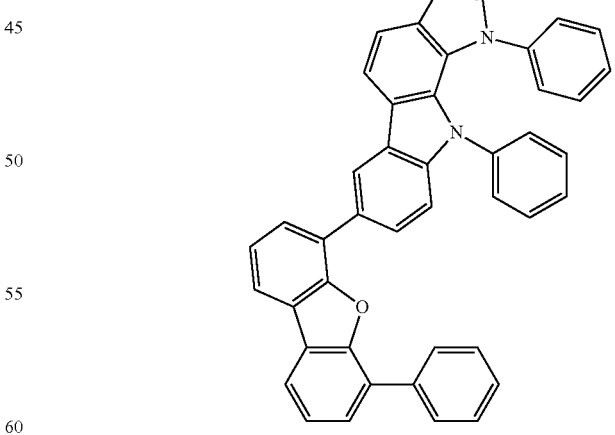

The target compound Inv1176 (3.3 g, yield: 80%) was obtained in the same manner as in Synthesis Example 72, except that 4,4,5,5-tetramethyl-2-(3-(triphenylen-2-yl)phenyl)-1,3,2-dioxaborolane was used instead of 4,4,5,5-tetramethyl-2-(6-phenyldibenzo[b,d]furan-4-yl)-1,3,2-dioxaborolane.

GC-Mass (theoretical value: 600.71 g/mol, measured value: 600 g/mol)

Synthesis Example 79

Synthesis of Inv1177

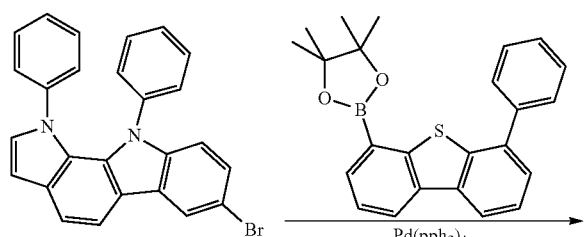

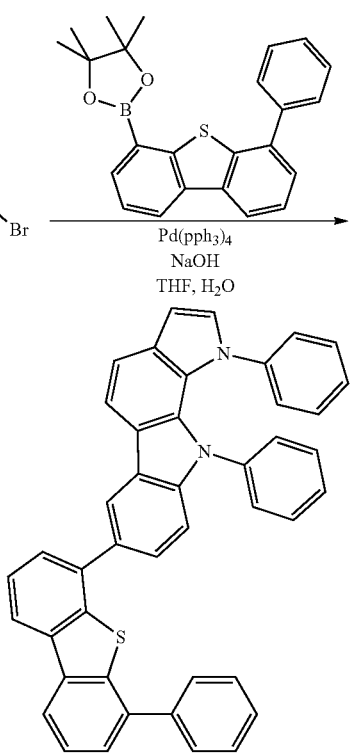

The target compound Inv1177 (3.4 g, yield: 80%) was obtained in the same manner as in Synthesis Example 72, except that 4,4,5,5-tetramethyl-2-(6-phenyldibenzo[b,d]thiophen-4-yl)-1,3,2-dioxaborolane was used instead of 4,4,5,5-tetramethyl-2-(6-phenyldibenzo[b,d]furan-4-yl)-1,3,2-dioxaborolane.

GC-Mass (theoretical value: 616.77 g/mol, measured value: 616 g/mol)

Synthesis Example 80

Synthesis of Inv1185

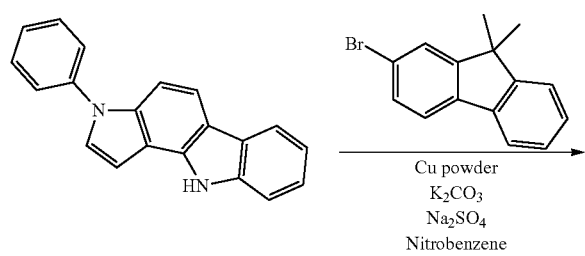

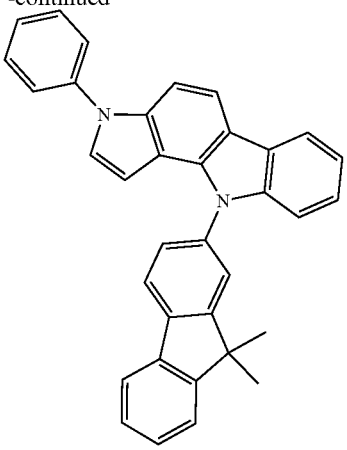

The target compound Inv1185 (2.5 g, yield: 59%) was obtained in the same manner as in Synthesis Example 1, except that 2-bromo-9,9-dimethyl-9H-fluorene was used instead of 2-(3-bromophenyl)triphenylene.

GC-Mass (theoretical value: 474.59 g/mol, measured value: 474 g/mol)

Synthesis Example 81

Synthesis of Inv1206

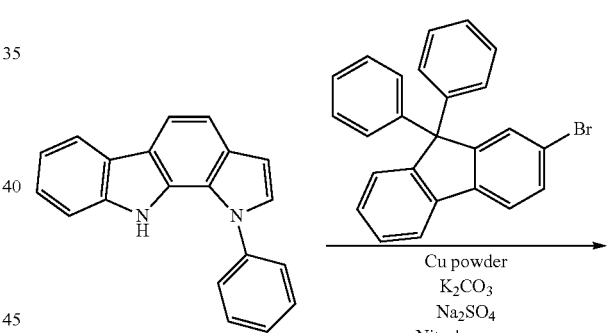

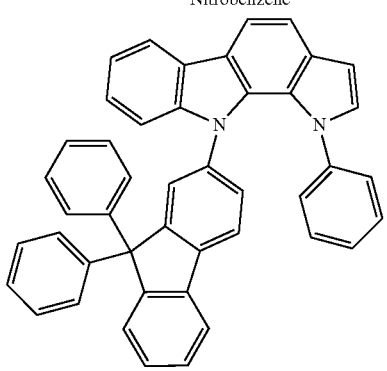

The target compound Inv1206 (3.1 g, yield: 58%) was obtained in the same manner as in Synthesis Example 11, except that 2-bromo-9,9-diphenyl-9H-fluorene was used instead of 2-(3-bromophenyl)triphenylene.

GC-Mass (theoretical value: 598.73 g/mol, measured value: 598 g/mol)

Synthesis Example 82

Synthesis of Inv1254

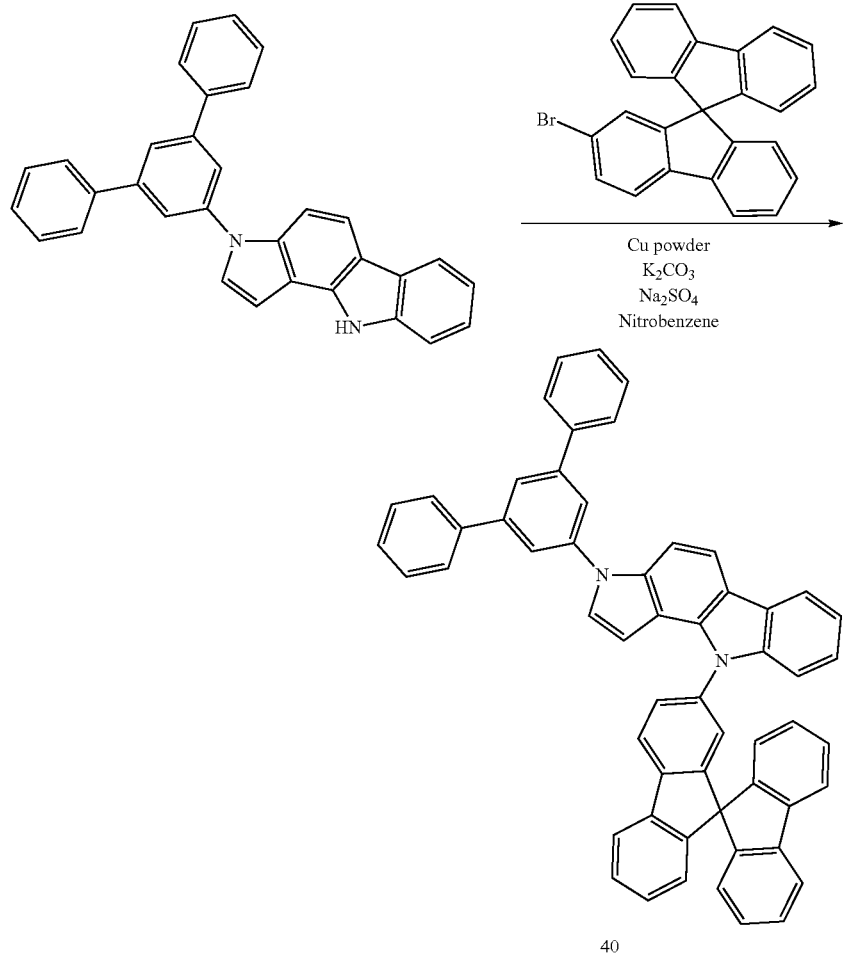

The target compound Inv1254 (2.7 g, yield: 53%) was obtained in the same manner as in Synthesis Example 19, except that 2-bromo-9,9'-spirobi[fluorene] was used instead of 2-(3-bromophenyl)triphenylene.

GC-Mass (theoretical value: 748.91 g/mol, measured value: 748 g/mol)

Synthesis Example 83

Synthesis of Inv1259

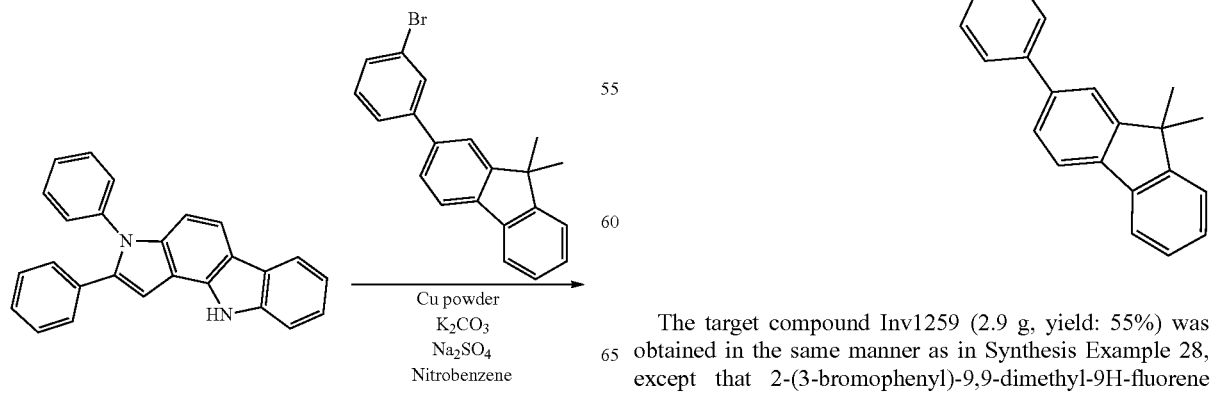

The target compound Inv1259 (2.9 g, yield: 55%) was obtained in the same manner as in Synthesis Example 28, except that 2-(3-bromophenyl)-9,9-dimethyl-9H-fluorene was used instead of 2-(3-bromophenyl)triphenylene.

GC-Mass (theoretical value: 626.79 g/mol, measured value: 626.79 g/mol)

Synthesis Example 84

Synthesis of Inv1289

Synthesis Example 85

Synthesis of Inv1319

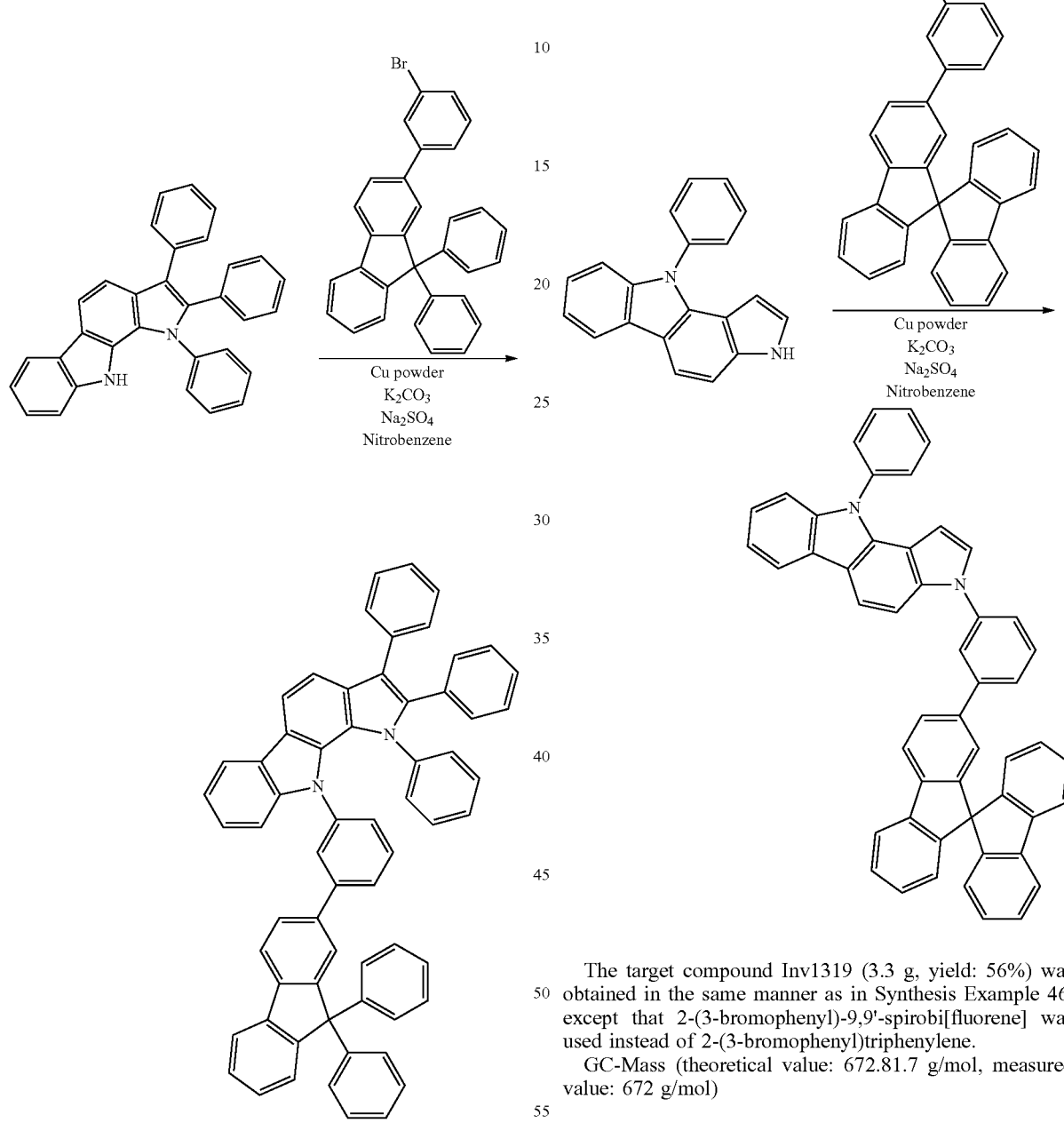

The target compound Inv1289 (3.1 g, yield: 60%) was obtained in the same manner as in Synthesis Example 37, except that 4-(4-bromophenyl)-6-phenyldibenzo[b,d]furan was used instead of 2-(3-bromophenyl)triphenylene.

GC-Mass (theoretical value: 827.02 g/mol, measured value: 827 g/mol)

The target compound Inv1319 (3.3 g, yield: 56%) was obtained in the same manner as in Synthesis Example 46, except that 2-(3-bromophenyl)-9,9'-spirobi[fluorene] was used instead of 2-(3-bromophenyl)triphenylene.

GC-Mass (theoretical value: 672.81.7 g/mol, measured value: 672 g/mol)

Examples 1 to 85

Manufacture of Green Organic Electroluminescence Device

The compounds synthesized in Synthesis Examples 1 to 85 were subjected to highly-pure sublimation purification by a typically known method, and then green organic electroluminescence devices were manufactured according to the following procedure.

First, a glass substrate thinly coated with indium tin oxide (ITO) to have a thickness of 1,500 Å was ultrasonically washed with distilled water. When the washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescence device was manufactured by stacking m-MTDATA (60 nm)/TCTA (80 nm)/each compound of Synthesis Examples 1 to 85+10% Ir(ppy)$_3$ (300 nm)/BCP (10 nm)/Alq$_3$ (30 nm)/LiF (1 nm)/Al (200 nm) in this order on the thus prepared ITO transparent substrate (electrode).

Comparative Example

A green organic electroluminescence device was manufactured by the same procedure as in Example 1, except that when a light-emitting layer is formed, CBP was used as a light-emitting host material instead of the compound of Synthesis Example 1.

The structures of m-MTDATA, TCTA, Ir(ppy)$_3$, CBP, and BCP used in Examples 1 to 85 and the Comparative Example are as follows.

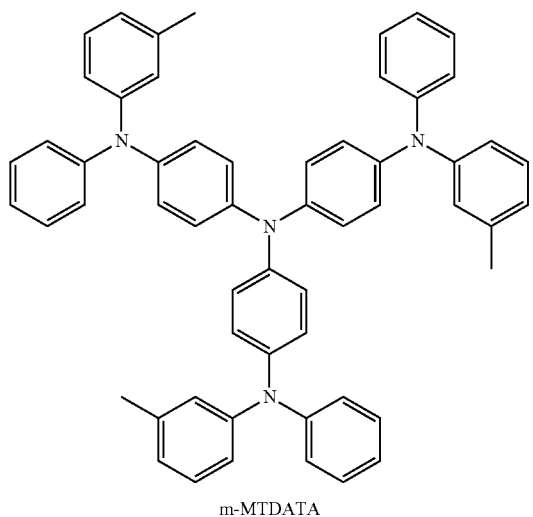

m-MTDATA

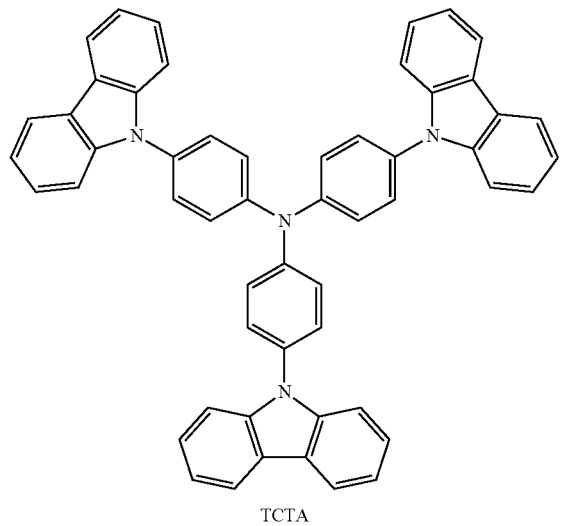

TCTA

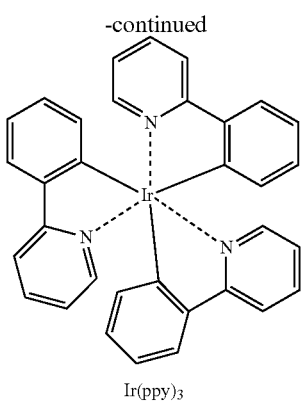

Ir(ppy)$_3$

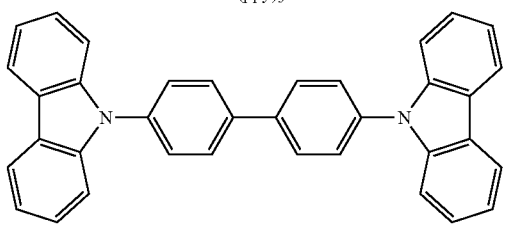

CBP

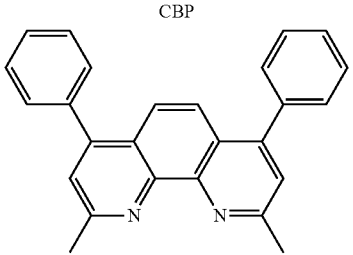

BCP

Evaluation Example

For each of the organic electroluminescence devices manufactured in Examples 1 to 85 and Comparative Example, the driving voltage, current efficiency, and light-emitting peaks thereof were measured at a current density of 10 mA/cm$^2$, and the results are shown in the following Table 1.

TABLE 1

| Sample | Host | Driving voltage (V) | Light-emitting peak (nm) | Current efficiency (cd/A) |
|---|---|---|---|---|
| Example 1 | Inv5 | 6.68 | 521 | 41.8 |
| Example 2 | Inv29 | 6.65 | 521 | 41.9 |
| Example 3 | Inv38 | 6.60 | 520 | 42.1 |
| Example 4 | Inv39 | 6.65 | 520 | 42.5 |
| Example 5 | Inv42 | 6.70 | 520 | 41.8 |
| Example 6 | Inv46 | 6.66 | 521 | 42.2 |
| Example 7 | Inv47 | 6.70 | 521 | 42.7 |
| Example 8 | Inv48 | 6.61 | 521 | 41.4 |
| Example 9 | Inv58 | 6.55 | 520 | 42.8 |
| Example 10 | Inv65 | 6.60 | 519 | 41.5 |
| Example 11 | Inv167 | 6.64 | 519 | 41.1 |
| Example 12 | Inv192 | 6.63 | 519 | 42.5 |
| Example 13 | Inv200 | 6.55 | 520 | 41.4 |
| Example 14 | Inv205 | 6.63 | 521 | 41.9 |
| Example 15 | Inv208 | 6.65 | 521 | 41.5 |
| Example 16 | Inv222 | 6.58 | 521 | 41.3 |
| Example 17 | Inv219 | 6.57 | 521 | 42.4 |
| Example 18 | Inv224 | 6.61 | 522 | 41.1 |
| Example 19 | Inv572 | 6.60 | 522 | 41.5 |

TABLE 1-continued

| Sample | Host | Driving voltage (V) | Light-emitting peak (nm) | Current efficiency (cd/A) |
|---|---|---|---|---|
| Example 20 | Inv596 | 6.61 | 522 | 40.7 |
| Example 21 | Inv606 | 6.62 | 520 | 41.9 |
| Example 22 | Inv609 | 6.57 | 520 | 41.8 |
| Example 23 | Inv611 | 6.61 | 519 | 41.1 |
| Example 24 | Inv614 | 6.63 | 518 | 41.5 |
| Example 25 | Inv615 | 6.68 | 520 | 42.0 |
| Example 26 | Inv625 | 6.51 | 520 | 41.3 |
| Example 27 | Inv632 | 6.62 | 521 | 42.2 |
| Example 28 | Inv653 | 6.64 | 521 | 41.7 |
| Example 29 | Inv678 | 6.60 | 520 | 41.9 |
| Example 30 | Inv686 | 6.73 | 519 | 41.5 |
| Example 31 | Inv691 | 6.62 | 522 | 41.3 |
| Example 32 | Inv694 | 6.60 | 522 | 42.1 |
| Example 33 | Inv705 | 6.61 | 522 | 41.6 |
| Example 34 | Inv707 | 6.50 | 523 | 41.6 |
| Example 35 | Inv708 | 6.52 | 520 | 40.9 |
| Example 36 | Inv710 | 6.60 | 521 | 42.6 |
| Example 37 | Inv896 | 6.65 | 521 | 42.3 |
| Example 38 | Inv920 | 6.65 | 520 | 41.7 |
| Example 39 | Inv930 | 6.61 | 520 | 41.9 |
| Example 40 | Inv933 | 6.59 | 521 | 41.3 |
| Example 41 | Inv935 | 6.60 | 522 | 41.9 |
| Example 42 | Inv938 | 6.62 | 522 | 42.2 |
| Example 43 | Inv939 | 6.60 | 523 | 41.8 |
| Example 44 | Inv949 | 6.53 | 520 | 42.1 |
| Example 45 | Inv956 | 6.65 | 519 | 41.5 |
| Example 46 | Inv977 | 6.63 | 520 | 42.5 |
| Example 47 | Inv1002 | 6.60 | 519 | 42.3 |
| Example 48 | Inv1010 | 6.51 | 519 | 42.6 |
| Example 49 | Inv1015 | 6.66 | 520 | 43.1 |
| Example 50 | Inv1018 | 6.55 | 520 | 41.8 |
| Example 51 | Inv1029 | 6.56 | 521 | 41.5 |
| Example 52 | Inv1032 | 6.63 | 521 | 41.3 |
| Example 53 | Inv1031 | 6.66 | 521 | 41.0 |
| Example 54 | Inv1034 | 6.57 | 522 | 40.8 |
| Example 55 | Inv1058 | 6.50 | 523 | 41.3 |
| Example 56 | Inv1082 | 6.55 | 521 | 41.3 |
| Example 57 | Inv1092 | 6.70 | 520 | 42.1 |
| Example 58 | Inv1095 | 6.63 | 521 | 41.9 |
| Example 59 | Inv1097 | 6.65 | 520 | 42.9 |
| Example 60 | Inv1100 | 6.60 | 519 | 42.3 |
| Example 61 | Inv1101 | 6.69 | 519 | 41.7 |
| Example 62 | Inv1111 | 6.73 | 520 | 41.8 |
| Example 63 | Inv1118 | 6.72 | 521 | 42.3 |
| Example 64 | Inv1139 | 6.63 | 521 | 41.7 |
| Example 65 | Inv1141 | 6.57 | 521 | 41.8 |
| Example 66 | Inv1142 | 6.50 | 520 | 42.5 |
| Example 67 | Inv1144 | 6.55 | 520 | 42.3 |
| Example 68 | Inv1145 | 6.62 | 521 | 42.2 |
| Example 69 | Inv1150 | 6.60 | 522 | 42.1 |
| Example 70 | Inv1151 | 6.63 | 523 | 41.9 |
| Example 71 | Inv1152 | 6.65 | 522 | 41.5 |
| Example 72 | Inv1164 | 6.70 | 520 | 42.3 |
| Example 73 | Inv1166 | 6.71 | 521 | 42.2 |
| Example 74 | Inv1167 | 6.64 | 521 | 41.1 |
| Example 75 | Inv1169 | 6.70 | 521 | 40.9 |
| Example 76 | Inv1170 | 6.61 | 523 | 41.2 |
| Example 77 | Inv1175 | 6.60 | 523 | 40.7 |
| Example 78 | Inv1176 | 6.55 | 522 | 41.3 |
| Example 79 | Inv1177 | 6.61 | 523 | 40.8 |
| Example 80 | Inv1185 | 6.60 | 522 | 42.9 |
| Example 81 | Inv1206 | 6.63 | 521 | 41.6 |
| Example 82 | Inv1254 | 6.59 | 522 | 41.1 |
| Example 83 | Inv1259 | 6.64 | 523 | 41.9 |
| Example 84 | Inv1289 | 6.61 | 523 | 42.6 |
| Example 85 | Inv1319 | 6.55 | 523 | 42.3 |
| Comparative Example | CBP | 6.93 | 516 | 38.2 |

As shown in Table 1, it can be seen that when the compound according to the present invention is used as a material for a light-emitting layer of a green organic electroluminescence device (Examples 1 to 85), the green organic electroluminescence devices exhibit better performance in terms of efficiency and driving voltage than the green organic electroluminescence device (Comparative Example) in the related art in which the CBP is used as a material for a light-emitting layer.

INDUSTRIAL APPLICABILITY

The indole-based compound represented by Formula 1 according to the present invention has excellent heat resistance, hole injection and transport capabilities, light-emitting capabilities, and the like. Therefore, an organic electroluminescence device including the compound in a hole injection layer, a hole transporting layer or a light-emitting layer may be greatly enhanced in terms of light-emitting performance, driving voltage, lifespan, efficiency, and the like, and thus, may be effectively applied to a full-color display panel, and the like.

The invention claimed is:

1. A compound of the following Formula 1:

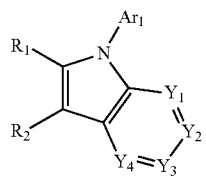

Formula 1 in Formula 1, $Y_1$ to $Y_4$ are each independently N or $CR_3$, one of $Y_1$ and $Y_2$, $Y_2$ and $Y_3$, and $Y_3$ and $Y_4$ forms a fused ring of the following Formula 2,

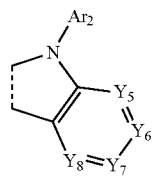

Formula 2 in Formula 2, $Y_5$ to $Y_8$ are each independently N or $CR_4$, and a dotted line means a site where a fusion with the compound of Formula 1 occurs, $Ar_1$ and $Ar_2$ are each independently selected from the group consisting of a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and in this case, one or more of $Ar_1$ and $Ar_2$ are selected from the group consisting of the structures of the following A1 to A100, 599
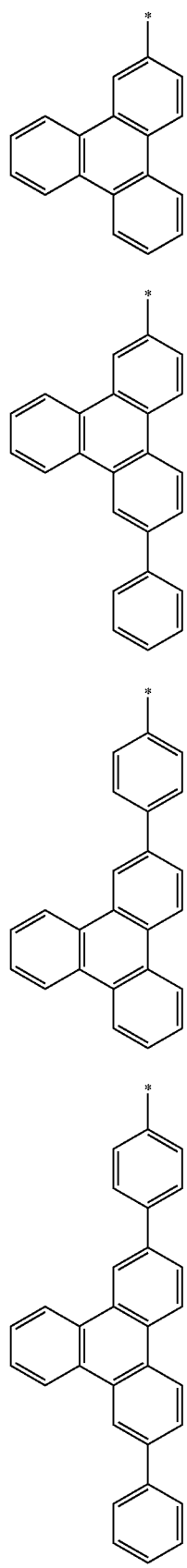
600
-continued
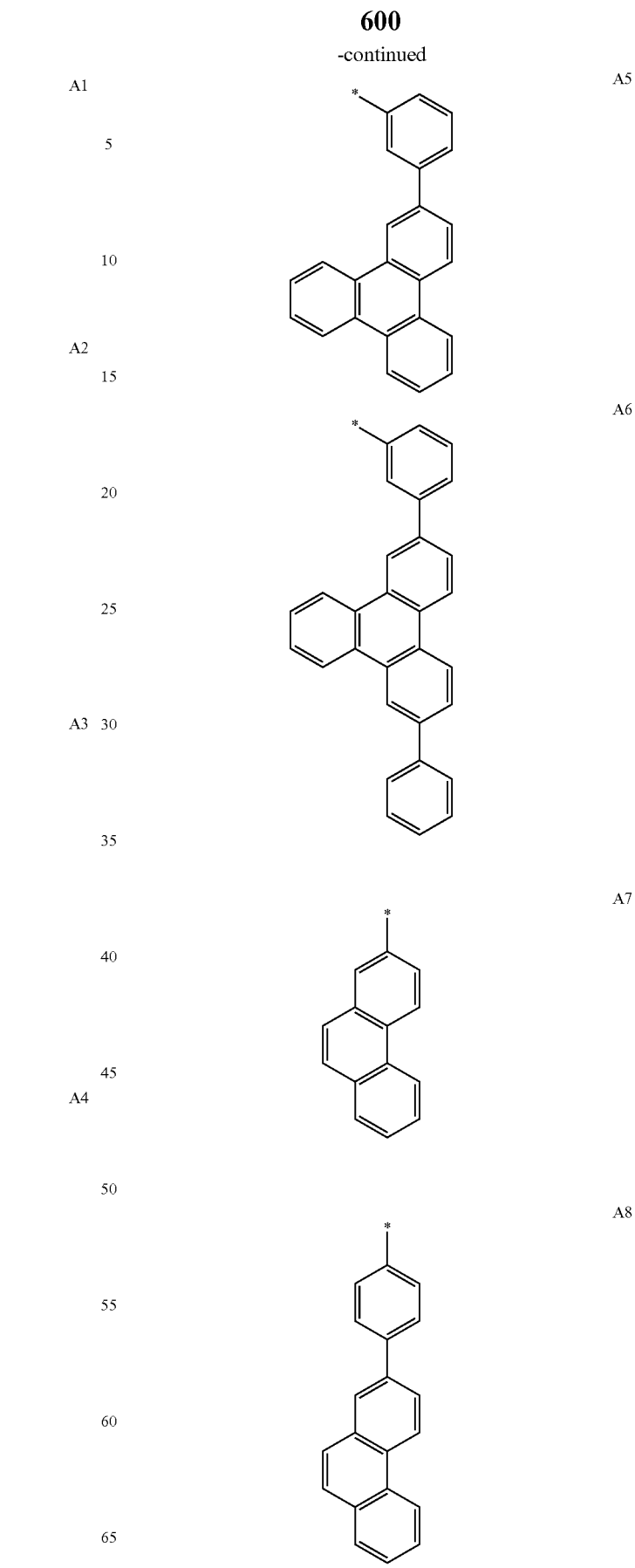

| 601 | 602 |
|---|---|
| -continued | -continued |
A9 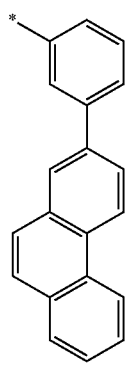
A10 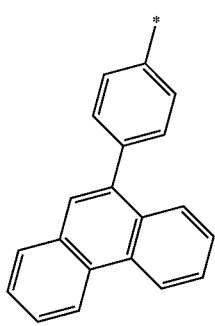
A11 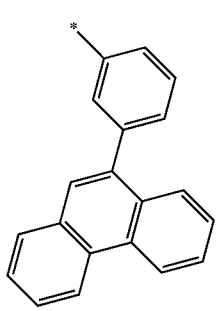
A12 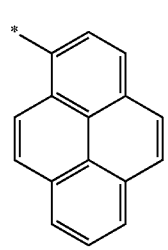
A13
A14 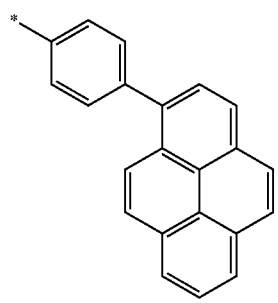
A15 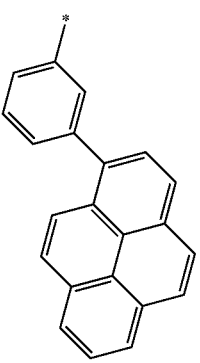
A16 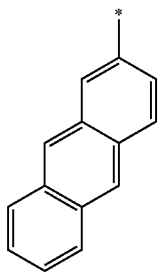
A17 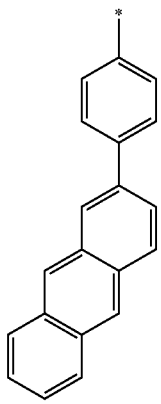

-continued
A18 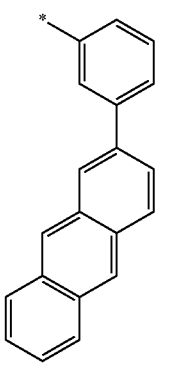
A19 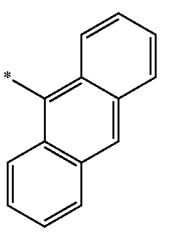
A20 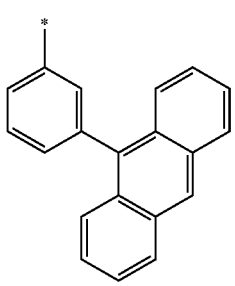
A21 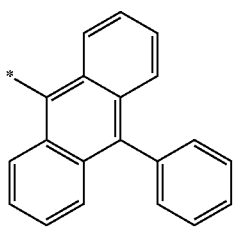
A22 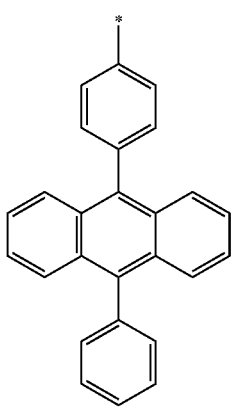
-continued
A23 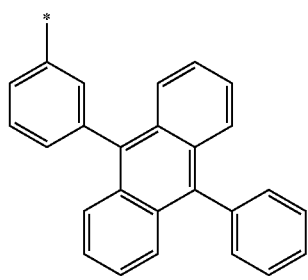
A24 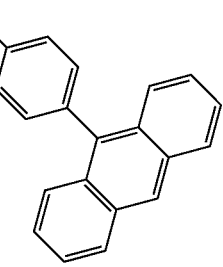
A25 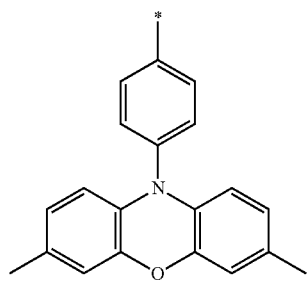
A26 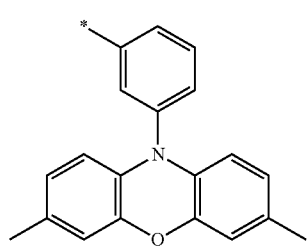
A27 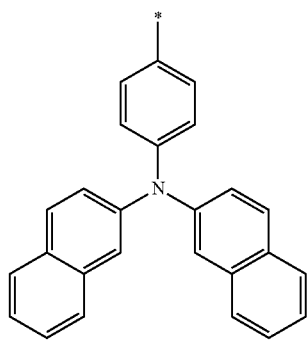

| | |
|---|---|
| A28 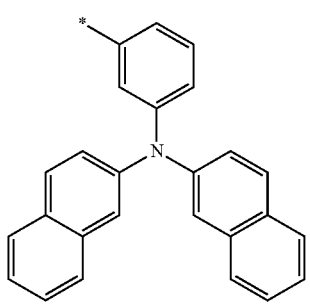 | A34 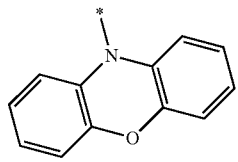 |
| A29 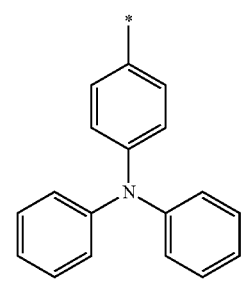 | A35 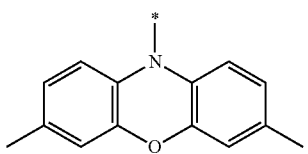 |
| A30 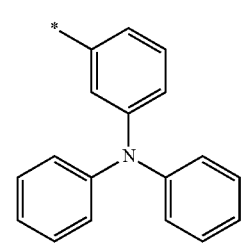 | A36 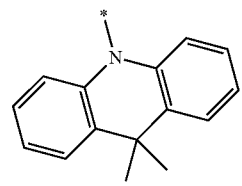 |
| A31 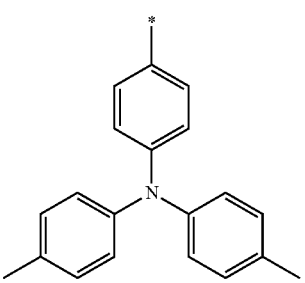 | A37 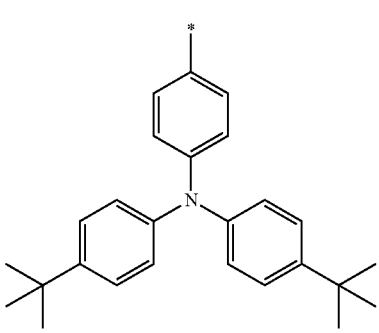 |
| A32 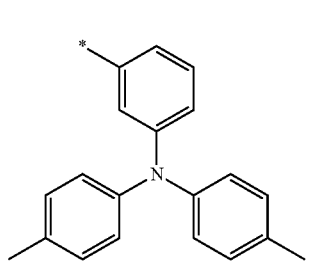 | A38 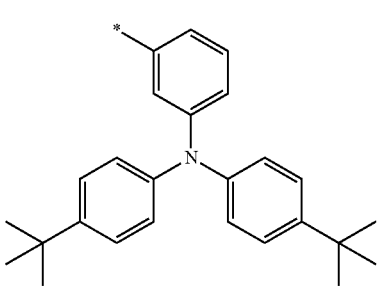 |
| A33 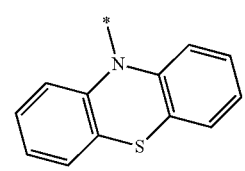 | A39 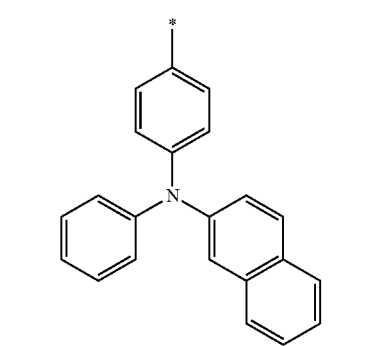 |

607
-continued
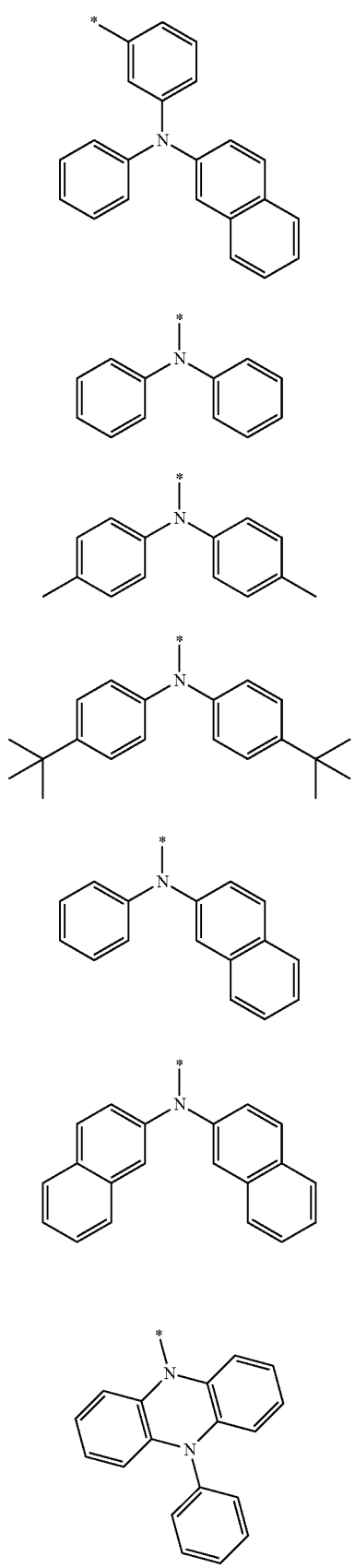
608
-continued
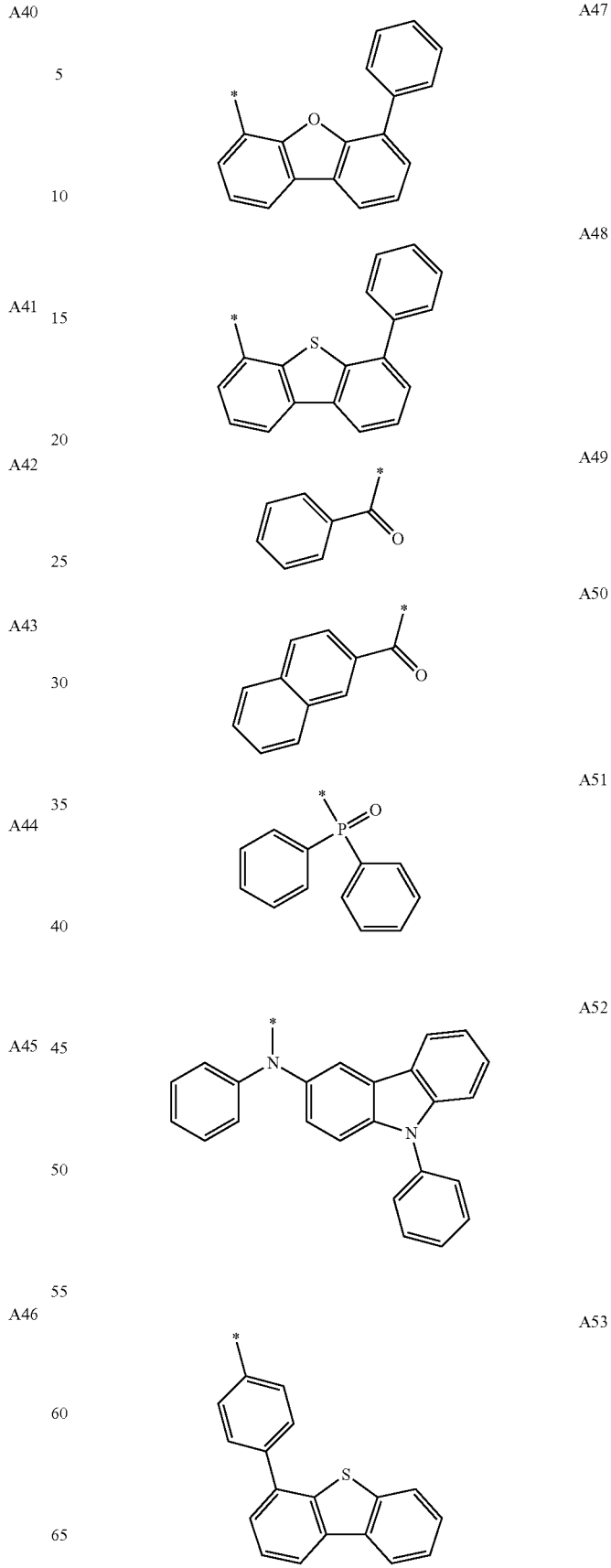

A54 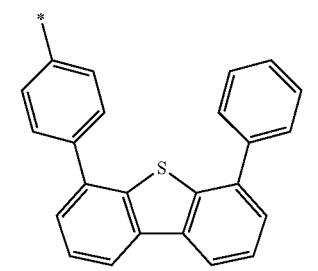
A55 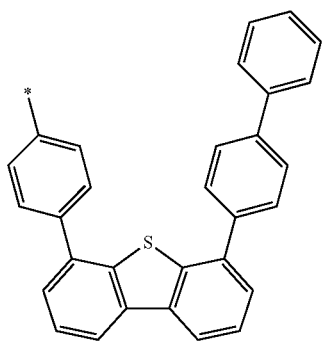
A56 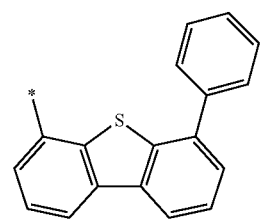
A57 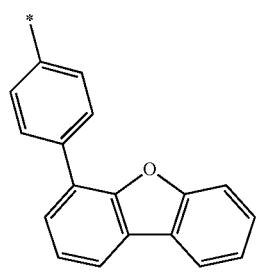
A58 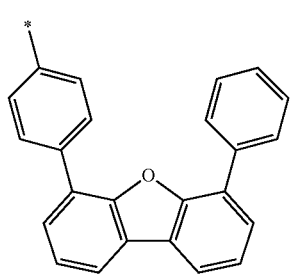
A59 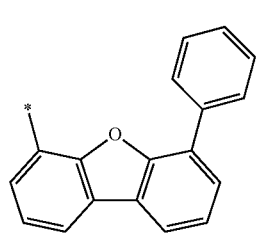
A60 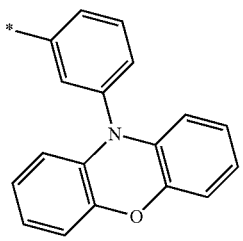
A61 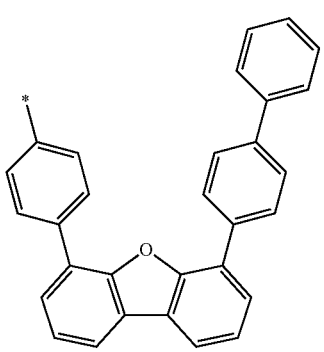
A62 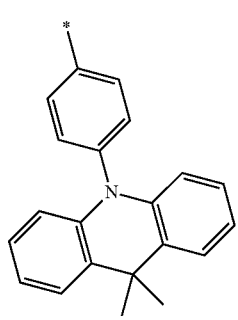
A63 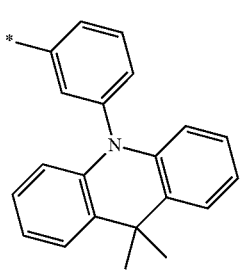
A64 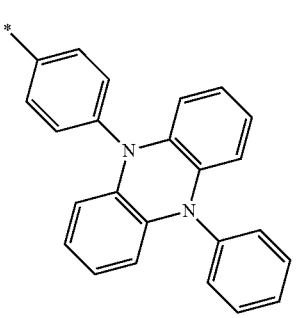

611
-continued
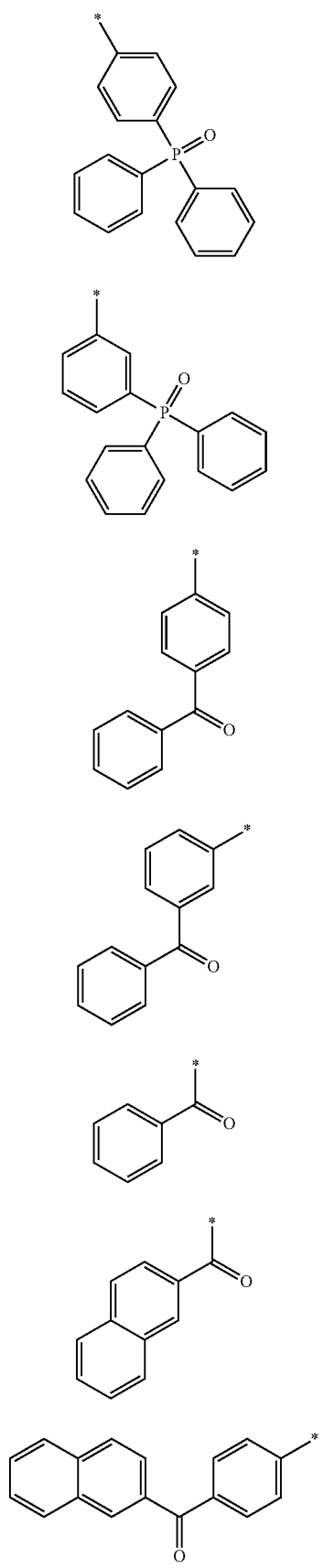
A65
A66
A67
A68
A69
A70
A71
612
-continued
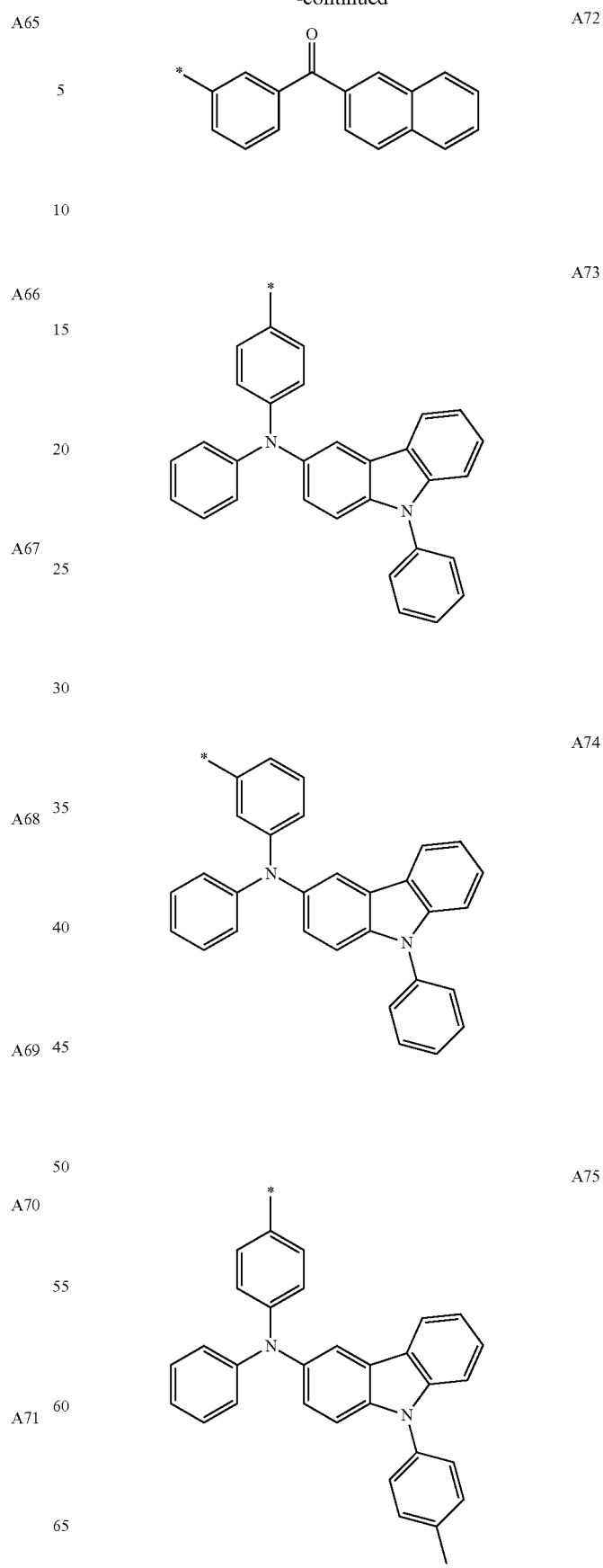
A72
A73
A74
A75

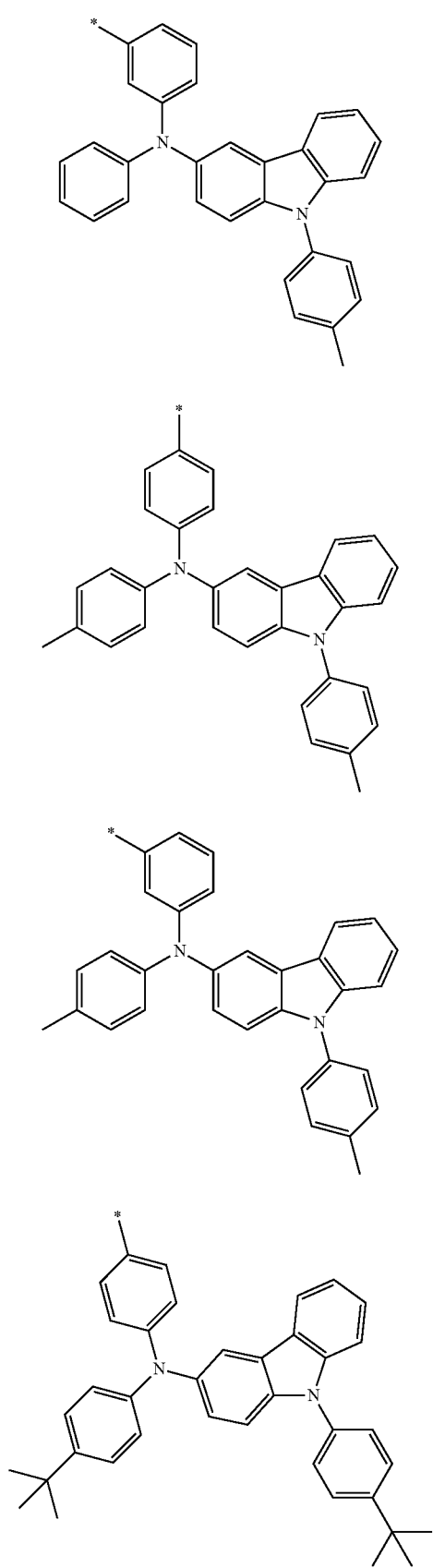
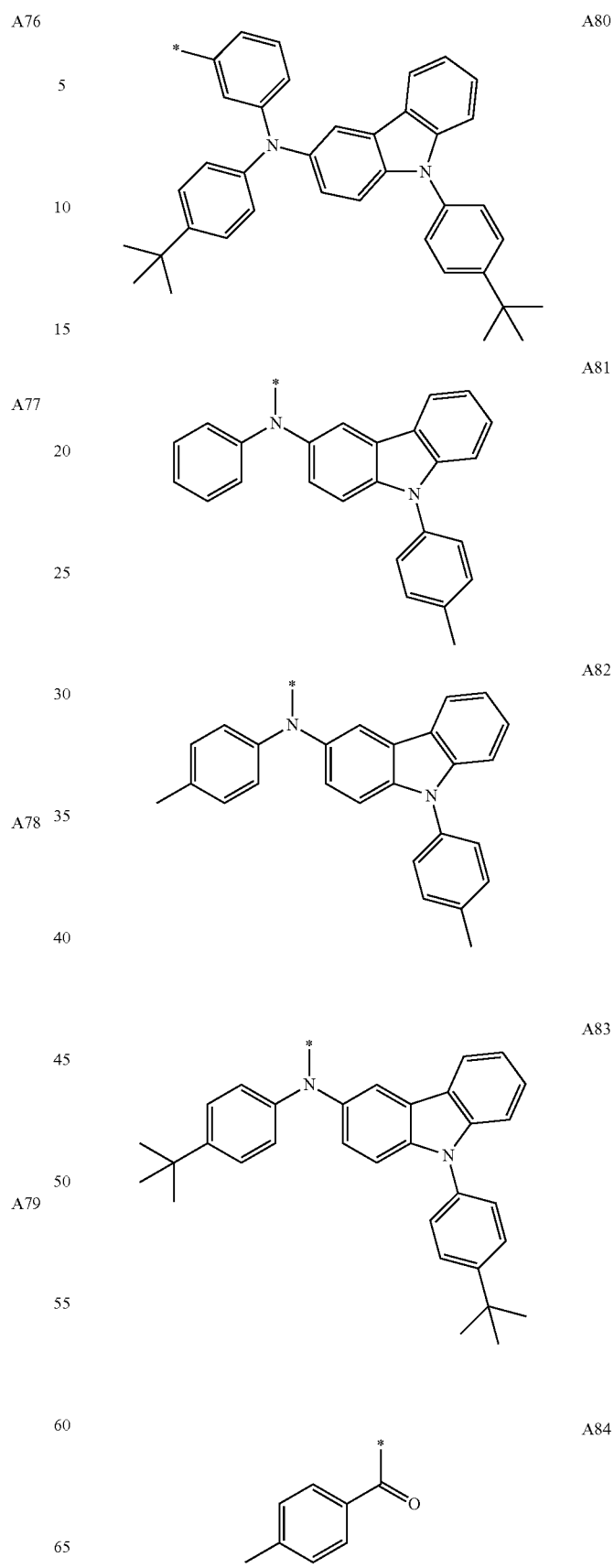

| 615 -continued | | 616 -continued | |
|---|---|---|---|
| 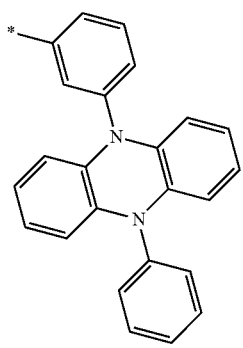 | A85 | 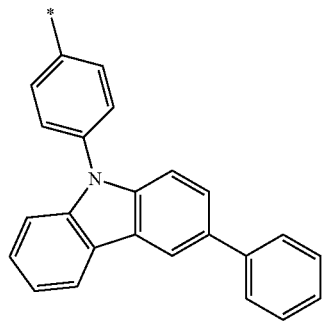 | A90 |
| 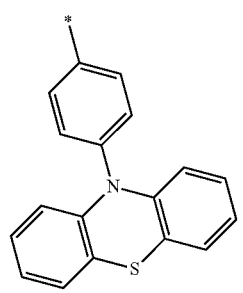 | A86 | 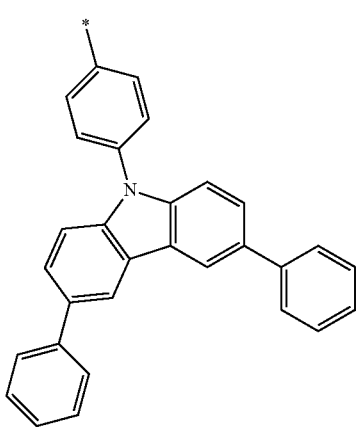 | A91 |
| 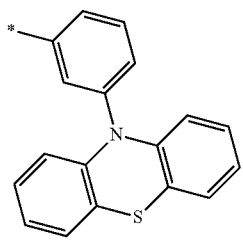 | A87 | 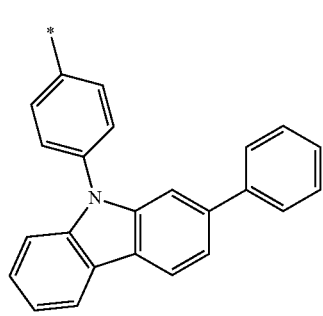 | A92 |
| 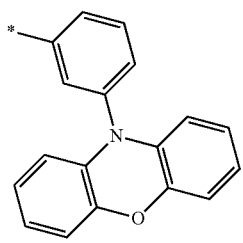 | A88 | 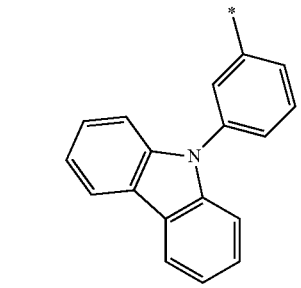 | A93 |
| 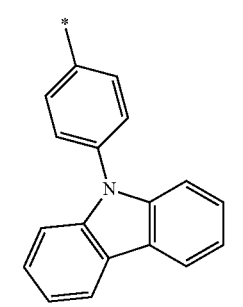 | A89 | 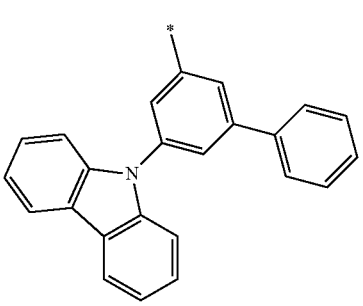 | A94 |

A95 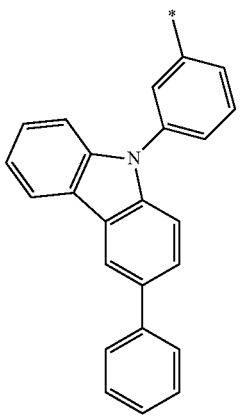

A96 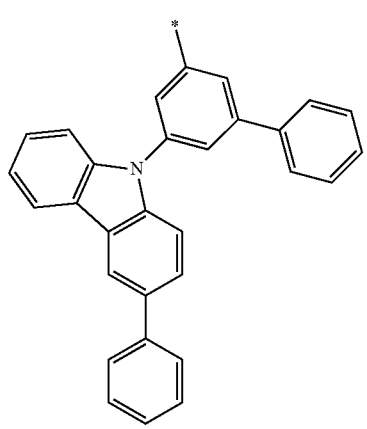

A97 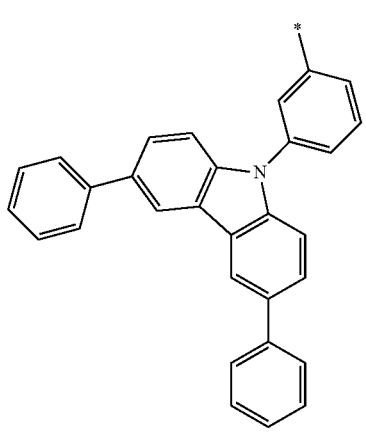

A98 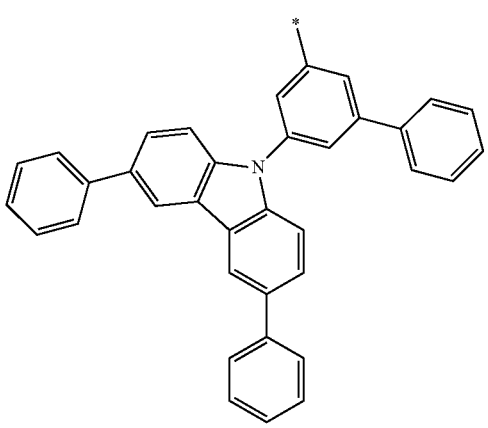

A99 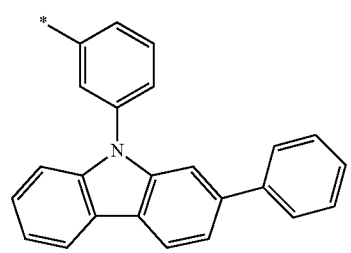

A100 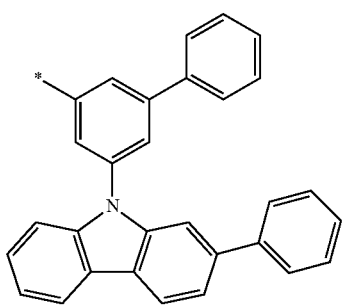

$R_1$ to $R_4$ are each independently selected from the group consisting of hydrogen, deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or adjacent group form a fused ring, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_1$ to $R_4$ is each independently unsubstituted or substituted with one or more selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkyl boron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

2. The compound of claim 1, wherein the compound of Formula 1 is selected from the group consisting of compounds of the following Formulae 4 to 9:

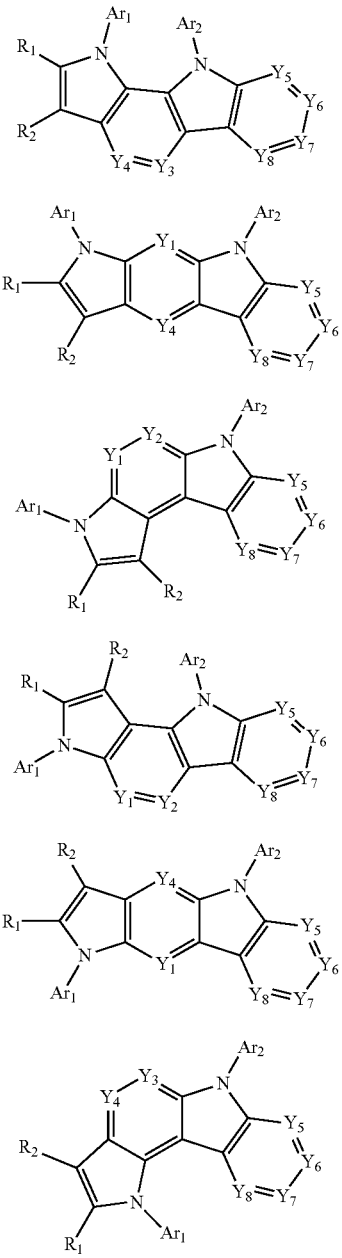

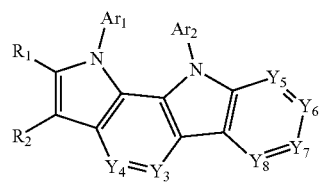

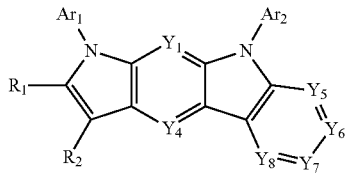

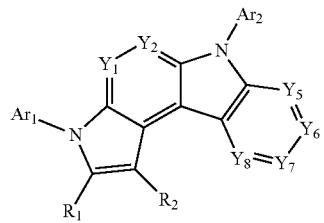

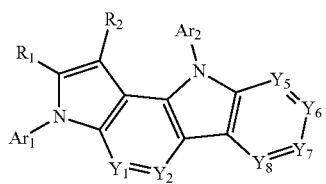

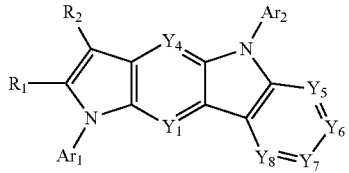

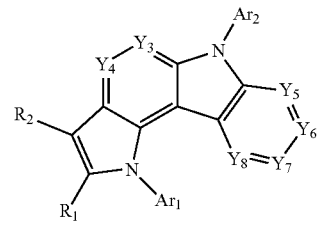

in Formulae 4 to 9, $Ar_1$ and $Ar_2$, $Y_1$ to $Y_8$, and $R_1$ to $R_4$ are the same as those defined in claim 1.

3. The compound of claim 1, wherein which does not form a fused ring in $Y_1$ to $Y_4$ is $CR_3$, and which does not form a fused ring in $Y_5$ to $Y_8$ is $CR_4$.

4. A compound selected from the group consisting of compounds of the following Formulae 4 to 9:

in Formulae 4 to 9, $Y_1$ to $Y_4$ are each independently N or $CR_3$, $Y_5$ to $Y_8$ are each independently N or $CR_4$, $Ar_1$ and $Ar_2$ are different from each other, and are a $C_6$ to $C_{60}$ aryl group or a heteroaryl group having 5 to 60 nuclear atoms, and in this case, one or more of $Ar_1$ and $Ar_2$ have the following Formula 3,

Formula 3 in Formula 3,

L is a single bond or phenylene,

Ra is selected from the group consisting of structures of the following S-1 to S-17:

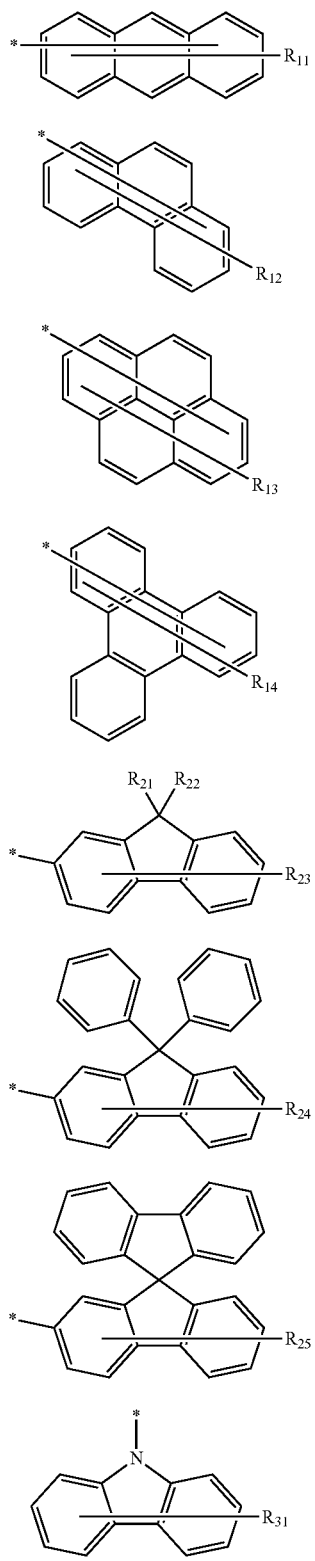

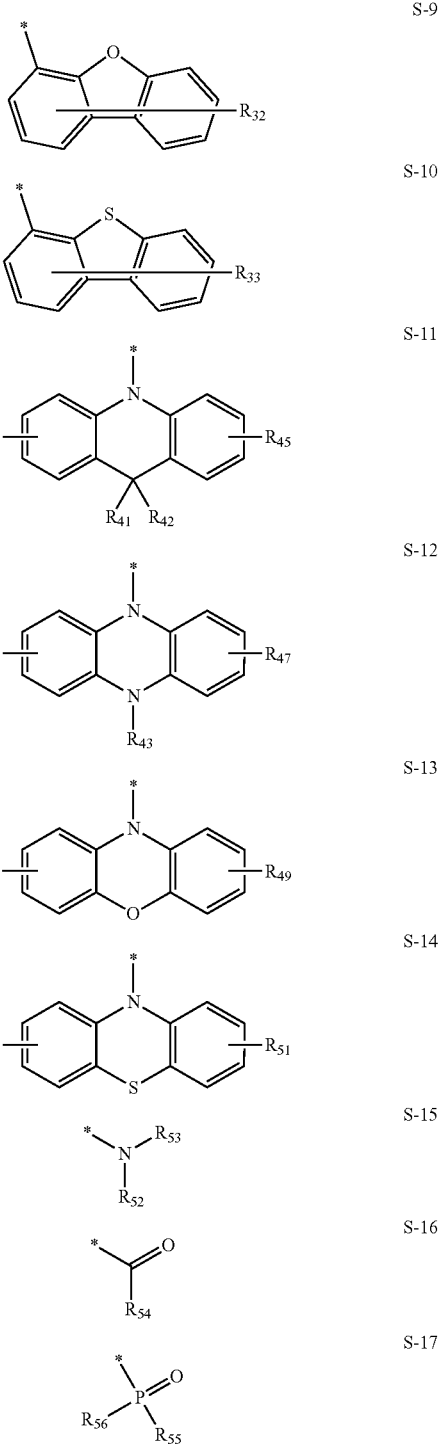

$R_{11}$ to $R_{14}$, $R_{21}$ to $R_{25}$, $R_{31}$ to $R_{33}$, and $R_{41}$ to $R_{56}$ are each independently selected from the group consisting of hydrogen, deuterium, halogen, nitro, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and $R_1$ to $R_4$ are each independently selected from the group consisting of hydrogen, deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, or adjacent group form a fused ring, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_1$ to $R_4$, $R_{11}$ to $R_{14}$, $R_{21}$ to $R_{25}$, $R_{31}$ to $R_{33}$, and $R_{41}$ to $R_{56}$ are each independently unsubstituted or substituted with one or more selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

5. An organic electroluminescence device comprising:

an anode;

a cathode; and an organic material layer comprising one or more layers interposed between the anode and the cathode, wherein at least one of the organic material layers comprising one or more layers comprises the compound of claim 1.

6. The organic electroluminescence device of claim 5, wherein the organic material layer comprising the compound is selected from the group consisting of a hole injection layer, a hole transporting layer, and a light-emitting layer.

7. The organic electroluminescence device of claim 5, wherein the organic material layer comprising the compound is a phosphorescent light-emitting layer.

8. The organic electroluminescence device of claim 5, wherein the compound of Formula 1 is selected from the group consisting of compounds of the following Formulae 4 to 9:

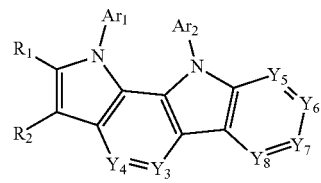

Formula 4

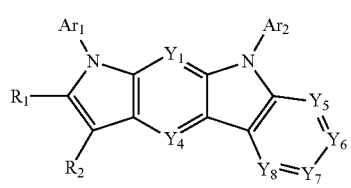

Formula 5

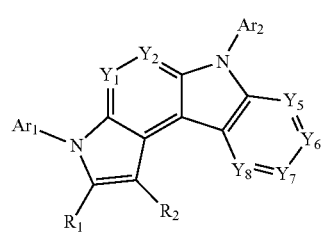

Formula 6

Formula 7

Formula 8

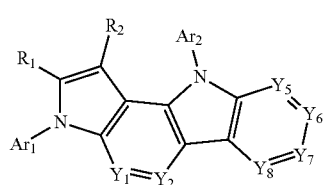

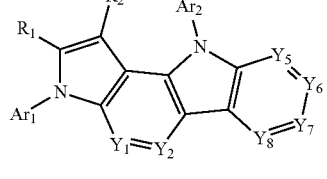

Formula 9

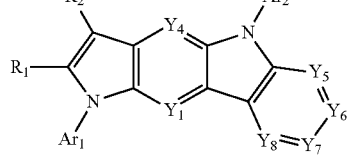

in Formulae 4 to 9, $Ar_1$ and $Ar_2$, $Y_1$ to $Y_8$, and $R_1$ to $R_4$ are the same as those defined in claim 1.

9. The organic electroluminescence device of claim 5, wherein what does not form a fused ring in $Y_1$ to $Y_4$ is $CR_3$, and what does not form a fused ring in $Y_5$ to $Y_8$ is $CR_4$.

* * * * *